US012747436B2

(12) United States Patent
Madani et al.

(10) Patent No.: US 12,747,436 B2
(45) Date of Patent: Sep. 29, 2026

(54) ADENINE DEAMINASES AND COMPOSITIONS, SYSTEMS, AND METHODS THEREOF

(71) Applicant: Profluent Bio Inc., Emeryville, CA (US)

(72) Inventors: Ali Madani, Emeryville, CA (US); Jeffrey A. Ruffolo, Emeryville, CA (US); Stephen Nayfach, Emeryville, CA (US); Joel Beazer, Emeryville, CA (US)

(73) Assignee: Profluent Bio Inc., Emeryville, CA (US)

( * ) Notice: Subject to any disclaimer, the term of this patent is extended or adjusted under 35 U.S.C. 154(b) by 0 days.

(21) Appl. No.: 19/255,359

(22) Filed: Jun. 30, 2025

(65) Prior Publication Data

US 2025/0327055 A1 Oct. 23, 2025

Related U.S. Application Data

(63) Continuation of application No. PCT/US2024/056236, filed on Nov. 15, 2024.

(60) Provisional application No. 63/599,141, filed on Nov. 15, 2023.

(51) Int. Cl.

| | |
|---|---|
| ***C12N 9/78*** | (2006.01) |
| ***C12N 9/22*** | (2006.01) |
| ***C12N 15/11*** | (2006.01) |
| ***C12N 15/90*** | (2006.01) |

(52) U.S. Cl.

CPC ............... *C12N 9/78* (2013.01); *C12N 9/226* (2025.05); *C12N 15/11* (2013.01); *C12N 15/907* (2013.01); *C12Y 305/04004* (2013.01); *C07K 2319/00* (2013.01); *C12N 2310/20* (2017.05)

(58) Field of Classification Search

CPC .......... C12N 9/78; C12N 9/226; C12N 15/11; C12N 15/907; C12N 2310/20; C12Y 305/04004; C07K 2319/00

USPC ........................................................ 424/94.6

See application file for complete search history.

(56) References Cited

U.S. PATENT DOCUMENTS

| | | | | |
|---|---|---|---|---|
| 5,034,506 | A | 7/1991 | Summerton et al. | |
| 12,123,016 | B1 | 10/2024 | Madani et al. | |
| 2017/0051312 | A1 | 2/2017 | Jinek et al. | |
| 2022/0364067 | A1* | 11/2022 | Lin ..................... | C12N 15/907 |

OTHER PUBLICATIONS

Uniprot (“A0A931VZPO_UNCAI”, published on Feb. 22, 2023, downloaded from https://www.uniprot.org/uniparc/UPI001DA0F361/entry/A0A931VZP0#sequence, 4 pages (Year: 2023).*

Valerio et al., “One adenosine deaminase allele in a patient with severe combined immunodeficiency contains a point mutation abolishing enzyme activity”, published in 1986, The EMBO Journal , vol. 5, No. 1, pp. 113-119. (Year: 1986).*

Wolf et al., “tadA, an essential tRNA-specific adenosine deaminase from *Escherichia coli*”, published in 2002, The Embo Journal, vol. 21, No. 14, pp. 3841-3851. (Year: 2002).*

Altschul S.F., et al., “Basic Local Alignment Search Tool,” Journal of Molecular Biology, PMID: 2231712, Oct. 5, 1990, vol. 215, No. 3, pp. 403-410, Doi: 10.1016/S0022-2836(05)80360-2.

Altschul S.F., et al., “Gapped BLAST and PSI-BLAST: A New Generation of Protein Database Search Programs”, Nucleic Acids Research, Sep. 1, 1997, vol. 25, No. 17, pp. 3389-3402.

Ausubel F.M., et al., “Current Protocols in Molecular Biology,” John Wiley & Sons, New York, 1989, vol. 1, 14 Pages, TOC only.

Beigert A., et al., “Sequence Context-Specific Profiles for Homology Searching”, Proceedings of the National Academy of Sciences of the United States of America, Mar. 10, 2009, vol. 106, No. 10, pp. 3770-3775.

Bonas U., et al., “Genetic and Structural Characterization of the Avirulence Gene AvrBs3 From Xanthomonas Campestris Pv. Vesicatoria,” Molecular Genetics and Genomics, Jul. 1989, vol. 218, No. 1, pp. 127-136.

Braasch D.A., et al., “Novel Antisense and Peptide Nucleic Acid Strategies for Controlling Gene Expression,” Biochemistry, Apr. 9, 2002, vol. 41, No. 14, pp. 4503-4510.

Durbin R., et al., “Biological Sequence Analysis: Probabilistic Models of Proteins and Nucleic Acids,” Cambridge University Press, Cambridge, UK, 2002, 7 Pages, TOC Only.

Gelinas A.D., et al.. “Embracing Proteins: Structural Themes in Aptamer-protein Complexes”, Current Opinion in Structural Biology, Feb. 2016, vol. 36, pp. 122-132.

Glick B.R., et al., “Methods in Plant Molecular Biology and Biotechnology”, Boca Raton, Taylor & Francis, CRC Press, 1993, 21 pages, TOC Only.

Gusfield D., “Algorithms on Strings, Trees and Sequences”, Computer Science and Computational Biology, Cambridge University Press, Cambridge UK, 1997, 6 Pages, TOC only.

Hasegawa H., et al., “Methods for Improving Aptamer Binding Affinity”, Molecules, Mar. 28, 2016, vol. 21, No. 4, 421, 15 Pages.

Heigwer F., et al.. “E-CRISP: Fast CRISPR Target Site Identification,” Nature Methods, Febraury 2014, vol. 11, No. 2, pp. 122-123.

Hu J.H., et al., “Evolved Cas9 Variants With Broad PAM Compatibility and High DNA Specificity,” Nature, Apr. 5, 2018, vol. 556, No. 7699, pp. 57-63 (28 Pages).

Ibraheem D., et al., “Gene Therapy and DNA Delivery Systems”, International Journal of Pharmaceutics, vol. 459, No. 1-2, Jan. 1, 2014, pp. 70-83.

(Continued)

*Primary Examiner* — Sharmila G Landau
*Assistant Examiner* — Sandra Zingarelli
(74) *Attorney, Agent, or Firm* — Casimir Jones, S.C.; Kelly A. Barton

(57) ABSTRACT

The present disclosure provides components, compositions, methods, and systems thereof for nucleic acid editing. Particularly, the invention relates to adenine deaminases, fusion proteins of the adenine deaminases, systems including the adenine deaminases, and methods of using thereof.

6 Claims, 15 Drawing Sheets

Specification includes a Sequence Listing.

(56) References Cited

OTHER PUBLICATIONS

International Search Report and Written Opinion for PCT/US2024/056236, dated Mar. 19, 2025, 12 pages.
IUPAC-IUB: "Nomenclature of Alpha-Amino Acids (Recommendations, 1974)," Biochemistry, IUPAC Commission on the Nomenclature of Organic Chemistry and the IUPAC-IUB Commission on Biochemical Nomenclature 1975, vol. 14, No. 2, pp. 449-462.
Jayasena S.D., "Aptamers: an Emerging Class of Molecules That Rival Antibodies in Diagnostics," Clinical Chemistry, Sep. 1999, vol. 45, No. 9, pp. 1628-1650.
Jinek M., et al., "A Programmable Dual-RNA-Guided DNA Endonuclease in Adaptive Bacterial Immunity", Science, 2012, vol. 337, No. 6096, pp. 816-821.
Kaufman R.J., et al., "Translational Efficiency of Polycistronic mRNAs and Their Utilization to Express Heterologous Genes in Mammalian Cells," The EMBO Journal, Jan. 1987, vol. 6, No. 1, pp. 187-193.
Kay M.A., et al., "Viral Vectors for Gene Therapy: The Art of Turning Infectious Agents into Vehicles of Therapeutics," Nature Medicine, Jan. 2001, vol. 7, No. 1, pp. 33-40.
Kay S., et al., "Characterization of AvrBs3-like Effectors From a Brassicaceae Pathogen Reveals Virulence and Avirulence Activities and a Protein With a Novel Repeat Architecture," Molecular Plant Microbe Interactions, Aug. 2005, vol. 18, No. 8, pp. 838-848.
Kim Y.B., et al., "Increasing the Genome-targeting Scope and Precision of Base Editing with Engineered Cas9-cytidine Deaminase Fusions", Nature Biotechnology, Apr. 2017, vol. 35, No. 4, pp. 371-376 (15 pages).
Klein T.M., et al., "High-Velocity Microprojectiles for Delivering Nucleic Acids into Living Cells," Nature, May 7, 1987, vol. 327, pp. 70-73.
Kleinstiver B.P., et al., "Engineered CRISPR-Cas9 Nucleases With Altered PAM Specificities," Nature, Jul. 23, 2015, vol. 523, No. 7561, pp. 481-485 (27 Pages).
Kleinstiver B.P., et al., "High-fidelity CRISPR-Cas9 Variants with Undetectable genome-wide off-targets" Nature, Jan. 28, 2016, vol. 529, No. 7587, pp. 490-495, (24 Pages).
Lehninger A.L., "Principles of Biochemistry", Worth Publication 1982, pp. 793-800 (24 Pages).
Miller S.M., et al., "Continuous Evolution of SpCas9 Variants Compatible with non-G PAMs", Nature biotechnology, vol. 38, No. 4, Apr. 2020, pp. 471-481 (32 Pages).
Nayerossadat N., et al., "Viral and Nonviral Delivery Systems for Gene Delivery", Advanced Biomedical Research, Apr.-Jun. 2012, vol. 1, No. 2, Article No. 27, pp. 1-11.
Nishimasu H., et al., "Engineered CRISPR-Cas9 Nuclease with Expanded Targeting Space", Science, 2018, vol. 361, pp. 1259-1262 (5 Pages).
Noguchi H., et al., "PDX-1 Protein Containing Its Own Antennapedia-Like Protein Transduction Domain Can Transduce Pancreatic Duct and Islet Cells", Diabetes, Jul. 2003, vol. 52, No. 7, pp. 1732-1737.
Prykhozhij S.V., et al., "CRISPR Multitargeter: A Web Tool to Find Common and Unique CRISPR Single Guide RNA Targets in a Set of Similar Sequences", PLoS One, Mar. 5, 2015, vol. 10, No. 3, Article No. e0119372, pp. 1-18.
Ran F.A., et al., "Genome Engineering Using the CRISPR-Cas9 System", Nature Protocols, Oct. 24, 2013, vol. 8, No. 11, pp. 2281-2308.
Ruffolo J.A., et al., "Design of Highly Functional Genome Editors by Modeling the Universe of CRISPR-Cas Sequences", bioRxiv 2024.04.22.590591, Apr. 21, 2024, 35 Pages.
Sambrook J., et al., "Molecular Cloning: A Laboratory Manual", 2nd Edition, Cold Spring Harbor Laboratory Press, Cold Spring Harbor, NY, Toc Only, 1989, 30 Pages.
Seed B., "An LFA-3 cDNA Encodes a Phospholipid-Linked Membrane Protein Homologous to Its Receptor CD2," Nature, Oct. 29, 1987, vol. 329, No. 6142, pp. 840-842.
Sharei A., et al., "A Vector-free Microfluidic Platform for Intracellular Delivery," Proceedings of the National Academy of Sciences, Feb. 5, 2013, vol. 110, No. 6, pp. 2082-2087.
Soding J., "Protein Homology Detection by HMM-HMM Comparison", Bioinformatics, vol. 21, No. 7, Apr. 2005,pp. 951-960.
Trehin R., et al., "Cellular Uptake But Low Permeation of Human Calcitonin-Derived Cell Penetrating Peptides and Tat(47-57) Through Well-Differentiated Epithelial Models," Pharmaceutical Research, vol. 21, No. 7, Jul. 2004, pp. 1248-1256.
Trehin R., et al., "Metabolic Cleavage of Cell-penetrating Peptides in Contact with Epithelial Models: Human Calcitonin (hCT)-Derived Peptides, Tat(4757) and Penetratin(4358)", Biochemical Journal, 2004, vol. 382, pp. 945-956.
UNIPROT: "UniProtKB Accession No. C1F7L7, tRNA-Specific Adenosine Deaminase", May 26, 2009 [online], 7 Pages, full document, especially sequence https://www.uniprot.org/uniprotkb/C1F7L7/entry.
Wahlestedt C., et al., "Potent and Nontoxic Antisense Oligonucleotides Containing Locked Nucleic Acids", Proceedings of the National Academy of Sciences of the United States of America, vol. 97, No. 10, May 9, 2000, pp. 5633-5638.
Walther W., et al., "Viral Vectors for Gene Transfer: A Review of Their Use in the Treatment of Human Diseases", Drugs, vol. 60, No. 2, Aug. 2000, pp. 249-271.
Walton R.T., et al., "Unconstrained Genome Targeting With Near-PAMless Engineered CRISPR-Cas9 Variants," Science, Apr. 17, 2020, vol. 368, No. 6488, pp. 290-296 (18 Pages).
Wang J., et al., "Cyclohexene Nucleic Acids (CeNA): Serum Stable Oligonucleotides that Activate RNase H and Increase Duplex Stability with Complementary RNA", Journal of the American Chemical Society, vol. 122, No. 36, 2000, pp. 8595-8602.
Wender P.A., et al., "The Design, Synthesis, and Evaluation of Molecules That Enable or Enhance Cellular Uptake: Peptoid Molecular Transporters", Proceedings of the National Academy of Sciences of the United States of America, vol. 97, No. 24, Nov. 21, 2000, pp. 13003-13008.
Xiao A., et al., "CasOT: A Genome-Wide Cas9/gRNA Off-Target Searching Tool," Bioinformatics, Apr. 15, 2014, vol. 30, No. 8, pp. 1180-1182, Jan. 21, 2014.
Xu L., et al., "BEAT: A Python Program to Quantify Base Editing from Sanger Sequencing," The CRISPR Journal, 2019, vol. 2, No. 4, 7 Pages.
Yang L., et al., "Increasing Targeting Scope of Adenosine Base Editors in Mouse and Rat Embryos Through Fusion of TadA Deaminase with Cas9 Variants", Protein and Cell, 2018, vol. 9, No. 9, pp. 814-819.
Zender L., et al., "VP22-Mediated Intercellular Transport of p53 in Hepatoma Cells in Vitro and in Vivo", Cancer Gene Therapy, vol. 9, No. 6, 2002, pp. 489-496.
Zhu L.J., "Overview of Guide RNA Design Tools for CRISPR-Cas9 Genome Editing Technology", Frontiers in Biology, vol. 10, No. 4, 2015, pp. 289-296.
Zhu P., et al., "The Relationship of Retinal Vessel Diameters and Fractal Dimensions with Blood Pressure and Cardiovascular Risk Factors", PLOS ONE, vol. 9, Issue 9, Article No. e106551,Sep. 4, 2014, pp. 1-10.

* cited by examiner

FIG. 2, continued
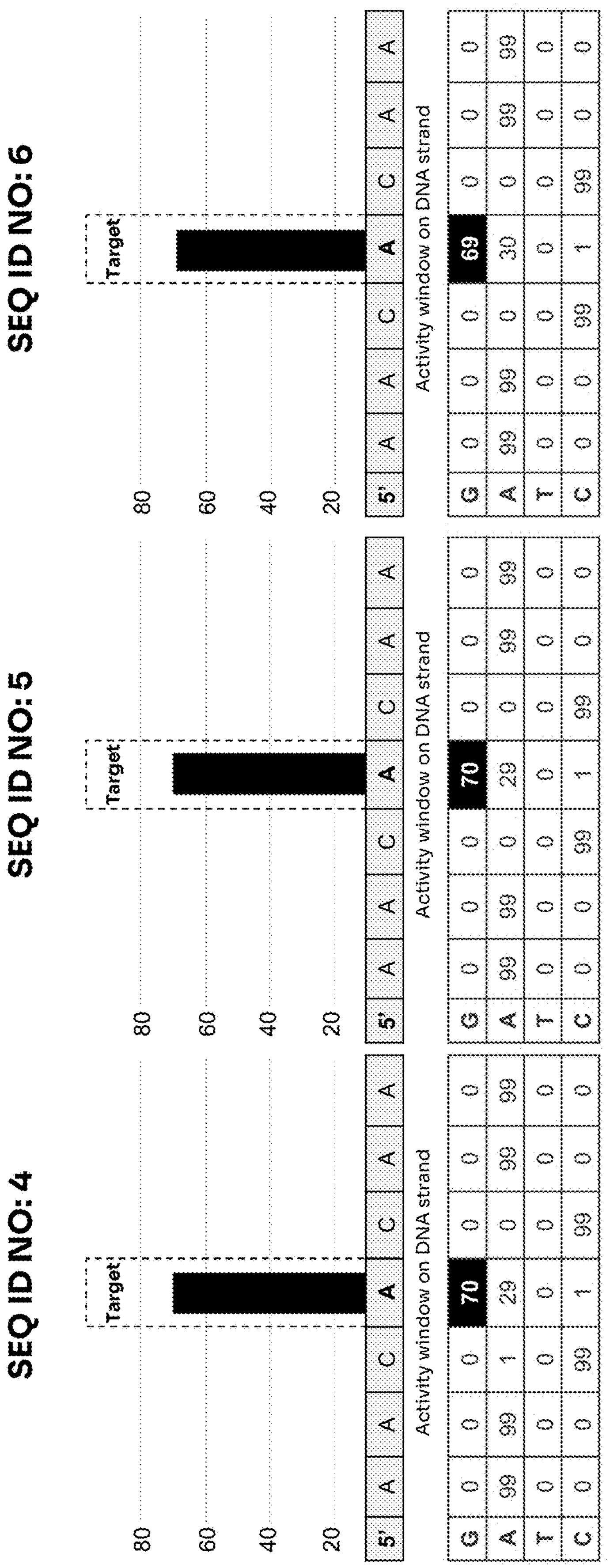

FIG. 2, continued
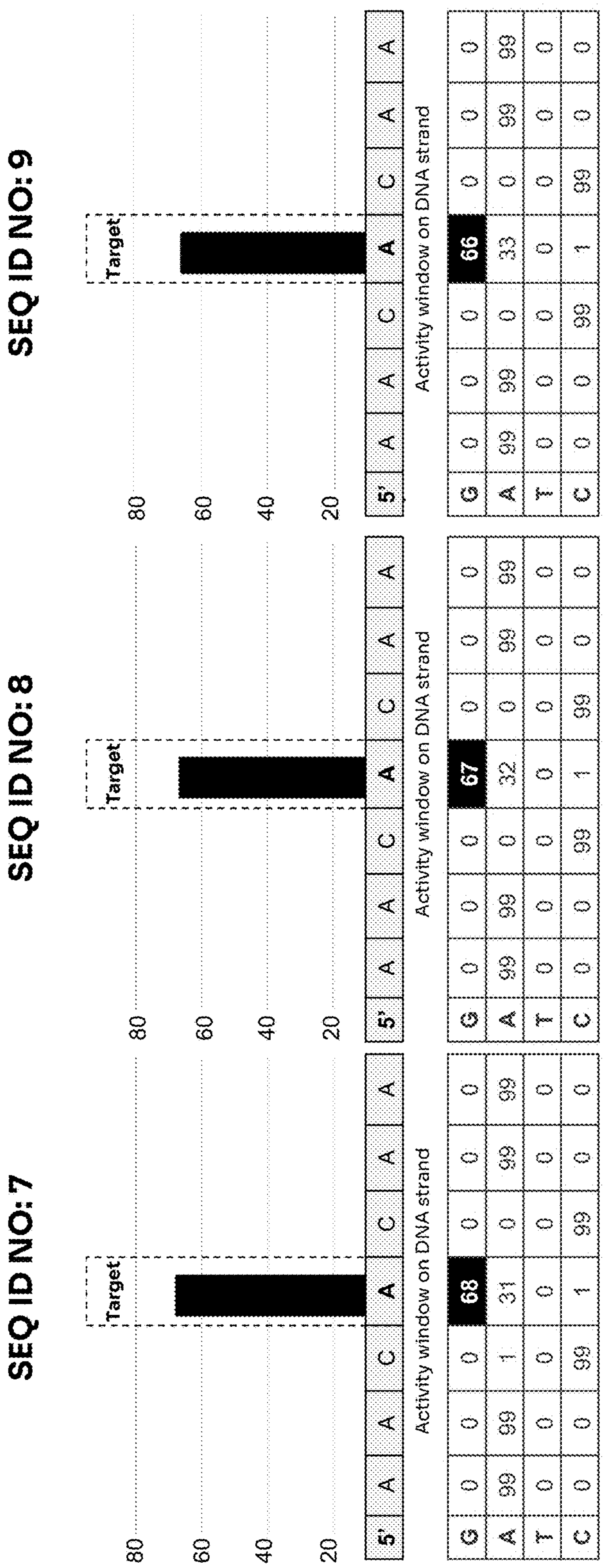

FIG. 2, continued
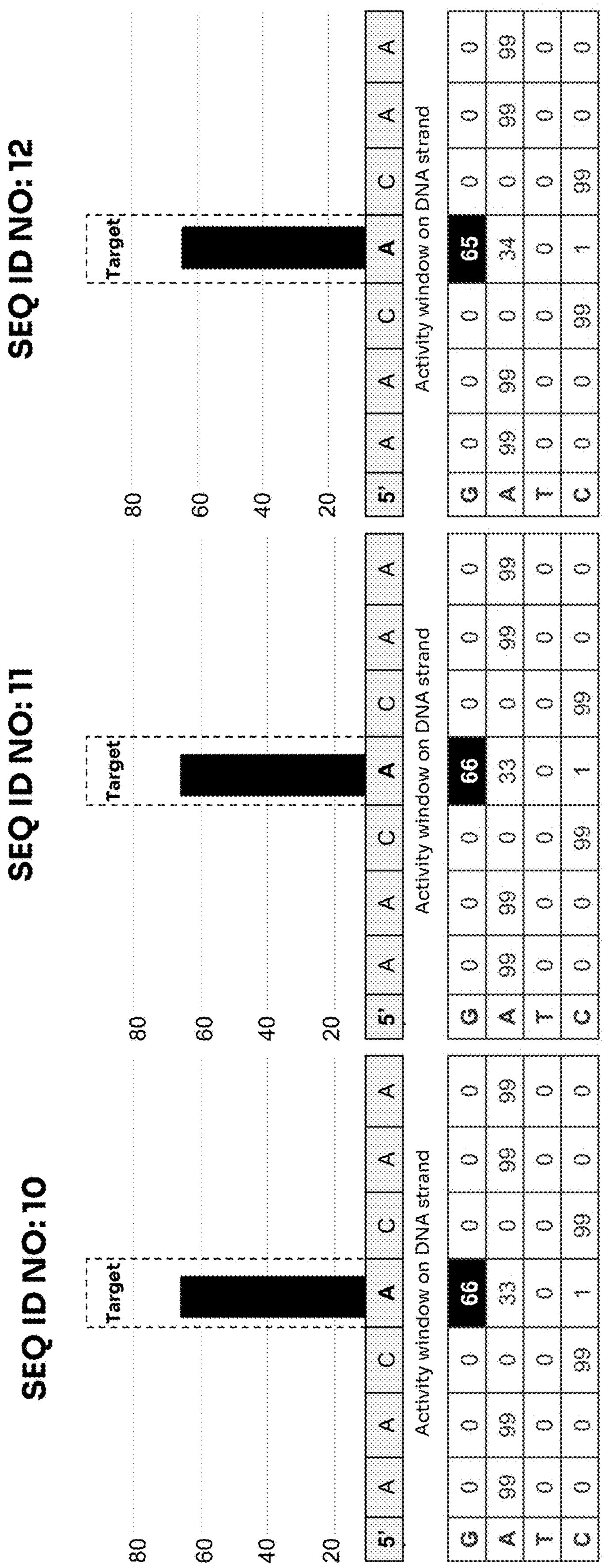

FIG. 2, continued
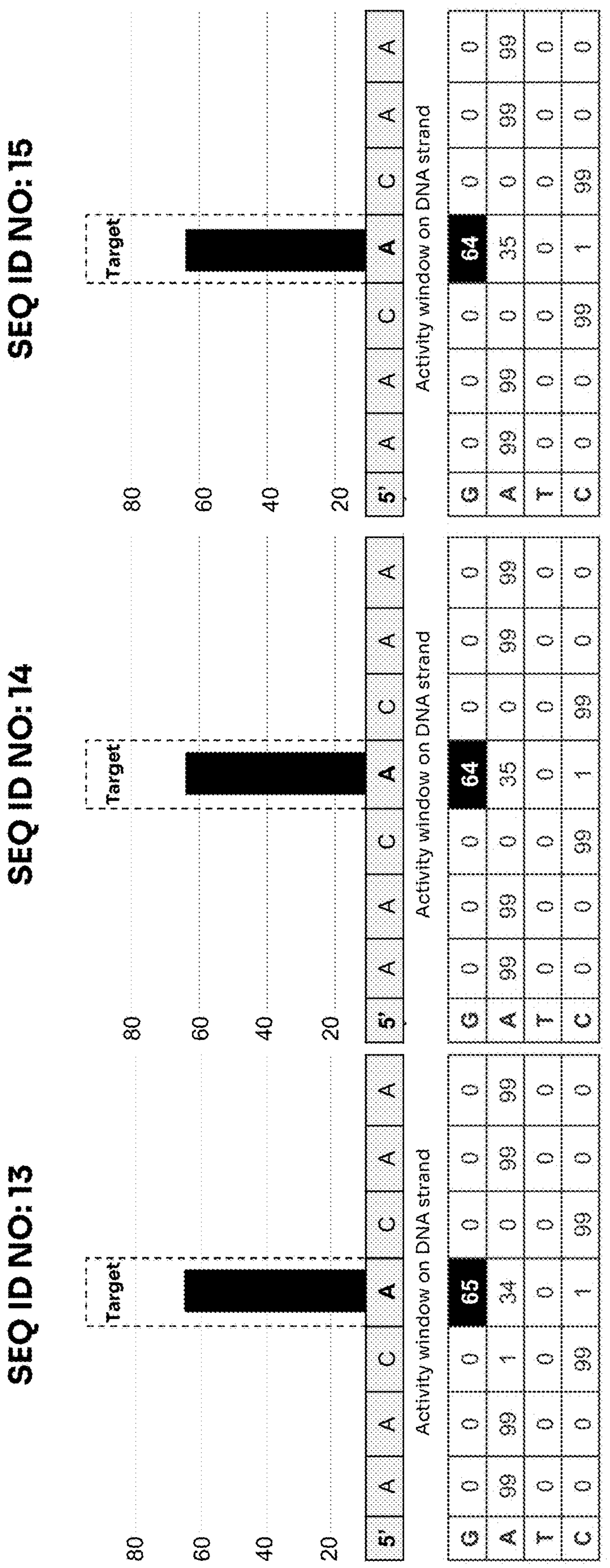

FIG. 2, continued
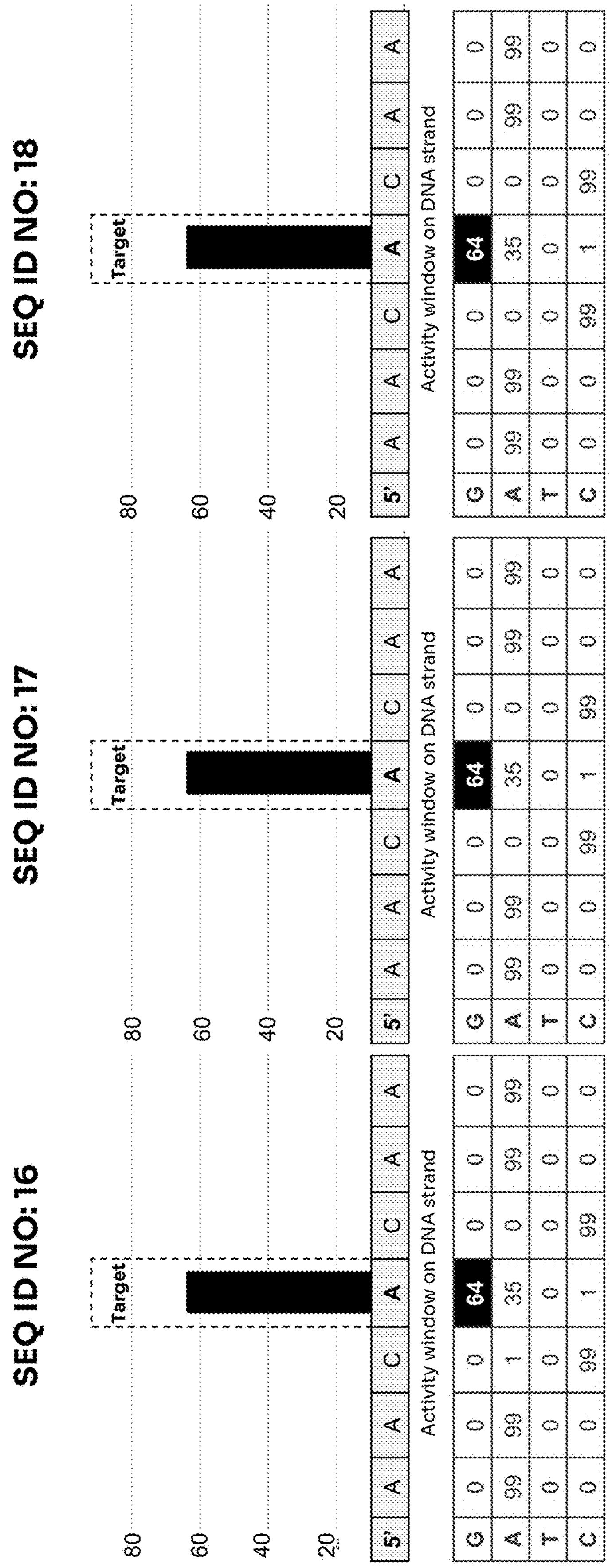

FIG. 2, continued
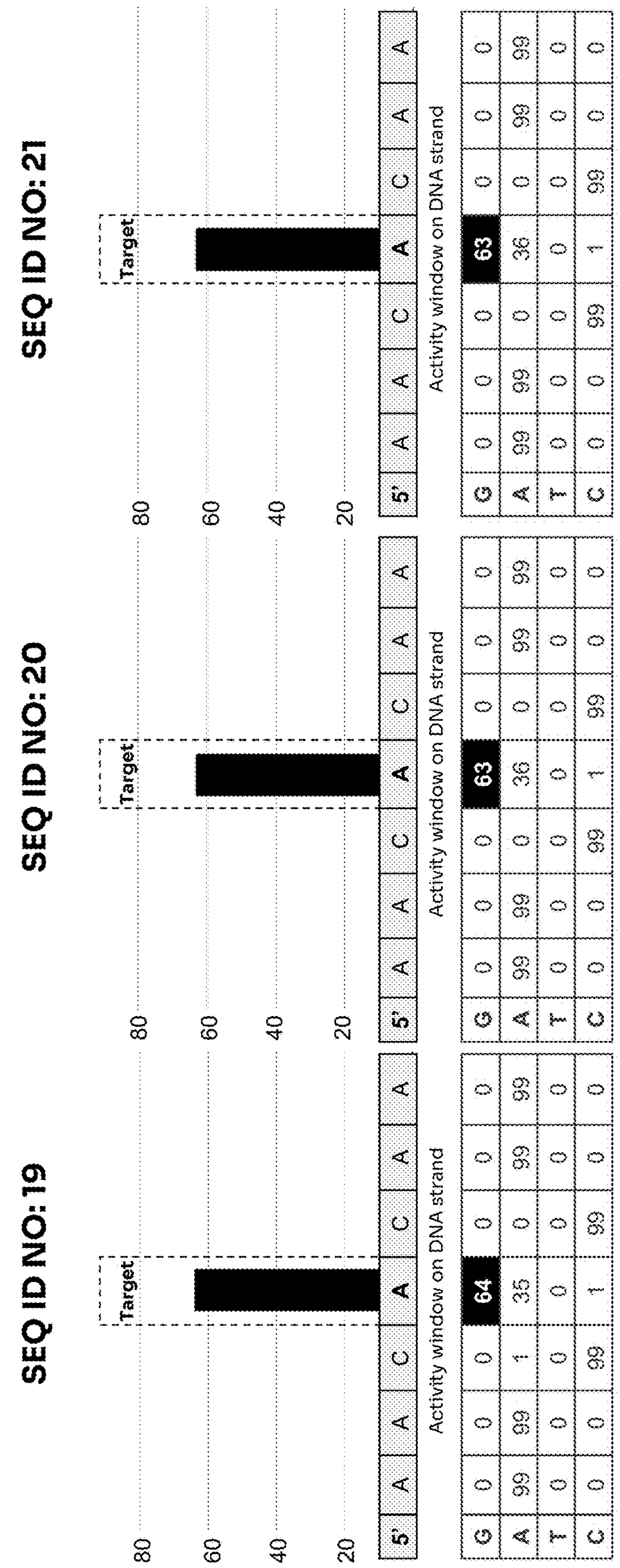

FIG. 2, continued
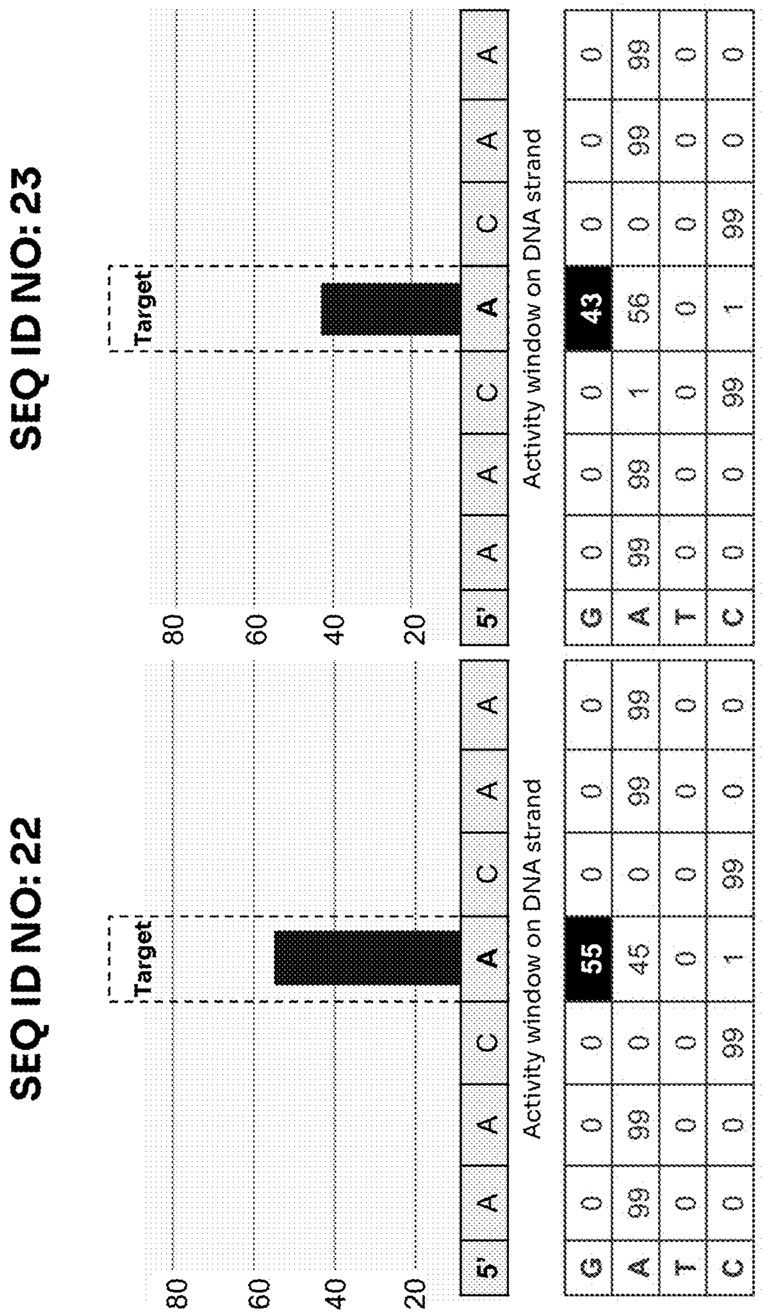

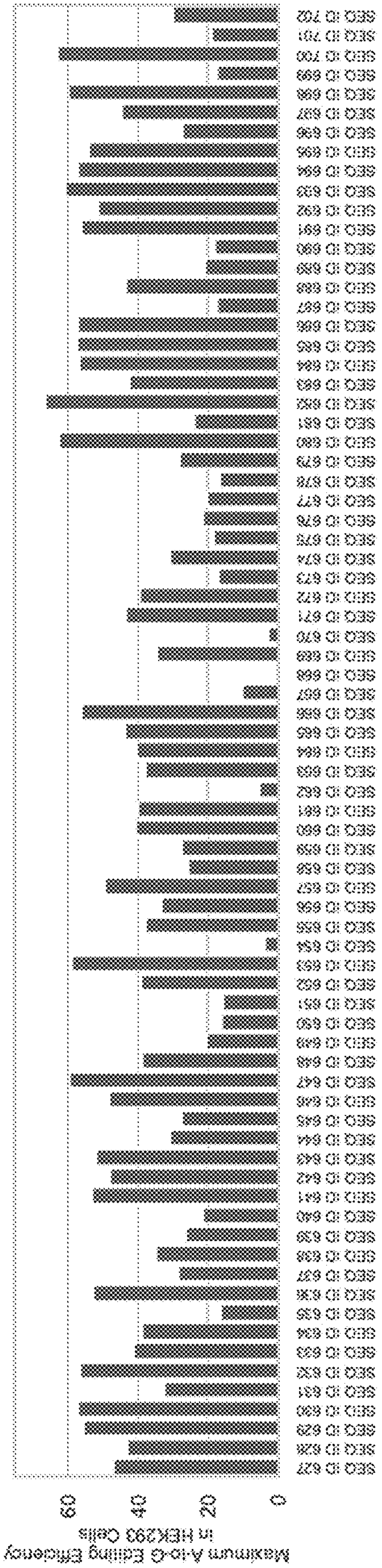
FIG. 4, continued

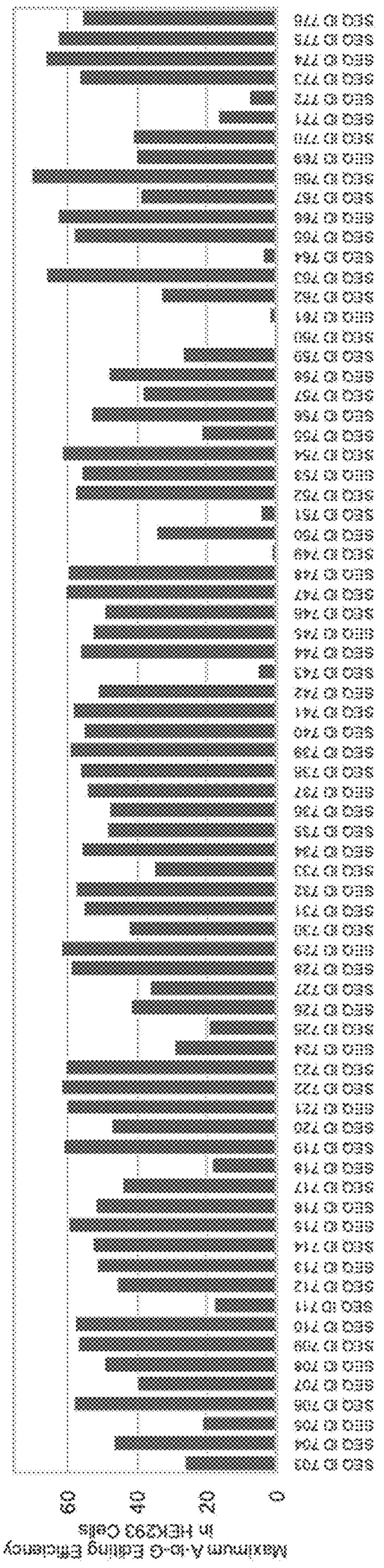
FIG. 4, continued

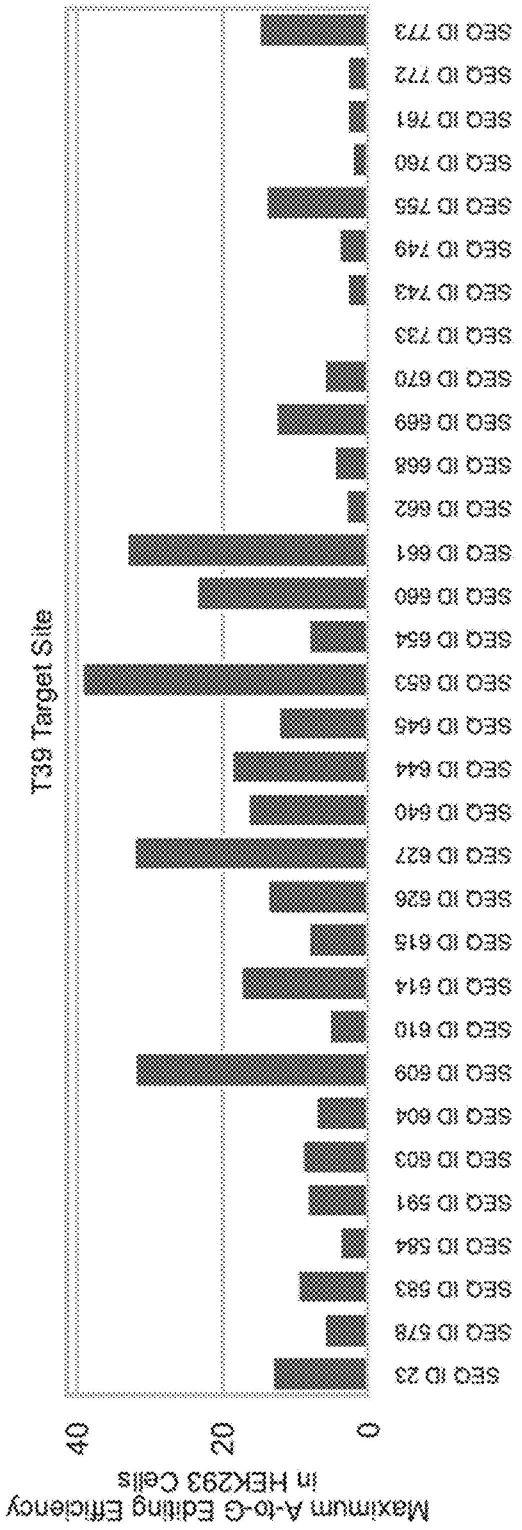
FIG. 5, continued

ADENINE DEAMINASES AND COMPOSITIONS, SYSTEMS, AND METHODS THEREOF

CROSS-REFERENCE TO RELATED APPLICATIONS

This application is a continuation of PCT International Application No. PCT/US2024/056236, filed Nov. 15, 2024, which claims the benefit of U.S. Provisional Application No. 63/599,141, filed Nov. 15, 2023, the contents of each are herein incorporated by reference in their entirety.

FIELD

The present disclosure relates to components, compositions, methods, and systems thereof for nucleic acid editing. Particularly, the disclosure relates to adenine deaminases, fusion proteins of the adenine deaminases, systems including the adenine deaminases, and methods of using thereof.

SEQUENCE LISTING STATEMENT

The content of the electronic sequence listing titled PROF_42422_601_SequenceListing.xml (Size: 817,420 bytes; and Date of Creation: Nov. 14, 2024) is herein incorporated by reference in its entirety.

BACKGROUND

Methods for precisely and efficiently editing nucleic acid sequences, particularly in vivo, are challenging to develop but when successful enable studies of gene function and open doors to new therapies for human genetic diseases. Theoretically, genetic diseases can be treated by altering nucleic acid sequences as specific locations in the genome, even a single nucleotide alteration from T to C or A to G can affect gene product expression and function resulting in a change in disease state. Deaminases, enzymes utilized in metabolic and salvage pathways, can be harnessed to facilitate single nucleotide modifications of a nucleic acid. For example, cytidine deaminases can ultimately result in conversion of C-G base pairs to T-A base pairs whereas adenosine deaminases can support conversion of A-T base pairs to G-C base pairs. However, there is a continuing need to expand the available deaminases which are efficient, precise, and suitable for use in genetic engineering methods and therapies, particularly in eukaryotic cells and organisms.

SUMMARY

Provided herein are polypeptides comprising an adenosine deaminase having an amino acid sequence with at least 75% identity to any of SEQ ID NOs: 1-23. In some embodiments, the adenosine deaminase has an amino acid sequence of any of SEQ ID NO: 1-23. In some embodiments, the adenosine deaminase has an amino acid sequence with at least 75% identity to any of SEQ ID NOs: 24-776. In some embodiments, the adenosine deaminase has an amino acid sequence of any of SEQ ID NO: 24-776.

Also provided herein are fusion proteins comprising a polypeptide or deaminase disclosed herein and a nucleic acid binding domain.

In some embodiments, the nucleic acid binding domain comprises a programmable nucleic acid binding domain.

In some embodiments, the nucleic acid binding domain is a Clustered Regularly Interspaced Short Palindromic Repeats associated (Cas) protein or a fragment or variant thereof capable of nucleic acid binding. In some embodiments, the Cas protein is at least partially catalytically inactivated. In some embodiments, the Cas protein is catalytically inactivated Cas9.

In some embodiments, the fusion proteins further comprise a linker separating the polypeptide and the nucleic acid binding domain.

In some embodiments, the fusion proteins further comprise at least one nuclear localization sequence.

Further provided are nucleic acids encoding a polypeptide, deaminase, or fusion protein disclosed herein and vectors comprising the nucleic acid.

Additionally provided are systems comprising a polypeptide or deaminase disclosed herein and a nucleic acid binding polypeptide. In some embodiments, the polypeptide or deaminase and the nucleic acid binding polypeptide are fused as a single protein. In some embodiments, the polypeptide or deaminase is linked to a first half of a binding pair and the nucleic acid binding polypeptide is linked to a second half of the binding pair.

In some embodiments, the nucleic acid binding domain comprises a programmable nucleic acid binding domain.

In some embodiments, the nucleic acid binding polypeptide is a Cas protein. In some embodiments, the Cas protein is at least partially catalytically inactivated. In some embodiments, the Cas protein is catalytically inactivated Cas9.

In some embodiments, the systems further comprise at least one guide RNA. In some embodiments, at least one gRNA is complexed with the Cas protein.

Compositions and cells comprising a nucleic acid binding polypeptide or deaminase, a fusion protein, a nucleic acid, a vector, or a system as disclosed herein are also provided.

In some embodiments, the cell is a prokaryotic cell or a eukaryotic cell. In some embodiments, the cell is a mammalian cell. In some embodiments, the cell is a human cell.

Methods of modifying a target nucleic acid are likewise provided. In some embodiments, the methods comprise contacting the target nucleic acid with a polypeptide or deaminase, a fusion protein, a nucleic acid, a vector, or a system as disclosed herein. In some embodiments, the target nucleic acid is DNA. In some embodiments, the target nucleic acid is RNA.

In some embodiments, the target nucleic acid is associated with a disease or disorder. In some embodiments, the disease or disorder is associated with a point mutation in the target nucleic acid.

In some embodiments, the target nucleic acid encodes a gene product.

In some embodiments, the target nucleic acid is in a cell. In some embodiments, the contacting comprises introducing into the cell. In some embodiments, the cell is in vitro or ex vivo. In some embodiments, the cell is in vivo. In some embodiments, the introducing comprises administering to a subject.

In some embodiments, the cell is in a plant. In some embodiments, the method comprises administering to a plant, plant cell, seed, fruit, plant part, or propagation material of a plant the polypeptide, fusion protein, nucleic acid, vector, or system.

In some embodiments, the methods treat a disease or disorder in a subject. In some embodiments, the methods comprise administering to the subject in need thereof an effective amount of a polypeptide or deaminase, a fusion protein, a nucleic acid, a vector, or a system as disclosed herein. In some embodiments, the subject is a human.

In some embodiments, the target nucleic acid encodes a gene product. In some embodiments, the target nucleic acid is a disease-associated gene. In some embodiments, the disease-associated gene is associated with a point mutation, single nucleotide variant (SNV), or single nucleotide polymorphism (SNP).

Other aspects and embodiments of the disclosure will be apparent in light of the following detailed description.

DETAILED DESCRIPTION

Figure 1:
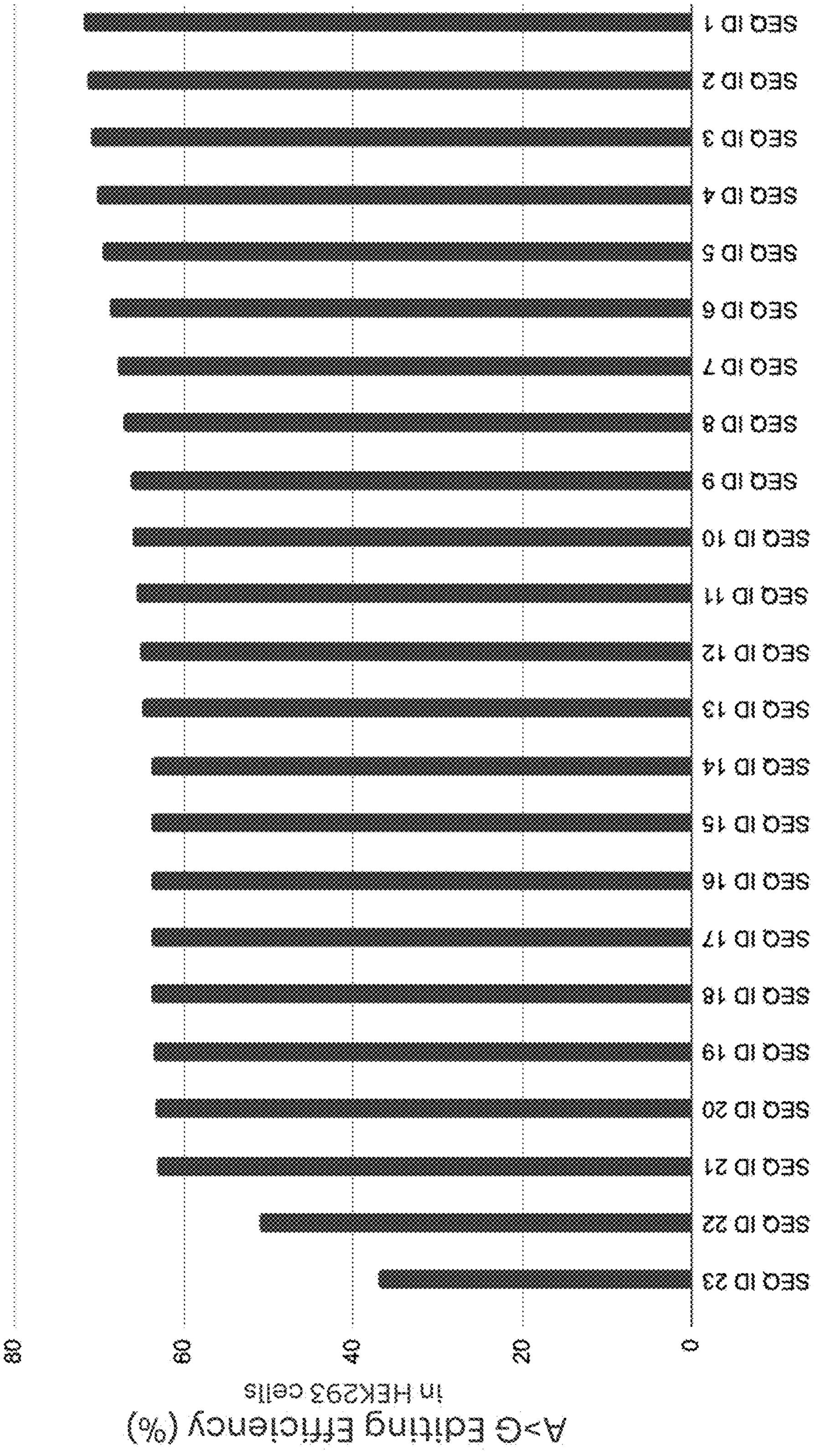
FIG. 1 is a graph of the A to G editing efficiency of deaminase enzymes linked to Cas9n as disclosed herein (SEQ ID NOs: 1-23, as indicated).
Figure 2:
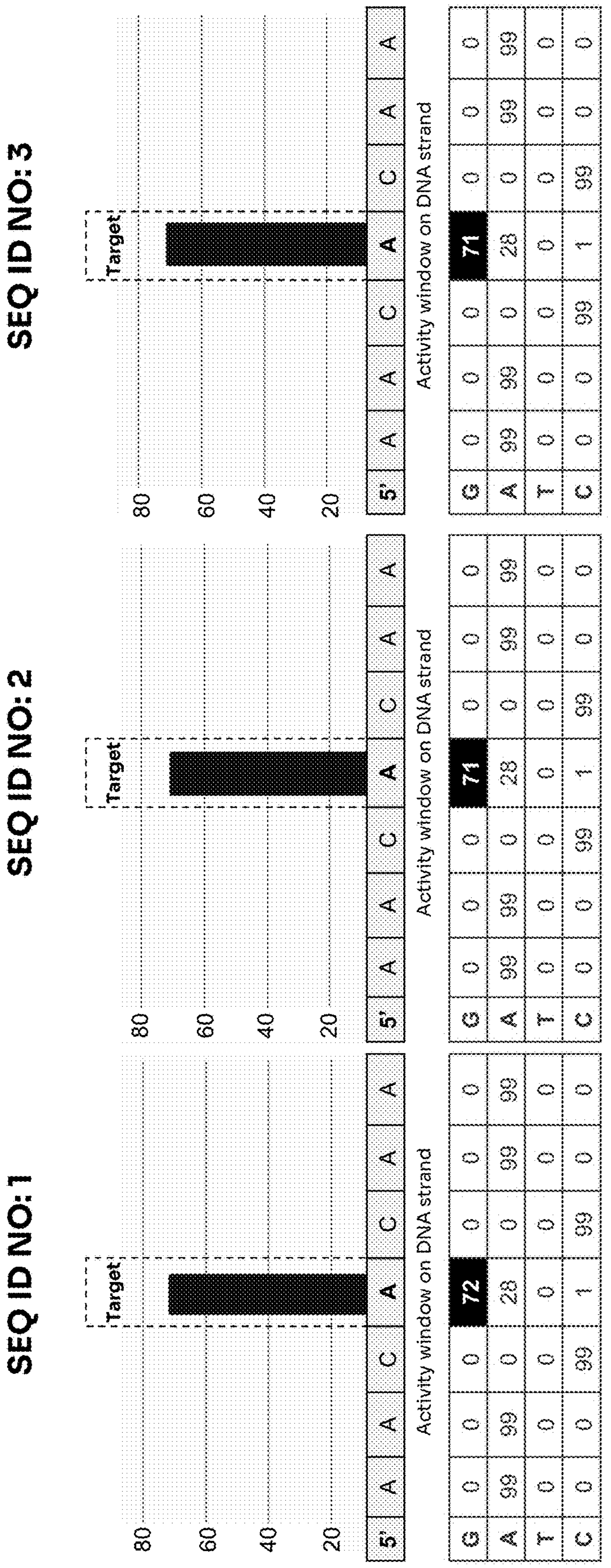
FIG. 2 is a graph showing the specificity of the deaminase enzymes linked to Cas9n on the target strand as disclosed herein (SEQ ID NOs: 1-23, as indicated). Efficiency of nucleotide changes at each position on the target strand, including at the target site, are shown.
Figure 3:
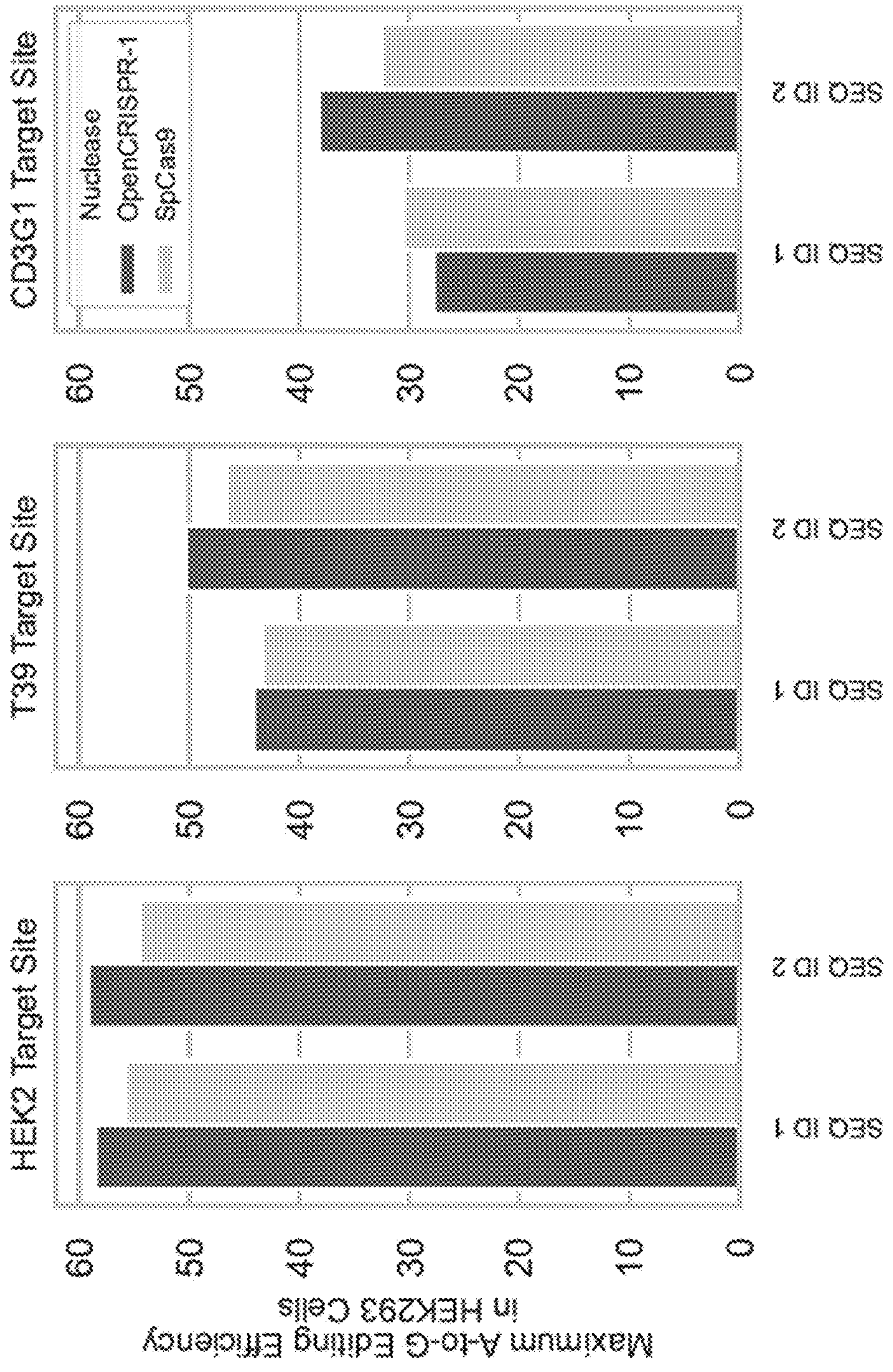
FIG. 3 is graphs showing the A to G editing efficiency of deaminase enzymes as disclosed herein (SEQ ID NOs: 1-2, as indicated) at three different target sites (HEK2, T39, and CD3G1) using when linked to two different nucleases, OpenCRISPR-1 (Ruffolo, et al., bioRxiv 2024.04.22.590591) and spCas9, both partially catalytically inactivated (nickases).
Figure 4:
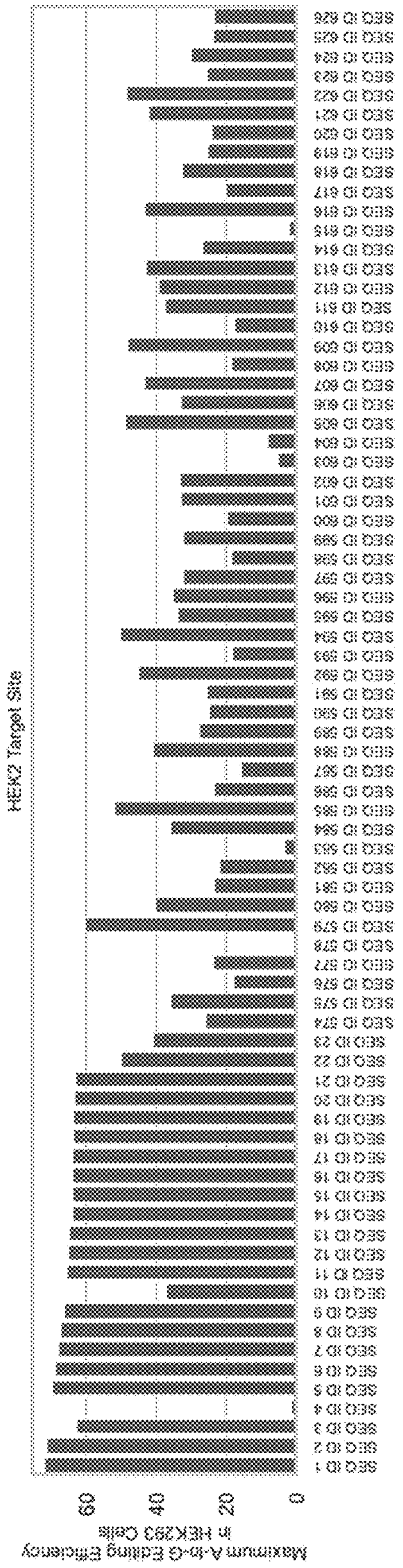
FIG. 4 is graphs of the A to G editing efficiency of deaminase enzymes as disclosed herein (SEQ ID NOs: 1-23 and 574-776, as indicated) when tethered to spCas9n.

The disclosed polypeptides, compositions, systems, kits, and methods include deaminases useful for nucleic acid modification.

Section headings as used in this section and the entire disclosure herein are merely for organizational purposes and are not intended to be limiting.

Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. As used herein, comprising a certain sequence or a certain SEQ ID NO usually implies that at least one copy of said sequence is present in recited peptide or polynucleotide. However, two or more copies are also contemplated. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined herein, scientific, and technical terms used in connection with the present disclosure shall have the meanings that are commonly understood by those of ordinary skill in the art. For example, any nomenclature used in connection with, and techniques of cell and tissue culture, molecular biology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein, "nucleic acid" or "nucleic acid sequence" refers to a polymer or oligomer of pyrimidine and/or purine bases, preferably cytosine, thymine, and uracil, and adenine and guanine, respectively (See Albert L. Lehninger, *Principles of Biochemistry,* 793-800 (Worth Pub. 1982)). The present technology contemplates any deoxyribonucleotide, ribonucleotide, or nucleoprotein component, and any chemical variants thereof, such as methylated, hydroxymethylated, or glycosylated forms of these bases, and the like. The polymers or oligomers may be heterogenous or homogenous in composition and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see, e.g., Braasch and Corey, *Biochemistry,* 41 (14): 4503-4510 (2002) and U.S. Pat. No. 5,034,506), locked nucleic acid (LNA; see Wahlestedt et al., Proc. Natl. Acad. Sci. U.S.A., 97:5633-5638 (2000)), cyclohexenyl nucleic acids (sec Wang, J. Am. Chem. Soc., 122: 8595-8602 (2000)), and/or a ribozyme. Hence, the term "nucleic acid" or "nucleic acid sequence" may also encompass a chain comprising non-natural nucleotides, modified nucleotides, and/or non-nucleotide building blocks that can exhibit the same function as natural nucleotides (e.g., "nucleotide analogs"); further, the term "nucleic acid sequence" as used herein refers to an oligonucleotide, nucleotide or polynucleotide, and fragments or portions thereof, and to DNA or RNA of genomic or synthetic origin, which may be single or double-stranded, and represent the sense or antisense strand. The terms "nucleic acid," "polynucleotide," "nucleotide sequence," and "oligonucleotide" are used interchangeably. They refer to a polymeric form of nucleotides of any length, either deoxyribonucleotides or ribonucleotides, or analogs thereof.

As used herein, "peptide," "polypeptide," or "protein" refer to a sequence of two or more amino acids linked by peptide bonds. The polypeptide can be natural, synthetic, or a modification or combination of natural and synthetic. The peptide or polypeptide may be modified by the addition of sugars, lipids or other moieties not included in the amino acid chain. The terms "polypeptide," "oligopeptide," and "peptide" are used interchangeably herein. The peptide(s) may be produced by recombinant genetic technology or chemical synthesis. The peptide(s) may be isolated and purified by any number of standard methods including, but not limited to, differential solubility (e.g., precipitation), centrifugation, chromatography (e.g., affinity, ion exchange, and size exclusion), or by any other standard techniques known in the art.

The term "amino acid" or "any amino acid" as used here refers to any and all amino acids, including naturally occurring amino acids (e.g., α-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Throughout the present specification, unless naturally occurring amino acids are referred to by their full name (e.g., alanine, arginine, etc.), they are designated by their conventional three-letter or single-letter abbreviations (e.g., Ala or A for alanine, Arg or R for arginine, etc.). The term "L-amino acid," as used herein, refers to the "L" isomeric form of a peptide, and conversely the term "D-amino acid" refers to the "D" isomeric form of a peptide (e.g., Dphe, (D)Phe, D-Phe, or $^{D}$F for the D isomeric form of Phenylalanine). Amino acid residues in the D isomeric form can be substituted for any L-amino acid residue, as long as the desired function is retained by the peptide.

Nucleic acid or amino acid sequence "identity," as described herein, can be determined by comparing a nucleic acid or amino acid sequence of interest to a reference nucleic acid or amino acid sequence. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FAS™, and SSEARCH for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106 (10): 3770-3775 (2009), Durbin et al., eds., *Biological Sequence Analysis: Probabilistic Models of Proteins and Nucleic Acids*, Cambridge University Press, Cambridge, UK (2009), Soding, *Bioinformatics,* 21(7): 951-60 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

The term "gene" refers to a nucleic acid sequence that comprises control and coding sequences necessary for the production of a gene product (e.g., an RNA having a non-coding function (e.g., a ribosomal or transfer RNA), a polypeptide, or a precursor of any of the foregoing). The RNA or polypeptide can be encoded by a full-length coding sequence or by any portion of the coding sequence so long as the desired activity or function is retained. Thus, a "gene" refers to a DNA or RNA, or portion thereof, that encodes a polypeptide or an RNA chain that has functional role to play in an organism. For the purpose of this disclosure, it may be considered that genes include regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

A cell has been "genetically modified," "transformed," or "transfected" by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell. For example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

The terms "non-naturally occurring," "engineered," and "synthetic" are used interchangeably and indicate the involvement of the hand of man. The terms, when referring to nucleic acid molecules or polypeptides mean that the nucleic acid molecule or the polypeptide is at least substantially free from at least one other component with which it is naturally associated in nature and as found in nature, and/or the nucleic acid molecule or the polypeptide is associated with at least one other component with which it is not naturally associated in nature and/or that there is one or more changes in nucleic acid or amino acid sequence as compared with such sequence as it is found in nature and/or that the nucleic acid or polypeptide sequence was generated de novo, e.g., not based on or derived from any naturally occurring sequence.

A "vector" or "expression vector" is a replicon, such as plasmid, phage, virus, or cosmid, to which another DNA segment, e.g., an "insert," may be attached or incorporated so as to bring about the replication of the attached segment in a cell.

The term "contacting" as used herein refers to bring or put in contact, to be in or come into contact. The term "contact" as used herein refers to a state or condition of touching or of immediate or local proximity.

As used herein, the terms "providing," "administering," and "introducing," are used interchangeably herein and refer to the placement of the composition or systems of the disclosure into a cell, organism, or subject by a method or route which results in at least partial localization to a desired site. The composition or systems can be administered by any appropriate route which results in delivery to a desired location in the cell, organism, or subject.

A "subject" or "patient" may be human or non-human and may include, for example, animal strains or species used as "model systems" for research purposes, such a mouse model as described herein. Likewise, a patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents such as rats, mice, and guinea pigs, and the like. Examples of non-mammals include, but are not limited to, birds, fish, and the like. In one embodiment of the methods and compositions provided herein, the mammal is a human.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

Deaminases

Disclosed herein are synthetic deaminases. A deaminase catalyzes removal of an amino group from a compound or molecule (e.g., a nucleic acid/nucleotide or protein/amino acid). In some embodiments, the deaminase is an adenosine deaminase, also sometimes referred to as an adenine deaminase. Adenosine deaminases catalyze the deamination of adenosine and deoxyadenosine to inosine and deoxyinosine, respectively. Accordingly, with repair and replication mechanisms adenosine deaminase can ultimately lead to the conversion of an A:T base pair to a G:C base pair.

In some embodiments, the deaminases comprise an amino acid sequence having at least 75% identity (e.g., at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) to any one of SEQ ID NOs: 1-23. In some embodiments, the deaminases comprise an amino acid sequence having at least 70% identity to any one of SEQ ID NOs: 24-776. In some embodiments, the deaminases comprise an amino acid sequence having at least 70% identity to any one of SEQ ID NOs: 1-776. In some embodiments, the deaminases comprise an amino acid sequence having any one of SEQ ID NOs: 1-776.

Any of the deaminases described herein may comprise one or more (e.g., 1, 2, 3, 4, 5, 6, 7, 8, 9, 10, 15, 20, 25, or more, etc.) amino acid substitutions as compared to SEQ ID NOs: 1-776. An amino acid "replacement" or "substitution" refers to the replacement of one amino acid at a given position or residue by another amino acid at the same position or residue within a polypeptide sequence. Amino acids are broadly grouped as "aromatic" or "aliphatic." An aromatic amino acid includes an aromatic ring. Examples of aromatic amino acids include histidine (H or His), phenylalanine (F or Phe), tyrosine (Y or Tyr), and tryptophan (W or Trp). Non-aromatic amino acids are broadly grouped as aliphatic. Examples of aliphatic amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gin), lysine (K or Lys), and arginine (R or Arg).

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, Principles of Protein Structure, Springer-Verlag, New York (1979)). According to such analyses, groups of amino acids may be defined where amino acids within a group exchange preferentially with each other and therefore resemble each other most in their impact on the overall protein structure (Schulz and Schirmer). Examples of conservative amino acid substitutions include substitutions of amino acids within the subgroups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —$NH_2$ can be maintained. "Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

Fusion Proteins

The present disclosure also provides fusion proteins comprising one or more of the deaminases fused to a nucleic acid binding domain. The fusion proteins are not limited by orientation or directionality of the deaminase and the nucleic acid binding domain. For example, the nucleic acid binding domain may be fused to the N-terminus or C-terminus of the deaminase, in any orientation, e.g., N-terminus to N-terminus, C-terminus to C-terminus, N-terminus to C-terminus, or C-terminus to N-terminus.

Nucleic acid binding domains include polypeptides, proteins, or moieties which are capable of binding double- or single-stranded DNA, RNA, or combinations thereof, generally or with sequence specificity either alone or in coordination with another molecule. In some embodiments, the nucleic acid binding domain is capable of binding directly to the target nucleic acid sequences. In some embodiments, the nucleic acid binding domain is capable of binding indirectly to the target nucleic acid sequences, through an additional molecule. Exemplary nucleic acid binding domains include polypeptides having helix-turn-helix motifs, zinc fingers, leucine zippers, HMG-box (high mobility group box) domains, winged helix regions, winged helix-turn-helix regions, helix-loop-helix regions, immunoglobulin folds, B3 domains, Wor3 domains, TAL effector DNA-binding domains, and the like. The nucleic acid binding domain may be a natural binding domain. In some embodiments, the nucleic acid binding domain comprises a programmable nucleic acid binding domain, e.g., a nucleic acid binding domain engineered, for example by altering one or more amino acid of a natural nucleic acid binding domain, to bind to a predetermined nucleotide sequence.

The nucleic acid binding domain may be derived from domains found in naturally occurring transcription activator-like effectors (TALEs) such as AvrBs3, Hax2, Hax3 or Hax4 (Bonas et al. Mol Gen Genet 218(1):127-36, 1989; Kay et al. Mol Plant Microbe Interact 18(8): 838-48, 2005). TALEs have a modular binding domain consisting of repetitive sequences of residues; each repeat region consists of 34 amino acids. A pair of residues at the 12th and 13th position of each repeat region determines the nucleotide specificity and combining of the regions allows synthesis of sequence-specific TALE binding domains. In some embodiments, the TALE binding domains may be engineered using known methods to provide a binding domain with chosen specificity for any target sequence. The binding domain may comprise multiple (e.g., 2, 3, 4, 5, 6, 10, 20, or more) TALE effector binding motifs. In particular, any number of nucleotide-specific TALE effector motifs can be combined to form a sequence-specific binding domain to be employed in the fusion protein.

In some embodiments, the nucleic acid binding domain is derived from an RNA-guided protein (e.g., an RNA-guided nuclease). These proteins associate with an RNA molecule which guides the protein to the target DNA based on sequence complementarity of the RNA molecule to the target DNA. Exemplary RNA-guided proteins include for example, Cas proteins, transposon proteins (e.g., ISC transposon proteins or TnpB proteins, and other homologous proteins), and the Fanzor protein.

In some embodiments, the nucleic acid binding domain is derived from a Clustered Regularly Interspaced Short Palindromic Repeats associated (Cas) protein and associates with the target nucleic acid through a guide RNA (gRNA), a full description of which is provided elsewhere herein. The gRNA itself comprises a sequence complementary to one strand of the target sequence and a scaffold sequence binds and recruits the Cas protein to the target sequence. Thus, the disclosure provides base editors, which are fusion proteins of a Cas protein, generally a fully or partially catalytically inactivated Cas nuclease, as described below, and a deaminase or "base editing" enzyme.

The Cas protein can be from any Type or Class of CRISPR-Cas systems (e.g., Class 1, Class 2, Class 3, Types I-VI, or any subtypes thereof) from any species. Exemplary Cas proteins include: Cas1, Cas2, Cas3, Cas4, Cas5, Cas6, Cas7, Cas8, Cas9, Cas10, Cas12, Cas13, and the like. In some embodiments, the Cas protein is Cas9 or Cas 12. Fragments or variants of any Cas protein which retain their nucleic acid binding capability may also be suitable for use as a nucleic acid binding domain in a fusion protein disclosed herein.

In some embodiments, the Cas protein is Cas9, or a fragment thereof. The Cas9 protein may be obtained from any suitable organism. For example, a number of bacteria express Cas9 protein orthologs or variants. Cas9 proteins of other species are known in the art (see, e.g., U.S. Patent Application Publication 2017/0051312, incorporated herein by reference) and may be used in connection with the present disclosure. The amino acid sequences of Cas proteins from a variety of species are publicly available through the GenBank, UniProt, and JGI Integrated Microbial Genomes and Microbiomes (IMG/M) databases. The Cas9 protein may be from *Streptococcus pyogenes, Staphylococcus aureus* (*S. aureus*), *Campylobacter jejuni, Corynebacterium diphtheria, Eubacterium ventriosum, Streptococcus pasteurianus, Lactobacillus farciminis, Sphaerochaeta globus, Azospirillum* (strain B510), *Gluconacetobacter diazotrophicus, Neisseria cinerea, Roseburia intestinalis, Parvibaculum lavamentivorans, Nitratifractor salsuginis* (strain DSM 16511), *Campylobacter lari* (strain CF89-12), or *Streptococcus thermophilus* (strain LMD-9). In some embodiments, the Cas9 is from *Streptococcus pyogenes* or *Staphylococcus aureus*.

Engineered Cas protein variants having one or more inactivated nuclease domains; alterations in the PAM requirements of target nucleic acids; decreased off-target binding or increased on-target binding; decreased editing windows on target nucleic acid; decreased 'bystander' effects, editing of nucleotides outside but near editing window; and the like are suitable for use in the disclosed fusion proteins. For example, *Streptococcus pyogenes* Cas 9 (SpCas9) variants SpCas9-VQR, -VRQR, -EQR, -VRER, xCas9, SpCas9-NG, SpG, and SaKKHn allow targeting of genomic regions containing non-NGG PAMs and SpRY is a near-PAMless variant of SpCas9 (See, Kleinstiver B P et al., Nature. 523, 481-5 (2015); Kleinstiver B P et al., Nature. 529, 490-5 (2016); Kim et al., Nat. Biotechnol. 35, 371-376 (2017); Nishimasu, H. et al., Science 361, 1259-1262 (2018); Hu J H, et al., Nature. 556, 57-63 (2018); Miller, et al. Nat. Biotechnol. 38, 471-481(2020); Yang, L. et al., Protein Cell 9, 814-819 (2018); Walton, et al., Science 268, 290-296 (2020), incorporated herein by reference).

In some embodiments, the Cas9 protein is a Cas9 nickase (Cas9n). Wild-type Cas9 has two catalytic nuclease domains (HNH and RuvC) facilitating double-stranded DNA breaks. A Cas9 nickase protein is typically engineered through inactivating point mutation(s) in one of the catalytic nuclease domains causing Cas9 to nick or enzymatically break only one of the two DNA strands using the remaining active nuclease domain. Cas9 nickases are known in the art (see, e.g., U.S. Patent Application Publication 2017/0051312, incorporated herein by reference) and include, for example, *Streptococcus pyogenes* with point mutations at D10 or H840. In select embodiments, the Cas9 nickase is *Streptococcus pyogenes* Cas9n (D10A).

In some embodiments, the Cas9 protein is a catalytically dead Cas9. Catalytically dead Cas 9 (dCas9) can be obtained, for example, by introducing point mutations (e.g., substitutions, deletions, or additions) in the Cas9 molecule at the DNA-cleavage domain, e.g., the nuclease domain, the RuvC and/or HNH domain. Sec, e.g., Jinek et al., Science 337:816-21 (2012), incorporated by reference herein in its entirety. For example, introducing two point mutations in the RuvC and HNH domains reduces the Cas9 nuclease activity while retaining the Cas9 nucleic acid binding activity. For example, *Streptococcus pyogenes* Cas9 may be rendered catalytically dead by mutations of D10 and at least one of E762, H840, N854, N863, or D986, typically H840 and/or N863A (see, e.g., U.S. Patent Application Publication 2017/0051312, incorporated herein by reference). Mutations in corresponding orthologs are known, such as N580 in *Staphylococcus aureus* Cas9. Similar mutations can also apply to any other naturally occurring Cas9 (e.g., Cas9 from other species) or engineered Cas9 molecules. Oftentimes, such mutations result in the catalytically dead Cas9 possessing no more than 3% of the normal nuclease activity.

In some embodiments, the deaminase and the nucleic acid binding domain are covalently linked in a single amino acid chain through a linker. The linker may have any of a variety of amino acid sequences. Proteins can be joined by a linker polypeptide, generally of a flexible nature, although other chemical linkages are not excluded. Suitable linkers include polypeptides of between 1 amino acid and 100 amino acids in length, 4 amino acids and 40 amino acids in length, or between 4 amino acids and 25 amino acids in length. The linking peptides may have virtually any amino acid sequence, bearing in mind that the preferred linkers will have a sequence that results in a generally flexible peptide. Small amino acids, such as glycine and alanine, are useful in creating a flexible peptide linker. A variety of different linkers are considered suitable for use, including but not limited to, glycine-serine polymers, glycine-alanine polymers, and alanine-serine polymers. Such fusion proteins can be expressed recombinantly from a single nucleic acid encoding the amino acid chain.

Alternatively, the nucleic acid binding domain and the deaminase may be individually fused to one half of a binding pair (e.g., from a recruitment system) and, when introduced into the same system or location, the deaminase and nucleic acid binding domain form a protein conjugate through the recruitment system. The recruitment system can comprise any binding pair. For example, the recruitment system may comprise an aptamer and an aptamer binding protein. The recruitment system may be a so-called split system. Split systems include two or more polypeptide chains that reassemble into an operable fusion protein or protein conjugate upon association of the two binding partners. Split systems include, but are not limited to, intein, MS2, or SunTag based systems.

In some embodiments, the aptamer sequence is a nucleic acid (e.g., RNA aptamer) sequence. In some embodiments, the guide RNA also comprises a sequence of one or more RNA aptamers, or distinct RNA secondary structures or sequences that can recruit and bind another molecular species, an adaptor molecule, such as a nucleic acid or protein. Any RNA aptamer/aptamer binding protein pair known may be selected and used in connection with the present disclosure (see, e.g., Jayasena, S. D., Clinical Chemistry. 45(9): p. 1628-1650, (1999); Gelinas, et al., Current Opinion in Structural Biology 36: p. 122-132, (2016); and Hasegawa, H., Molecules, 21(4): p. 421 (2016), incorporated herein by reference).

In some embodiments, the aptamer sequence is a peptide aptamer sequence. In some embodiments, the nucleic acid binding domain comprises the peptide aptamer sequence and the deaminase comprises the peptide aptamer binding protein. In some embodiments, the deaminase comprises the peptide aptamer sequence and the nucleic acid binding domain comprises the peptide aptamer binding protein. The peptide aptamer sequence or peptide aptamer binding protein may be fused in any orientation (e.g., N-terminus to C-terminus, C-terminus to N-terminus, N-terminus to N-terminus). The peptide aptamer sequence or peptide aptamer binding protein may be fused by a linker region. Suitable linker regions are known in the art. The linker may be flexible or configured to allow the functionality and association with the DNA or other proteins with decreased steric hindrance. The linker sequences may provide an unstructured or linear region of the polypeptide, for example, with the inclusion of one or more glycine and/or serine residues. The linker sequences can be at least about 2, 3, 4, 5, 6, 7, 8, 9, 10 or more amino acids in length.

The peptide aptamers can be naturally occurring or synthetic peptides that are specifically recognized by an affinity agent. Such aptamers include, but are not limited to, a c-Myc affinity tag, an HA affinity tag, a His affinity tag, an S affinity tag, a methionine-His affinity tag, an RGD-His affinity tag, a 7× His tag, a FLAG octapeptide, a strep tag or strep tag II, a V5 tag, or a VSV-G epitope. Corresponding aptamer binding proteins are well-known in the art and include, for example, primary antibodies, biotin, affimers, single domain antibodies, and antibody mimetics.

Any of the deaminases and/or fusion proteins disclosed herein may further comprise one or more proteins, polypeptides (e.g., protein domain sequences), or peptides. For example, the deaminases and/or fusion proteins disclosed herein may be fused to another protein or protein domain that provides for tagging or visualization (e.g., GFP). The one or more proteins, polypeptides (e.g., protein domain sequences), or peptides may be appended at an N-terminus, a C-terminus, internally, or a combination thereof. The one or more proteins, polypeptides (e.g., protein domain sequences), or peptides may be fused in any orientation in relationship to the disclosed protein. The one or more proteins, polypeptides (e.g., protein domain sequences), or peptides may be fused via a linker, as described above.

In some embodiments, the deaminases and/or fusion proteins comprise one or more nuclear localization sequences (NLSs). The nuclear localization sequence may be appended, for example, to the N-terminus, a C-terminus, internally, or a combination thereof. In such cases when the deaminase and/or fusion protein comprises two or more NLSs, the NLSs may be in tandem, separated by a linker, at either end of the protein, or one or more may be embedded in the protein.

The nuclear localization sequence may comprise any amino acid sequence known in the art to functionally tag or direct a protein for import into a cell's nucleus (e.g., for nuclear transport). Usually, a nuclear localization sequence comprises one or more positively charged amino acids, such as lysine and arginine. The NLS may be appended by a linker.

In some embodiments, the NLS is a monopartite sequence. A monopartite NLS comprises a single cluster of positively charged or basic amino acids. In some embodiments, the monopartite NLS comprises a sequence of K-K/R-X-K/R, wherein X can be any amino acid. Exemplary monopartite NLS sequences include those from the SV40 large T-antigen, c-Myc, and TUS-proteins. In some embodiments, the NLS is a bipartite sequence. Bipartite NLSs comprise two clusters of basic amino acids, separated by a spacer of about 9-12 amino acids. Exemplary bipartite NLSs include the nuclear localization sequences of nucleoplasmin, EGL-12, or bipartite SV40. In some embodiments, the NLS comprises a sequence of: KR(K/R)R (SEQ ID NOs: 792-793); K(K/R)RK (SEQ ID NOs: 794-795); (R/P)XXKR(K/R)(^DE) (SEQ ID NOS: 796-799) or (R/P)XXKR(^DE)(K/R) (SEQ ID NOs: 800-803) wherein (^DE) represents any amino acid except for Asp or Glu; KRX(W/F/Y)XXAF (SEQ ID NOs: 804-806); LGKR(K/R)(W/F/Y) (SEQ ID NO: 807-808); or a bipartite sequence thereof.

The deaminases and/or fusion proteins may also comprise an epitope tag (e.g., 3×FLAG tag, an HA tag, a Myc tag, and the like). In some embodiments, the epitope tag may be adjacent, either upstream or downstream, to a nuclear localization sequence. The epitope tags may be at the N-terminus, a C-terminus, or a combination thereof of the corresponding protein or polypeptide.

In some embodiments, the deaminases and/or fusion proteins may be fused with one or more (e.g., two, three, four, or more) protein transduction moieties. A protein transduction moiety is a polypeptide, polynucleotide, carbohydrate, or organic or inorganic compound that facilitates traversing a lipid bilayer, micelle, cell membrane, organelle membrane, or vesicle membrane. A protein transduction moiety attached to another molecule facilitates the molecule traversing a membrane, for example going from extracellular space to intracellular space, or cytosol to within an organelle. The protein transduction moiety may be linked to the terminus of the deaminase or fusion protein, or alternatively be inserted internally. Examples of protein transduction moieties include but are not limited to a minimal undecapeptide protein transduction domain (corresponding to residues 47-57 of HIV-1 TAT comprising); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); a *Drosophila Antennapedia* protein transduction domain (Noguchi et al. (2003) *Diabetes*

52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); Transportan, and the like.

Systems and Compositions

Disclosed herein are systems and compositions that comprise a deaminase or a nucleic acid encoding thereof. In some embodiments, the systems and compositions comprise a deaminase and a nucleic acid binding polypeptide, or one or more nucleic acids encoding thereof. In some embodiments, the deaminase and the nucleic acid binding polypeptide are fused as a single protein, for example as described above for the fusion protein. In some embodiments, the deaminase and the nucleic acid binding polypeptide are each linked to a half of a binding pair. Descriptions of the deaminases, nucleic acid binding polypeptides, and fusion protein provided above are equally applicable to the systems and compositions.

In some embodiments, the nucleic acid sequences that encode the deaminase and the nucleic acid binding polypeptide are on the same nucleic acid. In some embodiments, the nucleic acid sequences that encode the deaminase and the nucleic acid binding polypeptide are on different nucleic acids. In some embodiments, the nucleic acids comprise one or more messenger RNAs, one or more vectors, or any combination thereof.

In some embodiments, for example when the nucleic acid binding polypeptide is an RNA-guided protein (e.g., a Cas protein) or fragment thereof, the compositions or systems further comprise at least one guide RNA (gRNA) or one or more nucleic acids comprising a sequence encoding the least one gRNA. In instances when the composition or system comprises more than one gRNA, each may be encoded on the same or different nucleic acid as the other gRNA, together or separate from either or both of the deaminase and the nucleic acid binding polypeptide. For example, the system and compositions may comprise a first nucleic acid encoding the deaminase and the nucleic acid binding polypeptide and a second nucleic acid encoding the gRNA; a first nucleic acid encoding the deaminase and the gRNA and a second nucleic acid encoding the nucleic acid binding polypeptide; a first nucleic acid encoding the deaminase and a second nucleic acid encoding the gRNA and the nucleic acid binding polypeptide; or a single nucleic acid encoding the deaminase, the nucleic acid binding polypeptide, and the gRNA. In some embodiments, the at least one gRNA is provided in a ribonucleoprotein (RNP) complex with the RNA-guided protein.

The gRNA may contain separate crRNA and tracrRNA sequences (or dual guide RNA) or having the crRNA and tracrRNA fused by a flexible linker (or single guide RNA, sgRNA). The terms “gRNA,” “guide RNA,” and “guide sequence” may be used interchangeably throughout and refer to a nucleic acid comprising a sequence that determines the sequence specificity of the CRISPR-associated protein. A gRNA hybridizes to (complementary to, partially or completely) a target nucleic acid sequence (e.g., the genome in a host cell).

In some embodiments, at least one gRNA is encoded in a CRISPR array. CRISPR arrays contain a series of direct repeats separated by short sequences called spacers. The CRISPR-associated protein described herein may have a preference for direct repeat sequences. These can be determined by methods known in the art. For example, the CRISPR RNA (crRNA) may contain multiple gRNAs or may contain more than one different sequence each configured to hybridize a distinct target nucleic acid sequence.

The gRNA or portion thereof that hybridizes to the target nucleic acid (a target site) may be between 15-40 nucleotides in length. gRNAs or sgRNA(s) used in the present disclosure can be between about 5 and 100 nucleotides long, or longer. The gRNA may be a non-naturally occurring or engineered gRNA.

To facilitate gRNA design, many computational tools have been developed (See Prykhozhij et al. (PLoS ONE, 10(3): (2015)); Zhu et al. (PLoS ONE, 9(9) (2014)); Xiao et al. (Bioinformatics. January 21 (2014)); Heigwer et al. (Nat Methods, 11(2): 122-123 (2014)). Methods and tools for guide RNA design are discussed by Zhu (Frontiers in Biology, 10 (4) pp. 289-296 (2015)), which is incorporated by reference herein. Additionally, there are many publicly available software tools that can be used to facilitate the design of sgRNA(s); including but not limited to, Genscript Interactive CRISPR gRNA Design Tool, WU-CRISPR, and Broad Institute GPP sgRNA Designer. There are also publicly available pre-designed gRNA sequences to target many genes and locations within the genomes of many species (human, mouse, rat, zebrafish, *C. elegans*), including but not limited to, IDT DNA Predesigned Alt-R CRISPR-Cas9 guide RNAs, Addgene Validated gRNA Target Sequences, and GenScript Genome-wide gRNA databases.

In some embodiments, the gRNA sequence that binds to the target nucleic acid may be fused to a scaffold sequence (e.g., tracrRNA). In some embodiments, such a chimeric gRNA may be referred to as a single guide RNA (sgRNA). Exemplary scaffold sequences will be evident to one of skill in the art and can be found, for example, in Jinek, et al. Science (2012) 337(6096):816-821, and Ran, et al. Nature Protocols (2013) 8:2281-2308, incorporated herein by reference in their entireties.

In some embodiments, the targeting gRNA sequence and tracrRNA scaffold sequence are expressed as separate transcripts. In some embodiments, this may be referred to as a dual guide RNA In such embodiments, the gRNA sequence further comprises an additional sequence that is complementary to a portion of the scaffold sequence and functions to bind (hybridize) the scaffold sequence.

“Complementarity” refers to the ability of a nucleic acid to form hydrogen bond(s) with another nucleic acid sequence by either traditional Watson-Crick or other non-traditional types. A percent complementarity indicates the percentage of residues in a nucleic acid molecule, which can form hydrogen bonds (e.g., Watson-Crick base pairing) with a second nucleic acid sequence. Full complementarity is not necessarily required, provided there is sufficient complementarity to cause hybridization. There may be mismatches distal from the PAM.

In some embodiments, the compositions and systems may further comprise one or more additional genome engineering tools. For example, the compositions may further comprise nucleases, such as zinc finger nucleases (ZFNs) and/or transcription activator like effector nucleases (TALENs); transcriptional activators, transcriptional repressors, histone-modifying proteins, integrases, recombinases, and the like.

The compositions or systems may further comprise an excipient or carrier. Excipients and carriers may include any and all solvents, dispersion media, coatings, antibacterial and antifungal agents, isotonic and absorption delaying agents. Some examples of materials which can serve as excipients and/or carriers are sugars including, but not limited to, lactose, glucose and sucrose; starches including, but not limited to, corn starch and potato starch; cellulose and its derivatives including, but not limited to, sodium carboxymethyl cellulose, ethyl cellulose and cellulose acetate; powdered tragacanth; malt; gelatin; talc; excipients including, but not limited to, cocoa butter and suppository waxes; oils including, but not limited to, peanut oil, cottonseed oil, safflower oil, sesame oil, olive oil, corn oil and soybean oil; glycols; including propylene glycol; esters including, but not limited to, ethyl oleate and ethyl laurate; agar; buffering agents including, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants including, but not limited to, sodium lauryl sulfate and magnesium stearate, as well as coloring agents, releasing agents, coating agents, sweetening, flavoring and perfuming agents, preservatives and antioxidants. The compositions of the present invention and methods for their preparation will be readily apparent to those skilled in the art. Techniques and formulations may be found, for example, in Remington's Pharmaceutical Sciences, 19th Edition (Mack Publishing Company, 1995).

In some embodiments, the excipient or carrier is pharmaceutically acceptable. Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. Sec, e.g., Remington: The Science and Practice of Pharmacy 20th Ed. (2000) Lippincott Williams and Wilkins, Ed. K. E. Hoover.

The carrier may include a delivery vehicle. Delivery vehicles such as nanoparticle- and lipid-based delivery systems can be used. Exemplary delivery vehicles include, but are not limited to, microparticle compositions comprising a variety of polymers, liposomes or lipid nanoparticles, viral vectors, ribonucleoprotein (RNP) complexes, and the like.

Microparticles can include, but are not limited to, liposomes, nanoparticles, microspheres, nanospheres, microcapsules, and nanocapsules. In some cases, microparticle can include one or more of the following: a poly(lactide-co-glycolide), aliphatic polyesters including, but not limited to, poly-glycolic acid and poly-lactic acid, hyaluronic acid, modified polysaccharides, chitosan, cellulose, dextran, polyurethanes, polyacrylic acids, pseudo-poly(amino acids), polyhydroxybutyrate-related copolymers, polyanhydrides, polymethylmethacrylate, poly(ethylene oxide), lecithin, lipids, and phospholipids, in any combination thereof.

In some embodiments, a liposome or lipid nanoparticle encapsulates the disclosed systems, nucleic acids, or proteins (e.g., deaminases and nucleic acid binding polypeptides). Methods of making lipid compositions include, for example, lipid film hydration, optionally coupled with sonication or extrusion, solvent evaporation (e.g., ethanol injection, ether injection, or reverse phase evaporation), solvent-diffusion method, hot homogenization process, detergent removal methods, or combinations thereof. Any naturally occurring or synthetic vesicle forming lipid or combinations thereof can be used, including for example, di-aliphatic chain lipids, such as phospholipids; diglycerides; di-aliphatic glycolipids; single lipids such as sphingomyelin or glycosphingolipid; steroidal lipids; hydrophilic polymer derivatized lipids; or mixtures thereof. Liposome and lipid nanoparticle compositions of the disclosure may include one or more cationic and/or ionizable lipids, phospholipids, neutral or non-cationic lipids, polyethyleneglycol (PEG)-lipid conjugates, and/or sterols. In some embodiments, the lipid nanoparticle comprises a cationic lipid and/or ionizable lipid, a neutral or non-cationic lipid, and cholesterol.

The liposomes and lipid nanoparticles described herein may also include other components typically used in the formation of vesicles (e.g., for stabilization). Examples of such other components includes, without being limited thereto, fatty alcohols, fatty acids, and/or any other pharmaceutically acceptable excipients which may affect the surface charge, the membrane fluidity and assist in the incorporation of the lipid into the lipid assembly.

The liposome and lipid nanoparticle compositions of the disclosure can also be targeting compositions, e.g., contain one or more targeting moieties or biodistribution modifiers on the surface. A targeting moiety can be any agent that is capable of specifically binding or interacting with a desired target and are generally known in the art, for example ligands such as folic acid, proteins, antibody or antibody fragments, and the like).

The phrase "pharmaceutically acceptable," as used in connection with the present disclosure, refers to molecular entities and other ingredients of such compositions that are physiologically tolerable and do not typically produce untoward reactions when administered to a subject (e.g., a mammal, a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. "Acceptable" means that the carrier is compatible with the composition (e.g., the nucleic acids, vectors, cells, proteins, or polypeptides) and does not negatively affect the subject to which the composition(s) are administered. Any of the compositions to be used in the present methods can comprise pharmaceutically acceptable carriers, excipients, or stabilizers in the form of lyophilized formations or aqueous solutions.

Nucleic Acids

Also disclosed herein are nucleic acids encoding the deaminases or fusion proteins as described herein. The nucleic acids may be DNA, RNA, or combinations thereof. In some embodiments, the nucleic acids comprise one or more messenger RNAs, one or more vectors, or any combination thereof.

In certain embodiments, the nucleic acids are engineered for codon-optimization. It will be appreciated altering codons to those most frequently used in the cells or subject of interest allows for maximum expression. Such modified nucleic acid sequences are commonly described in the art as "codon-optimized." In some embodiments, the nucleic acid sequence is considered codon-optimized if at least about 60% (e.g., about 65%, about 70%, about 75%, about 80%, about 85%, about 90%, about 95%, or about 98%) of the codons encoded therein are preferred codons to the subject of interest.

The present disclosure also provides for DNA segments encoding the deaminases or fusion proteins disclosed herein, vectors containing these segments, and cells containing the vectors. The vectors may be used to propagate the DNA segment in an appropriate cell and/or to allow expression from the segment (e.g., an expression vector). The person of ordinary skill in the art would be aware of the various vectors available for propagation and expression of a nucleic acid sequence.

The present disclosure further provides engineered, non-naturally occurring vectors and vector systems, which can encode the deaminases, fusion proteins, or one or more or all of the components of the systems or compositions, as disclosed herein. The vector(s) can be introduced into a cell that is capable of expressing the polypeptide encoded thereby, including any suitable prokaryotic or eukaryotic cell.

The vectors of the present disclosure may be delivered to a eukaryotic cell. Modification of the eukaryotic cells via the present system can take place in a cell culture, where the method comprises isolating the eukaryotic cell from a subject prior to the modification. In some embodiments, the method further comprises returning said eukaryotic cell and/or cells derived therefrom to the subject.

Viral and non-viral based gene transfer methods can be used to introduce nucleic acids encoding components of the present system into cells, tissues, or a subject. Such methods can be used to administer nucleic acids encoding components of the present system to cells in culture, or in a host organism. Non-viral vector delivery systems include DNA plasmids, cosmids, RNA (e.g., a transcript of a vector described herein), nucleic acids, and nucleic acids complexed with a delivery vehicle. Viral vector delivery systems include DNA and RNA viruses, which have either episomal or integrated genomes after delivery to the cell. Viral vectors include, for example, retroviral, lentiviral, adenoviral, adeno-associated and herpes simplex viral vectors.

In certain embodiments, plasmids that are non-replicative, or plasmids that can be cured by high temperature may be used, such that any or all of the necessary components of the system may be removed from the cells under certain conditions. For example, this may allow for DNA integration by transforming bacteria of interest, but then being left with engineered strains that have no memory of the plasmids or vectors used for the integration.

Drug selection strategies may be adopted by positively selecting for cells that underwent DNA integration. A donor nucleic acid may contain one or more drug-selectable markers within the cargo. Then presuming that the original donor plasmid is removed, drug selection may be used to enrich for integrated clones. Colony screenings may be used to isolate clonal events.

A variety of viral constructs may be used to deliver deaminases, fusion proteins, or one or more or all of the components of the system or compositions (such as a deaminase, fusion protein, and/or a guide RNA) to the targeted cells and/or a subject. Nonlimiting examples of such recombinant viruses include recombinant adeno-associated virus (AAV), recombinant adenoviruses, recombinant lentiviruses, recombinant retroviruses, recombinant herpes simplex viruses, recombinant poxviruses, phages, etc. The present disclosure provides vectors capable of integration in the host genome, such as retrovirus or lentivirus. See, e.g., Ausubel et al., Current Protocols in Molecular Biology, John Wiley & Sons, New York, 1989; Kay, M. A., et al., 2001 Nat. Medic. 7(1):33-40; and Walther W. and Stein U., 2000 Drugs, 60(2): 249-71, incorporated herein by reference.

In one embodiment, a DNA segment encoding deaminases, fusion proteins, or one or more or all of the components of the system or compositions is contained in a plasmid vector that allows expression of the protein(s) and subsequent isolation and purification produced by the recombinant vector. Accordingly, the proteins disclosed herein can be purified following expression, obtained by chemical synthesis, or obtained by recombinant methods.

To construct cells that express the deaminases, fusion proteins, or one or more or all of the components of the system or compositions, expression vectors for stable or transient expression may be constructed via conventional methods as described herein and introduced into cells. For example, nucleic acids encoding the deaminases, fusion proteins, or one or more or all of the components of the system or compositions may be cloned into a suitable expression vector, such as a plasmid or a viral vector in operable linkage to a suitable promoter. The selection of expression vectors/plasmids/viral vectors should be suitable for integration and replication in eukaryotic cells.

In certain embodiments, vectors of the present disclosure can drive the expression of one or more sequences in prokaryotic cells. Promoters that may be used include T7 RNA polymerase promoters, constitutive *E. coli* promoters, and promoters that could be broadly recognized by transcriptional machinery in a wide range of bacterial organisms. The system may be used with various bacterial hosts.

In certain embodiments, vectors of the present disclosure can drive the expression of one or more sequences in mammalian cells using a mammalian expression vector. Examples of mammalian expression vectors include pCDM8 (Seed, Nature (1987) 329:840, incorporated herein by reference) and pMT2PC (Kaufman, et al., EMBO J. (1987) 6:187, incorporated herein by reference). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd eds., Cold Spring Harbor Laboratory, Cold Spring Harbor Laboratory Press, Cold Spring Harbor, N.Y., 1989, incorporated herein by reference.

Vectors of the present disclosure can comprise any of a number of promoters known to the art, wherein the promoter is constitutive, regulatable or inducible, cell type specific, tissue-specific, or species specific. In addition to the sequence sufficient to direct transcription, a promoter sequence of the invention can also include sequences of other regulatory elements that are involved in modulating transcription (e.g., enhancers, Kozak sequences and introns). Many promoter/regulatory sequences useful for driving constitutive expression of a gene are available in the art and include, but are not limited to, for example, CMV (cytomegalovirus promoter), EF1a (human elongation factor 1 alpha promoter), SV40 (simian vacuolating virus 40 promoter), PGK (mammalian phosphoglycerate kinase promoter), Ubc (human ubiquitin C promoter), human beta-actin promoter, rodent beta-actin promoter, CBh (chicken beta-actin promoter), CAG (hybrid promoter contains CMV enhancer, chicken beta actin promoter, and rabbit beta-globin splice acceptor), TRE (Tetracycline response element promoter), H1 (human polymerase III RNA promoter), U6 (human U6 small nuclear promoter), and the like. Additional promoters that can be used for expression of the components of the present system, include, without limitation, cytomegalovirus (CMV) intermediate early promoter, a viral LTR such as the Rous sarcoma virus LTR, HIV-LTR, HTLV-1 LTR, Maloney murine leukemia virus (MMLV) LTR, mycoloproliferative sarcoma virus (MPSV) LTR, spleen focus-forming virus (SFFV) LTR, the simian virus 40 (SV40) early promoter, herpes simplex tk virus promoter, elongation factor 1-alpha (EF1-α) promoter with or without the EF1-α intron. Additional promoters include any constitutively active promoter. Alternatively, any regulatable promoter may be used, such that its expression can be modulated within a cell.

Moreover, inducible and tissue specific expression can be accomplished by placing the nucleic acid encoding such a molecule under the control of an inducible or tissue specific promoter/regulatory sequence. Examples of tissue specific or inducible promoter/regulatory sequences which are useful for this purpose include, but are not limited to, the rhodopsin promoter, the MMTV LTR inducible promoter, the SV40 late enhancer/promoter, synapsin 1 promoter, ET hepatocyte promoter, GS glutamine synthase promoter and many others. In addition, promoters which are well known in the art can be induced in response to inducing agents such as metals, glucocorticoids, tetracycline, hormones, and the like, are also contemplated for use with the invention. Thus, it will be appreciated that the present disclosure includes the use of any promoter/regulatory sequence capable of driving expression of the desired protein operably linked thereto.

The vectors of the present disclosure may direct expression of the nucleic acid in a particular cell type (e.g., tissue-specific regulatory elements are used to express the nucleic acid). Such regulatory elements include promoters that may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining.

Additionally, the vector may contain, for example, some or all of the following: a selectable marker gene, such as the neomycin gene for selection of stable or transient transfectants in host cells; enhancer/promoter sequences from the immediate early gene of human CMV for high levels of transcription; transcription termination and RNA processing signals from SV40 for mRNA stability; 5'- and 3'-untranslated regions for mRNA stability and translation efficiency from highly-expressed genes like α-globin or β-globin; SV40 polyoma origins of replication and ColE1 for proper episomal replication; internal ribosome binding sites (IRESes), versatile multiple cloning sites; T7 and SP6 RNA promoters for in vitro transcription of sense and antisense RNA; a "suicide switch" or "suicide gene" which when triggered causes cells carrying the vector to die (e.g., HSV thymidine kinase, an inducible caspase such as iCasp9), and reporter gene for assessing expression of the chimeric receptor. Suitable vectors and methods for producing vectors containing transgenes are well known and available in the art. Selectable markers also include chloramphenicol resistance, tetracycline resistance, spectinomycin resistance, streptomycin resistance, erythromycin resistance, rifampicin resistance, bleomycin resistance, thermally adapted kanamycin resistance, gentamycin resistance, hygromycin resistance, trimethoprim resistance, dihydrofolate reductase (DHFR), GPT; the URA3, HIS4, LEU2, and TRPI genes of *S. cerevisiae.*

When introduced into the cell, the vectors may be maintained as an autonomously replicating sequence or extrachromosomal element or may be integrated into host DNA.

The proteins, polynucleotides encoding these proteins, and systems and compositions comprising the proteins and/or polynucleotides described herein may be delivered by any suitable means. In certain embodiments, the delivery is in vivo. In other embodiments, the delivery is to isolated/cultured cells (e.g., autologous iPS cells) in vitro to provide modified cells useful for in vivo delivery to patients afflicted with a disease or condition.

Vectors according to the present disclosure can be transformed, transfected, or otherwise introduced into a wide variety of cells. Transfection refers to the taking up of a vector by a cell whether or not any coding sequences are in fact expressed. Numerous methods of transfection are known to the ordinarily skilled artisan, for example, lipofectamine, calcium phosphate co-precipitation, electroporation, DEAE-dextran treatment, microinjection, viral infection, and other methods known in the art. Transduction refers to entry of a virus into the cell and expression (e.g., transcription and/or translation) of sequences delivered by the viral vector genome. In the case of a recombinant vector, "transduction" generally refers to entry of the recombinant viral vector into the cell and expression of a nucleic acid of interest delivered by the vector genome.

Any of the vectors comprising a nucleic acid sequence that encodes the deaminases, fusion proteins, or one or more or all of the components of the system or compositions is also within the scope of the present disclosure. Such a vector may be delivered into host cells by a suitable method. Methods of delivering vectors to cells are well known in the art and may include DNA or RNA electroporation, transfection reagents such as liposomes or nanoparticles to delivery DNA or RNA; delivery of DNA, RNA, or protein by mechanical deformation (see, e.g., Sharei et al. Proc. Natl. Acad. Sci. USA 110(6): 2082-2087 (2013) incorporated herein by reference); or viral transduction. In some embodiments, the vectors are delivered to host cells by viral transduction. Nucleic acids can be delivered as part of a larger construct, such as a plasmid or viral vector, or directly, e.g., by electroporation, lipid vesicles, viral transporters, microinjection, and biolistics (high-speed particle bombardment). Similarly, the construct containing the one or more transgenes can be delivered by any method appropriate for introducing nucleic acids into a cell. In some embodiments, the construct or the nucleic acid encoding the components of the present system is a DNA molecule. In some embodiments, the nucleic acid encoding the components of the present system is a DNA vector and may be electroporated to cells. In some embodiments, the nucleic acid encoding the components of the present system is an RNA molecule, which may be electroporated to cells.

Additionally, delivery vehicles such as nanoparticle- and lipid-based mRNA or protein delivery systems can be used. Further examples of delivery vehicles include lentiviral vectors, ribonucleoprotein (RNP) complexes, lipid-based delivery system, gene gun, hydrodynamic, electroporation or nucleofection microinjection, and biolistics. Various gene delivery methods are discussed in detail by Nayerossadat et al. (Adv Biomed Res. 2012; 1:27) and Ibraheem et al. (Int J Pharm. 2014 Jan. 1; 459(1-2):70-83), incorporated herein by reference.

In some embodiments, the deaminases, fusion proteins, or one or more or all of the components of the system or compositions may be mixed, individually or in any combination, with a carrier which are also within the scope of the present disclosure. Exemplary carriers include buffers, antioxidants, preservatives, carbohydrates, surfactants, and the like, and are described in detail elsewhere herein.

Also disclosed is a cell comprising the deaminases, fusion proteins, nucleic acids, or one or more or all of the components of the system or compositions described herein. In some embodiments, the cell is a prokaryotic cell. In some embodiments, the cell is a eukaryotic cell. In some embodiments, the cell is a mammalian cell. In some embodiments, the cell is a human cell.

Methods

The disclosure also provides methods of modifying a target nucleic acid sequence (e.g., DNA or RNA). The phrase "modifying a nucleic acid sequence," as used herein, refers to modifying at least one physical feature of a nucleic acid sequence of interest. In some embodiments, the modifications comprise base editing. In some embodiments, the base editing edits an adenine in the target nucleic acid.

The methods comprise contacting a target nucleic acid sequence with a deaminase, fusion protein, composition, or system as described herein. In some embodiments, contacting a target nucleic acid sequence comprises introducing the deaminase, fusion protein, composition, or system into the cell. The deaminase, fusion protein, composition, or system may be introduced into eukaryotic or prokaryotic cells by methods known in the art, as described elsewhere herein.

The cell may be a prokaryotic cell, a plant cell, an insect cell, a vertebrate cell, an invertebrate cell, an animal cell, a mammalian cell, or a human cell. In some embodiments, the cell is a stem cell.

In some embodiments, the cell is ex vivo (e.g., fresh isolate—early passage). In some cases, the cell is in vivo. In some cases, the cell is in culture or in vitro (e.g., immortalized cell line). Cells may be from established cell lines or they may be primary cells, where "primary cells," "primary cell lines," and "primary cultures" are used interchangeably herein to refer to cells and cells cultures that have been derived from a subject and allowed to grow in vitro for a limited number of passages of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in culture.

In some embodiments, introducing the deaminase, fusion protein, composition, or system into a cell comprises administering the deaminase, fusion protein, composition, or system to a subject. In some embodiments, the subject is human. The administering may comprise in vivo administration of the deaminase, fusion protein, composition, system, or a nucleic acid encoding the deaminase, fusion protein, or system. In alternative embodiments, an in vitro or ex vivo treated cell is transplanted into a subject.

In some embodiments, the target nucleic acid is a nucleic acid endogenous to a target cell. In some embodiments, the target nucleic acid is a genomic DNA sequence. The term "genomic," as used herein, refers to a nucleic acid sequence (e.g., a gene or locus) that is located on a chromosome in a cell.

In some embodiments, the target nucleic acid encodes a gene or gene product. The term "gene product," as used herein, refers to any biochemical product resulting from expression of a gene. Gene products may be RNA or protein. RNA gene products include non-coding RNA, such as tRNA, rRNA, microRNA (miRNA), and small interfering RNA (siRNA), and coding RNA, such as messenger RNA (mRNA). In some embodiments, the target nucleic acid sequence encodes a protein or polypeptide.

In some embodiments, the methods described herein result in an adenine (A) to guanine (G) point mutation within a gene (e.g., a coding region or non-coding region (e.g., a promoter or regulatory sequences) of a gene).

In some embodiments, the methods described herein alter the regulatory sequence of a gene (e.g., a gene promoter or gene repressor). Accordingly, in some embodiments, the methods described herein lead to modulation (increase, decrease, or cessation) of transcription of a gene. In some embodiments, the methods described herein alter the splicing of a gene (e.g., introduce or remove a splice site). Accordingly, in some embodiments, the method results in the introduction of a splice site in a gene. In alternative embodiments, the method results in the removal of a splice site.

In some embodiments, the methods described herein alter the coding sequence of a gene. In some embodiments, the alteration is silent or synonymous. In some embodiments, the alteration is non-synonymous and results in an amino-acid change. In some embodiments, the methods described herein generate a stop codon, for example, a premature stop codon within the coding region of a gene. In some embodiments, the methods described herein eliminate a stop codon, e.g., a stop codon in a target nucleic acid comprising the nucleic acid sequence TAG, TAA, or TGA.

In some embodiments, the methods described herein may be used to correct one or more defects or mutations in one or more genes (referred to as "gene correction"). In some cases, the target sequence encodes a defective version of a gene, and the disclosed systems and compositions are configured to correct, or ablate e.g., by mutating the start codon (ATG) and abolishing gene expression, the defective version of the gene. Alternatively, the target sequence may encode the wild-type version of the gene, and the disclosed systems and compositions are configured to confer the disease-causing mutation to the gene, for example, for use in cell and organismal models of the disease or disorder.

In some embodiments, the defective version of the gene includes a point mutation. Point mutations are the largest class of known pathogenic genetic variants and approximately half of which result from a change of a G-C to an A-T base pair. The deaminases and fusion proteins (e.g., base editors) disclosed herein may install or reverse point mutations, thereby providing methods for the study and treatment of disease-associated point mutations.

The present methods may be used in various bacterial hosts, including human pathogens that are medically important, and bacterial pests that are key targets within the agricultural industry, as well as antibiotic resistant versions thereof. The method may be designed to target any gene or any set of genes, such as virulence or metabolic genes, for clinical and industrial applications in other embodiments. The present methods may be used to inactivate microbial genes. In some embodiments, the gene is an antibiotic resistance gene. The present methods may be used to treat a multi-drug resistance bacterial infection in a subject. The present methods may also be used for genomic engineering within complex bacterial consortia.

The methods described here also provide for treating a disease or disorder in a subject. The method may comprise administering to the subject, in vivo, an effective amount of the deaminase, fusion protein, composition, or system, or by transplantation of ex vivo treated cells. A "subject" or "patient" may be human or non-human and may include, for example, animal strains or species used as "model systems" for research purposes, such a mouse model as described herein. Within the context of the present disclosure, the term "effective amount" refers to that quantity such that modification of the target nucleic acid is achieved.

In some embodiments, the systems and methods target one or more "disease-associated" genes. The term "disease-associated gene," refers to any gene or polynucleotide whose gene products are expressed at an abnormal level or in an abnormal form in cells obtained from a disease-affected individual as compared with tissues or cells obtained from an individual not affected by the disease. A disease-associated gene may refer to a gene, the mutation or genetic variation of which is directly responsible or is in linkage disequilibrium with a gene(s) that is responsible for the etiology of a disease. In another embodiment, the target genomic DNA sequence can comprise a gene, the mutation of which contributes to a particular disease in combination with mutations in other genes.

In some embodiments, the one or more disease-associated gene comprises one or more point mutations, single nucleotide variants (SNVs), or single-nucleotide polymorphisms (SNPs). In some embodiments, the point mutation, SNV, or SNP comprises a mutation of a wild-type base to an adenine. In some embodiments, the point mutation, SNV, or SNP comprises a G to A point mutation. Accordingly, correction of the G to A point mutation, SNV, or SNP with the deaminases or fusion proteins disclosed herein results in a reversion to wild-type or non-disease-associated sequence. In some embodiments, the point mutation, SNV, or SNP comprises a C to T point mutation. Accordingly, correction of the A which base pairs with the T mutation results in a wild-type or non-disease-associated sequence following cellular replication/repair processes. Exemplary diseases associated with a point mutation, SNV, or SNP that may be treated with the disclosed methods include, but are not limited to, proliferative diseases, metabolic diseases, and lysosomal storage diseases.

When utilized as a method of treatment, the effective amount may depend on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human.

A wide range of additional therapies may be used in conjunction with the methods of the present disclosure. The additional therapy may be administration of a therapeutic agent or may be an additional therapy not connected to administration of a therapeutic agent. Such additional therapies include, but are not limited to, surgery, immunotherapy, radiotherapy. The additional therapy may be administered at the same time as the above methods. In some embodiments, the additional therapy may precede or follow the treatment of the disclosed methods by time intervals ranging from hours to months.

In some embodiments, effective combination therapy is achieved with a single composition or pharmacological formulation or with two distinct compositions or formulations, administered at the same time or separated by a time interval. The therapeutic agent may comprise any manner of therapeutic, including protein, small molecule, nucleic acids, and the like. For example, therapeutic agents include, but are not limited to, immune modulators, chemotherapeutic agents, a nucleic acid (e.g., mRNA, aptamers, antisense oligonucleotides, ribozyme nucleic acids, interfering RNAs, antigene nucleic acids), decongestants, steroids, analgesics, antimicrobial agents, immunotherapies, or any combination thereof.

In the context of the present disclosure insofar as it relates to any of the disease conditions recited herein, the terms "treat," "treatment," and the like mean to relieve or alleviate at least one symptom associated with such condition, or to slow or reverse the progression of such condition. Within the meaning of the present disclosure, the term "treat" also denotes to arrest, delay the onset (e.g., the period prior to clinical manifestation of a disease) and/or reduce the risk of developing or worsening a disease. For example, in connection with cancer the term "treat" may mean elimination or reduction of a patient's tumor burden, or prevention, delay, or inhibition of metastasis, etc.

The methods disclosed herein are also applicable to plants. For example, the methods can be used to generate novel engineered plants to improve agronomic traits, for example, herbicidal resistance, resistance to environmental stress, resistance to pests, etc.

The disclosed deaminases, fusion proteins, compositions, and systems can be introduced into a plant, or a plant cell, seed, fruit, plant part, or propagation material of the plant. The term "plant propagation material" refers to generative parts of a plant, which can be used for the multiplication of the plant, and vegetative plant material such as cuttings and tubers (e.g., potatoes). In some embodiments, the propagation material is a root, a corm, a tuber, a bulb, a slip, a cutting of the plant, and a rhizome. Parts of a plant are any sections of a plant (e.g., roots, cotyledons, tendrils, leaves, flowers, seeds, stems, callus tissue, nuts, and fruit) that develop from a plant propagation material or grow at a later time. The methods described herein can be used on any plant part. Examples of plant parts include but are not limited to the root, corm, tuber, bulb, slip and rhizome.

Methods of introducing exogenous nucleic acids into plant cells are well known in the art. Such plant cells are considered transformed. DNA constructs can be introduced into plant cells by various methods, including, but not limited to PEG- or electroporation-mediated protoplast transformation, tissue culture or plant tissue transformation by biolistic bombardment, or the *Agrobacterium*-mediated transient and stable transformation.

The transformation can be a transient or a stable transformation. As used herein, the term "stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant. In select embodiments, the nucleic acid encoding the RNA hairpin may be stably integrated into the plant genome, for example via *Agrobacterium*-mediated transformation.

Suitable methods also include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation, and the like. The choice of method is generally dependent on the type of cell being transformed and the circumstances under which the transformation is taking place (e.g., in vitro, ex vivo, or in vivo). Transformation methods based upon the soil bacterium *Agrobacterium tumefaciens* are useful for introducing an exogenous nucleic acid molecule into a vascular plant. The wild-type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of co-culturing *Agrobacterium* with cultured plant cells or wounded tissue such as leaf tissue, root explants, hypocotyledons, stem pieces or tubers, for example, also are well known in the art. Sec., e.g., Glick and Thompson, (eds.), Methods in Plant Molecular Biology and Biotechnology, Boca Raton, Fla.: CRC Press (1993), incorporated herein by reference.

Microprojectile-mediated transformation also can be used. This method, first described by Klein et al. (Nature 327:70-73 (1987), incorporated herein by reference), relies on microprojectiles such as gold or tungsten that are coated with the desired nucleic acid molecule by precipitation with calcium chloride, spermidine, or polyethylene glycol. The microprojectile particles are accelerated at high speed into an angiosperm tissue using a device such as the BIOLISTIC PD-1000 (Biorad; Hercules Calif.).

As such, the disclosure also provides plants and plant propagation materials (e.g., plant cell, seed, fruit, or plant parts) produced using the methods disclosed herein. Genetically modified, transformed or transgenic plants include a plant into which an exogenous polynucleotide, e.g., a polynucleotide encoding the deaminase or fusion protein disclosed herein, has been introduced.

The methods disclosed herein are suitable for use with any plant, for example, grain crops, fruit crops, forage crops, root vegetable crops, leafy vegetable crops, flowering plants, conifers, trees, oil crops, plants used in phytoremediation, industrial crops, medicinal crops, laboratory model plants, and the like. As such, non-limiting examples of plants that may be used with the present methods include: grains, forage crops, fruits, vegetables, oil seed crops, palms, forestry, vines, maize (corn, *Zea mays*), banana, peanut, field peas, sunflower, tomato, canola, tobacco, wheat, barley, oats, potato, soybeans, cotton, carnations, sorghum, lupin, rice, rutabaga, celery, switchgrass, apple, petunias, *Arabidopsis thaliana, Medicago truncatula, Medicago sativa, Brachypodium distachyon, Nicotiana benthamiana*, or *Setaria viridis.*

Additionally, the disclosed methods can also be used as a synthetic biology tool to record cellular signaling and exposure to stimuli. The disclosed deaminases and fusion proteins can generate predictable single point mutations and by coupling the stimulus of interest to the activity or expression of the deaminase or fusion protein, the resulting stimulus-dependent single point mutations can be used to record exposure to signals into the genome. Accordingly, the methods may further comprise exposing the cell, subject, or plant, to stimulus of interest, wherein the deaminase or fusion protein is configured for activation to the stimulus of interest (e.g., transcriptionally or translationally controlled activation).

Kits

Also within the scope of the present disclosure are kits that include the deaminases, fusion proteins, nucleic acids, cells, compositions, systems, or components thereof as disclosed herein.

The kits may contain one or more reagents or other components useful, necessary, or sufficient for practicing any of the methods described herein, such as, transfection or administration reagents, negative and positive control samples (e.g., cells, template DNA), cells, containers housing one or more components (e.g., microcentrifuge tubes, boxes), detectable labels, detection and analysis instruments, software, instructions, and the like.

The kit may include instructions for use in any of the methods described herein. Kits optionally may provide additional components such as buffers and interpretive information. Normally, the kit comprises a container and a label or package insert(s) on or associated with the container. Instructions supplied in the kits of the disclosure are typically written instructions on a label or package insert. In some embodiment, the disclosure provides articles of manufacture comprising contents of the kits described above.

The kits provided herein are in suitable packaging. Suitable packaging includes, but is not limited to, vials, bottles, jars, flexible packaging, and the like. A kit may have a sterile access port (for example, the container may be an intravenous solution bag or a vial having a stopper pierceable by a hypodermic injection needle). The container may also have a sterile access port.

The packaging may be unit doses, bulk packages (e.g., multi-dose packages) or sub-unit doses.

The kit will typically be provided with its various components in one or more packages, e.g., a fiber-based, a cardboard, a polymeric, or a Styrofoam box. The enclosure(s) can be configured so as to maintain a temperature differential between the interior and the exterior, for example, to provide insulating properties to keep the reagents at a preselected temperature for a preselected time. The packaging can be air-tight, waterproof (e.g., impermeable to changes in moisture or evaporation), and/or light-tight.

EXAMPLES

The following are examples of the present invention and are not to be construed as limiting.

Materials and Methods

Cell Culture, Plasmid Construction, and Transient Transfection

HEK293T cells (ATCC) were cultured at 37° C. and 5% (v/v) $CO_2$ in high glucose DMEM with 4 mM L-glutamine, 1 mM sodium pyruvate and phenol red pH indicator (Gibco), supplemented with 10% FBS and 1× penicillin-streptomycin. 24 hours prior to transfection, cells were seeded at a density of $10^3$ cells/well in 96 well tissue culture-treated plates.

guide RNAs (gRNA) were cloned into pGuide plasmid with a U6 promoter driving their expression and a CMV-driven GFP transfection reporter using HiFi DNA Assembly protocols (New England Biolabs). Deaminase enzyme constructs, e.g., deaminases linked to Cas9n (nickase (D10A)), in pTwist CMV were purchased from Twist Bioscience, or a nickase version of OpenCRISPR-1 (Ruffolo, et al., bioRxiv 2024.04.22.590591).

For each transfection well, 50 ng of gRNA plasmid and 50 ng of deaminase enzyme plasmid were added to 5 μL of Opti-MEM (Gibco). One non-targeting guide RNA negative control was included for each experiment. 0.2 μL of TransIT®-2020 transfection reagent (Mirus Bio) was diluted into 4 μL of Opti-MEM. Plasmid and TransIT®-2020 mixtures were combined, incubated for 15-30 min at room temperature, and added to HEK293T cells in a dropwise manner. Plates were gently rocked to mix and incubated for 72 hours. Guide RNA sequences are listed in Table 1.

Microscopy, Sample Preparation, and Sequencing 72 hours post-transfection, qualitative assessments of transfection efficiency and cell health were made using fluorescence and brightfield microscopy (Revolve Echo). Quantitative transfection efficiency measurements were made using 96 well plate-based fluorescence measurements (Tecan Spark). Culture media was aspirated from cells prior to washing with PBS (Gibco). 35 μL lysis buffer (100 mM Tris-HCl, pH 7.5; 0.05% SDS; 25 μg/mL Proteinase K) was added to each well. The samples were then incubated at 37° C. for 1 hour before being transferred to 96-well PCR plates and boiled at 98° C. for 15 min. Guide-specific primers were used to PCR amplify the genomic target region of interest from the cell lysates (Q5 DNA Polymerase NEB). Five samples per plate were spot-checked via gel electrophoresis to confirm the presence of the expected amplicon size. The Mag-Bind® RxnPure Plus (Omega Bio-tek) PCR clean-up kit was used to purify the PCR products prior to sequencing submission. Once cluted, DNA yields were quantified via the QuantiFluor® kit (Promega). DNA concentrations were normalized to 2 ng/100 bp of amplicon length and submitted to the UC Berkeley Sequencing facility for Sanger sequencing along with the appropriate forward PCR primer. PCR and Sanger sequencing primers are listed in Table 2.

Sequencing Analysis

To quantify base editing efficiency from Sanger sequencing data (FIGS. 1-4), an open-source program called Beat using default parameters (Xu et al. CRISPR J 2019). Beat is a Python-based program that determines editing efficiency after subtracting the background noise and without the need to normalize to control samples. Beat produces results that are concordant with EditR (another commonly used software for base editing) and agree with base editing quantification based on NGS.

Figure 5:
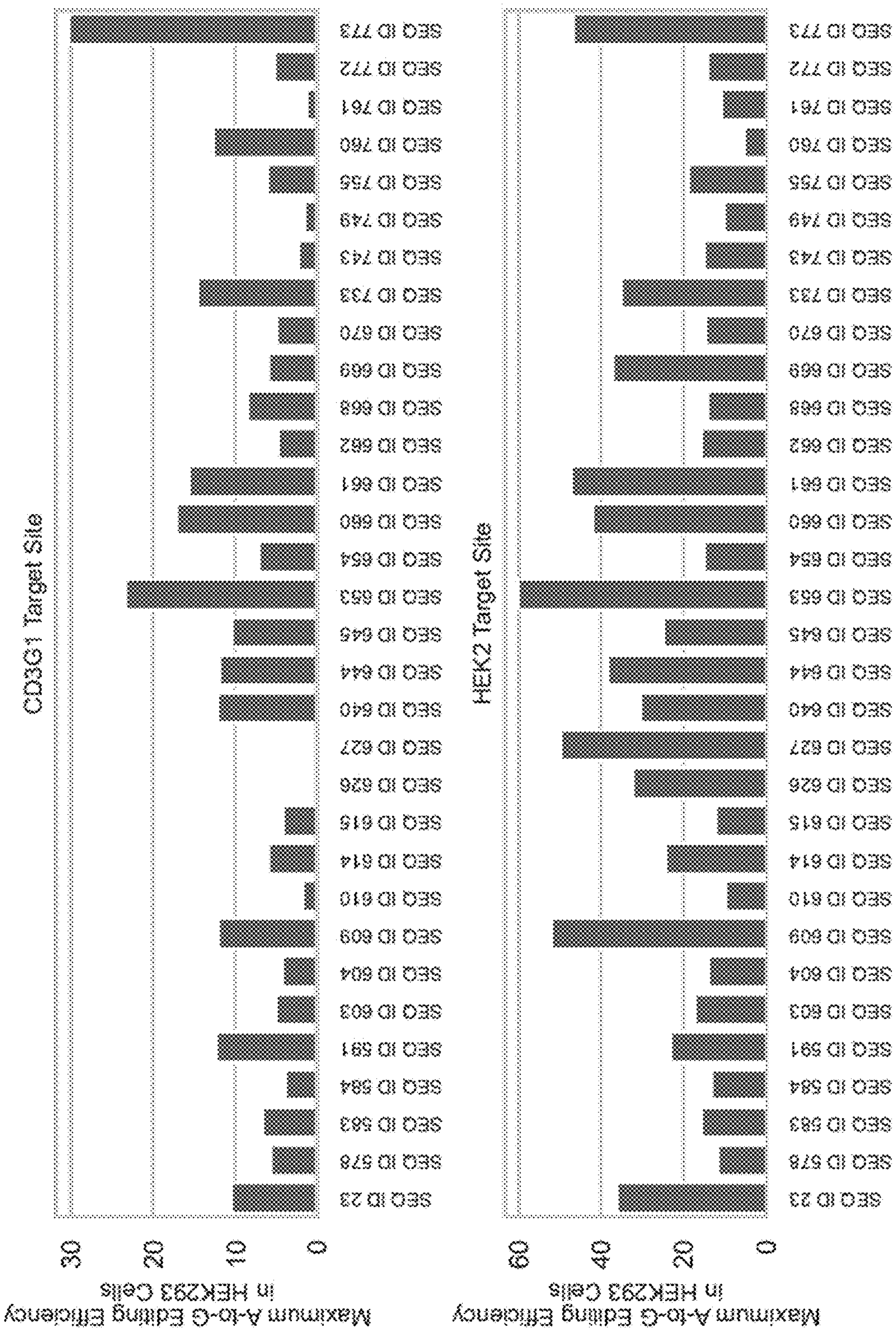
FIG. 5 is graphs of the A to G editing efficiency of deaminase enzymes, as indicated, when tether to spCas9n. The editing efficiency was determined by NGS analysis with CRISPResso.

For short read Illumina NGS analysis, target sites were amplified for base editing quantification using a two-step PCR reaction. First, 5 μL of lysate (corresponding to 1×10^3 cells) was used as a template for PCR (Invitrogen™ Platinum™ SuperFi II PCR Master Mix) with unique primer pairs containing an internal locus-specific region and an outer Illumina-compatible adapter sequence (Table 2). The resulting product was then diluted 1:100 in nuclease-free water and used as a template in a second PCR reaction targeting the outer-adapter sequence, appending unique indices (xGen UDI 10 nt Primer Plates 1-16, IDT) to each amplicon for pooled sequencing. Amplicons were pooled 1:1 and sequenced on a NovaseqX with 2×151 paired end reads (Seqmatic). All amplicons across experiments included reference samples that were not treated with active base editors to control for any variant reads relative to reference genome that are not due to editing. Base editing efficiencies were calculated using CRISPResso analysis (FIG. 5). Reads were trimmed and filtered using fastp. CRISPResso2 was run in base editing mode with default parameters using the processed reads, amplicon sequences, and spacer sequences as input.

TABLE 1

| Guide RNA | Sequence | SEQ ID NO: |
|---|---|---|
| HEK2-gRNA | GAACACAAAGCAUAGACUGC | 777 |
| HEK3-gRNA | GGCCCAGACUGAGCACGUGA | 778 |
| CD3G1 | ACAUACUUCUGUAAUACACU | 779 |
| T39 | GGACAGCUUUUCCUAGACAG | 780 |
| Non-targeting-gRNA control | GAGCAGAUCGUUGAUUGUAG | 781 |

TABLE 2

| Sequencing Primer | Sequence | SEQ ID NO: |
|---|---|---|
| HEK2 forward(A) | CTGGTGGTACTTGAATCAAGCAC | 782 |
| HEK2 reverse(A) | GAAGGAGACTTGTGCACATTCTATAG | 783 |
| HEK3 forward | ATGTGGGCTGCCTAGAAAGG | 784 |
| HEK3 reverse | CCCAGCCAAACTTGTCAACC | 785 |
| HEK2 forward(B) | ACACTCTTTCCCTACACGACGCTCTTCCGATCTCAAGACCTGGCTGAGCTAAC | 786 |
| HEK2 reverse(B) | GACTGGAGTTCAGACGTGTGCTCTTCCGATCTAAATTGTCCAGCCCCATCTG | 787 |
| CD3G1 forward | ACACTCTTTCCCTACACGACGCTCTTCCGATCTTGATCGGCTTCCTAACTGAAG | 788 |
| CD3G1 reverse | GACTGGAGTTCAGACGTGTGCTCTTCCGATCTAAGCTCACCAGAACAGCAAA | 789 |
| T39 forward | ACACTCTTTCCCTACACGACGCTCTTCCGATCTCTGGCCTGGGTCAATCCTTG | 790 |
| T39 reverse | GACTGGAGTTCAGACGTGTGCTCTTCCGATCTTCCCTAGGTGCTGGCTTCCA | 791 |

Sequences

| SEQ ID NO: | Deaminase Sequence |
|---|---|
| 1 | MDDQGWMKLALEEARASRAAGEVPVGAVVVRDGQIVASAGNRTRELCDPTAHAEIVALRQAARALGNYRLPGCTLYVTLEPCAMCAGAMVHARLDRLVYGVPNPKAGAAGSVLDVLHHPRLNHRLEVTGGVLEDECGALLRDFFRAR |

-continued

| Sequences | |
|---|---|
| SEQ ID NO: | Deaminase Sequence |
| 2 | MDPEDVAFMRKALDEARKAREAGEVPVGAVVVKDGEIVARAHNRTIQKSDPTAHA EILALRKAARALGNYRLTGCTLYATLEPCAMCAGAILHARIERLVYGVPNPKAGATG SVLNVLNHPRLNHRVEVTGGVLAEECGALLRGFFRAR |
| 3 | MDPTDLAFMREALAEARAAAEAGEVPVGAVVVCDGRIVARAHNRPIALSDPTAHAE ILALREAARALGNYRLTGCTLYATLEPCAMCAGAILHARIARLVYGVANPKAGACGS VLDVMNHPRLNHRVEVTGGVLAEECGALLSGFFRAR |
| 4 | MDDAGFMRLALEEARAAAAAGEVPVGAVVVRDGEVLARAGNRTVRDNDPTAHAEI VALREAARRLGSYRLAGCTLYVTLEPCPMCAGAMIHARLDRLVYGVANPKAGAAG TVLDVLGHPRLNHRMEVEGGVLAAECGALLRDFFRAR |
| 5 | MDDKGFMQLALEEARAAQAAGEVPVGAVVVRDGEVLARAGNRTRELCDPTAHAEI VALREAARKRGNYRLPGCTLYVTLEPCAMCAGAMLHARLDRLVYGVANPKAGAAG SVLDVLGHPRLNHRLEVTGGVLEAECGALLRDFFRAR |
| 6 | MDDKGWMRLALEEARAAKAAGEVPVGAVVVRDGQVLARAGNQVRELCDPTAHAE IVALREAARKLGNYRLPGCTLYVTLEPCAMCAGAMLHARLDRLVYGVANPKAGAA GSVLDVLGHPRLNHRLEVEGGVLADECGQLLRDFFRAR |
| 7 | MDPEDLRFMRQALAEARRAAEAGEVPVGAVVVLDGEVVAQAFNRTRAQSDPTAHA EILALREAARATGNYRLTGCTLYVTLEPCAMCAGAILHARIARLVYGVANPKAGAAG SVLDVLNHPRLNHRVEVTGGVLAEECGALLRDFFRAR |
| 8 | MNDEGWMQLALEEARKAKAAGEVPVGAVVVRDGEVIAMAGNRTRERCDPTAHAEI VALREAARRLGNYRLPGCTLYVTLEPCAMCAGAMLHARLDRLVYGVPNPKAGAAG SVLDVLGHPRLNHRMEVTGGVLEEECGRLLRDFFRAR |
| 9 | MDDEGWMKLALEEARAARAAGEVPVGAVVVKDGEVIARAGNRTRELCDPTAHAEII ALREAARRLGNYRLPGCTLYVTLEPCAMCAGAMLHARLDRLVYGVANPKAGAAGS VLDVLGHPRLNHRMEVTGGVLEAECGQLLRDFFRAR |
| 10 | MDPTDLAFMREALAEARAAAEAGEVPVGAVVVCDGRIVARAHNRPIALNDPTAHAE ILALREAAKALGNYRLTGCTLYATLEPCPMCAGAILHARIARLVYGVANPKAGACGT VLDVMNHPRLNHRVEVTGGVLAEECGALLSGFFRAR |
| 11 | MDPTDIAFMRQALAEARKAKDAGEVPVGAVVVHDGEIVARAHNRTILESDPTAHAEI LALRAAARRLGNYRLTGCTLYVTLEPCAMCAGAILHARIERLVYGVANPKAGAAGS VLNVLNHPRLNHRVEVTGGVLADECGALLSGFFRAR |
| 12 | MDDEDWMRLALEEARKARAAGEVPVGAVVVRDGQVLARAGNRTRELCDPTAHAEI IALRQAARRRGNYRLAGCTLYVTLEPCAMCAGAMIHARLDRLVYGVPNPKAGAAGS VLDVLHHPRLNHRLEVTGGVLEAECGALLRDFFRAR |
| 13 | MDPDDVEFMRQALDEARRARDAGEVPVGAVVVHDGRVVARAHNRVIAESDPTAHA EIRALREAARALGNYRLTGCTLYATLEPCAMCAGAILHARIARLVYGVPNPKAGATG SVLDVLNHPRLNHRVEVTGGVLEEECGRLLSGFFRAR |
| 14 | MDDQGWMQLALEEARAARAAGEVPVGAVVVRDGEVLARAGNRTRELCDPTAHAEI RALREAARALGNYRLAGCTLYVTLEPCAMCAGAMIHARLDRLVYGVRNPKAGAAG SVLDVLGHPRLNHRLEVTGGVLEAECGALLRDFFRAR |
| 15 | MDPEDIEFMKKALAEARAAKEAGEVPVGAVVVSDGEVVARAHNQTIERSDPTAHAE ILALRAAARALGNYRLTGCTLYVTLEPCAMCAGAILHARIERLVYGVANPKAGAAGS VLDVLNHPRLNHRVEVTGGVLAEECGALLSDFFRAR |
| 16 | MDDEGWMRLALEEARAARAAGEVPVGAVVVRDGQVLAQAGNRTRELCDPTAHAEI VALREAARALGNYRLAGCTLYVTLEPCAMCAGAMLHARLDRLVYGVANPKAGAA GSVLDVLGHPRLNHRAEVEGGVLADECGALLRDFFRAR |
| 17 | MDPEDREFMRKALEEARKAREAGEVPVGAVVVLDGRIVARAHNQTRAESDPTAHAE ILALREAARALGNYRLTGCTLYVTLEPCAMCAGAILHARIERLVYGVPNPKAGATGS VLNVLNHPRLNHRVEVTGGVLAEECGALLSGFFRAR |
| 18 | MDDEGWMQLALEEARASKAAGEVPVGAVVVRDGRVLARAGNRTRERCDPTAHAEI VALREAARRLGNYRLTGCTLYVTLEPCAMCAGAMLHARLDRLVYGVPNPKAGAAG SVLDVLHHPRLNHRLEVEGGVLEAECGQLLRDFFRAR |
| 19 | MDDRGWMKLALEEARAAKAAGEVPVGAVVVRDGEVIARAGNRTRLKCDPTAHAEI VALREAARRLGNYRLPGCTLYVTLEPCAMCAGAMLHARLDRLVYGVPNPKAGAAG SVLDVLGHPRLNHRLEVTGGVLAAECAALLRDFFRAR |

-continued

| Sequences | |
|---|---|
| SEQ ID NO: | Deaminase Sequence |
| 20 | MDDEGWMRLALEEARKAKAAGEVPVGAVVVRNGEVIARAGNRTRELCDPTAHAEI VALREAARRLGNYRLAGCTLYVTLEPCAMCAGAMIHARLDRLVYGVANPKAGAAG SVLDVLGHPRLNHRLEVEGGVLEAECGALLRDFFRAR |
| 21 | MDPMDIAFMQQALDEARKAKEAGEVPVGAVVVHDGQIVARAHNRTIALSDPTAHA EILALREAARALGNYRLQGCTLYATLEPCAMCAGAILHARIARLVYGVPNPKAGACG SVLNVLNHPRLNHRVEVTGGVLAEECGALLRGFFRAR |
| 22 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGVANPKAGAAG SVLDVLGHPRLNHRMEVEGGVLAAECGALLRDFFRAR |
| 23 | MTDEYFMRQALREARRAYDEGEVPVGAVVVRDGRVIARGRNQVERLKDPTAHAEM LALTAAAGHLGSKYLTGCTLYVTVEPCAMCAGALVWARVERVVFGVRNPKAGACG SVFDIPGDRRLNHRPEVVGGVLEAECAALMRDFFRER |
| 24 | MDAALEEARRAAAAGEVPVGAVLVRDGAVLARGGNRTIRDCDPTAHAEIVALRAA ARAAGNYRLPGATLYVTLEPCAMCAGAMIHARLDRLVYGAADPRAGAAGSVFDVL RHPALNHQMAVEGGVRAAECGALLRDFFRARR |
| 25 | MTDADFMALALEEARAAAALGEVPVGAVVVRDGAVIARAGNRTIRDCDPTAHAEIV ALREAARALGNYRLAGCTLYVTLEPCAMCAGAMIHARLDRLVYGAADPKTGAAGS VLDVLNHPKLNHQMQVEAGVLAEECGAMLRDFFQQRR |
| 26 | MRDALAEARKAADAGEVPVGAVVVRGGEILARAHNRTVADHDPTAHAEILALREA ARVLGNHRLTGCTLYVTLEPCAMCAGAIVHARLDRLVYGAADPKAGAAGSVLDVL NHPRLNHRMEVEGGVLAEESGELLRGFFRARR |
| 27 | MDDAGFMREALAEARAAAAAGEVPVGAVVVKDGEIIARAGNRTLRDNDPTAHAEIV ALRAAARALGNHRLTGCTLYVTLEPCAMCAGAISHARIARLVYGADDPKGGAVAHG PRFFAQPTCHHRPEVTGGVGAEEAGALLRDFFRARR |
| 28 | MREALAEARAAAEAGEVPVGAVVVRDGEIIARARNRMVADCDPTAHAEIVALREAA RVLGNHRLTGCTLYATLEPCAMCAGAIAHARIARLVYAADDPKGGAVWHGPRFFEQ PTCHHRPEVTSGVLADEAAALLRDFFRARR |
| 29 | MREALAEARAAAAAGEVPVGAVVVRDGAVLARAGNASIRARDPTAHAEVLALRAA ARALGNHRLTGCTLYVTLEPCAMCAGAIAHARVARLVYGAADPKGGAVAHGPRFFE QPTCHHRPEVTGGVLAEEAGALLRDFFRARR |
| 30 | MREALAEARAAAAAGEVPVGAVVVRDGAVLARAGNRTVRDADPTAHAEIVALREA ARALGNHRLGGCTLYVTLEPCAMCAGAIAQARVARLVYGADDPKGGAVAHGPRLF AQPTCHHRPEVVGGVGAAEAGALLRDFFAARR |
| 31 | MTEALAEARKAAAAGEVPVGAVLVRDGAVLARGGNRTIRDCDPTAHAEIVALRAA ARALGNYRLPGTTLYVTLEPCAMCAGAMIHARVARLVYGAADPKTGAAGSVEDVL RHPALNHRMEVEGGVLAEECGALLREFFRARR |
| 32 | MREALAEARAAAAAGEVPVGAVVVRDGAVLARAGNRTVRDADPTAHAEIVALREA ARALGNHRLTGCTLYVTLEPCAMCAGAISHARVARLVYGADDPKGGAVAHGPRFFA QPTCHHRPEVTGGVLAAEAGELLRGFFRARR |
| 33 | MRDALAEARAAAAAGEVPVGAVVVRDGAIVARARNRMVADCDPTAHAEIVALRAA ARALGNHRVDGCTLYVTLEPCAMCAGAMIHARLARLVYGAADPRAGAAGSVLDVL GHPALNHRMEVTAGVLAEECGALLRDFFAARR |
| 34 | MTEALAEARKAAAAGEVPVGAVLVRDGAVLARGGNRTIRDCDPTAHAEIVALRAA ARALGNYRLPGTTLYVTLEPCAMCAGAMIHARVARLVYGAADPKTGAAGSVFDILR HPALNHRMEVEGGVLAEECGALLRDFFRARR |
| 35 | MREALAEARAAAAAGEVPVGAVVVRDGAVLARAGNRTVRDADPTAHAEIVALRAA ARALGNHRLDGCTLYVTLEPCAMCAGAIAQARVARLVYGAADPKGGAVAHGPRLF EQPTTHHRPEVVGGVLAEEAAALLRGFFAARR |
| 36 | MRAALAEARAAAAAGEVPVGAVVVRDGAVLARAGNASIRARDPTAHAEILALRAA ARALGNHRLTGCTLYVTLEPCAMCAGAIAHARIARLVYGAADPKGGAVAHGPRFFE QPTCHHRPEVTGGVLAEEAGALLRAFFRARR |
| 37 | MRDALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPEVVGGVGAAEAGALLRDFFRARR |

-continued

| Sequences | |
|---|---|
| SEQ ID NO: | Deaminase Sequence |
| 38 | MREALAEARAAAAAGEVPVGAVVVRDGAVLARAGNRTVRDADPTAHAEIVALRAA ARALGNHRLDGCTLYVTLEPCAMCAGAMVQARLARLVYGAADPKAGAVDSVLDV LDHPRLNHRMEVTGGVLAEECGALLREFFAARR |
| 39 | MRDALAEARAAAAAGEVPVGAVVVRDGAILARAGNASIRARDPTAHAEILALRAAA RALGNHRLDGCTLYVTLEPCAMCAGAIAHARIARLVYGAADPKGGAVAHGPRFFEQ PTCHHRPDVTGGVGAAEAAALLRDFFRARR |
| 40 | MDDAGFMRLALEEARAAAAAGEVPVGAVVVRDGEVLARARNAPVAAHDPTAHAEI LALRAAAAALGNYRLDGCTLYVTLEPCAMCSGAMLHARLARVVYGAADPKTGAAG SVLDLFAQPRLNHHTAVEGGVLAAECGALLRDFFRARRG |
| 41 | MDDEFFMREALRLAEEAAAAGEVPVGAVVVRDGEIVGRGRNRVLEDRDPTAHAEIV ALREAARRLGNYRLEGCELYVTLEPCAMCAGAMVHARLARLVYGAADPKAGAAGS VLDVLGHPRLNHRMEVTGGVLAEECGALLREFFRARR |
| 42 | MRDALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPDVTGGVGAAEAAALLRDFFRARR |
| 43 | MREALAEARAAAAAGEVPVGAVVVRDGAVLARAGNRTVRDADPTAHAEVVALRE AARALGNHRLGGCTLYVTLEPCAMCAGAIAQARVARLVYGADDPKGGAVAHGPRL FAQPTCHHRPEVVGGVGAAEAAALLRGFFAARR |
| 44 | MDDAGFMRLALAEARAAAAAGEVPVGAVVVRDGAVLAAAGNRTLRDCDPTAHAE VVALRAAARALGNHRLGGCDLYVTLEPCAMCAGAISFARIRRLYFGADDPKGGAVE HGPRFFAQPTCHHAPEVYGGLAESEAAALLRDFFRARR |
| 45 | MDDAGFMRLALAEARAAAAAGEVPVGAVVVRDGAVLAAAGNRTLRDCDPTAHAE VVALRAAARALGNHRLEGCTLYVTLEPCAMCAGAMLHARLARVVYGAADPKTGA AGSVLDLFANPRLNHHTRVEGGVLAEECGALLQDFFRARRG |
| 46 | MSDEDYMRLALEEARAAAAAGEVPIGAVVVRDGEVLARAGNRTVRDCDPTAHAEI VALREAARKLGNYRLAGCTLYVTVEPCAMCAGALVWARVDRLVYGADDPKAGAV RSALAVVDHPRLNHRMEVVSGVLAGECAALLQEFFAARR |
| 47 | MREALAEARAAAAAGEVPVGAVVVRDGAVLARAGNASIRARDPTAHAEILALRAA ARALGNHRLTGCTLYVTLEPCAMCAGAIAHARVARLVYGAADPKGGAVAHGPRFFE QPTCHHRPEVTGGVLAEEAGALLRDFFRARR |
| 48 | MREALAEARAAAAAGEVPVGAVVVRDGAVLARAGNASIRARDPTAHAEILALRAA ARALGNHRLDGCTLYVTLEPCAMCAGAIAQARVARLVYGAADPKGGAVAHGPRLF AQPTCHHRPEVTGGVGEAEAAALLRDFFAARR |
| 49 | MTDEYFMRQALREARKAYDEDEVPVGAVVVRDGKVIARGRNQVERLKDPTAHAEM IALTSAANYLGSKRLEGCTVYVTLEPCPMCAGALVLARVERLVFGAFDPKAGACGTL YDIPGDRRLNHRIEVVGGVLEEESAALLREFFEKRR |
| 50 | MREALAEARAAAAAGEVPVGAVVVRDGAVLARAGNASIRARDPTAHAEMLALRAA ARALGNHRLDGCTLYVTLEPCAMCAGAIAHARIARLVYGAADPKGGAVAHGPRFFA QPTCHHRPEVTGGVLAEEAGALLRDFFRARR |
| 51 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPEVVGGVGAGEAAALLRDFFAARR |
| 52 | MDDAGFMRLALAEARAAAAAGEVPVGAVVVRDGAVLAAAGNRTLRDCDPTAHAE VVALRAAARALGNHRLEGCDLYVTLEPCAMCAGAISFARIRRLYFGAADPKGGAVE HGPRFFAQPTCHHAPEVYGGLAESEAAALLRGFFAARR |
| 53 | MREALAEARAAAAAGEVPVGAVVVRDGAVLARAGNRTVRDADPTAHAEIVALRAA ARALGNHRLDGCTLYVTLEPCAMCAGAIAQARVARLVYGAADPKGGAVAHGPRLF EQPTTHHRPEVVGGVLAAEAGALLRAFFAARR |
| 54 | MTEALAEARKAAALGEVPVGAVVVRDGAVIARGHNRTVTDADPTAHAEIVALREA ARALGNHRLTGCTLYVTLEPCAMCAGAIVHARVDRLVYGAADPKAGAAGSVLDVIG HPRLNHRPEVEGGVLGEECGALLRDFFRARR |
| 55 | MRSALDLAAAAAAAGEVPVGAVVVRDGAIVGRGENRVLRDSDPTAHAEIVAMREA ARALGNYRLTGCTLYVTLEPCAMCAGAMVHARLDRLVYGAADPKAGAAGSVLDVL GHPRLNHQMEVEGGVLAAESAALLRDFFRARR |

-continued

| Sequences | |
|---|---|
| SEQ ID NO: | Deaminase Sequence |
| 56 | MREALAEARAAAAAGEVPVGAVVVRDGAVLARAGNASIRARDPTAHAEILALRAA ARALGNHRLTGCTLYVTLEPCAMCAGAIAHARIARLVYGAADPKGGAVAHGPRFFE QPTCHHRPEVTGGVLAEEAGALLRDFFRARR |
| 57 | MDDAGFMRLALAEAEAAAAAGEVPVGAVVVRDGEVIARAGNRTVRDCDPTAHAEI VALRAAARALGNHRLTGCTLYVTLEPCAMCAGAISHARVARLVYGADDPKGGAVA HGPRFFAQPTCHHRPEVAGGVLAEEAGALLRGFFRARR |
| 58 | MDDAGFMRLALAEARAAAAAGEVPVGAVVVRDGAVLAAAGNRTLRDCDPTAHAEI VALRAAARALGNYRLDGCDLYVTLEPCAMCAGAMLHARLRRVVFGAADPKTGAA GSVLDLFAERRLNHRTAVAGGVLADECGALLRDFFRARR |
| 59 | MDDAGFMRLALAEARAAAAAGEVPVGAVVVRDGAVLAAAGNRTLRDCDPTAHAE VVALRAAARALGNHRLDGCDLYVTLEPCAMCAGAISHARIRRLYYGADDPKGGAV DNGVRFFASPTCHHAPEVYGGLAEGEAAALLRDFFRER |
| 60 | MREALAEARAAAAAGEVPVGAVVVRDGAVLARAGNRTVRDADPTAHAEIVALRAA ARALGNHRLGGCTLYVTLEPCAMCAGAIAQARVARLVYGADDPKGGAVAHGPRFF AQPTCHHRPEVVGGVGAEEAGALLRGFFAARR |
| 61 | MTEALREARRAAAAGEVPVGAVVVRDGAVLARAGNRTVRDADPTAHAEIVALREA ARALGNHRLTGCTLYVTLEPCAMCAGAISHARIARLVYGAADPKGGAVAHGPRFFE QPTCHHRPEVTGGVGEAEAAALLRDFFRARR |
| 62 | MREALAEARAAAAAGEVPVGAVVVRDGAVLARAGNRTVRDADPTAHAEVVALRA AARALGNHRLGGCTLYVTLEPCAMCAGAIAQARVARLVYGAADPKGGAVAHGPRL FAQPTCHHRPEVVGGVGEAEAAALLRDFFAARR |
| 63 | MREALAEARAAAAAGEVPVGAVVVRDGAVLARAGNASIRARDPTAHAEVLALRAA ARALGNHRLTGCTLYVTLEPCAMCAGAIAHARIARLVYGAADPKGGAVAHGPRFFE QPTCHHRPEVTGGVLAEEAGALLRDFFRARR |
| 64 | MTDEYFMRQALREARRAYEEDEVPVGAVVVRDGRVIARGRNQVERLKDPTAHAEM IALTAAANHLGSKRLEGCTVYVTLEPCPMCAGALVLARVPRLVFGAFDPKAGACGTL YDIVRDPRLNHRVEVVGGVLEEECGELLKRFFRERR |
| 65 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVAHGPRLF AQPTCHHRPEVVGGVGAAEAGALLRDFFAARR |
| 66 | MTEALAEARKAAAEGEVPVGAVVVRDGVVLARAHNRTVADHDPTAHAELLAIREA ARVLGNHRLTGCTLYVTLEPCAMCAGAIVHARLDRLVYGAADPKAGAAGSVLDVL GHPRLNHRPEVEGGVLAAESAALLRDFFRARR |
| 67 | MDDAGFMRLALAEAERAAALGEVPVGAVLVRDGEVLAAAGNRTVADCDPTAHAE MLALREGARRLGNYRLTGCTLYVTLEPCAMCAGAMVHARLDRLVYAAADPKAGA AGSVLDVLNHPALNHRMQVEGGVLAEESAALLRGFFRARR |
| 68 | MREALAEARAAAAAGEVPVGAVVVRDGAVLARAGNRTVRDADPTAHAEIVALREA ARALGNHRVGGATLYVTLEPCAMCAGAISQARVARLVYGADDPKGGAVAHGPRFF EQPTCHHRPEVTGGVLAEESAALLRGFFAARR |
| 69 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPEVVGGVGAAEAGALLRDFFRARR |
| 70 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVAHGPRFF EQPTCHHRPDVTGGVLAEEAGALLRDFFRARR |
| 71 | MTDEYFMRQALREARRAYDEGEVPVGAVVVRDGRVIARGRNQVERLKDPTAHAEM IALTAAADYLGSKRLEGCTLYVTLEPCAMCAGAIVLARIPRLVFGAFDPKAGACGTL YDIVRDRRLNHRAEVVSGVLEEECGALLKEFFARLR |
| 72 | MDDEFFMREALRLAEEAAAAGEVPVGAVVVRDGEIVGRGRNRVLEDRDPTAHAEIV AMREAARRLGNYRLEGCTLYVTLEPCAMCAGAMVHARVARLVYGAADPKAGAAG SVLDVLGHPRLNHRMEVTGGVLAEECGALLREFFRRRR |
| 73 | MREALAEARAAAAAGEVPVGAVVVRDGAVLARAGNRTVRDADPTAHAELVAIRAA AAALGQERLTGCTLYVTLEPCAMCAGAISHARIARLVYGAADPKGGAVAHGPRFFE QPTCHHRPEVTGGVLAEEAGALLRDFFRARR |

-continued

Sequences

| SEQ ID NO: | Deaminase Sequence |
|---|---|
| 74 | MREALAEARAAAAAGEVPVGAVVVRDGAIVARARNRMVADCDPTAHAEIVALREAARALGNHRLDGCTLYVTLEPCAMCAGAMVHARVARLVYGAADPRAGAAGSVLDVLGHPALNHRMEVAGGVLAEECGALLREFFAARR |
| 75 | MRAALAEARAAAAAGEVPVGAVVVRDGAVLARAGNASIRARDPTAHAEILALRAAARALGNHRLDGCTLYVTLEPCAMCAGAIAHARVARLVYGAADPKGGAVAHGPRFFEQPTCHHRPEVTGGVLAEEAGALLRDFFRARR |
| 76 | MRAALDEARAAAAAGEVPVGAVVVRDGAILARAGNRTVRDCDPTAHAEIVALREAARALGNHRLTGCTLYVTLEPCAMCAGAISHARVARLVYGADDPKGGAVRHGPRFFEQPTCHHRPEVVGGVGAEEAAALLRGFFAARR |
| 77 | MDDEAWMRRAIALAHQAEAEGEVPVGAVLVKDGEVIAEGWNRSIGHHDATAHAEIETLRQAGQALQNYRLLDTTLYVTLEPCPMCAGALLHSRVKRVVFGAPDLKAGAAGTVLNLFESQASYHYAEVESGLLEQECREQLQAFFKRRRKEIKALRQAQRDAE |
| 78 | MDDAGFMRLALAEARAAAAAGEVPVGAVVVRDGAVLAAAGNRTLRDCDPTAHAEVVALRAAARALGNHRLEGCDLYVTLEPCAMCAGAIAHARIARLYYGAADPKGGAVEHGARVFDQPQCLHRPEVYGGIGEAEAAALLRGFFAARR |
| 79 | MREALAEARAAAAAGEVPVGAVVVRDGAVLARAGNRTVRDADPTAHAEIVALRAAARALGNHRLGGCTLYVTLEPCAMCAGAIAQARVARLVYGADDPKGGAVAHGPRFFAQPTCHHRPEVAGGLGEAEAGALLRDFFAARR |
| 80 | MREALAEARAAAAAGEVPVGAVVVRDGAVLARAGNRTVRDADPTAHAEIVALRAAARALGNHRLGGCTLYVTLEPCAMCAGAIAQARVARLVYGAADPKGGAVAHGPRLFAQPTCHHRPEVVGGVGEAEAAALLRAFFAARR |
| 81 | MRDALAEARAAAAAGEVPVGAVVVRDGAVLARAGNASIRARDPTAHAEILALRAAARALGNHRLDGCTLYVTLEPCAMCAGAIAHARIARLVYGAADPKGGAVAHGPRFFAQPTCHHRPEVTGGVGEAEAAALLRAFFAARR |
| 82 | MTDEYFMRQALREARRAYEEDEVPVGAVVVRDGRVIARGRNQVERLKDPTAHAEMIALTAAANHLGSKRLEGCTVYVTLEPCPMCAGALVLARVERLVFGAFDPKAGACGTLYDIPGDRRLNHRLEVVGGVLEEESAALLREFFRKRR |
| 83 | MTDEDYMRLALEEARAAAAAGEVPIGAVVVRDGEVLARAGNRTVRDCDPTAHAEIVALREAARVLGNYRLAGCTLYVTVEPCAMCAGAIVHARVARLVYGADDPKGGAVRSCLEVLDHPRLNHRVEVTAGVLAGECAALLQDFFAARR |
| 84 | MREALAEARAAAAAGEVPVGAVVVRDGAVLARAGNRTVRDADPTAHAEVLALRAAARALGSERLTGCTLYVTLEPCAMCAGAISHARVARLVYGAADPKGGAVEHGARVFEQPTCHHRPEVVGGVGAAEAGALLRDFFAARR |
| 85 | MREALAEARAAAAAGEVPVGAVVVRDGAILARAGNASIRARDPTAHAEILALRAAARALGNHRLTGCTLYVTLEPCAMCAGAIAHARIARLVYGAADPKGGAVAHGPRFFEQPTCHHRPEVTGGVLAEEAGALLRAFFRARR |
| 86 | MDDAGFMRLALEEARAAAAAGEVPVGAVVVRDGAVLARAGNRTLRDRDPTAHAEMVALRAAARALGSERLTGCDLYVTLEPCAMCAGAISFARIRRLYFGAADPKGGAVENGVRFFASPTCHHAPEVYGGLAESEAAALLRDFFRARR |
| 87 | MTDEYFMRQALREARRAYDEGEVPVGAVVVRDGRVIARGRNQVERLKDPTAHAEMLALTAAAGHLGSKYLTGCTLYVTVEPCAMCAGALVWARVERVVFGARDPKAGACGSVFDIPGDRRLNHRPEVVGGVLEAECAALMRDFFRERR |
| 88 | MREALAEARAAAAAGEVPVGAVVVRDGAVLARAGNASIRARDPTAHAEMLALRAAARALGNHRLDGCTLYVTLEPCAMCAGAIAHARVARLVYGAADPKGGAVAHGPRFFEQPTCHHRPEVTGGVLAEEAGALLREFFRARR |
| 89 | MREALAEARAAAAAGEVPVGAVVVRDGAILARAGNASIRARDPTAHAEILALRAAARALGNHRLTGCTLYVTLEPCAMCAGAIAHARIARLVYGAADPKGGAVAHGPRFFAQPTCHHRPEVTGGVLAEEAGALLRAFFRARR |
| 90 | MSDEQYMRRALELARQAEQAGEVPVGAVLVKDGEIIAEGWNQSISAHDATAHAEIMALRAAGQALENYRLLDTTLYVTLEPCPMCAGALLHSRVKRVVFGAPDLKAGAAGTVLNLFESQASYHYADVESGLLEDECREQLQAFFKRRRKEIKALRQAQREAEE |
| 91 | MSEEQYMRRALELARQAEQEGEVPVGAVLVKDGEVIAEGWNRSIGSHDATGHAEIMALRAAGEKLENYRLLDTTLYVTLEPCPMCAGALLHSRVKRVVFGAPDLKAGAAGTVLNLFESQASYHYADVESGLLEEECREQLQAFFKRRRKEIKALRQAQKEAE |

-continued

| Sequences | |
|---|---|
| SEQ ID NO: | Deaminase Sequence |
| 92 | MDDAGFMRLALAEARRAAEAGEVPVGAVVVRDGAVLAAAGNRTLRDCDPTAHAE VVALREAARALGNHRLGGCDLYVTLEPCAMCAGAISHARIARLYYGADDPKGGAV AHGARVFDQPTCHHRPEVYGGIGAAEAAALLRDFFRARR |
| 93 | MREALAEARAAAAAGEVPVGAVVVRDGAVLARAGNASIRARDPTAHAEVLALRAA ARALGNHRLTGCTLYVTLEPCAMCAGAIAHARVARLVYGAADPKGGAVAHGPRFFE QPTCHHRPEVTGGVLAAEAGALLRDFFRARR |
| 94 | MREALAEARAAAAAGEVPVGAVVVRDGAVLARAGNASIRARDPTAHAEMLALRAA ARALGNHRLDGCTLYVTLEPCAMCAGAIAHARIARLVYGAADPKGGAVAHGPRFFA QPTCHHRPDVTGGVLAEEAGALLRDFFRARR |
| 95 | MREALAEARAAAAAGEVPVGAVVVRDGAVLARAGNRTVRDADPTAHAEIVALRAA ARALGNHRLGGCTLYVTLEPCAMCAGAIAQARVARLVYGADDPKGGAVAHGPRFF AQPTCHHRPEVVGGVGEAEAGALLRDFFAARR |
| 96 | MTDEYFMRQALREARRAYDEGEVPVGAVVVRDGRVIARGRNQVERLKDPTAHAEM LALTAAAAHLGSKRLEGCTVYVTLEPCAMCAGALVLARVDRLVFGAFDPKAGACGT VYDIPRDRRLNHRVEVVGGVLEEESAALLRAFFEERR |
| 97 | MREALAEARAAAAAGEVPVGAVVVRDGAVLARAGNASIRARDPTAHAEILALRAA ARALGNHRLDGCTLYVTLEPCAMCAGAIAQARVARLVYGAADPKGGAVAHGPRLF AQPTCHHRPEVVGGVGAEEAAALLRGFFAARR |
| 98 | MTDEYFMRQALREARRAYDEGEVPVGAVVVRDGRVIARGRNQVERLKDPTAHAEM IALTAAADHLGSKRLEGCTLYVTLEPCAMCAGAIVLARIPRLVFGAFDPKAGACGTL YDIVRDRRLNHRVEVVSGVLEEESAALLREFFAERR |
| 99 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPDVVGGVGAAEAGALLRDFFRARR |
| 100 | MTDEYFMRQALREARRAYDEDEVPVGAVVVRDGRVIARGRNQVERLKDPTAHAEM IALTSAANHLGSKRLEGCTVYVTLEPCPMCAGALVLARVPRLVFGAFDPKAGACGTL YDIPRDRRLNHRVEVVGGVLEEESAALLREFFARRR |
| 101 | MTEALAEARKAAAAGEVPVGAVLVRDGEILARGGNRTIRDCDPTAHAEIVALREAA RKLGNYRLAGCTLYVTLEPCAMCAGAMIHARLDRLVYGADDPKAGAAGSVLDVLN HPRLNHQMEVTRGVLADECGALLRDFFQARR |
| 102 | MTDEYFMRQALREARRAFDEDEVPVGAVVVRDGRVIARGRNQVERLKDPTAHAEM IAITSAANYLGSKRLEGCTVYVTLEPCPMCAGALVLARVPRLVFGAFDPKAGACGTL YDIPRDRRLNHRLEVVGGVLEEESAALLREFFARRR |
| 103 | MTDEDYMRLALEEARAAAAAGEVPVGAVVVRDGAVLARAGNRTVRDCDPTAHAEI VALRAAARALGNYRLPGCTLYVTVEPCAMCAGAMIHARLDRLVYGADDPKAGAVR STLRVLDHPALNHRMAVTAGVLADECAALLQDFFRARR |
| 104 | MREALAEARAAAAAGEVPIGAVVVRDGAVLARAGNRTVRDCDPTAHAEIVALREA ARALGNHRLTGCTLYVTVEPCAMCAGAISWARVARLVYGAADPKGGAVRHGPRLF EQPTCHHAPEVVDGVCAEEAAALLRDFFRARR |
| 105 | MDDEALMGLALDEARAAAAAGEAPIGAVVARGGEVLAAAGNRTLRDCDPTAHAEI LALREAARKLGNYRLTGCTLYATLEPCAMCAGAISHARIARLVYGADDPKGGAVRH GPRFFEQPTCHHRPEVAGGVGAAEAGALLRDFFRARR |
| 106 | MDDEALMGLALDEARAAAAAGEAPIGAVVARGGEVLAAAGNRTLRDCDPTAHAEV LALREAARRLGNYRLTGCTLYVTLEPCAMCAGAISHARVARLVYGAADPKGGAVA HGPRFFEQPTCHHRPEVTGGVGAAEAGALLRDFFRARR |
| 107 | MSDEQYMRRALELARQAEAEGEVPVGAVLVRDGEVIAEGWNRSIGSHDATGHAEIM ALRAAGQALQNYRLLDTTLYVTLEPCPMCAGALLHSRVKRVVFGAPDLKAGAAGT VLNLFESQASYHYADVESGLLEEECREQLQAFFKRRRKEIKALRQAQREAEEK |
| 108 | MTEALAEARKAAAAGEVPVGAVLVRDGAVLARGGNRTIRDCDPTAHAEIVALRAA ARALGNYRLPGTTLYVTLEPCAMCAGAMIHARVDRLVYGAADPRAGAAGSVLDVIG HPALNHRMAVEGGVLAEECGALLRDFFRARR |
| 109 | MTDEYFMRQALREARRAYDEGEVPVGAVVVRDGRVIARGRNQVERLKDPTAHAEM LALTAAAAHLGSKRLEGCTLYVTLEPCAMCAGAIVLARVPRLVFGAFDPKAGACGT LYDIVRDRRLNHRVEVVSGVLEEESAALLREFFARLR |

-continued

| Sequences | |
|---|---|
| SEQ ID NO: | Deaminase Sequence |
| 110 | MREALAEARAAAAAGEVPVGAVVVRDGAVLARAGNRTVRDADPTAHAEIVALRAA ARALGNHRLDGCTLYVTLEPCAMCAGAIAQARVARLVYGAADPKGGAVAHGPRLF EQPTTHHRPEVVGGVLAEEAGALLRGFFAARR |
| 111 | MREALAEARAAAAAGEVPVGAVVVRDGAVLARAGNASIRARDPTAHAEILALRAA ARALGNHRLDGCTLYVTLEPCAMCAGAIAHARVARLVYGAADPKGGAVAHGPRFF EQPTCHHRPEVTGGVLAAEAGALLRDFFRARR |
| 112 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPEVVGGVGAAEAGALLREFFAARR |
| 113 | MRDALAEARAAAAAGEVPVGAVVVRDGAILARAGNASIRARDPTAHAEILALRAAA RALGNHRLTGCTLYVTLEPCAMCAGAIAHARIARLVYGAADPKGGAVAHGPRFFEQ PTCHHRPEVTGGVLAEEAGALLRDFFRARR |
| 114 | MDDAGFMRLALAEAEAAAAAGEVPVGAVVVRDGEVIARAGNRTVRDCDPTAHAEI VALREAARKLGNYRLPGCTLYVTLEPCAMCAGAMIHARLDRVVYGAADPKTGAAG SVLDLFADRRLNHHTAVVGGVLAEEAGALLRAFFAARR |
| 115 | MREALAEARAAAAAGEVPVGAVVVRDGAVLARAGNASIRARDPTAHAEILALRAA ARALGNHRLTGCTLYVTLEPCAMCAGAIAHARVARLVYGAADPKGGAVAHGPRFFE QPTCHHRPEVTGGVLAEEAGALLRAFFRARR |
| 116 | MREALAEARAAAAAGEVPVGAVVVRDGAVLARAGNASIRARDPTAHAEMLALRAA ARALGNHRLTGCTLYVTLEPCAMCAGAIAHARVARLVYGAADPKGGAVAHGPRFFE QPTCHHRPEVTGGVLAEEAGALLRDFFRARR |
| 117 | MRAALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPEVVGGVGAAEAGALLRDFFRARR |
| 118 | MREALAEARAAAAAGEVPVGAVVVRDGAVLARAGNASIRARDPTAHAEVLALRAA ARALGNHRLTGCTLYVTLEPCAMCAGAIAHARLARLVYGAADPKGGAVEHGPRFFA QPTCHHRPEVTGGVGAAEAGALLRAFFAARR |
| 119 | MSDEQFMRRAIELAKKGEELGEVPVGAVLVKDGEIIAEGWNQSISTHDATAHAEIMA LRAAGEKLQNYRLLDTTLYVTLEPCPMCAGALLHSRVKRVVFGAPDLKAGAAGTVL NLFESQASYHYADVESGLLEEECREQLQAFFKRRRKEIKALKKAKKEAEQK |
| 120 | MREALAEARAAAAAGEVPIGAVVVRDGAVLARAGNRTVRDCDPTAHAEIVALREA ARALGNYRLDGCTLYVTLEPCAMCAGAMLHARLARVVYGAADPKTGAAGSVLDLF AERRLNHQTEVAGGVLAEECGALLRDFFRARRG |
| 121 | MTEALAEARKAAALGEVPVGAVVVRDGAVIARGHNRTVTDTDPTAHAEIVALREAA RALGNHRLTGCTLYVTLEPCAMCAGAIVHARLDRVVYGAADPKAGAAGSVLDVLG HPRLNHRPEVAGGVLAAESAALLRDFFRARR |
| 122 | MTDEYFMRQALREARRAYDEGEVPVGAVVVRDGRVIARGRNQVERLKDPTAHAEM LALTAAAAHLGSKRLEGCTLYVTLEPCAMCAGAIVLARIPRLVFGAFDPKAGACGTL YDIVRDRRLNHRAEVVSGVLEEECGALLKEFFARLR |
| 123 | MREALAEARAAAAAGEVPVGAVVVRDGAVLARAGNRTVRDADPTAHAEIVALRAA ARALGNHRLGGCTLYVTLEPCAMCAGAIAQARVARLVYGADDPKGGAVAHGPRFF AQPTCHHRPEVVGGVGEAEAAALLRGFFAARR |
| 124 | MREALAEARAAAAAGEVPVGAVVVRDGAVLARAGNRTVRDADPTAHAELVAIRAA ARALGSERLTGCTLYVTLEPCAMCAGAISHARVARLVYGAADPKGGAVAHGPRFFE QPTCHHRPEVTGGVLAEEAGALLRDFFRARR |
| 125 | MTDEYFMRQALREARRAYEEDEVPVGAVVVREGRVIARGRNQVERLKDPTAHAEMI ALTSAANYLGSKRLEGCTVYVTLEPCPMCAGALVLARVERLVFGAFDPKAGACGTL YDIPGDRRLNHRIEVVGGVLEEESAALLREFFRRRR |
| 126 | MSEALAEARKAAALGEVPVGAVVVRDGAVIARGHNRTVADADPTAHAEIVALREA ARALGNHRLTGCTLYVTLEPCAMCAGAIVHARLDRLVYGAADPKAGAAGSVLDVL GHPRLNHRPEVEGGVLAAESAALLRDFFRARR |
| 127 | MSDEQYMRRALELARQAEQEGEVPVGAVLVKDGEVIAEGWNRSIGSHDATGHAEIM ALRAAGEKLGNYRLLDTTLYVTLEPCPMCAGALLHSRVKRVVFGAPDLKAGAAGTV LNLFESQASYHYADVESGLLEEECREQLQAFFKRRRKEIKAARKAKREAEEK |

-continued

| Sequences | |
|---|---|
| SEQ ID NO: | Deaminase Sequence |
| 128 | MREALAEARAAAAAGEVPVGAVVVRDGAVLARAGNASIRARDPTAHAEMLALRAA ARALGNHRLTGCTLYVTLEPCAMCAGAIAHARVARLVYGAADPKGGAVAHGPRFFE QPTCHHRPEVTGGVLAEEAGALLRAFFRARR |
| 129 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGAADPKAGAAG SVLDVLGHPRLNHRMEVEGGVLAAECGALLRDFFRARR |
| 130 | MRAALDEARAAAAAGEVPVGAVVVRDGAVLARAGNASIRARDPTAHAEILALRAA ARALGNHRLTGCTLYVTLEPCAMCAGAIAHARVARLVYGAADPKGGAVEHGPRFFA QPTCHHRPEVTGGVLAAEAGALLRDFFRARR |
| 131 | MTEALAEARKAAAAGEVPVGAVVVRDGEILARAHNRTVADHDPTAHAEILALREAA RRLGNHRLTGCELYVTLEPCAMCAGAISHARIARLVYGAADPKGGAVEHGPRFFAQP TCHHRPEVVGGVGASEAAALLRDFFRARR |
| 132 | MRAALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVAHGPRFF EQPTCHHRPEVTGGVLAEEAGALLRAFFRARR |
| 133 | MDDAGFMRLALEEARAAAAAGEVPVGAVVVRDGEVLARAGNRTVRDCDPTAHAE VVALREAARKLGNHRLTGCTLYVTLEPCAMCAGAISHARVARLVYGADDPKGGAV AHGPRFFAQPTCHHRPEVAGGLLAGEAAALLRDFFAARR |
| 134 | MRDALAEARAAAAAGEVPVGAVVVRDGAVLARAGNASIRARDPTAHAEILALRAA ARALGNHRLTGCTLYVTLEPCAMCAGAIAHARIARLVYGAADPKGGAVAHGPRFFE QPTCHHRPEVTGGVLAEEAGALLREFFRARR |
| 135 | MTEALAEARKAAAAGEVPVGAVLVRDGAVLARGGNRTIRDCDPTAHAEIVALRAA ARALGNYRLPGTTLYVTLEPCAMCAGAMIHARVDRLVYGAADPRAGAAGSVEDVIR HPALNHRMEVEGGVLAEECGALLRDFFRARR |
| 136 | MREALAEARAAAAAGEVPVGAVVVRDGAVLARAGNRTVRDADPTAHAEIVALREA ARALGNHRLTGCTLYVTLEPCAMCAGAISHARVARLVYGADDPKGGAVAHGPRFFA QPTCHHRPEVVGGVGAEEAGALLRDFFRARR |
| 137 | MTDEYFMRQALREARRAYDEGEVPVGAVVVRDGRVIARGRNQVERLKDPTAHAEM LALTAAAAHLGSKRLEGCTLYVTLEPCAMCAGAIVLARIPRLVFGAFDPKAGACGTL YDIVRDRRLNHRVEVVSGVLEEESAALLREFFARLRA |
| 138 | MSDEQYMRRALELARQAEEEGEVPVGAVLVKDGEIVAEGWNRSIGSHDATGHAEIM ALRAAGEKLENYRLLDTTLYVTLEPCPMCAGALLHSRVKRVVFGAPDLKAGAAGTV LNLFESQASYHYADVESGLLEEECREQLQAFFKRRRKEIKAQRDAEKAAAE |
| 139 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPEVVGGVGAAEAGALLRAFFAARR |
| 140 | MRDALAEARAAAAAGEVPVGAVVVRDGAILARAGNASIRARDPTAHAEVLALRAA ARALGNHRLDGCTLYVTLEPCAMCAGAIAHARVARLVYGAADPKGGAVEHGPRFF AQPTCHHRPDVTGGVGAAEAAALLRDFFRARR |
| 141 | MRDALAEARAAAAAGEVPVGAVVVRDGAVLARAGNRTVRDCDPTAHAEIVALRAA ARALGNHRLDGCTLYVTLEPCAMCAGAIAQARVARLVYGADDPKGGAVAHGPRLF AQPTCHHRPEVVGGVGAEEAAALLRGFFAARR |
| 142 | MTDEYFMRQALREARRAYDEDEVPVGAVVVRDGKVIARGRNQVERLKDPTAHAEM IALTSAANHLGSKRLEGCTVYVTLEPCAMCAGALVLARVDRLVFGAFDPKAGACGT LYDIPRDRRLNHRVEVVGGVLEEESAALLREFFRRRR |
| 143 | MTDEYFMRQALREARRAYDEGEVPVGAVVVRDGKVIARGRNQVERLKDPTAHAEM IALTAAANHLGAKRLEGCTVYVTLEPCAMCAGALVLARVDRLVFGAFDPKAGACGT LYDIPRDARLNHRVEVVSGVLEEESAALLREFFARLR |
| 144 | MSEALAEARKAAAAGEVPVGAVLVRDGAVLARGGNRTIRDCDPTAHAEIVALRAAA RALGNYRLPGTTLYVTLEPCAMCAGAMIHARVDRLVYGAADPRAGAAGSVFDILRH PALNHRMEVEGGVLADECGALLRDFFRARR |
| 145 | MRAALAEARAAAAAGEVPVGAVVVRDGAILARAGNASIRARDPTAHAEVLALRAA ARALGNHRLTGCTLYVTLEPCAMCAGAIAHARIARLVYGAADPKGGAVAHGPRFFA QPTCHHRPEVTGGLGEAEAAALLRAFFAARR |

-continued

| SEQ ID NO: | Deaminase Sequence |
|---|---|
| 146 | MRAALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVAHGPRFF EQPTCHHRPEVTGGVLAAEAGALLRDFFRARR |
| 147 | MTEALAEARKAAALGEVPVGAVVVRDGAVIARGHNRTVADADPTAHAEIVALREA ARALGNHRLTGCTLYVTLEPCAMCAGAIVHARLDRVVYGAADPKAGAAGSVLDVL GHPRLNHRPEVAGGVLAEECGALLRDFFRARR |
| 148 | MREALAEARAAAAAGEVPVGAVVVRDGAVLARAGNRTVRDADPTAHAEIVALREA ARALGNHRLGGCTLYVTLEPCAMCAGAIAQARVARLVYGAADPKGGAVAHGPRLF EQPTCHHRPEVVGGVLAEEAGALLRGFFAARR |
| 149 | MTDEYFMRQALREARRAYEEGEVPVGAVVVRDGRVIARGRNQVERLKDPTAHAEM IALTAAAAHLGNKRLEGCTLYVTLEPCAMCAGAIVLARIPRLVFGAFDPKAGACGTL YDIVRDRRLNHRAEVVSGVLEEECGALLKEFFARLR |
| 150 | MREALAEARAAAAAGEVPVGAVVVRDGAVLARAGNRTVRDADPTAHAEIVALRAA ARALGNHRLGGCTLYVTLEPCAMCAGAIAQARVARLVYGAADPKGGAVAHGPRLF AQPTCHHRPEVVGGVGEAEAAALLRDFFAARR |
| 151 | MDDEFYMRRALELAALAEEHNEVPVGAVLVLNGEIIGEGWNRSIGHHDATAHAEIM ALRQAGKKLENYRLLDTTLYVTLEPCPMCAGALLHSRVKRVVFGAPDLKAGAAGTV LNLFESQASYHYADVESGLLEQECREQLQAFFKRRRKEIKALKKAKREAE |
| 152 | MREALAEARAAAAAGEVPVGAVVVRDGAILARAGNASIRARDPTAHAEVLALRAA ARALGNHRLTGCTLYVTLEPCAMCAGAIAHARVARLVYGAADPKGGAVEHGPRFFA QPTCHHRPEVTGGVLAAEAGALLRDFFRARR |
| 153 | MTDEYFMRQALREARRAYDEGEVPVGAVVVRDGRVIARGRNQVERLKDPTAHAEM IALTAAANHLGAKRLEGCTVYVTLEPCAMCAGALVLARVDRLVFGAFDPKAGACGT LYDIPRDPRLNHRVEVVSGVLAEESAALLREFFAARR |
| 154 | MTDEYFMRQALREARRAYEEDEVPVGAVVVREGRVIARGRNQVERLKDPTAHAEMI ALTAAANHLGSKRLEGCTVYVTLEPCPMCAGALVLARVRRLVFGAFDPKAGACGTL YDIPRDRRLNHRVEVVGGVLEEESAALLREFFRRRR |
| 155 | MSDEQYMRRALELARQAEQEGEVPVGAVLVKDGEVVAEGWNRSIGSHDATGHAEI MALRAAGQVLQNYRLLDTTLYVTLEPCPMCAGALLHSRVKRVVYGAPDLKAGAAG TVLNLFESQASYHYADVESGLLEEECREQLQAFFKRRRKEIKAARQAKRDAE |
| 156 | MREALAEARAAAAAGEVPVGAVVVRDGAVLARAGNRTVRDADPTAHAEVVALRA AARALGNHRLGGCTLYVTLEPCAMCAGAIAQARVARLVYGADDPKGGAVAHGPRL FAQPTCHHRPEVVGGVGAAEAAALLRDFFAARR |
| 157 | MDDAGFMRLALAEARAAAAAGEVPVGAVVVRDGAVLAAAGNRTLRDCDPTAHAE VVALRAAARALGNYRLDGCTLYVTLEPCAMCAGAMLHARLARVVYGAADPKTGA AGSVLDLFAQPRLNHHTQVEGGVLAAECGALLQDFFRARRG |
| 158 | MSDEQFMRRAIELARKGEELGEVPVGAVLVKDGEIIAEGWNQSISTHDATAHAEIMA LRAAGEKLQNYRLLDTTLYVTLEPCPMCAGALLHSRVKRVVFGAPDLKAGAAGTVL NLFESQASYHYADVESGLLEEECREQLQAFFKRRRKEIKALKKAKREAEEK |
| 159 | MREALAEARAAAAAGEVPVGAVVVRDGVVLARAGNRTVRDADPTAHAEVVALRA AARALGNHRLGGCTLYVTLEPCAMCAGAIAQARVARLVYGAADPKGGAVAHGPRL FEQPTCHHRPEVVGGVLAEEAGALLRDFFAARR |
| 160 | MRDALAEARAAAAAGEVPVGAVVVRDGAVLARAGNASIRARDPTAHAEILALRAA ARALGNHRLDGCTLYVTLEPCAMCAGAIAHARIARLVYGAADPKGGAVEHGPRFFA QPTCHHRPEVVGGVGAAEAGALLRDFFRARR |
| 161 | MSDEDYMRLALEEARAAAAAGEVPVGAVVVRDGAVLARAGNRTVRDCDPTAHAEI VALREAARALGNHRLTGCTLYVTLEPCAMCAGAISHARVARLVYGADDPKGGAVA HGPRFFAQPTCHHRPEVTGGVLAEEAGALLRGFFAARR |
| 162 | MTDEYFMRQALREARRAYDEDEVPVGAVVVRDGRVIARGRNQVERLKDPTAHAEM IALTSAANYLGSKRLEGCTVYVTLEPCAMCAGALVLARVDRLVFGAFDPKAGACGT LYDIPGDRRLNHRVAVTGGVLEEESAALLREFFRERR |
| 163 | MSDEQYMRRALELARQAEQEGEVPVGAVLVKDGEIVAEGWNRSIGSHDATAHAEIE TLRKAGQALENYRLLDTTLYVTLEPCPMCAGALLHSRVKRVVFGAPDLKAGAAGTV LNLFESQASYHYAEVESGLLEEECREQLQAFFKRRRKEIKALRQAEKEAAEK |

-continued

| Sequences | |
|---|---|
| SEQ ID NO: | Deaminase Sequence |
| 164 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVAHGPRFF EQPTCHHRPEVTGGVLAEEAGALLRDFFRARR |
| 165 | MRDALAEARAAAARGEVPVGAVVVRDGAVLARAGNASIAARDPTAHAEILALRAA ARALGNHRLAGCTLYVTLEPCAMCAGAIAHARIARLVYGAADPKGGAVAHGPRFFE QPTCHHRPEVTGGVGAAEAGALLRDFFAARR |
| 166 | MREALAEARAAAAAGEVPVGAVVVRDGAVLARAGNRTVRDADPTAHAELVAIRAA ARALGSERLTGCTLYVTLEPCAMCAGAISHARVARLVYGADDPKGGAVAHGPRFFA QPTCHHRPDVTGGVGEAEAGALLRAFFAARR |
| 167 | MDDAGFMRLALAEARKAAAAGEVPVGAVVVRDGAVLAAAGNRTLRDCDPTAHAE VVALREAARALGNHRLGGCDLYVTLEPCAMCAGAISHARIARLYYGADDPKGGAV AHGARVFDQPTCHHRPEVYGGIGAAEAAALLRGFFAARR |
| 168 | MTDEYFMRQALREARRAYDEGEVPVGAVVVRDGRVIARGRNQVERLKDPTAHAEM LALTAAAAHLGSKRLEGCTLYVTLEPCAMCAGAIVLARLPRLVFGAFDPKAGACGTL YDIVRDRRLNHRVEVVSGVLEEECGALLKEFFARLR |
| 169 | MSDEQYMRRALELARQAEQEGEVPVGAVLVKDGEVIAEGWNRSIGSHDATGHAEIM ALRAAGEKLQNYRLLDTTLYVTLEPCPMCAGALLHSRVKRVVFGAPDLKAGAAGTV LNLFESQASYHYADVESGLLEEECREQLQAFFKRRRKEIKALRQAQKAAE |
| 170 | MRDALAEARAAAAAGEVPVGAVVVRDGAILARAGNASIRARDPTAHAEILALRAAA RALGNHRLTGCTLYVTLEPCAMCAGAIAHARVARLVYGAADPKGGAVAHGPRFFEQ PTCHHRPEVTGGVGAAEAGALLRDFFAARR |
| 171 | MTEALAEARKAAAAGEVPVGAVLVRDGAVLARGGNRTIRDCDPTAHAEIVVLREAA RALGNYRLEGCTLYVTLEPCAMCAGAMIHARLDRLVYGADDPKAGAAGSVLDVLN HPRLNHQMEVTAGVLAEECGALLREFFRARR |
| 172 | MREALAEARAAAAAGEVPVGAVVVRDGAVLARAGNRTVRDADPTAHAELVAIRAA ARALGSERLTGCTLYVTLEPCAMCAGAISHARIARLVYGADDPKGGGVAHGARVFD HPQCHHRPEVVGGVGAAEAAALLRDFFAARR |
| 173 | MREALAEARAAAAAGEVPVGAVVVRDGAVLARAGNRTVRDADPTAHAELVAIRAA AAALGSERLTGCTLYVTLEPCAMCAGAISHARIARLVYGAADPKGGAVAHGPRLFA QPTCHHRPEVVGGVGEAEAAALLRDFFAARR |
| 174 | MREALAEARAAAAAGEVPVGAVVVRDGAVLARAGNASIRARDPTAHAEILALRAA ARALGNHRLTGCTLYVTLEPCAMCAGAIAHARIARLVYGAADPKGGAVAHGPRFFE QPTCHHRPEVTGGVLAEEAGALLRAFFRARR |
| 175 | MRDALAEARAAAARGEVPVGAVVVRDGAILARAGNATVAASDPTAHAEILALRAA ARALGSQRLPGAVLYVTLEPCAMCAGAISHARIARLVYGAADPKGGAVAHGPRFFE QPTCHHRPEVTGGVLAEEAGALLRDFFRARR |
| 176 | MRDALAEARAAAAAGEVPVGAVVVRDGAILARAGNASIRARDPTAHAEILALRAAA RALGNHRLDGCTLYVTLEPCAMCAGAIAHARIARLVYGAADPKGGAVAHGPRLFAQ PTCHHRPEVTGGVGAAEAAALLRDFFRARR |
| 177 | MTDEYFMRQALREARRAYDEGEVPVGAVVVRDGRVIARGRNQVERLKDPTAHAEM IALTAAAAHLGNKRLEGCTLYVTLEPCAMCAGALVLARVPRLVFGAFDPKAGACGT LYDIVRDRRLNHRVEVVSGVLEEESAALLKEFFARLR |
| 178 | MDDAGFMRLALEEARAAAAAGEVPVGAVVVRDGEVLARAGNRTVRDCDPTAHAE VVALREAARKLGNHRVTGATLYVTLEPCAMCAGAISLARVARLVYAADDPKGGGV AHGARVFDQPTCHHRPEVVSGVLAEESAALLRGFFAARR |
| 179 | MTDEYFMRQALREARRAYDEDEVPVGAVVVREGKVIARGRNQVERLKDPTAHAEM IALTSAANHLGSKRLEGCTVYVTLEPCAMCAGALVLARVERLVFGAFDPKAGACGT LYNIPADRRLNHRVEVVGGVLEEESAALLREFFRKRR |
| 180 | MDDEAWMRRAIALAHQAEAEGEVPVGAVLVKDGEVVAEGWNRSIGSHDATAHAEI ETLRKAGQALENYRLLDTTLYVTLEPCPMCAGALLHSRVKRVVFGAPDLKAGAAGT VLNLFESQASYHYADVESGLLEEECREQLQAFFKRRRKEIKALRQAQREAE |
| 181 | MDDAGFMRLALAEARAAAAAGEVPVGAVVVRDGAVLAAAGNRTLRDCDPTAHAE VVALRAAARALGNHRLEGCTLYVTLEPCAMCAGAALQARLARLVYGAAEPKTGAA GSVLDVFANPALNHHTAVTGGVLAAEAAALLRDFFAARR |

-continued

| SEQ ID NO: | Deaminase Sequence |
|---|---|
| 182 | MTEALAEARKAAAAGEVPVGAVLVRDGAVLARGGNRTIRDCDPTAHAEIVALRAA ARAAGNYRLPGATLYVTLEPCAMCAGAMIHARVDRLVYGAADPRAGAAGSVFDVV RHPALNHRMAVEGGVLAEECGALLRDFFRARR |
| 183 | MTEKDKFFMQRAIELAKLAEENGEVPVGAVLVKDGEIIAEGWNQSIGSHDATAHAEI MALRQAGKVLENYRLLDTTLYVTLEPCPMCAGALLHSRVKRIVFGAPDLKAGAAGT VLNLFESQASYHYADVESGLLEEECREQLQAFFKRRRKEIKALKKAKKEAE |
| 184 | MTDEYFMRQALREARRAYDEDEVPVGAVVVRDGKVIARGRNQVERLKDPTAHAEM IALTSAANYLGSKRLEGCTVYVTLEPCPMCAGALVLARVERLVFGAFDPKAGACGTL YDIPGDRRLNHRLEVVGGVLEEESAALLREFFRRRR |
| 185 | MREALAEARAAAAAGEVPVGAVVVRDGAVLARAGNASIRARDPTAHAEMLALRAA ARALGNHRLDGCTLYVTLEPCAMCAGAIAHARVARLVYGAADPKGGAVAHGPRFF EQPTCHHRPEVTGGVLAAEAGALLRDFFRARR |
| 186 | MTDEYFMRQALREARRAYDEGEVPVGAVVVRDGRVIARGRNQVERLKDPTAHAEM IALTAAAAHLGNKRLEGCTLYVTLEPCAMCAGAIVLARIPRLVFGAFDPKAGACGTL YDIVRDRRLNHRAEVVSGVLEEECGALLKEFFARLR |
| 187 | MSDEQYMRRALELARQAEQAGEVPVGAVLVKDGEIIAEGWNQSISSHDATAHAEIM ALRAAGQALENYRLLDTTLYVTLEPCPMCAGALLHSRVKRVVFGAPDLKAGAAGTV LNLFESQASYHYAEVESGLLEEECREQLQAFFKRRRKEIKALKQAKREAEQK |
| 188 | MDDAGFMRLALAEARAAAAAGEVPVGAVVVRDGAVLAAAGNRTLRDCDPTAHAE VVALRAAARALGNYRLDGCTLYVTLEPCAMCAGAMLHARLARVVYGAADPKTGA AGSVLDLFAEPRLNHHTRVEGGVLAAECGALLRDFFRARRG |
| 189 | MDDAGFMRLALAEARAAAAAGEVPVGAVVVRDGAVLAAAGNRTLRDRDPTAHAE MVAIRAAAAALGQERLTDCDLYVTLEPCAMCAGAISFARIRRLYFGAADPKGGAVE HGPRFFAQPTCHHAPEVYGGIGEGEAAALLRDFFRARR |
| 190 | MREALAEARAAAAAGEVPVGAVVVRDGAVLARAGNRTVRDADPTAHAEVVALRA AARALGNHRLDGCTLYVTLEPCAMCAGAIAQARVARLVYGAADPKGGAVAHGPRL FEQPTTHHRPEVVGGVLAEEAAALLRGFFAARR |
| 191 | MREALAEARAAAAAGEVPVGAVVVRDGAVLARAGNRTVRDADPTAHAEIVALRAA ARALGNHRLGGCTLYVTLEPCAMCAGAIAQARVARLVYGAADPKGGAVAHGARVF DQPQTHHRPEVTGGVLAEEAGALLRAFFAARR |
| 192 | MDDAGFMRLALAEARRAAEAGEVPVGAVVVRGGEVLAAAGNRTLRDCDPTAHAEI VALREAARRVGNYRLADCDLYVTLEPCAMCAGAIVHARVRRLVYGADDPKAGAVR SALRVLDAPALNHRVEVTAGVLAEECGALLRDFFRARR |
| 193 | MTEALAEARKAAALGEVPVGAVVVRDGAVIARGHNRTVTDADPTAHAEIVALREA ARALGNHRLTGCTLYVTLEPCAMCAGAMVHARLDRLVYGAADPKAGAAGSVLDVL GHPRLNHQMEVTAGVLADESAALLRDFFRARR |
| 194 | MREALAEARAAAAAGEVPVGAVVVRDGAVLARAGNASIRARDPTAHAEMLALRAA ARALGNHRLDGCTLYVTLEPCAMCAGAIAHARIARLVYGAADPKGGAVAHGPRFFE QPTCHHRPEVVGGVGAAEAGALLRDFFAARR |
| 195 | MTEALAEARKAAALGEVPVGAVVVRDGAVIARGHNRTVTDTDPTAHAEIVALREAA RALGNHRLTGCTLYVTLEPCAMCAGAIVHARLDRVVYGAADPKAGAAGSVLDVLG HPRLNHRPEVEGGVLGEECGALLRDFFRARR |
| 196 | MREALAEARAAAAAGEVPVGAVVVRDGAVLARAGNRTVRDADPTAHAEVVALRE AARALGNHRLGGCTLYVTLEPCAMCAGAISHARVARLVYGADDPKGGAVRHGARV FDQPTCHHRPEVVGGVLAEESAALLRGFFAARR |
| 197 | MREALAEARAAAAAGEVPVGAVVVRDGAVLARAGNASIRARDPTAHAEILALRAA ARALGNHRLDGCTLYVTLEPCAMCAGAIAHARVARLVYGAADPKGGAVEHGPRFF AQPTCHHRPEVVGGVGAAEAGALLRAFFAARR |
| 198 | MDDAGFMRLALAEARAAAAAGEVPVGAVVVRDGAVLAAAGNRTLRDCDPTAHAE VVALRAAARALGNHRLGGCDLYVTLEPCAMCAGAISHARIARLYYGADDPKGGAV AHGARVFAHPQCHHRPEVYGGIGAAEAAALLRDFFAARR |
| 199 | MTDEYFMRQALREARRAYDEDEVPVGAVVVRDGKVIARGRNQVERLKDPTAHAEM IALTSAANHLGSKRLEGCTVYVTLEPCPMCAGALVLARVERLVFGAFDPKAGACGTL YDIPGDRRLNHRVEVVGGVLEEESAALLREFFRRRR |

-continued

Sequences

| SEQ ID NO: | Deaminase Sequence |
|---|---|
| 200 | MDDEFYMRRALELAALAEEHNEVPVGAVLVLNGEIIGEGWNRSIGHHDATAHAEIMALRQAGKKLENYRLLDTTLYVTLEPCPMCAGALLHSRVKRVVFGAPDLKAGAAGTVLNLFESQASYHYADVESGLLEQECREQLQAFFKRRRKEKKALKQAQKEAE |
| 201 | MRDALAEARAAAAAGEVPVGAVVVRDGAILARAGNASIRARDPTAHAEVLALRAAARALGNHRLDGCTLYVTLEPCAMCAGAIAHARIARLVYGAADPKGGAVEHGPRFFAQPTCHHRPEVVGGVGAAEAAALLRDFFRARR |
| 202 | MRAALDEARAAAAAGEVPVGAVVVRDGAILARAGNRTVRDCDPTAHAEIVALREAARALGNHRLTGCTLYVTLEPCAMCAGAISHARVARLVYGADDPKGGAVAHGPRFFAQPTCHHRPEVVGGVGAGEAAALLRDFFAARR |
| 203 | MREALAEARAAAAAGEVPVGAVVVRDGAILARAGNASIRARDPTAHAEVLALRAAARALGNHRLTGCTLYVTLEPCAMCAGAIAHARIARLVYGAADPKGGAVAHGPRFFEQPTCHHRPEVTGGVLAEEAGALLRAFFRARR |
| 204 | MRDALAEARAAAARGEVPVGAVVVRDGAVLARAGNATVAASDPTAHAEILALRAAARAAGNHRLPGAVLYVTLEPCAMCAGAISHARIARLVYGAADPKGGAVAHGPRFFEQPTCHHRPEVTGGVLAEEAGALLRDFFRARR |
| 205 | MREALAEARAAAAAGEVPVGAVVVRDGAILARAGNRTVRDADPTAHAEIVALREAARALGNHRLGGCTLYVTLEPCAMCAGAISQARVARLVYGADDPKGGAVAHGPRFFAQPTCHHRPEVAGGLGEAEAAALLRDFFAARR |
| 206 | MTEALAEARKAAAAGEVPVGAVLVRDGAVLARGGNRTIRDCDPTAHAEIVALRAAARALGNYRLPGTTLYVTLEPCAMCAGAMIHARVARLVYGAADPKTGAAGSVEDVLRHPALNHRMEVEGGVLAEECGALLRDFFRARR |
| 207 | MTEKDKFFMQRAIELAKKGEENGEVPVGAVLVKDGEIIAEGWNQSIGSHDATAHAEIMTLREAGKVLQNYRLLDTTLYVTLEPCPMCAGALLHSRVKRVVFGAPDLKAGAAGTVLNLFESQASYHYADVESGLLEEECREQLQAFFKRRRKEKKALKQAKREAEQK |
| 208 | MTDEDYMRLALEEARAAAAAGEVPIGAVVVRDGEVLARAGNRTVRDCDPTAHAEIVALREAARALGNYRLTGCTLYVTIEPCAMCAGAMIHARVDRLVYGAADPKAGAVRSTLRVLDHPALNHRVEVTAGVLADECAALLQDFFRSRR |
| 209 | MRDALAEARAAAAAGEVPVGAVVVRDGAVLARAGNRTVRDADPTAHAELVAIRAAARALGSERLTGCTLYVTLEPCAMCAGAISHARIARLVYGAADPKGGAVAHGPRFFAQPTCHHRPDVTGGVGEAEAGALLRDFFAARR |
| 210 | MREALAEARAAAAAGEVPIGAVVVRDGAVLARAGNRTVRDCDPTAHAEVVALREAARALGNHRLTGCTLYVTVEPCAMCAGAISHARVARLVYGADDPKGGAVRHGPRFFEQPTCHHRPEVVGGVGAEEAAALLRDFFRARR |
| 211 | MREALAEARAAAAAGEVPVGAVVVRDGAVLARAGNASIRARDPTAHAEVLALRAAARALGNHRLDGCTLYVTLEPCAMCAGAIAHARVARLVYGAADPKGGAVAHGPRFFEQPTCHHRPEVTGGVLAEEAGALLRAFFAARR |
| 212 | MTDEYFMRQALREARRAYDEGEVPVGAVVVRDGRVIARGRNQVERLKDPTAHAEMLALTAAAAHLGSKRLEGCTLYVTLEPCAMCAGAIVLARVPRLVFGAFDPKAGACGTLYDIPRDRRLNHRAEVVGGVLEEESAALLREFFAARR |
| 213 | MREALAEARAAAAAGEVPVGAVVVRDGAVLARAGNRTVRDADPTAHAEIVALREAARALGNHRLGGCTLYVTLEPCAMCAGAIAQARVARLVYGADDPKGGAVAHGPRFFAQPTCHHRPEVVGGVGAAEAGALLRGFFAARR |
| 214 | MDDEAWMRRAIALAHKAEQEGEVPVGAVLVKDGEVIAEGWNRSIGHHDATAHAEIETLRKAGQVLENYRLLDTTLYVTLEPCPMCAGALLHSRVKRIVFGAPDLKAGAAGTVLNLFESQASYHYADVESGLLEEECREQLQAFFKRRRKEIKALRQAQKAAE |
| 215 | MREALAEARAAAAAGEVPVGAVVVRDGAVLARAGNRTVRDADPTAHAEIVALREAARALGNHRLGGCTLYVTLEPCAMCAGAIAQARVARLVYGAADPKGGAVAHGPRLFAQPTCHHRPEVVGGVGEAEAAALLRGFFAARR |
| 216 | MRDALAEARAAAAAGEVPVGAVVVRDGAILARAGNASIRARDPTAHAEILALRAAARALGNHRLTGCTLYVTLEPCAMCAGAISHARIARLVYGAADPKGGAVAHGPRFFEQPTCHHRPEVTGGVLAEEAGALLRAFFRARR |
| 217 | MSDEQYMRRAIELARQAEQEGEVPVGAVLVKDGEIIAEGWNRSIGSHDATAHAEIETLRKAGQVLENYRLLDTTLYVTLEPCPMCAGALLHSRVKRIVYGAPDLKAGAAGTVLNLFESQASYHYADVESGLLEEECREQLQAFFKRRRKEIKAARKAKREAEQ |

-continued

Sequences

| SEQ ID NO: | Deaminase Sequence |
|---|---|
| 218 | MDDAGFMRLALAEARAAAAAGEVPVGAVVVRDGEVLAAAGNRTLRDCDPTAHAE VVALRAAARALGNHRLDGCDLYVTLEPCAMCAGAISHARIRRLYYGADDPKGGAV DNGVRFFASPTCHHAPEVYSGLAESEAAALLRDFFRERR |
| 219 | MREALAEARAAAAAGEVPVGAVVVRDGAVLARAGNRTVRDADPTAHAEVVALRA AARALGNHRLDGCTLYVTLEPCAMCAGAIAQARVARLVYGAADPKGGAVAHGPRL FEQPTCHHRPEVVGGVGEAEAAALLRGFFAARR |
| 220 | MTDEYFMRQALREARRAYDEDEVPVGAVVVREGKVIARGRNQVERLKDPTAHAEM IALTSAANYLGSKRLEGCTVYVTLEPCPMCAGALVLARVERLVFGAFDPKAGACGTL YDIPGDRRLNHRVEVVGGVLEEESAALLREFFRRRR |
| 221 | MREALAEARAAAAAGEVPVGAVVVRDGAILARAGNASIRARDPTAHAEILALRAAA RALGNHRLTGCTLYVTLEPCAMCAGAIAHARIARLVYGAADPKGGAVAHGPRFFEQ PTCHHRPEVTGGLGEAEAAALLRDFFRARR |
| 222 | MTDEYFMRQALREARRAYEEDEVPVGAVVVREGRVIARGRNQVERLKDPTAHAEMI ALTAAANHLGSKRLEGCTVYVTLEPCPMCAGALVLARVERLVFGAFDPKAGACGTL YDIPGDRRLNHRVEVVGGVLEEEAAALLREFFRRRR |
| 223 | MDDAGFMRLALAEARAAAAAGEVPVGAVVVRDGAVLAAAGNRTLRDCDPTAHAE VVALRAAARALGNYRLDGCTLYVTLEPCAMCSGAMLHARLARVVYGAADPKTGA AGSVLDLFAEPRLNHHTRVEGGVLAGECGALLADFFRGRRG |
| 224 | MDDAGFMRLALAEARAAAAAGEVPVGAVVVRDGAVLAAAGNRTLRDCDPTAHAE VVALRAAARALGNHRLDGCDLYVTLEPCAMCAGAIAHARIRRLYYGAADPKGGAV EHGARVFDQPTCHHRPEVYGGIGEAEAAALLRDFFRDR |
| 225 | MSDEQYMRRALELARQAEQEGEVPVGAVLVKDGEIIAEGWNRSIGSHDATGHAEIM ALRAAGEKLQNYRLLDTTLYVTLEPCPMCAGALLHSRVKRVVFGAPDLKAGAAGTV LNLFESQASYHYADVESGLLEEECREQLQAFFKRRRKEIKALRQAQKAAE |
| 226 | MREALAEARAAAAAGEVPVGAVVVRDGAVLARAGNASIRARDPTAHAEVLALRAA ARALGNHRLDGCTLYVTLEPCAMCAGAIAHARVARLVYGAADPKGGAVEHGPRFF AQPTCHHRPDVTGGVGAAEAAALLRDFFRARR |
| 227 | MREALAEARAAAAAGEVPVGAVVVRDGAILARAGNRTVRDADPTAHAEIVALRAA ARALGNHRLDGCTLYVTLEPCAMCAGAAVLARVARLVFGADDPKGGAVRTGVRLF DAPTCHHRPEVTGGVLAEEAGALLREFFAARR |
| 228 | MREALAEARAAAAAGEVPVGAVVVRDGAVLARAGNRTVRDADPTAHAELVAIRAA ARALGSERLTGCTLYVTLEPCAMCAGAISHARIARLVYGAADPKGGAVAHGPRFFAQ PTCHHRPEVTGGVGEAEAAALLRGFFAARR |
| 229 | MTDEDYMRLALEEARAAAAAGEVPVGAVVVRDGEVIARARNAPVSACDPTAHAEIL ALREAARRLGNYRLDGCTLYVTLEPCAMCSGAMLHARLARVVYGAADPKTGAAGS VLDLFAEPRLNHHTAVEGGVLAAECGALLRDFFRARRG |
| 230 | MSDEQYMRRALELARQAEAEGEVPVGAVLVKDGEVVAEGWNRSIGSHDATGHAEI MALRAAGQALENYRLLDTTLYVTLEPCPMCAGALLHSRVKRVVFGAPDLKAGAAG TVLNLFESQASYHYAEVESGLLEEECREQLQAFFKRRRKEIKAARKAAKAAAE |
| 231 | MREALAEARAAAAAGEVPVGAVVVRDGAVLARAGNASIRAHDPTAHAEVLALRAA ARALGNHRLTGCTLYVTLEPCAMCAGAIAHARVARLVYGAADPKGGAVAHGPRFFE QPTCHHRPEVTGGVLAEEAGALLREFFRARR |
| 232 | MREALAEARAAAAAGEVPVGAVVVRDGAVLARAGNRTVRDADPTAHAEVVALRA AARALGNHRLDGCTLYVTLEPCAMCAGAIAQARVARLVYGAADPKGGAVAHGPRL FEQPTCHHRPEVVGGVGEAEAAALLRAFFAARR |
| 233 | MTEALAEARKAAALGEVPVGAVVVRDGAVIARGHNRTIADSDPTAHAEIVALREAA RVLGNYRLTGCTLYVTVEPCAMCAGAMVHARLDRLVYGAADPKAGAAGSVLDVL GHPRLNHQMEVTGGVLAEECAALLRDFFRARR |
| 234 | MDDEFYMRRALELAALAEEHNEVPVGAVLVLNGEIIGEGWNRSIGHHDATAHAEIM ALRQAGKVLQNYRLLDTTLYVTLEPCPMCAGALVHSRVKRVVYGTPDLKTGAAGS VMNLLSYEGVNHHVEVTSGVLAEECREQLQAFFRRRRAEKKALKKAQREAE |
| 235 | MDDEAWMRRAIALAHQAEAEGEVPVGAVLVKDGEVIAEGWNRSIGHHDATAHAEI ETLRQAGQVLQNYRLLDTTLYVTLEPCPMCAGALLHSRVKRVVFGAPDLKAGAAGT VLNLFESQASYHYADVESGLLEQECREQLQAFFKRRRKEIKAQRDAQRAAQE |

-continued

Sequences

| SEQ ID NO: | Deaminase Sequence |
|---|---|
| 236 | MREALAEARAAAAAGEVPVGAVVVRDGAVLARAGNASIRARDPTAHAEILALRAA ARALGNHRLTGCTLYVTLEPCAMCAGAISHARIARLVYGAADPKGGAVAHGPRFFE QPTCHHRPDVTGGVLAAEAGALLRDFFRARR |
| 237 | MDDAGFMRLALEEARAAAAAGEVPVGAVVVRDGAVLARAGNRTLRDRDPTAHAE VVALRAAARALGSERLTGCDLYVTLEPCAMCAGAISFARIRRLYFGAADPKGGAVEN GVRFFASPTCHHAPEVYGGLAESEAAALLRDFFRARR |
| 238 | MDDAGFMRLALAEARAAAAAGEVPVGAVVVRDGAVLAAAGNRTLRDCDPTAHAE VVALRAAARALGNHRLGGCDLYVTLEPCAMCAGAISHARIARLYYGADDPKGGAV AHGARVFDQPTCHHRPEVYGGIGAAEAAALLRDFFRARR |
| 239 | MREALAEARAAAAAGEVPVGAVVVRDGAVLARAGNASIRARDPTAHAEILALRAA ARALGNHRLDGCTLYVTLEPCAMCAGAIAHARVARLVYGAADPKGGAVEHGPRFF AQPTCHHRPEVTGGVLAAEAGALLRDFFRARR |
| 240 | MREALAEARAAAAAGEVPVGAVVVRDGAVLARAGNASIRARDPTAHAEILALRAA ARALGNHRLDGCTLYVTLEPCAMCAGAIAHARIARLVYGAADPKGGAVAHGPRFFA QPTCHHRPDVTGGVLAAEAGALLRDFFRARR |
| 241 | MREALAEARAAAAAGEVPVGAVVVRDGAVLARAGNASIRARDPTAHAEVLALRAA ARALGNHRLTGCTLYVTLEPCAMCAGAIAHARVARLVYGAADPKGGAVAHGPRFFE QPTCHHRPEVTGGVLAEEAGALLRGFFRARR |
| 242 | DDDDRRWMREALAEARAAADAGEVPVGAVVVRDGVLLARAGNASIRDRDPTAHA EMLALRAAARALGNHRLTGCTLYVTLEPCAMCAGAIAHARIARLVYGASDPKAGAV EHGPRLFAQPTIHHRPEVTAGVLAEECGALLRDFFRARR |
| 243 | DPTDLAFMREALAEARAAAEAGEVPVGAVVVCDGRIVARAHNRPIALSDPTAHAEIL ALREAARALGNYRLTGCTLYATLEPCAMCAGAILHARIARLVYGAADPKAGACGSV LDVMNHPRLNHRVEVTGGVLAEECGALLSGFFRARR |
| 244 | DDDHAWMGAALAEARAAAEAGEVPVGAVLVADGRVLARAGNRTIRDRDPTAHAE MLALRAAARALGNHRLTGTTLYVTLEPCAMCAGAISLARVARLVYAASDPKGGAVE HGPRFFAQPTCHHRPEVVGGVGEGEAGALLRDFFRARR |
| 245 | MTAEDDRFMRLALAEARAAAEAGEVPVGAVVVAGGRVVARAHNRPIALHDPTAHA EVLALRAAARELGNYRLTGCTLYATLEPCAMCAGAVLHARIARLVYGAADPKAGAC GSVLAVMNHPRLNHRVEVTGGVLAEECGALLREFFRARR |
| 246 | MDSDLAFMREALAEARAAAEAGEVPVGAVVVHEGKIVARAANRMRTDRDPTAHAE LLALRAAARALETTRLTGCTLYVTLEPCAMCAGAISHARVARLVYGASDPKGGAVE HGPRFFAQPTCHHRPEVVGGVGEAEAGALLRGFFRARR |
| 247 | DPDDARWMREALAEARAAAEAGEVPVGAVVVRDGRLLARAGNRTIRDRDPTAHAE MLALRAAARALGNHRLEGCTLYVTLEPCAMCAGAMVQARVARLVYGAADPKAGA AGSVLDVLGDPRLNHRVEVTGGVLAEECGALLREFFRARR |
| 248 | MDSDLEFMREALAEARAAAEAGEVPVGAVVVRDGVILARAGNRPIRDHDPTAHAEI LALREAARAVGNYRLTGCTLYVTLEPCAMCAGAILHARVERLVYGAADPKAGAAGS VLDVFGNARLNHHTRVEGGVLAEECGALLSGFFRARRG |
| 249 | DPDAEFMRLALAEAEAAARAGEVPVGAVVVADGRVIARAGNRTIRDRDPTAHAEML ALRAAARALGSHRLTGCDLYVTLEPCAMCAGAISHARIRRLYYGAADAKGGAVEHG PRFFAQPTCHHRPEVYGGIGETAAAALLRDFFRARR |
| 250 | DPDAAFMRAALAEARAAAEAGEVPVGAVVVAGGRIVARAHNRPIELNDPTAHAEIL ALRQAAAALGNYRLTGCTLYATLEPCAMCAGAILHARIERLVYGAADPKAGAVGSV LDVFANPRLNHRTQVTAGVLADECGALLREFFRARR |
| 251 | DESSDEEFMRAALEEARAAAAEGEVPVGAVVVAGGRIVARAHNRPIALNDPTAHAEI LALRQAAAALGNYRLTGCTLYATLEPCAMCAGAILHARIARVVYGAADPKAGACGS VLAVMNHPQLNHRAEVTGGVLAEECGALLSEFFRARR |
| 252 | DDDHRFMRAALAEARAAAEAGEVPVGAVVVHGGEIIARAHNRPIALHDPTAHAEILA LRAAARRLGNYRLTGCTLYATLEPCAMCAGAILHARIARLVYGAADPKAGACGSVL AVMNHPRLNHRVEVTAGVLADECGALLSEFFRARR |
| 253 | MNDEDYMRAALEQARQAAAAGEVPVGAVVVCGGEIVARAHNRPISASDPTAHAEIL ALREAARKLGNYRLTGCTLYATLEPCAMCSGAILHARIARLVYGAADPKAGAVGSV LDVINHPRLNHRVEVTSGVLADECGALLKEFFRARR |

-continued

Sequences

| SEQ ID NO: | Deaminase Sequence |
|---|---|
| 254 | MNDEDYMRAALEQARQAAAAGEVPVGAVVVCDGKIVARAHNRPISANDPTAHAEI LALREAARQLGNYRLTGCTLYATLEPCAMCSGAILHARIARLVYGAADPKAGACGS VLNVINHPQLNHQTEVTGGVLADECGALLKDFFRARR |
| 255 | MRAALEEARRAAAAGEVPVGAVVVRDGAIVARAHNRPIALHDPTAHAEILALREAA RALGNYRLTGCTLYATLEPCAMCAGAILHARIDRLVYGAADPKAGACGSVLSVMNH PRLNHRVEVTGGVLAEECGALLTGFFRARR |
| 256 | MSEEDRFMRAALAEARAAAEAGEVPVGAVVVCGGRIVARAHNRPIALNDPTAHAEI LALREAARELGNYRLTGCTLYATLEPCAMCAGAILHARIARLVYGARDPKAGAVESL YRLLDDTRLNHRVEAVGGVLAGECGALLSGFFRARR |
| 257 | MDEEFMRLALAEARAAAEAGEVPVGAVVVAGGRVVARAHNRPVALHDPTAHAEV LALRAAARELGNYRLTGCTLYATLEPCAMCAGAILHARLDRVVYGAADPKAGAAGS VLDVFANPRLNHRTAVTGGVLAEECGALLREFFRARR |
| 258 | MSEEDRFMRAALAEARAAAEAGEVPVGAVVVAGGRIVARAHNRPIALNDPTAHAEI LALRAAARALGNYRLTGCTLYATLEPCAMCAGAILHARIARLVYGARDPKAGAVES LYRLLDDRRLNHRVEAVGGVLAAECGALLSGFFRARRG |
| 259 | MREALAEARAAAAAGEVPVGAVVVRDGAVLARAGNRTLRDRDPTAHAEMLAIRAA ARALGSERLTGCDLYVTLEPCAMCAGAISHARIARLYYGAADPKGGAVEHGPRFFAQ PTCHHRPEVYGGIGEGEAAALLRGFFRARR |
| 260 | MRAALEEARRAAAAGEVPVGAVVVRDGAIVARAHNRPIALHDPTAHAEILALREAA RALGNYRLTGCTLYATLEPCAMCSGAILHARLDRVVYGAADPKTGAAGSVLDVFAN PRLNHHAAVTGGVLAEECGALLSGFFRARR |
| 261 | MREALAEARAAAAAGEVPVGAVVVRDGAIVARAHNRPIALHDPTAHAEVLALREA ARALGNYRLTGCTLYATLEPCAMCAGAILHARLDRVVYGAADPKAGAAGSVLDVF ANPRLNHRTAVTGGVLADECGALLSGFFRARR |
| 262 | MRAALEEARRAAAAGEVPVGAVVVRDGAIVARAHNRPIALHDPTAHAEILALREAA RALGNYRLTGCTLYATLEPCAMCAGAILHARLDRVVYGAADPKAGAAGSVLQVFD HPRLNHRTAVTGGVLAEECGALLRDFFRARR |
| 263 | MDDDALMREALAEARAAAAAGEVPVGAVVARGGEIVARAANAPRALCDPTAHAEI LALRAAARALGNYRLTGCTLYATLEPCAMCAGAILHARIARLVYAAPDPKAGACGS VLAVLNHPQLNHRVEVTAGLLADECGALLTDFFRARRG |
| 264 | MRAALEEARRAAAAGEVPVGAVVVRDGAIVARAHNRPIALHDPTAHAEILALREAA RALGNYRLTGCTLYATLEPCAMCAGAILHARIDRLVYGAADPKAGACGSVLSVMNH PQLNHRVEVTGGVLAEECGALLSGFFRARR |
| 265 | MNDEDFMRAALAQAREAAAAGEVPVGAVVVCDGEIVARAHNRPIALNDPTAHAEIL ALREAARRLGNYRLTGCTLYATLEPCAMCAGAILHARIARLVYGAADPKAGAVGSV LDVLNHPRLNHRVEVTRGVLAEECGALLSEFFRARRR |
| 266 | MDEEFMRRALELARQAEAAGEVPVGAVLVKDGEIVAEGWNQSIGRHDATAHAEIQV LRKAGQVLENYRLLDTTLYVTLEPCPMCAGALLHSRVKRIVYGAPDLKAGAAGTVL NLFEHQAAYHYADVEHGLLEEECREQLQAFFKRRRKEKKALKQAQREAEEK |
| 267 | MSEEDRFMRAALAEARAAAEAGEVPVGAVVVAGGRIVARAHNRPIALNDPTAHAEI LALREAARALGNYRLTGCTLYATLEPCAMCAGAILHARIARLVYGAADPKAGAVES LYRLLDDTRLNHRVEATGGVLAGECGALLSEFFRARRR |
| 268 | MSEEDRFMRAALAEARAAAEAGEVPVGAVVVAGGRIIARAHNRPIALNDPTAHAEIL ALRAAARALGNYRLTGCTLYATLEPCAMCAGAILHARIARLVYGARDAKAGAVESV LRLFDHPALNHRVEAVGGVLADECGALLSEFFRARRA |
| 269 | MREALAEARAAAAAGEVPVGAVVVRDGAIVARAHNRPIALHDPTAHAEILALREAA RALGNYRLTGCTLYATLEPCAMCAGAILHARLDRVVYGAADPKAGAAGSVLDVFA NPRLNHRTAVTGGVLADECGALLRDFFRARR |
| 270 | MNDEDYMRAALEQARQAAAAGEVPVGAVVVCGGEIVARAHNRPISASDPTAHAEIL ALREAARKLGNYRLTGCTLYATLEPCAMCSGAILHARIARLVYGAADPKAGAVGSV LDVINHPRLNHRVEVTGGVLAGECGALLSGFFRARR |
| 271 | MREALAEARAAAAAGEVPVGAVVVRDGAIVARAHNRPIALHDPTAHAEVLALRAA ARELGNYRLTGCTLYATLEPCAMCAGAILHARLDRVVFGARDPKAGAAGSVLDVFA NPRLNHRTAVTGGVLAEECGALLSGFFRARR |

-continued

| Sequences | |
|---|---|
| SEQ ID NO: | Deaminase Sequence |
| 272 | MNDEDYMRAALEQARQAAAAGEVPVGAVVVCDGKIVARAHNRPISANDPTAHAEI LALREAARQLGNYRLTGCTLYATLEPCAMCSGAILHARIARLVYGASDPKAGACGSV LNVINHPQLNHRVEVTGGVLADECGALLKDFFRARR |
| 273 | MSEEDRFMRAALAEARAAAAEGEVPVGAVVVAGGRIVARAHNRPVALNDPTAHAEI LALRAAARALGNYRLTGCTLYATVEPCAMCAGAILHARIARLVYGAADPKAGAVRS VLRVLDHPALNHRVEVTAGVLAEECAALLQEFFRARR |
| 274 | MNDEDYMRAALEQARQAAAAGEVPVGAVVVCGGEIVARAHNRPISANDPTAHAEIL ALREAARKLGNYRLTGCTLYATLEPCAMCSGAILHARIARLVYGAADPKAGACGSV LNVINHPQLNHRVEVTGGILADECGALLKDFFRARR |
| 275 | MRAALEEARRAAAAGEVPVGAVVVRDGAIVARAHNRPIALHDPTAHAEILALREAA RRLGNYRLTGCTLYATLEPCAMCAGAILHARIDRLVYGAADPKAGACGSVLSVMNH PRLNHRVEVTSGVLAEECGALLTDFFRARR |
| 276 | MRAALEEARRAAAAGEVPVGAVVVRDGEIVARAHNRPIALHDPTAHAEILALREAA RRLGNYRLTGCTLYATLEPCAMCAGAILHARLDRVVYGAADPKAGACGSVLSVFDQ PRLNHRTTVTGGVLAEECGALLSGFFRARRG |
| 277 | MREALAEARAAAAAGEVPVGAVVVRDGAVLARAGNASIRARDPTAHAEVLALRAA ARALGNHRLTGCTLYVTLEPCAMCAGAIAHARVARLVYGAADPKGGAVAHGPRFFE QPTCHHRPEVVGGVGAAEAGALLRDFFAARR |
| 278 | MTDEYFMRQALREARRAYDEGEVPVGAVVVRDGRVIARGRNQVERLKDPTAHAEM IALTAAANYLGSKRLEGCTVYVTLEPCPMCAGALVLARVERLVFGAFDPKAGACGT LYDIVRDRRLNHRLEVVGGVLEEESAALLREFFEKRR |
| 279 | MSDEQYMRRALELARQAEQEGEVPVGAVLVKDGEVIAEGWNRSIGSHDATGHAEIM ALRAAGEKLQNYRLLDTTLYVTLEPCPMCAGALLHSRVKRVVFGAPDLKAGAAGTV LNLFESQASYHYADVESGLLEEECREQLQAFFKRRRKEIKAARQAKRDAE |
| 280 | MREALAEARAAAAAGEVPVGAVVVRDGAVLARAGNRTVRDADPTAHAEIVALRAA ARALGNHRLGGCTLYVTLEPCAMCAGAIAQARVARLVYGADDPKGGAVAHGPRLF AQPTCHHRPEVVGGVGAAEAAALLRDFFAARR |
| 281 | MDDEALMGLALDEARAAAAAGEVPIGAVVARGGEVLARAGNRTLRDCDPTAHAEI VALREAARALGNYRLTGCTLYVTLEPCAMCAGAAIQARLDRVVYGAADPKAGAAG SVLDVLGHPRLNHRPAVEGGVLAAESAALLREFFAARR |
| 282 | MREALAEARAAAAAGEVPVGAVVVRDGAVLARAGNASIRARDPTAHAEILALRAA ARALGNHRLTGCTLYVTLEPCAMCAGAIAHARLARLVYGAADPKGGAVAHGPRLF AQPTCHHRPEVTGGVGAAEAAALLRDFFAARR |
| 283 | MSDEQFMRRAIELAKKGEELGEVPVGAVLVKDGEIIAEGWNQSISTHDATAHAEIMA IRAAGEKLENYRLLDTTLYVTLEPCPMCAGALLHSRVKRVVFGAPDLKAGAAGTVL NLFESQASYHYADVESGLLEEECREQLQAFFKRRRKEIKAAKQAKREAEEK |
| 284 | MDDEFYMRRALELAALAEEHNEVPVGAVLVLNGEIIGEGWNRSIGHHDATAHAEIM ALRQAGKKLENYRLLDTTLYVTLEPCPMCAGALLHSRVKRVVFGAPDLKAGAAGTV LNLFESQASYHYADVESGLLEQECREQLQAFFKRRRKEIKALKKAQKEAE |
| 285 | MDDAGFMRLALAEARKAAAAGEVPVGAVVVRDGAVLAAAGNRTLRDCDPTAHAE VVALRAAARALGNHRLGGCDLYVTLEPCAMCAGAISHARIARLYYGADDPKGGAV AHGARVFDQPTCHHRPEVYGGIGAGEAAALLRDFFAARR |
| 286 | DLDDARFMREALAEARAAAEAGEVPVGAVVVADGRIVARAHNRPVALNDPTAHAEI LALREAARALGNYRLTGCTLYATLEPCAMCAGAILHARIARLVYGARDAKAGAVES LYRLLDDARLNHRVEVAAGVLADECGALLTEFFRARR |
| 287 | DESFMREALAEARAAAEAGEVPVGAVVVHGGQIVARAHNRPIELSDPTAHAEILALR AAARALGNYRLTGCTLYATLEPCAMCAGAILHARIDRVVYGASDPKAGAAGSVLSV FDHPALNHRVDVTAGVLAEECGALLREFFRARRR |
| 288 | DPDAAFMRAALAEARAAAEAGEVPVGAVVVADGAIVARAHNRPIALNDPTAHAEIL ALREAARALGNYRLTGATLYATLEPCAMCAGAILHARIARLVYGARDPKAGAVESL YRLLDDARLNHRVAVTGGVLAAECGALLTAFFRARR |
| 289 | DERFMREALAEARAAAAAGEVPVGAVVVRDGEIVARAANRTVRDNDPTAHAEILAL REAARALGSYRLTGCTLYATLEPCAMCAGAILHARIARLVYAAADPKAGACGSVLS VMNHPQLNHRVEVESGLLAEECGALLTEFFRARRG |

-continued

| SEQ ID NO: | Deaminase Sequence |
|---|---|
| 290 | MTADEQYMRRALELARQAEAEGEVPVGAVLVKDGEIVAEGWNRSIGHHDATAHAEI QVLRKAGQVLQNYRLLDTTLYVTLEPCPMCAGALLHSRVKRIVYGAPDLKAGAAGT VLNLFEHQAAYHYADVEHGLLEDECREQLQAFFKRRRKEKKALKQALKESN |
| 291 | RIRSDEDFMRQALAEARAAAAAGEVPVGAVVVAGGRIVARAHNRPIDLVDPTAHAEI LALREAARALGNYRLTGCTLYATLEPCAMCAGAILHARIARLVYGAADPKAGAVES VLRLLDHPALNHRVEAVSGVLAGECGALLREFFRARR |
| 292 | DLDEALMREALAEARRAAEAGEVPVGAVVARGGRIVARAHNQPVALHDPTAHAEIL ALRQAAREAGNYRLEGCTLYATLEPCAMCAGALLHARVARLVYGARDPKAGAVGS LYDLLRDPRLNHRVEVTAGVLAEECGALLSGFFRARR |
| 293 | MREALAEARAAAAAGEVPVGAVVVDPAGEIVARAGNAPRALCDPTAHAEILALRAA AAAAGNYRLPGHVLYVTLEPCAMCAGAISHARIARLVYGAADPKGGAVAHGPRFFA QPTCHHRPEVTGGVLAEECGALLRDFFRARR |
| 294 | RLDEQFMRRALELAAHAEAEGEVPVGAVLVLDGQVIGEGWNRSIGQHDATAHAEIM ALRQAGQVVQNYRLLDTTLYVTLEPCPMCAGALLHSRVKRIVYGAPDLKAGAAGTV LNLFEHQAAYHYADVEHGLLEEECREQLQAFFKRRRKEKKALKQAQRAAE |
| 295 | DPDDVAFMREALAEAERAAAAGEVPVGAVVVHDGVIVGRGHNRPIASRDPTAHAEI VALREAAAALGNYRLTGCSLYVTIEPCAMCAGAILHARIARLVYGAADPKAGACGS VLDVFAEPRLNHHAEVTGGVLADECAALLRSFFAARR |
| 296 | DPDERFMRAALAQARAAAEAGEVPVGAVVVRDGRIVARAHNQPIALNDPTAHAEIL ALREAARELGNYRLTGCTLYATLEPCAMCAGAILHARIARLVYGARDAKAGAVESK LRLFENGSFNHRVEVTGGVLAGECGALLSEFFRARR |
| 297 | MDEEFMREALAEARAAAEAGEVPVGAVVVAGGRIVGRGRNRPVELADPTAHAEILA LREAARALGNYRLEGCTLYATLEPCAMCAGAILHARIARLVYGAADPKAGAAGSVL DVFALPRLNHRTAVTGGVLAEECGALLSGFFRARRG |
| 298 | RSSDAALMREALAEARAAAEAGEVPVGAVVVAGGRIVARAHNRPVALSDPTAHAE VLALREAARELGNYRLEGCTLYATLEPCAMCSGALLHARVARLVYGAADPKAGAV GSVLDLFANPRLNHRVEVTGGVLAEECGALLSGFFRARRG |
| 299 | DDDERWMREALAEARAAAAAGEVPVGAVVVRDGVLLARAGNASIRERDPTAHAE MLALRAAARALGNHRLGGCTLYVTLEPCAMCAGAIAHARIARLVYGAADPKAGAV DHGPRLFAQPTVHHRPEVVAGVGAEESAALLRDFFRARR |
| 300 | DPDSDEAFMRAALAEARAAAEAGEVPVGAVVVADGAIVARAHNRPIALHDPTAHAE ILALRAAARRLGNYRLTGCTLYATLEPCAMCAGAILHARIARLVYGAADPKAGACGS VLAVMNHPQLNHRVEVTGGILAEECGALLRDFFRARR |
| 301 | MREALAEARAAAEAGEVPVGAVVVAGGRIVARAHNRPVALHDPTAHAEILALRQA AAELGNYRLEGCTLYATLEPCAMCAGAMLHARLARVVYGAADPKAGAAGSVLDLF ANPRLNHRTEVVGGVLAEECGALLSGFFRSRR |
| 302 | DERFMREALAEARAAAAAGEVPVGAVVVRDGVVLARAGNRTLRDRDPTAHAEML ALRQAARALGSHRLTGCDLYVTLEPCAMCAGAISHARIARLYYGAADAKGGAVEHG PRFFAQPTCHHRPEVYGGIGETEAAALLRGFFRERR |
| 303 | MDSDLEFMRLALAEARAAAEAGEVPVGAVVVAGGRVVARAHNRPVALHDPTAHAE ILALRAAARELGNYRLTGCTLYATLEPCAMCAGAILHARIARLVYGAADPKAGACGS VLDVIHHPRLNHRVEVTGGVLAEECGALLSGFFRARR |
| 304 | MREALAEARAAAEAGEVPVGAVVVAGGRIVARAHNRPVALHDPTAHAEILALREAA RALGNYRLEGCTLYATLEPCAMCAGALLHARVARLVYGARDPKAGAVGSVLDLLD HPRLNHRVEVVGGVLAEECGALLSGFFRARRG |
| 305 | DDRRWMREALAEARAAAEAGEVPVGAVVVRDGRLLARAGNASIRDRDPTAHAELL ALRAAARALGNHRLTGCTLYVTLEPCAMCAGAIAHARIARLVYGAADPKGGAVAH GPRLFEQPTLHHRPEVTGGVLAAEAGELLRAFFRARR |
| 306 | MNDEDFMRAALAQARLAAEAGEVPVGAVVVCDGEIVARAHNRPISASDPTAHAEIL ALREAARRLGNYRLTGCTLYATLEPCAMCAGAILHARIARLVYGAADPKAGAVGSV LDVLNHPRLNHRVEVTGGVLAEECGALLRDFFRARR |
| 307 | DESSDLRFMREALAEARAAAEAGEVPVGAVVVCGGRIVARAHNRPIALSDPTAHAEI LALREAARELGNYRLTGCTLYATLEPCAMCAGAILHARIARLVYGAADPKAGACGS VLDVINHPRLNHRVEVTGGVLAGECGALLSGFFRARRG |

-continued

Sequences

| SEQ ID NO: | Deaminase Sequence |
|---|---|
| 308 | DDLFFMREALAEARRAAAEGEVPVGAVVVCGGRIIARAHNRPIALNDPTAHAEILAL RAAARALGNYRLTDCTLYATLEPCAMCAGAILHARIRRLVYGAADPKAGAVRSVLR LLDAPALNHRVAVTAGVLAEECGALLSEFFRARR |
| 309 | DPPSADEAFMREALAEARAAAEAGEVPVGAVVVAGGRIVARAHNRPIALSDPTAHA EILALRAAARALGNYRLTGTTLYATVEPCAMCAGAIVQARVARLVYGAADPKAGAV ESLFRILDHPALNHRVEVTAGVLAEECAALLREFFRARR |
| 310 | DETEAFMRAALAEARAAAEAGEVPVGAVVVADGRIVARAHNRPVALHDPTAHAEIL ALREAARRLGNYRLTGCTLYATLEPCAMCAGAVLHARLARLVYGARDAKAGAVGS VLDLLAHPRLNHRTAVTAGVLADECGALLSAFFRARRG |
| 311 | DDDERWMREALAEARAAAAAGEVPVGAVVVRDGVLLARAGNASIRDRDPTAHAE MLALRAAARALGNHRLTGCTLYVTLEPCAMCAGAIAHARIARLVYGASDPKAGAVD HGPRLFEQPTIHHRPEVTAGVLADECGALLRDFFRARR |
| 312 | DPTTDEALMREALAEARAAAEAGEVPVGAVVARDGEIVARAANAPRALCDPTAHAE ILALRAAARALGNYRLTGCTLYATLEPCAMCAGAALHARFARIVYGAADPKAGAAG SVLDVLDQPRLNHRTRVTGGVLADECGALLTEFFRARR |
| 313 | MNKDEFYMKRALELAQKAEEEGEVPVGAVLVLDDEIIGEGWNRPIGSHDATAHAEIQ ALRDAGQKLENYRLLDTTLYVTLEPCPMCAGALLHSRVKRVVYGAPDLKAGAAGT VLNLFEHEAAYHYADVEHGLLEDECREQLQAFFKRRRKEIKAKKEAEKKALE |
| 314 | MNSDEFYMQRALELAQKAEQEDEVPVGAVLVLDGEIIGEGWNRSIGHHDATAHAEM MALKQGGKQIQNYRLLDATLYVTLEPCPMCAGALLHSRVKRIVYGAPDLKAGAAGT VLNLFEHQAAYHYADVEQGLMEEECREQLQAFFKRRRKEKKALKQAKREAEE |
| 315 | DERFMREALAEARAAAAAGEVPVGAVVVRDGVVLARAGNRTLRDRDPTAHAEML ALRQAARALGSWRLTGCTLYVTLEPCAMCAGAMVQARVDRLVYGAADPKAGAAG SVLDVLGHPRLNHRPEVAAGVLAEECGALLREFFRERR |
| 316 | MRAALEEARRAAAEGEVPVGAVVVRDGAIVARAHNRPIALNDPTAHAEILALREAA RALGNYRLTGCTLYATLEPCAMCAGAILHARIARLVYGAADPKAGACGSVLSVINHP RLNHRVEVTGGVLAEECGALLTGFFRARR |
| 317 | DPDAAFMREALAEARAAAAAGEVPVGAVVVRAGRIVARAHNRPVELHDPTAHAEIL ALRAAARELGNYRLTGCTLYATLEPCAMCAGAILHARIERLVYGARDAKAGAAGSV LDVFANPRLNHRVAVEGGVLADECAALLREFFRARR |
| 318 | MDDEALMRVALEEARAAAAAGEVPVGAVVARGGEIVARAANAPIAASDPTAHAEIL ALRAAARALGNYRLTGCTLYATLEPCAMCAGAILHARIARLVYAAPDPKAGACGSV LAVLDHPALNHRVEVTGGVLAEECGALLREFFRARR |
| 319 | MSDEQYMRRALELARQAEQEGEVPVGAVLVKDGEIIAEGWNRSIGHHDATAHAEM QVLRKAGQVLENYRLLDTTLYVTLEPCPMCAGALLHSRVKRIVYGAPDLKAGAAGT VLNLFEHQAAYHYADVEHGLLEEECREQLQAFFKRRRKEIKARKQAEKEAEAR |
| 320 | DPLEQDERWMREALAEARAAAEAGEVPVGAVLVRDGVLLARAGNRTIRDRDPTAH AEMLALRAAARALGNHRLTGCTLYVTLEPCAMCAGAIAHARIARLVYGASDPKGGA VAHGPRLFEQPTLHHRPEVTGGVLAEEAGELLRAFFRARR |
| 321 | MREALAEARAAAEAGEVPVGAVVVAGGRIVARAHNQPIALNDPTAHAEVLALRQA ARELGNYRLTGCTLYATLEPCAMCAGAILHARLDRVVYGAADPKAGAAGSVLDVFA NPRLNHHAQVTGGVLAEECGALLSGFFRARR |
| 322 | DDLSFMREALAEAEAAAEAGEVPVGAVLVRDGEIVARGRNRVIEDRDPTAHAEIVAL REAGRALGNYRLEGCTLYVTLEPCAMCAGALVHARLDRLVYGAADPKAGAAGSVL DVLNHPRLNHRMEVTGGVLADECGAMLRAFFRARR |
| 323 | DRLRADEQFMRAALAEARAAAAAGEVPVGAVVVRDGEIVARAHNRPIALHDPTAH AEILALRAAARALGNYRLTGCTLYATLEPCAMCAGAILHARLDRVVYGAADPKAGA CGSVLSVMNHPRLNHRVEVTGGVLADECGALLTEFFRARR |
| 324 | MREALAEARAAAAAGEVPVGAVVVRGGEIVARAHNRPVALSDPTAHAEVLALREA ARRLGNYRLEGCTLYATLEPCAMCSGAVLHARLARLVYGAPDPKAGAAGSVLDVL DHPRLNHRTAVTGGVLAEECGALLSGFFRARRG |
| 325 | DDRRWMREALAEARAAGAAGEVPVGAVVVRDGELLARAGNASIRDRDPTAHAEML ALRAAARALGNHRLTGCTLYVTLEPCAMCAGAIAHARIARLVYGASDPKGGAVAHG PRLFEQPTLHHRPEVTAGVLADECGALLRDFFRARR |

-continued

| Sequences | |
|---|---|
| SEQ ID NO: | Deaminase Sequence |
| 326 | MREALAEARRAAEAGEVPVGAVVVRDGEIVARAHNRPIALHDPTAHAEILALREAA RRLGNYRLTGCTLYATLEPCAMCAGAILHARLDRVVYGAPDPKAGACGSVLSVFDQ PRLNHRTRVEGGVLAEECGALLSGFFRARR |
| 327 | DDRDRRWMRAALAEARAAAEAGEVPVGAVVVRDGELLARAGNASIRDRDPTAHAE MLALRAAARALGNHRLTGCTLYVTLEPCAMCAGAIAHARIARLVYGAADPKGGAV AHGPRLFEQPTLHHRPEVTAGVLAEEAGELLRAFFRARR |
| 328 | MREALAEARAAAAAGEVPVGAVVVRGGEIVARAHNRPIALNDPTAHAEILALREAA RVLGNYRLTGCTLYATLEPCAMCAGAILHARIDRLVYGAADPKAGACGSVLSVMNH PQLNHRVEVTSGVLAEECGALLTDFFRARR |
| 329 | MREALAEARAAAEAGEVPVGAVVVRDGEIVARAHNRPIALNDPTAHAEILALREAA RRLGNYRLTGCTLYATLEPCAMCAGAILHARLARLVYGAADPKAGACGSVLSVINH PRLNHRVEVTSGVLADECGALLSDFFRARRRAA |
| 330 | DDRFMRAALAEARAAAEAGEVPVGAVVVVDGRIVARAHNRPVELSDPTAHAEVLA LREAARALGNYRLEGATLYATLEPCAMCSGAILHARVERVVYGAADSRAGAAGSVL DVFATRRLNHQTTVTGGVLAEECGALLSGFFRARR |
| 331 | DDDQRFMREALAEARAAAAAGEVPIGAVVVCDGAIVARAGNRTIRDNDPTAHAEIL ALRQAARALGNYRLTGCTLYVTLEPCAMCAGAIVQARIARLVYGAADPKAGAVDSV LDVLNHPRLNHRVEVTRGVLAEECGALLRDFFRARR |
| 332 | MSDDERFMRLALEQARLAAEAGEVPVGAVVVCDGRVVARAHNRPIALNDPTAHAEI LALREAARELGNYRLTGCTLYATLEPCAMCSGAVLHARLARVVYGAADPKTGAAGS VLDLFAEPRLNHHAEVTGGVLAGECGALLSGFFRARRG |
| 333 | DPTDLAFMREALAEAEAAAAAGEVPVGAVVVHEGRIVGRGRNRMIAASDPTAHAEI VALREAARALGNYRLTGCTLYVTLEPCAMCAGAILHARIARLVYGAADPKAGACGS VLDVLNHPRLNHRTEVTAGVLAEECGAMLSGFFRARRAQQRAARVAAS |
| 334 | DPPDAVEMRAALEEARAAAEAGEVPVGAVLVHDGQILARAGNRTIRDRDPTAHAEIL ALRQAARVLGSHRLTGATLYVTLEPCAMCAGAISHARIARLVYGADDPKGGAVRHG PRFFEQPTCHHRPEVTGGILAEESAALLRGFFRARR |
| 335 | MRAALEEARRAAEAGEVPVGAVVVRDGAIVARAHNRPIALHDPTAHAEILALREAA RRLGNYRLTGCTLYATLEPCAMCAGAILHARLDRVVYGAADPKAGACGSVLSVFDQ PRLNHRTRVEGGVLAEECGALLSGFFRARR |
| 336 | DDDQRFMALALAQAQAAADAGEVPVGAVVVCDGRVVARAHNRPIALNDPTAHAEI LALREAARALGNYRLTGCTLYATLEPCAMCAGAILHARIARLVYGARDPKAGAVES LYRLLDDDRLNHRVAVTGGVLAAACGALLSGFFRARRR |
| 337 | DLTDEQLMRAALAEARAAAAAGEVPVGAVVAKDGEIIARAHNRPIAAHDPTAHAEIL ALRAAARALGNYRLTGCTLYATLEPCAMCSGAILHARIARLVYGAADPKAGACGSV LAVMNHPQLNHRVEVTGGVLAEECGALLRDFFRARR |
| 338 | DDDERWMREALAEARAAAEAGEVPVGAVVVRDGELLARAGNASIRDRDPTAHAEM LALRAAARALGNHRLTGCTLYVTLEPCAMCAGAIAHARIARLVYGASDPKGGAVAH GPRLFEQPTLHHRPEVTGGVLAEEAGALLRAFFRARR |
| 339 | DLEFMREALAEARAAAEAGEVPVGAVVVRDGAIVARAGNRTLRDRDPTAHAEMLA LRQAARALDSWRLSGCTLYVTLEPCAMCAGAMVQARLDRLVYGAADPKAGAAGS VLDVLGHPRLNHRVEVTGGVLAEECGALLREFFRARR |
| 340 | RSESDEALMREALAEARRAADAGEVPVGAVVVRDGAILARAGNAPIAASDPTAHAEI LALRAAARALGNYRLTGCTLYATLEPCAMCAGAILHARIARLVYGARDPKAGAVES VLDLLDRPALNHRVEVTGGVLAAECGALLSGFFRARR |
| 341 | MDDAGFMRAALAEARAAAEAGEVPVGAVVVCDGRIVARAGNRTLRDRDPTAHAE MLALRAAARALGSHRLTGCDLYVTLEPCAMCAGAISHARIRRLYYGASDPKGGAVE NGVRFFAQPTCHHAPEVYGGIGEAEAAALLRGFFRARR |
| 342 | MRDEDYMRAALAQAREAAAAGEVPVGAVVVADGRIVARAHNRPIALNDPTAHAEI LALREAARQLGNYRLTGCTLYATLEPCAMCAGAILHARIARLVYGAADPKAGAVGS VLDVLNHPRLNHRVEVTSGVLAAECGALLTEFFRSRRR |
| 343 | DETEAFMRAALAEARAAAAEGEVPVGAVVVADGAIVARAHNRPIALNDPTAHAEIL ALREAARALGNYRLTGCTLYATLEPCAMCAGAILHARIARLVYGARDPKAGAVESL YRLLDDTRLNHRVEAVGGVLADECGALLTEFFRARRG |

-continued

| Sequences | |
|---|---|
| SEQ ID NO: | Deaminase Sequence |
| 344 | DDDERWMREALAEARAAAAAGEVPVGAVVVRDGVLLARAGNASIRDRDPTAHAE MLALRAAARALGNHRLGGCTLYVTLEPCAMCAGAIAHARIARLVYGAADPKAGAV DHGPRLFEQPTCHHRPEVVSGVGAAESAALLRDFFRARR |
| 345 | MRAALEEARRAAEAGEVPVGAVVVRDGAIVARAHNRPIALNDPTAHAEILALREAA RALGNYRLTGCTLYATLEPCAMCAGAILHARLDRVVYGAADPKAGACGSVLSVFDQ PRLNHRTTLTGGVLAEECGALLSGFFRARRRAA |
| 346 | MDDDLFMRAALDEARAAAEAGEVPVGAVVVADGRIVARAHNRPIALNDPTAHAEIL ALRAAAAALGNYRLTGCELFVTLEPCAMCAGAILHARLARVVYGAADPKTGAAGSV LDVFANPRLNHRTEVRGGVLADECGALLTEFFRARRG |
| 347 | MDDEALMREALAEARAAAEAGEVPVGAVVARGGEIVARGRNRMIADGDPTAHAEI VALREAARALGNYRLTGCTLYATLEPCAMCAGAILHARIARLVYAAPDPKAGACGS VLSVMNHPQLNHRVEVASGLLAEECGALLTNFFRARRG |
| 348 | DPEDERFMREALAEAERAREAGEVPVGAVVVLDGRIVGRGHNRPIGAHDPTAHAEIV ALREAAAALGNYRLTGATLYVTLEPCAMCAGAILHARIARLVYGAADPKTGAVGSL LDLLAEPRLNHRTEVTGGVLAEECGALLSAFFRARR |
| 349 | DDLSFMREALAEAEAAAAAGEVPVGAVVVHGGRIVGRGRNRMIADHDPTAHAEIVA LREAARALGNYRLTGCTLYVTLEPCAMCAGAILHARIERLVYGAADPKAGACGSVLS VMNHPQLNHRVEVTSGVLADECGAMLSGFFRARR |
| 350 | DLEFMRLALEEARAAAAAGEVPVGAVLVRDGEVLARAGNRTIRDRDPTAHAEMLAI REAARRLDNYRLEGTTLYVTLEPCAMCSGAILHARVPRVVYGAADPKAGAAGSVLD VLGHPRLNHRTEVVGGVLAEECGALLREFFRARR |
| 351 | DDDHFMREALAEARRAADAGEVPVGAVVVRAGQIIARAHNRPVALHDPTAHAEILA LRAAARRLGNYRLTGCTLYATLEPCAMCAGAILHARIARLVYGAADPKAGACGSVL DVLNHPRLNHRVEVTAGVLAEECGALLSAFFRARR |
| 352 | DDDQRFMREALAEARAAAAAGEVPIGAVVVCDGEIVARAGNRTIRDNDPTAHAEIL ALRQAARALGNYRLTGCTLYVTLEPCAMCAGAIVHARIARLVYGAADPKAGAVNSV FDLLNHPRLNHRVEVTSGVLADECGALLRDFFRARR |
| 353 | DESFMREALAEARAAAEAGEVPVGAVVVHGGRIVARAHNRPIELSDPTAHAEILALR AAARALGNYRLTGCTLYATLEPCAMCAGAILHARIDRVVYGAADPKAGAAGSVLDV FANPRLNHHARVTGGVLADECGALLSGFFRARR |
| 354 | DPESDAAFMRAALAEAQAAAEAGEVPVGAVVVCDGRIVARAHNRPIGLNDPTAHAE ILALREAARELGNYRLTGCTLYVTLEPCAMCSGAILHARLARVVYGAADPKTGAAGS VLDLFANRRLNHQTQVEGGVLAEECGALLSGFFRARRG |
| 355 | MREALAEARAAAAAGEVPVGAVVVRGGEIVARAHNRPIALNDPTAHAEILALREAA RVLGNYRLTGCTLYATLEPCAMCAGAILHARIARLVYGAADPKAGACGSVLSVMNH PQLNHRVEVTGGVLAGECGALLSDFFRARR |
| 356 | MSDDERFMRLALAQAREAAAEGEVPVGAVVVCGGRVVARAHNRPIALNDPTAHAE VLALRAAARELGNYRLTGCTLYATLEPCAMCAGAILHARIARVVYGARDPKAGAAG SVLDVFANPRLNHHATVTGGVLAEECGALLSDFFRARRR |
| 357 | MDDDERWMREALAEARAAAEAGEVPVGAVVVRDGVLLARAGNASIRDRDPTAHA EMLALRAAARALGNHRLTGCTLYVTLEPCAMCAGAIAHARIARLVYGAADPKAGA VDHGPRLFEQPTCHHRPEVVSGVGAAESAALLRDFFRARR |
| 358 | DDDERWMRAALAEARAAAEAGEVPVGAVVVAGGRLVARAGNASIRDSDPTAHAEI LALRAAARALGNHRLAGCTLYVTLEPCAMCAGAIAHARIARLVYGASDPKGGAVAH GPRLFEQPTLHHRPEVTGGVLAAEAGALLRAFFRARR |
| 359 | MREALAEARRAAAEGEVPVGAVVVRDGAVIARAHNRPIALRDPTAHAEILALREAA RLLGNYRLTGCTLYVTLEPCAMCAGAIVHARIDRLVYGAADPKAGAVESVLRVLDH PRLNHRVEVTRGVLAEECGALLREFFRARR |
| 360 | MNDEDFMRAALAQAREAAAAGEVPVGAVVVCGGRIVARAHNRPISARDPTAHAEIL ALRAAARELGNYRLTGCELYVTLEPCAMCAGAILHARIARLVYGAADPKTGAAGSV LDVFANPRLNHRTEVTGGVLADECGALLSGFFRARRG |
| 361 | DDDQRFMAAALEEARAAAAEGEVPVGAVVVAGGRIVARAHNRPIALNDPTAHAEIL ALRAAARELGNYRLTGCTLYATLEPCAMCAGAILHARIDRVVYGARDPKAGAAGSV LDVFANPRLNHHAEVTGGVLAEECGALLSDFFRARR |

-continued

| Sequences | |
|---|---|
| SEQ ID NO: | Deaminase Sequence |
| 362 | MREALAEARAAAEAGEVPVGAVVVAGGRIVARAHNRPIALHDPTAHAEILALREAA RELGNYRLTGCTLYATLEPCAMCAGAILHARIARLVYGAADPKAGACGSVLAVMNH PQLNHRVEVVGGVLAEECGALLREFFRARR |
| 363 | MDSDLEFMREALAEARAAAEAGEVPVGAVVVRDGEIVARAANRTIRDGDPTAHAE MVALRAAARALGNYRLAGCTLYVTLEPCAMCAGAMIHARLDRVVYGAADPKAGA AGSVLDVLGHPALNHRTAVTAGVLAEECGALLRDFFRARR |
| 364 | DPTTDEALMREALAEARAAAADGEVPVGAVVARDGVIVARAHNAPVALSDPTAHA EILALREAARAAGNYRLPGCTLYATLEPCAMCCGAALHARLARVVYGARDPKAGAA GSVLDLLDDPRLNHRAEVVGGVLAEECGALLSGFFRARR |
| 365 | DPLSADDARFMRLALAEARAAAEAGEVPVGAVVVAGGRVVARAHNRPVALHDPTA HAEILALRAAARALGNYRLTGCTLYATLEPCAMCAGAILHARIARLVYGAADPKAG ACGSVLAVMNHPQLNHRVEVTGGVLAEECGALLRDFFRARR |
| 366 | MNDEDFMRAALAQAREAAAAGEVPVGAVVVCDGRIVARAHNRPIALNDPTAHAEIL ALREAARALGNYRLTGCTLYATLEPCAMCAGAILHARIARLVYGAADPKAGAVGSV LDVMNHPRLNHRVEVTSGVLAEECGALLKEFFRARR |
| 367 | DDDQRFMREALAEARAAAEAGEVPIGAVVVCDGEIVARAGNRTIRDNDPTAHAEILA LRQAARRLGNYRLTGCTLYVTLEPCAMCAGAIVQARIARLVYGAADPKAGAVDSVL QVLNHPRLNHRVEVTRGVLAEECGALLRDFFRARR |
| 368 | MREALAEARRAAEAGEVPVGAVVVRDGEIVARAHNRPIALHDPTAHAEILALREAA RRLGNYRLTGCTLYATLEPCAMCAGAILHARLDRVVYGAPDPKAGACGSVLSVFDQ PALNHRVAVTGGVLAEECGALLREFFRARR |
| 369 | DPDARFMREALAEAEAAAAAGEVPVGAVVVAGGRIVARAHNRPVELSDPTAHAEIL ALREAARELGNYRLEGCTLYATLEPCAMCSGAILHARLARVVYGAADPKAGAAGSV LDVFALPQLNHRTAVTGGVLADECGALLSGFFRARR |
| 370 | MNDEDYMRAALEQARLAASEGEVPVGAVVVCDGKIVARAHNRPIALNDPTAHAEIL ALREAARKLGNYRLTGCTLYATLEPCAMCSGAILHARIARLVYGAADPKAGAVGSV LDVINHPRLNHRVEVTSGVLAEECGALLSGFFRARRK |
| 371 | MRAALEEARRAAEAGEVPVGAVVVRDGAIVARAHNRPIALHDPTAHAEILALREAA RRLGNYRLTGCTLYATLEPCAMCAGAILHARIDRLVYGAADPKAGACGSVLSVMNH PRLNHRVEVERGVLAEECGALLTGFFRARR |
| 372 | MSTEDERFMRLALAEARRAAAEGEVPVGAVVVAGGEVVAAAHNRPIALADPTAHA EILALRAAARALGNYRLTGCTLYATLEPCAMCAGAILHARIARLVYGAADPKAGAVE SVLRLLDAPGLNHRVAVTGGVLAEECGALLREFFRARR |
| 373 | MREALAEARAAAEAGEVPVGAVVVRDGAIVARAHNRPIALNDPTAHAEILALREAA RALGNYRLTGCTLYATLEPCAMCAGAILHARLDRVVYGAADPKAGAAGSVLQVFD HPRLNHRTAVTGGVLAAECGALLSGFFRARRG |
| 374 | MREALAEARAAAAAGEVPVGAVVVRGGEIVARAHNRPIALNDPTAHAEILALREAA RALGNYRLTGCTLYATLEPCAMCAGAILHARIDRVVFGARDPKAGAAGSVLDVFAN PRLNHHAEVVGGVLADECGALLSGFFRARRG |
| 375 | DERFMREALAEARAAAAAGEVPVGAVVVRDGVVLARAGNRTLRDRDPTAHAEML ALRQAARALGSWRLAGCTLYVTLEPCAMCAGAMVLARVDRLVYGAADPKAGAAG SVLDVLGEPRLNHRPEVAAGVLAEECGELLRAFFRERR |
| 376 | DPTSDEAFMRAALAEARAAAEAGEVPVGAVVVCGGRIVARAGNRPIAARDPTAHAE ILALRAAARELGSYRLTGATLYVTLEPCAMCAGAILHARIERLVFGAADPKTGAAGS VLDLFAEPRLNHRTAVEGGVLAEECGALLRDFFRARRG |
| 377 | DPSPDEAFMRAALAEARAAAEAGEVPVGAVVVRDGRIVARAGNRPIALHDPTAHAEI LALRAAARELGNYRLTGCELYVTLEPCAMCAGAILHARLARLVYGAADPKTGAAGS VLDVFANRRLNHHTAVTGGVLADECGALLAGFFRARR |
| 378 | MDDAAFMRAALAEARAAAEAGEVPVGAVVVADGAIVARAHNRPIALNDPTAHAEIL ALRAAARALGNYRLTGCTLYATLEPCAMCAGAILHARIARLVYGARDPKAGAVESL YRLLDDTRLNHRVAVTGGVLADECGALLTEFFRARRR |
| 379 | DPESDAAFMRAALAEARAAAEAGEVPVGAVVVCDGRIVARAHNRPIGLNDPTAHAE ILALRAAARALGNYRLTGCTLYVTLEPCAMCAGAILHARLDRVVYGAADPKTGAAG SVLDLFAQPRLNHHARVEGGVLADECGALLRDFFRARR |

-continued

| SEQ ID NO: | Deaminase Sequence |
|---|---|
| 380 | DPDAAFMRAALAEARAAAAEAGEVPVGAVVVAGGRIVARAHNRPIELNDPTAHAEILALRQAAAALGNYRLEGCTLYVTLEPCAMCAGAILHARLARVVYGAADPKTGAAGSVLDLFANPRLNHHAEVTGGVLAEECGALLRDFFRARRG |
| 381 | MREALAEARRAAEAGEVPVGAVVVRDGEIVARAHNRPIALHDPTAHAEILALREAARRLGNYRLTGCTLYATLEPCAMCAGAILHARIDRLVYGAADPKAGACGSVLSVMNHPRLNHRVEVESGLLAGECGALLTEFFRRRRAAARG |
| 382 | MSTDLAFMREALAEARAAAAEAGEVPVGAVVVRDGAILARAGNRTLRDGDPTAHAEMVALRAAAAALGSERLTDCDLYVTLEPCAMCAGAISHARIRRLYYGAADPKGGAVEHGVRFFASPTCHHRPEVYGGIGEGEAAALLRDFFRARR |
| 383 | DDRFMREALAEARAAAAAGEVPVGAVVVRDGEIIARAGNRTLRDRDPTAHAEMLALRQAARALGSHRLTGCDLYVTLEPCAMCAGAIQHARIRRLVYGAADPKAGAVDHGVRLFDSPSCHHRPEVVAGVGEGEAAALLRDFFRERR |
| 384 | MREALAEARAAAAAGEVPVGAVVVRGGEIVARAHNRPIALHDPTAHAEILALREAARALGNYRLEGCTLYATLEPCAMCSGAILHARLARLVYGAADPKAGAVGSVLDVIGNPRLNHRVEVTGGVLAEECGALLSGFFRARR |
| 385 | MDDAGFMRAALAEARAAAAAGEVPVGAVVVRDGAIVARAGNRTLRDRDPTAHAEMLAIRAAARALGSERLTGCDLYVTLEPCAMCAGAISFARIRRLYYGAADPKGGAVENGVRFFASPTCHHAPEVYSGIGEAEAAALLRDFFRARR |
| 386 | RPPSDDERWMAEALAQARAAAAEGEVPVGAVVVRDGRLLARAHNRPIALNDPTAHAEILALRAAAREIGNYRLTGCTLYATLEPCAMCAGAILHARIARLVYGARDPKAGACGSVLDVLNHPRLNHRVEVTGGLLADECGALLSAFFRARR |
| 387 | DLEFMREALAEARAAAAEAGEVPVGAVVVAGGRIVARAHNRPIELHDPTAHAEILALRQAATALGNYRLTGCTLYATLEPCPMCAGAALHARLDRIVYGAADPKAGAAGSVLDLFADTRLNHHAAVAGGVLADECGALLSGFFRARR |
| 388 | DDDERWMRAALAEARAAAAAGEVPVGAVVVRDGELLARAGNASIRERDPTAHAELLALRAAARRLGNHRLTGCTLYVTLEPCAMCAGAIAHARIARLVYGAADPKGGAVAHGPRLFEQPTLHHRPEVTAGVLAEECGALLREFFRARR |
| 389 | MREALAEARAAAAAGEVPVGAVVVRGGEIVARAHNRPIALHDPTAHAEILALREAARRLGNYRLTGCTLYATLEPCAMCAGAILHARIDRLVYGAADPKAGACGSVLSVMNHPQLNHRVEVTSGVLAEECGALLTGFFRERR |
| 390 | DERWMREALAEARAAAAEGEVPVGAVVVRDGRLLARAGNASIRSRDPTAHAEILALRRAARRLGNHRLTGCTLYVTLEPCAMCAGAIAHARIARLVYGASDPKGGAVAHGPRLFEQPTCHHRPEVTGGVLAEECGALLREFFRARR |
| 391 | MDDAGFMRAALAEARAAAAEAGEVPVGAVVVADGRIVARAHNRPVALNDPTAHAEILALRAAARALGNYRLTGCTLYATLEPCAMCAGAILHARLDRVVYGAADPKAGAAGSVLDVFANPRLNHRTAVTGGVLADECGALLTGFFRARR |
| 392 | DDRFMRAALAEARAAAAEAGEVPVGAVVVCGGRIVARAHNRPIDLCDPTAHAEILALREAARELGNYRLTGCTLYATLEPCAMCAGAILHARIARLVYGARDEKAGAVESLYRLLDDTRLNHRVAVTGGVLAAECGALLSEFFRARRA |
| 393 | DPDAAFMRAALAEARAAAAEAGEVPVGAVVVHEGRIVARAHNRPVALNDPTAHAEILALRAAARALGNYRLTGCTLYATLEPCAMCAGAILHARIARLVYGARDPKAGAVESLYRLLDDTRLNHRVEAVGGVLADECGALLSEFFRARRR |
| 394 | DDRFMRAALAEARAAAAAGEVPVGAVVVAGGRIVARAHNQPVALVDPTAHAEVLALRAAARELGNYRLTGCTLYATLEPCAMCAGAILHARIDRLVYGAADPKAGAVGSVLDVFANPRLNHRTRVTGGVLAAECGALLSEFFRARRR |
| 395 | MTSAPAPSDLDFMRLALAEARLAAAEGEVPVGAVVVCDGEVVARAHNRPIALHDPTAHAEILALREAARKLGNYRLTGCTLYATLEPCAMCAGAILHARIARLVYGAADPKAGAVESRLRLLDAPFLNHRVEVTGGVLAEECGALLKDFFRARR |
| 396 | DDRFMRAALAEARAAAAEAGEVPVGAVVVCGGEIVARAHNRPIALNDPTAHAEILALREAARRLGNYRLTGCTLYATLEPCAMCAGAILHARIARLVYGAADPKAGAVESLYRLLDDTRLNHRVEAVGGVLAGECGALLSEFFRARRA |
| 397 | MREALAEARAAAAAGEVPVGAVVVAAGRIVARAHNRPVELSDPTAHAEILALREAARELGNYRLEGCTLYATLEPCAMCAGALLHARLARLVYGAADPKAGAVGSVLDVLDHPRLNHRVEVTAGVLAEECGALLRDFFRARR |

-continued

| Sequences | |
|---|---|
| SEQ ID NO: | Deaminase Sequence |
| 398 | MDEEFMREALAEARAAAEAGEVPVGAVVVAGGRIVGRGRNRPVELADPTAHAEILA LREAAAALGNYRLEGCTLYATLEPCAMCAGAILHARIARVVYGARDPKAGAAGSVL DVFALPRLNHHTRVTGGVLAEECGALLSGFFRARR |
| 399 | RLDEQFMRRALELAAHAEAEGEVPVGAVLVLDGQVIGEGWNRSIGHHDATAHAEM MAIEQAGKAVENYRLLDATLYVTLEPCPMCAGALLHSRVKRIVYGAPDLKAGAAGT VLNLFEHQAAYHYADVEHGLLEEECREQLQAFFKRRRKEKKALKQAQRDAEEK |
| 400 | MSTSEADLTFMREALAEARAAAEAGEVPVGAVVVAGGEIVARAHNRPIALHDPTAH AEILALRAAARRLGNYRLTGCTLYVTLEPCAMCAGAILHARLARLVYGAADPKTGA AGSVLDLFANRRLNHHTEVTGGVLADECGALLSDFFRARRA |
| 401 | MDDAGFMRLALAEARRAAEAGEVPVGAVVVRGGEVLAAAGNRTVRDCDPTAHAE VVALREAARKLGNHRLTGCDLYVTIEPCAMCAGAISHARIARLYYGADDPKGGAVE HGPRFFGQPTCHHRPEVYGGIGAAEAAELLRGFFRARR |
| 402 | MREALAEARAAAEAGEVPVGAVVVRDGEIIARARNRMVADCDPTAHAEIVALREAA RALGNHRLGGCTLYVTLEPCAMCAGAMIHARVDRLVYGAADPKAGAAGSVLDVIN HPRLNHRMEVESGVLADECGALLKEFFRSRR |
| 403 | MDAALAEARAAADAGEVPVGAVVVRDGAVLARAGNRTLRDSDPTAHAEIVALRAA ARALGNHRLPGCTLYVTLEPCAMCAGAISHARLARLHYGAADPKGGAVEHGPRFFA QPTCHHRPDVVGGLGETEAADLLRAFFAARR |
| 404 | MSDEQYMRRALELARQAEQQGEVPVGAVLVRDGEVIAEGWNQSISSHDATAHAEIM ALRAAGQALENYRLLDTTLYVTLEPCPMCAGALLHSRVKRVVFGAPDLKAGAAGTV LNLFESQASYHYADVESGLLEEECREQLQAFFKRRRKEIKAQRDAKRAADE |
| 405 | MDAALAEARAAADAGEVPVGAVVVRDGVVLARAGNRTVRDADPTAHAEIVALRA AARALGNHRLPGCTLYVTLEPCAMCAGAISHARLARLVYGAADPKGGAVAHGPRLF AQPTCHHRPEVTGGVGAAEAAALLRAFFAARR |
| 406 | MDDAGFMRLALAEARAAAAAGEVPVGAVVVRDGEVLAAAGNRTLRDRDPTAHAE VVALRAAARALGSERLPGCDLYVTLEPCAMCAGAISFARIRRLYFGAGDPKGGAVEH GPRFFAQPTCHHAPEVYGGLGEGEAAGLLRGFFAARR |
| 407 | MRSALDEARRAAAAGEVPVGAVVVRDGAVLAAAGNRTVRDCDPTAHAEIVALRAA AAALGNYRLDGCDLYVTLEPCAMCAGAMVHARLARLVYGAADPRAGAAGSVLDV VRHPALNHRMEVTGGVLADECGALLREFFAARR |
| 408 | MDSAAKDLCYMRRALELAALAEAEGEVPVGAVLVKDGEIVGEGWNRSIGSHDATA HAEIMALRQAGQALQNYRLLDTTLYVTLEPCPMCAGALLHSRVKRVVFGAPDLKAG AAGTVLNLFESQASYHYAEVESGLLEQECREQLQAFFKRRRKEIKALRQAEKEAQQK |
| 409 | MDSAAKDLCYMRRALELAALAEAEGEVPVGAVLVKDGEIVGEGWNRSIGSHDATA HAEIMALRQAGQALQNYRLLDTTLYVTLEPCPMCAGALLHSRVKRVVFGAPDLKAG AAGTVLNLFESQASYHYAEVESGLLEEECREQLQAFFKRRRKEIKAQRDAKRAAD |
| 410 | MTSAPEHEKYMRRALELARQAEEHGEVPVGAVLVKDGEIIAEGWNQSIGSHDATAH AEIMALRAAGKALENYRLLDTTLYVTLEPCPMCAGALLHSRVKRVVFGAPDLKAGA AGTVLNLFESQASYHYADVESGLLEEECREQLQAFFKRRRKEIKALKQAKREQEE |
| 411 | DTEFMREALAEARAAAAAGEVPVGAVVVHEGKIIARAGNRTIRDNDPTAHAEIVALR AAARALGNYRLAGCTLYVTLEPCAMCAGAMIHARLDRLVYGADDPKAGAAGSVLN VLNHPRLNHQMQVESGVLADECAALLQDFFRARR |
| 412 | MTDADFMALALEEARAAAALGEVPVGAVVVRDGAVIARAGNRTVRDNDPTAHAEI VALREAARALGNYRLDGCTLYVTLEPCAMCSGAMLHARLARVVYGAADPKTGAAG SVLDLFATAQLNHQTQVQGGVLAAECGALLQDFFRQRR |
| 413 | DESYMRRALELARQAEQHGEVPVGAVLVKDGEVIAEGWNQSIGSHDATAHAEIMAL RAAGQVLENYRLLDTTLYVTLEPCPMCAGALLHSRVKRVVFGAPDLKAGAAGTVLN LFESQASYHYAEVEGGLLEDECREQLQAFFKRRRKEIKAARQAKRAAE |
| 414 | MDEALAEARRAAAAGEVPVGAVLVRDGRVLARGGNRTIRDCDPTAHAEIVALREAA RAAGNYRLPGTTLYVTLEPCAMCAGAMIHARVARLVYGAADPRAGAAGSVFDVLR HPALNHRMEVEGGVRAEECGALLREFFRARRA |
| 415 | MTEADLRFMQLALEEARRAGEAGEVPVGAVLVRDGAVLARGGNRTIRDCDPTAHA EIVALREAARALGNYRLDGCTLYVTLEPCAMCAGAMIHARLDRLVYGADDPRAGAA GSVLDVLGHPALNHQTRVTAGVLAEECGALLREFFRARR |

-continued

| Sequences | |
|---|---|
| SEQ ID NO: | Deaminase Sequence |
| 416 | MTDEEYMRRALELARQAEQQGEVPVGAVLVKDGEVIAEGWNQSIGSHDATAHAEI MALRAAGQALENYRLLDTTLYVTLEPCPMCAGALLHSRVKRVVFGAPDLKAGAAG TVLNLFESQASYHYADVESGLLEEECREQLQAFFKRRRKEIKALKQAKRDAEE |
| 417 | MRDALAEARAAAARGEVPVGAVVVRDGAVLARAGNASIAARDPTAHAEILALRAA ARALGNHRLTGCTLYVTLEPCAMCAGAIAHARIARLVYGAADPKGGAVAHGPRFFA QPTCHHRPEVAGGLGEAEAAALLRDFFRARR |
| 418 | MTDEDFMRLALAEAQAAAAGEAPIGAVLVRDGQVLARGQNRVIRDNDPTAHAEIV ALREAARQLGNYRLDGCELYVTLEPCAMCAGAMIHARLARLVYGAADPKAGAAGS VLDVINHPRLNHRMQVTAGVLADECGALLRDFFRQRR |
| 419 | MRAALDEARAAADAGEVPVGAVVVRDGAILARAGNRTVRDADPTAHAEIVALRAA ARALGNHRLGGCTLYVTLEPCAMCAGAIAQARVARLVYGAADPKGGAVAHGPRLF AQPTCHHRPEVTGGVLADEAGELLRAFFAARR |
| 420 | DETYMRRALELARQAEQHGEVPVGAVLVKDGEVIAEGWNQSIGAHDATAHAEIMA LRAAGQALQNYRLLDTTLYVTLEPCPMCAGALLHSRVKRVVFGAPDLKAGAAGTVL NLFESQASYHYAEVESGLLEEECREQLQAFFKRRRKEIKAARQAARDAQ |
| 421 | MNDEFYMRRALELAKMAEERGEVPVGAVLVRDGEVIAEGWNQSIGSHDATAHAEI MALRAAGQVLQNYRLLDTTLYVTLEPCPMCAGALLHSRVKRVVFGAPDLKAGAAG TVLNLFESQASYHYAEVESGLLEEECREQLQAFFKRRRKEIKALKQAQREAEEK |
| 422 | DTSPADLRFMRLALAEARAAAAAGEVPVGAVVVRDGAVLARAGNRTLRDRDPTAH AEIVALRAAARALGSHRLGGCTLYVTLEPCAMCAGAIAQARVARLVYGADDPKGGA VAHGPRLFAQPTCHHRPEVVGGVGAEEAAALLRDFFAARR |
| 423 | MTAADERFMRRAIELAAQAEAAGEVPVGAVLVKDGEIVAEGWNQSIGSHDATAHAE IQTLRQAGQALENYRLLDTTLYVTLEPCPMCAGALLHSRVKRVVFGAPDLKAGAAG TVLNLFESQASYHYADVEGGLLEDECREQLQAFFKRRRKEIKAARQAAKEAE |
| 424 | MDDDGLMRAAIAEAEAAAAAGEVPVGAVLVRDGVVLARGRNRMIADSDPTAHAEI VALREAARALGNYRLEGCELYVTLEPCAMCAGAMVHARLARLVYGAADPKAGAA GSVLDVLGHPRLNHRMEVTGGVLADECGAMLRDFFRARRA |
| 425 | DDTFYMRRALELAALAESEGEVPVGAVLVKDGEIIAEGWNRSIGSHDATAHAEIETL RKAGQALQNYRLLDTTLYVTLEPCPMCAGALLHSRVKRIVFGAPDLKAGAAGTVLN LFESQASYHYAEVESGLLEEECREQLQAFFKRRRKEIKALRQAEKAAQE |
| 426 | MDDAGFMREALAEARAAAAAGEVPVGAVVVKDGEIIARAGNRTIRDCDPTAHAEIV ALRAAAQALGNYRLDGCTLYVTLEPCAMCSGAMLHARLPRVVYGAADPKTGAAGS VLDLFAEPRLNHHTRVEGGVLAAECGALLTDFFRARRG |
| 427 | MDAALEEARRAAAAGEVPVGAVLVRDGVVLARAGNRTVRDCDPTAHAEIVALRAA AAALGNYRLPGTTLYVTLEPCAMCAGAMIHARVARLVYGAADPKTGAAGSVFDVL GSPRLNHRVEVEGGVRAAECGALLQDFFRARRAG |
| 428 | MTDDERWMAEALREAEAAAAEGEVPVGAVVVRDGELIARGRNRVVRDCDPTAHAE IVALREAARALGNYRLTGCTLYVTLEPCAMCAGAMVHARLDRLVYGAADPKAGAA GSVLAVLNHPRLNHQMEVAGGVLAGESAALLRDFFRARR |
| 429 | DSEFMAEALAEARAAAEAGEVPIGAVVVCDGEIVARAGNRTIRDNDPTAHAEIVALR EAAAKLGNYRLAGCTLYVTLEPCAMCAGAMIHARLDRLVYGAADPKAGAAGSVLD VLGHPQLNHQTEVEGGVLAEECGALLKDFFASRR |
| 430 | DPEYMRRALELAAQAEAEGEVPVGAVLVKDGEVVAEGWNRSIGDHDATAHAEIQV LRKAGQALQNYRLLDTTLYVTLEPCPMCAGALLHSRVKRVVFGAPDLKAGAAGTVL NLFESQASYHYADVESGLLEDECREQLQAFFKRRRKEIKAARKAAKEAE |
| 431 | DTEMMRLALAEARAAAEAGEVPVGAVVVRDGVVLARAGNRTVRDNDPTAHAEIVA LREAARALGNHRLEGCTLYVTLEPCAMCAGAIAQARVARLVYGAADPKGGAVAHG PRLFEQPTTHHRPEVTGGVLAEEAGALLREFFAARR |
| 432 | MTDADFMALALEEARAAAALGEVPVGAVVVRDGAVVARAGNRTVRDCDPTAHAE VVALREAARVLGNYRVDGATLYVTLEPCAMCAGAMIHARLPRLVYGAADPRAGAA GSVLDVLGHPALNHRVEVTGGVLADESAALLREFFRERR |
| 433 | DEPLDRDRYFMEIALAEARAAAAAGEVPVGAVVVRDGEVIARAGNRTVRDNDPTAH AEIVALREAARALGNHRLTGCTLYVTLEPCAMCAGAISHARVARLVYGADDPKGGA VAHGPRFFEQPTCHHRPEVTGGVLAAESAALLRGFFAARR |

-continued

Sequences

| SEQ ID NO: | Deaminase Sequence |
|---|---|
| 434 | MTSDAEFMALALEEARAAAALGEVPVGAVVVRDGAVIARAGNRTIRDCDPTAHAE MVALREAARALGNYRLAGCDLYVTLEPCAMCAGAIVHARLARLVYGAADPKTGAA GSVFDVLGSGRLNHRPEVVAGVLADECGALLTDFFRARR |
| 435 | MTEEDKYFMQRAIELAKLAEENGEVPVGAVLVKDGEIIAEGWNQSIGNHDATAHAEI MTLRQAGQVLQNYRLLDTTLYVTLEPCPMCAGALLHSRVKRIVFGAPDLKAGAAGT VLNLFESQASYHYADVESGLLEEECREQLQAFFKRRRKEIKALKKQQKLEQE |
| 436 | MSAALDEARRAAAAGEVPVGAVVVRDGVVLAAAGNRTLRDCDPTAHAEIVALRAA ARALGNYRLDGCDLYVTLEPCAMCAGAMIHARLARLVYGAADPKTGAAGSVLDVL GHPRLNHRTAVTGGVLADECGALLRDFFAARR |
| 437 | DTSERDERFMRLALEEARAAAEAGEAPIGAVVVRDGAVLARAGNRTVRDNDPTAHA EVVALREAARALGNHRLTGCTLYVTLEPCAMCAGAISHARVARLVYGADDPKGGA VAHGPRFFAQPTCHHRPEVTGGVLAEESAELLRGFFRARR |
| 438 | DPDSRFMQAALAEARAAAEAGEVPIGAVVVRDGEIVARAGNRTIRDNDPTAHAEIVA LREAARVLGNYRLTGCTLYVTLEPCAMCAGAMIHARIDRLVYGAADPKAGAAGSVL DVLNHPKLNHQMEVEAGVLADECGALLRDFFRARR |
| 439 | MDDDERWMRLALEEARLAEEAGEVPVGAVVVRDGELLARGRNRVLRDCDPTAHAE IVALREAARRLGNYRLDGCTLYATLEPCAMCAGAMVHARLARLVYGAPDPKAGAA GSVLDVLNHPRLNHRMEVTAGVLAEECGALLRRFFQARR |
| 440 | MSAALAEARRAAAAGEVPVGAVVVRDGAVLAAAGNRTVRDCDPTAHAEIVALRAA ARALGNHRLEGCTLYVTLEPCAMCAGAIAQARVARLVYGAADPKGGAVAHGPRLF AQPTCHHRPEVVGGVGEAEAAALLRDFFAARR |
| 441 | MRSALALAAAAGAAGEVPVGAVVVRDGVVIGRGENRVIRDSDPTAHAEIVALRDAA RALGNYRLTGCTLYVTLEPCAMCAGAMIHARIDRLVYGAADPKAGAAGSVLDVLN HPQLNHQMEVEGGVLAEECGALLRDFFRARR |
| 442 | RTADERWMRLALEEARAAEAAGEVPVGAVVVRDGELIARGRNRVLRDCDPTAHAEI VALREAARALGNYRVEGCTLYVTLEPCAMCAGAMIHARLDRLVYGAADPRAGAAG SVLDVLGHPALNHQTQVTGGVLAEECGALLREFFRARRG |
| 443 | DDLSFMQEALAEARAAAEAGEVPIGAVVVRDGAILARAGNRTVRDNDPTAHAEIVA LREAARALGNYRLAGCTLYVTLEPCAMCAGAMIHARVDRLVYGAADPKAGAAGSV LDVLGHPRLNHRMEVEGGVLAEECGALLREFFRARR |
| 444 | MSSDAGFMAEALAEAEAAAAAGEVPVGAVVVCGGEIVARAGNRTIRDCDPTAHAE MVALREAARKLGNYRLAGCTLYVTLEPCAMCAGAMIHARLDRLVYGAADPKAGAA GSVLDVINHPRLNHQMEVEAGVLADECGAMLRRFFQERR |
| 445 | MDDDRWMRLALEEARRAEEEGEVPVGAVVVLGGEVIGRGRNRVIRDSDPTAHAEIV ALREAARTLGNYRLDGCELYVTLEPCAMCAGAMVHARLARLVYGAADPRAGAAGS VLDVLGHPRLNHRMEVTGGVLAEECGALLRDFFRRRR |
| 446 | MDDAGFMREALAEAEAAAAAGEVPVGAVVVCDGRIVARAGNRTVRDNDPTAHAEI VALREAARALGNHRLGGCTLYVTLEPCAMCAGAMIHARIDRLVYGADDPKAGAVR SVLQVLDHPRLNHRMAVESGVLAGECAAVLQAFFAARR |
| 447 | MDAALEEARRAAAAGEVPVGAVLVRDGEVLARGGNRTIRDCDPTAHAEIVALRAAA RAAGNYRLPGTTLYVTLEPCAMCAGAMIHARVARLVYGAADPRAGAAGSVFDVLR HPALNHRMEVEGGVLAEESAALLRGFFRARR |
| 448 | MRDALALARAAAAAGEVPVGAVVVKDGVVVGRGENRVVRDSDPTAHAEIVAMRE AARALGNYRLTGCTLYVTLEPCAMCAGAMIHARLDRVVYGAADPKTGAAGSVLDV LGHPRLNHQTQVEGGVLAAECGALLSDFFRARR |
| 449 | MDDAGFMREALAEAEAAAAAGEVPVGAVVVKDGEIIARAGNRTVRDCDPTAHAEIV ALREAARKLGNYRLAGCTLYVTLEPCAMCAGAMIHARLDRLVYGADDPKAGAAGS VLNVLNHPRLNHQMQVEAGVLAEECGAMLRRFFETRR |
| 450 | MDDAAFMGEALAEARAAAAAGEVPIGAVVVCDGEIVARAGNRTVRDNDPTAHAEI VALREAARKLGNYRLAGCTLYVTLEPCAMCAGAMIHARVDRLVYGADDPKAGAAR SVLNVVDHPALNHRLEVTSGVLAAECAELLRGFFERRR |
| 451 | MTAADAAAMRAALAEARAAAARGEVPVGAVVMRDGVIVARAGNATVAGHDPTAH AEIVALRRAARALGNHRLTGCALYVTLEPCAMCAGAIAHARIARLVYGAADPKGGA VAHGPRFFAQPTCHHRPEVTGGVLAEEAGALLRAFFRARR |

-continued

| Sequences | |
|---|---|
| SEQ ID NO: | Deaminase Sequence |
| 452 | DTEMMALALAEARAAAEAGEVPVGAVVVRDGEVLARAGNRTVRDCDPTAHAEIVA LREAARRLGNYRLPGCTLYVTLEPCAMCAGAIMHARLDRVVYGAADPKTGAAGSV LDLFAEPRLNHHTAVVGGVLADEAGALLRGFFAARR |
| 453 | MTEEDKYFMKRAIELAKLAEENGEVPVGAVLVKDGEIISEGWNQSIGNNDATAHAEI MALREAGKVLENYRLLDTTLYVTLEPCPMCAGALLHSRVKRIVFGAPDLKAGAAGT VLNLFESQASYHYADVESGLLEEECREQLQAFFKRRRKEKKELKKLKREEN |
| 454 | MDSAAKDLCYMRRALELAALAEAEGEVPVGAVLVKDGEIVGEGWNRSIGSHDATA HAEIMALRQAGQALQNYRLLDTTLYVTLEPCPMCAGALLHSRVKRVVFGAPDLKAG AAGTVLNLFESQASYHYADVESGLLEEECRAQLQAFFKRRRKEIKAQRDAQRAAQE K |
| 455 | MRTALEEARRAAEAGEVPVGAVVVRDGVVLARAHNRTVADHDPTAHAEILALREA ARVLGNHRLTGCTLYVTLEPCAMCAGAIVHARLDRLVYGAADPKAGAAGSVLDVL GHPRLNHRPEVAAGVLAEECGELLRGFFRERR |
| 456 | DDDERWMREALAEARAAEEAGEVPVGAVVVRDGELVGRGRNRVLRDSDPTAHAEI VALREAARALGNYRLDGCTLYATLEPCAMCAGAMLHARLARLVYGAADPKAGAA GSVLDVLNHPRLNHRMEVTGGVLAEECGALLRGFFRARRG |
| 457 | RSSPDERFMALALAEARRAAEAGEVPVGAVLVRDGAVLAAAGNRTIRDNDPTAHAE IVVLREAARRLGNYRLEGCTLYVTLEPCAMCAGAMVNARLGRLVYGAADPRAGAA GSVLDVLRHPALNHRMEVTGGVLAAECGALLRDFFAARR |
| 458 | MRDALAEARKAAALGEVPVGAVVVKDGAVIARGHNRTVADSDPTAHAEIVAIRAA ARALGNHRLTGCTLYVTLEPCAMCAGAIAHARIARLVYGAADPKGGAVDHGVRFFE SPTCHHRPEVTGGVLAAEAAALLRDFFRARR |
| 459 | DETYMRRALELARQAEEHGEVPVGAVLVKDGEIIAEGWNQSIGAHDATAHAEIMAL RAAGQALENYRLLDTTLYVTLEPCPMCAGALLHSRVKRIVFGAPDLKAGAAGTVLN LFESQASYHYADVESGLLEEECREQLQAFFKRRRKEIKALKQAQREAEEK |
| 460 | MDEALAEARRAAAAGEVPVGAVVVRDGAVLARAGNRTVRDCDPTAHAEIVALRAA ARALGNHRLTGCDLYVTLEPCAMCAGAISHARIARLYYGADDPKGGAVAHGPRFFG QPTCHHRPEVYGGIGEGAAAALLRAFFAARR |
| 461 | DESYMRRALELARQAEAEGEVPVGAVLVKDGEVVAEGWNRSIGAHDATAHAEIETL RKAGQALENYRLLDTTLYVTLEPCPMCAGALLHSRVKRVVFGAPDLKAGAAGTVLN LFESQASYHYAEVESGLLEDECREQLQAFFKRRRKEIKAQRQAQKEAEQK |
| 462 | MSEQDRYFMQRAIELAQQAELNGEVPVGAVLVKDGEVIAEGWNQSIGSHDATAHAE IMALRKAGQVLENYRLLDTTLYVTLEPCPMCAGALLHSRVKRVVFGAPDLKAGAAG TVLNLFESQASYHYADVESGLLEDECREQLQAFFKRRRKEKKALKQAQKEAAQ |
| 463 | MTDADFMALALEEARAAAALGEVPVGAVVVKDGEVIARAGNRTVRDCDPTAHAEI VALREAARKLGNYRLDGCTLYVTLEPCAMCAGAMLHARLPRVVYGAADPKTGAAG SVLDLFAEPRLNHQTAVQGGVLADEAGALLRDFFKARRA |
| 464 | MDAALEEARRAAAAGEVPVGAVLVRDGVVLARAGNRTVRDCDPTAHAEIVALRAA AAALGNYRLDGCTLYVTLEPCAMCAGAMIHARLARLVYGAADPRTGAAGSVLDVL GHPALNHRTEVTGGVLAEECGALLREFFRTRRG |
| 465 | MSDKDLRFMQLALEEARAAADAGEVPVGAVLVRDGQVLARGRNRVILDNDPTAHA EIVALREGARRLGNYRLAGCTLYVTLEPCAMCAGAIVHARLDRLVYGAADPKAGAA GSVLDVLNHPKLNHQMEVEGGVLAAESGELLRSFFRARR |
| 466 | DTLYMRRALELAAQAEAEGEVPVGAVLVKDGEVIAEGWNRSIGSHDATAHAEIETL RKAGQVLQNYRLLDTTLYVTLEPCPMCAGALLHSRVKRIVYGAPDLKAGAAGTVLN LFESQASYHYAEVESGLLEEECREQLQAFFKRRRKEIKALRQAQKEAE |
| 467 | MDAALEEARRAAEAGEVPVGAVLVRDGAVLARAGNRTIRDCDPTAHAEIVALRAAA RALGNYRLPGTTLYVTLEPCAMCAGAMIHARVDRLVYGAADPRAGAAGSVLDVIGH PALNHRMEVEGGVLAEECGALLREFFRARRG |
| 468 | DPLMDEFMGEALAEARAAAAAGEVPVGAVVVRDGAVIARAGNRTVRDCDPTAHAE IVALRAAARALGNHRLDGCDLYVTLEPCAMCAGAISHARIRRLYYGADDPKGGAVA HGARVFAHPTCHHRPEVYGGIGAAEAAGLLRAFFAARR |
| 469 | DESYMRRALELARQAEQEGEVPVGAVLVKDGEVIAEGWNRSIGAHDATAHAEIETL RKAGQVLQNYRLLDTTLYVTLEPCPMCAGALLHSRVKRVVFGAPDLKAGAAGTVL NLFESQASYHYADVESGLLEDECREQLQAFFKRRRKEIKAQRDAEKAAK |

-continued

Sequences

| SEQ ID NO: | Deaminase Sequence |
|---|---|
| 470 | MRDALAEARAAAARGEVPVGAVVVRDGAVLARAGNATIADCDPTAHAEMRALRA AARALGNYRLPGCTLYVTVEPCAMCAGAMIHARLARLVYGAADPKAGAAGSVLDV LGHPALNHRMEVTGGVLAAECAALLRDFFAARRGR |
| 471 | MTEEDKKFMQRAIELARKGEQEGEVPVGAVLVKDGEIIAEGWNRSIGDHDATAHAEI ETLRKAGKALENYRLLDTTLYVTLEPCPMCAGALLHSRVKRVVFGAPDLKAGAAGT VLNLFESQASYHYADVESGLLEEECREQLQAFFKRRRKEKKALKQAKKEAEK |
| 472 | MDDDALMGLALDEARAAAAAGEVPIGAVVARDGAVVARAGNRTVRDCDPTAHAE VVALREAARALGNYRLAGCTLYVTLEPCAMCAGAMIHARLDRVVYGAADPKTGAA GSVLDVLGHPALNHQTRVEGGVLAAECGALLRDFFAARR |
| 473 | MTRDEQYMRRALELARQAEQEGEVPVGAVLVKDGEIVAEGWNRSIGDHDATAHAEI ETLRKAGQVLENYRLLDTTLYVTLEPCPMCAGALLHSRVKRVVFGAPDLKAGAAGT VLNLFESQASYHYAEVESGLLEEECREQLQAFFKRRRKEIKALRQAEKEAEQK |
| 474 | DSEFMAEALAEARAAAAAGEVPVGAVVVKDGEIIARAGNRTLRDNDPTAHAEIVAL RAAARALGNQRLEGCDLYVTLEPCAMCAGAISHARIRRLYYGAEDPKGGAVDNGVR FFASPTCHHRPEVYGGIGETEAAELLRGFFRER |
| 475 | DDDERFMRLALEEARKAEEAGEVPVGAVLVKDGEVIARGRNRVISDSDPTAHAEIVA LREAGRALGNYRLDGCTLYVTLEPCAMCAGAMVHARLDRLVYGAADPRAGAAGSV LDVLNHPALNHRMEVEGGVLADECGALLRDFFRRRR |
| 476 | MDAALAEARAAADAGEVPVGAVVVRDGAVLARAGNRTLRDSDPTAHAEIVALRAA ARALGNHRLGGCTLYVTLEPCAMCAGAISHARLARLHYGADDPKGGAVAHGPRFFA QPTCHHRPDVYGGIGEGEAAALLRGFFAARR |
| 477 | DTEFMREALAEARAAAAAGEVPVGAVVVKDGEIIARAGNRTLRDNDPTAHAEIVAL REAARKLGNHRLTGCTLYVTLEPCAMCAGAISHARIARLVYGADDPKGGAVAHGPR FFAQPTCHHRPEVTGGVLAEEAGELLRGFFRERR |
| 478 | MDAALEEARRAAAAGEVPVGAVLVAGGRVLARAGNRTIRDCDPTAHAEIVALREAA RALGNYRLAGTTLYVTLEPCAMCAGAMIHARVDRLVYGAADPRAGAAGSVFDVVR HPALNHRLEVEGGVLAEECGALLRDFFRARRGR |
| 479 | MRAALDEARRAAAAGEVPVGAVVVRDGVVLARAHNRTVADHDPTAHAEILALREA ARVLGNHRLTGCTLYVTLEPCAMCAGAIVHARLDRLVYGAADPKAGAAGSVLDVL DHPRLNHRMEVTGGVLAEESAALLRGFFAARR |
| 480 | MSSDADFMRLALAEARAAAAAGEVPVGAVVVRGGEVIARAGNRTVRDCDPTAHAE VVALREAARKLGNHRLTGCTLYVTLEPCAMCAGAISHARVARLVYGADDPKGGAV AHGPRFFAQPTCHHRPEVTGGVLAEEAGELLRGFFRARR |
| 481 | MDAALEEARRAAAAGEVPVGAVLVRDGAVLARGGNRTIRDCDPTAHAEIVALRAA ARALGNYRLPGTTLYVTLEPCAMCAGAMIHARVARLVYGAADPKTGAAGSVFDVL GSARLNHRVEVEGGVRAAECGALLRDFFAARRGR |
| 482 | MRAALAEARRAAAEGEVPVGAVVVRDGAVLARAGNRTVRDCDPTAHAEVLALREA ARALGNHRLTGCTLYVTVEPCAMCAGAISHARVARLVYGADDPKGGAVRHGPRVF DQPTCHHRPEVVGGVLAEEAGALLRDFFAARR |
| 483 | DTSFMQQALDEARAAAAAGEVPVGAVVVKDGEIIARAGNRTLRDNDPTAHAEIVAL RAAARALGSQRLGGCDLYVTLEPCAMCAGAISHARIARLYYGADDPKGGAVAHGA RVFSHPQCHHVPEVYDGIGAGEAAALLRDFFAGR |
| 484 | DTEFMREALAEARAAAAAGEVPVGAVVVRDGAIIARAGNRTIRDRDPTAHAEVVAL REAARALGNHRLTGCTLYVTLEPCAMCAGAISHARVARLVYGAADPKGGAVAHGP RFFEQPTCHHRPEVTGGVLAEEAGALLRDFFRARR |
| 485 | MSEQDEFYMRRAIELARKGEENGEVPVGAVLVKDGEIIAEGWNQSIGSHDATAHAEI VTLRKAGQVLENYRLLDTTLYVTLEPCPMCAGALLHSRVKRVVFGAPDLKAGAAGT VLNLFESQASYHYADVESGLLEEECREQLQAFFKRRRKEKKALKQAQKELE |
| 486 | MTDADFMALALAEARAAAAAGEVPVGAVVVRDGVVLAAAGNRTLRDCDPTAHAE VVALRAAARALGNYRLDGCTLYVTLEPCAMCAGAMLHARLARVVYGAADPKTGA AGSVLDLFAQPRLNHHTAVAGGVLAAECGALLADFFRQRRG |
| 487 | MSDEQYMRRALELARQAEQQGEVPVGAVLVRDGEVIAEGWNQSISSHDATAHAEM MAIRAAGAALENYRLLDTTLYVTLEPCPMCAGALLHSRVKRVVFGAPDLKAGAAGT VLNLFESQASYHYADVESGLLEEECREQLQAFFKRRRKEIKALRQAEKEAAAK |

-continued

| Sequences | |
|---|---|
| SEQ ID NO: | Deaminase Sequence |
| 488 | MSSETSTDAAADAAFMAEALAEARAAAAAGEVPVGAVVVCGGRIVARAGNRTVRD NDPTAHAEIVALREAARVLGNHRLTGCTLYVTLEPCAMCAGAISHARIARLVYGADD PKGGAVRHGPRFFAQPTCHHRPDVAGGVGEAEAAELLRAFFRARR |
| 489 | MTDADFMALALEEARAAAALGEVPVGAVVVKDGEVIARAGNRTIRDCDPTAHAEIV ALREAARKLGNYRLDGCDLYVTLEPCAMCAGAMIHARLARLVYGAADPKTGAAGS VLDVFANPQLNHHTAVVGGVLADEAGALLREFFAARR |
| 490 | MDDDARFMGEALAEARAAAAAGEVPIGAVVVRDGAVVARAGNRTVRDNDPTAHA EVLALREAARALGSQRLTGCTLYVTLEPCAMCAGAISHARVARLVYGAADPKGGAV AHGPRFFAQPTCHHRPEVTGGVGEAEAAALLRDFFRARR |
| 491 | DRLFMEEALAEARAAAAAGEVPIGAVVVRDGEIVARAGNRTVRDCDPTAHAEIVAL REAARALGNYRLTGCTLYVTIEPCAMCAGAMIHARLDRLVYGADDPKAGAVRSVLQ VLDHPALNHRVEVESGVLAAECAALLQEFFASRR |
| 492 | DSLTRDELYMRRALELAALAEAEGEVPVGAVLVKDGEIVGEGWNRSIGSHDATAHA EIMALRQAGQALQNYRLLDTTLYVTLEPCPMCAGALLHSRVKRVVFGASDLKAGAA GTVLNLFESQASYHYADVESGLLEQECREQLQAFFKRRRKEIKAQRQAEKAAQ |
| 493 | MRAALAEARRAAEAGEVPVGAVVVRDGAVLAAAGNRTVRDCDPTAHAEIVALRAA ARAAGNHRLTGCTLYVTLEPCAMCAGAISHARVARLVYGAADPKGGAVAHGPRFFE QPTCHHRPEVTGGVLAEEAGALLRDFFRARR |
| 494 | MSAALEEARRAAAAGEVPVGAVLVRDGAVLARGGNRTIRDCDPTAHAEIVALRAAA RALGNYRLPGTTLYVTLEPCAMCAGAMIHARVARLVYGAADPKTGAAGSVEDVLR HPALNHRMEVEGGVLAEECGALLRDFFRARR |
| 495 | DDTEFMRLALAEAEAAAAAGEVPVGAVVVRDGEVIARAGNRTIRDCDPTAHAEVVA LREAARKLGNYRLAGCTLYVTLEPCAMCAGAMIHARLDRVVYGAADPKTGAAGSV LDLFATRQLNHHTQVTGGVLAEECGALLRGFFEARR |
| 496 | DTLYMRRALELAAQAEAEGEVPVGAVLVKDGEVIAEGWNRSIGDHDATAHAEIQTL RKAGQVLQNYRLLDTTLYVTLEPCPMCAGALLHSRVKRIVYGAPDLKAGAAGTVLN LFESQASYHYADVESGLLEDECREQLQAFFKRRRKEIKALRQAEKAAEQ |
| 497 | DDPYMALALEEARAAAAAGEVPIGAVVVRDGEVVARAGNRTVRDNDPTAHAEVVA LREAARALGNHRLTGCTLYVTLEPCAMCAGAISHARVARLVYGADDPKGGAVRHG ARVFEHPQCHHRPEVTGGVGAAEAGELLRGFFRARR |
| 498 | MDSKEKDEFFMRRALELARLGEEKGEVPVGAVLVKDGEIIAEGWNQSIGENDATAH AEIMALRKAGKALENYRLLDTTLYVTLEPCPMCAGALLHSRVKRIVFGAPDLKAGA AGTVLNLFESQASYHYADVESGLLEEECREQLQAFFKRRRKEIKEKKKAEKAALEA |
| 499 | MRSALDLAAAAAAAGEVPVGAVVVRDGAIVGRGENRVLRDSDPTAHAEIVALREAA RALGNYRLTGCTLYVTLEPCAMCAGAMIHARIDRLVYGAADPKAGAAGSVLDVLG HPALNHQMEVEGGVLAEECGALLRDFFRARR |
| 500 | MDAALAEARAAADAGEVPVGAVVVRDGVVLARAGNRTVRDADPTAHAEIVALRA AARALGNHRLGGCTLYVTLEPCAMCAGAISHARVARLVYGADDPKGGAVRHGPRL FASPTCHHRPEVVSGVGEAEAAALLRDFFAARR |
| 501 | MDAALEEARRAAAAGEVPVGAVLVRDGVVLARAGNRTIRDCDPTAHAEIVALREAA RAAGNYRLPGTTLYVTLEPCAMCAGAMIHARVDRLVYGAADPRAGAAGSVFDVVR HPALNHRMEVEGGVLADESAALLRGFFRARR |
| 502 | MTSEDEKYMRRALELARQAEQEGEVPVGAVLVKDGEIVAEGWNRSIGDHDATAHA EIETLRKAGQVLENYRLLDTTLYVTLEPCPMCAGALLHSRVKRVVFGAPDLKAGAA GTVLNLFESQASYHYADVESGLLEEECREQLQAFFKRRRKEIKALRQAQKEAEQK |
| 503 | DEPYMRLALDEARAAAAAGEVPIGAVVVRDGEVLARAGNRTVRDNDPTAHAEVLA LREAARALGNHRLTGCTLYVTLEPCAMCAGAISHARVARLVYGADDPKGGAVAHG PRFFAQPTCHHRPEVTGGVLAEEAGALLRDFFRARR |
| 504 | MDAALAEARAAADAGEVPVGAVVVRDGAVLARAGNRTLRDADPTAHAEIVALRAA ARALGNHRLGGCTLYVTLEPCAMCAGAISHARLARLVYGADDPKGGAVAHGPRFFG QPTCHHRPEVVGGVGAAAAGDLLRGFFRARR |
| 505 | RSSPEEAAMDDAGFMRLALAEAEAAAAAGEVPVGAVVVLGGEVIARAGNRTVRDN DPTAHAEIVALREAARKLGNYRLAGCTLYVTLEPCAMCAGAMIHARLARLVYGAAD PKTGAAGSVLDLVAHPALNHRMEVEGGVLAAECGALLRDFFAARRG |

-continued

| SEQ ID NO: | Deaminase Sequence |
|---|---|
| 506 | MTRDEQYMRRALELARQAEAEGEVPVGAVLVRDGEVIAEGWNRSIGAHDATAHAEI MALRQAGQVLENYRLLDTTLYVTLEPCPMCAGALLHSRVKRVVYGAPDLKAGAAG TVLNLFESQASYHYAEVEGGLLEEECREQLQAFFKRRRKEIKAARQARRAAEE |
| 507 | MRAALAEARAAAEAGEVPVGAVVVHEGRIIARAQNRVERDHDPTAHAEILALRAAA AALGATRLGGCTLYVTLEPCAMCAGAIAHARVARLVYGADDPKGGAVAHGPRFFT QPTCHHRPEVTGGVGEAEAAALLRDFFRARR |
| 508 | MDDAGFMREALAEAEAAAAAGEVPVGAVVVKDGEIIARARNATVARNDPTAHAEIL ALREAARVLGNYRLTGCTLYATLEPCAMCAGAILHARIARLVYGAADPKAGACGSV LDVIGHPRLNHRVEVAGGVLAEECGALLREFFRSRR |
| 509 | DETYMRRALELARQAEQAGEVPVGAVLVKDGEIVAEGWNQSIGTHDATAHAEIMAL RAAGQALENYRLVDTTLYVTLEPCPMCAGALLHSRVKRVVFGAADLKAGAAGTVL NLFESQASYHYAEVESGLLEEECREQLQAFFKRRRKEIKALKQAEKAAQE |
| 510 | MNSDDLYMRRALELARQAEEEGEVPVGAVLVKDGEIVAEGWNRSIGSHDATAHAEI ETLRKAGQVLQNYRLLDTTLYVTLEPCPMCAGALLHSRVKRVVFGAPDLKAGAAGT VLNLFESQASYHYADVESGLLEDECREQLQAFFKRRRKEIKALRQAQKEAEE |
| 511 | MDAALAEARAAADAGEVPVGAVLVRDGVVLARAGNRTVRDCDPTAHAEIVALRAA ARALGNYRLPGTTLYVTLEPCAMCAGAMIHARVDRLVFGARDPRAGAAGSVFDVLR HPALNHRVEVVEGVRAEECGALLRDFFRARR |
| 512 | DRLFMRRALELAAQAEAEGEVPVGAVLVKDGEVIAEGWNRSIGSHDATAHAEIETLR KAGQVLENYRLLDTTLYVTLEPCPMCAGALLHSRVKRIVYGAPDLKAGAAGTVLNL FESQASYHYADVESGLLEDECREQLQAFFKRRRKEIKAARQAKREQE |
| 513 | MDDARFMAEALAEARAAAAAGEVPVGAVVVRDGAVLARAGNRTVRDCDPTAHAE IVALREAARALGNYRLDGCTLYVTLEPCAMCAGAMLHARLPRLVYGAADPKTGAA GSVLDLFAERRLNHQTEVRGGVLAEACGALLTDFFRSRRA |
| 514 | DSEFMAEALAEARAAAEAGEVPIGAVVVCDGEIVARAGNRTIRDNDPTAHAEIVALR EAARKLGNYRLTGCTVYVTLEPCAMCAGAMIHARLDRLVYGAADPKAGAAGSVLD VLGHPRLNHQMAVESGVLADECGALLRDFFRSRR |
| 515 | MDSESDLRFMREALAEARAAAAAGEVPVGAVVVRDGAILARAGNRTLRDNDPTAH AEIVALRAAAAALGNHRLTGCTLYVTLEPCAMCAGAISHARIARLVYGAADPKGGA VAHGPRFFEQPTCHHRPEVAGGVLAEEAGALLRAFFAARR |
| 516 | MSSDAGFMAEALAEARAAAAAGEVPVGAVVVRDGAIVARAGNRTVRDNDPTAHAE VVALREAARALGNHRLGGCELYVTLEPCAMCAGAISHARIARLYYGADDPKGGAVA HGARVFSHPQCHHRPEVYDGIGAGEAAALLRDFFAARR |
| 517 | DRDDRYMRLALEEARAAAEAGEVPIGAVVVRDGEVLARAGNRTVRDCDPTAHAEIV ALREAARVLGNYRLAGCTLYVTVEPCAMCAGAMIHARVDRLVYGADDPKGGAVRS CLQVLDHPRLNHRVEVTAGVLAEECAALLQSFFAARR |
| 518 | DSEFMAEALAEARAAAAAGEVPVGAVVVRDGEIVARAGNRTLRDNDPTAHAEIVAL REAARALGNHRLTGCTLYVTLEPCAMCAGAISHARIARLVYGADDPKGGGVAHGAR VFEHPQCHHRPEVVGGVGAAEAGELLRGFFAARR |
| 519 | DREEYLMRKALELAAKAEQLGEVPVGAVLVKDGEIIAEGWNQSIGNHDATAHAEIM TLRQAGQALENYRLLDTTLYVTLEPCPMCAGALLHSRVKRIVFGAPDLKAGAAGTV LNLFESQASYHYADVESGLLEDECREQLQAFFKRRRKEIKALKQAKRDAEEN |
| 520 | MDAALAEARAAADAGEVPVGAVVVRDGAVLARAGNRTLRDADPTAHAEIVALRAA ARALGNHRLGGCTLYVTLEPCAMCAGAISHARLARLHYGAADPKGGAVEHGPRFFA QPTCHHRPDVYGGIGEGEAAALLRGFFAARR |
| 521 | DEPYMRLALDEARAAAAAGEVPIGAVVVKDGEVIARARNRTLADNDPTAHAEIVAL RAAAAALGNHRLTGCELYVTLEPCAMCAGAISHARIARLVYGADDPKGGAVAHGPR FFAQPTCHHRPEVVGGVGEGEAAELLRGFFAARR |
| 522 | DRDSRFMREALAEARAAAEAGEVPIGAVVVRDGEIVARAGNRTVRDCDPTAHAEIV ALREAARALGNYRLTGCTLYVTIEPCAMCAGAMIHARIDRLVYGAADPKAGAAGSV LDVLGHPRLNHRMEVTAGVLAEECAALLRDFFAARR |
| 523 | MDAALEEARRAAAAGEVPVGAVLVHDGQILARAGNRTIRDNDPTAHAEIVVLREAA RALGNYRLEGCTLYVTLEPCAMCAGAMIHARLPRLVYGADDPKAGAAGSVLDVLN HPALNHRMEVEGGVLAAECGALLRDFFRARR |

-continued

| SEQ ID NO: | Deaminase Sequence |
|---|---|
| 524 | MSAADDIRFMREALAEARAAAAAGEVPVGAVVVRDGAILARAGNRTIRDCDPTAHA EVVALREAARALGNHRLTGCTLYVTLEPCAMCAGAISQARVARLVYGADDPKGGA VAHGPRFFAQPTCHHRPEVTGGVLAEEAGALLRDFFRARR |
| 525 | MTDADFMALALEEARAAAALGEVPVGAVVVKDGEVIARAGNRTIRDCDPTAHAEV VALREAARKLGNYRLPGLTLYVTLEPCAMCAGAMIHARLDRVVYGADDPKGGAAR SVYRILDDPRLNHQVAVTSGVLAEECGALLRDFFRARR |
| 526 | MDSAAKDLCYMRRALELAALAEAEGEVPVGAVLVRDGEIVGEGWNRSIGSHDATA HAEIMALRQAGQALQNYRLLDTTLYVTLEPCPMCAGALLHSRVKRVVFGAPDLKAG AAGTVLNLFESQASYHYADVEGGLLAEECRAQLQAFFKRRRKEQKALRQAQKEAA |
| 527 | DEEFMREALAEAQAAADAGEVPIGAVVVCDGEIVARAGNRTIRDNDPTAHAEIVALR EAARKLGNYRLAGCTLYVTLEPCAMCAGAMIHARVDRLVYGADDPKAGAAGSVLD VIGHPRLNHRMEVTSGVLAEECGAMLREFFRRRRA |
| 528 | MDDAGFMRLALAEARAAAAAGEVPVGAVVVRGGEVLAAAGNRTLRDCDPTAHAE VVALRAAARALGNHRLDGCDLYVTLEPCAMCAGAISHARIARLYYGADDPKGGAV AHGPRFFAQPTCHHRPEVYGGIGESEAAALLRDFFAARR |
| 529 | MSDEDYMRLALAEAQAAADAGEVPVGAVLVAGGEVVARGRNRMIADSDPTAHAEI VALREAARRLGNYRLTGCTLYVTLEPCAMCAGAIVHARLDRVVYGAADPKAGAAG SVLDVLGHPRLNHRTEVTGGVLADECGALLKDFFRARR |
| 530 | MSSEDEKYMRRALELARQAEEEGEVPVGAVLVKDGEIVAEGWNRSIGSHDATAHAE IETLRKAGQALENYRLLDTTLYVTLEPCPMCAGALLHSRVKRIVFGAPDLKAGAAGT VLNLFESQASYHYADVESGLLEDECREQLQAFFKRRRKEIKAARKAAKAE |
| 531 | MSDDAAFMGEALAEARAAAAAGEVPIGAVVVCDGAIVARAGNRTVRDNDPTAHAE IVALREAAARLGNYRLTGCTLYVTLEPCAMCAGAMIHARIDRLVYGAADPKAGAAG SVLDVIGHPRLNHRMEVEGGVLAAECGALLRDFFASRR |
| 532 | MRAALAEAERAAAAGEVPVGAVVVRDGAVLAAAGNRTVRDCDPTAHAEVLALRA AARALGNHRLTGCTLYVTLEPCAMCAGAISHARVARLVYGADDPKGGAVAHGPRFF AQPTCHHRPEVAGGLGAAAAGELLRAFFRARR |
| 533 | MRAALDEARAAAAAGEVPVGAVVVHEGRIVARAQNRMRRDNDPTAHAEIVALRAA AAALGSMRLTGCTLYVTLEPCAMCAGAISHARIDRLVYGAADPKGGAVAHGPRFFE QPTCHHRPDVVGGVLAEEAGALLRGFFAARR |
| 534 | MDSAAKDLCYMRRALELAALAEAEGEVPVGAVLVKDGEIVGEGWNRSIGSHDATA HAEIMALRQAGQALQNYRLLDTTLYVTLEPCPMCAGALLHSRVKRVVFGAPDLKAG AAGTVLNLFESQASYHYADVESGLLEQECREQLQAFFKRRRKEIKAQRDAQRAADE |
| 535 | MNDEFYMRRALELAALAEEHNEVPVGAVLVLNGEIIGEGWNRSIGQHDATAHAEIM ALRQAGKVLQNYRLLDTTLYVTLEPCPMCAGALVHSRVKRVVYGTPDLKAGAAGT VMNLLSYDAVNHHVAITSGVLAEECREQLQAFFRRRRAEKKALKQAQRA |
| 536 | DDTFYMRRALELARQAEAEGEVPVGAVLVRDGEVIAEGWNRSIGDHDATAHAEIQV LRKAGQVLQNYRLLDTTLYVTLEPCPMCAGALLHSRVKRVVYGAPDLKAGAAGTV LNLFESQASYHYADVESGLLEEECREQLQAFFKRRRKEIKAARQAKRAAE |
| 537 | MRSALDLAAAAAAAGEVPVGAVVVRDGAIVGRGENRVLRDSDPTAHAEIVAMREA ARALGNYRLTGCTLYVTLEPCAMCAGAMIHARIDRLVYGAADPKAGAAGSVLDVL NHPRLNHQMEVEGGVLAAECGAMLRDFFRARR |
| 538 | MDDDALMGLALDEARAAAAAGEVPIGAVVARDGEVVARAGNRTVRDCDPTAHAEI VALREAARKLGNYRLTGCTLYVTLEPCAMCAGAMIHARLDRLVYGAADPKTGAAG SVLDVLGHPALNHQTQVEGGVLAEECGALLRDFFRERR |
| 539 | MTEEDKYFMRRAIELAKLAEENGEVPVGAVLVKDGEIIAEGWNQSIGSHDATAHAE MMAIREAGKVLENYRLLDTTLYVTLEPCPMCAGALLHSRVKRIVFGAPDLKAGAAG TVLNLFESQASYHYADVESGLLEEECREQLQAFFKRRRKEIKALKKAQKEAEE |
| 540 | DDDYMRLALAEARAAAEAGEVPIGAVVVCGGEVVARAGNRTVADCDPTAHAEIVA LREAARKLGNYRLTGCTLYVTLEPCAMCAGAMIHARLDRLVYGADDPKAGAAGSV LDVLGHPALNHQMQVTAGVLADECAALLRDFFRARR |
| 541 | DDSFYMRRALELAALAEREGEVPVGAVLVKDGEIIAEGWNRSIGSHDATAHAEIETL RKAGQALQNYRLLDTTLYVTLEPCPMCAGALLHSRVKRIVFGAPDLKAGAAGTVLN LFESQASYHYADVESGLLEEECREQLQAFFKRRRKEIKAQRDAEKAAAEK |

-continued

| Sequences | |
|---|---|
| SEQ ID NO: | Deaminase Sequence |
| 542 | MDAALAEARAAADAGEVPVGAVVVRDGAVLARAGNRTLRDSDPTAHAEIVALRAA ARALGNHRLGGCDLYVTLEPCAMCAGAISHARIARLYYGADDPKGGAVAHGARVF AHPQCHHRPEVYDGIGAAEAAALLRDFFAARR |
| 543 | MTRDEQYMRRALELARQAEAEGEVPVGAVLVKDGEIIAEGWNRSIGSHDATGHAEI MALRAAGQALENYRLLDTTLYVTLEPCPMCAGALLHSRVKRVVFGAPDLKAGAAG TVLNLFESQASYHYADVESGLLEEECREQLQAFFKRRRKEIKALRQAEKAAAE |
| 544 | MTDADFMALALEEARAAAALGEVPVGAVVVKDGEVIARAGNRTIRDCDPTAHAEIV ALREAARKLGNYRLPGLALYVTLEPCAMCAGAMIHARLARLVYGAADPKTGAAGS VLDVLGHPALNHQTAVTGGVLAEEAGALLRDFFAARRAAG |
| 545 | MDAALAEARAAADAGEVPVGAVVVRDGAVLARAGNRTLRDADPTAHAEIVALRAA ARALGNHRLPGCTLYVTLEPCAMCAGAISHARIARLVYGAADPKGGAVAHGPRFFE QPTCHHRPEVVGGLGETEAAALLRAFFAARR |
| 546 | MDAALEEARRAAAAGEVPVGAVLVAGGRVLARAGNRTIRDCDPTAHAEIVALRAA ARALGNYRLPGTTLYVTLEPCAMCAGAMIHARVARLVYGAADPKTGAAGSVEDVL GSGRLNHRVAVEGGVRAEECGALLRDFFRARR |
| 547 | DDDERWMREALAEARAAAEAGEVPVGAVVVRDGELIARGRNRVEADADPSAHAEI VALREAARRLGNHRLTGCTLYVTLEPCAMCAGAISHARVARLVYGADDPKGGAVR HGARVFEQPTCHHRPEVVGGVLASESAALLRDFFRARR |
| 548 | MSAADEQFMRRAIELARQAEAEGEVPVGAVLVKDGEIVAEGWNRSIGAHDATAHAE IETLRKAGQALENYRLLDTTLYVTLEPCPMCAGALLHSRVKRVVFGAPDLKAGAAG TVLNLFESQASYHYADVESGLLEEECREQLQAFFKRRRKEIKALRQAQKAAEE |
| 549 | MSSAPSDADFMGLALEQARLAAAAGEVPVGAVVVRDGEVIAQAHNRTVADCDPTA HAEVVALRAAARALGNHRLTGCTLYVTLEPCAMCAGAIAHARVARVVYGAADPKG GAVEHGPRFFAQPTCHHRPEVVGGVGAAEAGALLRDFFRARR |
| 550 | MDEALAEARRAAAAGEVPVGAVVVRDGVVLARAGNRTVRDADPTAHAEIVALRAA AAALGNYRLDGCTLYVTLEPCAMCAGAMVHARLARLVYGAADPRAGAAGSVLDV LGHPALNHRMEVAGGVRAEECAALLRDFFAARRG |
| 551 | MDEALAEARRAAEAGEVPVGAVVVRDGAVLARAGNRTVRDCDPTAHAEVLALREA ARALGNHRLAGCTLYVTLEPCAMCAGAISHARVARLVYGADDPKGGAVAHGPRFF GQPTCHHRPEVAAGLGAAEAGALLRDFFAARR |
| 552 | DTSFMRLALDEARAAADAGEVPVGAVVVCDGEVIARAGNRTVRDCDPTAHAEIVAL REAARRLGNYRLAGCTLYVTLEPCAMCAGAMIHARLDRLVYGAADPKAGAAGSVL DVLGHPALNHQTQVEGGVLAAECGALLRDFFRARR |
| 553 | DTLFMRRALELAAQAEAEGEVPVGAVLVKDGEVIAEGWNRSIGSHDATAHAEIETLR KAGQVLQNYRLLDTTLYVTLEPCPMCAGALLHSRVKRIVYGAPDLKAGAAGTVLNL FESQASYHYAEVESGLLEEECREQLQAFFKRRRKEIKALRQAEKEAEK |
| 554 | MDDEFFMRQALREARKAYDEGEVPVGAVVVRDGKVIARGRNQVERLKDPTAHAEM IALTAAAAHLGSKWLKGCTLYVTVEPCAMCAGALVLARLERLVFGARDPKAGACGS VLDIVRHPRLNHRVEVVSGVLEEECGALLKEFFRRLR |
| 555 | MTRDEQYMRRALALARQAEAEGEVPVGAVLVKDGEVIAEGWNRSIGRHDATAHAEI ETLRKAGQVLGNYRLLDTTLYVTLEPCPMCAGALLHSRVKRVVFGAPDLKAGAAGT VLNLFESQASYHYADVESGLLEDECREQLQAFFKRRRKEIKAARKAAKEAE |
| 556 | MDAALEEARRAAAAGEVPVGAVLVRDGEVLARAGNRTVRDNDPTAHAEILVIREAA RRLGNYRLEGCVLYVTLEPCAMCAGAMVHARLPRLVYGAADPKAGAAGSVLDVLG HPALNHRVEVTGGVLADACGALLRDFFAARR |
| 557 | MDEALAEARRAAAAGEVPVGAVLVRDGEVLARGGNRTIRDCDPTAHAEIVALREAA RRAGNYRLPGTTLYVTLEPCAMCAGAMIHARVARLVYGAADPRAGAAGSVEDVLR HPALNHRMEVEGGVRAEECGALLREFFRARR |
| 558 | MTEKDEFYMKRAIELARKGEEEGEVPVGAVLVKDGEIIAEGWNRSIGSHDATAHAEI ETLRKAGQALENYRLLDTTLYVTLEPCPMCAGALLHSRVKRVVFGAPDLKAGAAGT VLNLFESQASYHYADVESGLLEEECREQLQAFFKRRRKEIKALKKAKKEEQDK |
| 559 | DDDFMALALEEARAAAEAGEVPIGAVVVCDGEVVARAGNRTVRDNDPTAHAEIVAL REAARKLGNYRLAGCTLYVTLEPCAMCAGAMIHARLDRVVYGADDPKAGAARSVL NVLDHPALNHRVAVEGGVLADECGALLREFFRARR |

-continued

| Sequences | |
|---|---|
| SEQ ID NO: | Deaminase Sequence |
| 560 | MTEEDKYFMQRAIELARQAELAGEVPVGAVLVKDGEIIAEGWNQSIGSHDATAHAEIMALRQAGQVLQNYRLLDTTLYVTLEPCPMCAGALLHSRVKRVVFGAPDLKAGAAGTVLNLFESQASYHYADVESGLLEQECREQLQAFFKRRRKEIKALKQAQKEAEN |
| 561 | MTDEEYMRRALELARQAEQQGEVPVGAVLVKDGEVIAEGWNQSIGSHDATAHAEIMALRAAGQALENYRLLDTTLYVTLEPCPMCAGALLHSRVKRVVFGAPDLKAGAAGTVLNLFESQASYHYADVESGLLEEECREQLQAFFKRRRKEIKAARQAKREAE |
| 562 | MSEQDEFYMRRAIELARQAEAEGEVPVGAVLVKDGEIVAEGWNRSIGSHDATAHAEIETLRKAGQALQNYRLLDTTLYVTLEPCPMCAGALLHSRVKRVVFGAPDLKAGAAGTVLNLFESQASYHYAEVESGLLEEECREQLQAFFKRRRKEIKALRQAQKEAEEK |
| 563 | DDTLYMKRALELARQAEAEGEVPVGAVLVKDGEVIAEGWNRSIGSHDATAHAEIETLRKAGQALQNYRLLDTTLYVTLEPCPMCAGALLHSRVKRIVFGAPDLKAGAAGTVLNLFESQASYHYAEVESGLLEEECREQLQAFFKRRRKEIKALRQAEKEAE |
| 564 | DETYMRRALELARQAEEHGEVPVGAVLVKDGEIIAEGWNRSIGDHDATAHAEIMALREAGKTLENYRLLDTTLYVTLEPCPMCAGALLHSRVKRVVYGAPDLKAGAAGTVLNLFESQASYHYAEVESGLLEEECREQLQAFFKRRRKEIKAARKARREAEEK |
| 565 | MTDADFMALALEEARAAAALGEVPVGAVVVRDGAVIARAGNRTIRDCDPTAHAEIVALRAAARALGNYRLDGCDLYVTLEPCAMCAGAMIHARLARLVYGAADPKTGAAGSVLDVFANPRLNHHTAVVGGVLADEAAALLRGFFAARR |
| 566 | DDEKWMRYALSLADKAEALGEVPVGAVLVKDNQVIGEGWNQSISGHDATAHAEIMAIRDAGKNLQNYRLIDCTLYVTLEPCPMCAGAIVHSRIKRVVFGASDYKTGAAGSVFNLLSNEQLNHQAEVTAGVLAEECGEKISAFFKRRRKEKKAAKKAAKLAE |
| 567 | MTEEDKYFMRRAIELAKLAEENGEVPVGAVLVKDGEIIAEGWNQSIGSHDATAHAEMMAIRQAGQVLENYRLLDTTLYVTLEPCPMCAGALLHSRVKRIVFGAPDLKAGAAGTVLNLFESQASYHYADVESGLLEEECREQLQAFFKRRRKEIKALKKAQKEAE |
| 568 | MTDDERWMREALAEARAAEAAGEVPVGAVVVRDGELIARGRNRVLRDSDPTAHAEIVALREAARALGNYRLDGCTLYATLEPCAMCAGAMLHARLARLVYGAADPKAGAAGSVLDVLGHPRLNHRMEVTGGVLAEEAGALLREFFRARR |
| 569 | DDSFYMRRALELAALAEAEGEVPVGAVLVKDGEIIAEGWNRSIGDHDATAHAEIQVLRKAGQALQNYRLLDTTLYVTLEPCPMCAGALLHSRVKRIVYGAPDLKAGAAGTVLNLFESQASYHYAEVESGLLEEECREQLQAFFKRRRKEIKALRQAEKEAQN |
| 570 | DEEFMREALAEAQAAADAGEVPIGAVVVCDGEIVARAGNRTIRDNDPTAHAEIVALREAARKLGNYRLAGCTLYVTLEPCAMCAGAMIHARIDRLVYGADDPKAGAAGSVLDVLGHPRLNHQMQVERGVLAAECGAMLTRFFQARR |
| 571 | MTEADEKFMRRAIELAREAEEHGEVPVGAVLVKDGEIIAEGWNRSIGEHDATAHAEIETLRKAGQVLENYRLLDTTLYVTLEPCPMCAGALLHSRVKRIVFGAPDLKAGAAGTVLNLFESQASYHYADVESGLLEEECREQLQAFFKRRRKEIKALRQAEKAAG |
| 572 | MRDALALAAAAAAAGEVPVGAVVVHGGEIVGRGENRVLRDSDPTAHAEIVALREAARALGNYRLTGCDLYVTLEPCAMCAGAMIHARIARLVYGAADPKAGAAGSVLDVLNHPRLNHRMEVTGGVLAEECGALLRDFFRARR |
| 573 | MTEEDKYFMQRAIELARLAEENGEVPVGAVLVKDGEIIAEGWNQSIGNHDATAHAEIMTLRQAGQVLQNYRLLDTTLYVTLEPCPMCAGALLHSRVKRIVFGAPDLKAGAAGTVLNLFESQASYHYADVESGLLEDECREQLQAFFKRRRKEIKALKKAKRDAEN |
| 574 | MDPTDLAFMREALAEARAAAEAGEFPIGAVVVCDGRIVARAHNRPIALSDPTAHAEILALREAARALGNYRLTGCTLYATLEPCAMCAGAILHARIARLVYGVANPGAGACGSVLDVMNHPRLNHRVEVTGGVLAEECGALLSGFFRAR |
| 575 | MDPTDLAFMREALAEARAAAEAGEVPVGAVVVCDGRIVARAHNRPIALSDPTAHAEILALREAARALGNIRLTGCTLYATLEPCAMCAGAILHARIARLVYGVANPGAGACGSVLDVMNHPRLNHRVEVTGGVLAEECGALLSGFFRAR |
| 576 | MDDAGFMRLALEEARAAAAAGEVPVGAVVVRDGEVLARAGNRTVRDCDPTAHAEIVALREAARRLGNYRLAGCTLYVTLEPCAMCAGAMIHARLDRLVYGVANPKTGAAGSVLDVLGHPRLNHRMEVEGGVLAAECGALLRDFFRAR |
| 577 | MDDAGFMRLALEEARAAAAAGEVPVGAVVVRDGEVLARAGNRTVRDCDPTAHAEIVALREAARRLGNYRLAGCTLYVTLEPCAMCAGAMIHARLDRLVYGVANPGCGAAGSVLDVLGHPRLNHRMEVEGGVLAAECGALLRDFFRAR |

-continued

| Sequences | |
|---|---|
| SEQ ID NO: | Deaminase Sequence |
| 578 | MTDEYFMRQALREARRAYDEGEVPVGAVVVRDGRVIARGRNQVERLKDPTAHAEMLALTAAAGHLGSGRLTGCTLYVTVEPCAMCAGALVWARVERVVFGVRNPKTGACGSVFDIPGDRRLNHRPEVVGGVLEAECAALMRDFFRER |
| 579 | MDPTDLAFMREALAEARAAAEAGEVPVGAVVVCDGRIVARAHNRPIALSDPTAHAEILALREAARALGNYRLTGCTLYATLEPCAMCAGAILHARIARLVYGVANPGAGACGSVLDVMNHPRLNHRVEVTGGVLAEECGALLSGFFRAR |
| 580 | MDPTDLAFMREALAEARAAAEAGEVPIGAVVVCDGRIVARAHNRPIALSDPTAHAEILALREAARALGNYRLTGCTLYATLEPCAMCAGAILHARIARLVYGVANAGAGACGSVLDVMNHPRLNHRVEVTGGVLAEECGALLSGFFRAR |
| 581 | MDDAGFMRLALEEARAAAAAGEVPIGAVVVRDGEVLARAGNRTVRDCDPTAHAEIVALREAARRLGNYRLAGCTLYVTLEPCAMCAGAMIHARLDRLVYGVANPKTGAAGSVLDVLGHPRLNHRMEVEGGVLAAECGALLRDFFRAR |
| 582 | MDDAGFMRLALEEARAAAAAGEVPIGAVVVRDGEVLARAGNRTVRDCDPTAHAEIVALREAARRLGNYRLAGCTLYVTLEPCAMCAGAMIHARLDRLVYGVANPGAGAAGSVLDVLGHPRLNHRMEVEGGVLAAECGALLRDFFRAR |
| 583 | MTDEYFMRQALREARRAYDEGEVPVGAVVVRDGRVIARGRNQVERLKDPTAHAEMLALTAAAGHLGSSRLTGCTLYVTVEPCAMCAGALVWARVERVVFGVRNPKTGACGSVFDIPGDRRLNHRPEVVGGVLEAECAALMRDFFRER |
| 584 | MTDEYFMRQALREARRAYDEGEVPVGAVVVRDGRVIARGRNQVRRLKDPTAHAEMLALTAAAGHLGSPRLTGCTLYVTVEPCAMCAGALVWARVERVVFGVRNPKTGACGSVFDIPGDRRLNHRPEVVGGVLEAECAALMRDFFRER |
| 585 | MDPTDLAFMREALAEARAAAEAGEVPIGAVVVCDGRIVARAHNRPIALSDPTAHAEILALREAARALGNYRLTGCTLYATLEPCAMCAGAILHARIARLVYGVANPGAGACGSVLDVMNHPRLNHRVEVTGGVLAEECGALLSGFFRAR |
| 586 | MDPTDLAFMREALAEARAAAEAGELPIGAVVVCDGRIVARAHNRPIALSDPTAHAEILALREAARALGNYRLTGCTLYATLEPCAMCAGAILHARIARLVYGVANPGTGACGSVLDVMNHPRLNHRVEVTGGVLAEECGALLSGFFRAR |
| 587 | MDPTDLAFMREALAEARAAAEAGEMPVGAVVVCDGRIVARAHNRPIALSDPTAHAEILALREAARALGNYRLTGCTLYATLEPCAMCAGAILHARIARLVYGVANPGAGACGSVLDVMNHPRLNHRVEVTGGVLAEECGALLSGFFRAR |
| 588 | MDDAGFMRLALEEARAAAAAGEVPIGAVVVRDGEVLARAGNRTVRDCDPTAHAEIVALREAARRLGNYRLAGCTLYVTLEPCAMCAGAMIHARLDRLVYGVANPKAGAAGSVLDVLGHPRLNHRMEVEGGVLAAECGALLRDFFRAR |
| 589 | MDDAGFMRLALEEARAAAAAGEVPVGAVVVRDGEVLARAGNRTVRDCDPTAHAEIVALREAARRLGNYRLAGCTLYVTLEPCAMCAGAMIHARLDRLVYGVANPGRGAAGSVLDVLGHPRLNHRMEVEGGVLAAECGALLRDFFRAR |
| 590 | MDDAGFMRLALEEARAAAAAGEVPIGAVVVRDGEVLARAGNRTVRDCDPTAHAEIVALREAARRLGNYRLAGCTLYVTLEPCAMCAGAMIHARLDRLVYGVANPGSGAAGSVLDVLGHPRLNHRMEVEGGVLAAECGALLRDFFRAR |
| 591 | MTDEYFMRQALREARRAYDEGEVPVGAVVVRDGRVIARGRNQVIRLKDPTAHAEMLALTAAAGHLGSPRLTGCTLYVTVEPCAMCAGALVWARVERVVFGVRNPKTGACGSVFDIPGDRRLNHRPEVVGGVLEAECAALMRDFFRER |
| 592 | MDPTDLAFMREALAEARAAAEAGEIPVGAVVVCDGRIVARAHNRPIALSDPTAHAEILALREAARALGNYRLTGCTLYATLEPCAMCAGAILHARIARLVYGVANPGAGACGSVLDVMNHPRLNHRVEVTGGVLAEECGALLSGFFRAR |
| 593 | MDPTDLAFMREALAEARAAAEAGELPIGAVVVCDGRIVARAHNRPIALSDPTAHAEILALREAARALGNYRLTGCTLYATLEPCAMCAGAILHARIARLVYGVANPGAGACGSVLDVMNHPRLNHRVEVTGGVLAEECGALLSGFFRAR |
| 594 | MDPTDLAFMREALAEARAAAEAGEVPVGAVVVCDGRIVARAHNRPIALSDPTAHAEILALREAARALGNVRLTGCTLYATLEPCAMCAGAILHARIARLVYGVANPGAGACGSVLDVMNHPRLNHRVEVTGGVLAEECGALLSGFFRAR |
| 595 | MDPTDLAFMREALAEARAAAEAGEVPIGAVVVCDGRIVARAHNRPIALSDPTAHAEILALREAARALGNSRLTGCTLYATLEPCAMCAGAILHARIARLVYGVANPGAGACGSVLDVMNHPRLNHRVEVTGGVLAEECGALLSGFFRAR |

-continued

| Sequences | |
|---|---|
| SEQ ID NO: | Deaminase Sequence |
| 596 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGVANPKRGAAG SVLDVLGHPRLNHRMEVEGGVLAAECGALLRDFFRAR |
| 597 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGVANPGSGAAG SVLDVLGHPRLNHRMEVEGGVLAAECGALLRDFFRAR |
| 598 | MDDAGFMRLALEEARAAAAAGEVPVGAVVVRDGEVLARAGNRTVRDCDPTAHAEI VALREAARRLGNFRLAGCTLYVTLEPCAMCAGAMIHARLDRLVYGVANPGRGAAG SVLDVLGHPRLNHRMEVEGGVLAAECGALLRDFFRAR |
| 599 | MDPTDLAFMREALAEARAAAEAGEVPVGAVVVCDGRIVARAHNRPIALSDPTAHAE ILALREAARALGNYRLTGCTLYATLEPCAMCAGAILHARIARLVYGVANDGAGACG SVLDVMNHPRLNHRVEVTGGVLAEECGALLSGFFRAR |
| 600 | MDPTDLAFMREALAEARAAAEAGEFPVGAVVVCDGRIVARAHNRPIALSDPTAHAEI LALREAARALGNYRLTGCTLYATLEPCAMCAGAILHARIARLVYGVANPGTGACGS VLDVMNHPRLNHRVEVTGGVLAEECGALLSGFFRAR |
| 601 | MDPTDLAFMREALAEARAAAEAGEVPIGAVVVCDGRIVARAHNRPIALSDPTAHAEI LALREAARALGNWRLTGCTLYATLEPCAMCAGAILHARIARLVYGVANPGAGACGS VLDVMNHPRLNHRVEVTGGVLAEECGALLSGFFRAR |
| 602 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGVANAGSGAAG SVLDVLGHPRLNHRMEVEGGVLAAECGALLRDFFRAR |
| 603 | MTDEYFMRQALREARRAYDEGEVPVGAVVVRDGRVIARGRNQVERLKDPTAHAEM LALTAAAGHLGSGRLTGCTLYVTVEPCAMCAGALVWARVERVVFGVRNPKTGACG SVFDIPGDRRLSHRPEVVGGVLEAECAALMRDFFRER |
| 604 | MTDEYFMRQALREARRAYDEGEVPVGAVVVRDGRVIARGRNQVRRLKDPTAHAEM LALTAAAGHLGSRRLTGCTLYVTVEPCAMCAGALVWARVERVVFGVRNPKTGACG SVFDIPGDRRLNHRPEVVGGVLEAECAALMRDFFRER |
| 605 | MDPTDLAFMREALAEARAAAEAGEIPIGAVVVCDGRIVARAHNRPIALSDPTAHAEIL ALREAARALGNYRLTGCTLYATLEPCAMCAGAILHARIARLVYGVANPGAGACGSV LDVMNHPRLNHRVEVTGGVLAEECGALLSGFFRAR |
| 606 | MDPTDLAFMREALAEARAAAEAGEFPVGAVVVCDGRIVARAHNRPIALSDPTAHAEI LALREAARALGNYRLTGCTLYATLEPCAMCAGAILHARIARLVYGVANPGAGACGS VLDVMNHPRLNHRVEVTGGVLAEECGALLSGFFRAR |
| 607 | MDPTDLAFMREALAEARAAAEAGEIPVGAVVVCDGRIVARAHNRPIALSDPTAHAEI LALREAARALGNYRLTGCTLYATLEPCAMCAGAILHARIARLVYGVANAGAGACGS VLDVMNHPRLNHRVEVTGGVLAEECGALLSGFFRAR |
| 608 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGVANPGTGAAG SVLDVLGHPRLNHRMEVEGGVLAAECGALLRDFFRAR |
| 609 | MTDEYFMRQALREARRAYDEGEVPVGAVVVRDGRVIARGRNQVERLKDPTAHAEM LALTAAAGHLGSRSLTGCTLYVTVEPCAMCAGALVWARVERVVFGVRNPRAGACG SVFDIPGDRRLNHRPEVVGGVLEAECAALMRDFFRER |
| 610 | MTDEYFMRQALREARRAYDEGEVPVGAVVVRDGRVIARGRNQVVRLKDPTAHAEM LALTAAAGHLGSPRLTGCTLYVTVEPCAMCAGALVWARVERVVFGVRNPKTGACG SVFDIPGDRRLNHRPEVVGGVLEAECAALMRDFFRER |
| 611 | MDPTDLAFMREALAEARAAAEAGEVPIGAVVVCDGRIVARAHNRPIALSDPTAHAEI LALREAARALGNYRLTGCTLYATLEPCAMCAGAILHARIARLVYGVANDGAGACGS VLDVMNHPRLNHRVEVTGGVLAEECGALLSGFFRAR |
| 612 | MDPTDLAFMREALAEARAAAEAGEVPVGAVVVCDGRIVARAHNRPIALSDPTAHAE ILALREAARALGNYRLTGCTLYATLEPCAMCAGAILHARIARLVYGVANSGAGACGS VLDVMNHPRLNHRVEVTGGVLAEECGALLSGFFRAR |
| 613 | MDPTDLAFMREALAEARAAAEAGEVPIGAVVVCDGRIVARAHNRPIALSDPTAHAEI LALREAARALGNTRLTGCTLYATLEPCAMCAGAILHARIARLVYGVANPGAGACGS VLDVMNHPRLNHRVEVTGGVLAEECGALLSGFFRAR |

-continued

| Sequences | |
|---|---|
| SEQ ID NO: | Deaminase Sequence |
| 614 | MTDEYFMRQALREARRAYDEGEVPVGAVVVRDGRVIARGRNQVNRLKDPTAHAEM LALTAAAGHLGSPRLTGCTLYVTVEPCAMCAGALVWARVERVVFGVRNPKAGACG SVFDIPGDRRLNHRPEVVGGVLEAECAALMRDFFRER |
| 615 | MTDEYFMRQALREARRAYDEGEVPVGAVVVRDGRVIARGRNQVNRLKDPTAHAEM LALTAAAGHLGSRSLTGCTLYVTVEPCAMCAGALVWARVERVVFGVRNPKTGACG SVFDIPGDRRLNHRPEVVGGVLEAECAALMRDFFRER |
| 616 | MDPTDLAFMREALAEARAAAEAGEVPIGAVVVCDGRIVARAHNRPIALSDPTAHAEI LALREAARALGNYRLTGCTLYATLEPCAMCAGAILHARIARLVYGVANAGTGACGS VLDVMNHPRLNHRVEVTGGVLAEECGALLSGFFRAR |
| 617 | MDPTDLAFMREALAEARAAAEAGEFPIGAVVVCDGRIVARAHNRPIALSDPTAHAEI LALREAARALGNYRLTGCTLYATLEPCAMCAGAILHARIARLVYGVANPGTGACGS VLDVMNHPRLNHRVEVTGGVLAEECGALLSGFFRAR |
| 618 | MDPTDLAFMREALAEARAAAEAGEVPIGAVVVCDGRIVARAHNRPIALSDPTAHAEI LALREAARALGNIRLTGCTLYATLEPCAMCAGAILHARIARLVYGVANPGTGACGSV LDVMNHPRLNHRVEVTGGVLAEECGALLSGFFRAR |
| 619 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGVANPGAGAAG SVLDVLGHPRLNHRMEVEGGVLAAECGALLRDFFRAR |
| 620 | MDDAGFMRLALEEARAAAAAGEVPVGAVVVRDGEVLARAGNRTVRDCDPTAHAEI VALREAARRLGNYRLAGCTLYVTLEPCAMCAGAMIHARLDRLVYGVANAGRGAAG SVLDVLGHPRLNHRMEVEGGVLAAECGALLRDFFRAR |
| 621 | MDPTDLAFMREALAEARAAAEAGEVPVGAVVVCDGRIVARAHNRPIALRDPTAHAE VLALREAAAALGSYRLTGCTLYATLEPCPMCAGAILHARIARLVYGVANPKAGACGS VLDVMNHPRLNHRVEVTGGVLAEECGALLSGFFRAR |
| 622 | MDPTDLAFMREALAEARAAAEAGEVPVGAVVVCDGRIVARAHNRPIALKDPTAHAE VLALREAAAALGSYRLTGCTLYATLEPCPMCAGAILHARIARLVYGVANPKAGACGS VLDVMNHPRLNHRVEVTGGVLAEECGALLSGFFRAR |
| 623 | MDPTDLAFMREALAEARAAAEAGEVPVGAVVVCDGRIVARAHNRPIALNDPTAHAE VLALREAGKALGSYRLTGCTLYATLEPCPMCAGAILHARIARLVYGVANPKAGACGS VLDVMNHPRLNHRVEVTGGVLAEECGALLSGFFRAR |
| 624 | MDPTDLAFMREALAEARAAAEAGEVPVGAVVVCDGRIVARAHNRPIALRDPTAHAE VLALREAARALGSYRLTGCTLYATLEPCPMCAGAILHARIARLVYGVANPKAGACGT VLDVMNHPRLNHRVEVTGGVLAEECGALLSGFFRAR |
| 625 | MDDAGFMRLALEEARAAAAAGEVPVGAVVVRDGEVLARAGNRTVRDRDPTAHAEI VAIREAARRLGSYRLAGCTLYVTLEPCPMCAGAMIHARLDRLVYGVANPKAGAAGT VLDVLGHPRLNHRMEVEGGVLAAECGALLRDFFRAR |
| 626 | MTDEYFMRQALREARRAYDEGEVPVGAVVVRDGRVIARGRNQVRRLKDPTAHAEM LALTAAAGHLGSRSLTGCTLYVTVEPCAMCAGALVWARVERVVFGVRNPKAGACG SVFDIPGDRRLNHRPEVVGGVLEAECAALMRDFFRER |
| 627 | MTDEYFMRQALREARRAYDEGEVPVGAVVVRDGRVIARGRNQVRRLKDPTAHAEM LALTAAAGHLGSARLTGCTLYVTVEPCAMCAGALVWARVERVVFGVRNPRAGACG SVFDIPGDRRLNHRPEVVGGVLEAECAALMRDFFRER |
| 628 | MDPTDLAFMREALAEARAAAEAGEVPVGAVVVCDGRIVARAHNRPIALNDPTAHAE VLALREAARALGDYRLTGCTLYATLEPCPMCAGAILHARIARLVYGVANPKAGACG SVLDVMNHPRLNHRVEVTGGVLAEECGALLSGFFRAR |
| 629 | MDPTDLAFMREALAEARAAAEAGEVPVGAVVVCDGRIVARAHNRPIALKDPTAHAE ILALREAAAALGSYRLTGCTLYATLEPCAMCAGAILHARIARLVYGVANPKAGACGS VLDVMNHPRLNHRVEVTGGVLAEECGALLSGFFRAR |
| 630 | MDPTDLAFMREALAEARAAAEAGEVPVGAVVVCDGRIVARAHNRPIALKDPTAHAE ILALREAGRALGSYRLTGCTLYATLEPCPMCAGAILHARIARLVYGVANPKAGACGS VLDVMNHPRLNHRVEVTGGVLAEECGALLSGFFRAR |
| 631 | MDPTDLAFMREALAEARAAAEAGEVPVGAVVVCDGRIVARAHNRPIALADPTAHAE VLALREAARALGSYRLTGCTLYATLEPCPMCAGAILHARIARLVYGVANPKAGACGS VLDVMNHPKLNHRVEVTGGVLAEECGALLSGFFRAR |

-continued

| Sequences | |
|---|---|
| SEQ ID NO: | Deaminase Sequence |
| 632 | MDPTDLAFMREALAEARAAAEAGEVPVGAVVVCDGRIVARAHNRPIALNDPTAHAE ILALREAGRALGSYRLTGCTLYATLEPCPMCAGAILHARIARLVYGVANPKAGACGS VLDVMNHPRLNHRVEVTGGVLAEECGALLSGFFRAR |
| 633 | MDPTDLAFMREALAEARAAAEAGEVPVGAVVVCDGRIVARAHNRPIALRDPTAHAE ILALREAGRALGNYRLTGCTLYATLEPCPMCAGAILHARIARLVYGVANPKAGACGS VLDVMNHPKLNHRVEVTGGVLAEECGALLSGFFRAR |
| 634 | MDPTDLAFMREALAEARAAAEAGEVPVGAVVVCDGRIVARAHNRPIALNDPTAHAE VLALREAAAALGSYRLTGCTLYATLEPCPMCAGAILHARIARLVYGVANPKAGACG TVLDVMNHPRLNHRVEVTGGVLAEECGALLSGFFRAR |
| 635 | MDPTDLAFMREALAEARAAAEAGEVPVGAVVVCDGRIVARAHNRPIALNDPTAHAE ILALREAGRALGSYRLTGCTLYATLEPCPMCAGAILHARIARLVYGVANPKAGACGT VLDVMNHPRLNHRVEVTGGVLAEECGALLSGFFRAR |
| 636 | MDPTDLAFMREALAEARAAAEAGEVPVGAVVVCDGRIVARAHNRPIALADPTAHAE VLALREAARALGSYRLTGCTLYATLEPCAMCAGAILHARIARLVYGVANPKAGACG SVLDVMNHPKLNHRVEVTGGVLAEECGALLSGFFRAR |
| 637 | MDDAGFMRLALEEARAAAAAGEVPVGAVVVRDGEVLARAGNRTVRDRDPTAHAE VVALREAARRLGSYRLAGCTLYVTLEPCAMCAGAMIHARLDRLVYGVANPKAGAA GTVLDVLGHPRLNHRMEVEGGVLAAECGALLRDFFRAR |
| 638 | MDDAGFMRLALEEARAAAAAGEVPVGAVVVRDGEVLARAGNRTVRDRDPTAHAEI VAIREAARRLGSYRLAGCTLYVTLEPCAMCAGAMIHARLDRLVYGVANPKAGAAGT VLDVLGHPRLNHRMEVEGGVLAAECGALLRDFFRAR |
| 639 | MDDAGFMRLALEEARAAAAAGEVPVGAVVVRDGEVLARAGNRTVRDKDPTAHAEI VALREAARRLGSYRLAGCTLYVTLEPCAMCAGAMIHARLDRLVYGVANPKAGAAG TVLDVLGHPRLNHRMEVEGGVLAAECGALLRDFFRAR |
| 640 | MTDEYFMRQALREARRAYDEGEVPVGAVVVRDGRVIARGRNQVVRLKDPTAHAEM LALTAAAGHLGSPRLTGCTLYVTVEPCAMCAGALVWARVERVVFGVRNPKTGACG SVFDIPGDRRLSHRPEVVGGVLEAECAALMRDFFRER |
| 641 | MDPTDLAFMREALAEARAAAEAGEVPVGAVVVCDGRIVARAHNRPIALNDPTAHAE ILALREAARALGSYRLTGCTLYATLEPCAMCAGAILHARIARLVYGVANPKAGACGS VLDVMNHPKLNHRVEVTGGVLAEECGALLSGFFRAR |
| 642 | MDPTDLAFMREALAEARAAAEAGEVPVGAVVVCDGRIVARAHNRPIALRDPTAHAE ILALREAARALGSYRLTGCTLYATLEPCAMCAGAILHARIARLVYGVANPKAGACGT VLDVMNHPRLNHRVEVTGGVLAEECGALLSGFFRAR |
| 643 | MDPTDLAFMREALAEARAAAEAGEVPVGAVVVCDGRIVARAHNRPIALNDPTAHAE VLALREAAAALGSYRLTGCTLYATLEPCAMCAGAILHARIARLVYGVANPKAGACG TVLDVMNHPRLNHRVEVTGGVLAEECGALLSGFFRAR |
| 644 | MTDEYFMRQALREARRAYDEGEVPVGAVVVRDGRVIARGRNQVVRLKDPTAHAEM LALTAAAGHLGSSRLTGCTLYVTVEPCAMCAGALVWARVERVVFGVRNPRTGACG SVFDIPGDRRLNHRPEVVGGVLEAECAALMRDFFRER |
| 645 | MTDEYFMRQALREARRAYDEGEVPVGAVVVRDGRVIARGRNQVRRLKDPTAHAEM LALTAAAGHLGSPSLTGCTLYVTVEPCAMCAGALVWARVERVVFGVRNPRTGACGS VFDIPGDRRLNHRPEVVGGVLEAECAALMRDFFRER |
| 646 | MDPTDLAFMREALAEARAAAEAGEVPVGAVVVCDGRIVARAHNRPIALKDPTAHAE ILALREAARALGSYRLTGCTLYATLEPCPMCAGAILHARIARLVYGVANPKAGACGS VLDVMNHPRLNHRVEVTGGVLAEECGALLSGFFRAR |
| 647 | MDPTDLAFMREALAEARAAAEAGEVPVGAVVVCDGRIVARAHNRPIALNDPTAHAE VLALREAGRALGSYRLTGCTLYATLEPCPMCAGAILHARIARLVYGVANPKAGACGS VLDVMNHPRLNHRVEVTGGVLAEECGALLSGFFRAR |
| 648 | MDPTDLAFMREALAEARAAAEAGEVPVGAVVVCDGRIVARAHNRPIALNDPTAHAE VLALREAAKALGSYRLTGCTLYATLEPCPMCAGAILHARIARLVYGVANPKAGACGS VLDVMNHPKLNHRVEVTGGVLAEECGALLSGFFRAR |
| 649 | MDPTDLAFMREALAEARAAAEAGEVPVGAVVVCDGRIVARAHNRPIALKDPTAHAE ILALREAAAALGDYRLTGCTLYATLEPCPMCAGAILHARIARLVYGVANPKAGACGS VLDVMNHPKLNHRVEVTGGVLAEECGALLSGFFRAR |

-continued

| Sequences | |
|---|---|
| SEQ ID NO: | Deaminase Sequence |
| 650 | MDPTDLAFMREALAEARAAAEAGEVPVGAVVVCDGRIVARAHNRPIALRDPTAHAE ILALREAGRALGSYRLTGCTLYATLEPCPMCAGAILHARIARLVYGVANPKAGACGS VLDVMNHPKLNHRVEVTGGVLAEECGALLSGFFRAR |
| 651 | MDDAGFMRLALEEARAAAAAGEVPVGAVVVRDGEVLARAGNRTVRDRDPTAHAEI VALREAARRLGSYRLAGCTLYVTLEPCPMCAGAMIHARLDRLVYGVANPKAGAAG TVLDILGHPRLNHRMEVEGGVLAAECGALLRDFFRAR |
| 652 | MDDAGFMRLALEEARAAAAAGEVPVGAVVVRDGEVLARAGNRTVRDRDPTAHAE VVAIREAARRLGSYRLAGCTLYVTLEPCAMCAGAMIHARLDRLVYGVANPKAGAA GTVLDVLGHPRLNHRMEVEGGVLAAECGALLRDFFRAR |
| 653 | MTDEYFMRQALREARRAYDEGEVPVGAVVVRDGRVIARGRNQVNRLKDPTAHAEM LALTAAAGHLGSPRLTGCTLYVTVEPCAMCAGALVWARVERVVFGVRNPRTGACG SVFDIPGDRRLSHRPEVVGGVLEAECAALMRDFFRER |
| 654 | MTDEYFMRQALREARRAYDEGEVPVGAVVVRDGRVIARGRNQVRRLKDPTAHAEM LALTAAAGHLGSPQLTGCTLYVTVEPCAMCAGALVWARVERVVFGVRNPKTGACG SVFDIPGDRRLNHRPEVVGGVLEAECAALMRDFFRER |
| 655 | MDPTDLAFMREALAEARAAAEAGEVPVGAVVVCDGRIVARAHNRPIALNDPTAHAE ILALREAGRALGNYRLTGCTLYATLEPCPMCAGAILHARIARLVYGVANPKAGACGT VLDVMNHPRLNHRVEVTGGVLAEECGALLSGFFRAR |
| 656 | MDPTDLAFMREALAEARAAAEAGEVPVGAVVVCDGRIVARAHNRPIALRDPTAHAE ILALREAARALGSYRLTGCTLYATLEPCPMCAGAILHARIARLVYGVANPKAGACGT VLDVMNHPRLNHRVEVTGGVLAEECGALLSGFFRAR |
| 657 | MDPTDLAFMREALAEARAAAEAGEVPVGAVVVCDGRIVARAHNRPIALNDPTAHAE VLALREAARALGSYRLTGCTLYATLEPCAMCAGAILHARIARLVYGVANPKAGACG TVLDVMNHPRLNHRVEVTGGVLAEECGALLSGFFRAR |
| 658 | MDPTDLAFMREALAEARAAAEAGEVPVGAVVVCDGRIVARAHNRPIALNDPTAHAE ILALREAARALGSYRLTGCTLYATLEPCAMCAGAILHARIARLVYGVANPKAGACGT VLDVMNHPKLNHRVEVTGGVLAEECGALLSGFFRAR |
| 659 | MDPTDLAFMREALAEARAAAEAGEVPVGAVVVCDGRIVARAHNRPIALADPTAHAE ILALREAAKALGSYRLTGCTLYATLEPCPMCAGAILHARIARLVYGVANPKAGACGT VLDVMNHPRLNHRVEVTGGVLAEECGALLSGFFRAR |
| 660 | MTDEYFMRQALREARRAYDEGEVPVGAVVVRDGRVIARGRNQVRRLKDPTAHAEM LALTAAAGHLGSPRLTGCTLYVTVEPCAMCAGALVWARVERVVFGVRNPKTGACG SVFDIPGDRRLSHRPEVVGGVLEAECAALMRDFFRER |
| 661 | MTDEYFMRQALREARRAYDEGEVPVGAVVVRDGRVIARGRNQVRRLKDPTAHAEM LALTAAAGHLGSARLTGCTLYVTVEPCAMCAGALVWARVERVVFGVRNPRTGACG SVFDIPGDRRLNHRPEVVGGVLEAECAALMRDFFRER |
| 662 | MTDEYFMRQALREARRAYDEGEVPVGAVVVRDGRVIARGRNQVIRLKDPTAHAEM LALTAAAGHLGSPSLTGCTLYVTVEPCAMCAGALVWARVERVVFGVRNPRTGACGS VFDIPGDRRLNHRPEVVGGVLEAECAALMRDFFRER |
| 663 | MDPTDLAFMREALAEARAAAEAGEVPVGAVVVCDGRIVARAHNRPIALNDPTAHAE ILALREAARALGSYRLTGCTLYATLEPCPMCAGAILHARIARLVYGVANPKAGACGT VLDVMNHPRLNHRVEVTGGVLAEECGALLSGFFRAR |
| 664 | MDPTDLAFMREALAEARAAAEAGEVPVGAVVVCDGRIVARAHNRPIALNDPTAHAE VLALREAARALGSYRLTGCTLYATLEPCPMCAGAILHARIARLVYGVANPKAGACGT VLDVMNHPRLNHRVEVTGGVLAEECGALLSGFFRAR |
| 665 | MDPTDLAFMREALAEARAAAEAGEVPVGAVVVCDGRIVARAHNRPIALNDPTAHAE VLALREAAKALGSYRLTGCTLYATLEPCPMCAGAILHARIARLVYGVANPKAGACG TVLDVMNHPRLNHRVEVTGGVLAEECGALLSGFFRAR |
| 666 | MDPTDLAFMREALAEARAAAEAGEVPVGAVVVCDGRIVARAHNRPIALNDPTAHAE VLALREAGRALGSYRLTGCTLYATLEPCPMCAGAILHARIARLVYGVANPKAGACGS VLDVMNHPKLNHRVEVTGGVLAEECGALLSGFFRAR |
| 667 | MDDAGFMRLALEEARAAAAAGEVPVGAVVVRDGEVLARAGNRTVRDKDPTAHAEI VAIREAARRLGSYRLAGCTLYVTLEPCPMCAGAMIHARLDRLVYGVANPKAGAAGT VLDVLGHPRLNHRMEVEGGVLAAECGALLRDFFRAR |

-continued

| SEQ ID NO: | Sequences<br>Deaminase Sequence |
|---|---|
| 668 | MTDEYFMRQALREARRAYDEGEVPVGAVVVRDGRVIARGRNQVRRLKDPTAHAEM LALTAAAGHLGSPSLTGCTLYVTVEPCAMCAGALVWARVERVVFGVRNPKTGACGS VFDIPGDRRLNHRPEVVGGVLEAECAALMRDFFRER |
| 669 | MTDEYFMRQALREARRAYDEGEVPVGAVVVRDGRVIARGRNQVIRLKDPTAHAEM LALTAAAGHLGSRSLTGCTLYVTVEPCAMCAGALVWARVERVVFGVRNPRAGACG SVFDIPGDRRLNHRPEVVGGVLEAECAALMRDFFRER |
| 670 | MTDEYFMRQALREARRAYDEGEVPVGAVVVRDGRVIARGRNQVVRLKDPTAHAEM LALTAAAGHLGSPSLTGCTLYVTVEPCAMCAGALVWARVERVVFGVRNPRTGACGS VFDIPGDRRLNHRPEVVGGVLEAECAALMRDFFRER |
| 671 | MDPTDLAFMREALAEARAAAEAGEVPVGAVVVCDGRIVARAHNRPIALKDPTAHAE ILALREAAAALGNYRLTGCTLYATLEPCPMCAGAILHARIARLVYGVANPKAGACGS VLDVMNHPLLNHRVEVTGGVLAEECGALLSGFFRAR |
| 672 | MDPTDLAFMREALAEARAAAEAGEVPVGAVVVCDGRIVARAHNRPIALRDPTAHAE ILALREAAAALGSYRLTGCTLYATLEPCPMCAGAILHARIARLVYGVANPKAGACGT VLDVMNHPRLNHRVEVTGGVLAEECGALLSGFFRAR |
| 673 | MDPTDLAFMREALAEARAAAEAGEVPVGAVVVCDGRIVARAHNRPIALNDPTAHAE ILALREAARALGSYRLTGCTLYATLEPCPMCAGAILHARIARLVYGVANPKAGACGT VLDVMNHPKLNHRVEVTGGVLAEECGALLSGFFRAR |
| 674 | MDPTDLAFMREALAEARAAAEAGEVPVGAVVVCDGRIVARAHNRPIALKDPTAHAE ILALREAARALGSYRLTGCTLYATLEPCPMCAGAILHARIARLVYGVANPKAGACGT VLDVMNHPRLNHRVEVTGGVLAEECGALLSGFFRAR |
| 675 | MDPTDLAFMREALAEARAAAEAGEVPVGAVVVCDGRIVARAHNRPIALKDPTAHAE ILALREAAAALGDYRLTGCTLYATLEPCPMCAGAILHARIARLVYGVANPKAGACGT VLDVMNHPRLNHRVEVTGGVLAEECGALLSGFFRAR |
| 676 | MTDEYFMRQALREARRAYDEGEVPVGAVVVRDGRVIARGRNQVERLKDPTAHAEIL ALRAACRHLGSKYLTGCTLYVTVEPCAMCAGALVWARVERVVFGVRNPKAGACGS VLDIPGDRRLNHRPEVVGGVLEAECAALMRDFFRER |
| 677 | MTDEYFMRQALREARRAYDEGEVPVGAVVVRDGRVIARGRNQVERLKDPTAHAEIL ALSAACRHLGSKYLTGCTLYVTVEPCAMCAGALVWARVERVVFGVRNPKAGACGS VLDIPGDRRLNHRPEVVGGVLEAECAALMRDFFRER |
| 678 | MTDEYFMRQALREARRAYDEGEVPVGAVVVRDGRVIARGRNQVERLKDATAHAEI LALRAACAHLGSKYLTGCTLYVTVEPCAMCAGALVWARVERVVFGVRNPKAGACG SVLDIPGDRRLNHRPEVVGGVLEAECAALMRDFFRER |
| 679 | MTDEYFMRQALREARRAYDEGEVPVGAVVVRDGRVIARGRNQVERLRDATAHAEI LALRAACEHLGSKYLTGCTLYVTVEPCAMCAGALVWARVERVVFGVRNPKAGACG SVLDIPGNRRLNHRPEVVGGVLEAECAALMRDFFRER |
| 680 | MDPEDLAFMRKALEEARQARDAGEVPVGAVVVLDGEIVARAHNRTIQLSDPTAHAE ILALREAARALGNYRLEGCTLYVTLEPCAMCAGAILHARIERLVFGVANPKAGAAGS VLDVLNHPRLNHRVEVTGGVLAEECGALLRDFFRAR |
| 681 | MDPTDEAFMKKALDEAKKAAEAGEVPVGAVVVYDGKVVARAHNRRIAESDPTAHA EILALREAARALGNYRLTGCTLYVTLEPCAMCAGAILHARIARLVYGVPNPKAGATG SVLNVLNHPRLNHRVEVTGGVLAEECGDLLRGFFRAR |
| 682 | MDDEGWMQLALEEARASRAAGEVPVGAVVVRDGEVLARAGNRTRELCDPTAHAEI VALREAARRLGNYRLPGCTLYVTLEPCAMCAGAMLHARLDRLVYGVPNPKAGAAG SVLDVLGHPRLNHRLEVTGGVLAAECGQLLRDFFRAR |
| 683 | MTDEYFMRQALREARRAYDEGEVPVGAVVVRDGRVIARGRNQVERLKDPTAHAEIL ALKAACAHLGSKYLTGCTLYVTVEPCAMCAGALVWARVERVVFGVRNPKAGACGS VLDIPGNRRLNHRPEVVGGVLEAECAALMRDFFRER |
| 684 | MDPTDVAFMQQALDEARAAREAGEVPVGAVVVYDGRVVARAHNRTIARSDPTAHA EILALREAARALGNYRLAGCTLYVTLEPCAMCAGAILHARIERLVYGVPNPKAGATG SVLNVLNHPRLNHRVEVTGGVLAEECGALLRGFFRAR |
| 685 | MDPEDLRFMRKALAEARKAKEAGEVPVGAVVVKDGKIVAQAHNRTIALSDPTAHAE ILALREAARALGNYRLTGCTLYATLEPCAMCAGAILHARIARLVYGVPNPKAGASGS VLNVLNHPRLNHQVEVTGGVLAEECGALLRDFFRAR |

-continued

Sequences

| SEQ ID NO: | Deaminase Sequence |
|---|---|
| 686 | MDPKDLRFMQKALAEAREAKAAGEVPVGAVVVRNGKIVARAHNRTRALSDPTAHA<br>EILALREAARALGNYRLEGCTLYVTLEPCAMCAGAILHARIERLVYGVANPKAGAAG<br>SVLDVLNHPRLNHRVEVTGGVLAEECGALLRGFFRAR |
| 687 | MTDEYFMRQALREARRAYDEGEVPVGAVVVRDGRVIARGRNQVERLKDPTAHAEIL<br>ALRAACAHLGSKYLTGCTLYVTVEPCAMCAGALVWARVERVVFGVRNPKAGACGS<br>VLDIPGDRRLNHRPEVVGGVLEAECAALMRDFFRER |
| 688 | MTDEYFMRQALREARRAYDEGEVPVGAVVVRDGRVIARGRNQVERLQDPTAHAEIL<br>ALRAACAHLGSKYLTGCTLYVTVEPCAMCAGALVWARVERVVFGVRNPKAGACGS<br>VLDIPGNRRLNHRPEVVGGVLEAECAALMRDFFRER |
| 689 | MTDEYFMRQALREARRAYDEGEVPVGAVVVRDGRVIARGRNQVERLRDPTAHAEV<br>LALRAACAHLGSKYLTGCTLYVTVEPCAMCAGALVWARVERVVFGVRNPKAGACG<br>SVLDIPGDRRMNHRPEVVGGVLEAECAALMRDFFRER |
| 690 | MTDEYFMRQALREARRAYDEGEVPVGAVVVRDGRVIARGRNQVERLKDATAHAEI<br>LALRAACRHLGSKYLTGCTLYVTVEPCAMCAGALVWARVERVVFGVRNPKAGACG<br>SVLDIPGNRRLNHRPEVVGGVLEAECAALMRDFFRER |
| 691 | MDALDIEFMRKALAEARAAKEAGEVPVGAVVVRDGKIVARAHNRTIALSDPTAHAE<br>ILALRAAARALGNYRLTGCTLYVTLEPCAMCAGAILHARIERLVYGVPNPKAGATGS<br>VLNVLNHPRLNHRVEVTGGVLAEECGRLLSDFFRAR |
| 692 | MDPDDIAFMREALAEARRAKEAGEVPVGAVVVKDGRIVARAHNRTIAESDPTAHAEI<br>LALREAARQLGNYRLTGCTLYATLEPCAMCAGAILHARIARLVYGVPNPKAGATGS<br>VLDVMNHPRLNHRVEVTGGVLADECGDLLRDFFRAR |
| 693 | MDPEDIAFMEQALAEARAARDAGEVPVGAVVVLDGEIVAQAHNRTRQLSDPTAHAE<br>ILALRQAARALGNYRLTGCTLYVTLEPCAMCAGAILHARVERLVYGVANPKAGATG<br>SVLNVLNHPRLNHRVEVTGGVLAEECGDLLRGFFRAR |
| 694 | MDDQDLRFMKMALDEARKAKDAGEVPVGAVVVHEGEVVARAHNRTIARSDPTAH<br>AEIRALREAARALGNYRLTGCTLYVTLEPCAMCAGAILHARIARLVYGVPNPKAGAT<br>GSVLNVLNHPRLNHRVEVTGGVLAEECGDLLRDFFRAR |
| 695 | MDDEGWMRLALEEARASRAAGEVPVGAVVVRDGQVLARAGNRTRERCDPTAHAEI<br>VALREAARKLGNYRLAGCTLYVTLEPCAMCAGAMLHARLDRLVYGVANPKAGAA<br>GSVLDVLGHPRLNHRLEVTGGVLEAECGQLLRDFFRAR |
| 696 | MTDEYFMRQALREARRAYDEGEVPVGAVVVRDGRVIARGRNQVERLRDPTAHAEL<br>LALRAACEHLGSKYLTGCTLYVTVEPCAMCAGALVWARVERVVFGVRNPKAGACG<br>SVLDIPGDRRLNHRPEVVGGVLEAECAALMRDFFRER |
| 697 | MTDEYFMRQALREARRAYDEGEVPVGAVVVRDGRVIARGRNQVERLRDATAHAEI<br>LALRAAARHLGSKYLTGCTLYVTVEPCAMCAGALVWARVERVVFGVRNPKAGACG<br>SVLDIPGNRRLNHRPEVVGGVLEAECAALMRDFFRER |
| 698 | MDAEDLAFMRQALAEAREAKEAGEVPVGAVVVHDGRVVARAHNRTIRLSDPTAHA<br>EILALREAARALGNYRLAGCTLYVTLEPCAMCAGAILHARIQRLVYGVPNPKAGAAG<br>SVLDVLNHPRLNHRVEVTGGVLAEECAALLTDFFRAR |
| 699 | MDPEDVEFMRKALAEAREARQAGEVPVGAVVVHDGKIVARAHNRPIALSDPTAHAE<br>ILALREAARALGNYRLEGCTLYVTLEPCAMCAGAILHARIQRLVYGVPNPKAGATGS<br>VLNVMNHPRLNHRVEVTGGVLAEECGALLSDFFRAR |
| 700 | MDPEDLRFMREALDEAREAREAGEVPVGAVVVRDGRIVARAHNRTKELSDPTAHAE<br>ILALRAAARALGNYRLAGCTLYCTLEPCAMCAGAILHARIARLVYGVPNPKAGAAGS<br>VLDVLNHPRLNHRVEVTGGVLAEECGALLRGFFRAR |
| 701 | MDDAGFMRLALEEARAAAAAGEVPVGAVVVRDGEVLARAGNRTVRDADPTAHAE<br>VVAIREAARRLGSYRLAGCTLYVTLEPCPMCAGAMIHARLDRLVYGVANPKAGAAG<br>TVLDVLGHPRLNHRMEVEGGVLAAECGALLRDFFRAR |
| 702 | MTDEYFMRQALREARRAYDEGEVPVGAVVVRDGRVIARGRNQVERLRDPTAHAEIL<br>ALRAACAHLGSKYLTGCTLYVTVEPCAMCAGALVWARVERVVFGVRNPKAGACGS<br>VLDIPGNRRLNHRPEVVGGVLEAECAALMRDFFRER |
| 703 | MTDEYFMRQALREARRAYDEGEVPVGAVVVRDGRVIARGRNQVERLRDPTAHAEL<br>LALRAACAHLGSKYLTGCTLYVTVEPCAMCAGALVWARVERVVFGVRNPKAGACG<br>SVLDIPGDRRLNHRPEVVGGVLEAECAALMRDFFRER |

-continued

| SEQ ID NO: | Deaminase Sequence |
|---|---|
| 704 | MTDEYFMRQALREARRAYDEGEVPVGAVVVRDGRVIARGRNQVERLRDATAHAEI LALRAAAAHLGSKYLTGCTLYVTVEPCAMCAGALVWARVERVVFGVRNPKAGACG SVLDIPGNRRLNHRPEVVGGVLEAECAALMRDFFRER |
| 705 | MTDEYFMRQALREARRAYDEGEVPVGAVVVRDGRVIARGRNQVERLKDATAHAEI LALRAACAHLGSKYLTGCTLYVTVEPCAMCAGALVWARVERVVFGVRNPKAGACG SVLDIPGNRRLNHRPEVVGGVLEAECAALMRDFFRER |
| 706 | MDPKDIRFMRKALAEAREARDAGEVPVGAVVVHDGEIVAQAHNRPIAESDPTAHAEI LALREAARALGNYRLEGCTLYVTLEPCAMCAGAILHARIARLVYGVANPKAGAAGS VLNVLNHPRLNHRVEVTGGVLADECGDLLRDFFRAR |
| 707 | MDSEDIKFMRQALAEAREAREAGEVPVGAVVVHDGRIVARAHNRRILESDPTAHAEI LALRQAARALGNYRLTGCTLYATLEPCAMCAGAILHARIERLVYGVANPKAGATGS VLNVLNHPRLNHRVEVTGGVLEEECGALLRDFFRAR |
| 708 | MDPVDVRFMKKALAEAREAKEAGEVPVGAVVVKDGEVVARAHNRTIARSDPTAHA EINALRAAARALGNYRLEGCTLYVTLEPCAMCAGAILHARIQRLVYGVPNPKAGAA GSVLDVLNHPRLNHRVEVTGGVLAEECGALLSDFFRAR |
| 709 | MDPDDIKFMRQALAEARKAREAGEVPVGAVVVKDGRVVARAHNRTIALSDPTAHA EIRALREAARALGNYRLVGCTLYVTLEPCAMCAGAILHARIARLVYGVPNPKAGAAG SVLDVMNHPRLNHRVEVTGGVLAEECGALMSDFFRAR |
| 710 | MDDEGWMQLALEEARASRAAGEVPVGAVVVRDGEVLARAGNRTRERCDPTAHAEI VALREAARRLGNYRLPGCTLYVTLEPCAMCAGAMLHARLDRLVYGVANPKAGAAG SVLDVLGHPRLNHRMEVTGGVLADECGRLLRDFFRAR |
| 711 | MTDEYFMRQALREARRAYDEGEVPVGAVVVRDGRVIARGRNQVERLRDATAHAEI LALKAAAAHLGSKYLTGCTLYVTVEPCAMCAGALVWARVERVVFGVRNPKAGACG SVLDIPGDRRLNHRPEVVGGVLEAECAALMRDFFRER |
| 712 | MDPEDIEFMEQALAEAKAAREAGEVPVGAVVVHDGKIVARAHNRTRALSDPTAHAE ILALREAARALGNYRLEGCTLYATLEPCAMCAGAILHARIERLVYGVANPKAGATGS VLDVLNHPRLNHRVEVTGGVLAEECGALLSDFFRAR |
| 713 | MDPEDIAFMRMALAEARKAKEAGEVPVGAVVVLNGEIVARAHNRPIALSDPTAHAEI LALREAARALGNYRLPGCTLYVTLEPCAMCAGAILHARIERLVYGVANPKAGATGS VLDVLNHPRLNHKVEVTGGVLAEECGALLRGFFRAR |
| 714 | MDAEDLEFMQQALDEAREAREAGEVPVGAVVVLDGRIVARAHNRPIAESDPTAHAE ILALRAAARALGNYRLTGCTLYVTLEPCAMCAGAILHARIERLVYGVPNPKAGACGS VLNVMNHPRLNHRVEVVGGVLAEECGALLTGFFRAR |
| 715 | MDPKDIKFMEKALEEARKAKEAGEVPVGAVVVKDGRIVARAHNRTIELSDPTAHAEI RALREAARALGNYRLEGCTLYATLEPCAMCAGAILHARIERLVYGVPNPKAGATGSV LDVLNHPRLNHRVEVTGGVLAEECGALLRGFFRAR |
| 716 | MDDEGWMRLALEEARASRAAGEVPVGAVVVRDGEVLARAGNRTRELCDPTAHAEI VALREAARRLGNYRLPGCTLYVTLEPCAMCAGAMIHARLDRLVYGVANPKAGAAG SVLDVLGHPRLNHRMEVTGGVLAEECGALMRDFFRAR |
| 717 | MTDEYFMRQALREARRAYDEGEVPVGAVVVRDGRVIARGRNQVERLKDPTAHAEIL ALRAACAHLGSKYLTGCTLYVTVEPCAMCAGALVWARVERVVFGVRNPKAGACGS VLDIPGNRKLNHRPEVVGGVLEAECAALMRDFFRER |
| 718 | MTDEYFMRQALREARRAYDEGEVPVGAVVVRDGRVIARGRNQVERLRDATAHAEI LALRAACRHLGSKYLTGCTLYVTVEPCAMCAGALVWARVERVVFGVRNPKAGACG SVLDIPGNRRLNHRPEVVGGVLEAECAALMRDFFRER |
| 719 | MDPEDIAFMRKALAEARKAKEAGEVPVGAVVVKDGKIVARAHNRTIALSDPTAHAE ILALREAARALGNYRLTGCTLYVTLEPCAMCAGAILHARIEKLVYGVPNPKAGACGS VLNVLNHPRLNHRVEVTGGVLAEECGALLKDFFRAR |
| 720 | MDPEDVRYMRKALAEARKAKEAGEVPVGAVVVHDGRVVARAHNRTIALSDPTAHA EILALREAARALGNYRLEGCTLYATLEPCAMCAGAILHARIQRLVYGVANPKAGAAG SVLDVMNHPRLNHRVEVTGGVLEEECGALLSDFFRAR |
| 721 | MDPEDVAFMKKALAEARAAQEAGEVPVGAVVVKDGEVVARAHNRTRERSDPTAH AEILALREAARALGNYRLAGCTLYVTLEPCAMCAGAILHARIERLVYGVANPKAGAA GSVLNVLNHPRLNHRVEVTGGVLAEECGDLLRGFFRAR |

-continued

Sequences

| SEQ ID NO: | Deaminase Sequence |
|---|---|
| 722 | MDPTDLEFMRQALAEAREARDAGEVPVGAVVVHDGRIVARAHNRTRELSDPTAHAE ILALRAAARALGNYRLTGCTLYATLEPCAMCAGAILHARIERLVYGVANPKAGACGS VLHVLNHPRLNHRVEVTGGVLAEECGRLLRGFFRAR |
| 723 | MDDEGWMRLALEEARAAKAAGEVPVGAVVVRDGEVLARAGNRTRLDCDPTAHAEI VALREAARQLGNYRLAGCTLYVTLEPCAMCAGAMLHARLDRLVYGVPNPKAGAAG SVLDVLGHPRLNHRLEVTGGVLAEECGQLMRDFFRAR |
| 724 | MTDEYFMRQALREARRAYDEGEVPVGAVVVRDGRVIARGRNQVERLRDATAHAEI LALRAAAAHLGSKYLTGCTLYVTVEPCAMCAGALVWARVERVVFGVRNPKAGACG SVLDIPGDRRLNHRPEVVGGVLEAECAALMRDFFRER |
| 725 | MTDEYFMRQALREARRAYDEGEVPVGAVVVRDGRVIARGRNQVERLRDATAHAEI LALRAASAHLGSKYLTGCTLYVTVEPCAMCAGALVWARVERVVFGVRNPKAGACG SVLDIPGDRRLNHRPEVVGGVLEAECAALMRDFFRER |
| 726 | MTDEYFMRQALREARRAYDEGEVPVGAVVVRDGRVIARGRNQVERLRDPTAHAEIL ALRAACAHLGSKYLTGCTLYVTVEPCAMCAGALVWARVERVVFGVRNPKAGACGS VLDIPGNRRMNHRPEVVGGVLEAECAALMRDFFRER |
| 727 | MDPEDLAFMRKALAEARRAAEAGEVPVGAVVVHDGRIVARAHNRREALSDPTAHA EILALREAARALGNYRLAGCTLYATLEPCAMCAGAILHARIARLVYGVPNPKAGACG SVLDVLNHPRLNHRVEVTGGVLAEECGALLRDFFRAR |
| 728 | MDPYDLAFMQQALAEARQAKAAGEVPVGAVVVHDGRIVARAHNRTIELSDPTAHA EILALRQAARALGNYRLEGCTLYCTLEPCAMCAGAILHARIERLVYGVPNPKAGAAG SVLNVMNHPRLNHRVEVTGGVLAEECGALLRDFFRAR |
| 729 | MDPEDIEFMQKALAEAREAREAGEVPVGAVVVKDGEVVARAHNRVNALSDPTAHA EILALREAARALGNYRLTGCTLYATLEPCAMCAGAILHARIERLVYGVANPKAGATG SVLNVLNHPRLNHRVEVTGGVLAEECGDLLRDFFRAR |
| 730 | MDDRGWMRLALEEARAARARGEVPVGAVVVRDGQVLARAGNRTRELCDPTAHAEI VALREAARRLGNYRLAGCTLYVTLEPCAMCSGAMLHARLDRLVYGVANPKAGAAG SVLDVLGHPRLNHRLEVEGGVLEEECGALLRDFFRAR |
| 731 | MDDRGWMRLALEEARASRAAGEVPVGAVVVRDGEVLARAGNRVRELCDPTAHAEI VALREAARRLGNYRLPGCTLYVTLEPCAMCAGAMLHARLDRLVYGVANPKAGAAG SVLDVLGHPRLNHRMEVTGGVLEEECGALMRDFFRAR |
| 732 | MNDEGFMQLALEEARAARAAGEVPVGAVVVRDGEVIASAGNRTRERCDPTAHAEIV ALRAAARKLGNYRLPGCTLYVTLEPCAMCAGAMIHARLDRLVYGVANPKAGAAGS VLDVLGHPRLNHRMEVEGGVLAEECGRLLRDFFRAR |
| 733 | MSDEHFMKQALDEARKAKDRGEVPVGAVVVRDGEIIATGRNRVEELKDPTAHAEM LAITAAAGHLGSKYLTGCTLYVTLEPCVMCAGACIWARVDRVVFGVRNPKAGACGS VFNVPGDPRLNHHPEVTGGILEDECAKLLRDFFRER |
| 734 | MSEVDPTDLAFMREALAEARAAAEAGEVPVGAVVVCDGRIVARAHNRPIALSDPTA HAEILALREAARALGNYRLTGCTLYATLEPCAMCAGAILHARIARLVYGVANPKAGA CGSVLDVMNHPRLNHRVEVTGGVLAEECGALLSGFFRAPRRVFNAQKKAQSSTD |
| 735 | MSEVEFSHEYWMRHALTLAKRAWDEREVPVGAVLVHNNRVIGEGWNRPIGRHDPT AHAEIMALRQGGLVMQNYRLIDATLYVTLEPCVMCAGAMIHSRIGRVVFGVRNAKT GAAGSLMDVLHHPGMNHRVEITEGILADECAALLSDFFRMRRQEIKAQKKAQSSTDS GGSSGGSSGSETPGTSESATPESSGGSSGGSSEVEFTDEYFMRQALREARRAYDEGEV PVGAVVVRDGRVIARGRNQVERLKDPTAHAEMLALTAAAGHLGSKYLTGCTLYVT VEPCAMCAGALVWARVERVVFGVRNPKAGACGSVFDIPGDRRLNHRPEVVGGVLE AECAALMRDFFREPRRVFNAQKKAQSSTD |
| 736 | MDDEGWMRLALEEARAAKAAGEVPVGAVVVRDGQVIARAGNRTRERCDPTAHAEI RALREAARRLGNYRLEGCTLYVTLEPCAMCAGAMLHARLDRLVYGVANPKAGAAG SVLDVLGHPRLNHRLEVTGGVLAEECGQLLRDFFRAR |
| 737 | MDDAGWMQLALEEARASRAAGEVPVGAVVVRDGEVLASAGNRTRELCDPTAHAEI VALREAARRLGNYRLSGCTLYVTLEPCAMCAGAMLHARLDRLVYGVANPKAGAAG SVLDVLGHPRLNHRMEVTGGVLAEECAALLRDFFRAR |
| 738 | MDDEGWMRLALEEARAARDAGEVPVGAVVVRDGQVIARAGNRTRQLCDPTAHAEI VALRAAARRLGNYRLPGCTLYVTLEPCAMCAGAMVHARIDRLVYGVPNPKAGAAG SVLNVLHHPRLNHRMEVTGGVLAEECGALLTDFFRAR |

-continued

| SEQ ID NO: | Deaminase Sequence |
|---|---|
| 739 | MDDAGWMQLALEEARASKAAGEVPVGAVVVRDGRILARAGNRTRELCDPTAHAEI VALREAARRLGNYRLPGCTLYVTLEPCAMCAGAMLHARLDRLVYGVANPKAGAAG SVLDVLGHPRLNHRLEVEGGVLAAECSALLRDFFRAR |
| 740 | MSEVEFDDAGFMRLALEEARAAAAAGEVPVGAVVVRDGEVLARAGNRTVRDCDPT AHAEIVALREAARRLGNYRLAGCTLYVTLEPCAMCAGAMIHARLDRLVYGVANPKA GAAGSVLDVLGHPRLNHRMEVEGGVLAAECGALLRDFFRAPRRVFNAQKKAQSSTD |
| 741 | MDDRGWMKLALEEARASRAAGEVPVGAVVVRDGRVLASAGNRTRERCDPTAHAEI VALREAARKLGNYRLAGCTLYVTLEPCAMCAGAMLHARLDRLVYGVANPKAGAA GSVLDVLGHPRLNHRMEVTGGVLAEECGALLRDFFRAR |
| 742 | MDDEGWMQLALDEARKARDAGEVPVGAVVVRDGRVLASAGNRTRERCDPTAHAEI VALREAARKLGNYRLPGCTLYVTLEPCAMCAGAMLHARLDRLVYGVDNPKAGAAG SVLDVLGHPRLNHRMEVVGGVLAEECGALLRDFFRAR |
| 743 | MTDEYFMKQALAEARKAYDAGEVPVGAVVVRDGEVIARGHNRVERLKDPTAHAE MLAITAAAGHLGSKYLEGCTLYVTLEPCVMCAGALVWARVDRVVFGVPNPKAGAC GSVFDIPGDPRLNHRPEVTGGVLEAECAALIRDFFRER |
| 744 | MSEVEFTDEYFMRQALREARRAYDEGEVPVGAVVVRDGRVIARGRNQVERLKDPTA HAEMLALTAAAGHLGSKYLTGCTLYVTVEPCAMCAGALVWARVERVVFGVRNPKA GACGSVFDIPGDRRLNHRPEVVGGVLEAECAALMRDFFREPRRVFNAQKKAQSSTD |
| 745 | MSEVEFSHEYWMRHALTLAKRAWDEREVPVGAVLVHNNRVIGEGWNRPIGRHDPT AHAEIMALRQGGLVMQNYRLIDATLYVTLEPCVMCAGAMIHSRIGRVVFGVRNAKT GAAGSLMDVLHHPGMNHRVEITEGILADECAALLSDFFRMRRQEIKAQKKAQSSTDS GGSSGGSSGSETPGTSESATPESSGGSSGGSSEVEFDEKWMRYALSLADKAEALGEVP VGAVLVKDNQVIGEGWNQSISGHDATAHAEIMAIRDAGKNLQNYRLIDCTLYVTLEP CPMCAGAIVHSRIKRVVFGVSNYKTGAAGSVENLLSNEQLNHQAEVTAGVLAEECG EKISAFFKRPRRVFNAQKKAQSSTD |
| 746 | MDDEGWMQLALEEARASRAAGEVPVGAVVVRDGEVVARAGNRTRELCDPTAHAEI VALREAARARGNYRLTGCTLYVTLEPCAMCAGAMIHARLDRLVYGVPNPKAGAAG SVLDVLGHPRLNHRMEVTGGVLAEECGALLRDFFRAR |
| 747 | MDDQGWMQLALEEARASRARGEVPVGAVVVRDGEVIARAGNRVRERCDPTAHAEI VALREAARALGNYRLPGCTLYVTLEPCAMCAGAMLHARLDRLVYGVANPKAGAAG SVLDVLGHPRLNHRLEVTGGVLEAECGALLRDFFRAR |
| 748 | MDDEGWMRLALEEARASRARGEVPVGAVVVRDGEVLARAGNRTREKCDPTAHAEI VALREAARRLGNYRLAGCTLYVTLEPCAMCAGAMLHARLDRLVYGVPNPKAGAAG SVLDVLGHPRLNHRMEVVGGVLEAECGALLRDFFRAR |
| 749 | MTDEHFMREALREAQKAYDRGEVPVGAVVVRDGEIIARGRNQVEKLKDPTAHAEM LAITAAAGHLGSKYLRGCTLYVTLEPCVMCAGALVWARVERVVFGVDNPKAGAAG SVFNVPGDPRLNHRPEVVGGVLEAECAALLRDFFRER |
| 750 | MSEVEFSHEYWMRHALTLAKRAWDEREVPVGAVLVHNNRVIGEGWNRPIGRHDPT AHAEIMALRQGGLVMQNYRLIDATLYVTLEPCVMCAGAMIHSRIGRVVFGVRNAKT GAAGSLMDVLHHPGMNHRVEITEGILADECAALLSDFFRMRRQEIKAQKKAQSSTDS GGSSGGSSGSETPGTSESATPESSGGSSGGSSEVEFSDDAGFMREALAEARAAAAAGE VPVGAVVVKDGEIIARAGNRTLRDNDPTAHAEIVALRAAARALGNHRLTGCTLYVTL EPCAMCAGAISHARIARLVYGVDNPKGGAVAHGPRFFAQPTCHHRPEVTGGVGAEE AGALLRDFFRAPRRVFNAQKKAQSSTD |
| 751 | MDDEFYMRRALELAALAEEHNEVPVGAVLVLNGEIIGEGWNRSIGHHDATAHAEIM ALRQAGKKLENYRLLDTTLYVTLEPCPMCAGALLHSRVKRVVFGVPNLKAGAAGTV LNLFESQASYHYADVESGLLEQECREQLQAFFKRRRKEKKALKQAQKEAE |
| 752 | MDDRGWMRLALEEARAARAAGEVPVGAVVVRDGEVLARAGNRTRELCDPTAHAEI RALREAARQLGNYRLAGCTLYVTLEPCAMCAGAMLHARLDRLVYGVPNPKAGAAG SVLDVLGHPRLNHRLEVEGGVLAAECAQLLRDFFRAR |
| 753 | MDDAGWMQLALEEARAAREAGEVPVGAVVVRDGEVIARAGNRTRELCDPTAHAEI VALREAARKLGNYRLAGCTLYVTLEPCAMCAGAMLHARLDRLVYGVANPKAGAA GSVLDVLGHPRLNHRMEVTGGVLAAECGRLLRDFFRAR |
| 754 | MDDEGFMQLALEEARAARAAGEVPVGAVVVKDGEVLARAGNRTRELCDPTAHAEI VALREAARALGNYRLSGCTLYVTLEPCAMCAGAMVHARLDRLVYGVPNPKAGAAG SVLDVLHHPRLNHRMEVTGGVLAAECGALLRDFFRAR |

-continued

Sequences

| SEQ ID NO: | Deaminase Sequence |
|---|---|
| 755 | MSDEHFMRQALEEARKAYDEGEVPVGAVVVRDGEVIARGRNQVEILKDPTAHAEM LALTAAAGHLGSKYLRGCTLYVTLEPCVMCAGACIWARVDRVVFGVRNPKAGAAG SVFDVPGDPRLNHRPEVVGGVLRDECAQLMRDFFRER |
| 756 | MSEVEFTDEYFMRQALREARRAYDEGEVPVGAVVVRDGRVIARGRNQVERLKDPTA HAEMLALTAAAGHLGSKYLTGCTLYVTVEPCAMCAGALVWARVERVVFGVRNPKA GACGSVFDIPGDRRLNHRPEVVGGVLEAECAALMRDFFREPRRVFNAQKKAQSSTDS GGSSGGSSGSETPGTSESATPESSGGSSGGSSEVEFTDEYFMRQALREARRAYDEGEV PVGAVVVRDGRVIARGRNQVERLKDPTAHAEMLALTAAAGHLGSKYLTGCTLYVT VEPCAMCAGALVWARVERVVFGVRNPKAGACGSVFDIPGDRRLNHRPEVVGGVLE AECAALMRDFFREPRRVFNAQKKAQSSTD |
| 757 | MDEKWMRYALSLADKAEALGEVPVGAVLVKDNQVIGEGWNQSISGHDATAHAEIM AIRDAGKNLQNYRLIDCTLYVTLEPCPMCAGAIVHSRIKRVVFGVSNYKTGAAGSVF NLLSNEQLNHQAEVTAGVLAEECGEKISAFFKRRRKEKKAAKKAAKLAE |
| 758 | MNDQGWMRLALEEARAARAAGEVPVGAVVVRDGEVLARAGNRVRLLCDPTAHAE IVALREAARRLGNYRLEGCTLYVTLEPCAMCAGAMIHARLDRLVYGVPNPKAGAAG SVLDVLGHPRLNHRLEVTGGVLADECGALMRDFFRAR |
| 759 | MDDEGWMRLALEEARASKAAGEVPVGAVVVRDGEVIARAGNRTRELCDPTAHAEI VALREAARRLGNYRLAGCTLYVTLEPCAMCAGAMIHARLDRLVYGVPNPKAGAAG SVLDVLGHPRLNHRMEVEGGVLAEECRALLTDFFRAR |
| 760 | MTDEHFMRQALAEARKAYDEGEVPVGAVVVRDGEIVATGRNQVERLKDPTAHAEM LAITAAAGHLGSKYLRGCTLYVTVEPCVMCAGACVWARVDRVVFGVRNPKAGACG SVFDIPGDPRLNHHPEVTGGVLEDECRQLLRDFFRER |
| 761 | MTDEHFMRQALEEARKAYDQGEVPVGAVVVRDGEVIARGRNQVERLKDPTAHAEM LAITAAAGTLGSKYLEGCTLYVTLEPCVMCAGACIWARVERVVFGVRNPKAGACGS VFDIPGDPRLNHRPEVVGGVLEAECAALMRDFFRER |
| 762 | MSEVEFSDDAGFMREALAEARAAAAAGEVPVGAVVVKDGEIIARAGNRTLRDNDPT AHAEIVALRAAARALGNHRLTGCTLYVTLEPCAMCAGAISHARIARLVYGVDNPKG GAVAHGPRFFAQPTCHHRPEVTGGVGAEEAGALLRDFFRAPRRVFNAQKKAQSSTD |
| 763 | MSEVDPTDLAFMREALAEARAAAEAGEVPVGAVVVCDGRIVARAHNRPIALNDPTA HAEILALREAAKALGNYRLTGCTLYATLEPCPMCAGAILHARIARLVYGVANPKAGA CGTVLDVMNHPRLNHRVEVTGGVLAEECGALLSGFFRAPRRVFNAQKKAQSSTDSG GSSGGSSGSETPGTSESATPESSGGSSGGSSEVDPTDLAFMREALAEARAAAEAGEVP VGAVVVCDGRIVARAHNRPIALNDPTAHAEILALREAAKALGNYRLTGCTLYATLEP CPMCAGAILHARIARLVYGVANPKAGACGTVLDVMNHPRLNHRVEVTGGVLAEEC GALLSGFFRAPRRVFNAQKKAQSSTD |
| 764 | MDDAGFMREALAEARAAAAAGEVPVGAVVVKDGEIIARAGNRTLRDNDPTAHAEIV ALRAAARALGNHRLTGCTLYVTLEPCAMCAGAISHARIARLVYGVDNPKGGAVAHG PRFFAQPTCHHRPEVTGGVGAEEAGALLRDFFRAR |
| 765 | MDDEGWMRLALEEARKSRAAGEVPVGAVVVRDGEVLATAGNRTRELCDPTAHAEI VALREAARRLGNYRLPGCTLYVTLEPCAMCAGAMIHARLDRLVYGVANPKAGAAG SVLDVLGHPRLNHRMEVEGGVLEAECAALLRDFFRAR |
| 766 | MDDEGWMQLALEEARQSRAAGEVPVGAVVVRDGEVIARAGNRTREKCDPTAHAEI VALREAARKLGNYRLPGCTLYVTLEPCAMCAGAMVHARLDRLVYGVANPKAGAA GSVLDVLHHPRLNHRMEVTGGVLAEECGALLRDFFRAR |
| 767 | MDDAGWMRLALEEARKSRARGEVPVGAVVVRDGQVLARAGNRTRELCDPTAHAEI VALRAAARKLGNYRLPGCTLYVTLEPCAMCAGAMVHARLDRLVYGVRNPKAGAA GSVLDVLGHPRLNHQMEVTGGVLADECAALLRDFFRAR |
| 768 | MSEVEFDDAGFMRLALEEARAAAAAGEVPVGAVVVRDGEVLARAGNRTVRDNDPT AHAEIVALREAARRLGSYRLAGCTLYVTLEPCPMCAGAMIHARLDRLVYGVANPKA GAAGTVLDVLGHPRLNHRMEVEGGVLAAECGALLRDFFRAPRRVFNAQKKAQSSTD SGGSSGGSSGSETPGTSESATPESSGGSSGGSSEVEFDDAGFMRLALEEARAAAAAGE VPVGAVVVRDGEVLARAGNRTVRDNDPTAHAEIVALREAARRLGSYRLAGCTLYVT LEPCPMCAGAMIHARLDRLVYGVANPKAGAAGTVLDVLGHPRLNHRMEVEGGVLA AECGALLRDFFRAPRRVFNAQKKAQSSTD |
| 769 | MDDAGFMELALDEARAARAAGEVPVGAVVVRDGEVLARAGNRTRELCDPTAHAEI VALREAARKLGNYRLEGCTLYVTLEPCAMCAGAMLHARLDRLVYGVANPKAGAAG SVLDVLGHPRLNHRMEVTGGVLEDECAALLRDFFRAR |

-continued

| Sequences | |
|---|---|
| SEQ ID NO: | Deaminase Sequence |
| 770 | MDDAGWMQLALEEARAARAAGEVPVGAVVVRDGEVLARAGNRTRERCDPTAHAE IVALRAAARHLGNYRLEGCTLYVTLEPCAMCAGAMLHARLDRLVYGVDNPKAGAA GSVLDVLGHPRLNHRLEVTGGVLADECGQLLRDFFRAR |
| 771 | MNDKGWMRLALEEARAARAAGEVPVGAVVVRDGEVIAAAGNRRRELCDPTAHAEI VALREAARRLGNYRLPGCTLYVTLEPCAMCAGAMIHARLDRLVFGVANPKAGAAGS VLDVLGHPRLNHRLEVTGGVLEEECGQLLRDFFRAR |
| 772 | MSDEHFMQQALAEARKAYDLGEVPVGAVVVRDGRIIARGHNQVEKLKDPTAHAEM LAITAAAGHLGSKYLEGCTLYVTLEPCIMCAGACVWARVERVVYGVRNPKAGACGS VFDIPGDPRLNHHPEVTGGVLEAECARLMRDFFRER |
| 773 | MSDEFFMKQALEEARLAYDEGEVPVGAVVVRDGEVIARGRNQIEELKDPTAHAEML AITAAAGHLGSKYLLGCTLYVTLEPCVMCAGACVWARVDRVVYGVRNPKAGAAGS VFDIPGDPRLNHHPEVVGGVLQAECAALMRDFFRER |
| 774 | MSEVEFSHEYWMRHALTLAKRAWDEREVPVGAVLVHNNRVIGEGWNRPIGRHDPT AHAEIMALRQGGLVMQNYRLIDATLYVTLEPCVMCAGAMIHSRIGRVVFGVRNAKT GAAGSLMDVLHHPGMNHRVEITEGILADECAALLSDFFRMRRQEIKAQKKAQSSTDS GGSSGGSSGSETPGTSESATPESSGGSSGGSSEVEFDDAGFMRLALEEARAAAAAGEV PVGAVVVRDGEVLARAGNRTVRDCDPTAHAEIVALREAARRLGNYRLAGCTLYVTL EPCAMCAGAMIHARLDRLVYGVANPKAGAAGSVLDVLGHPRLNHRMEVEGGVLAA ECGALLRDFFRAPRRVFNAQKKAQSSTD |
| 775 | MSEVEFTDEYFMRQALREARRAYDEGEVPVGAVVVRDGRVIARGRNQVERLKDPTA HAEILALRAACRHLGSKYLTGCTLYVTVEPCAMCAGALVWARVERVVFGVRNPKA GACGSVLDIPGDRRLNHRPEVVGGVLEAECAALMRDFFREPRRVFNAQKKAQSSTDS GGSSGGSSGSETPGTSESATPESSGGSSGGSSEVEFTDEYFMRQALREARRAYDEGEV PVGAVVVRDGRVIARGRNQVERLKDPTAHAEILALRAACRHLGSKYLTGCTLYVTV EPCAMCAGALVWARVERVVFGVRNPKAGACGSVLDIPGDRRLNHRPEVVGGVLEA ECAALMRDFFREPRRVFNAQKKAQSSTD |
| 776 | MDPTDLAFMREALAEARAAAEAGEVPVGAVVVCDGRIVARAHNRPIALSDPTAHAE ILALREAARALGNYRLTGCTLYATLEPCAMCAGAILHARIARLVYGVANPGTGACGS VLDVMNHPRLNHRVEVTGGVLAEECGALLSGFFRAR |

The scope of the present invention is not limited by what has been specifically shown and described hereinabove. Those skilled in the art will recognize that there are suitable alternatives to the depicted examples of materials, configurations, constructions, and dimensions. Variations, modifications, and other implementations of what is described herein will occur to those of ordinary skill in the art without departing from the spirit and scope of the invention.

Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety.

SEQUENCE LISTING

```
Sequence total quantity: 808
SEQ ID NO: 1           moltype = AA  length = 147
FEATURE                Location/Qualifiers
source                 1..147
                       mol_type = protein
                       organism = synthetic construct
SEQUENCE: 1
MDDQGWMKLA LEEARASRAA GEVPVGAVVV RDGQIVASAG NRTRELCDPT AHAEIVALRQ  60
AARALGNYRL PGCTLYVTLE PCAMCAGAMV HARLDRLVYG VPNPKAGAAG SVLDVLHHPR  120
LNHRLEVTGG VLEDECGALL RDFFRAR                                      147

SEQ ID NO: 2           moltype = AA  length = 149
FEATURE                Location/Qualifiers
source                 1..149
                       mol_type = protein
                       organism = synthetic construct
SEQUENCE: 2
MDPEDVAFMR KALDEARKAR EAGEVPVGAV VVKDGEIVAR AHNRTIQKSD PTAHAEILAL  60
RKAARALGNY RLTGCTLYAT LEPCAMCAGA ILHARIERLV YGVPNPKAGA TGSVLNVLNH  120
PRLNHRVEVT GGVLAEECGA LLRGFFRAR                                    149
```

```
SEQ ID NO: 3            moltype = AA  length = 149
FEATURE                 Location/Qualifiers
source                  1..149
                        mol_type = protein
                        organism = synthetic construct
SEQUENCE: 3
MDPTDLAFMR EALAEARAAA EAGEVPVGAV VVCDGRIVAR AHNRPIALSD PTAHAEILAL  60
REAARALGNY RLTGCTLYAT LEPCAMCAGA ILHARIARLV YGVANPKAGA CGSVLDVMNH  120
PRLNHRVEVT GGVLAEECGA LLSGFFRAR                                    149

SEQ ID NO: 4            moltype = AA  length = 147
FEATURE                 Location/Qualifiers
source                  1..147
                        mol_type = protein
                        organism = synthetic construct
SEQUENCE: 4
MDDAGFMRLA LEEARAAAAA GEVPVGAVVV RDGEVLARAG NRTVRDNDPT AHAEIVALRE  60
AARRLGSYRL AGCTLYVTLE PCPMCAGAMI HARLDRLVYG VANPKAGAAG TVLDVLGHPR  120
LNHRMEVEGG VLAAECGALL RDFFRAR                                      147

SEQ ID NO: 5            moltype = AA  length = 147
FEATURE                 Location/Qualifiers
source                  1..147
                        mol_type = protein
                        organism = synthetic construct
SEQUENCE: 5
MDDKGFMQLA LEEARAAQAA GEVPVGAVVV RDGEVLARAG NRTRELCDPT AHAEIVALRE  60
AARKRGNYRL PGCTLYVTLE PCAMCAGAML HARLDRLVYG VANPKAGAAG SVLDVLGHPR  120
LNHRLEVTGG VLEAECGALL RDFFRAR                                      147

SEQ ID NO: 6            moltype = AA  length = 147
FEATURE                 Location/Qualifiers
source                  1..147
                        mol_type = protein
                        organism = synthetic construct
SEQUENCE: 6
MDDKGWMRLA LEEARAAKAA GEVPVGAVVV RDGQVLARAG NQVRELCDPT AHAEIVALRE  60
AARKLGNYRL PGCTLYVTLE PCAMCAGAML HARLDRLVYG VANPKAGAAG SVLDVLGHPR  120
LNHRLEVEGG VLADECGQLL RDFFRAR                                      147

SEQ ID NO: 7            moltype = AA  length = 149
FEATURE                 Location/Qualifiers
source                  1..149
                        mol_type = protein
                        organism = synthetic construct
SEQUENCE: 7
MDPEDLRFMR QALAEARRAA EAGEVPVGAV VVLDGEVVAQ AFNRTRAQSD PTAHAEILAL  60
REAARATGNY RLTGCTLYVT LEPCAMCAGA ILHARIARLV YGVANPKAGA AGSVLDVLNH  120
PRLNHRVEVT GGVLAEECGA LLRDFFRAR                                    149

SEQ ID NO: 8            moltype = AA  length = 147
FEATURE                 Location/Qualifiers
source                  1..147
                        mol_type = protein
                        organism = synthetic construct
SEQUENCE: 8
MNDEGWMQLA LEEARKAKAA GEVPVGAVVV RDGEVIAMAG NRTRERCDPT AHAEIVALRE  60
AARRLGNYRL PGCTLYVTLE PCAMCAGAML HARLDRLVYG VPNPKAGAAG SVLDVLGHPR  120
LNHRMEVTGG VLEEECGRLL RDFFRAR                                      147

SEQ ID NO: 9            moltype = AA  length = 147
FEATURE                 Location/Qualifiers
source                  1..147
                        mol_type = protein
                        organism = synthetic construct
SEQUENCE: 9
MDDEGWMKLA LEEARAARAA GEVPVGAVVV KDGEVIARAG NRTRELCDPT AHAEIIALRE  60
AARRLGNYRL PGCTLYVTLE PCAMCAGAML HARLDRLVYG VANPKAGAAG SVLDVLGHPR  120
LNHRMEVTGG VLEAECGQLL RDFFRAR                                      147

SEQ ID NO: 10           moltype = AA  length = 149
FEATURE                 Location/Qualifiers
source                  1..149
                        mol_type = protein
                        organism = synthetic construct
SEQUENCE: 10
MDPTDLAFMR EALAEARAAA EAGEVPVGAV VVCDGRIVAR AHNRPIALND PTAHAEILAL  60
REAAKALGNY RLTGCTLYAT LEPCPMCAGA ILHARIARLV YGVANPKAGA CGTVLDVMNH  120
PRLNHRVEVT GGVLAEECGA LLSGFFRAR                                    149
```

```
SEQ ID NO: 11          moltype = AA  length = 149
FEATURE                Location/Qualifiers
source                 1..149
                       mol_type = protein
                       organism = synthetic construct
SEQUENCE: 11
MDPTDIAFMR QALAEARKAK DAGEVPVGAV VVHDGEIVAR AHNRTILESD PTAHAEILAL  60
RAAARRLGNY RLTGCTLYVT LEPCAMCAGA ILHARIERLV YGVANPKAGA AGSVLNVLNH  120
PRLNHRVEVT GGVLADECGA LLSGFFRAR                                    149

SEQ ID NO: 12          moltype = AA  length = 147
FEATURE                Location/Qualifiers
source                 1..147
                       mol_type = protein
                       organism = synthetic construct
SEQUENCE: 12
MDDEDWMRLA LEEARKARAA GEVPVGAVVV RDGQVLARAG NRTRELCDPT AHAEIIALRQ  60
AARRRGNYRL AGCTLYVTLE PCAMCAGAMI HARLDRLVYG VPNPKAGAAG SVLDVLHHPR  120
LNHRLEVTGG VLEAECGALL RDFFRAR                                      147

SEQ ID NO: 13          moltype = AA  length = 149
FEATURE                Location/Qualifiers
source                 1..149
                       mol_type = protein
                       organism = synthetic construct
SEQUENCE: 13
MDPDDVEFMR QALDEARRAR DAGEVPVGAV VVHDGRVVAR AHNRVIAESD PTAHAEIRAL  60
REAARALGNY RLTGCTLYAT LEPCAMCAGA ILHARIARLV YGVPNPKAGA TGSVLDVLNH  120
PRLNHRVEVT GGVLEEECGR LLSGFFRAR                                    149

SEQ ID NO: 14          moltype = AA  length = 147
FEATURE                Location/Qualifiers
source                 1..147
                       mol_type = protein
                       organism = synthetic construct
SEQUENCE: 14
MDDQGWMQLA LEEARAARAA GEVPVGAVVV RDGEVLARAG NRTRELCDPT AHAEIRALRE  60
AARALGNYRL AGCTLYVTLE PCAMCAGAMI HARLDRLVYG VRNPKAGAAG SVLDVLGHPR  120
LNHRLEVTGG VLEAECGALL RDFFRAR                                      147

SEQ ID NO: 15          moltype = AA  length = 149
FEATURE                Location/Qualifiers
source                 1..149
                       mol_type = protein
                       organism = synthetic construct
SEQUENCE: 15
MDPEDIEFMK KALAEARAAK EAGEVPVGAV VVSDGEVVAR AHNQTIERSD PTAHAEILAL  60
RAAARALGNY RLTGCTLYVT LEPCAMCAGA ILHARIERLV YGVANPKAGA AGSVLDVLNH  120
PRLNHRVEVT GGVLAEECGA LLSDFFRAR                                    149

SEQ ID NO: 16          moltype = AA  length = 147
FEATURE                Location/Qualifiers
source                 1..147
                       mol_type = protein
                       organism = synthetic construct
SEQUENCE: 16
MDDEGWMRLA LEEARAARAA GEVPVGAVVV RDGQVLAQAG NRTRELCDPT AHAEIVALRE  60
AARALGNYRL AGCTLYVTLE PCAMCAGAML HARLDRLVYG VANPKAGAAG SVLDVLGHPR  120
LNHRAEVEGG VLADECGALL RDFFRAR                                      147

SEQ ID NO: 17          moltype = AA  length = 149
FEATURE                Location/Qualifiers
source                 1..149
                       mol_type = protein
                       organism = synthetic construct
SEQUENCE: 17
MDPEDREFMR KALEEARKAR EAGEVPVGAV VVLDGRIVAR AHNQTRAESD PTAHAEILAL  60
REAARALGNY RLTGCTLYVT LEPCAMCAGA ILHARIERLV YGVPNPKAGA TGSVLNVLNH  120
PRLNHRVEVT GGVLAEECGA LLSGFFRAR                                    149

SEQ ID NO: 18          moltype = AA  length = 147
FEATURE                Location/Qualifiers
source                 1..147
                       mol_type = protein
                       organism = synthetic construct
SEQUENCE: 18
MDDEGWMQLA LEEARASKAA GEVPVGAVVV RDGRVLARAG NRTRERCDPT AHAEIVALRE  60
AARRLGNYRL TGCTLYVTLE PCAMCAGAML HARLDRLVYG VPNPKAGAAG SVLDVLHHPR  120
```

```
LNHRLEVEGG VLEAECGQLL RDFFRAR                                147

SEQ ID NO: 19          moltype = AA  length = 147
FEATURE                Location/Qualifiers
source                 1..147
                       mol_type = protein
                       organism = synthetic construct
SEQUENCE: 19
MDDRGWMKLA LEEARAAKAA GEVPVGAVVV RDGEVIARAG NRTRLKCDPT AHAEIVALRE  60
AARRLGNYRL PGCTLYVTLE PCAMCAGAML HARLDRLVYG VPNPKAGAAG SVLDVLGHPR  120
LNHRLEVTGG VLAAECAALL RDFFRAR                                147

SEQ ID NO: 20          moltype = AA  length = 147
FEATURE                Location/Qualifiers
source                 1..147
                       mol_type = protein
                       organism = synthetic construct
SEQUENCE: 20
MDDEGWMRLA LEEARKAKAA GEVPVGAVVV RNGEVIARAG NRTRELCDPT AHAEIVALRE  60
AARRLGNYRL AGCTLYVTLE PCAMCAGAMI HARLDRLVYG VANPKAGAAG SVLDVLGHPR  120
LNHRLEVEGG VLEAECGALL RDFFRAR                                147

SEQ ID NO: 21          moltype = AA  length = 149
FEATURE                Location/Qualifiers
source                 1..149
                       mol_type = protein
                       organism = synthetic construct
SEQUENCE: 21
MDPMDIAFMQ QALDEARKAK EAGEVPVGAV VVHDGQIVAR AHNRTIALSD PTAHAEILAL  60
REAARALGNY RLQGCTLYAT LEPCAMCAGA ILHARIARLV YGVPNPKAGA CGSVLNVLNH  120
PRLNHRVEVT GGVLAEECGA LLRGFFRAR                              149

SEQ ID NO: 22          moltype = AA  length = 147
FEATURE                Location/Qualifiers
source                 1..147
                       mol_type = protein
                       organism = synthetic construct
SEQUENCE: 22
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPKAGAAG SVLDVLGHPR  120
LNHRMEVEGG VLAAECGALL RDFFRAR                                147

SEQ ID NO: 23          moltype = AA  length = 147
FEATURE                Location/Qualifiers
source                 1..147
                       mol_type = protein
                       organism = synthetic construct
SEQUENCE: 23
MTDEYFMRQA LREARRAYDE GEVPVGAVVV RDGRVIARGR NQVERLKDPT AHAEMLALTA  60
AAGHLGSKYL TGCTLYVTVE PCAMCAGALV WARVERVVFG VRNPKAGACG SVFDIPGDRR  120
LNHRPEVVGG VLEAECAALM RDFFRER                                147

SEQ ID NO: 24          moltype = AA  length = 142
FEATURE                Location/Qualifiers
source                 1..142
                       mol_type = protein
                       organism = synthetic construct
SEQUENCE: 24
MDAALEEARR AAAAGEVPVG AVLVRDGAVL ARGGNRTIRD CDPTAHAEIV ALRAAARAAG  60
NYRLPGATLY VTLEPCAMCA GAMIHARLDR LVYGAADPRA GAAGSVFDVL RHPALNHQMA  120
VEGGVRAAEC GALLRDFFRA RR                                     142

SEQ ID NO: 25          moltype = AA  length = 148
FEATURE                Location/Qualifiers
source                 1..148
                       mol_type = protein
                       organism = synthetic construct
SEQUENCE: 25
MTDADFMALA LEEARAAAAL GEVPVGAVVV RDGAVIARAG NRTIRDCDPT AHAEIVALRE  60
AARALGNYRL AGCTLYVTLE PCAMCAGAMI HARLDRLVYG AADPKTGAAG SVLDVLNHPK  120
LNHQMQVEAG VLAEECGAML RDFFQQRR                               148

SEQ ID NO: 26          moltype = AA  length = 142
FEATURE                Location/Qualifiers
source                 1..142
                       mol_type = protein
                       organism = synthetic construct
SEQUENCE: 26
MRDALAEARK AADAGEVPVG AVVVRGGEIL ARAHNRTVAD HDPTAHAEIL ALREAARVLG  60
```

```
NHRLTGCTLY VTLEPCAMCA GAIVHARLDR LVYGAADPKA GAAGSVLDVL NHPRLNHRME  120
VEGGVLAEES GELLRGFFRA RR                                          142

SEQ ID NO: 27          moltype = AA  length = 148
FEATURE                Location/Qualifiers
source                 1..148
                       mol_type = protein
                       organism = synthetic construct
SEQUENCE: 27
MDDAGFMREA LAEARAAAAA GEVPVGAVVV KDGEIIARAG NRTLRDNDPT AHAEIVALRA  60
AARALGNHRL TGCTLYVTLE PCAMCAGAIS HARIARLVYG ADDPKGGAVA HGPRFFAQPT  120
CHHRPEVTGG VGAEEAGALL RDFFRARR                                    148

SEQ ID NO: 28          moltype = AA  length = 142
FEATURE                Location/Qualifiers
source                 1..142
                       mol_type = protein
                       organism = synthetic construct
SEQUENCE: 28
MREALAEARA AAEAGEVPVG AVVVRDGEII ARARNRMVAD CDPTAHAEIV ALREAARVLG  60
NHRLTGCTLY ATLEPCAMCA GAIAHARIAR LVYAADDPKG GAVWHGPRFF EQPTCHHRPE  120
VTSGVLADEA AALLRDFFRA RR                                          142

SEQ ID NO: 29          moltype = AA  length = 142
FEATURE                Location/Qualifiers
source                 1..142
                       mol_type = protein
                       organism = synthetic construct
SEQUENCE: 29
MREALAEARA AAAAGEVPVG AVVVRDGAVL ARAGNASIRA RDPTAHAEVL ALRAAARALG  60
NHRLTGCTLY VTLEPCAMCA GAIAHARVAR LVYGAADPKG GAVAHGPRFF EQPTCHHRPE  120
VTGGVLAEEA GALLRDFFRA RR                                          142

SEQ ID NO: 30          moltype = AA  length = 142
FEATURE                Location/Qualifiers
source                 1..142
                       mol_type = protein
                       organism = synthetic construct
SEQUENCE: 30
MREALAEARA AAAAGEVPVG AVVVRDGAVL ARAGNRTVRD ADPTAHAEIV ALREAARALG  60
NHRLGGCTLY VTLEPCAMCA GAIAQARVAR LVYGADDPKG GAVAHGPRLF AQPTCHHRPE  120
VVGGVGAAEA GALLRDFFAA RR                                          142

SEQ ID NO: 31          moltype = AA  length = 142
FEATURE                Location/Qualifiers
source                 1..142
                       mol_type = protein
                       organism = synthetic construct
SEQUENCE: 31
MTEALAEARK AAAAGEVPVG AVLVRDGAVL ARGGNRTIRD CDPTAHAEIV ALRAAARALG  60
NYRLPGTTLY VTLEPCAMCA GAMIHARVAR LVYGAADPKT GAAGSVFDVL RHPALNHRME  120
VEGGVLAEEC GALLREFFRA RR                                          142

SEQ ID NO: 32          moltype = AA  length = 142
FEATURE                Location/Qualifiers
source                 1..142
                       mol_type = protein
                       organism = synthetic construct
SEQUENCE: 32
MREALAEARA AAAAGEVPVG AVVVRDGAVL ARAGNRTVRD ADPTAHAEIV ALREAARALG  60
NHRLTGCTLY VTLEPCAMCA GAISHARVAR LVYGADDPKG GAVAHGPRFF AQPTCHHRPE  120
VTGGVLAAEA GELLRGFFRA RR                                          142

SEQ ID NO: 33          moltype = AA  length = 142
FEATURE                Location/Qualifiers
source                 1..142
                       mol_type = protein
                       organism = synthetic construct
SEQUENCE: 33
MRDALAEARA AAAAGEVPVG AVVVRDGAIV ARARNRMVAD CDPTAHAEIV ALRAAARALG  60
NHRVDGCTLY VTLEPCAMCA GAMIHARLAR LVYGAADPRA GAAGSVLDVL GHPALNHRME  120
VTAGVLAEEC GALLRDFFAA RR                                          142

SEQ ID NO: 34          moltype = AA  length = 142
FEATURE                Location/Qualifiers
source                 1..142
                       mol_type = protein
                       organism = synthetic construct
SEQUENCE: 34
```

```
MTEALAEARK AAAAGEVPVG AVLVRDGAVL ARGGNRTIRD CDPTAHAEIV ALRAAARALG  60
NYRLPGTTLY VTLEPCAMCA GAMIHARVAR LVYGAADPKT GAAGSVFDIL RHPALNHRME  120
VEGGVLAEEC GALLRDFFRA RR                                           142

SEQ ID NO: 35          moltype = AA  length = 142
FEATURE                Location/Qualifiers
source                 1..142
                       mol_type = protein
                       organism = synthetic construct
SEQUENCE: 35
MREALAEARA AAAAGEVPVG AVVVRDGAVL ARAGNRTVRD ADPTAHAEIV ALRAAARALG  60
NHRLDGCTLY VTLEPCAMCA GAIAQARVAR LVYGAADPKG GAVAHGPRLF EQPTTHHRPE  120
VVGGVLAEEA AALLRGFFAA RR                                           142

SEQ ID NO: 36          moltype = AA  length = 142
FEATURE                Location/Qualifiers
source                 1..142
                       mol_type = protein
                       organism = synthetic construct
SEQUENCE: 36
MRAALAEARA AAAAGEVPVG AVVVRDGAVL ARAGNASIRA RDPTAHAEIL ALRAAARALG  60
NHRLTGCTLY VTLEPCAMCA GAIAHARIAR LVYGAADPKG GAVAHGPRFF EQPTCHHRPE  120
VTGGVLAEEA GALLRAFFRA RR                                           142

SEQ ID NO: 37          moltype = AA  length = 142
FEATURE                Location/Qualifiers
source                 1..142
                       mol_type = protein
                       organism = synthetic construct
SEQUENCE: 37
MRDALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPE  120
VVGGVGAAEA GALLRDFFRA RR                                           142

SEQ ID NO: 38          moltype = AA  length = 142
FEATURE                Location/Qualifiers
source                 1..142
                       mol_type = protein
                       organism = synthetic construct
SEQUENCE: 38
MREALAEARA AAAAGEVPVG AVVVRDGAVL ARAGNRTVRD ADPTAHAEIV ALRAAARALG  60
NHRLDGCTLY VTLEPCAMCA GAMVQARLAR LVYGAADPKA GAVDSVLDVL DHPRLNHRME  120
VTGGVLAEEC GALLREFFAA RR                                           142

SEQ ID NO: 39          moltype = AA  length = 142
FEATURE                Location/Qualifiers
source                 1..142
                       mol_type = protein
                       organism = synthetic construct
SEQUENCE: 39
MRDALAEARA AAAAGEVPVG AVVVRDGAIL ARAGNASIRA RDPTAHAEIL ALRAAARALG  60
NHRLDGCTLY VTLEPCAMCA GAIAHARIAR LVYGAADPKG GAVAHGPRFF EQPTCHHRPD  120
VTGGVGAAEA AALLRDFFRA RR                                           142

SEQ ID NO: 40          moltype = AA  length = 149
FEATURE                Location/Qualifiers
source                 1..149
                       mol_type = protein
                       organism = synthetic construct
SEQUENCE: 40
MDDAGFMRLA LEEARAAAAA GEVPVGAVVV RDGEVLARAR NAPVAAHDPT AHAEILALRA  60
AAAALGNYRL DGCTLYVTLE PCAMCSGAML HARLARVVYG AADPKTGAAG SVLDLFAQPR  120
LNHHTAVEGG VLAAECGALL RDFFRARRG                                    149

SEQ ID NO: 41          moltype = AA  length = 148
FEATURE                Location/Qualifiers
source                 1..148
                       mol_type = protein
                       organism = synthetic construct
SEQUENCE: 41
MDDEFFMREA LRLAEEAAAA GEVPVGAVVV RDGEIVGRGR NRVLEDRDPT AHAEIVALRE  60
AARRLGNYRL EGCELYVTLE PCAMCAGAMV HARLARLVYG AADPKAGAAG SVLDVLGHPR  120
LNHRMEVTGG VLAEECGALL REFFRARR                                     148

SEQ ID NO: 42          moltype = AA  length = 142
FEATURE                Location/Qualifiers
source                 1..142
                       mol_type = protein
                       organism = synthetic construct
```

```
SEQUENCE: 42
MRDALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPD  120
VTGGVGAAEA AALLRDFFRA RR                                           142

SEQ ID NO: 43          moltype = AA  length = 142
FEATURE                Location/Qualifiers
source                 1..142
                       mol_type = protein
                       organism = synthetic construct
SEQUENCE: 43
MREALAEARA AAAAGEVPVG AVVVRDGAVL ARAGNRTVRD ADPTAHAEVV ALREAARALG  60
NHRLGGCTLY VTLEPCAMCA GAIAQARVAR LVYGADDPKG GAVAHGPRLF AQPTCHHRPE  120
VVGGVGAAEA AALLRGFFAA RR                                           142

SEQ ID NO: 44          moltype = AA  length = 148
FEATURE                Location/Qualifiers
source                 1..148
                       mol_type = protein
                       organism = synthetic construct
SEQUENCE: 44
MDDAGFMRLA LAEARAAAAA GEVPVGAVVV RDGAVLAAAG NRTLRDCDPT AHAEVVALRA  60
AARALGNHRL GGCDLYVTLE PCAMCAGAIS FARIRRLYFG ADDPKGGAVE HGPRFFAQPT  120
CHHAPEVYGG LAESEAAALL RDFFRARR                                     148

SEQ ID NO: 45          moltype = AA  length = 149
FEATURE                Location/Qualifiers
source                 1..149
                       mol_type = protein
                       organism = synthetic construct
SEQUENCE: 45
MDDAGFMRLA LAEARAAAAA GEVPVGAVVV RDGAVLAAAG NRTLRDCDPT AHAEVVALRA  60
AARALGNHRL EGCTLYVTLE PCAMCAGAML HARLARVVYG AADPKTGAAG SVLDLFANPR  120
LNHHTRVEGG VLAEECGALL QDFFRARRG                                    149

SEQ ID NO: 46          moltype = AA  length = 148
FEATURE                Location/Qualifiers
source                 1..148
                       mol_type = protein
                       organism = synthetic construct
SEQUENCE: 46
MSDEDYMRLA LEEARAAAAA GEVPIGAVVV RDGEVLARAG NRTVRDCDPT AHAEIVALRE  60
AARKLGNYRL AGCTLYVTVE PCAMCAGALV WARVDRLVYG ADDPKAGAVR SALAVVDHPR  120
LNHRMEVVSG VLAGECAALL QEFFAARR                                     148

SEQ ID NO: 47          moltype = AA  length = 142
FEATURE                Location/Qualifiers
source                 1..142
                       mol_type = protein
                       organism = synthetic construct
SEQUENCE: 47
MREALAEARA AAAAGEVPVG AVVVRDGAVL ARAGNASIRA RDPTAHAEIL ALRAAARALG  60
NHRLTGCTLY VTLEPCAMCA GAIAHARVAR LVYGAADPKG GAVAHGPRFF EQPTCHHRPE  120
VTGGVLAEEA GALLRDFFRA RR                                           142

SEQ ID NO: 48          moltype = AA  length = 142
FEATURE                Location/Qualifiers
source                 1..142
                       mol_type = protein
                       organism = synthetic construct
SEQUENCE: 48
MREALAEARA AAAAGEVPVG AVVVRDGAVL ARAGNASIRA RDPTAHAEIL ALRAAARALG  60
NHRLDGCTLY VTLEPCAMCA GAIAQARVAR LVYGAADPKG GAVAHGPRLF AQPTCHHRPE  120
VTGGVGEAEA AALLRDFFAA RR                                           142

SEQ ID NO: 49          moltype = AA  length = 148
FEATURE                Location/Qualifiers
source                 1..148
                       mol_type = protein
                       organism = synthetic construct
SEQUENCE: 49
MTDEYFMRQA LREARKAYDE DEVPVGAVVV RDGKVIARGR NQVERLKDPT AHAEMIALTS  60
AANYLGSKRL EGCTVYVTLE PCPMCAGALV LARVERLVFG AFDPKAGACG TLYDIPGDRR  120
LNHRIEVVGG VLEEESAALL REFFEKRR                                     148

SEQ ID NO: 50          moltype = AA  length = 142
FEATURE                Location/Qualifiers
source                 1..142
                       mol_type = protein
```

```
                         organism = synthetic construct
SEQUENCE: 50
MREALAEARA AAAAGEVPVG AVVVRDGAVL ARAGNASIRA RDPTAHAEML ALRAAARALG  60
NHRLDGCTLY VTLEPCAMCA GAIAHARIAR LVYGAADPKG GAVAHGPRFF AQPTCHHRPE  120
VTGGVLAEEA GALLRDFFRA RR                                           142

SEQ ID NO: 51            moltype = AA  length = 142
FEATURE                  Location/Qualifiers
source                   1..142
                         mol_type = protein
                         organism = synthetic construct
SEQUENCE: 51
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPE  120
VVGGVGAGEA AALLRDFFAA RR                                           142

SEQ ID NO: 52            moltype = AA  length = 148
FEATURE                  Location/Qualifiers
source                   1..148
                         mol_type = protein
                         organism = synthetic construct
SEQUENCE: 52
MDDAGFMRLA LAEARAAAAA GEVPVGAVVV RDGAVLAAAG NRTLRDCDPT AHAEVVALRA  60
AARALGNHRL EGCDLYVTLE PCAMCAGAIS FARIRRLYFG AADPKGGAVE HGPRFFAQPT  120
CHHAPEVYGG LAESEAAALL RGFFAARR                                     148

SEQ ID NO: 53            moltype = AA  length = 142
FEATURE                  Location/Qualifiers
source                   1..142
                         mol_type = protein
                         organism = synthetic construct
SEQUENCE: 53
MREALAEARA AAAAGEVPVG AVVVRDGAVL ARAGNRTVRD ADPTAHAEIV ALRAAARALG  60
NHRLDGCTLY VTLEPCAMCA GAIAQARVAR LVYGAADPKG GAVAHGPRLF EQPTTHHRPE  120
VVGGVLAAEA GALLRAFFAA RR                                           142

SEQ ID NO: 54            moltype = AA  length = 142
FEATURE                  Location/Qualifiers
source                   1..142
                         mol_type = protein
                         organism = synthetic construct
SEQUENCE: 54
MTEALAEARK AAALGEVPVG AVVVRDGAVI ARGHNRTVTD ADPTAHAEIV ALREAARALG  60
NHRLTGCTLY VTLEPCAMCA GAIVHARVDR LVYGAADPKA GAAGSVLDVI GHPRLNHRPE  120
VEGGVLGEEC GALLRDFFRA RR                                           142

SEQ ID NO: 55            moltype = AA  length = 142
FEATURE                  Location/Qualifiers
source                   1..142
                         mol_type = protein
                         organism = synthetic construct
SEQUENCE: 55
MRSALDLAAA AAAAGEVPVG AVVVRDGAIV GRGENRVLRD SDPTAHAEIV AMREAARALG  60
NYRLTGCTLY VTLEPCAMCA GAMVHARLDR LVYGAADPKA GAAGSVLDVL GHPRLNHQME  120
VEGGVLAAES AALLRDFFRA RR                                           142

SEQ ID NO: 56            moltype = AA  length = 142
FEATURE                  Location/Qualifiers
source                   1..142
                         mol_type = protein
                         organism = synthetic construct
SEQUENCE: 56
MREALAEARA AAAAGEVPVG AVVVRDGAVL ARAGNASIRA RDPTAHAEIL ALRAAARALG  60
NHRLTGCTLY VTLEPCAMCA GAIAHARIAR LVYGAADPKG GAVAHGPRFF EQPTCHHRPE  120
VTGGVLAEEA GALLRDFFRA RR                                           142

SEQ ID NO: 57            moltype = AA  length = 148
FEATURE                  Location/Qualifiers
source                   1..148
                         mol_type = protein
                         organism = synthetic construct
SEQUENCE: 57
MDDAGFMRLA LAEAEAAAAA GEVPVGAVVV RDGEVIARAG NRTVRDCDPT AHAEIVALRA  60
AARALGNHRL TGCTLYVTLE PCAMCAGAIS HARVARLVYG ADDPKGGAVA HGPRFFAQPT  120
CHHRPEVAGG VLAEEAGALL RGFFRARR                                     148

SEQ ID NO: 58            moltype = AA  length = 148
FEATURE                  Location/Qualifiers
source                   1..148
```

```
                         mol_type = protein
                         organism = synthetic construct
SEQUENCE: 58
MDDAGFMRLA LAEARAAAAA GEVPVGAVVV RDGAVLAAAG NRTLRDCDPT AHAEIVALRA  60
AARALGNYRL DGCDLYVTLE PCAMCAGAML HARLRRVVFG AADPKTGAAG SVLDLFAERR  120
LNHRTAVAGG VLADECGALL RDFFRARR                                     148

SEQ ID NO: 59            moltype = AA  length = 147
FEATURE                  Location/Qualifiers
source                   1..147
                         mol_type = protein
                         organism = synthetic construct
SEQUENCE: 59
MDDAGFMRLA LAEARAAAAA GEVPVGAVVV RDGAVLAAAG NRTLRDCDPT AHAEVVALRA  60
AARALGNHRL DGCDLYVTLE PCAMCAGAIS HARIRRLYYG ADDPKGGAVD NGVRFFASPT  120
CHHAPEVYGG LAEGEAAALL RDFFRER                                      147

SEQ ID NO: 60            moltype = AA  length = 142
FEATURE                  Location/Qualifiers
source                   1..142
                         mol_type = protein
                         organism = synthetic construct
SEQUENCE: 60
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGADDPKG GAVAHGPRFF AQPTCHHRPE  120
VVGGVGAEEA GALLRGFFAA RR                                           142

SEQ ID NO: 61            moltype = AA  length = 142
FEATURE                  Location/Qualifiers
source                   1..142
                         mol_type = protein
                         organism = synthetic construct
SEQUENCE: 61
MTEALREARR AAAAGEVPVG AVVVRDGAVL ARAGNRTVRD ADPTAHAEIV ALREAARALG  60
NHRLTGCTLY VTLEPCAMCA GAISHARIAR LVYGAADPKG GAVAHGPRFF EQPTCHHRPE  120
VTGGVGEAEA AALLRDFFRA RR                                           142

SEQ ID NO: 62            moltype = AA  length = 142
FEATURE                  Location/Qualifiers
source                   1..142
                         mol_type = protein
                         organism = synthetic construct
SEQUENCE: 62
MREALAEARA AAAAGEVPVG AVVVRDGAVL ARAGNRTVRD ADPTAHAEVV ALRAAARALG  60
NHRLGGCTLY VTLEPCAMCA GAIAQARVAR LVYGAADPKG GAVAHGPRLF AQPTCHHRPE  120
VVGGVGEAEA AALLRDFFAA RR                                           142

SEQ ID NO: 63            moltype = AA  length = 142
FEATURE                  Location/Qualifiers
source                   1..142
                         mol_type = protein
                         organism = synthetic construct
SEQUENCE: 63
MREALAEARA AAAAGEVPVG AVVVRDGAVL ARAGNASIRA RDPTAHAEVL ALRAAARALG  60
NHRLTGCTLY VTLEPCAMCA GAIAHARIAR LVYGAADPKG GAVAHGPRFF EQPTCHHRPE  120
VTGGVLAEEA GALLRDFFRA RR                                           142

SEQ ID NO: 64            moltype = AA  length = 148
FEATURE                  Location/Qualifiers
source                   1..148
                         mol_type = protein
                         organism = synthetic construct
SEQUENCE: 64
MTDEYFMRQA LREARRAYEE DEVPVGAVVV RDGRVIARGR NQVERLKDPT AHAEMIALTA  60
AANHLGSKRL EGCTVYVTLE PCPMCAGALV LARVPRLVFG AFDPKAGACG TLYDIVRDPR  120
LNHRVEVVGG VLEEECGELL KRFFRERR                                     148

SEQ ID NO: 65            moltype = AA  length = 142
FEATURE                  Location/Qualifiers
source                   1..142
                         mol_type = protein
                         organism = synthetic construct
SEQUENCE: 65
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVAHGPRLF AQPTCHHRPE  120
VVGGVGAAEA GALLRDFFAA RR                                           142

SEQ ID NO: 66            moltype = AA  length = 142
FEATURE                  Location/Qualifiers
```

```
source                  1..142
                        mol_type = protein
                        organism = synthetic construct
SEQUENCE: 66
MTEALAEARK AAAEGEVPVG AVVVRDGVVL ARAHNRTVAD HDPTAHAELL AIREAARVLG  60
NHRLTGCTLY VTLEPCAMCA GAIVHARLDR LVYGAADPKA GAAGSVLDVL GHPRLNHRPE  120
VEGGVLAAES AALLRDFFRA RR                                          142

SEQ ID NO: 67           moltype = AA  length = 148
FEATURE                 Location/Qualifiers
source                  1..148
                        mol_type = protein
                        organism = synthetic construct
SEQUENCE: 67
MDDAGFMRLA LAEAERAAAL GEVPVGAVLV RDGEVLAAAG NRTVADCDPT AHAEMLALRE  60
GARRLGNYRL TGCTLYVTLE PCAMCAGAMV HARLDRLVYA AADPKAGAAG SVLDVLNHPA  120
LNHRMQVEGG VLAEESAALL RGFFRARR                                    148

SEQ ID NO: 68           moltype = AA  length = 142
FEATURE                 Location/Qualifiers
source                  1..142
                        mol_type = protein
                        organism = synthetic construct
SEQUENCE: 68
MREALAEARA AAAAGEVPVG AVVVRDGAVL ARAGNRTVRD ADPTAHAEIV ALREAARALG  60
NHRVGGATLY VTLEPCAMCA GAISQARVAR LVYGADDPKG GAVAHGPRFF EQPTCHHRPE  120
VTGGVLAEES AALLRGFFAA RR                                          142

SEQ ID NO: 69           moltype = AA  length = 142
FEATURE                 Location/Qualifiers
source                  1..142
                        mol_type = protein
                        organism = synthetic construct
SEQUENCE: 69
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPE  120
VVGGVGAAEA GALLRDFFRA RR                                          142

SEQ ID NO: 70           moltype = AA  length = 142
FEATURE                 Location/Qualifiers
source                  1..142
                        mol_type = protein
                        organism = synthetic construct
SEQUENCE: 70
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVAHGPRFF EQPTCHHRPD  120
VTGGVLAEEA GALLRDFFRA RR                                          142

SEQ ID NO: 71           moltype = AA  length = 148
FEATURE                 Location/Qualifiers
source                  1..148
                        mol_type = protein
                        organism = synthetic construct
SEQUENCE: 71
MTDEYFMRQA LREARRAYDE GEVPVGAVVV RDGRVIARGR NQVERLKDPT AHAEMIALTA  60
AADYLGSKRL EGCTLYVTLE PCAMCAGAIV LARIPRLVFG AFDPKAGACG TLYDIVRDRR  120
LNHRAEVVSG VLEEECGALL KEFFARLR                                    148

SEQ ID NO: 72           moltype = AA  length = 148
FEATURE                 Location/Qualifiers
source                  1..148
                        mol_type = protein
                        organism = synthetic construct
SEQUENCE: 72
MDDEFFMREA LRLAEEAAAA GEVPVGAVVV RDGEIVGRGR NRVLEDRDPT AHAEIVAMRE  60
AARRLGNYRL EGCTLYVTLE PCAMCAGAMV HARVARLVYG AADPKAGAAG SVLDVLGHPR  120
LNHRMEVTGG VLAEECGALL REFFRRRR                                    148

SEQ ID NO: 73           moltype = AA  length = 142
FEATURE                 Location/Qualifiers
source                  1..142
                        mol_type = protein
                        organism = synthetic construct
SEQUENCE: 73
MREALAEARA AAAAGEVPVG AVVVRDGAVL ARAGNRTVRD ADPTAHAELV AIRAAAAALG  60
QERLTGCTLY VTLEPCAMCA GAISHARIAR LVYGAADPKG GAVAHGPRFF EQPTCHHRPE  120
VTGGVLAEEA GALLRDFFRA RR                                          142

SEQ ID NO: 74           moltype = AA  length = 142
```

```
FEATURE                 Location/Qualifiers
source                  1..142
                        mol_type = protein
                        organism = synthetic construct
SEQUENCE: 74
MREALAEARA AAAAGEVPVG AVVVRDGAIV ARARNRMVAD CDPTAHAEIV ALREAARALG  60
NHRLDGCTLY VTLEPCAMCA GAMVHARVAR LVYGAADPRA GAAGSVLDVL GHPALNHRME  120
VAGGVLAEEC GALLREFFAA RR                                           142

SEQ ID NO: 75           moltype = AA  length = 142
FEATURE                 Location/Qualifiers
source                  1..142
                        mol_type = protein
                        organism = synthetic construct
SEQUENCE: 75
MRAALAEARA AAAAGEVPVG AVVVRDGAVL ARAGNASIRA RDPTAHAEIL ALRAAARALG  60
NHRLDGCTLY VTLEPCAMCA GAIAHARVAR LVYGAADPKG GAVAHGPRFF EQPTCHHRPE  120
VTGGVLAEEA GALLRDFFRA RR                                           142

SEQ ID NO: 76           moltype = AA  length = 142
FEATURE                 Location/Qualifiers
source                  1..142
                        mol_type = protein
                        organism = synthetic construct
SEQUENCE: 76
MRAALDEARA AAAAGEVPVG AVVVRDGAIL ARAGNRTVRD CDPTAHAEIV ALREAARALG  60
NHRLTGCTLY VTLEPCAMCA GAISHARVAR LVYGADDPKG GAVRHGPRFF EQPTCHHRPE  120
VVGGVGAEEA AALLRGFFAA RR                                           142

SEQ ID NO: 77           moltype = AA  length = 162
FEATURE                 Location/Qualifiers
source                  1..162
                        mol_type = protein
                        organism = synthetic construct
SEQUENCE: 77
MDDEAWMRRA IALAHQAEAE GEVPVGAVLV KDGEVIAEGW NRSIGHHDAT AHAEIETLRQ  60
AGQALQNYRL LDTTLYVTLE PCPMCAGALL HSRVKRVVFG APDLKAGAAG TVLNLFESQA  120
SYHYAEVESG LLEQECREQL QAFFKRRRKE IKALRQAQRD AE                     162

SEQ ID NO: 78           moltype = AA  length = 148
FEATURE                 Location/Qualifiers
source                  1..148
                        mol_type = protein
                        organism = synthetic construct
SEQUENCE: 78
MDDAGFMRLA LAEARAAAAA GEVPVGAVVV RDGAVLAAAG NRTLRDCDPT AHAEVVALRA  60
AARALGNHRL EGCDLYVTLE PCAMCAGAIA HARIARLYYG AADPKGGAVE HGARVFDQPQ  120
CLHRPEVYGG IGEAEAAALL RGFFAARR                                     148

SEQ ID NO: 79           moltype = AA  length = 142
FEATURE                 Location/Qualifiers
source                  1..142
                        mol_type = protein
                        organism = synthetic construct
SEQUENCE: 79
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGADDPKG GAVAHGPRFF AQPTCHHRPE  120
VAGGLGEAEA GALLRDFFAA RR                                           142

SEQ ID NO: 80           moltype = AA  length = 142
FEATURE                 Location/Qualifiers
source                  1..142
                        mol_type = protein
                        organism = synthetic construct
SEQUENCE: 80
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGAADPKG GAVAHGPRLF AQPTCHHRPE  120
VVGGVGEAEA AALLRAFFAA RR                                           142

SEQ ID NO: 81           moltype = AA  length = 142
FEATURE                 Location/Qualifiers
source                  1..142
                        mol_type = protein
                        organism = synthetic construct
SEQUENCE: 81
MRDALAEARA AAAAGEVPVG AVVVRDGAVL ARAGNASIRA RDPTAHAEIL ALRAAARALG  60
NHRLDGCTLY VTLEPCAMCA GAIAHARIAR LVYGAADPKG GAVAHGPRFF AQPTCHHRPE  120
VTGGVGEAEA AALLRAFFAA RR                                           142
```

```
SEQ ID NO: 82          moltype = AA  length = 148
FEATURE                Location/Qualifiers
source                 1..148
                       mol_type = protein
                       organism = synthetic construct
SEQUENCE: 82
MTDEYFMRQA LREARRAYEE DEVPVGAVVV RDGRVIARGR NQVERLKDPT AHAEMIALTA  60
AANHLGSKRL EGCTVYVTLE PCPMCAGALV LARVERLVFG AFDPKAGACG TLYDIPGDRR  120
LNHRLEVVGG VLEEESAALL REFFRKRR                                     148

SEQ ID NO: 83          moltype = AA  length = 148
FEATURE                Location/Qualifiers
source                 1..148
                       mol_type = protein
                       organism = synthetic construct
SEQUENCE: 83
MTDEDYMRLA LEEARAAAAA GEVPIGAVVV RDGEVLARAG NRTVRDCDPT AHAEIVALRE  60
AARVLGNYRL AGCTLYVTVE PCAMCAGAIV HARVARLVYG ADDPKGGAVR SCLEVLDHPR  120
LNHRVEVTAG VLAGECAALL QDFFAARR                                     148

SEQ ID NO: 84          moltype = AA  length = 142
FEATURE                Location/Qualifiers
source                 1..142
                       mol_type = protein
                       organism = synthetic construct
SEQUENCE: 84
MREALAEARA AAAAGEVPVG AVVVRDGAVL ARAGNRTVRD ADPTAHAEVL ALRAAARALG  60
SERLTGCTLY VTLEPCAMCA GAISHARVAR LVYGAADPKG GAVEHGARVF EQPTCHHRPE  120
VVGGVGAAEA GALLRDFFAA RR                                           142

SEQ ID NO: 85          moltype = AA  length = 142
FEATURE                Location/Qualifiers
source                 1..142
                       mol_type = protein
                       organism = synthetic construct
SEQUENCE: 85
MREALAEARA AAAAGEVPVG AVVVRDGAIL ARAGNASIRA RDPTAHAEIL ALRAAARALG  60
NHRLTGCTLY VTLEPCAMCA GAIAHARIAR LVYGAADPKG GAVAHGPRFF EQPTCHHRPE  120
VTGGVLAEEA GALLRAFFRA RR                                           142

SEQ ID NO: 86          moltype = AA  length = 148
FEATURE                Location/Qualifiers
source                 1..148
                       mol_type = protein
                       organism = synthetic construct
SEQUENCE: 86
MDDAGFMRLA LEEARAAAAA GEVPVGAVVV RDGAVLARAG NRTLRDRDPT AHAEMVALRA  60
AARALGSERL TGCDLYVTLE PCAMCAGAIS FARIRRLYFG AADPKGGAVE NGVRFFASPT  120
CHHAPEVYGG LAESEAAALL RDFFRARR                                     148

SEQ ID NO: 87          moltype = AA  length = 148
FEATURE                Location/Qualifiers
source                 1..148
                       mol_type = protein
                       organism = synthetic construct
SEQUENCE: 87
MTDEYFMRQA LREARRAYDE GEVPVGAVVV RDGRVIARGR NQVERLKDPT AHAEMLALTA  60
AAGHLGSKYL TGCTLYVTVE PCAMCAGALV WARVERVVFG ARDPKAGACG SVFDIPGDRR  120
LNHRPEVVGG VLEAECAALM RDFFRERR                                     148

SEQ ID NO: 88          moltype = AA  length = 142
FEATURE                Location/Qualifiers
source                 1..142
                       mol_type = protein
                       organism = synthetic construct
SEQUENCE: 88
MREALAEARA AAAAGEVPVG AVVVRDGAVL ARAGNASIRA RDPTAHAEML ALRAAARALG  60
NHRLDGCTLY VTLEPCAMCA GAIAHARVAR LVYGAADPKG GAVAHGPRFF EQPTCHHRPE  120
VTGGVLAEEA GALLREFFRA RR                                           142

SEQ ID NO: 89          moltype = AA  length = 142
FEATURE                Location/Qualifiers
source                 1..142
                       mol_type = protein
                       organism = synthetic construct
SEQUENCE: 89
MREALAEARA AAAAGEVPVG AVVVRDGAIL ARAGNASIRA RDPTAHAEIL ALRAAARALG  60
NHRLTGCTLY VTLEPCAMCA GAIAHARIAR LVYGAADPKG GAVAHGPRFF AQPTCHHRPE  120
VTGGVLAEEA GALLRAFFRA RR                                           142
```

```
SEQ ID NO: 90          moltype = AA  length = 163
FEATURE                Location/Qualifiers
source                 1..163
                       mol_type = protein
                       organism = synthetic construct
SEQUENCE: 90
MSDEQYMRRA LELARQAEQA GEVPVGAVLV KDGEIIAEGW NQSISAHDAT AHAEIMALRA  60
AGQALENYRL LDTTLYVTLE PCPMCAGALL HSRVKRVVFG APDLKAGAAG TVLNLFESQA  120
SYHYADVESG LLEDECREQL QAFFKRRRKE IKALRQAQRE AEE                    163

SEQ ID NO: 91          moltype = AA  length = 162
FEATURE                Location/Qualifiers
source                 1..162
                       mol_type = protein
                       organism = synthetic construct
SEQUENCE: 91
MSEEQYMRRA LELARQAEQE GEVPVGAVLV KDGEVIAEGW NRSIGSHDAT GHAEIMALRA  60
AGEKLENYRL LDTTLYVTLE PCPMCAGALL HSRVKRVVFG APDLKAGAAG TVLNLFESQA  120
SYHYADVESG LLEEECREQL QAFFKRRRKE IKALRQAQKE AE                     162

SEQ ID NO: 92          moltype = AA  length = 148
FEATURE                Location/Qualifiers
source                 1..148
                       mol_type = protein
                       organism = synthetic construct
SEQUENCE: 92
MDDAGFMRLA LAEARRAAEA GEVPVGAVVV RDGAVLAAAG NRTLRDCDPT AHAEVVALRE  60
AARALGNHRL GGCDLYVTLE PCAMCAGAIS HARIARLYYG ADDPKGGAVA HGARVFDQPT  120
CHHRPEVYGG IGAAEAAALL RDFFRARR                                     148

SEQ ID NO: 93          moltype = AA  length = 142
FEATURE                Location/Qualifiers
source                 1..142
                       mol_type = protein
                       organism = synthetic construct
SEQUENCE: 93
MREALAEARA AAAAGEVPVG AVVVRDGAVL ARAGNASIRA RDPTAHAEVL ALRAAARALG  60
NHRLTGCTLY VTLEPCAMCA GAIAHARVAR LVYGAADPKG GAVAHGPRFF EQPTCHHRPE  120
VTGGVLAAEA GALLRDFFRA RR                                           142

SEQ ID NO: 94          moltype = AA  length = 142
FEATURE                Location/Qualifiers
source                 1..142
                       mol_type = protein
                       organism = synthetic construct
SEQUENCE: 94
MREALAEARA AAAAGEVPVG AVVVRDGAVL ARAGNASIRA RDPTAHAEML ALRAAARALG  60
NHRLDGCTLY VTLEPCAMCA GAIAHARIAR LVYGAADPKG GAVAHGPRFF AQPTCHHRPD  120
VTGGVLAEEA GALLRDFFRA RR                                           142

SEQ ID NO: 95          moltype = AA  length = 142
FEATURE                Location/Qualifiers
source                 1..142
                       mol_type = protein
                       organism = synthetic construct
SEQUENCE: 95
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGADDPKG GAVAHGPRFF AQPTCHHRPE  120
VVGGVGEAEA GALLRDFFAA RR                                           142

SEQ ID NO: 96          moltype = AA  length = 148
FEATURE                Location/Qualifiers
source                 1..148
                       mol_type = protein
                       organism = synthetic construct
SEQUENCE: 96
MTDEYFMRQA LREARRAYDE GEVPVGAVVV RDGRVIARGR NQVERLKDPT AHAEMLALTA  60
AAAHLGSKRL EGCTVYVTLE PCAMCAGALV LARVDRLVFG AFDPKAGACG TVYDIPRDRR  120
LNHRVEVVGG VLEEESAALL RAFFEERR                                     148

SEQ ID NO: 97          moltype = AA  length = 142
FEATURE                Location/Qualifiers
source                 1..142
                       mol_type = protein
                       organism = synthetic construct
SEQUENCE: 97
MREALAEARA AAAAGEVPVG AVVVRDGAVL ARAGNASIRA RDPTAHAEIL ALRAAARALG  60
NHRLDGCTLY VTLEPCAMCA GAIAQARVAR LVYGAADPKG GAVAHGPRLF AQPTCHHRPE  120
```

```
VVGGVGAEEA AALLRGFFAA RR                                          142

SEQ ID NO: 98          moltype = AA  length = 148
FEATURE                Location/Qualifiers
source                 1..148
                       mol_type = protein
                       organism = synthetic construct
SEQUENCE: 98
MTDEYFMRQA LREARRAYDE GEVPVGAVVV RDGRVIARGR NQVERLKDPT AHAEMIALTA  60
AADHLGSKRL EGCTLYVTLE PCAMCAGAIV LARIPRLVFG AFDPKAGACG TLYDIVRDRR  120
LNHRVEVVSG VLEEESAALL REFFAERR                                    148

SEQ ID NO: 99          moltype = AA  length = 142
FEATURE                Location/Qualifiers
source                 1..142
                       mol_type = protein
                       organism = synthetic construct
SEQUENCE: 99
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPD  120
VVGGVGAAEA GALLRDFFRA RR                                          142

SEQ ID NO: 100         moltype = AA  length = 148
FEATURE                Location/Qualifiers
source                 1..148
                       mol_type = protein
                       organism = synthetic construct
SEQUENCE: 100
MTDEYFMRQA LREARRAYDE DEVPVGAVVV RDGRVIARGR NQVERLKDPT AHAEMIALTS  60
AANHLGSKRL EGCTVYVTLE PCPMCAGALV LARVPRLVFG AFDPKAGACG TLYDIPRDRR  120
LNHRVEVVGG VLEEESAALL REFFARRR                                    148

SEQ ID NO: 101         moltype = AA  length = 142
FEATURE                Location/Qualifiers
source                 1..142
                       mol_type = protein
                       organism = synthetic construct
SEQUENCE: 101
MTEALAEARK AAAAGEVPVG AVLVRDGEIL ARGGNRTIRD CDPTAHAEIV ALREAARKLG  60
NYRLAGCTLY VTLEPCAMCA GAMIHARLDR LVYGADDPKA GAAGSVLDVL NHPRLNHQME  120
VTRGVLADEC GALLRDFFQA RR                                          142

SEQ ID NO: 102         moltype = AA  length = 148
FEATURE                Location/Qualifiers
source                 1..148
                       mol_type = protein
                       organism = synthetic construct
SEQUENCE: 102
MTDEYFMRQA LREARRAFDE DEVPVGAVVV RDGRVIARGR NQVERLKDPT AHAEMIAITS  60
AANYLGSKRL EGCTVYVTLE PCPMCAGALV LARVPRLVFG AFDPKAGACG TLYDIPRDRR  120
LNHRLEVVGG VLEEESAALL REFFARRR                                    148

SEQ ID NO: 103         moltype = AA  length = 148
FEATURE                Location/Qualifiers
source                 1..148
                       mol_type = protein
                       organism = synthetic construct
SEQUENCE: 103
MTDEDYMRLA LEEARAAAAA GEVPVGAVVV RDGAVLARAG NRTVRDCDPT AHAEIVALRA  60
AARALGNYRL PGCTLYVTVE PCAMCAGAMI HARLDRLVYG ADDPKAGAVR STLRVLDHPA  120
LNHRMAVTAG VLADECAALL QDFFRARR                                    148

SEQ ID NO: 104         moltype = AA  length = 142
FEATURE                Location/Qualifiers
source                 1..142
                       mol_type = protein
                       organism = synthetic construct
SEQUENCE: 104
MREALAEARA AAAAGEVPIG AVVVRDGAVL ARAGNRTVRD CDPTAHAEIV ALREAARALG  60
NHRLTGCTLY VTVEPCAMCA GAISWARVAR LVYGAADPKG GAVRHGPRLF EQPTCHHAPE  120
VVDGVCAEEA AALLRDFFRA RR                                          142

SEQ ID NO: 105         moltype = AA  length = 148
FEATURE                Location/Qualifiers
source                 1..148
                       mol_type = protein
                       organism = synthetic construct
SEQUENCE: 105
MDDEALMGLA LDEARAAAAA GEAPIGAVVA RGGEVLAAAG NRTLRDCDPT AHAEILALRE  60
```

```
AARKLGNYRL TGCTLYATLE PCAMCAGAIS HARIARLVYG ADDPKGGAVR HGPRFFEQPT  120
CHHRPEVAGG VGAAEAGALL RDFFRARR                                     148

SEQ ID NO: 106          moltype = AA  length = 148
FEATURE                 Location/Qualifiers
source                  1..148
                        mol_type = protein
                        organism = synthetic construct
SEQUENCE: 106
MDDEALMGLA LDEARAAAAA GEAPIGAVVA RGGEVLAAAG NRTLRDCDPT AHAEVLALRE  60
AARRLGNYRL TGCTLYVTLE PCAMCAGAIS HARVARLVYG AADPKGGAVA HGPRFFEQPT  120
CHHRPEVTGG VGAAEAGALL RDFFRARR                                     148

SEQ ID NO: 107          moltype = AA  length = 164
FEATURE                 Location/Qualifiers
source                  1..164
                        mol_type = protein
                        organism = synthetic construct
SEQUENCE: 107
MSDEQYMRRA LELARQAEAE GEVPVGAVLV RDGEVIAEGW NRSIGSHDAT GHAEIMALRA  60
AGQALQNYRL LDTTLYVTLE PCPMCAGALL HSRVKRVVFG APDLKAGAAG TVLNLFESQA  120
SYHYADVESG LLEEECREQL QAFFKRRRKE IKALRQAQRE AEEK                   164

SEQ ID NO: 108          moltype = AA  length = 142
FEATURE                 Location/Qualifiers
source                  1..142
                        mol_type = protein
                        organism = synthetic construct
SEQUENCE: 108
MTEALAEARK AAAAGEVPVG AVLVRDGAVL ARGGNRTIRD CDPTAHAEIV ALRAAARALG  60
NYRLPGTTLY VTLEPCAMCA GAMIHARVDR LVYGAADPRA GAAGSVLDVI GHPALNHRMA  120
VEGGVLAEEC GALLRDFFRA RR                                           142

SEQ ID NO: 109          moltype = AA  length = 148
FEATURE                 Location/Qualifiers
source                  1..148
                        mol_type = protein
                        organism = synthetic construct
SEQUENCE: 109
MTDEYFMRQA LREARRAYDE GEVPVGAVVV RDGRVIARGR NQVERLKDPT AHAEMLALTA  60
AAAHLGSKRL EGCTLYVTLE PCAMCAGAIV LARVPRLVFG AFDPKAGACG TLYDIVRDRR  120
LNHRVEVVSG VLEEESAALL REFFARLR                                     148

SEQ ID NO: 110          moltype = AA  length = 142
FEATURE                 Location/Qualifiers
source                  1..142
                        mol_type = protein
                        organism = synthetic construct
SEQUENCE: 110
MREALAEARA AAAAGEVPVG AVVVRDGAVL ARAGNRTVRD ADPTAHAEIV ALRAAARALG  60
NHRLDGCTLY VTLEPCAMCA GAIAQARVAR LVYGAADPKG GAVAHGPRLF EQPTTHHRPE  120
VVGGVLAEEA GALLRGFFAA RR                                           142

SEQ ID NO: 111          moltype = AA  length = 142
FEATURE                 Location/Qualifiers
source                  1..142
                        mol_type = protein
                        organism = synthetic construct
SEQUENCE: 111
MREALAEARA AAAAGEVPVG AVVVRDGAVL ARAGNASIRA RDPTAHAEIL ALRAAARALG  60
NHRLDGCTLY VTLEPCAMCA GAIAHARVAR LVYGAADPKG GAVAHGPRFF EQPTCHHRPE  120
VTGGVLAAEA GALLRDFFRA RR                                           142

SEQ ID NO: 112          moltype = AA  length = 142
FEATURE                 Location/Qualifiers
source                  1..142
                        mol_type = protein
                        organism = synthetic construct
SEQUENCE: 112
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPE  120
VVGGVGAAEA GALLREFFAA RR                                           142

SEQ ID NO: 113          moltype = AA  length = 142
FEATURE                 Location/Qualifiers
source                  1..142
                        mol_type = protein
                        organism = synthetic construct
SEQUENCE: 113
```

```
MRDALAEARA AAAAGEVPVG AVVVRDGAIL ARAGNASIRA RDPTAHAEIL ALRAAARALG  60
NHRLTGCTLY VTLEPCAMCA GAIAHARIAR LVYGAADPKG GAVAHGPRFF EQPTCHHRPE  120
VTGGVLAEEA GALLRDFFRA RR                                           142

SEQ ID NO: 114         moltype = AA  length = 148
FEATURE                Location/Qualifiers
source                 1..148
                       mol_type = protein
                       organism = synthetic construct
SEQUENCE: 114
MDDAGFMRLA LAEAEAAAAA GEVPVGAVVV RDGEVIARAG NRTVRDCDPT AHAEIVALRE  60
AARKLGNYRL PGCTLYVTLE PCAMCAGAMI HARLDRVVYG AADPKTGAAG SVLDLFADRR  120
LNHHTAVVGG VLAEEAGALL RAFFAARR                                     148

SEQ ID NO: 115         moltype = AA  length = 142
FEATURE                Location/Qualifiers
source                 1..142
                       mol_type = protein
                       organism = synthetic construct
SEQUENCE: 115
MREALAEARA AAAAGEVPVG AVVVRDGAVL ARAGNASIRA RDPTAHAEIL ALRAAARALG  60
NHRLTGCTLY VTLEPCAMCA GAIAHARVAR LVYGAADPKG GAVAHGPRFF EQPTCHHRPE  120
VTGGVLAEEA GALLRAFFRA RR                                           142

SEQ ID NO: 116         moltype = AA  length = 142
FEATURE                Location/Qualifiers
source                 1..142
                       mol_type = protein
                       organism = synthetic construct
SEQUENCE: 116
MREALAEARA AAAAGEVPVG AVVVRDGAVL ARAGNASIRA RDPTAHAEML ALRAAARALG  60
NHRLTGCTLY VTLEPCAMCA GAIAHARVAR LVYGAADPKG GAVAHGPRFF EQPTCHHRPE  120
VTGGVLAEEA GALLRDFFRA RR                                           142

SEQ ID NO: 117         moltype = AA  length = 142
FEATURE                Location/Qualifiers
source                 1..142
                       mol_type = protein
                       organism = synthetic construct
SEQUENCE: 117
MRAALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPE  120
VVGGVGAAEA GALLRDFFRA RR                                           142

SEQ ID NO: 118         moltype = AA  length = 142
FEATURE                Location/Qualifiers
source                 1..142
                       mol_type = protein
                       organism = synthetic construct
SEQUENCE: 118
MREALAEARA AAAAGEVPVG AVVVRDGAVL ARAGNASIRA RDPTAHAEVL ALRAAARALG  60
NHRLTGCTLY VTLEPCAMCA GAIAHARLAR LVYGAADPKG GAVEHGPRFF AQPTCHHRPE  120
VTGGVGAAEA GALLRAFFAA RR                                           142

SEQ ID NO: 119         moltype = AA  length = 164
FEATURE                Location/Qualifiers
source                 1..164
                       mol_type = protein
                       organism = synthetic construct
SEQUENCE: 119
MSDEQFMRRA IELAKKGEEL GEVPVGAVLV KDGEIIAEGW NQSISTHDAT AHAEIMALRA  60
AGEKLQNYRL LDTTLYVTLE PCPMCAGALL HSRVKRVVFG APDLKAGAAG TVLNLFESQA  120
SYHYADVESG LLEEECREQL QAFFKRRRKE IKALKKAKKE AEQK                   164

SEQ ID NO: 120         moltype = AA  length = 143
FEATURE                Location/Qualifiers
source                 1..143
                       mol_type = protein
                       organism = synthetic construct
SEQUENCE: 120
MREALAEARA AAAAGEVPIG AVVVRDGAVL ARAGNRTVRD CDPTAHAEIV ALREAARALG  60
NYRLDGCTLY VTLEPCAMCA GAMLHARLAR VVYGAADPKT GAAGSVLDLF AERRLNHQTE  120
VAGGVLAEEC GALLRDFFRA RRG                                          143

SEQ ID NO: 121         moltype = AA  length = 142
FEATURE                Location/Qualifiers
source                 1..142
                       mol_type = protein
                       organism = synthetic construct
```

```
SEQUENCE: 121
MTEALAEARK AAALGEVPVG AVVVRDGAVI ARGHNRTVTD TDPTAHAEIV ALREAARALG  60
NHRLTGCTLY VTLEPCAMCA GAIVHARLDR VVYGAADPKA GAAGSVLDVL GHPRLNHRPE  120
VAGGVLAAES AALLRDFFRA RR                                           142

SEQ ID NO: 122          moltype = AA  length = 148
FEATURE                 Location/Qualifiers
source                  1..148
                        mol_type = protein
                        organism = synthetic construct
SEQUENCE: 122
MTDEYFMRQA LREARRAYDE GEVPVGAVVV RDGRVIARGR NQVERLKDPT AHAEMLALTA  60
AAAHLGSKRL EGCTLYVTLE PCAMCAGAIV LARIPRLVFG AFDPKAGACG TLYDIVRDRR  120
LNHRAEVVSG VLEEECGALL KEFFARLR                                     148

SEQ ID NO: 123          moltype = AA  length = 142
FEATURE                 Location/Qualifiers
source                  1..142
                        mol_type = protein
                        organism = synthetic construct
SEQUENCE: 123
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGADDPKG GAVAHGPRFF AQPTCHHRPE  120
VVGGVGEAEA AALLRGFFAA RR                                           142

SEQ ID NO: 124          moltype = AA  length = 142
FEATURE                 Location/Qualifiers
source                  1..142
                        mol_type = protein
                        organism = synthetic construct
SEQUENCE: 124
MREALAEARA AAAAGEVPVG AVVVRDGAVL ARAGNRTVRD ADPTAHAELV AIRAAARALG  60
SERLTGCTLY VTLEPCAMCA GAISHARVAR LVYGAADPKG GAVAHGPRFF EQPTCHHRPE  120
VTGGVLAEEA GALLRDFFRA RR                                           142

SEQ ID NO: 125          moltype = AA  length = 148
FEATURE                 Location/Qualifiers
source                  1..148
                        mol_type = protein
                        organism = synthetic construct
SEQUENCE: 125
MTDEYFMRQA LREARRAYEE DEVPVGAVVV REGRVIARGR NQVERLKDPT AHAEMIALTS  60
AANYLGSKRL EGCTVYVTLE PCPMCAGALV LARVERLVFG AFDPKAGACG TLYDIPGDRR  120
LNHRIEVVGG VLEEESAALL REFFRRRR                                     148

SEQ ID NO: 126          moltype = AA  length = 142
FEATURE                 Location/Qualifiers
source                  1..142
                        mol_type = protein
                        organism = synthetic construct
SEQUENCE: 126
MSEALAEARK AAALGEVPVG AVVVRDGAVI ARGHNRTVAD ADPTAHAEIV ALREAARALG  60
NHRLTGCTLY VTLEPCAMCA GAIVHARLDR LVYGAADPKA GAAGSVLDVL GHPRLNHRPE  120
VEGGVLAAES AALLRDFFRA RR                                           142

SEQ ID NO: 127          moltype = AA  length = 164
FEATURE                 Location/Qualifiers
source                  1..164
                        mol_type = protein
                        organism = synthetic construct
SEQUENCE: 127
MSDEQYMRRA LELARQAEQE GEVPVGAVLV KDGEVIAEGW NRSIGSHDAT GHAEIMALRA  60
AGEKLGNYRL LDTTLYVTLE PCPMCAGALL HSRVKRVVFG APDLKAGAAG TVLNLFESQA  120
SYHYADVESG LLEEECREQL QAFFKRRRKE IKAARKAKRE AEEK                   164

SEQ ID NO: 128          moltype = AA  length = 142
FEATURE                 Location/Qualifiers
source                  1..142
                        mol_type = protein
                        organism = synthetic construct
SEQUENCE: 128
MREALAEARA AAAAGEVPVG AVVVRDGAVL ARAGNASIRA RDPTAHAEML ALRAAARALG  60
NHRLTGCTLY VTLEPCAMCA GAIAHARVAR LVYGAADPKG GAVAHGPRFF EQPTCHHRPE  120
VTGGVLAEEA GALLRAFFRA RR                                           142

SEQ ID NO: 129          moltype = AA  length = 148
FEATURE                 Location/Qualifiers
source                  1..148
                        mol_type = protein
```

```
                         organism = synthetic construct
SEQUENCE: 129
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG AADPKAGAAG SVLDVLGHPR  120
LNHRMEVEGG VLAAECGALL RDFFRARR                                     148

SEQ ID NO: 130           moltype = AA  length = 142
FEATURE                  Location/Qualifiers
source                   1..142
                         mol_type = protein
                         organism = synthetic construct
SEQUENCE: 130
MRAALDEARA AAAAGEVPVG AVVVRDGAVL ARAGNASIRA RDPTAHAEIL ALRAAARALG  60
NHRLTGCTLY VTLEPCAMCA GAIAHARVAR LVYGAADPKG GAVEHGPRFF AQPTCHHRPE  120
VTGGVLAAEA GALLRDFFRA RR                                           142

SEQ ID NO: 131           moltype = AA  length = 142
FEATURE                  Location/Qualifiers
source                   1..142
                         mol_type = protein
                         organism = synthetic construct
SEQUENCE: 131
MTEALAEARK AAAAGEVPVG AVVVRDGEIL ARAHNRTVAD HDPTAHAEIL ALREAARRLG  60
NHRLTGCELY VTLEPCAMCA GAISHARIAR LVYGAADPKG GAVEHGPRFF AQPTCHHRPE  120
VVGGVGASEA AALLRDFFRA RR                                           142

SEQ ID NO: 132           moltype = AA  length = 142
FEATURE                  Location/Qualifiers
source                   1..142
                         mol_type = protein
                         organism = synthetic construct
SEQUENCE: 132
MRAALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVAHGPRFF EQPTCHHRPE  120
VTGGVLAEEA GALLRAFFRA RR                                           142

SEQ ID NO: 133           moltype = AA  length = 148
FEATURE                  Location/Qualifiers
source                   1..148
                         mol_type = protein
                         organism = synthetic construct
SEQUENCE: 133
MDDAGFMRLA LEEARAAAAA GEVPVGAVVV RDGEVLARAG NRTVRDCDPT AHAEVVALRE  60
AARKLGNHRL TGCTLYVTLE PCAMCAGAIS HARVARLVYG ADDPKGGAVA HGPRFFAQPT  120
CHHRPEVAGG LLAGEAAALL RDFFAARR                                     148

SEQ ID NO: 134           moltype = AA  length = 142
FEATURE                  Location/Qualifiers
source                   1..142
                         mol_type = protein
                         organism = synthetic construct
SEQUENCE: 134
MRDALAEARA AAAAGEVPVG AVVVRDGAVL ARAGNASIRA RDPTAHAEIL ALRAAARALG  60
NHRLTGCTLY VTLEPCAMCA GAIAHARIAR LVYGAADPKG GAVAHGPRFF EQPTCHHRPE  120
VTGGVLAEEA GALLREFFRA RR                                           142

SEQ ID NO: 135           moltype = AA  length = 142
FEATURE                  Location/Qualifiers
source                   1..142
                         mol_type = protein
                         organism = synthetic construct
SEQUENCE: 135
MTEALAEARK AAAAGEVPVG AVLVRDGAVL ARGGNRTIRD CDPTAHAEIV ALRAAARALG  60
NYRLPGTTLY VTLEPCAMCA GAMIHARVDR LVYGAADPRA GAAGSVFDVI RHPALNHRME  120
VEGGVLAEEC GALLRDFFRA RR                                           142

SEQ ID NO: 136           moltype = AA  length = 142
FEATURE                  Location/Qualifiers
source                   1..142
                         mol_type = protein
                         organism = synthetic construct
SEQUENCE: 136
MREALAEARA AAAAGEVPVG AVVVRDGAVL ARAGNRTVRD ADPTAHAEIV ALREAARALG  60
NHRLTGCTLY VTLEPCAMCA GAISHARVAR LVYGADDPKG GAVAHGPRFF AQPTCHHRPE  120
VVGGVGAEEA GALLRDFFRA RR                                           142

SEQ ID NO: 137           moltype = AA  length = 149
FEATURE                  Location/Qualifiers
source                   1..149
```

```
                        mol_type = protein
                        organism = synthetic construct
SEQUENCE: 137
MTDEYFMRQA LREARRAYDE GEVPVGAVVV RDGRVIARGR NQVERLKDPT AHAEMLALTA  60
AAAHLGSKRL EGCTLYVTLE PCAMCAGAIV LARIPRLVFG AFDPKAGACG TLYDIVRDRR  120
LNHRVEVVSG VLEEESAALL REFFARLRA                                    149

SEQ ID NO: 138          moltype = AA  length = 163
FEATURE                 Location/Qualifiers
source                  1..163
                        mol_type = protein
                        organism = synthetic construct
SEQUENCE: 138
MSDEQYMRRA LELARQAEEE GEVPVGAVLV KDGEIVAEGW NRSIGSHDAT GHAEIMALRA  60
AGEKLENYRL LDTTLYVTLE PCPMCAGALL HSRVKRVVFG APDLKAGAAG TVLNLFESQA  120
SYHYADVESG LLEEECREQL QAFFKRRRKE IKAQRDAEKA AAE                    163

SEQ ID NO: 139          moltype = AA  length = 142
FEATURE                 Location/Qualifiers
source                  1..142
                        mol_type = protein
                        organism = synthetic construct
SEQUENCE: 139
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPE  120
VVGGVGAAEA GALLRAFFAA RR                                           142

SEQ ID NO: 140          moltype = AA  length = 142
FEATURE                 Location/Qualifiers
source                  1..142
                        mol_type = protein
                        organism = synthetic construct
SEQUENCE: 140
MRDALAEARA AAAAGEVPVG AVVVRDGAIL ARAGNASIRA RDPTAHAEVL ALRAAARALG  60
NHRLDGCTLY VTLEPCAMCA GAIAHARVAR LVYGAADPKG GAVEHGPRFF AQPTCHHRPD  120
VTGGVGAAEA AALLRDFFRA RR                                           142

SEQ ID NO: 141          moltype = AA  length = 142
FEATURE                 Location/Qualifiers
source                  1..142
                        mol_type = protein
                        organism = synthetic construct
SEQUENCE: 141
MRDALAEARA AAAAGEVPVG AVVVRDGAVL ARAGNRTVRD CDPTAHAEIV ALRAAARALG  60
NHRLDGCTLY VTLEPCAMCA GAIAQARVAR LVYGADDPKG GAVAHGPRLF AQPTCHHRPE  120
VVGGVGAEEA AALLRGFFAA RR                                           142

SEQ ID NO: 142          moltype = AA  length = 148
FEATURE                 Location/Qualifiers
source                  1..148
                        mol_type = protein
                        organism = synthetic construct
SEQUENCE: 142
MTDEYFMRQA LREARRAYDE DEVPVGAVVV RDGKVIARGR NQVERLKDPT AHAEMIALTS  60
AANHLGSKRL EGCTVYVTLE PCAMCAGALV LARVDRLVFG AFDPKAGACG TLYDIPRDRR  120
LNHRVEVVGG VLEEESAALL REFFRRRR                                     148

SEQ ID NO: 143          moltype = AA  length = 148
FEATURE                 Location/Qualifiers
source                  1..148
                        mol_type = protein
                        organism = synthetic construct
SEQUENCE: 143
MTDEYFMRQA LREARRAYDE GEVPVGAVVV RDGKVIARGR NQVERLKDPT AHAEMIALTA  60
AANHLGAKRL EGCTVYVTLE PCAMCAGALV LARVDRLVFG AFDPKAGACG TLYDIPRDAR  120
LNHRVEVVSG VLEEESAALL REFFARLR                                     148

SEQ ID NO: 144          moltype = AA  length = 142
FEATURE                 Location/Qualifiers
source                  1..142
                        mol_type = protein
                        organism = synthetic construct
SEQUENCE: 144
MSEALAEARK AAAAGEVPVG AVLVRDGAVL ARGGNRTIRD CDPTAHAEIV ALRAAARALG  60
NYRLPGTTLY VTLEPCAMCA GAMIHARVDR LVYGAADPRA GAAGSVFDIL RHPALNHRME  120
VEGGVLADEC GALLRDFFRA RR                                           142

SEQ ID NO: 145          moltype = AA  length = 142
FEATURE                 Location/Qualifiers
```

```
source                  1..142
                        mol_type = protein
                        organism = synthetic construct
SEQUENCE: 145
MRAALAEARA AAAAGEVPVG AVVVRDGAIL ARAGNASIRA RDPTAHAEVL ALRAAARALG  60
NHRLTGCTLY VTLEPCAMCA GAIAHARIAR LVYGAADPKG GAVAHGPRFF AQPTCHHRPE  120
VTGGLGEAEA AALLRAFFAA RR                                           142

SEQ ID NO: 146          moltype = AA  length = 142
FEATURE                 Location/Qualifiers
source                  1..142
                        mol_type = protein
                        organism = synthetic construct
SEQUENCE: 146
MRAALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVAHGPRFF EQPTCHHRPE  120
VTGGVLAAEA GALLRDFFRA RR                                           142

SEQ ID NO: 147          moltype = AA  length = 142
FEATURE                 Location/Qualifiers
source                  1..142
                        mol_type = protein
                        organism = synthetic construct
SEQUENCE: 147
MTEALAEARK AAALGEVPVG AVVVRDGAVI ARGHNRTVAD ADPTAHAEIV ALREAARALG  60
NHRLTGCTLY VTLEPCAMCA GAIVHARLDR VVYGAADPKA GAAGSVLDVL GHPRLNHRPE  120
VAGGVLAEEC GALLRDFFRA RR                                           142

SEQ ID NO: 148          moltype = AA  length = 142
FEATURE                 Location/Qualifiers
source                  1..142
                        mol_type = protein
                        organism = synthetic construct
SEQUENCE: 148
MREALAEARA AAAAGEVPVG AVVVRDGAVL ARAGNRTVRD ADPTAHAEIV ALREAARALG  60
NHRLGGCTLY VTLEPCAMCA GAIAQARVAR LVYGAADPKG GAVAHGPRLF EQPTCHHRPE  120
VVGGVLAEEA GALLRGFFAA RR                                           142

SEQ ID NO: 149          moltype = AA  length = 148
FEATURE                 Location/Qualifiers
source                  1..148
                        mol_type = protein
                        organism = synthetic construct
SEQUENCE: 149
MTDEYFMRQA LREARRAYEE GEVPVGAVVV RDGRVIARGR NQVERLKDPT AHAEMIALTA  60
AAAHLGNKRL EGCTLYVTLE PCAMCAGAIV LARIPRLVFG AFDPKAGACG TLYDIVRDRR  120
LNHRAEVVSG VLEEECGALL KEFFARLR                                     148

SEQ ID NO: 150          moltype = AA  length = 142
FEATURE                 Location/Qualifiers
source                  1..142
                        mol_type = protein
                        organism = synthetic construct
SEQUENCE: 150
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGAADPKG GAVAHGPRLF AQPTCHHRPE  120
VVGGVGEAEA AALLRDFFAA RR                                           142

SEQ ID NO: 151          moltype = AA  length = 162
FEATURE                 Location/Qualifiers
source                  1..162
                        mol_type = protein
                        organism = synthetic construct
SEQUENCE: 151
MDDEFYMRRA LELAALAEEH NEVPVGAVLV LNGEIIGEGW NRSIGHHDAT AHAEIMALRQ  60
AGKKLENYRL LDTTLYVTLE PCPMCAGALL HSRVKRVVFG APDLKAGAAG TVLNLFESQA  120
SYHYADVESG LLEQECREQL QAFFKRRRKE IKALKKAKRE AE                     162

SEQ ID NO: 152          moltype = AA  length = 142
FEATURE                 Location/Qualifiers
source                  1..142
                        mol_type = protein
                        organism = synthetic construct
SEQUENCE: 152
MREALAEARA AAAAGEVPVG AVVVRDGAIL ARAGNASIRA RDPTAHAEVL ALRAAARALG  60
NHRLTGCTLY VTLEPCAMCA GAIAHARVAR LVYGAADPKG GAVEHGPRFF AQPTCHHRPE  120
VTGGVLAAEA GALLRDFFRA RR                                           142

SEQ ID NO: 153          moltype = AA  length = 148
```

```
FEATURE                Location/Qualifiers
source                 1..148
                       mol_type = protein
                       organism = synthetic construct
SEQUENCE: 153
MTDEYFMRQA LREARRAYDE GEVPVGAVVV RDGRVIARGR NQVERLKDPT AHAEMIALTA  60
AANHLGAKRL EGCTVYVTLE PCAMCAGALV LARVDRLVFG AFDPKAGACG TLYDIPRDPR  120
LNHRVEVVSG VLAEESAALL REFFAARR                                     148

SEQ ID NO: 154         moltype = AA  length = 148
FEATURE                Location/Qualifiers
source                 1..148
                       mol_type = protein
                       organism = synthetic construct
SEQUENCE: 154
MTDEYFMRQA LREARRAYEE DEVPVGAVVV REGRVIARGR NQVERLKDPT AHAEMIALTA  60
AANHLGSKRL EGCTVYVTLE PCPMCAGALV LARVRRLVFG AFDPKAGACG TLYDIPRDRR  120
LNHRVEVVGG VLEEESAALL REFFRRRR                                     148

SEQ ID NO: 155         moltype = AA  length = 162
FEATURE                Location/Qualifiers
source                 1..162
                       mol_type = protein
                       organism = synthetic construct
SEQUENCE: 155
MSDEQYMRRA LELARQAEQE GEVPVGAVLV KDGEVVAEGW NRSIGSHDAT GHAEIMALRA  60
AGQVLQNYRL LDTTLYVTLE PCPMCAGALL HSRVKRVVYG APDLKAGAAG TVLNLFESQA  120
SYHYADVESG LLEEECREQL QAFFKRRRKE IKAARQAKRD AE                     162

SEQ ID NO: 156         moltype = AA  length = 142
FEATURE                Location/Qualifiers
source                 1..142
                       mol_type = protein
                       organism = synthetic construct
SEQUENCE: 156
MREALAEARA AAAAGEVPVG AVVVRDGAVL ARAGNRTVRD ADPTAHAEVV ALRAAARALG  60
NHRLGGCTLY VTLEPCAMCA GAIAQARVAR LVYGADDPKG GAVAHGPRLF AQPTCHHRPE  120
VVGGVGAAEA AALLRDFFAA RR                                           142

SEQ ID NO: 157         moltype = AA  length = 149
FEATURE                Location/Qualifiers
source                 1..149
                       mol_type = protein
                       organism = synthetic construct
SEQUENCE: 157
MDDAGFMRLA LAEARAAAAA GEVPVGAVVV RDGAVLAAAG NRTLRDCDPT AHAEVVALRA  60
AARALGNYRL DGCTLYVTLE PCAMCAGAML HARLARVVYG AADPKTGAAG SVLDLFAQPR  120
LNHHTQVEGG VLAAECGALL QDFFRARRG                                    149

SEQ ID NO: 158         moltype = AA  length = 164
FEATURE                Location/Qualifiers
source                 1..164
                       mol_type = protein
                       organism = synthetic construct
SEQUENCE: 158
MSDEQFMRRA IELARKGEEL GEVPVGAVLV KDGEIIAEGW NQSISTHDAT AHAEIMALRA  60
AGEKLQNYRL LDTTLYVTLE PCPMCAGALL HSRVKRVVFG APDLKAGAAG TVLNLFESQA  120
SYHYADVESG LLEEECREQL QAFFKRRRKE IKALKKAKRE AEEK                   164

SEQ ID NO: 159         moltype = AA  length = 142
FEATURE                Location/Qualifiers
source                 1..142
                       mol_type = protein
                       organism = synthetic construct
SEQUENCE: 159
MREALAEARA AAAAGEVPVG AVVVRDGVVL ARAGNRTVRD ADPTAHAEVV ALRAAARALG  60
NHRLGGCTLY VTLEPCAMCA GAIAQARVAR LVYGAADPKG GAVAHGPRLF EQPTCHHRPE  120
VVGGVLAEEA GALLRDFFAA RR                                           142

SEQ ID NO: 160         moltype = AA  length = 142
FEATURE                Location/Qualifiers
source                 1..142
                       mol_type = protein
                       organism = synthetic construct
SEQUENCE: 160
MRDALAEARA AAAAGEVPVG AVVVRDGAVL ARAGNASIRA RDPTAHAEIL ALRAAARALG  60
NHRLDGCTLY VTLEPCAMCA GAIAHARIAR LVYGAADPKG GAVEHGPRFF AQPTCHHRPE  120
VVGGVGAAEA GALLRDFFRA RR                                           142
```

```
SEQ ID NO: 161         moltype = AA  length = 148
FEATURE                Location/Qualifiers
source                 1..148
                       mol_type = protein
                       organism = synthetic construct
SEQUENCE: 161
MSDEDYMRLA LEEARAAAAA GEVPVGAVVV RDGAVLARAG NRTVRDCDPT AHAEIVALRE  60
AARALGNHRL TGCTLYVTLE PCAMCAGAIS HARVARLVYG ADDPKGGAVA HGPRFFAQPT  120
CHHRPEVTGG VLAEEAGALL RGFFAARR                                     148

SEQ ID NO: 162         moltype = AA  length = 148
FEATURE                Location/Qualifiers
source                 1..148
                       mol_type = protein
                       organism = synthetic construct
SEQUENCE: 162
MTDEYFMRQA LREARRAYDE DEVPVGAVVV RDGRVIARGR NQVERLKDPT AHAEMIALTS  60
AANYLGSKRL EGCTVYVTLE PCAMCAGALV LARVDRLVFG AFDPKAGACG TLYDIPGDRR  120
LNHRVAVTGG VLEEESAALL REFFRERR                                     148

SEQ ID NO: 163         moltype = AA  length = 164
FEATURE                Location/Qualifiers
source                 1..164
                       mol_type = protein
                       organism = synthetic construct
SEQUENCE: 163
MSDEQYMRRA LELARQAEQE GEVPVGAVLV KDGEIVAEGW NRSIGSHDAT AHAEIETLRK  60
AGQALENYRL LDTTLYVTLE PCPMCAGALL HSRVKRVVFG APDLKAGAAG TVLNLFESQA  120
SYHYAEVESG LLEEECREQL QAFFKRRRKE IKALRQAEKE AAEK                   164

SEQ ID NO: 164         moltype = AA  length = 142
FEATURE                Location/Qualifiers
source                 1..142
                       mol_type = protein
                       organism = synthetic construct
SEQUENCE: 164
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVAHGPRFF EQPTCHHRPE  120
VTGGVLAEEA GALLRDFFRA RR                                           142

SEQ ID NO: 165         moltype = AA  length = 142
FEATURE                Location/Qualifiers
source                 1..142
                       mol_type = protein
                       organism = synthetic construct
SEQUENCE: 165
MRDALAEARA AAARGEVPVG AVVVRDGAVL ARAGNASIAA RDPTAHAEIL ALRAAARALG  60
NHRLAGCTLY VTLEPCAMCA GAIAHARIAR LVYGAADPKG GAVAHGPRFF EQPTCHHRPE  120
VTGGVGAAEA GALLRDFFAA RR                                           142

SEQ ID NO: 166         moltype = AA  length = 142
FEATURE                Location/Qualifiers
source                 1..142
                       mol_type = protein
                       organism = synthetic construct
SEQUENCE: 166
MREALAEARA AAAAGEVPVG AVVVRDGAVL ARAGNRTVRD ADPTAHAELV AIRAAARALG  60
SERLTGCTLY VTLEPCAMCA GAISHARVAR LVYGADDPKG GAVAHGPRFF AQPTCHHRPD  120
VTGGVGEAEA GALLRAFFAA RR                                           142

SEQ ID NO: 167         moltype = AA  length = 148
FEATURE                Location/Qualifiers
source                 1..148
                       mol_type = protein
                       organism = synthetic construct
SEQUENCE: 167
MDDAGFMRLA LAEARKAAAA GEVPVGAVVV RDGAVLAAAG NRTLRDCDPT AHAEVVALRE  60
AARALGNHRL GGCDLYVTLE PCAMCAGAIS HARIARLYYG ADDPKGGAVA HGARVFDQPT  120
CHHRPEVYGG IGAAEAAALL RGFFAARR                                     148

SEQ ID NO: 168         moltype = AA  length = 148
FEATURE                Location/Qualifiers
source                 1..148
                       mol_type = protein
                       organism = synthetic construct
SEQUENCE: 168
MTDEYFMRQA LREARRAYDE GEVPVGAVVV RDGRVIARGR NQVERLKDPT AHAEMLALTA  60
AAAHLGSKRL EGCTLYVTLE PCAMCAGAIV LARLPRLVFG AFDPKAGACG TLYDIVRDRR  120
LNHRVEVVSG VLEEECGALL KEFFARLR                                     148
```

```
SEQ ID NO: 169          moltype = AA  length = 162
FEATURE                 Location/Qualifiers
source                  1..162
                        mol_type = protein
                        organism = synthetic construct
SEQUENCE: 169
MSDEQYMRRA LELARQAEQE GEVPVGAVLV KDGEVIAEGW NRSIGSHDAT GHAEIMALRA  60
AGEKLQNYRL LDTTLYVTLE PCPMCAGALL HSRVKRVVFG APDLKAGAAG TVLNLFESQA  120
SYHYADVESG LLEEECREQL QAFFKRRRKE IKALRQAQKA AE                    162

SEQ ID NO: 170          moltype = AA  length = 142
FEATURE                 Location/Qualifiers
source                  1..142
                        mol_type = protein
                        organism = synthetic construct
SEQUENCE: 170
MRDALAEARA AAAAGEVPVG AVVVRDGAIL ARAGNASIRA RDPTAHAEIL ALRAAARALG  60
NHRLTGCTLY VTLEPCAMCA GAIAHARVAR LVYGAADPKG GAVAHGPRFF EQPTCHHRPE  120
VTGGVGAAEA GALLRDFFAA RR                                          142

SEQ ID NO: 171          moltype = AA  length = 142
FEATURE                 Location/Qualifiers
source                  1..142
                        mol_type = protein
                        organism = synthetic construct
SEQUENCE: 171
MTEALAEARK AAAAGEVPVG AVLVRDGAVL ARGGNRTIRD CDPTAHAEIV VLREAARALG  60
NYRLEGCTLY VTLEPCAMCA GAMIHARLDR LVYGADDPKA GAAGSVLDVL NHPRLNHQME  120
VTAGVLAEEC GALLREFFRA RR                                          142

SEQ ID NO: 172          moltype = AA  length = 142
FEATURE                 Location/Qualifiers
source                  1..142
                        mol_type = protein
                        organism = synthetic construct
SEQUENCE: 172
MREALAEARA AAAAGEVPVG AVVVRDGAVL ARAGNRTVRD ADPTAHAELV AIRAAARALG  60
SERLTGCTLY VTLEPCAMCA GAISHARIAR LVYGADDPKG GGVAHGARVF DHPQCHHRPE  120
VVGGVGAAEA AALLRDFFAA RR                                          142

SEQ ID NO: 173          moltype = AA  length = 142
FEATURE                 Location/Qualifiers
source                  1..142
                        mol_type = protein
                        organism = synthetic construct
SEQUENCE: 173
MREALAEARA AAAAGEVPVG AVVVRDGAVL ARAGNRTVRD ADPTAHAELV AIRAAAAALG  60
SERLTGCTLY VTLEPCAMCA GAISHARIAR LVYGAADPKG GAVAHGPRLF AQPTCHHRPE  120
VVGGVGEAEA AALLRDFFAA RR                                          142

SEQ ID NO: 174          moltype = AA  length = 142
FEATURE                 Location/Qualifiers
source                  1..142
                        mol_type = protein
                        organism = synthetic construct
SEQUENCE: 174
MREALAEARA AAAAGEVPVG AVVVRDGAVL ARAGNASIRA RDPTAHAEIL ALRAAARALG  60
NHRLTGCTLY VTLEPCAMCA GAIAHARIAR LVYGAADPKG GAVAHGPRFF EQPTCHHRPE  120
VTGGVLAEEA GALLRAFFRA RR                                          142

SEQ ID NO: 175          moltype = AA  length = 142
FEATURE                 Location/Qualifiers
source                  1..142
                        mol_type = protein
                        organism = synthetic construct
SEQUENCE: 175
MRDALAEARA AAARGEVPVG AVVVRDGAIL ARAGNATVAA SDPTAHAEIL ALRAAARALG  60
SQRLPGAVLY VTLEPCAMCA GAISHARIAR LVYGAADPKG GAVAHGPRFF EQPTCHHRPE  120
VTGGVLAEEA GALLRDFFRA RR                                          142

SEQ ID NO: 176          moltype = AA  length = 142
FEATURE                 Location/Qualifiers
source                  1..142
                        mol_type = protein
                        organism = synthetic construct
SEQUENCE: 176
MRDALAEARA AAAAGEVPVG AVVVRDGAIL ARAGNASIRA RDPTAHAEIL ALRAAARALG  60
NHRLDGCTLY VTLEPCAMCA GAIAHARIAR LVYGAADPKG GAVAHGPRLF AQPTCHHRPE  120
```

```
VTGGVGAAEA AALLRDFFRA RR                                          142

SEQ ID NO: 177         moltype = AA  length = 148
FEATURE                Location/Qualifiers
source                 1..148
                       mol_type = protein
                       organism = synthetic construct
SEQUENCE: 177
MTDEYFMRQA LREARRAYDE GEVPVGAVVV RDGRVIARGR NQVERLKDPT AHAEMIALTA  60
AAAHLGNKRL EGCTLYVTLE PCAMCAGALV LARVPRLVFG AFDPKAGACG TLYDIVRDRR  120
LNHRVEVVSG VLEEESAALL KEFFARLR                                    148

SEQ ID NO: 178         moltype = AA  length = 148
FEATURE                Location/Qualifiers
source                 1..148
                       mol_type = protein
                       organism = synthetic construct
SEQUENCE: 178
MDDAGFMRLA LEEARAAAAA GEVPVGAVVV RDGEVLARAG NRTVRDCDPT AHAEVVALRE  60
AARKLGNHRV TGATLYVTLE PCAMCAGAIS LARVARLVYA ADDPKGGGVA HGARVFDQPT  120
CHHRPEVVSG VLAEESAALL RGFFAARR                                    148

SEQ ID NO: 179         moltype = AA  length = 148
FEATURE                Location/Qualifiers
source                 1..148
                       mol_type = protein
                       organism = synthetic construct
SEQUENCE: 179
MTDEYFMRQA LREARRAYDE DEVPVGAVVV REGKVIARGR NQVERLKDPT AHAEMIALTS  60
AANHLGSKRL EGCTLYVTLE PCAMCAGALV LARVERLVFG AFDPKAGACG TLYNIPADRR  120
LNHRVEVVGG VLEEESAALL REFFRKRR                                    148

SEQ ID NO: 180         moltype = AA  length = 162
FEATURE                Location/Qualifiers
source                 1..162
                       mol_type = protein
                       organism = synthetic construct
SEQUENCE: 180
MDDEAWMRRA IALAHQAEAE GEVPVGAVLV KDGEVVAEGW NRSIGSHDAT AHAEIETLRK  60
AGQALENYRL LDTTLYVTLE PCPMCAGALL HSRVKRVVFG APDLKAGAAG TVLNLFESQA  120
SYHYADVESG LLEEECREQL QAFFKRRRKE IKALRQAQRE AE                    162

SEQ ID NO: 181         moltype = AA  length = 148
FEATURE                Location/Qualifiers
source                 1..148
                       mol_type = protein
                       organism = synthetic construct
SEQUENCE: 181
MDDAGFMRLA LAEARAAAAA GEVPVGAVVV RDGAVLAAAG NRTLRDCDPT AHAEVVALRA  60
AARALGNHRL EGCTLYVTLE PCAMCAGAAL QARLARLVYG AAEPKTGAAG SVLDVFANPA  120
LNHHTAVTGG VLAAEAAALL RDFFAARR                                    148

SEQ ID NO: 182         moltype = AA  length = 142
FEATURE                Location/Qualifiers
source                 1..142
                       mol_type = protein
                       organism = synthetic construct
SEQUENCE: 182
MTEALAEARK AAAAGEVPVG AVLVRDGAVL ARGGNRTIRD CDPTAHAEIV ALRAAARAAG  60
NYRLPGATLY VTLEPCAMCA GAMIHARVDR LVYGAADPRA GAAGSVFDVV RHPALNHRMA  120
VEGGVLAEEC GALLRDFFRA RR                                          142

SEQ ID NO: 183         moltype = AA  length = 164
FEATURE                Location/Qualifiers
source                 1..164
                       mol_type = protein
                       organism = synthetic construct
SEQUENCE: 183
MTEKDKFFMQ RAIELAKLAE ENGEVPVGAV LVKDGEIIAE GWNQSIGSHD ATAHAEIMAL  60
RQAGKVLENY RLLDTTLYVT LEPCPMCAGA LLHSRVKRIV FGAPDLKAGA AGTVLNLFES  120
QASYHYADVE SGLLEEECRE QLQAFFKRRR KEIKALKKAK KEAE                  164

SEQ ID NO: 184         moltype = AA  length = 148
FEATURE                Location/Qualifiers
source                 1..148
                       mol_type = protein
                       organism = synthetic construct
SEQUENCE: 184
MTDEYFMRQA LREARRAYDE DEVPVGAVVV RDGKVIARGR NQVERLKDPT AHAEMIALTS  60
```

```
AANYLGSKRL EGCTVYVTLE PCPMCAGALV LARVERLVFG AFDPKAGACG TLYDIPGDRR  120
LNHRLEVVGG VLEEESAALL REFFRRRR                                     148

SEQ ID NO: 185          moltype = AA  length = 142
FEATURE                 Location/Qualifiers
source                  1..142
                        mol_type = protein
                        organism = synthetic construct
SEQUENCE: 185
MREALAEARA AAAAGEVPVG AVVVRDGAVL ARAGNASIRA RDPTAHAEML ALRAAARALG  60
NHRLDGCTLY VTLEPCAMCA GAIAHARVAR LVYGAADPKG GAVAHGPRFF EQPTCHHRPE  120
VTGGVLAAEA GALLRDFFRA RR                                           142

SEQ ID NO: 186          moltype = AA  length = 148
FEATURE                 Location/Qualifiers
source                  1..148
                        mol_type = protein
                        organism = synthetic construct
SEQUENCE: 186
MTDEYFMRQA LREARRAYDE GEVPVGAVVV RDGRVIARGR NQVERLKDPT AHAEMIALTA  60
AAAHLGNKRL EGCTLYVTLE PCAMCAGAIV LARIPRLVFG AFDPKAGACG TLYDIVRDRR  120
LNHRAEVVSG VLEEECGALL KEFFARLR                                     148

SEQ ID NO: 187          moltype = AA  length = 164
FEATURE                 Location/Qualifiers
source                  1..164
                        mol_type = protein
                        organism = synthetic construct
SEQUENCE: 187
MSDEQYMRRA LELARQAEQA GEVPVGAVLV KDGEIIAEGW NQSISSHDAT AHAEIMALRA  60
AGQALENYRL LDTTLYVTLE PCPMCAGALL HSRVKRVVFG APDLKAGAAG TVLNLFESQA  120
SYHYAEVESG LLEEECREQL QAFFKRRRKE IKALKQAKRE AEQK                   164

SEQ ID NO: 188          moltype = AA  length = 149
FEATURE                 Location/Qualifiers
source                  1..149
                        mol_type = protein
                        organism = synthetic construct
SEQUENCE: 188
MDDAGFMRLA LAEARAAAAA GEVPVGAVVV RDGAVLAAAG NRTLRDCDPT AHAEVVALRA  60
AARALGNYRL DGCTLYVTLE PCAMCAGAML HARLARVVYG AADPKTGAAG SVLDLFAEPR  120
LNHHTRVEGG VLAAECGALL RDFFRARRG                                    149

SEQ ID NO: 189          moltype = AA  length = 148
FEATURE                 Location/Qualifiers
source                  1..148
                        mol_type = protein
                        organism = synthetic construct
SEQUENCE: 189
MDDAGFMRLA LAEARAAAAA GEVPVGAVVV RDGAVLAAAG NRTLRDRDPT AHAEMVAIRA  60
AAAALGQERL TDCDLYVTLE PCAMCAGAIS FARIRRLYFG AADPKGGAVE HGPRFFAQPT  120
CHHAPEVYGG IGEGEAAALL RDFFRARR                                     148

SEQ ID NO: 190          moltype = AA  length = 142
FEATURE                 Location/Qualifiers
source                  1..142
                        mol_type = protein
                        organism = synthetic construct
SEQUENCE: 190
MREALAEARA AAAAGEVPVG AVVVRDGAVL ARAGNRTVRD ADPTAHAEVV ALRAAARALG  60
NHRLDGCTLY VTLEPCAMCA GAIAQARVAR LVYGAADPKG GAVAHGPRLF EQPTTHHRPE  120
VVGGVLAEEA AALLRGFFAA RR                                           142

SEQ ID NO: 191          moltype = AA  length = 142
FEATURE                 Location/Qualifiers
source                  1..142
                        mol_type = protein
                        organism = synthetic construct
SEQUENCE: 191
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGAADPKG GAVAHGARVF DQPQTHHRPE  120
VTGGVLAEEA GALLRAFFAA RR                                           142

SEQ ID NO: 192          moltype = AA  length = 148
FEATURE                 Location/Qualifiers
source                  1..148
                        mol_type = protein
                        organism = synthetic construct
SEQUENCE: 192
```

```
MDDAGFMRLA LAEARRAAEA GEVPVGAVVV RGGEVLAAAG NRTLRDCDPT AHAEIVALRE  60
AARRVGNYRL ADCDLYVTLE PCAMCAGAIV HARVRRLVYG ADDPKAGAVR SALRVLDAPA  120
LNHRVEVTAG VLAEECGALL RDFFRARR                                     148

SEQ ID NO: 193         moltype = AA  length = 142
FEATURE                Location/Qualifiers
source                 1..142
                       mol_type = protein
                       organism = synthetic construct
SEQUENCE: 193
MTEALAEARK AAALGEVPVG AVVVRDGAVI ARGHNRTVTD ADPTAHAEIV ALREAARALG  60
NHRLTGCTLY VTLEPCAMCA GAMVHARLDR LVYGAADPKA GAAGSVLDVL GHPRLNHQME  120
VTAGVLADES AALLRDFFRA RR                                           142

SEQ ID NO: 194         moltype = AA  length = 142
FEATURE                Location/Qualifiers
source                 1..142
                       mol_type = protein
                       organism = synthetic construct
SEQUENCE: 194
MREALAEARA AAAAGEVPVG AVVVRDGAVL ARAGNASIRA RDPTAHAEML ALRAAARALG  60
NHRLDGCTLY VTLEPCAMCA GAIAHARIAR LVYGAADPKG GAVAHGPRFF EQPTCHHRPE  120
VVGGVGAAEA GALLRDFFAA RR                                           142

SEQ ID NO: 195         moltype = AA  length = 142
FEATURE                Location/Qualifiers
source                 1..142
                       mol_type = protein
                       organism = synthetic construct
SEQUENCE: 195
MTEALAEARK AAALGEVPVG AVVVRDGAVI ARGHNRTVTD TDPTAHAEIV ALREAARALG  60
NHRLTGCTLY VTLEPCAMCA GAIVHARLDR VVYGAADPKA GAAGSVLDVL GHPRLNHRPE  120
VEGGVLGEEC GALLRDFFRA RR                                           142

SEQ ID NO: 196         moltype = AA  length = 142
FEATURE                Location/Qualifiers
source                 1..142
                       mol_type = protein
                       organism = synthetic construct
SEQUENCE: 196
MREALAEARA AAAAGEVPVG AVVVRDGAVL ARAGNRTVRD ADPTAHAEVV ALREAARALG  60
NHRLGGCTLY VTLEPCAMCA GAISHARVAR LVYGADDPKG GAVRHGARVF DQPTCHHRPE  120
VVGGVLAEES AALLRGFFAA RR                                           142

SEQ ID NO: 197         moltype = AA  length = 142
FEATURE                Location/Qualifiers
source                 1..142
                       mol_type = protein
                       organism = synthetic construct
SEQUENCE: 197
MREALAEARA AAAAGEVPVG AVVVRDGAVL ARAGNASIRA RDPTAHAEIL ALRAAARALG  60
NHRLDGCTLY VTLEPCAMCA GAIAHARVAR LVYGAADPKG GAVEHGPRFF AQPTCHHRPE  120
VVGGVGAAEA GALLRAFFAA RR                                           142

SEQ ID NO: 198         moltype = AA  length = 148
FEATURE                Location/Qualifiers
source                 1..148
                       mol_type = protein
                       organism = synthetic construct
SEQUENCE: 198
MDDAGFMRLA LAEARAAAAA GEVPVGAVVV RDGAVLAAAG NRTLRDCDPT AHAEVVALRA  60
AARALGNHRL GGCDLYVTLE PCAMCAGAIS HARIARLYYG ADDPKGGAVA HGARVFAHPQ  120
CHHRPEVYGG IGAAEAAALL RDFFAARR                                     148

SEQ ID NO: 199         moltype = AA  length = 148
FEATURE                Location/Qualifiers
source                 1..148
                       mol_type = protein
                       organism = synthetic construct
SEQUENCE: 199
MTDEYFMRQA LREARRAYDE DEVPVGAVVV RDGKVIARGR NQVERLKDPT AHAEMIALTS  60
AANHLGSKRL EGCTVYVTLE PCPMCAGALV LARVERLVFG AFDPKAGACG TLYDIPGDRR  120
LNHRVEVVGG VLEEESAALL REFFRRRR                                     148

SEQ ID NO: 200         moltype = AA  length = 162
FEATURE                Location/Qualifiers
source                 1..162
                       mol_type = protein
                       organism = synthetic construct
```

```
SEQUENCE: 200
MDDEFYMRRA LELAALAEEH NEVPVGAVLV LNGEIIGEGW NRSIGHHDAT AHAEIMALRQ  60
AGKKLENYRL LDTTLYVTLE PCPMCAGALL HSRVKRVVFG APDLKAGAAG TVLNLFESQA  120
SYHYADVESG LLEQECREQL QAFFKRRRKE KKALKQAQKE AE                    162

SEQ ID NO: 201         moltype = AA  length = 142
FEATURE                Location/Qualifiers
source                 1..142
                       mol_type = protein
                       organism = synthetic construct
SEQUENCE: 201
MRDALAEARA AAAAGEVPVG AVVVRDGAIL ARAGNASIRA RDPTAHAEVL ALRAAARALG  60
NHRLDGCTLY VTLEPCAMCA GAIAHARIAR LVYGAADPKG GAVEHGPRFF AQPTCHHRPE  120
VVGGVGAAEA AALLRDFFRA RR                                           142

SEQ ID NO: 202         moltype = AA  length = 142
FEATURE                Location/Qualifiers
source                 1..142
                       mol_type = protein
                       organism = synthetic construct
SEQUENCE: 202
MRAALDEARA AAAAGEVPVG AVVVRDGAIL ARAGNRTVRD CDPTAHAEIV ALREAARALG  60
NHRLTGCTLY VTLEPCAMCA GAISHARVAR LVYGADDPKG GAVAHGPRFF AQPTCHHRPE  120
VVGGVGAGEA AALLRDFFAA RR                                           142

SEQ ID NO: 203         moltype = AA  length = 142
FEATURE                Location/Qualifiers
source                 1..142
                       mol_type = protein
                       organism = synthetic construct
SEQUENCE: 203
MREALAEARA AAAAGEVPVG AVVVRDGAIL ARAGNASIRA RDPTAHAEVL ALRAAARALG  60
NHRLTGCTLY VTLEPCAMCA GAIAHARIAR LVYGAADPKG GAVAHGPRFF EQPTCHHRPE  120
VTGGVLAEEA GALLRAFFRA RR                                           142

SEQ ID NO: 204         moltype = AA  length = 142
FEATURE                Location/Qualifiers
source                 1..142
                       mol_type = protein
                       organism = synthetic construct
SEQUENCE: 204
MRDALAEARA AAARGEVPVG AVVVRDGAVL ARAGNATVAA SDPTAHAEIL ALRAAARAAG  60
NHRLPGAVLY VTLEPCAMCA GAISHARIAR LVYGAADPKG GAVAHGPRFF EQPTCHHRPE  120
VTGGVLAEEA GALLRDFFRA RR                                           142

SEQ ID NO: 205         moltype = AA  length = 142
FEATURE                Location/Qualifiers
source                 1..142
                       mol_type = protein
                       organism = synthetic construct
SEQUENCE: 205
MREALAEARA AAAAGEVPVG AVVVRDGAIL ARAGNRTVRD ADPTAHAEIV ALREAARALG  60
NHRLGGCTLY VTLEPCAMCA GAISQARVAR LVYGADDPKG GAVAHGPRFF AQPTCHHRPE  120
VAGGLGEAEA AALLRDFFAA RR                                           142

SEQ ID NO: 206         moltype = AA  length = 142
FEATURE                Location/Qualifiers
source                 1..142
                       mol_type = protein
                       organism = synthetic construct
SEQUENCE: 206
MTEALAEARK AAAAGEVPVG AVLVRDGAVL ARGGNRTIRD CDPTAHAEIV ALRAAARALG  60
NYRLPGTTLY VTLEPCAMCA GAMIHARVAR LVYGAADPKT GAAGSVFDVL RHPALNHRME  120
VEGGVLAEEC GALLRDFFRA RR                                           142

SEQ ID NO: 207         moltype = AA  length = 166
FEATURE                Location/Qualifiers
source                 1..166
                       mol_type = protein
                       organism = synthetic construct
SEQUENCE: 207
MTEKDKFFMQ RAIELAKKGE ENGEVPVGAV LVKDGEIIAE GWNQSIGSHD ATAHAEIMTL  60
REAGKVLQNY RLLDTTLYVT LEPCPMCAGA LLHSRVKRVV FGAPDLKAGA AGTVLNLFES  120
QASYHYADVE SGLLEEECRE QLQAFFKRRR KEKKALKQAK REAEQK                 166

SEQ ID NO: 208         moltype = AA  length = 148
FEATURE                Location/Qualifiers
source                 1..148
                       mol_type = protein
```

```
                        organism = synthetic construct
SEQUENCE: 208
MTDEDYMRLA LEEARAAAAA GEVPIGAVVV RDGEVLARAG NRTVRDCDPT AHAEIVALRE  60
AARALGNYRL TGCTLYVTIE PCAMCAGAMI HARVDRLVYG AADPKAGAVR STLRVLDHPA  120
LNHRVEVTAG VLADECAALL QDFFRSRR                                      148

SEQ ID NO: 209          moltype = AA  length = 142
FEATURE                 Location/Qualifiers
source                  1..142
                        mol_type = protein
                        organism = synthetic construct
SEQUENCE: 209
MRDALAEARA AAAAGEVPVG AVVVRDGAVL ARAGNRTVRD ADPTAHAELV AIRAAARALG  60
SERLTGCTLY VTLEPCAMCA GAISHARIAR LVYGAADPKG GAVAHGPRFF AQPTCHHRPD  120
VTGGVGEAEA GALLRDFFAA RR                                            142

SEQ ID NO: 210          moltype = AA  length = 142
FEATURE                 Location/Qualifiers
source                  1..142
                        mol_type = protein
                        organism = synthetic construct
SEQUENCE: 210
MREALAEARA AAAAGEVPIG AVVVRDGAVL ARAGNRTVRD CDPTAHAEVV ALREAARALG  60
NHRLTGCTLY VTVEPCAMCA GAISHARVAR LVYGADDPKG GAVRHGPRFF EQPTCHHRPE  120
VVGGVGAEEA AALLRDFFRA RR                                            142

SEQ ID NO: 211          moltype = AA  length = 142
FEATURE                 Location/Qualifiers
source                  1..142
                        mol_type = protein
                        organism = synthetic construct
SEQUENCE: 211
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVAHGPRFF EQPTCHHRPE  120
VTGGVLAEEA GALLRAFFAA RR                                            142

SEQ ID NO: 212          moltype = AA  length = 148
FEATURE                 Location/Qualifiers
source                  1..148
                        mol_type = protein
                        organism = synthetic construct
SEQUENCE: 212
MTDEYFMRQA LREARRAYDE GEVPVGAVVV RDGRVIARGR NQVERLKDPT AHAEMLALTA  60
AAAHLGSKRL EGCTLYVTLE PCAMCAGAIV LARVPRLVFG AFDPKAGACG TLYDIPRDRR  120
LNHRAEVVGG VLEEESAALL REFFAARR                                      148

SEQ ID NO: 213          moltype = AA  length = 142
FEATURE                 Location/Qualifiers
source                  1..142
                        mol_type = protein
                        organism = synthetic construct
SEQUENCE: 213
MREALAEARA AAAAGEVPVG AVVVRDGAVL ARAGNRTVRD ADPTAHAEIV ALREAARALG  60
NHRLGGCTLY VTLEPCAMCA GAIAQARVAR LVYGADDPKG GAVAHGPRFF AQPTCHHRPE  120
VVGGVGAAEA GALLRGFFAA RR                                            142

SEQ ID NO: 214          moltype = AA  length = 162
FEATURE                 Location/Qualifiers
source                  1..162
                        mol_type = protein
                        organism = synthetic construct
SEQUENCE: 214
MDDEAWMRRA IALAHKAEQE GEVPVGAVLV KDGEVIAEGW NRSIGHHDAT AHAEIETLRK  60
AGQVLENYRL LDTTLYVTLE PCPMCAGALL HSRVKRIVFG APDLKAGAAG TVLNLFESQA  120
SYHYADVESG LLEEECREQL QAFFKRRRKE IKALRQAQKA AE                      162

SEQ ID NO: 215          moltype = AA  length = 142
FEATURE                 Location/Qualifiers
source                  1..142
                        mol_type = protein
                        organism = synthetic construct
SEQUENCE: 215
MREALAEARA AAAAGEVPVG AVVVRDGAVL ARAGNRTVRD ADPTAHAEIV ALREAARALG  60
NHRLGGCTLY VTLEPCAMCA GAIAQARVAR LVYGAADPKG GAVAHGPRLF AQPTCHHRPE  120
VVGGVGEAEA AALLRGFFAA RR                                            142

SEQ ID NO: 216          moltype = AA  length = 142
FEATURE                 Location/Qualifiers
source                  1..142
```

```
                        mol_type = protein
                        organism = synthetic construct
SEQUENCE: 216
MRDALAEARA AAAAGEVPVG AVVVRDGAIL ARAGNASIRA RDPTAHAEIL ALRAAARALG  60
NHRLTGCTLY VTLEPCAMCA GAISHARIAR LVYGAADPKG GAVAHGPRFF EQPTCHHRPE  120
VTGGVLAEEA GALLRAFFRA RR                                           142

SEQ ID NO: 217          moltype = AA  length = 163
FEATURE                 Location/Qualifiers
source                  1..163
                        mol_type = protein
                        organism = synthetic construct
SEQUENCE: 217
MSDEQYMRRA IELARQAEQE GEVPVGAVLV KDGEIIAEGW NRSIGSHDAT AHAEIETLRK  60
AGQVLENYRL LDTTLYVTLE PCPMCAGALL HSRVKRIVYG APDLKAGAAG TVLNLFESQA  120
SYHYADVESG LLEEECREQL QAFFKRRRKE IKAARKAKRE AEQ                    163

SEQ ID NO: 218          moltype = AA  length = 148
FEATURE                 Location/Qualifiers
source                  1..148
                        mol_type = protein
                        organism = synthetic construct
SEQUENCE: 218
MDDAGFMRLA LAEARAAAAA GEVPVGAVVV RDGEVLAAAG NRTLRDCDPT AHAEVVALRA  60
AARALGNHRL DGCDLYVTLE PCAMCAGAIS HARIRRLYYG ADDPKGGAVD NGVRFFASPT  120
CHHAPEVYSG LAESEAAALL RDFFRERR                                     148

SEQ ID NO: 219          moltype = AA  length = 142
FEATURE                 Location/Qualifiers
source                  1..142
                        mol_type = protein
                        organism = synthetic construct
SEQUENCE: 219
MREALAEARA AAAAGEVPVG AVVVRDGAVL ARAGNRTVRD ADPTAHAEVV ALRAAARALG  60
NHRLDGCTLY VTLEPCAMCA GAIAQARVAR LVYGAADPKG GAVAHGPRLF EQPTCHHRPE  120
VVGGVGEAEA AALLRGFFAA RR                                           142

SEQ ID NO: 220          moltype = AA  length = 148
FEATURE                 Location/Qualifiers
source                  1..148
                        mol_type = protein
                        organism = synthetic construct
SEQUENCE: 220
MTDEYFMRQA LREARRAYDE DEVPVGAVVV REGKVIARGR NQVERLKDPT AHAEMIALTS  60
AANYLGSKRL EGCTVYVTLE PCPMCAGALV LARVERLVFG AFDPKAGACG TLYDIPGDRR  120
LNHRVEVVGG VLEEESAALL REFFRRRR                                     148

SEQ ID NO: 221          moltype = AA  length = 142
FEATURE                 Location/Qualifiers
source                  1..142
                        mol_type = protein
                        organism = synthetic construct
SEQUENCE: 221
MREALAEARA AAAAGEVPVG AVVVRDGAIL ARAGNASIRA RDPTAHAEIL ALRAAARALG  60
NHRLTGCTLY VTLEPCAMCA GAIAHARIAR LVYGAADPKG GAVAHGPRFF EQPTCHHRPE  120
VTGGLGEAEA AALLRDFFRA RR                                           142

SEQ ID NO: 222          moltype = AA  length = 148
FEATURE                 Location/Qualifiers
source                  1..148
                        mol_type = protein
                        organism = synthetic construct
SEQUENCE: 222
MTDEYFMRQA LREARRAYEE DEVPVGAVVV REGRVIARGR NQVERLKDPT AHAEMIALTA  60
AANHLGSKRL EGCTVYVTLE PCPMCAGALV LARVERLVFG AFDPKAGACG TLYDIPGDRR  120
LNHRVEVVGG VLEEEAAALL REFFRRRR                                     148

SEQ ID NO: 223          moltype = AA  length = 149
FEATURE                 Location/Qualifiers
source                  1..149
                        mol_type = protein
                        organism = synthetic construct
SEQUENCE: 223
MDDAGFMRLA LAEARAAAAA GEVPVGAVVV RDGAVLAAAG NRTLRDCDPT AHAEVVALRA  60
AARALGNYRL DGCTLYVTLE PCAMCSGAML HARLARVVYG AADPKTGAAG SVLDLFAEPR  120
LNHHTRVEGG VLAGECGALL ADFFRGRRG                                    149

SEQ ID NO: 224          moltype = AA  length = 147
FEATURE                 Location/Qualifiers
```

```
source                  1..147
                        mol_type = protein
                        organism = synthetic construct
SEQUENCE: 224
MDDAGFMRLA LAEARAAAAA GEVPVGAVVV RDGAVLAAAG NRTLRDCDPT AHAEVVALRA  60
AARALGNHRL DGCDLYVTLE PCAMCAGAIA HARIRRLYYG AADPKGGAVE HGARVFDQPT  120
CHHRPEVYGG IGEAEAAALL RDFFRDR                                     147

SEQ ID NO: 225          moltype = AA  length = 162
FEATURE                 Location/Qualifiers
source                  1..162
                        mol_type = protein
                        organism = synthetic construct
SEQUENCE: 225
MSDEQYMRRA LELARQAEQE GEVPVGAVLV KDGEIIAEGW NRSIGSHDAT GHAEIMALRA  60
AGEKLQNYRL LDTTLYVTLE PCPMCAGALL HSRVKRVVFG APDLKAGAAG TVLNLFESQA  120
SYHYADVESG LLEEECREQL QAFFKRRRKE IKALRQAQKA AE                    162

SEQ ID NO: 226          moltype = AA  length = 142
FEATURE                 Location/Qualifiers
source                  1..142
                        mol_type = protein
                        organism = synthetic construct
SEQUENCE: 226
MREALAEARA AAAAGEVPVG AVVVRDGAVL ARAGNASIRA RDPTAHAEVL ALRAAARALG  60
NHRLDGCTLY VTLEPCAMCA GAIAHARVAR LVYGAADPKG GAVEHGPRFF AQPTCHHRPD  120
VTGGVGAAEA AALLRDFFRA RR                                          142

SEQ ID NO: 227          moltype = AA  length = 142
FEATURE                 Location/Qualifiers
source                  1..142
                        mol_type = protein
                        organism = synthetic construct
SEQUENCE: 227
MREALAEARA AAAAGEVPVG AVVVRDGAIL ARAGNRTVRD ADPTAHAEIV ALRAAARALG  60
NHRLDGCTLY VTLEPCAMCA GAAVLARVAR LVFGADDPKG GAVRTGVRLF DAPTCHHRPE  120
VTGGVLAEEA GALLREFFAA RR                                          142

SEQ ID NO: 228          moltype = AA  length = 142
FEATURE                 Location/Qualifiers
source                  1..142
                        mol_type = protein
                        organism = synthetic construct
SEQUENCE: 228
MREALAEARA AAAAGEVPVG AVVVRDGAVL ARAGNRTVRD ADPTAHAELV AIRAAARALG  60
SERLTGCTLY VTLEPCAMCA GAISHARIAR LVYGAADPKG GAVAHGPRFF AQPTCHHRPE  120
VTGGVGEAEA AALLRGFFAA RR                                          142

SEQ ID NO: 229          moltype = AA  length = 149
FEATURE                 Location/Qualifiers
source                  1..149
                        mol_type = protein
                        organism = synthetic construct
SEQUENCE: 229
MTDEDYMRLA LEEARAAAAA GEVPVGAVVV RDGEVIARAR NAPVSACDPT AHAEILALRE  60
AARRLGNYRL DGCTLYVTLE PCAMCSGAML HARLARVVYG AADPKTGAAG SVLDLFAEPR  120
LNHHTAVEGG VLAAECGALL RDFFRARRG                                   149

SEQ ID NO: 230          moltype = AA  length = 163
FEATURE                 Location/Qualifiers
source                  1..163
                        mol_type = protein
                        organism = synthetic construct
SEQUENCE: 230
MSDEQYMRRA LELARQAEAE GEVPVGAVLV KDGEVVAEGW NRSIGSHDAT GHAEIMALRA  60
AGQALENYRL LDTTLYVTLE PCPMCAGALL HSRVKRVVFG APDLKAGAAG TVLNLFESQA  120
SYHYAEVESG LLEEECREQL QAFFKRRRKE IKAARKAAKA AAE                   163

SEQ ID NO: 231          moltype = AA  length = 142
FEATURE                 Location/Qualifiers
source                  1..142
                        mol_type = protein
                        organism = synthetic construct
SEQUENCE: 231
MREALAEARA AAAAGEVPVG AVVVRDGAVL ARAGNASIRA HDPTAHAEVL ALRAAARALG  60
NHRLTGCTLY VTLEPCAMCA GAIAHARVAR LVYGAADPKG GAVAHGPRFF EQPTCHHRPE  120
VTGGVLAEEA GALLREFFRA RR                                          142

SEQ ID NO: 232          moltype = AA  length = 142
```

```
FEATURE                 Location/Qualifiers
source                  1..142
                        mol_type = protein
                        organism = synthetic construct
SEQUENCE: 232
MREALAEARA AAAAGEVPVG AVVVRDGAVL ARAGNRTVRD ADPTAHAEVV ALRAAARALG  60
NHRLDGCTLY VTLEPCAMCA GAIAQARVAR LVYGAADPKG GAVAHGPRLF EQPTCHHRPE  120
VVGGVGEAEA AALLRAFFAA RR                                           142

SEQ ID NO: 233          moltype = AA  length = 142
FEATURE                 Location/Qualifiers
source                  1..142
                        mol_type = protein
                        organism = synthetic construct
SEQUENCE: 233
MTEALAEARK AAALGEVPVG AVVVRDGAVI ARGHNRTIAD SDPTAHAEIV ALREAARVLG  60
NYRLTGCTLY VTVEPCAMCA GAMVHARLDR LVYGAADPKA GAAGSVLDVL GHPRLNHQME  120
VTGGVLAEEC AALLRDFFRA RR                                           142

SEQ ID NO: 234          moltype = AA  length = 162
FEATURE                 Location/Qualifiers
source                  1..162
                        mol_type = protein
                        organism = synthetic construct
SEQUENCE: 234
MDDEFYMRRA LELAALAEEH NEVPVGAVLV LNGEIIGEGW NRSIGHHDAT AHAEIMALRQ  60
AGKVLQNYRL LDTTLYVTLE PCPMCAGALV HSRVKRVVYG TPDLKTGAAG SVMNLLSYEG  120
VNHHVEVTSG VLAEECREQL QAFFRRRRAE KKALKKAQRE AE                     162

SEQ ID NO: 235          moltype = AA  length = 163
FEATURE                 Location/Qualifiers
source                  1..163
                        mol_type = protein
                        organism = synthetic construct
SEQUENCE: 235
MDDEAWMRRA IALAHQAEAE GEVPVGAVLV KDGEVIAEGW NRSIGHHDAT AHAEIETLRQ  60
AGQVLQNYRL LDTTLYVTLE PCPMCAGALL HSRVKRVVFG APDLKAGAAG TVLNLFESQA  120
SYHYADVESG LLEQECREQL QAFFKRRRKE IKAQRDAQRA AQE                    163

SEQ ID NO: 236          moltype = AA  length = 142
FEATURE                 Location/Qualifiers
source                  1..142
                        mol_type = protein
                        organism = synthetic construct
SEQUENCE: 236
MREALAEARA AAAAGEVPVG AVVVRDGAVL ARAGNASIRA RDPTAHAEIL ALRAAARALG  60
NHRLTGCTLY VTLEPCAMCA GAISHARIAR LVYGAADPKG GAVAHGPRFF EQPTCHHRPD  120
VTGGVLAAEA GALLRDFFRA RR                                           142

SEQ ID NO: 237          moltype = AA  length = 148
FEATURE                 Location/Qualifiers
source                  1..148
                        mol_type = protein
                        organism = synthetic construct
SEQUENCE: 237
MDDAGFMRLA LEEARAAAAA GEVPVGAVVV RDGAVLARAG NRTLRDRDPT AHAEVVALRA  60
AARALGSERL TGCDLYVTLE PCAMCAGAIS FARIRRLYFG AADPKGGAVE NGVRFFASPT  120
CHHAPEVYGG LAESEAAALL RDFFRARR                                     148

SEQ ID NO: 238          moltype = AA  length = 148
FEATURE                 Location/Qualifiers
source                  1..148
                        mol_type = protein
                        organism = synthetic construct
SEQUENCE: 238
MDDAGFMRLA LAEARAAAAA GEVPVGAVVV RDGAVLAAAG NRTLRDCDPT AHAEVVALRA  60
AARALGNHRL GGCDLYVTLE PCAMCAGAIS HARIARLYYG ADDPKGGAVA HGARVFDQPT  120
CHHRPEVYGG IGAAEAAALL RDFFRARR                                     148

SEQ ID NO: 239          moltype = AA  length = 142
FEATURE                 Location/Qualifiers
source                  1..142
                        mol_type = protein
                        organism = synthetic construct
SEQUENCE: 239
MREALAEARA AAAAGEVPVG AVVVRDGAVL ARAGNASIRA RDPTAHAEIL ALRAAARALG  60
NHRLDGCTLY VTLEPCAMCA GAIAHARVAR LVYGAADPKG GAVEHGPRFF AQPTCHHRPE  120
VTGGVLAAEA GALLRDFFRA RR                                           142
```

```
SEQ ID NO: 240          moltype = AA  length = 142
FEATURE                 Location/Qualifiers
source                  1..142
                        mol_type = protein
                        organism = synthetic construct
SEQUENCE: 240
MREALAEARA AAAAGEVPVG AVVVRDGAVL ARAGNASIRA RDPTAHAEIL ALRAAARALG  60
NHRLDGCTLY VTLEPCAMCA GAIAHARIAR LVYGAADPKG GAVAHGPRFF AQPTCHHRPD  120
VTGGVLAAEA GALLRDFFRA RR                                           142

SEQ ID NO: 241          moltype = AA  length = 142
FEATURE                 Location/Qualifiers
source                  1..142
                        mol_type = protein
                        organism = synthetic construct
SEQUENCE: 241
MREALAEARA AAAAGEVPVG AVVVRDGAVL ARAGNASIRA RDPTAHAEVL ALRAAARALG  60
NHRLTGCTLY VTLEPCAMCA GAIAHARVAR LVYGAADPKG GAVAHGPRFF EQPTCHHRPE  120
VTGGVLAEEA GALLRGFFRA RR                                           142

SEQ ID NO: 242          moltype = AA  length = 149
FEATURE                 Location/Qualifiers
source                  1..149
                        mol_type = protein
                        organism = synthetic construct
SEQUENCE: 242
DDDDRRWMRE ALAEARAAAD AGEVPVGAVV VRDGVLLARA GNASIRDRDP TAHAEMLALR  60
AAARALGNHR LTGCTLYVTL EPCAMCAGAI AHARIARLVY GASDPKAGAV EHGPRLFAQP  120
TIHHRPEVTA GVLAEECGAL LRDFFRARR                                    149

SEQ ID NO: 243          moltype = AA  length = 149
FEATURE                 Location/Qualifiers
source                  1..149
                        mol_type = protein
                        organism = synthetic construct
SEQUENCE: 243
DPTDLAFMRE ALAEARAAAE AGEVPVGAVV VCDGRIVARA HNRPIALSDP TAHAEILALR  60
EAARALGNYR LTGCTLYATL EPCAMCAGAI LHARIARLVY GAADPKAGAC GSVLDVMNHP  120
RLNHRVEVTG GVLAEECGAL LSGFFRARR                                    149

SEQ ID NO: 244          moltype = AA  length = 148
FEATURE                 Location/Qualifiers
source                  1..148
                        mol_type = protein
                        organism = synthetic construct
SEQUENCE: 244
DDDHAWMGAA LAEARAAAEA GEVPVGAVLV ADGRVLARAG NRTIRDRDPT AHAEMLALRA  60
AARALGNHRL TGTTLYVTLE PCAMCAGAIS LARVARLVYA ASDPKGGAVE HGPRFFAQPT  120
CHHRPEVVGG VGEGEAGALL RDFFRARR                                     148

SEQ ID NO: 245          moltype = AA  length = 150
FEATURE                 Location/Qualifiers
source                  1..150
                        mol_type = protein
                        organism = synthetic construct
SEQUENCE: 245
MTAEDDRFMR LALAEARAAA EAGEVPVGAV VVAGGRVVAR AHNRPIALHD PTAHAEVLAL  60
RAAARELGNY RLTGCTLYAT LEPCAMCAGA VLHARIARLV YGAADPKAGA CGSVLAVMNH  120
PRLNHRVEVT GGVLAEECGA LLREFFRARR                                   150

SEQ ID NO: 246          moltype = AA  length = 149
FEATURE                 Location/Qualifiers
source                  1..149
                        mol_type = protein
                        organism = synthetic construct
SEQUENCE: 246
MDSDLAFMRE ALAEARAAAE AGEVPVGAVV VHEGKIVARA ANRMRTDRDP TAHAELLALR  60
AAARALETTR LTGCTLYVTL EPCAMCAGAI SHARVARLVY GASDPKGGAV EHGPRFFAQP  120
TCHHRPEVVG GVGEAEAGAL LRGFFRARR                                    149

SEQ ID NO: 247          moltype = AA  length = 149
FEATURE                 Location/Qualifiers
source                  1..149
                        mol_type = protein
                        organism = synthetic construct
SEQUENCE: 247
DPDDARWMRE ALAEARAAAE AGEVPVGAVV VRDGRLLARA GNRTIRDRDP TAHAEMLALR  60
AAARALGNHR LEGCTLYVTL EPCAMCAGAM VQARVARLVY GAADPKAGAA GSVLDVLGDP  120
RLNHRVEVTG GVLAEECGAL LREFFRARR                                    149
```

```
SEQ ID NO: 248          moltype = AA  length = 150
FEATURE                 Location/Qualifiers
source                  1..150
                        mol_type = protein
                        organism = synthetic construct
SEQUENCE: 248
MDSDLEFMRE ALAEARAAAE AGEVPVGAVV VRDGVILARA GNRPIRDHDP TAHAEILALR  60
EAARAVGNYR LTGCTLYVTL EPCAMCAGAI LHARVERLVY GAADPKAGAA GSVLDVFGNA  120
RLNHHTRVEG GVLAEECGAL LSGFFRARRG                                   150

SEQ ID NO: 249          moltype = AA  length = 148
FEATURE                 Location/Qualifiers
source                  1..148
                        mol_type = protein
                        organism = synthetic construct
SEQUENCE: 249
DPDAEFMRLA LAEAEAAARA GEVPVGAVVV ADGRVIARAG NRTIRDRDPT AHAEMLALRA  60
AARALGSHRL TGCDLYVTLE PCAMCAGAIS HARIRRLYYG AADAKGGAVE HGPRFFAQPT  120
CHHRPEVYGG IGETAAAALL RDFFRARR                                     148

SEQ ID NO: 250          moltype = AA  length = 148
FEATURE                 Location/Qualifiers
source                  1..148
                        mol_type = protein
                        organism = synthetic construct
SEQUENCE: 250
DPDAAFMRAA LAEARAAAEA GEVPVGAVVV AGGRIVARAH NRPIELNDPT AHAEILALRQ  60
AAAALGNYRL TGCTLYATLE PCAMCAGAIL HARIERLVYG AADPKAGAVG SVLDVFANPR  120
LNHRTQVTAG VLADECGALL REFFRARR                                     148

SEQ ID NO: 251          moltype = AA  length = 150
FEATURE                 Location/Qualifiers
source                  1..150
                        mol_type = protein
                        organism = synthetic construct
SEQUENCE: 251
DESSDEEFMR AALEEARAAA AEGEVPVGAV VVAGGRIVAR AHNRPIALND PTAHAEILAL  60
RQAAAALGNY RLTGCTLYAT LEPCAMCAGA ILHARIARVV YGAADPKAGA CGSVLAVMNH  120
PQLNHRAEVT GGVLAEECGA LLSEFFRARR                                   150

SEQ ID NO: 252          moltype = AA  length = 148
FEATURE                 Location/Qualifiers
source                  1..148
                        mol_type = protein
                        organism = synthetic construct
SEQUENCE: 252
DDDHRFMRAA LAEARAAAEA GEVPVGAVVV HGGEIIARAH NRPIALHDPT AHAEILALRA  60
AARRLGNYRL TGCTLYATLE PCAMCAGAIL HARIARLVYG AADPKAGACG SVLAVMNHPR  120
LNHRVEVTAG VLADECGALL SEFFRARR                                     148

SEQ ID NO: 253          moltype = AA  length = 148
FEATURE                 Location/Qualifiers
source                  1..148
                        mol_type = protein
                        organism = synthetic construct
SEQUENCE: 253
MNDEDYMRAA LEQARQAAAA GEVPVGAVVV CGGEIVARAH NRPISASDPT AHAEILALRE  60
AARKLGNYRL TGCTLYATLE PCAMCSGAIL HARIARLVYG AADPKAGAVG SVLDVINHPR  120
LNHRVEVTSG VLADECGALL KEFFRARR                                     148

SEQ ID NO: 254          moltype = AA  length = 148
FEATURE                 Location/Qualifiers
source                  1..148
                        mol_type = protein
                        organism = synthetic construct
SEQUENCE: 254
MNDEDYMRAA LEQARQAAAA GEVPVGAVVV CDGKIVARAH NRPISANDPT AHAEILALRE  60
AARQLGNYRL TGCTLYATLE PCAMCSGAIL HARIARLVYG AADPKAGACG SVLNVINHPQ  120
LNHQTEVTGG VLADECGALL KDFFRARR                                     148

SEQ ID NO: 255          moltype = AA  length = 142
FEATURE                 Location/Qualifiers
source                  1..142
                        mol_type = protein
                        organism = synthetic construct
SEQUENCE: 255
MRAALEEARR AAAAGEVPVG AVVVRDGAIV ARAHNRPIAL HDPTAHAEIL ALREAARALG  60
NYRLTGCTLY ATLEPCAMCA GAILHARIDR LVYGAADPKA GACGSVLSVM NHPRLNHRVE  120
```

```
VTGGVLAEEC GALLTGFFRA RR                                          142

SEQ ID NO: 256          moltype = AA  length = 149
FEATURE                 Location/Qualifiers
source                  1..149
                        mol_type = protein
                        organism = synthetic construct
SEQUENCE: 256
MSEEDRFMRA ALAEARAAAE AGEVPVGAVV VCGGRIVARA HNRPIALNDP TAHAEILALR  60
EAARELGNYR LTGCTLYATL EPCAMCAGAI LHARIARLVY GARDPKAGAV ESLYRLLDDT  120
RLNHRVEAVG GVLAGECGAL LSGFFRARR                                   149

SEQ ID NO: 257          moltype = AA  length = 147
FEATURE                 Location/Qualifiers
source                  1..147
                        mol_type = protein
                        organism = synthetic construct
SEQUENCE: 257
MDEEFMRLAL AEARAAAEAG EVPVGAVVVA GGRVVARAHN RPVALHDPTA HAEVLALRAA  60
ARELGNYRLT GCTLYATLEP CAMCAGAILH ARLDRVVYGA ADPKAGAAGS VLDVFANPRL  120
NHRTAVTGGV LAEECGALLR EFFRARR                                     147

SEQ ID NO: 258          moltype = AA  length = 150
FEATURE                 Location/Qualifiers
source                  1..150
                        mol_type = protein
                        organism = synthetic construct
SEQUENCE: 258
MSEEDRFMRA ALAEARAAAE AGEVPVGAVV VAGGRIVARA HNRPIALNDP TAHAEILALR  60
AAARALGNYR LTGCTLYATL EPCAMCAGAI LHARIARLVY GARDPKAGAV ESLYRLLDDR  120
RLNHRVEAVG GVLAAECGAL LSGFFRARRG                                  150

SEQ ID NO: 259          moltype = AA  length = 142
FEATURE                 Location/Qualifiers
source                  1..142
                        mol_type = protein
                        organism = synthetic construct
SEQUENCE: 259
MREALAEARA AAAAGEVPVG AVVVRDGAVL ARAGNRTLRD RDPTAHAEML AIRAAARALG  60
SERLTGCDLY VTLEPCAMCA GAISHARIAR LYYGAADPKG GAVEHGPRFF AQPTCHHRPE  120
VYGGIGEGEA AALLRGFFRA RR                                          142

SEQ ID NO: 260          moltype = AA  length = 142
FEATURE                 Location/Qualifiers
source                  1..142
                        mol_type = protein
                        organism = synthetic construct
SEQUENCE: 260
MRAALEEARR AAAAGEVPVG AVVVRDGAIV ARAHNRPIAL HDPTAHAEIL ALREAARALG  60
NYRLTGCTLY ATLEPCAMCS GAILHARLDR VVYGAADPKT GAAGSVLDVF ANPRLNHHAA  120
VTGGVLAEEC GALLSGFFRA RR                                          142

SEQ ID NO: 261          moltype = AA  length = 142
FEATURE                 Location/Qualifiers
source                  1..142
                        mol_type = protein
                        organism = synthetic construct
SEQUENCE: 261
MREALAEARA AAAAGEVPVG AVVVRDGAIV ARAHNRPIAL HDPTAHAEVL ALREAARALG  60
NYRLTGCTLY ATLEPCAMCA GAILHARLDR VVYGAADPKA GAAGSVLDVF ANPRLNHRTA  120
VTGGVLADEC GALLSGFFRA RR                                          142

SEQ ID NO: 262          moltype = AA  length = 142
FEATURE                 Location/Qualifiers
source                  1..142
                        mol_type = protein
                        organism = synthetic construct
SEQUENCE: 262
MRAALEEARR AAAAGEVPVG AVVVRDGAIV ARAHNRPIAL HDPTAHAEIL ALREAARALG  60
NYRLTGCTLY ATLEPCAMCA GAILHARLDR VVYGAADPKA GAAGSVLQVF DHPRLNHRTA  120
VTGGVLAEEC GALLRDFFRA RR                                          142

SEQ ID NO: 263          moltype = AA  length = 149
FEATURE                 Location/Qualifiers
source                  1..149
                        mol_type = protein
                        organism = synthetic construct
SEQUENCE: 263
MDDDALMREA LAEARAAAAA GEVPVGAVVA RGGEIVARAA NAPRALCDPT AHAEILALRA  60
```

```
AARALGNYRL TGCTLYATLE PCAMCAGAIL HARIARLVYA APDPKAGACG SVLAVLNHPQ  120
LNHRVEVTAG LLADECGALL TDFFRARRG                                    149

SEQ ID NO: 264         moltype = AA  length = 142
FEATURE                Location/Qualifiers
source                 1..142
                       mol_type = protein
                       organism = synthetic construct
SEQUENCE: 264
MRAALEEARR AAAAGEVPVG AVVVRDGAIV ARAHNRPIAL HDPTAHAEIL ALREAARALG  60
NYRLTGCTLY ATLEPCAMCA GAILHARIDR LVYGAADPKA GACGSVLSVM NHPQLNHRVE  120
VTGGVLAEEC GALLSGFFRA RR                                           142

SEQ ID NO: 265         moltype = AA  length = 149
FEATURE                Location/Qualifiers
source                 1..149
                       mol_type = protein
                       organism = synthetic construct
SEQUENCE: 265
MNDEDFMRAA LAQAREAAAA GEVPVGAVVV CDGEIVARAH NRPIALNDPT AHAEILALRE  60
AARRLGNYRL TGCTLYATLE PCAMCAGAIL HARIARLVYG AADPKAGAVG SVLDVLNHPR  120
LNHRVEVTRG VLAEECGALL SEFFRARRR                                    149

SEQ ID NO: 266         moltype = AA  length = 163
FEATURE                Location/Qualifiers
source                 1..163
                       mol_type = protein
                       organism = synthetic construct
SEQUENCE: 266
MDEEFMRRAL ELARQAEAAG EVPVGAVLVK DGEIVAEGWN QSIGRHDATA HAEIQVLRKA  60
GQVLENYRLL DTTLYVTLEP CPMCAGALLH SRVKRIVYGA PDLKAGAAGT VLNLFEHQAA  120
YHYADVEHGL LEEECREQLQ AFFKRRRKEK KALKQAQREA EEK                    163

SEQ ID NO: 267         moltype = AA  length = 150
FEATURE                Location/Qualifiers
source                 1..150
                       mol_type = protein
                       organism = synthetic construct
SEQUENCE: 267
MSEEDRFMRA ALAEARAAAE AGEVPVGAVV VAGGRIVARA HNRPIALNDP TAHAEILALR  60
EAARALGNYR LTGCTLYATL EPCAMCAGAI LHARIARLVY GAADPKAGAV ESLYRLLDDT  120
RLNHRVEATG GVLAGECGAL LSEFFRARRR                                   150

SEQ ID NO: 268         moltype = AA  length = 150
FEATURE                Location/Qualifiers
source                 1..150
                       mol_type = protein
                       organism = synthetic construct
SEQUENCE: 268
MSEEDRFMRA ALAEARAAAE AGEVPVGAVV VAGGRIIARA HNRPIALNDP TAHAEILALR  60
AAARALGNYR LTGCTLYATL EPCAMCAGAI LHARIARLVY GARDAKAGAV ESVLRLFDHP  120
ALNHRVEAVG GVLADECGAL LSEFFRARRA                                   150

SEQ ID NO: 269         moltype = AA  length = 142
FEATURE                Location/Qualifiers
source                 1..142
                       mol_type = protein
                       organism = synthetic construct
SEQUENCE: 269
MREALAEARA AAAAGEVPVG AVVVRDGAIV ARAHNRPIAL HDPTAHAEIL ALREAARALG  60
NYRLTGCTLY ATLEPCAMCA GAILHARLDR VVYGAADPKA GAAGSVLDVF ANPRLNHRTA  120
VTGGVLADEC GALLRDFFRA RR                                           142

SEQ ID NO: 270         moltype = AA  length = 148
FEATURE                Location/Qualifiers
source                 1..148
                       mol_type = protein
                       organism = synthetic construct
SEQUENCE: 270
MNDEDYMRAA LEQARQAAAA GEVPVGAVVV CGGEIVARAH NRPISASDPT AHAEILALRE  60
AARKLGNYRL TGCTLYATLE PCAMCSGAIL HARIARLVYG AADPKAGAVG SVLDVINHPR  120
LNHRVEVTGG VLAGECGALL SGFFRARR                                     148

SEQ ID NO: 271         moltype = AA  length = 142
FEATURE                Location/Qualifiers
source                 1..142
                       mol_type = protein
                       organism = synthetic construct
SEQUENCE: 271
```

```
MREALAEARA AAAAGEVPVG AVVVRDGAIV ARAHNRPIAL HDPTAHAEVL ALRAAARELG  60
NYRLTGCTLY ATLEPCAMCA GAILHARLDR VVFGARDPKA GAAGSVLDVF ANPRLNHRTA  120
VTGGVLAEEC GALLSGFFRA RR                                           142

SEQ ID NO: 272         moltype = AA  length = 148
FEATURE                Location/Qualifiers
source                 1..148
                       mol_type = protein
                       organism = synthetic construct
SEQUENCE: 272
MNDEDYMRAA LEQARQAAAA GEVPVGAVVV CDGKIVARAH NRPISANDPT AHAEILALRE  60
AARQLGNYRL TGCTLYATLE PCAMCSGAIL HARIARLVYG ASDPKAGACG SVLNVINHPQ  120
LNHRVEVTGG VLADECGALL KDFFRARR                                     148

SEQ ID NO: 273         moltype = AA  length = 149
FEATURE                Location/Qualifiers
source                 1..149
                       mol_type = protein
                       organism = synthetic construct
SEQUENCE: 273
MSEEDRFMRA ALAEARAAAA EGEVPVGAVV VAGGRIVARA HNRPVALNDP TAHAEILALR  60
AAARALGNYR LTGCTLYATV EPCAMCAGAI LHARIARLVY GAADPKAGAV RSVLRVLDHP  120
ALNHRVEVTA GVLAEECAAL LQEFFRARR                                    149

SEQ ID NO: 274         moltype = AA  length = 148
FEATURE                Location/Qualifiers
source                 1..148
                       mol_type = protein
                       organism = synthetic construct
SEQUENCE: 274
MNDEDYMRAA LEQARQAAAA GEVPVGAVVV CGGEIVARAH NRPISANDPT AHAEILALRE  60
AARKLGNYRL TGCTLYATLE PCAMCSGAIL HARIARLVYG AADPKAGACG SVLNVINHPQ  120
LNHRVEVTGG ILADECGALL KDFFRARR                                     148

SEQ ID NO: 275         moltype = AA  length = 142
FEATURE                Location/Qualifiers
source                 1..142
                       mol_type = protein
                       organism = synthetic construct
SEQUENCE: 275
MRAALEEARR AAAAGEVPVG AVVVRDGAIV ARAHNRPIAL HDPTAHAEIL ALREAARRLG  60
NYRLTGCTLY ATLEPCAMCA GAILHARIDR LVYGAADPKA GACGSVLSVM NHPRLNHRVE  120
VTSGVLAEEC GALLTDFFRA RR                                           142

SEQ ID NO: 276         moltype = AA  length = 143
FEATURE                Location/Qualifiers
source                 1..143
                       mol_type = protein
                       organism = synthetic construct
SEQUENCE: 276
MRAALEEARR AAAAGEVPVG AVVVRDGEIV ARAHNRPIAL HDPTAHAEIL ALREAARRLG  60
NYRLTGCTLY ATLEPCAMCA GAILHARLDR VVYGAADPKA GACGSVLSVF DQPRLNHRTT  120
VTGGVLAEEC GALLSGFFRA RRG                                          143

SEQ ID NO: 277         moltype = AA  length = 142
FEATURE                Location/Qualifiers
source                 1..142
                       mol_type = protein
                       organism = synthetic construct
SEQUENCE: 277
MREALAEARA AAAAGEVPVG AVVVRDGAVL ARAGNASIRA RDPTAHAEVL ALRAAARALG  60
NHRLTGCTLY VTLEPCAMCA GAIAHARVAR LVYGAADPKG GAVAHGPRFF EQPTCHHRPE  120
VVGGVGAAEA GALLRDFFAA RR                                           142

SEQ ID NO: 278         moltype = AA  length = 148
FEATURE                Location/Qualifiers
source                 1..148
                       mol_type = protein
                       organism = synthetic construct
SEQUENCE: 278
MTDEYFMRQA LREARRAYDE GEVPVGAVVV RDGRVIARGR NQVERLKDPT AHAEMIALTA  60
AANYLGSKRL EGCTVYVTLE PCPMCAGALV LARVERLVFG AFDPKAGACG TLYDIVRDRR  120
LNHRLEVVGG VLEEESAALL REFFEKRR                                     148

SEQ ID NO: 279         moltype = AA  length = 162
FEATURE                Location/Qualifiers
source                 1..162
                       mol_type = protein
                       organism = synthetic construct
```

```
SEQUENCE: 279
MSDEQYMRRA LELARQAEQE GEVPVGAVLV KDGEVIAEGW NRSIGSHDAT GHAEIMALRA  60
AGEKLQNYRL LDTTLYVTLE PCPMCAGALL HSRVKRVVFG APDLKAGAAG TVLNLFESQA  120
SYHYADVESG LLEEECREQL QAFFKRRRKE IKAARQAKRD AE                    162

SEQ ID NO: 280          moltype = AA  length = 142
FEATURE                 Location/Qualifiers
source                  1..142
                        mol_type = protein
                        organism = synthetic construct
SEQUENCE: 280
MREALAEARA AAAAGEVPVG AVVVRDGAVL ARAGNRTVRD ADPTAHAEIV ALRAAARALG  60
NHRLGGCTLY VTLEPCAMCA GAIAQARVAR LVYGADDPKG GAVAHGPRLF AQPTCHHRPE  120
VVGGVGAAEA AALLRDFFAA RR                                          142

SEQ ID NO: 281          moltype = AA  length = 148
FEATURE                 Location/Qualifiers
source                  1..148
                        mol_type = protein
                        organism = synthetic construct
SEQUENCE: 281
MDDEALMGLA LDEARAAAAA GEVPIGAVVA RGGEVLARAG NRTLRDCDPT AHAEIVALRE  60
AARALGNYRL TGCTLYVTLE PCAMCAGAAI QARLDRVVYG AADPKAGAAG SVLDVLGHPR  120
LNHRPAVEGG VLAAESAALL REFFAARR                                    148

SEQ ID NO: 282          moltype = AA  length = 142
FEATURE                 Location/Qualifiers
source                  1..142
                        mol_type = protein
                        organism = synthetic construct
SEQUENCE: 282
MREALAEARA AAAAGEVPVG AVVVRDGAVL ARAGNASIRA RDPTAHAEIL ALRAAARALG  60
NHRLTGCTLY VTLEPCAMCA GAIAHARLAR LVYGAADPKG GAVAHGPRLF AQPTCHHRPE  120
VTGGVGAAEA AALLRDFFAA RR                                          142

SEQ ID NO: 283          moltype = AA  length = 164
FEATURE                 Location/Qualifiers
source                  1..164
                        mol_type = protein
                        organism = synthetic construct
SEQUENCE: 283
MSDEQFMRRA IELAKKGEEL GEVPVGAVLV KDGEIIAEGW NQSISTHDAT AHAEIMAIRA  60
AGEKLENYRL LDTTLYVTLE PCPMCAGALL HSRVKRVVFG APDLKAGAAG TVLNLFESQA  120
SYHYADVESG LLEEECREQL QAFFKRRRKE IKAAKQAKRE AEEK                  164

SEQ ID NO: 284          moltype = AA  length = 162
FEATURE                 Location/Qualifiers
source                  1..162
                        mol_type = protein
                        organism = synthetic construct
SEQUENCE: 284
MDDEFYMRRA LELAALAEEH NEVPVGAVLV LNGEIIGEGW NRSIGHHDAT AHAEIMALRQ  60
AGKKLENYRL LDTTLYVTLE PCPMCAGALL HSRVKRVVFG APDLKAGAAG TVLNLFESQA  120
SYHYADVESG LLEQECREQL QAFFKRRRKE IKALKKAQKE AE                    162

SEQ ID NO: 285          moltype = AA  length = 148
FEATURE                 Location/Qualifiers
source                  1..148
                        mol_type = protein
                        organism = synthetic construct
SEQUENCE: 285
MDDAGFMRLA LAEARKAAAA GEVPVGAVVV RDGAVLAAAG NRTLRDCDPT AHAEVVALRA  60
AARALGNHRL GGCDLYVTLE PCAMCAGAIS HARIARLYYG ADDPKGGAVA HGARVFDQPT  120
CHHRPEVYGG IGAGEAAALL RDFFAARR                                    148

SEQ ID NO: 286          moltype = AA  length = 149
FEATURE                 Location/Qualifiers
source                  1..149
                        mol_type = protein
                        organism = synthetic construct
SEQUENCE: 286
DLDDARFMRE ALAEARAAAE AGEVPVGAVV VADGRIVARA HNRPVALNDP TAHAEILALR  60
EAARALGNYR LTGCTLYATL EPCAMCAGAI LHARIARLVY GARDAKAGAV ESLYRLLDDA  120
RLNHRVEVAA GVLADECGAL LTEFFRARR                                   149

SEQ ID NO: 287          moltype = AA  length = 147
FEATURE                 Location/Qualifiers
source                  1..147
                        mol_type = protein
```

```
                        organism = synthetic construct
SEQUENCE: 287
DESFMREALA EARAAAEAGE VPVGAVVVHG GQIVARAHNR PIELSDPTAH AEILALRAAA  60
RALGNYRLTG CTLYATLEPC AMCAGAILHA RIDRVVYGAS DPKAGAAGSV LSVFDHPALN  120
HRVDVTAGVL AEECGALLRE FFRARRR                                      147

SEQ ID NO: 288          moltype = AA  length = 148
FEATURE                 Location/Qualifiers
source                  1..148
                        mol_type = protein
                        organism = synthetic construct
SEQUENCE: 288
DPDAAFMRAA LAEARAAAEA GEVPVGAVVV ADGAIVARAH NRPIALNDPT AHAEILALRE  60
AARALGNYRL TGATLYATLE PCAMCAGAIL HARIARLVYG ARDPKAGAVE SLYRLLDDAR  120
LNHRVAVTGG VLAAECGALL TAFFRARR                                     148

SEQ ID NO: 289          moltype = AA  length = 147
FEATURE                 Location/Qualifiers
source                  1..147
                        mol_type = protein
                        organism = synthetic construct
SEQUENCE: 289
DERFMREALA EARAAAAAGE VPVGAVVVRD GEIVARAANR TVRDNDPTAH AEILALREAA  60
RALGSYRLTG CTLYATLEPC AMCAGAILHA RIARLVYAAA DPKAGACGSV LSVMNHPQLN  120
HRVEVESGLL AEECGALLTE FFRARRG                                      147

SEQ ID NO: 290          moltype = AA  length = 163
FEATURE                 Location/Qualifiers
source                  1..163
                        mol_type = protein
                        organism = synthetic construct
SEQUENCE: 290
MTADEQYMRR ALELARQAEA EGEVPVGAVL VKDGEIVAEG WNRSIGHHDA TAHAEIQVLR  60
KAGQVLQNYR LLDTTLYVTL EPCPMCAGAL LHSRVKRIVY GAPDLKAGAA GTVLNLFEHQ  120
AAYHYADVEH GLLEDECREQ LQAFFKRRRK EKKALKQALK ESN                    163

SEQ ID NO: 291          moltype = AA  length = 150
FEATURE                 Location/Qualifiers
source                  1..150
                        mol_type = protein
                        organism = synthetic construct
SEQUENCE: 291
RIRSDEDFMR QALAEARAAA AAGEVPVGAV VVAGGRIVAR AHNRPIDLVD PTAHAEILAL  60
REAARALGNY RLTGCTLYAT LEPCAMCAGA ILHARIARLV YGAADPKAGA VESVLRLLDH  120
PALNHRVEAV SGVLAGECGA LLREFFRARR                                   150

SEQ ID NO: 292          moltype = AA  length = 148
FEATURE                 Location/Qualifiers
source                  1..148
                        mol_type = protein
                        organism = synthetic construct
SEQUENCE: 292
DLDEALMREA LAEARRAAEA GEVPVGAVVA RGGRIVARAH NQPVALHDPT AHAEILALRQ  60
AAREAGNYRL EGCTLYATLE PCAMCAGALL HARVARLVYG ARDPKAGAVG SLYDLLRDPR  120
LNHRVEVTAG VLAEECGALL SGFFRARR                                     148

SEQ ID NO: 293          moltype = AA  length = 143
FEATURE                 Location/Qualifiers
source                  1..143
                        mol_type = protein
                        organism = synthetic construct
SEQUENCE: 293
MREALAEARA AAAAGEVPVG AVVVDPAGEI VARAGNAPRA LCDPTAHAEI LALRAAAAAA  60
GNYRLPGHVL YVTLEPCAMC AGAISHARIA RLVYGAADPK GGAVAHGPRF FAQPTCHHRP  120
EVTGGVLAEE CGALLRDFFR ARR                                          143

SEQ ID NO: 294          moltype = AA  length = 162
FEATURE                 Location/Qualifiers
source                  1..162
                        mol_type = protein
                        organism = synthetic construct
SEQUENCE: 294
RLDEQFMRRA LELAAHAEAE GEVPVGAVLV LDGQVIGEGW NRSIGQHDAT AHAEIMALRQ  60
AGQVVQNYRL LDTTLYVTLE PCPMCAGALL HSRVKRIVYG APDLKAGAAG TVLNLFEHQA  120
AYHYADVEHG LLEEECREQL QAFFKRRRKE KKALKQAQRA AE                     162

SEQ ID NO: 295          moltype = AA  length = 149
FEATURE                 Location/Qualifiers
source                  1..149
```

```
                        mol_type = protein
                        organism = synthetic construct
SEQUENCE: 295
DPDDVAFMRE ALAEAERAAA AGEVPVGAVV VHDGVIVGRG HNRPIASRDP TAHAEIVALR  60
EAAAALGNYR LTGCSLYVTI EPCAMCAGAI LHARIARLVY GAADPKAGAC GSVLDVFAEP  120
RLNHHAEVTG GVLADECAAL LRSFFAARR                                   149

SEQ ID NO: 296          moltype = AA  length = 148
FEATURE                 Location/Qualifiers
source                  1..148
                        mol_type = protein
                        organism = synthetic construct
SEQUENCE: 296
DPDERFMRAA LAQARAAAEA GEVPVGAVVV RDGRIVARAH NQPIALNDPT AHAEILALRE  60
AARELGNYRL TGCTLYATLE PCAMCAGAIL HARIARLVYG ARDAKAGAVE SKLRLFENGS  120
FNHRVEVTGG VLAGECGALL SEFFRARR                                    148

SEQ ID NO: 297          moltype = AA  length = 148
FEATURE                 Location/Qualifiers
source                  1..148
                        mol_type = protein
                        organism = synthetic construct
SEQUENCE: 297
MDEEFMREAL AEARAAAEAG EVPVGAVVVA GGRIVGRGRN RPVELADPTA HAEILALREA  60
ARALGNYRLE GCTLYATLEP CAMCAGAILH ARIARLVYGA ADPKAGAAGS VLDVFALPRL  120
NHRTAVTGGV LAEECGALLS GFFRARRG                                    148

SEQ ID NO: 298          moltype = AA  length = 150
FEATURE                 Location/Qualifiers
source                  1..150
                        mol_type = protein
                        organism = synthetic construct
SEQUENCE: 298
RSSDAALMRE ALAEARAAAE AGEVPVGAVV VAGGRIVARA HNRPVALSDP TAHAEVLALR  60
EAARELGNYR LEGCTLYATL EPCAMCSGAL LHARVARLVY GAADPKAGAV GSVLDLFANP  120
RLNHRVEVTG GVLAEECGAL LSGFFRARRG                                  150

SEQ ID NO: 299          moltype = AA  length = 148
FEATURE                 Location/Qualifiers
source                  1..148
                        mol_type = protein
                        organism = synthetic construct
SEQUENCE: 299
DDDERWMREA LAEARAAAAA GEVPVGAVVV RDGVLLARAG NASIRERDPT AHAEMLALRA  60
AARALGNHRL GGCTLYVTLE PCAMCAGAIA HARIARLVYG AADPKAGAVD HGPRLFAQPT  120
VHHRPEVVAG VGAEESAALL RDFFRARR                                    148

SEQ ID NO: 300          moltype = AA  length = 150
FEATURE                 Location/Qualifiers
source                  1..150
                        mol_type = protein
                        organism = synthetic construct
SEQUENCE: 300
DPDSDEAFMR AALAEARAAA EAGEVPVGAV VVADGAIVAR AHNRPIALHD PTAHAEILAL  60
RAAARRLGNY RLTGCTLYAT LEPCAMCAGA ILHARIARLV YGAADPKAGA CGSVLAVMNH  120
PQLNHRVEVT GGILAEECGA LLRDFFRARR                                  150

SEQ ID NO: 301          moltype = AA  length = 142
FEATURE                 Location/Qualifiers
source                  1..142
                        mol_type = protein
                        organism = synthetic construct
SEQUENCE: 301
MREALAEARA AAEAGEVPVG AVVVAGGRIV ARAHNRPVAL HDPTAHAEIL ALRQAAAELG  60
NYRLEGCTLY ATLEPCAMCA GAMLHARLAR VVYGAADPKA GAAGSVLDLF ANPRLNHRTE  120
VVGGVLAEEC GALLSGFFRS RR                                          142

SEQ ID NO: 302          moltype = AA  length = 146
FEATURE                 Location/Qualifiers
source                  1..146
                        mol_type = protein
                        organism = synthetic construct
SEQUENCE: 302
DERFMREALA EARAAAAAGE VPVGAVVVRD GVVLARAGNR TLRDRDPTAH AEMLALRQAA  60
RALGSHRLTG CDLYVTLEPC AMCAGAISHA RIARLYYGAA DAKGGAVEHG PRFFAQPTCH  120
HRPEVYGGIG ETEAAALLRG FFRERR                                      146

SEQ ID NO: 303          moltype = AA  length = 149
FEATURE                 Location/Qualifiers
```

```
source                  1..149
                        mol_type = protein
                        organism = synthetic construct
SEQUENCE: 303
MDSDLEFMRL ALAEARAAAE AGEVPVGAVV VAGGRVVARA HNRPVALHDP TAHAEILALR  60
AAARELGNYR LTGCTLYATL EPCAMCAGAI LHARIARLVY GAADPKAGAC GSVLDVIHHP  120
RLNHRVEVTG GVLAEECGAL LSGFFRARR                                    149

SEQ ID NO: 304          moltype = AA  length = 143
FEATURE                 Location/Qualifiers
source                  1..143
                        mol_type = protein
                        organism = synthetic construct
SEQUENCE: 304
MREALAEARA AAEAGEVPVG AVVVAGGRIV ARAHNRPVAL HDPTAHAEIL ALREAARALG  60
NYRLEGCTLY ATLEPCAMCA GALLHARVAR LVYGARDPKA GAVGSVLDLL DHPRLNHRVE  120
VVGGVLAEEC GALLSGFFRA RRG                                          143

SEQ ID NO: 305          moltype = AA  length = 147
FEATURE                 Location/Qualifiers
source                  1..147
                        mol_type = protein
                        organism = synthetic construct
SEQUENCE: 305
DDRRWMREAL AEARAAAEAG EVPVGAVVVR DGRLLARAGN ASIRDRDPTA HAELLALRAA  60
ARALGNHRLT GCTLYVTLEP CAMCAGAIAH ARIARLVYGA ADPKGGAVAH GPRLFEQPTL  120
HHRPEVTGGV LAAEAGELLR AFFRARR                                      147

SEQ ID NO: 306          moltype = AA  length = 148
FEATURE                 Location/Qualifiers
source                  1..148
                        mol_type = protein
                        organism = synthetic construct
SEQUENCE: 306
MNDEDFMRAA LAQARLAAEA GEVPVGAVVV CDGEIVARAH NRPISASDPT AHAEILALRE  60
AARRLGNYRL TGCTLYATLE PCAMCAGAIL HARIARLVYG AADPKAGAVG SVLDVLNHPR  120
LNHRVEVTGG VLAEECGALL RDFFRARR                                     148

SEQ ID NO: 307          moltype = AA  length = 151
FEATURE                 Location/Qualifiers
source                  1..151
                        mol_type = protein
                        organism = synthetic construct
SEQUENCE: 307
DESSDLRFMR EALAEARAAA EAGEVPVGAV VVCGGRIVAR AHNRPIALSD PTAHAEILAL  60
REAARELGNY RLTGCTLYAT LEPCAMCAGA ILHARIARLV YGAADPKAGA CGSVLDVINH  120
PRLNHRVEVT GGVLAGECGA LLSGFFRARR G                                 151

SEQ ID NO: 308          moltype = AA  length = 147
FEATURE                 Location/Qualifiers
source                  1..147
                        mol_type = protein
                        organism = synthetic construct
SEQUENCE: 308
DDLFFMREAL AEARRAAAEG EVPVGAVVVC GGRIIARAHN RPIALNDPTA HAEILALRAA  60
ARALGNYRLT DCTLYATLEP CAMCAGAILH ARIRRLVYGA ADPKAGAVRS VLRLLDAPAL  120
NHRVAVTAGV LAEECGALLS EFFRARR                                      147

SEQ ID NO: 309          moltype = AA  length = 151
FEATURE                 Location/Qualifiers
source                  1..151
                        mol_type = protein
                        organism = synthetic construct
SEQUENCE: 309
DPPSADEAFM REALAEARAA AEAGEVPVGA VVVAGGRIVA RAHNRPIALS DPTAHAEILA  60
LRAAARALGN YRLTGTTLYA TVEPCAMCAG AIVQARVARL VYGAADPKAG AVESLFRILD  120
HPALNHRVEV TAGVLAEECA ALLREFFRAR R                                 151

SEQ ID NO: 310          moltype = AA  length = 149
FEATURE                 Location/Qualifiers
source                  1..149
                        mol_type = protein
                        organism = synthetic construct
SEQUENCE: 310
DETEAFMRAA LAEARAAAEA GEVPVGAVVV ADGRIVARAH NRPVALHDPT AHAEILALRE  60
AARRLGNYRL TGCTLYATLE PCAMCAGAVL HARLARLVYG ARDAKAGAVG SVLDLLAHPR  120
LNHRTAVTAG VLADECGALL SAFFRARRG                                    149

SEQ ID NO: 311          moltype = AA  length = 148
```

```
FEATURE                 Location/Qualifiers
source                  1..148
                        mol_type = protein
                        organism = synthetic construct
SEQUENCE: 311
DDDERWMREA LAEARAAAAA GEVPVGAVVV RDGVLLARAG NASIRDRDPT AHAEMLALRA  60
AARALGNHRL TGCTLYVTLE PCAMCAGAIA HARIARLVYG ASDPKAGAVD HGPRLFEQPT  120
IHHRPEVTAG VLADECGALL RDFFRARR                                     148

SEQ ID NO: 312          moltype = AA  length = 150
FEATURE                 Location/Qualifiers
source                  1..150
                        mol_type = protein
                        organism = synthetic construct
SEQUENCE: 312
DPTTDEALMR EALAEARAAA EAGEVPVGAV VARDGEIVAR AANAPRALCD PTAHAEILAL  60
RAAARALGNY RLTGCTLYAT LEPCAMCAGA ALHARFARIV YGAADPKAGA AGSVLDVLDQ  120
PRLNHRTRVT GGVLADECGA LLTEFFRARR                                   150

SEQ ID NO: 313          moltype = AA  length = 164
FEATURE                 Location/Qualifiers
source                  1..164
                        mol_type = protein
                        organism = synthetic construct
SEQUENCE: 313
MNKDEFYMKR ALELAQKAEE EGEVPVGAVL VLDDEIIGEG WNRPIGSHDA TAHAEIQALR  60
DAGQKLENYR LLDTTLYVTL EPCPMCAGAL LHSRVKRVVY GAPDLKAGAA GTVLNLFEHE  120
AAYHYADVEH GLLEDECREQ LQAFFKRRRK EIKAKKEAEK KALE                   164

SEQ ID NO: 314          moltype = AA  length = 164
FEATURE                 Location/Qualifiers
source                  1..164
                        mol_type = protein
                        organism = synthetic construct
SEQUENCE: 314
MNSDEFYMQR ALELAQKAEQ EDEVPVGAVL VLDGEIIGEG WNRSIGHHDA TAHAEMMALK  60
QGGKQIQNYR LLDATLYVTL EPCPMCAGAL LHSRVKRIVY GAPDLKAGAA GTVLNLFEHQ  120
AAYHYADVEQ GLMEEECREQ LQAFFKRRRK EKKALKQAKR EAEE                   164

SEQ ID NO: 315          moltype = AA  length = 146
FEATURE                 Location/Qualifiers
source                  1..146
                        mol_type = protein
                        organism = synthetic construct
SEQUENCE: 315
DERFMREALA EARAAAAAGE VPVGAVVVRD GVVLARAGNR TLRDRDPTAH AEMLALRQAA  60
RALGSWRLTG CTLYVTLEPC AMCAGAMVQA RVDRLVYGAA DPKAGAAGSV LDVLGHPRLN  120
HRPEVAAGVL AEECGALLRE FFRERR                                       146

SEQ ID NO: 316          moltype = AA  length = 142
FEATURE                 Location/Qualifiers
source                  1..142
                        mol_type = protein
                        organism = synthetic construct
SEQUENCE: 316
MRAALEEARR AAAEGEVPVG AVVVRDGAIV ARAHNRPIAL NDPTAHAEIL ALREAARALG  60
NYRLTGCTLY ATLEPCAMCA GAILHARIAR LVYGAADPKA GACGSVLSVI NHPRLNHRVE  120
VTGGVLAEEC GALLTGFFRA RR                                           142

SEQ ID NO: 317          moltype = AA  length = 148
FEATURE                 Location/Qualifiers
source                  1..148
                        mol_type = protein
                        organism = synthetic construct
SEQUENCE: 317
DPDAAFMREA LAEARAAAAA GEVPVGAVVV RAGRIVARAH NRPVELHDPT AHAEILALRA  60
AARELGNYRL TGCTLYATLE PCAMCAGAIL HARIERLVYG ARDAKAGAAG SVLDVFANPR  120
LNHRVAVEGG VLADECAALL REFFRARR                                     148

SEQ ID NO: 318          moltype = AA  length = 148
FEATURE                 Location/Qualifiers
source                  1..148
                        mol_type = protein
                        organism = synthetic construct
SEQUENCE: 318
MDDEALMRVA LEEARAAAAA GEVPVGAVVA RGGEIVARAA NAPIAASDPT AHAEILALRA  60
AARALGNYRL TGCTLYATLE PCAMCAGAIL HARIARLVYA APDPKAGACG SVLAVLDHPA  120
LNHRVEVTGG VLAEECGALL REFFRARR                                     148
```

```
SEQ ID NO: 319         moltype = AA  length = 164
FEATURE                Location/Qualifiers
source                 1..164
                       mol_type = protein
                       organism = synthetic construct
SEQUENCE: 319
MSDEQYMRRA LELARQAEQE GEVPVGAVLV KDGEIIAEGW NRSIGHHDAT AHAEMQVLRK  60
AGQVLENYRL LDTTLYVTLE PCPMCAGALL HSRVKRIVYG APDLKAGAAG TVLNLFEHQA  120
AYHYADVEHG LLEEECREQL QAFFKRRRKE IKARKQAEKE AEAR                   164

SEQ ID NO: 320         moltype = AA  length = 151
FEATURE                Location/Qualifiers
source                 1..151
                       mol_type = protein
                       organism = synthetic construct
SEQUENCE: 320
DPLEQDERWM REALAEARAA AEAGEVPVGA VLVRDGVLLA RAGNRTIRDR DPTAHAEMLA  60
LRAAARALGN HRLTGCTLYV TLEPCAMCAG AIAHARIARL VYGASDPKGG AVAHGPRLFE  120
QPTLHHRPEV TGGVLAEEAG ELLRAFFRAR R                                 151

SEQ ID NO: 321         moltype = AA  length = 142
FEATURE                Location/Qualifiers
source                 1..142
                       mol_type = protein
                       organism = synthetic construct
SEQUENCE: 321
MREALAEARA AAEAGEVPVG AVVVAGGRIV ARAHNQPIAL NDPTAHAEVL ALRQAARELG  60
NYRLTGCTLY ATLEPCAMCA GAILHARLDR VVYGAADPKA GAAGSVLDVF ANPRLNHHAQ  120
VTGGVLAEEC GALLSGFFRA RR                                           142

SEQ ID NO: 322         moltype = AA  length = 147
FEATURE                Location/Qualifiers
source                 1..147
                       mol_type = protein
                       organism = synthetic construct
SEQUENCE: 322
DDLSFMREAL AEAEAAAEAG EVPVGAVLVR DGEIVARGRN RVIEDRDPTA HAEIVALREA  60
GRALGNYRLE GCTLYVTLEP CAMCAGALVH ARLDRLVYGA ADPKAGAAGS VLDVLNHPRL  120
NHRMEVTGGV LADECGAMLR AFFRARR                                      147

SEQ ID NO: 323         moltype = AA  length = 151
FEATURE                Location/Qualifiers
source                 1..151
                       mol_type = protein
                       organism = synthetic construct
SEQUENCE: 323
DRLRADEQFM RAALAEARAA AAAGEVPVGA VVVRDGEIVA RAHNRPIALH DPTAHAEILA  60
LRAAARALGN YRLTGCTLYA TLEPCAMCAG AILHARLDRV VYGAADPKAG ACGSVLSVMN  120
HPRLNHRVEV TGGVLADECG ALLTEFFRAR R                                 151

SEQ ID NO: 324         moltype = AA  length = 143
FEATURE                Location/Qualifiers
source                 1..143
                       mol_type = protein
                       organism = synthetic construct
SEQUENCE: 324
MREALAEARA AAAAGEVPVG AVVVRGGEIV ARAHNRPVAL SDPTAHAEVL ALREAARRLG  60
NYRLEGCTLY ATLEPCAMCS GAVLHARLAR LVYGAPDPKA GAAGSVLDVL DHPRLNHRTA  120
VTGGVLAEEC GALLSGFFRA RRG                                          143

SEQ ID NO: 325         moltype = AA  length = 147
FEATURE                Location/Qualifiers
source                 1..147
                       mol_type = protein
                       organism = synthetic construct
SEQUENCE: 325
DDRRWMREAL AEARAAGAAG EVPVGAVVVR DGELLARAGN ASIRDRDPTA HAEMLALRAA  60
ARALGNHRLT GCTLYVTLEP CAMCAGAIAH ARIARLVYGA SDPKGGAVAH GPRLFEQPTL  120
HHRPEVTAGV LADECGALLR DFFRARR                                      147

SEQ ID NO: 326         moltype = AA  length = 142
FEATURE                Location/Qualifiers
source                 1..142
                       mol_type = protein
                       organism = synthetic construct
SEQUENCE: 326
MREALAEARR AAEAGEVPVG AVVVRDGEIV ARAHNRPIAL HDPTAHAEIL ALREAARRLG  60
NYRLTGCTLY ATLEPCAMCA GAILHARLDR VVYGAPDPKA GACGSVLSVF DQPRLNHRTR  120
VEGGVLAEEC GALLSGFFRA RR                                           142
```

```
SEQ ID NO: 327         moltype = AA  length = 149
FEATURE                Location/Qualifiers
source                 1..149
                       mol_type = protein
                       organism = synthetic construct
SEQUENCE: 327
DDRDRRWMRA ALAEARAAAE AGEVPVGAVV VRDGELLARA GNASIRDRDP TAHAEMLALR  60
AAARALGNHR LTGCTLYVTL EPCAMCAGAI AHARIARLVY GAADPKGGAV AHGPRLFEQP  120
TLHHRPEVTA GVLAEEAGEL LRAFFRARR                                    149

SEQ ID NO: 328         moltype = AA  length = 142
FEATURE                Location/Qualifiers
source                 1..142
                       mol_type = protein
                       organism = synthetic construct
SEQUENCE: 328
MREALAEARA AAAAGEVPVG AVVVRGGEIV ARAHNRPIAL NDPTAHAEIL ALREAARVLG  60
NYRLTGCTLY ATLEPCAMCA GAILHARIDR LVYGAADPKA GACGSVLSVM NHPQLNHRVE  120
VTSGVLAEEC GALLTDFFRA RR                                           142

SEQ ID NO: 329         moltype = AA  length = 145
FEATURE                Location/Qualifiers
source                 1..145
                       mol_type = protein
                       organism = synthetic construct
SEQUENCE: 329
MREALAEARA AAEAGEVPVG AVVVRDGEIV ARAHNRPIAL NDPTAHAEIL ALREAARRLG  60
NYRLTGCTLY ATLEPCAMCA GAILHARLAR LVYGAADPKA GACGSVLSVI NHPRLNHRVE  120
VTSGVLADEC GALLSDFFRA RRRAA                                        145

SEQ ID NO: 330         moltype = AA  length = 146
FEATURE                Location/Qualifiers
source                 1..146
                       mol_type = protein
                       organism = synthetic construct
SEQUENCE: 330
DDRFMRAALA EARAAAEAGE VPVGAVVVVD GRIVARAHNR PVELSDPTAH AEVLALREAA  60
RALGNYRLEG ATLYATLEPC AMCSGAILHA RVERVVYGAA DSRAGAAGSV LDVFATRRLN  120
HQTTVTGGVL AEECGALLSG FFRARR                                       146

SEQ ID NO: 331         moltype = AA  length = 148
FEATURE                Location/Qualifiers
source                 1..148
                       mol_type = protein
                       organism = synthetic construct
SEQUENCE: 331
DDDQRFMREA LAEARAAAAA GEVPIGAVVV CDGAIVARAG NRTIRDNDPT AHAEILALRQ  60
AARALGNYRL TGCTLYVTLE PCAMCAGAIV QARIARLVYG AADPKAGAVD SVLDVLNHPR  120
LNHRVEVTRG VLAEECGALL RDFFRARR                                     148

SEQ ID NO: 332         moltype = AA  length = 150
FEATURE                Location/Qualifiers
source                 1..150
                       mol_type = protein
                       organism = synthetic construct
SEQUENCE: 332
MSDDERFMRL ALEQARLAAE AGEVPVGAVV VCDGRVVARA HNRPIALNDP TAHAEILALR  60
EAARELGNYR LTGCTLYATL EPCAMCSGAV LHARLARVVY GAADPKTGAA GSVLDLFAEP  120
RLNHHAEVTG GVLAGECGAL LSGFFRARRG                                   150

SEQ ID NO: 333         moltype = AA  length = 160
FEATURE                Location/Qualifiers
source                 1..160
                       mol_type = protein
                       organism = synthetic construct
SEQUENCE: 333
DPTDLAFMRE ALAEAEAAAA AGEVPVGAVV VHEGRIVGRG RNRMIAASDP TAHAEIVALR  60
EAARALGNYR LTGCTLYVTL EPCAMCAGAI LHARIARLVY GAADPKAGAC GSVLDVLNHP  120
RLNHRTEVTA GVLAEECGAM LSGFFRARRA QQRAARVAAS                        160

SEQ ID NO: 334         moltype = AA  length = 149
FEATURE                Location/Qualifiers
source                 1..149
                       mol_type = protein
                       organism = synthetic construct
SEQUENCE: 334
DPPDAVFMRA ALEEARAAAE AGEVPVGAVL VHDGQILARA GNRTIRDRDP TAHAEILALR  60
QAARVLGSHR LTGATLYVTL EPCAMCAGAI SHARIARLVY GADDPKGGAV RHGPRFFEQP  120
```

```
TCHHRPEVTG GILAEESAAL LRGFFRARR                                   149

SEQ ID NO: 335          moltype = AA  length = 142
FEATURE                 Location/Qualifiers
source                  1..142
                        mol_type = protein
                        organism = synthetic construct
SEQUENCE: 335
MRAALEEARR AAEAGEVPVG AVVVRDGAIV ARAHNRPIAL HDPTAHAEIL ALREAARRLG  60
NYRLTGCTLY ATLEPCAMCA GAILHARLDR VVYGAADPKA GACGSVLSVF DQPRLNHRTR  120
VEGGVLAEEC GALLSGFFRA RR                                          142

SEQ ID NO: 336          moltype = AA  length = 149
FEATURE                 Location/Qualifiers
source                  1..149
                        mol_type = protein
                        organism = synthetic construct
SEQUENCE: 336
DDDQRFMALA LAQAQAAADA GEVPVGAVVV CDGRVVARAH NRPIALNDPT AHAEILALRE  60
AARALGNYRL TGCTLYATLE PCAMCAGAIL HARIARLVYG ARDPKAGAVE SLYRLLDDDR  120
LNHRVAVTGG VLAAACGALL SGFFRARRR                                   149

SEQ ID NO: 337          moltype = AA  length = 149
FEATURE                 Location/Qualifiers
source                  1..149
                        mol_type = protein
                        organism = synthetic construct
SEQUENCE: 337
DLTDEQLMRA ALAEARAAAA AGEVPVGAVV AKDGEIIARA HNRPIAAHDP TAHAEILALR  60
AAARALGNYR LTGCTLYATL EPCAMCSGAI LHARIARLVY GAADPKAGAC GSVLAVMNHP  120
QLNHRVEVTG GVLAEECGAL LRDFFRARR                                   149

SEQ ID NO: 338          moltype = AA  length = 148
FEATURE                 Location/Qualifiers
source                  1..148
                        mol_type = protein
                        organism = synthetic construct
SEQUENCE: 338
DDDERWMREA LAEARAAAEA GEVPVGAVVV RDGELLARAG NASIRDRDPT AHAEMLALRA  60
AARALGNHRL TGCTLYVTLE PCAMCAGAIA HARIARLVYG ASDPKGGAVA HGPRLFEQPT  120
LHHRPEVTGG VLAEEAGALL RAFFRARR                                    148

SEQ ID NO: 339          moltype = AA  length = 146
FEATURE                 Location/Qualifiers
source                  1..146
                        mol_type = protein
                        organism = synthetic construct
SEQUENCE: 339
DLEFMREALA EARAAAEAGE VPVGAVVVRD GAIVARAGNR TLRDRDPTAH AEMLALRQAA  60
RALDSWRLSG CTLYVTLEPC AMCAGAMVQA RLDRLVYGAA DPKAGAAGSV LDVLGHPRLN  120
HRVEVTGGVL AEECGALLRE FFRARR                                      146

SEQ ID NO: 340          moltype = AA  length = 150
FEATURE                 Location/Qualifiers
source                  1..150
                        mol_type = protein
                        organism = synthetic construct
SEQUENCE: 340
RSESDEALMR EALAEARRAA DAGEVPVGAV VVRDGAILAR AGNAPIAASD PTAHAEILAL  60
RAAARALGNY RLTGCTLYAT LEPCAMCAGA ILHARIARLV YGARDPKAGA VESVLDLLDR  120
PALNHRVEVT GGVLAAECGA LLSGFFRARR                                  150

SEQ ID NO: 341          moltype = AA  length = 148
FEATURE                 Location/Qualifiers
source                  1..148
                        mol_type = protein
                        organism = synthetic construct
SEQUENCE: 341
MDDAGFMRAA LAEARAAAEA GEVPVGAVVV CDGRIVARAG NRTLRDRDPT AHAEMLALRA  60
AARALGSHRL TGCDLYVTLE PCAMCAGAIS HARIRRLYYG ASDPKGGAVE NGVRFFAQPT  120
CHHAPEVYGG IGEAEAAALL RGFFRARR                                    148

SEQ ID NO: 342          moltype = AA  length = 149
FEATURE                 Location/Qualifiers
source                  1..149
                        mol_type = protein
                        organism = synthetic construct
SEQUENCE: 342
MRDEDYMRAA LAQAREAAAA GEVPVGAVVV ADGRIVARAH NRPIALNDPT AHAEILALRE  60
```

```
AARQLGNYRL TGCTLYATLE PCAMCAGAIL HARIARLVYG AADPKAGAVG SVLDVLNHPR  120
LNHRVEVTSG VLAAECGALL TEFFRSRRR                                   149

SEQ ID NO: 343         moltype = AA  length = 149
FEATURE                Location/Qualifiers
source                 1..149
                       mol_type = protein
                       organism = synthetic construct
SEQUENCE: 343
DETEAFMRAA LAEARAAAAE GEVPVGAVVV ADGAIVARAH NRPIALNDPT AHAEILALRE  60
AARALGNYRL TGCTLYATLE PCAMCAGAIL HARIARLVYG ARDPKAGAVE SLYRLLDDTR  120
LNHRVEAVGG VLADECGALL TEFFRARRG                                   149

SEQ ID NO: 344         moltype = AA  length = 148
FEATURE                Location/Qualifiers
source                 1..148
                       mol_type = protein
                       organism = synthetic construct
SEQUENCE: 344
DDDERWMREA LAEARAAAAA GEVPVGAVVV RDGVLLARAG NASIRDRDPT AHAEMLALRA  60
AARALGNHRL GGCTLYVTLE PCAMCAGAIA HARIARLVYG AADPKAGAVD HGPRLFEQPT  120
CHHRPEVVSG VGAAESAALL RDFFRARR                                    148

SEQ ID NO: 345         moltype = AA  length = 145
FEATURE                Location/Qualifiers
source                 1..145
                       mol_type = protein
                       organism = synthetic construct
SEQUENCE: 345
MRAALEEARR AAEAGEVPVG AVVVRDGAIV ARAHNRPIAL NDPTAHAEIL ALREAARALG  60
NYRLTGCTLY ATLEPCAMCA GAILHARLDR VVYGAADPKA GACGSVLSVF DQPRLNHRTT  120
LTGGVLAEEC GALLSGFFRA RRRAA                                       145

SEQ ID NO: 346         moltype = AA  length = 149
FEATURE                Location/Qualifiers
source                 1..149
                       mol_type = protein
                       organism = synthetic construct
SEQUENCE: 346
MDDDLFMRAA LDEARAAAEA GEVPVGAVVV ADGRIVARAH NRPIALNDPT AHAEILALRA  60
AAAALGNYRL TGCELFVTLE PCAMCAGAIL HARLARVVYG AADPKTGAAG SVLDVFANPR  120
LNHRTEVRGG VLADECGALL TEFFRARRG                                   149

SEQ ID NO: 347         moltype = AA  length = 149
FEATURE                Location/Qualifiers
source                 1..149
                       mol_type = protein
                       organism = synthetic construct
SEQUENCE: 347
MDDEALMREA LAEARAAAEA GEVPVGAVVA RGGEIVARGR NRMIADGDPT AHAEIVALRE  60
AARALGNYRL TGCTLYATLE PCAMCAGAIL HARIARLVYA APDPKAGACG SVLSVMNHPQ  120
LNHRVEVASG LLAEECGALL TNFFRARRG                                   149

SEQ ID NO: 348         moltype = AA  length = 149
FEATURE                Location/Qualifiers
source                 1..149
                       mol_type = protein
                       organism = synthetic construct
SEQUENCE: 348
DPEDERFMRE ALAEAERARE AGEVPVGAVV VLDGRIVGRG HNRPIGAHDP TAHAEIVALR  60
EAAAALGNYR LTGATLYVTL EPCAMCAGAI LHARIARLVY GAADPKTGAV GSLLDLLAEP  120
RLNHRTEVTG GVLAEECGAL LSAFFRARR                                   149

SEQ ID NO: 349         moltype = AA  length = 147
FEATURE                Location/Qualifiers
source                 1..147
                       mol_type = protein
                       organism = synthetic construct
SEQUENCE: 349
DDLSFMREAL AEAEAAAAAG EVPVGAVVVH GGRIVGRGRN RMIADHDPTA HAEIVALREA  60
ARALGNYRLT GCTLYVTLEP CAMCAGAILH ARIERLVYGA ADPKAGACGS VLSVMNHPQL  120
NHRVEVTSGV LADECGAMLS GFFRARR                                     147

SEQ ID NO: 350         moltype = AA  length = 146
FEATURE                Location/Qualifiers
source                 1..146
                       mol_type = protein
                       organism = synthetic construct
SEQUENCE: 350
```

```
DLEFMRLALE EARAAAAAGE VPVGAVLVRD GEVLARAGNR TIRDRDPTAH AEMLAIREAA  60
RRLDNYRLEG TTLYVTLEPC AMCSGAILHA RVPRVVYGAA DPKAGAAGSV LDVLGHPRLN  120
HRTEVVGGVL AEECGALLRE FFRARR                                       146

SEQ ID NO: 351         moltype = AA  length = 147
FEATURE                Location/Qualifiers
source                 1..147
                       mol_type = protein
                       organism = synthetic construct
SEQUENCE: 351
DDDHFMREAL AEARRAADAG EVPVGAVVVR AGQIIARAHN RPVALHDPTA HAEILALRAA  60
ARRLGNYRLT GCTLYATLEP CAMCAGAILH ARIARLVYGA ADPKAGACGS VLDVLNHPRL  120
NHRVEVTAGV LAEECGALLS AFFRARR                                      147

SEQ ID NO: 352         moltype = AA  length = 148
FEATURE                Location/Qualifiers
source                 1..148
                       mol_type = protein
                       organism = synthetic construct
SEQUENCE: 352
DDDQRFMREA LAEARAAAAA GEVPIGAVVV CDGEIVARAG NRTIRDNDPT AHAEILALRQ  60
AARALGNYRL TGCTLYVTLE PCAMCAGAIV HARIARLVYG AADPKAGAVN SVFDLLNHPR  120
LNHRVEVTSG VLADECGALL RDFFRARR                                     148

SEQ ID NO: 353         moltype = AA  length = 146
FEATURE                Location/Qualifiers
source                 1..146
                       mol_type = protein
                       organism = synthetic construct
SEQUENCE: 353
DESFMREALA EARAAAEAGE VPVGAVVVHG GRIVARAHNR PIELSDPTAH AEILALRAAA  60
RALGNYRLTG CTLYATLEPC AMCAGAILHA RIDRVVYGAA DPKAGAAGSV LDVFANPRLN  120
HHARVTGGVL ADECGALLSG FFRARR                                       146

SEQ ID NO: 354         moltype = AA  length = 151
FEATURE                Location/Qualifiers
source                 1..151
                       mol_type = protein
                       organism = synthetic construct
SEQUENCE: 354
DPESDAAFMR AALAEAQAAA EAGEVPVGAV VVCDGRIVAR AHNRPIGLND PTAHAEILAL  60
REAARELGNY RLTGCTLYVT LEPCAMCSGA ILHARLARVV YGAADPKTGA AGSVLDLFAN  120
RRLNHQTQVE GGVLAEECGA LLSGFFRARR G                                 151

SEQ ID NO: 355         moltype = AA  length = 142
FEATURE                Location/Qualifiers
source                 1..142
                       mol_type = protein
                       organism = synthetic construct
SEQUENCE: 355
MREALAEARA AAAAGEVPVG AVVVRGGEIV ARAHNRPIAL NDPTAHAEIL ALREAARVLG  60
NYRLTGCTLY ATLEPCAMCA GAILHARIAR LVYGAADPKA GACGSVLSVM NHPQLNHRVE  120
VTGGVLAGEC GALLSDFFRA RR                                           142

SEQ ID NO: 356         moltype = AA  length = 150
FEATURE                Location/Qualifiers
source                 1..150
                       mol_type = protein
                       organism = synthetic construct
SEQUENCE: 356
MSDDERFMRL ALAQAREAAA EGEVPVGAVV VCGGRVVARA HNRPIALNDP TAHAEVLALR  60
AAARELGNYR LTGCTLYATL EPCAMCAGAI LHARIARVVY GARDPKAGAA GSVLDVFANP  120
RLNHHATVTG GVLAEECGAL LSDFFRARRR                                   150

SEQ ID NO: 357         moltype = AA  length = 149
FEATURE                Location/Qualifiers
source                 1..149
                       mol_type = protein
                       organism = synthetic construct
SEQUENCE: 357
MDDDERWMRE ALAEARAAAE AGEVPVGAVV VRDGVLLARA GNASIRDRDP TAHAEMLALR  60
AAARALGNHR LTGCTLYVTL EPCAMCAGAI AHARIARLVY GAADPKAGAV DHGPRLFEQP  120
TCHHRPEVVS GVGAAESAAL LRDFFRARR                                    149

SEQ ID NO: 358         moltype = AA  length = 148
FEATURE                Location/Qualifiers
source                 1..148
                       mol_type = protein
                       organism = synthetic construct
```

```
SEQUENCE: 358
DDDERWMRAA LAEARAAAEA GEVPVGAVVV AGGRLVARAG NASIRDSDPT AHAEILALRA  60
AARALGNHRL AGCTLYVTLE PCAMCAGAIA HARIARLVYG ASDPKGGAVA HGPRLFEQPT  120
LHHRPEVTGG VLAAEAGALL RAFFRARR                                     148

SEQ ID NO: 359          moltype = AA  length = 142
FEATURE                 Location/Qualifiers
source                  1..142
                        mol_type = protein
                        organism = synthetic construct
SEQUENCE: 359
MREALAEARR AAAEGEVPVG AVVVRDGAVI ARAHNRPIAL RDPTAHAEIL ALREAARLLG  60
NYRLTGCTLY VTLEPCAMCA GAIVHARIDR LVYGAADPKA GAVESVLRVL DHPRLNHRVE  120
VTRGVLAEEC GALLREFFRA RR                                           142

SEQ ID NO: 360          moltype = AA  length = 149
FEATURE                 Location/Qualifiers
source                  1..149
                        mol_type = protein
                        organism = synthetic construct
SEQUENCE: 360
MNDEDFMRAA LAQAREAAAA GEVPVGAVVV CGGRIVARAH NRPISARDPT AHAEILALRA  60
AARELGNYRL TGCELYVTLE PCAMCAGAIL HARIARLVYG AADPKTGAAG SVLDVFANPR  120
LNHRTEVTGG VLADECGALL SGFFRARRG                                    149

SEQ ID NO: 361          moltype = AA  length = 148
FEATURE                 Location/Qualifiers
source                  1..148
                        mol_type = protein
                        organism = synthetic construct
SEQUENCE: 361
DDDQRFMAAA LEEARAAAAE GEVPVGAVVV AGGRIVARAH NRPIALNDPT AHAEILALRA  60
AARELGNYRL TGCTLYATLE PCAMCAGAIL HARIDRVVYG ARDPKAGAAG SVLDVFANPR  120
LNHHAEVTGG VLAEECGALL SDFFRARR                                     148

SEQ ID NO: 362          moltype = AA  length = 142
FEATURE                 Location/Qualifiers
source                  1..142
                        mol_type = protein
                        organism = synthetic construct
SEQUENCE: 362
MREALAEARA AAEAGEVPVG AVVVAGGRIV ARAHNRPIAL HDPTAHAEIL ALREAARELG  60
NYRLTGCTLY ATLEPCAMCA GAILHARIAR LVYGAADPKA GACGSVLAVM NHPQLNHRVE  120
VVGGVLAEEC GALLREFFRA RR                                           142

SEQ ID NO: 363          moltype = AA  length = 149
FEATURE                 Location/Qualifiers
source                  1..149
                        mol_type = protein
                        organism = synthetic construct
SEQUENCE: 363
MDSDLEFMRE ALAEARAAAE AGEVPVGAVV VRDGEIVARA ANRTIRDGDP TAHAEMVALR  60
AAARALGNYR LAGCTLYVTL EPCAMCAGAM IHARLDRVVY GAADPKAGAA GSVLDVLGHP  120
ALNHRTAVTA GVLAEECGAL LRDFFRARR                                    149

SEQ ID NO: 364          moltype = AA  length = 150
FEATURE                 Location/Qualifiers
source                  1..150
                        mol_type = protein
                        organism = synthetic construct
SEQUENCE: 364
DPTTDEALMR EALAEARAAA ADGEVPVGAV VARDGVIVAR AHNAPVALSD PTAHAEILAL  60
REAARAAGNY RLPGCTLYAT LEPCAMCCGA ALHARLARVV YGARDPKAGA AGSVLDLLDD  120
PRLNHRAEVV GGVLAEECGA LLSGFFRARR                                   150

SEQ ID NO: 365          moltype = AA  length = 152
FEATURE                 Location/Qualifiers
source                  1..152
                        mol_type = protein
                        organism = synthetic construct
SEQUENCE: 365
DPLSADDARF MRLALAEARA AAEAGEVPVG AVVVAGGRVV ARAHNRPVAL HDPTAHAEIL  60
ALRAAARALG NYRLTGCTLY ATLEPCAMCA GAILHARIAR LVYGAADPKA GACGSVLAVM  120
NHPQLNHRVE VTGGVLAEEC GALLRDFFRA RR                                152

SEQ ID NO: 366          moltype = AA  length = 148
FEATURE                 Location/Qualifiers
source                  1..148
                        mol_type = protein
```

```
                         organism = synthetic construct
SEQUENCE: 366
MNDEDFMRAA LAQAREAAAA GEVPVGAVVV CDGRIVARAH NRPIALNDPT AHAEILALRE  60
AARALGNYRL TGCTLYATLE PCAMCAGAIL HARIARLVYG AADPKAGAVG SVLDVMNHPR  120
LNHRVEVTSG VLAEECGALL KEFFRARR                                    148

SEQ ID NO: 367           moltype = AA  length = 148
FEATURE                  Location/Qualifiers
source                   1..148
                         mol_type = protein
                         organism = synthetic construct
SEQUENCE: 367
DDDQRFMREA LAEARAAAEA GEVPIGAVVV CDGEIVARAG NRTIRDNDPT AHAEILALRQ  60
AARRLGNYRL TGCTLYVTLE PCAMCAGAIV QARIARLVYG AADPKAGAVD SVLQVLNHPR  120
LNHRVEVTRG VLAEECGALL RDFFRARR                                    148

SEQ ID NO: 368           moltype = AA  length = 142
FEATURE                  Location/Qualifiers
source                   1..142
                         mol_type = protein
                         organism = synthetic construct
SEQUENCE: 368
MREALAEARR AAEAGEVPVG AVVVRDGEIV ARAHNRPIAL HDPTAHAEIL ALREAARRLG  60
NYRLTGCTLY ATLEPCAMCA GAILHARLDR VVYGAPDPKA GACGSVLSVF DQPALNHRVA  120
VTGGVLAEEC GALLREFFRA RR                                          142

SEQ ID NO: 369           moltype = AA  length = 148
FEATURE                  Location/Qualifiers
source                   1..148
                         mol_type = protein
                         organism = synthetic construct
SEQUENCE: 369
DPDARFMREA LAEAEAAAAA GEVPVGAVVV AGGRIVARAH NRPVELSDPT AHAEILALRE  60
AARELGNYRL EGCTLYATLE PCAMCSGAIL HARLARVVYG AADPKAGAAG SVLDVFALPQ  120
LNHRTAVTGG VLADECGALL SGFFRARR                                    148

SEQ ID NO: 370           moltype = AA  length = 149
FEATURE                  Location/Qualifiers
source                   1..149
                         mol_type = protein
                         organism = synthetic construct
SEQUENCE: 370
MNDEDYMRAA LEQARLAASE GEVPVGAVVV CDGKIVARAH NRPIALNDPT AHAEILALRE  60
AARKLGNYRL TGCTLYATLE PCAMCSGAIL HARIARLVYG AADPKAGAVG SVLDVINHPR  120
LNHRVEVTSG VLAEECGALL SGFFRARRK                                   149

SEQ ID NO: 371           moltype = AA  length = 142
FEATURE                  Location/Qualifiers
source                   1..142
                         mol_type = protein
                         organism = synthetic construct
SEQUENCE: 371
MRAALEEARR AAEAGEVPVG AVVVRDGAIV ARAHNRPIAL HDPTAHAEIL ALREAARRLG  60
NYRLTGCTLY ATLEPCAMCA GAILHARIDR LVYGAADPKA GACGSVLSVM NHPRLNHRVE  120
VERGVLAEEC GALLTGFFRA RR                                          142

SEQ ID NO: 372           moltype = AA  length = 150
FEATURE                  Location/Qualifiers
source                   1..150
                         mol_type = protein
                         organism = synthetic construct
SEQUENCE: 372
MSTEDERFMR LALAEARRAA AEGEVPVGAV VVAGGEVVAA AHNRPIALAD PTAHAEILAL  60
RAAARALGNY RLTGCTLYAT LEPCAMCAGA ILHARIARLV YGAADPKAGA VESVLRLLDA  120
PGLNHRVAVT GGVLAEECGA LLREFFRARR                                  150

SEQ ID NO: 373           moltype = AA  length = 143
FEATURE                  Location/Qualifiers
source                   1..143
                         mol_type = protein
                         organism = synthetic construct
SEQUENCE: 373
MREALAEARA AAEAGEVPVG AVVVRDGAIV ARAHNRPIAL NDPTAHAEIL ALREAARALG  60
NYRLTGCTLY ATLEPCAMCA GAILHARLDR VVYGAADPKA GAAGSVLQVF DHPRLNHRTA  120
VTGGVLAAEC GALLSGFFRA RRG                                         143

SEQ ID NO: 374           moltype = AA  length = 143
FEATURE                  Location/Qualifiers
source                   1..143
```

```
                        mol_type = protein
                        organism = synthetic construct
SEQUENCE: 374
MREALAEARA AAAAGEVPVG AVVVRGGEIV ARAHNRPIAL NDPTAHAEIL ALREAARALG  60
NYRLTGCTLY ATLEPCAMCA GAILHARIDR VVFGARDPKA GAAGSVLDVF ANPRLNHHAE  120
VVGGVLADEC GALLSGFFRA RRG                                          143

SEQ ID NO: 375          moltype = AA  length = 146
FEATURE                 Location/Qualifiers
source                  1..146
                        mol_type = protein
                        organism = synthetic construct
SEQUENCE: 375
DERFMREALA EARAAAAAGE VPVGAVVVRD GVVLARAGNR TLRDRDPTAH AEMLALRQAA  60
RALGSWRLAG CTLYVTLEPC AMCAGAMVLA RVDRLVYGAA DPKAGAAGSV LDVLGEPRLN  120
HRPEVAAGVL AEECGELLRA FFRERR                                       146

SEQ ID NO: 376          moltype = AA  length = 151
FEATURE                 Location/Qualifiers
source                  1..151
                        mol_type = protein
                        organism = synthetic construct
SEQUENCE: 376
DPTSDEAFMR AALAEARAAA EAGEVPVGAV VVCGGRIVAR AGNRPIAARD PTAHAEILAL  60
RAAARELGSY RLTGATLYVT LEPCAMCAGA ILHARIERLV FGAADPKTGA AGSVLDLFAE  120
PRLNHRTAVE GGVLAEECGA LLRDFFRARR G                                 151

SEQ ID NO: 377          moltype = AA  length = 150
FEATURE                 Location/Qualifiers
source                  1..150
                        mol_type = protein
                        organism = synthetic construct
SEQUENCE: 377
DPSPDEAFMR AALAEARAAA EAGEVPVGAV VVRDGRIVAR AGNRPIALHD PTAHAEILAL  60
RAAARELGNY RLTGCELYVT LEPCAMCAGA ILHARLARLV YGAADPKTGA AGSVLDVFAN  120
RRLNHHTAVT GGVLADECGA LLAGFFRARR                                   150

SEQ ID NO: 378          moltype = AA  length = 149
FEATURE                 Location/Qualifiers
source                  1..149
                        mol_type = protein
                        organism = synthetic construct
SEQUENCE: 378
MDDAAFMRAA LAEARAAAEA GEVPVGAVVV ADGAIVARAH NRPIALNDPT AHAEILALRA  60
AARALGNYRL TGCTLYATLE PCAMCAGAIL HARIARLVYG ARDPKAGAVE SLYRLLDDTR  120
LNHRVAVTGG VLADECGALL TEFFRARRR                                    149

SEQ ID NO: 379          moltype = AA  length = 150
FEATURE                 Location/Qualifiers
source                  1..150
                        mol_type = protein
                        organism = synthetic construct
SEQUENCE: 379
DPESDAAFMR AALAEARAAA EAGEVPVGAV VVCDGRIVAR AHNRPIGLND PTAHAEILAL  60
RAAARALGNY RLTGCTLYVT LEPCAMCAGA ILHARLDRVV YGAADPKTGA AGSVLDLFAQ  120
PRLNHHARVE GGVLADECGA LLRDFFRARR                                   150

SEQ ID NO: 380          moltype = AA  length = 149
FEATURE                 Location/Qualifiers
source                  1..149
                        mol_type = protein
                        organism = synthetic construct
SEQUENCE: 380
DPDAAFMRAA LAEARAAAEA GEVPVGAVVV AGGRIVARAH NRPIELNDPT AHAEILALRQ  60
AAAALGNYRL EGCTLYVTLE PCAMCAGAIL HARLARVVYG AADPKTGAAG SVLDLFANPR  120
LNHHAEVTGG VLAEECGALL RDFFRARRG                                    149

SEQ ID NO: 381          moltype = AA  length = 147
FEATURE                 Location/Qualifiers
source                  1..147
                        mol_type = protein
                        organism = synthetic construct
SEQUENCE: 381
MREALAEARR AAEAGEVPVG AVVVRDGEIV ARAHNRPIAL HDPTAHAEIL ALREAARRLG  60
NYRLTGCTLY ATLEPCAMCA GAILHARIDR LVYGAADPKA GACGSVLSVM NHPRLNHRVE  120
VESGLLAGEC GALLTEFFRR RRAAARG                                      147

SEQ ID NO: 382          moltype = AA  length = 149
FEATURE                 Location/Qualifiers
```

```
source                 1..149
                       mol_type = protein
                       organism = synthetic construct
SEQUENCE: 382
MSTDLAFMRE ALAEARAAAE AGEVPVGAVV VRDGAILARA GNRTLRDGDP TAHAEMVALR  60
AAAAALGSER LTDCDLYVTL EPCAMCAGAI SHARIRRLYY GAADPKGGAV EHGVRFFASP  120
TCHHRPEVYG GIGEGEAAAL LRDFFRARR                                   149

SEQ ID NO: 383         moltype = AA  length = 146
FEATURE                Location/Qualifiers
source                 1..146
                       mol_type = protein
                       organism = synthetic construct
SEQUENCE: 383
DDRFMREALA EARAAAAAGE VPVGAVVVRD GEIIARAGNR TLRDRDPTAH AEMLALRQAA  60
RALGSHRLTG CDLYVTLEPC AMCAGAIQHA RIRRLVYGAA DPKAGAVDHG VRLFDSPSCH  120
HRPEVVAGVG EGEAAALLRD FFRERR                                      146

SEQ ID NO: 384         moltype = AA  length = 142
FEATURE                Location/Qualifiers
source                 1..142
                       mol_type = protein
                       organism = synthetic construct
SEQUENCE: 384
MREALAEARA AAAAGEVPVG AVVVRGGEIV ARAHNRPIAL HDPTAHAEIL ALREAARALG  60
NYRLEGCTLY ATLEPCAMCS GAILHARLAR LVYGAADPKA GAVGSVLDVI GNPRLNHRVE  120
VTGGVLAEEC GALLSGFFRA RR                                          142

SEQ ID NO: 385         moltype = AA  length = 148
FEATURE                Location/Qualifiers
source                 1..148
                       mol_type = protein
                       organism = synthetic construct
SEQUENCE: 385
MDDAGFMRAA LAEARAAAAA GEVPVGAVVV RDGAIVARAG NRTLRDRDPT AHAEMLAIRA  60
AARALGSERL TGCDLYVTLE PCAMCAGAIS FARIRRLYYG AADPKGGAVE NGVRFFASPT  120
CHHAPEVYSG IGEAEAAALL RDFFRARR                                    148

SEQ ID NO: 386         moltype = AA  length = 151
FEATURE                Location/Qualifiers
source                 1..151
                       mol_type = protein
                       organism = synthetic construct
SEQUENCE: 386
RPPSDDERWM AEALAQARAA AAEGEVPVGA VVVRDGRLLA RAHNRPIALN DPTAHAEILA  60
LRAAAREIGN YRLTGCTLYA TLEPCAMCAG AILHARIARL VYGARDPKAG ACGSVLDVLN  120
HPRLNHRVEV TGGLLADECG ALLSAFFRAR R                                151

SEQ ID NO: 387         moltype = AA  length = 146
FEATURE                Location/Qualifiers
source                 1..146
                       mol_type = protein
                       organism = synthetic construct
SEQUENCE: 387
DLEFMREALA EARAAAEAGE VPVGAVVVAG GRIVARAHNR PIELHDPTAH AEILALRQAA  60
TALGNYRLTG CTLYATLEPC PMCAGAALHA RLDRIVYGAA DPKAGAAGSV LDLFADTRLN  120
HHAAVAGGVL ADECGALLSG FFRARR                                      146

SEQ ID NO: 388         moltype = AA  length = 148
FEATURE                Location/Qualifiers
source                 1..148
                       mol_type = protein
                       organism = synthetic construct
SEQUENCE: 388
DDDERWMRAA LAEARAAAAA GEVPVGAVVV RDGELLARAG NASIRERDPT AHAELLALRA  60
AARRLGNHRL TGCTLYVTLE PCAMCAGAIA HARIARLVYG AADPKGGAVA HGPRLFEQPT  120
LHHRPEVTAG VLAEECGALL REFFRARR                                    148

SEQ ID NO: 389         moltype = AA  length = 142
FEATURE                Location/Qualifiers
source                 1..142
                       mol_type = protein
                       organism = synthetic construct
SEQUENCE: 389
MREALAEARA AAAAGEVPVG AVVVRGGEIV ARAHNRPIAL HDPTAHAEIL ALREAARRLG  60
NYRLTGCTLY ATLEPCAMCA GAILHARIDR LVYGAADPKA GACGSVLSVM NHPQLNHRVE  120
VTSGVLAEEC GALLTGFFRE RR                                          142

SEQ ID NO: 390         moltype = AA  length = 146
```

```
FEATURE                 Location/Qualifiers
source                  1..146
                        mol_type = protein
                        organism = synthetic construct
SEQUENCE: 390
DERWMREALA EARAAAAEGE VPVGAVVVRD GRLLARAGNA SIRSRDPTAH AEILALRRAA  60
RRLGNHRLTG CTLYVTLEPC AMCAGAIAHA RIARLVYGAS DPKGGAVAHG PRLFEQPTCH  120
HRPEVTGGVL AEECGALLRE FFRARR                                       146

SEQ ID NO: 391          moltype = AA  length = 148
FEATURE                 Location/Qualifiers
source                  1..148
                        mol_type = protein
                        organism = synthetic construct
SEQUENCE: 391
MDDAGFMRAA LAEARAAAEA GEVPVGAVVV ADGRIVARAH NRPVALNDPT AHAEILALRA  60
AARALGNYRL TGCTLYATLE PCAMCAGAIL HARLDRVVYG AADPKAGAAG SVLDVFANPR  120
LNHRTAVTGG VLADECGALL TGFFRARR                                     148

SEQ ID NO: 392          moltype = AA  length = 147
FEATURE                 Location/Qualifiers
source                  1..147
                        mol_type = protein
                        organism = synthetic construct
SEQUENCE: 392
DDRFMRAALA EARAAAEAGE VPVGAVVVCG GRIVARAHNR PIDLCDPTAH AEILALREAA  60
RELGNYRLTG CTLYATLEPC AMCAGAILHA RIARLVYGAR DEKAGAVESL YRLLDDTRLN  120
HRVAVTGGVL AAECGALLSE FFRARRA                                      147

SEQ ID NO: 393          moltype = AA  length = 149
FEATURE                 Location/Qualifiers
source                  1..149
                        mol_type = protein
                        organism = synthetic construct
SEQUENCE: 393
DPDAAFMRAA LAEARAAAEA GEVPVGAVVV HEGRIVARAH NRPVALNDPT AHAEILALRA  60
AARALGNYRL TGCTLYATLE PCAMCAGAIL HARIARLVYG ARDPKAGAVE SLYRLLDDTR  120
LNHRVEAVGG VLADECGALL SEFFRARRR                                    149

SEQ ID NO: 394          moltype = AA  length = 147
FEATURE                 Location/Qualifiers
source                  1..147
                        mol_type = protein
                        organism = synthetic construct
SEQUENCE: 394
DDRFMRAALA EARAAAAAGE VPVGAVVVAG GRIVARAHNQ PVALVDPTAH AEVLALRAAA  60
RELGNYRLTG CTLYATLEPC AMCAGAILHA RIDRLVYGAA DPKAGAVGSV LDVFANPRLN  120
HRTRVTGGVL AAECGALLSE FFRARRR                                      147

SEQ ID NO: 395          moltype = AA  length = 154
FEATURE                 Location/Qualifiers
source                  1..154
                        mol_type = protein
                        organism = synthetic construct
SEQUENCE: 395
MTSAPAPSDL DFMRLALAEA RLAAAEGEVP VGAVVVCDGE VVARAHNRPI ALHDPTAHAE  60
ILALREAARK LGNYRLTGCT LYATLEPCAM CAGAILHARI ARLVYGAADP KAGAVESRLR  120
LLDAPFLNHR VEVTGGVLAE ECGALLKDFF RARR                              154

SEQ ID NO: 396          moltype = AA  length = 147
FEATURE                 Location/Qualifiers
source                  1..147
                        mol_type = protein
                        organism = synthetic construct
SEQUENCE: 396
DDRFMRAALA EARAAAEAGE VPVGAVVVCG GEIVARAHNR PIALNDPTAH AEILALREAA  60
RRLGNYRLTG CTLYATLEPC AMCAGAILHA RIARLVYGAA DPKAGAVESL YRLLDDTRLN  120
HRVEAVGGVL AGECGALLSE FFRARRA                                      147

SEQ ID NO: 397          moltype = AA  length = 142
FEATURE                 Location/Qualifiers
source                  1..142
                        mol_type = protein
                        organism = synthetic construct
SEQUENCE: 397
MREALAEARA AAAGEVPVG AVVVAAGRIV ARAHNRPVEL SDPTAHAEIL ALREAARELG  60
NYRLEGCTLY ATLEPCAMCA GALLHARLAR LVYGAADPKA GAVGSVLDVL DHPRLNHRVE  120
VTAGVLAEEC GALLRDFFRA RR                                           142
```

```
SEQ ID NO: 398          moltype = AA  length = 147
FEATURE                 Location/Qualifiers
source                  1..147
                        mol_type = protein
                        organism = synthetic construct
SEQUENCE: 398
MDEEFMREAL AEARAAAEAG EVPVGAVVVA GGRIVGRGRN RPVELADPTA HAEILALREA  60
AAALGNYRLE GCTLYATLEP CAMCAGAILH ARIARVVYGA RDPKAGAAGS VLDVFALPRL  120
NHHTRVTGGV LAEECGALLS GFFRARR                                      147

SEQ ID NO: 399          moltype = AA  length = 164
FEATURE                 Location/Qualifiers
source                  1..164
                        mol_type = protein
                        organism = synthetic construct
SEQUENCE: 399
RLDEQFMRRA LELAAHAEAE GEVPVGAVLV LDGQVIGEGW NRSIGHHDAT AHAEMMAIEQ  60
AGKAVENYRL LDATLYVTLE PCPMCAGALL HSRVKRIVYG APDLKAGAAG TVLNLFEHQA  120
AYHYADVEHG LLEEECREQL QAFFKRRRKE KKALKQAQRD AEEK                   164

SEQ ID NO: 400          moltype = AA  length = 153
FEATURE                 Location/Qualifiers
source                  1..153
                        mol_type = protein
                        organism = synthetic construct
SEQUENCE: 400
MSTSEADLTF MREALAEARA AAEAGEVPVG AVVVAGGEIV ARAHNRPIAL HDPTAHAEIL  60
ALRAAARRLG NYRLTGCTLY VTLEPCAMCA GAILHARLAR LVYGAADPKT GAAGSVLDLF  120
ANRRLNHHTE VTGGVLADEC GALLSDFFRA RRA                               153

SEQ ID NO: 401          moltype = AA  length = 148
FEATURE                 Location/Qualifiers
source                  1..148
                        mol_type = protein
                        organism = synthetic construct
SEQUENCE: 401
MDDAGFMRLA LAEARRAAEA GEVPVGAVVV RGGEVLAAAG NRTVRDCDPT AHAEVVALRE  60
AARKLGNHRL TGCDLYVTIE PCAMCAGAIS HARIARLYYG ADDPKGGAVE HGPRFFGQPT  120
CHHRPEVYGG IGAAEAAELL RGFFRARR                                     148

SEQ ID NO: 402          moltype = AA  length = 142
FEATURE                 Location/Qualifiers
source                  1..142
                        mol_type = protein
                        organism = synthetic construct
SEQUENCE: 402
MREALAEARA AAEAGEVPVG AVVVRDGEII ARARNRMVAD CDPTAHAEIV ALREAARALG  60
NHRLGGCTLY VTLEPCAMCA GAMIHARVDR LVYGAADPKA GAAGSVLDVI NHPRLNHRME  120
VESGVLADEC GALLKEFFRS RR                                           142

SEQ ID NO: 403          moltype = AA  length = 142
FEATURE                 Location/Qualifiers
source                  1..142
                        mol_type = protein
                        organism = synthetic construct
SEQUENCE: 403
MDAALAEARA AADAGEVPVG AVVVRDGAVL ARAGNRTLRD SDPTAHAEIV ALRAAARALG  60
NHRLPGCTLY VTLEPCAMCA GAISHARLAR LHYGAADPKG GAVEHGPRFF AQPTCHHRPD  120
VVGGLGETEA ADLLRAFFAA RR                                           142

SEQ ID NO: 404          moltype = AA  length = 163
FEATURE                 Location/Qualifiers
source                  1..163
                        mol_type = protein
                        organism = synthetic construct
SEQUENCE: 404
MSDEQYMRRA LELARQAEQQ GEVPVGAVLV RDGEVIAEGW NQSISSHDAT AHAEIMALRA  60
AGQALENYRL LDTTLYVTLE PCPMCAGALL HSRVKRVVFG APDLKAGAAG TVLNLFESQA  120
SYHYADVESG LLEEECREQL QAFFKRRRKE IKAQRDAKRA ADE                    163

SEQ ID NO: 405          moltype = AA  length = 142
FEATURE                 Location/Qualifiers
source                  1..142
                        mol_type = protein
                        organism = synthetic construct
SEQUENCE: 405
MDAALAEARA AADAGEVPVG AVVVRDGVVL ARAGNRTVRD ADPTAHAEIV ALRAAARALG  60
NHRLPGCTLY VTLEPCAMCA GAISHARLAR LVYGAADPKG GAVAHGPRLF AQPTCHHRPE  120
VTGGVGAAEA AALLRAFFAA RR                                           142
```

```
SEQ ID NO: 406          moltype = AA  length = 148
FEATURE                 Location/Qualifiers
source                  1..148
                        mol_type = protein
                        organism = synthetic construct
SEQUENCE: 406
MDDAGFMRLA LAEARAAAAA GEVPVGAVVV RDGEVLAAAG NRTLRDRDPT AHAEVVALRA  60
AARALGSERL PGCDLYVTLE PCAMCAGAIS FARIRRLYFG AGDPKGGAVE HGPRFFAQPT  120
CHHAPEVYGG LGEGEAAGLL RGFFAARR                                     148

SEQ ID NO: 407          moltype = AA  length = 142
FEATURE                 Location/Qualifiers
source                  1..142
                        mol_type = protein
                        organism = synthetic construct
SEQUENCE: 407
MRSALDEARR AAAAGEVPVG AVVVRDGAVL AAAGNRTVRD CDPTAHAEIV ALRAAAAALG  60
NYRLDGCDLY VTLEPCAMCA GAMVHARLAR LVYGAADPRA GAAGSVLDVV RHPALNHRME  120
VTGGVLADEC GALLREFFAA RR                                           142

SEQ ID NO: 408          moltype = AA  length = 168
FEATURE                 Location/Qualifiers
source                  1..168
                        mol_type = protein
                        organism = synthetic construct
SEQUENCE: 408
MDSAAKDLCY MRRALELAAL AEAEGEVPVG AVLVKDGEIV GEGWNRSIGS HDATAHAEIM  60
ALRQAGQALQ NYRLLDTTLY VTLEPCPMCA GALLHSRVKR VVFGAPDLKA GAAGTVLNLF  120
ESQASYHYAE VESGLLEQEC REQLQAFFKR RRKEIKALRQ AEKEAQQK               168

SEQ ID NO: 409          moltype = AA  length = 166
FEATURE                 Location/Qualifiers
source                  1..166
                        mol_type = protein
                        organism = synthetic construct
SEQUENCE: 409
MDSAAKDLCY MRRALELAAL AEAEGEVPVG AVLVKDGEIV GEGWNRSIGS HDATAHAEIM  60
ALRQAGQALQ NYRLLDTTLY VTLEPCPMCA GALLHSRVKR VVFGAPDLKA GAAGTVLNLF  120
ESQASYHYAE VESGLLEEEC REQLQAFFKR RRKEIKAQRD AKRAAD                 166

SEQ ID NO: 410          moltype = AA  length = 167
FEATURE                 Location/Qualifiers
source                  1..167
                        mol_type = protein
                        organism = synthetic construct
SEQUENCE: 410
MTSAPEHEKY MRRALELARQ AEEHGEVPVG AVLVKDGEII AEGWNQSIGS HDATAHAEIM  60
ALRAAGKALE NYRLLDTTLY VTLEPCPMCA GALLHSRVKR VVFGAPDLKA GAAGTVLNLF  120
ESQASYHYAD VESGLLEEEC REQLQAFFKR RRKEIKALKQ AKREQEE                167

SEQ ID NO: 411          moltype = AA  length = 146
FEATURE                 Location/Qualifiers
source                  1..146
                        mol_type = protein
                        organism = synthetic construct
SEQUENCE: 411
DTEFMREALA EARAAAAAGE VPVGAVVVHE GKIIARAGNR TIRDNDPTAH AEIVALRAAA  60
RALGNYRLAG CTLYVTLEPC AMCAGAMIHA RLDRLVYGAD DPKAGAAGSV LNVLNHPRLN  120
HQMQVESGVL ADECAALLQD FFRARR                                       146

SEQ ID NO: 412          moltype = AA  length = 148
FEATURE                 Location/Qualifiers
source                  1..148
                        mol_type = protein
                        organism = synthetic construct
SEQUENCE: 412
MTDADFMALA LEEARAAAAL GEVPVGAVVV RDGAVIARAG NRTVRDNDPT AHAEIVALRE  60
AARALGNYRL DGCTLYVTLE PCAMCSGAML HARLARVVYG AADPKTGAAG SVLDLFATAQ  120
LNHQTQVQGG VLAAECGALL QDFFRQRR                                     148

SEQ ID NO: 413          moltype = AA  length = 160
FEATURE                 Location/Qualifiers
source                  1..160
                        mol_type = protein
                        organism = synthetic construct
SEQUENCE: 413
DESYMRRALE LARQAEQHGE VPVGAVLVKD GEVIAEGWNQ SIGSHDATAH AEIMALRAAG  60
QVLENYRLLD TTLYVTLEPC PMCAGALLHS RVKRVVFGAP DLKAGAAGTV LNLFESQASY  120
```

```
HYAEVEGGLL EDECREQLQA FFKRRRKEIK AARQAKRAAE                    160

SEQ ID NO: 414          moltype = AA  length = 143
FEATURE                 Location/Qualifiers
source                  1..143
                        mol_type = protein
                        organism = synthetic construct
SEQUENCE: 414
MDEALAEARR AAAAGEVPVG AVLVRDGRVL ARGGNRTIRD CDPTAHAEIV ALREAARAAG  60
NYRLPGTTLY VTLEPCAMCA GAMIHARVAR LVYGAADPRA GAAGSVFDVL RHPALNHRME  120
VEGGVRAEEC GALLREFFRA RRA                                      143

SEQ ID NO: 415          moltype = AA  length = 150
FEATURE                 Location/Qualifiers
source                  1..150
                        mol_type = protein
                        organism = synthetic construct
SEQUENCE: 415
MTEADLRFMQ LALEEARRAG EAGEVPVGAV LVRDGAVLAR GGNRTIRDCD PTAHAEIVAL  60
REAARALGNY RLDGCTLYVT LEPCAMCAGA MIHARLDRLV YGADDPRAGA AGSVLDVLGH  120
PALNHQTRVT AGVLAEECGA LLREFFRARR                               150

SEQ ID NO: 416          moltype = AA  length = 163
FEATURE                 Location/Qualifiers
source                  1..163
                        mol_type = protein
                        organism = synthetic construct
SEQUENCE: 416
MTDEEYMRRA LELARQAEQQ GEVPVGAVLV KDGEVIAEGW NQSIGSHDAT AHAEIMALRA  60
AGQALENYRL LDTTLYVTLE PCPMCAGALL HSRVKRVVFG APDLKAGAAG TVLNLFESQA  120
SYHYADVESG LLEEECREQL QAFFKRRRKE IKALKQAKRD AEE                163

SEQ ID NO: 417          moltype = AA  length = 142
FEATURE                 Location/Qualifiers
source                  1..142
                        mol_type = protein
                        organism = synthetic construct
SEQUENCE: 417
MRDALAEARA AAARGEVPVG AVVVRDGAVL ARAGNASIAA RDPTAHAEIL ALRAAARALG  60
NHRLTGCTLY VTLEPCAMCA GAIAHARIAR LVYGAADPKG GAVAHGPRFF AQPTCHHRPE  120
VAGGLGEAEA AALLRDFFRA RR                                       142

SEQ ID NO: 418          moltype = AA  length = 148
FEATURE                 Location/Qualifiers
source                  1..148
                        mol_type = protein
                        organism = synthetic construct
SEQUENCE: 418
MTDEDFMRLA LAEAQAAAAA GEAPIGAVLV RDGQVLARGQ NRVIRDNDPT AHAEIVALRE  60
AARQLGNYRL DGCELYVTLE PCAMCAGAMI HARLARLVYG AADPKAGAAG SVLDVINHPR  120
LNHRMQVTAG VLADECGALL RDFFRQRR                                 148

SEQ ID NO: 419          moltype = AA  length = 142
FEATURE                 Location/Qualifiers
source                  1..142
                        mol_type = protein
                        organism = synthetic construct
SEQUENCE: 419
MRAALDEARA AADAGEVPVG AVVVRDGAIL ARAGNRTVRD ADPTAHAEIV ALRAAARALG  60
NHRLGGCTLY VTLEPCAMCA GAIAQARVAR LVYGAADPKG GAVAHGPRLF AQPTCHHRPE  120
VTGGVLADEA GELLRAFFAA RR                                       142

SEQ ID NO: 420          moltype = AA  length = 160
FEATURE                 Location/Qualifiers
source                  1..160
                        mol_type = protein
                        organism = synthetic construct
SEQUENCE: 420
DETYMRRALE LARQAEQHGE VPVGAVLVKD GEVIAEGWNQ SIGAHDATAH AEIMALRAAG  60
QALQNYRLLD TTLYVTLEPC PMCAGALLHS RVKRVVFGAP DLKAGAAGTV LNLFESQASY  120
HYAEVESGLL EEECREQLQA FFKRRRKEIK AARQAARDAQ                    160

SEQ ID NO: 421          moltype = AA  length = 164
FEATURE                 Location/Qualifiers
source                  1..164
                        mol_type = protein
                        organism = synthetic construct
SEQUENCE: 421
MNDEFYMRRA LELAKMAEER GEVPVGAVLV RDGEVIAEGW NQSIGSHDAT AHAEIMALRA  60
```

```
AGQVLQNYRL LDTTLYVTLE PCPMCAGALL HSRVKRVVFG APDLKAGAAG TVLNLFESQA  120
SYHYAEVESG LLEEECREQL QAFFKRRRKE IKALKQAQRE AEEK                  164

SEQ ID NO: 422          moltype = AA  length = 151
FEATURE                 Location/Qualifiers
source                  1..151
                        mol_type = protein
                        organism = synthetic construct
SEQUENCE: 422
DTSPADLRFM RLALAEARAA AAAGEVPVGA VVVRDGAVLA RAGNRTLRDR DPTAHAEIVA  60
LRAAARALGS HRLGGCTLYV TLEPCAMCAG AIAQARVARL VYGADDPKGG AVAHGPRLFA  120
QPTCHHRPEV VGGVGAEEAA ALLRDFFAAR R                                151

SEQ ID NO: 423          moltype = AA  length = 164
FEATURE                 Location/Qualifiers
source                  1..164
                        mol_type = protein
                        organism = synthetic construct
SEQUENCE: 423
MTAADERFMR RAIELAAQAE AAGEVPVGAV LVKDGEIVAE GWNQSIGSHD ATAHAEIQTL  60
RQAGQALENY RLLDTTLYVT LEPCPMCAGA LLHSRVKRVV FGAPDLKAGA AGTVLNLFES  120
QASYHYADVE GGLLEDECRE QLQAFFKRRR KEIKAARQAA KEAE                  164

SEQ ID NO: 424          moltype = AA  length = 149
FEATURE                 Location/Qualifiers
source                  1..149
                        mol_type = protein
                        organism = synthetic construct
SEQUENCE: 424
MDDDGLMRAA IAEAEAAAAA GEVPVGAVLV RDGVVLARGR NRMIADSDPT AHAEIVALRE  60
AARALGNYRL EGCELYVTLE PCAMCAGAMV HARLARLVYG AADPKAGAAG SVLDVLGHPR  120
LNHRMEVTGG VLADECGAML RDFFRARRA                                   149

SEQ ID NO: 425          moltype = AA  length = 162
FEATURE                 Location/Qualifiers
source                  1..162
                        mol_type = protein
                        organism = synthetic construct
SEQUENCE: 425
DDTFYMRRAL ELAALAESEG EVPVGAVLVK DGEIIAEGWN RSIGSHDATA HAEIETLRKA  60
GQALQNYRLL DTTLYVTLEP CPMCAGALLH SRVKRIVFGA PDLKAGAAGT VLNLFESQAS  120
YHYAEVESGL LEEECREQLQ AFFKRRRKEI KALRQAEKAA QE                    162

SEQ ID NO: 426          moltype = AA  length = 149
FEATURE                 Location/Qualifiers
source                  1..149
                        mol_type = protein
                        organism = synthetic construct
SEQUENCE: 426
MDDAGFMREA LAEARAAAAA GEVPVGAVVV KDGEIIARAG NRTIRDCDPT AHAEIVALRA  60
AAQALGNYRL DGCTLYVTLE PCAMCSGAML HARLPRVVYG AADPKTGAAG SVLDLFAEPR  120
LNHHTRVEGG VLAAECGALL TDFFRARRG                                   149

SEQ ID NO: 427          moltype = AA  length = 144
FEATURE                 Location/Qualifiers
source                  1..144
                        mol_type = protein
                        organism = synthetic construct
SEQUENCE: 427
MDAALEEARR AAAAGEVPVG AVLVRDGVVL ARAGNRTVRD CDPTAHAEIV ALRAAAAALG  60
NYRLPGTTLY VTLEPCAMCA GAMIHARVAR LVYGAADPKT GAAGSVFDVL GSPRLNHRVE  120
VEGGVRAAEC GALLQDFFRA RRAG                                        144

SEQ ID NO: 428          moltype = AA  length = 149
FEATURE                 Location/Qualifiers
source                  1..149
                        mol_type = protein
                        organism = synthetic construct
SEQUENCE: 428
MTDDERWMAE ALREAEAAAA EGEVPVGAVV VRDGELIARG RNRVVRDCDP TAHAEIVALR  60
EAARALGNYR LTGCTLYVTL EPCAMCAGAM VHARLDRLVY GAADPKAGAA GSVLAVLNHP  120
RLNHQMEVAG GVLAGESAAL LRDFFRARR                                   149

SEQ ID NO: 429          moltype = AA  length = 146
FEATURE                 Location/Qualifiers
source                  1..146
                        mol_type = protein
                        organism = synthetic construct
SEQUENCE: 429
```

```
DSEFMAEALA EARAAAEAGE VPIGAVVVCD GEIVARAGNR TIRDNDPTAH AEIVALREAA  60
AKLGNYRLAG CTLYVTLEPC AMCAGAMIHA RLDRLVYGAA DPKAGAAGSV LDVLGHPQLN  120
HQTEVEGGVL AEECGALLKD FFASRR                                       146

SEQ ID NO: 430         moltype = AA  length = 160
FEATURE                Location/Qualifiers
source                 1..160
                       mol_type = protein
                       organism = synthetic construct
SEQUENCE: 430
DPEYMRRALE LAAQAEAEGE VPVGAVLVKD GEVVAEGWNR SIGDHDATAH AEIQVLRKAG  60
QALQNYRLLD TTLYVTLEPC PMCAGALLHS RVKRVVFGAP DLKAGAAGTV LNLFESQASY  120
HYADVESGLL EDECREQLQA FFKRRRKEIK AARKAAKEAE                        160

SEQ ID NO: 431         moltype = AA  length = 146
FEATURE                Location/Qualifiers
source                 1..146
                       mol_type = protein
                       organism = synthetic construct
SEQUENCE: 431
DTEMMRLALA EARAAAEAGE VPVGAVVVRD GVVLARAGNR TVRDNDPTAH AEIVALREAA  60
RALGNHRLEG CTLYVTLEPC AMCAGAIAQA RVARLVYGAA DPKGGAVAHG PRLFEQPTTH  120
HRPEVTGGVL AEEAGALLRE FFAARR                                       146

SEQ ID NO: 432         moltype = AA  length = 148
FEATURE                Location/Qualifiers
source                 1..148
                       mol_type = protein
                       organism = synthetic construct
SEQUENCE: 432
MTDADFMALA LEEARAAAAL GEVPVGAVVV RDGAVVARAG NRTVRDCDPT AHAEVVALRE  60
AARVLGNYRV DGATLYVTLE PCAMCAGAMI HARLPRLVYG AADPRAGAAG SVLDVLGHPA  120
LNHRVEVTGG VLADESAALL REFFRERR                                     148

SEQ ID NO: 433         moltype = AA  length = 152
FEATURE                Location/Qualifiers
source                 1..152
                       mol_type = protein
                       organism = synthetic construct
SEQUENCE: 433
DEPLDRDRYF MEIALAEARA AAAAGEVPVG AVVVRDGEVI ARAGNRTVRD NDPTAHAEIV  60
ALREAARALG NHRLTGCTLY VTLEPCAMCA GAISHARVAR LVYGADDPKG GAVAHGPRFF  120
EQPTCHHRPE VTGGVLAAES AALLRGFFAA RR                                152

SEQ ID NO: 434         moltype = AA  length = 149
FEATURE                Location/Qualifiers
source                 1..149
                       mol_type = protein
                       organism = synthetic construct
SEQUENCE: 434
MTSDAEFMAL ALEEARAAAA LGEVPVGAVV VRDGAVIARA GNRTIRDCDP TAHAEMVALR  60
EAARALGNYR LAGCDLYVTL EPCAMCAGAI VHARLARLVY GAADPKTGAA GSVFDVLGSG  120
RLNHRPEVVA GVLADECGAL LTDFFRARR                                    149

SEQ ID NO: 435         moltype = AA  length = 165
FEATURE                Location/Qualifiers
source                 1..165
                       mol_type = protein
                       organism = synthetic construct
SEQUENCE: 435
MTEEDKYFMQ RAIELAKLAE ENGEVPVGAV LVKDGEIIAE GWNQSIGNHD ATAHAEIMTL  60
RQAGQVLQNY RLLDTTLYVT LEPCPMCAGA LLHSRVKRIV FGAPDLKAGA AGTVLNLFES  120
QASYHYADVE SGLLEEECRE QLQAFFKRRR KEIKALKKQQ KLEQE                  165

SEQ ID NO: 436         moltype = AA  length = 142
FEATURE                Location/Qualifiers
source                 1..142
                       mol_type = protein
                       organism = synthetic construct
SEQUENCE: 436
MSAALDEARR AAAAGEVPVG AVVVRDGVVL AAAGNRTLRD CDPTAHAEIV ALRAAARALG  60
NYRLDGCDLY VTLEPCAMCA GAMIHARLAR LVYGAADPKT GAAGSVLDVL GHPRLNHRTA  120
VTGGVLADEC GALLRDFFAA RR                                           142

SEQ ID NO: 437         moltype = AA  length = 151
FEATURE                Location/Qualifiers
source                 1..151
                       mol_type = protein
                       organism = synthetic construct
```

```
SEQUENCE: 437
DTSERDERFM RLALEEARAA AEAGEAPIGA VVVRDGAVLA RAGNRTVRDN DPTAHAEVVA  60
LREAARALGN HRLTGCTLYV TLEPCAMCAG AISHARVARL VYGADDPKGG AVAHGPRFFA  120
QPTCHHRPEV TGGVLAEESA ELLRGFFRAR R                                 151

SEQ ID NO: 438         moltype = AA  length = 148
FEATURE                Location/Qualifiers
source                 1..148
                       mol_type = protein
                       organism = synthetic construct
SEQUENCE: 438
DPDSRFMQAA LAEARAAAEA GEVPIGAVVV RDGEIVARAG NRTIRDNDPT AHAEIVALRE  60
AARVLGNYRL TGCTLYVTLE PCAMCAGAMI HARIDRLVYG AADPKAGAAG SVLDVLNHPK  120
LNHQMEVEAG VLADECGALL RDFFRARR                                     148

SEQ ID NO: 439         moltype = AA  length = 149
FEATURE                Location/Qualifiers
source                 1..149
                       mol_type = protein
                       organism = synthetic construct
SEQUENCE: 439
MDDDERWMRL ALEEARLAEE AGEVPVGAVV VRDGELLARG RNRVLRDCDP TAHAEIVALR  60
EAARRLGNYR LDGCTLYATL EPCAMCAGAM VHARLARLVY GAPDPKAGAA GSVLDVLNHP  120
RLNHRMEVTA GVLAEECGAL LRRFFQARR                                    149

SEQ ID NO: 440         moltype = AA  length = 142
FEATURE                Location/Qualifiers
source                 1..142
                       mol_type = protein
                       organism = synthetic construct
SEQUENCE: 440
MSAALAEARR AAAAGEVPVG AVVVRDGAVL AAAGNRTVRD CDPTAHAEIV ALRAAARALG  60
NHRLEGCTLY VTLEPCAMCA GAIAQARVAR LVYGAADPKG GAVAHGPRLF AQPTCHHRPE  120
VVGGVGEAEA AALLRDFFAA RR                                           142

SEQ ID NO: 441         moltype = AA  length = 142
FEATURE                Location/Qualifiers
source                 1..142
                       mol_type = protein
                       organism = synthetic construct
SEQUENCE: 441
MRSALALAAA AGAAGEVPVG AVVVRDGVVI GRGENRVIRD SDPTAHAEIV ALRDAARALG  60
NYRLTGCTLY VTLEPCAMCA GAMIHARIDR LVYGAADPKA GAAGSVLDVL NHPQLNHQME  120
VEGGVLAEEC GALLRDFFRA RR                                           142

SEQ ID NO: 442         moltype = AA  length = 150
FEATURE                Location/Qualifiers
source                 1..150
                       mol_type = protein
                       organism = synthetic construct
SEQUENCE: 442
RTADERWMRL ALEEARAAEA AGEVPVGAVV VRDGELIARG RNRVLRDCDP TAHAEIVALR  60
EAARALGNYR VEGCTLYVTL EPCAMCAGAM IHARLDRLVY GAADPRAGAA GSVLDVLGHP  120
ALNHQTQVTG GVLAEECGAL LREFFRARRG                                   150

SEQ ID NO: 443         moltype = AA  length = 147
FEATURE                Location/Qualifiers
source                 1..147
                       mol_type = protein
                       organism = synthetic construct
SEQUENCE: 443
DDLSFMQEAL AEARAAAEAG EVPIGAVVVR DGAILARAGN RTVRDNDPTA HAEIVALREA  60
ARALGNYRLA GCTLYVTLEP CAMCAGAMIH ARVDRLVYGA ADPKAGAAGS VLDVLGHPRL  120
NHRMEVEGGV LAEECGALLR EFFRARR                                      147

SEQ ID NO: 444         moltype = AA  length = 149
FEATURE                Location/Qualifiers
source                 1..149
                       mol_type = protein
                       organism = synthetic construct
SEQUENCE: 444
MSSDAGFMAE ALAEAEAAAA AGEVPVGAVV VCGGEIVARA GNRTIRDCDP TAHAEMVALR  60
EAARKLGNYR LAGCTLYVTL EPCAMCAGAM IHARLDRLVY GAADPKAGAA GSVLDVINHP  120
RLNHQMEVEA GVLADECGAM LRRFFQERR                                    149

SEQ ID NO: 445         moltype = AA  length = 148
FEATURE                Location/Qualifiers
source                 1..148
                       mol_type = protein
```

```
                         organism = synthetic construct
SEQUENCE: 445
MDDDRWMRLA LEEARRAEEE GEVPVGAVVV LGGEVIGRGR NRVIRDSDPT AHAEIVALRE  60
AARTLGNYRL DGCELYVTLE PCAMCAGAMV HARLARLVYG AADPRAGAAG SVLDVLGHPR  120
LNHRMEVTGG VLAEECGALL RDFFRRRR                                     148

SEQ ID NO: 446          moltype = AA  length = 148
FEATURE                 Location/Qualifiers
source                  1..148
                        mol_type = protein
                        organism = synthetic construct
SEQUENCE: 446
MDDAGFMREA LAEAEAAAAA GEVPVGAVVV CDGRIVARAG NRTVRDNDPT AHAEIVALRE  60
AARALGNHRL GGCTLYVTLE PCAMCAGAMI HARIDRLVYG ADDPKAGAVR SVLQVLDHPR  120
LNHRMAVESG VLAGECAAVL QAFFAARR                                     148

SEQ ID NO: 447          moltype = AA  length = 142
FEATURE                 Location/Qualifiers
source                  1..142
                        mol_type = protein
                        organism = synthetic construct
SEQUENCE: 447
MDAALEEARR AAAAGEVPVG AVLVRDGEVL ARGGNRTIRD CDPTAHAEIV ALRAAARAAG  60
NYRLPGTTLY VTLEPCAMCA GAMIHARVAR LVYGAADPRA GAAGSVFDVL RHPALNHRME  120
VEGGVLAEES AALLRGFFRA RR                                           142

SEQ ID NO: 448          moltype = AA  length = 142
FEATURE                 Location/Qualifiers
source                  1..142
                        mol_type = protein
                        organism = synthetic construct
SEQUENCE: 448
MRDALALARA AAAAGEVPVG AVVVKDGVVV GRGENRVVRD SDPTAHAEIV AMREAARALG  60
NYRLTGCTLY VTLEPCAMCA GAMIHARLDR VVYGAADPKT GAAGSVLDVL GHPRLNHQTQ  120
VEGGVLAAEC GALLSDFFRA RR                                           142

SEQ ID NO: 449          moltype = AA  length = 148
FEATURE                 Location/Qualifiers
source                  1..148
                        mol_type = protein
                        organism = synthetic construct
SEQUENCE: 449
MDDAGFMREA LAEAEAAAAA GEVPVGAVVV KDGEIIARAG NRTVRDCDPT AHAEIVALRE  60
AARKLGNYRL AGCTLYVTLE PCAMCAGAMI HARLDRLVYG ADDPKAGAAG SVLNVLNHPR  120
LNHQMQVEAG VLAEECGAML RRFFETRR                                     148

SEQ ID NO: 450          moltype = AA  length = 148
FEATURE                 Location/Qualifiers
source                  1..148
                        mol_type = protein
                        organism = synthetic construct
SEQUENCE: 450
MDDAAFMGEA LAEARAAAAA GEVPIGAVVV CDGEIVARAG NRTVRDNDPT AHAEIVALRE  60
AARKLGNYRL AGCTLYVTLE PCAMCAGAMI HARVDRLVYG ADDPKAGAAR SVLNVVDHPA  120
LNHRLEVTSG VLAAECAELL RGFFERRR                                     148

SEQ ID NO: 451          moltype = AA  length = 150
FEATURE                 Location/Qualifiers
source                  1..150
                        mol_type = protein
                        organism = synthetic construct
SEQUENCE: 451
MTAADAAAMR AALAEARAAA ARGEVPVGAV VMRDGVIVAR AGNATVAGHD PTAHAEIVAL  60
RRAARALGNH RLTGCALYVT LEPCAMCAGA IAHARIARLV YGAADPKGGA VAHGPRFFAQ  120
PTCHHRPEVT GGVLAEEAGA LLRAFFRARR                                   150

SEQ ID NO: 452          moltype = AA  length = 146
FEATURE                 Location/Qualifiers
source                  1..146
                        mol_type = protein
                        organism = synthetic construct
SEQUENCE: 452
DTEMMALALA EARAAAEAGE VPVGAVVVRD GEVLARAGNR TVRDCDPTAH AEIVALREAA  60
RRLGNYRLPG CTLYVTLEPC AMCAGAIMHA RLDRVVYGAA DPKTGAAGSV LDLFAEPRLN  120
HHTAVVGGVL ADEAGALLRG FFAARR                                       146

SEQ ID NO: 453          moltype = AA  length = 164
FEATURE                 Location/Qualifiers
source                  1..164
```

```
                         mol_type = protein
                         organism = synthetic construct
SEQUENCE: 453
MTEEDKYFMK RAIELAKLAE ENGEVPVGAV LVKDGEIISE GWNQSIGNND ATAHAEIMAL  60
REAGKVLENY RLLDTTLYVT LEPCPMCAGA LLHSRVKRIV FGAPDLKAGA AGTVLNLFES  120
QASYHYADVE SGLLEEECRE QLQAFFKRRR KEKKELKKLK REEN                  164

SEQ ID NO: 454           moltype = AA  length = 168
FEATURE                  Location/Qualifiers
source                   1..168
                         mol_type = protein
                         organism = synthetic construct
SEQUENCE: 454
MDSAAKDLCY MRRALELAAL AEAEGEVPVG AVLVKDGEIV GEGWNRSIGS HDATAHAEIM  60
ALRQAGQALQ NYRLLDTTLY VTLEPCPMCA GALLHSRVKR VVFGAPDLKA GAAGTVLNLF  120
ESQASYHYAD VESGLLEEEC RAQLQAFFKR RRKEIKAQRD AQRAAQEK              168

SEQ ID NO: 455           moltype = AA  length = 142
FEATURE                  Location/Qualifiers
source                   1..142
                         mol_type = protein
                         organism = synthetic construct
SEQUENCE: 455
MRTALEEARR AAEAGEVPVG AVVVRDGVVL ARAHNRTVAD HDPTAHAEIL ALREAARVLG  60
NHRLTGCTLY VTLEPCAMCA GAIVHARLDR LVYGAADPKA GAAGSVLDVL GHPRLNHRPE  120
VAAGVLAEEC GELLRGFFRE RR                                          142

SEQ ID NO: 456           moltype = AA  length = 149
FEATURE                  Location/Qualifiers
source                   1..149
                         mol_type = protein
                         organism = synthetic construct
SEQUENCE: 456
DDDERWMREA LAEARAAEEA GEVPVGAVVV RDGELVGRGR NRVLRDSDPT AHAEIVALRE  60
AARALGNYRL DGCTLYATLE PCAMCAGAML HARLARLVYG AADPKAGAAG SVLDVLNHPR  120
LNHRMEVTGG VLAEECGALL RGFFRARRG                                   149

SEQ ID NO: 457           moltype = AA  length = 150
FEATURE                  Location/Qualifiers
source                   1..150
                         mol_type = protein
                         organism = synthetic construct
SEQUENCE: 457
RSSPDERFMA LALAEARRAA EAGEVPVGAV LVRDGAVLAA AGNRTIRDND PTAHAEIVVL  60
REAARRLGNY RLEGCTLYVT LEPCAMCAGA MVNARLGRLV YGAADPRAGA AGSVLDVLRH  120
PALNHRMEVT GGVLAAECGA LLRDFFAARR                                  150

SEQ ID NO: 458           moltype = AA  length = 142
FEATURE                  Location/Qualifiers
source                   1..142
                         mol_type = protein
                         organism = synthetic construct
SEQUENCE: 458
MRDALAEARK AAALGEVPVG AVVVKDGAVI ARGHNRTVAD SDPTAHAEIV AIRAAARALG  60
NHRLTGCTLY VTLEPCAMCA GAIAHARIAR LVYGAADPKG GAVDHGVRFF ESPTCHHRPE  120
VTGGVLAAEA AALLRDFFRA RR                                          142

SEQ ID NO: 459           moltype = AA  length = 162
FEATURE                  Location/Qualifiers
source                   1..162
                         mol_type = protein
                         organism = synthetic construct
SEQUENCE: 459
DETYMRRALE LARQAEEHGE VPVGAVLVKD GEIIAEGWNQ SIGAHDATAH AEIMALRAAG  60
QALENYRLLD TTLYVTLEPC PMCAGALLHS RVKRIVFGAP DLKAGAAGTV LNLFESQASY  120
HYADVESGLL EEECREQLQA FFKRRRKEIK ALKQAQREAE EK                    162

SEQ ID NO: 460           moltype = AA  length = 142
FEATURE                  Location/Qualifiers
source                   1..142
                         mol_type = protein
                         organism = synthetic construct
SEQUENCE: 460
MDEALAEARR AAAAGEVPVG AVVVRDGAVL ARAGNRTVRD CDPTAHAEIV ALRAAARALG  60
NHRLTGCDLY VTLEPCAMCA GAISHARIAR LYYGADDPKG GAVAHGPRFF GQPTCHHRPE  120
VYGGIGEGAA AALLRAFFAA RR                                          142

SEQ ID NO: 461           moltype = AA  length = 162
FEATURE                  Location/Qualifiers
```

```
source                 1..162
                       mol_type = protein
                       organism = synthetic construct
SEQUENCE: 461
DESYMRRALE LARQAEAEGE VPVGAVLVKD GEVVAEGWNR SIGAHDATAH AEIETLRKAG  60
QALENYRLLD TTLYVTLEPC PMCAGALLHS RVKRVVFGAP DLKAGAAGTV LNLFESQASY  120
HYAEVESGLL EDECREQLQA FFKRRRKEIK AQRQAQKEAE QK                     162

SEQ ID NO: 462         moltype = AA  length = 165
FEATURE                Location/Qualifiers
source                 1..165
                       mol_type = protein
                       organism = synthetic construct
SEQUENCE: 462
MSEQDRYFMQ RAIELAQQAE LNGEVPVGAV LVKDGEVIAE GWNQSIGSHD ATAHAEIMAL  60
RKAGQVLENY RLLDTTLYVT LEPCPMCAGA LLHSRVKRVV FGAPDLKAGA AGTVLNLFES  120
QASYHYADVE SGLLEDECRE QLQAFFKRRR KEKKALKQAQ KEAAQ                  165

SEQ ID NO: 463         moltype = AA  length = 149
FEATURE                Location/Qualifiers
source                 1..149
                       mol_type = protein
                       organism = synthetic construct
SEQUENCE: 463
MTDADFMALA LEEARAAAAL GEVPVGAVVV KDGEVIARAG NRTVRDCDPT AHAEIVALRE  60
AARKLGNYRL DGCTLYVTLE PCAMCAGAML HARLPRVVYG AADPKTGAAG SVLDLFAEPR  120
LNHQTAVQGG VLADEAGALL RDFFKARRA                                    149

SEQ ID NO: 464         moltype = AA  length = 143
FEATURE                Location/Qualifiers
source                 1..143
                       mol_type = protein
                       organism = synthetic construct
SEQUENCE: 464
MDAALEEARR AAAAGEVPVG AVLVRDGVVL ARAGNRTVRD CDPTAHAEIV ALRAAAAALG  60
NYRLDGCTLY VTLEPCAMCA GAMIHARLAR LVYGAADPRT GAAGSVLDVL GHPALNHRTE  120
VTGGVLAEEC GALLREFFRT RRG                                          143

SEQ ID NO: 465         moltype = AA  length = 150
FEATURE                Location/Qualifiers
source                 1..150
                       mol_type = protein
                       organism = synthetic construct
SEQUENCE: 465
MSDKDLRFMQ LALEEARAAA DAGEVPVGAV LVRDGQVLAR GRNRVILDND PTAHAEIVAL  60
REGARRLGNY RLAGCTLYVT LEPCAMCAGA IVHARLDRLV YGAADPKAGA AGSVLDVLNH  120
PKLNHQMEVE GGVLAAESGE LLRSFFRARR                                   150

SEQ ID NO: 466         moltype = AA  length = 160
FEATURE                Location/Qualifiers
source                 1..160
                       mol_type = protein
                       organism = synthetic construct
SEQUENCE: 466
DTLYMRRALE LAAQAEAEGE VPVGAVLVKD GEVIAEGWNR SIGSHDATAH AEIETLRKAG  60
QVLQNYRLLD TTLYVTLEPC PMCAGALLHS RVKRIVYGAP DLKAGAAGTV LNLFESQASY  120
HYAEVESGLL EEECREQLQA FFKRRRKEIK ALRQAQKEAE                        160

SEQ ID NO: 467         moltype = AA  length = 143
FEATURE                Location/Qualifiers
source                 1..143
                       mol_type = protein
                       organism = synthetic construct
SEQUENCE: 467
MDAALEEARR AAEAGEVPVG AVLVRDGAVL ARAGNRTIRD CDPTAHAEIV ALRAAARALG  60
NYRLPGTTLY VTLEPCAMCA GAMIHARVDR LVYGAADPRA GAAGSVLDVI GHPALNHRME  120
VEGGVLAEEC GALLREFFRA RRG                                          143

SEQ ID NO: 468         moltype = AA  length = 149
FEATURE                Location/Qualifiers
source                 1..149
                       mol_type = protein
                       organism = synthetic construct
SEQUENCE: 468
DPLMDEFMGE ALAEARAAAA AGEVPVGAVV VRDGAVIARA GNRTVRDCDP TAHAEIVALR  60
AAARALGNHR LDGCDLYVTL EPCAMCAGAI SHARIRRLYY GADDPKGGAV AHGARVFAHP  120
TCHHRPEVYG GIGAAEAAGL LRAFFAARR                                    149

SEQ ID NO: 469         moltype = AA  length = 160
```

```
FEATURE               Location/Qualifiers
source                1..160
                      mol_type = protein
                      organism = synthetic construct
SEQUENCE: 469
DESYMRRALE LARQAEQEGE VPVGAVLVKD GEVIAEGWNR SIGAHDATAH AEIETLRKAG  60
QVLQNYRLLD TTLYVTLEPC PMCAGALLHS RVKRVVFGAP DLKAGAAGTV LNLFESQASY  120
HYADVESGLL EDECREQLQA FFKRRRKEIK AQRDAEKAAK                        160

SEQ ID NO: 470        moltype = AA  length = 144
FEATURE               Location/Qualifiers
source                1..144
                      mol_type = protein
                      organism = synthetic construct
SEQUENCE: 470
MRDALAEARA AAARGEVPVG AVVVRDGAVL ARAGNATIAD CDPTAHAEMR ALRAAARALG  60
NYRLPGCTLY VTVEPCAMCA GAMIHARLAR LVYGAADPKA GAAGSVLDVL GHPALNHRME  120
VTGGVLAAEC AALLRDFFAA RRGR                                        144

SEQ ID NO: 471        moltype = AA  length = 165
FEATURE               Location/Qualifiers
source                1..165
                      mol_type = protein
                      organism = synthetic construct
SEQUENCE: 471
MTEEDKKFMQ RAIELARKGE QEGEVPVGAV LVKDGEIIAE GWNRSIGDHD ATAHAEIETL  60
RKAGKALENY RLLDTTLYVT LEPCPMCAGA LLHSRVKRVV FGAPDLKAGA AGTVLNLFES  120
QASYHYADVE SGLLEEECRE QLQAFFKRRR KEKKALKQAK KEAEK                 165

SEQ ID NO: 472        moltype = AA  length = 148
FEATURE               Location/Qualifiers
source                1..148
                      mol_type = protein
                      organism = synthetic construct
SEQUENCE: 472
MDDDALMGLA LDEARAAAAA GEVPIGAVVA RDGAVVARAG NRTVRDCDPT AHAEVVALRE  60
AARALGNYRL AGCTLYVTLE PCAMCAGAMI HARLDRVVYG AADPKTGAAG SVLDVLGHPA  120
LNHQTRVEGG VLAAECGALL RDFFAARR                                    148

SEQ ID NO: 473        moltype = AA  length = 165
FEATURE               Location/Qualifiers
source                1..165
                      mol_type = protein
                      organism = synthetic construct
SEQUENCE: 473
MTRDEQYMRR ALELARQAEQ EGEVPVGAVL VKDGEIVAEG WNRSIGDHDA TAHAEIETLR  60
KAGQVLENYR LLDTTLYVTL EPCPMCAGAL LHSRVKRVVF GAPDLKAGAA GTVLNLFESQ  120
ASYHYAEVES GLLEEECREQ LQAFFKRRRK EIKALRQAEK EAEQK                 165

SEQ ID NO: 474        moltype = AA  length = 145
FEATURE               Location/Qualifiers
source                1..145
                      mol_type = protein
                      organism = synthetic construct
SEQUENCE: 474
DSEFMAEALA EARAAAAAGE VPVGAVVVKD GEIIARAGNR TLRDNDPTAH AEIVALRAAA  60
RALGNQRLEG CDLYVTLEPC AMCAGAISHA RIRRLYYGAE DPKGGAVDNG VRFFASPTCH  120
HRPEVYGGIG ETEAAELLRG FFRER                                       145

SEQ ID NO: 475        moltype = AA  length = 148
FEATURE               Location/Qualifiers
source                1..148
                      mol_type = protein
                      organism = synthetic construct
SEQUENCE: 475
DDDERFMRLA LEEARKAEEA GEVPVGAVLV KDGEVIARGR NRVISDSDPT AHAEIVALRE  60
AGRALGNYRL DGCTLYVTLE PCAMCAGAMV HARLDRLVYG AADPRAGAAG SVLDVLNHPA  120
LNHRMEVEGG VLADECGALL RDFFRRRR                                    148

SEQ ID NO: 476        moltype = AA  length = 142
FEATURE               Location/Qualifiers
source                1..142
                      mol_type = protein
                      organism = synthetic construct
SEQUENCE: 476
MDAALAEARA AADAGEVPVG AVVVRDGAVL ARAGNRTLRD SDPTAHAEIV ALRAAARALG  60
NHRLGGCTLY VTLEPCAMCA GAISHARLAR LHYGADDPKG GAVAHGPRFF AQPTCHHRPD  120
VYGGIGEGEA AALLRGFFAA RR                                          142
```

```
SEQ ID NO: 477         moltype = AA  length = 146
FEATURE                Location/Qualifiers
source                 1..146
                       mol_type = protein
                       organism = synthetic construct
SEQUENCE: 477
DTEFMREALA EARAAAAAGE VPVGAVVVKD GEIIARAGNR TLRDNDPTAH AEIVALREAA  60
RKLGNHRLTG CTLYVTLEPC AMCAGAISHA RIARLVYGAD DPKGGAVAHG PRFFAQPTCH  120
HRPEVTGGVL AEEAGELLRG FFRERR                                       146

SEQ ID NO: 478         moltype = AA  length = 144
FEATURE                Location/Qualifiers
source                 1..144
                       mol_type = protein
                       organism = synthetic construct
SEQUENCE: 478
MDAALEEARR AAAAGEVPVG AVLVAGGRVL ARAGNRTIRD CDPTAHAEIV ALREAARALG  60
NYRLAGTTLY VTLEPCAMCA GAMIHARVDR LVYGAADPRA GAAGSVFDVV RHPALNHRLE  120
VEGGVLAEEC GALLRDFFRA RRGR                                         144

SEQ ID NO: 479         moltype = AA  length = 142
FEATURE                Location/Qualifiers
source                 1..142
                       mol_type = protein
                       organism = synthetic construct
SEQUENCE: 479
MRAALDEARR AAAAGEVPVG AVVVRDGVVL ARAHNRTVAD HDPTAHAEIL ALREAARVLG  60
NHRLTGCTLY VTLEPCAMCA GAIVHARLDR LVYGAADPKA GAAGSVLDVL DHPRLNHRME  120
VTGGVLAEES AALLRGFFAA RR                                           142

SEQ ID NO: 480         moltype = AA  length = 149
FEATURE                Location/Qualifiers
source                 1..149
                       mol_type = protein
                       organism = synthetic construct
SEQUENCE: 480
MSSDADFMRL ALAEARAAAA AGEVPVGAVV VRGGEVIARA GNRTVRDCDP TAHAEVVALR  60
EAARKLGNHR LTGCTLYVTL EPCAMCAGAI SHARVARLVY GADDPKGGAV AHGPRFFAQP  120
TCHHRPEVTG GVLAEEAGEL LRGFFRARR                                    149

SEQ ID NO: 481         moltype = AA  length = 144
FEATURE                Location/Qualifiers
source                 1..144
                       mol_type = protein
                       organism = synthetic construct
SEQUENCE: 481
MDAALEEARR AAAAGEVPVG AVLVRDGAVL ARGGNRTIRD CDPTAHAEIV ALRAAARALG  60
NYRLPGTTLY VTLEPCAMCA GAMIHARVAR LVYGAADPKT GAAGSVFDVL GSARLNHRVE  120
VEGGVRAAEC GALLRDFFAA RRGR                                         144

SEQ ID NO: 482         moltype = AA  length = 142
FEATURE                Location/Qualifiers
source                 1..142
                       mol_type = protein
                       organism = synthetic construct
SEQUENCE: 482
MRAALAEARR AAAEGEVPVG AVVVRDGAVL ARAGNRTVRD CDPTAHAEVL ALREAARALG  60
NHRLTGCTLY VTVEPCAMCA GAISHARVAR LVYGADDPKG GAVRHGPRVF DQPTCHHRPE  120
VVGGVLAEEA GALLRDFFAA RR                                           142

SEQ ID NO: 483         moltype = AA  length = 145
FEATURE                Location/Qualifiers
source                 1..145
                       mol_type = protein
                       organism = synthetic construct
SEQUENCE: 483
DTSFMQQALD EARAAAAAGE VPVGAVVVKD GEIIARAGNR TLRDNDPTAH AEIVALRAAA  60
RALGSQRLGG CDLYVTLEPC AMCAGAISHA RIARLYYGAD DPKGGAVAHG ARVFSHPQCH  120
HVPEVYDGIG AGEAAALLRD FFAGR                                        145

SEQ ID NO: 484         moltype = AA  length = 146
FEATURE                Location/Qualifiers
source                 1..146
                       mol_type = protein
                       organism = synthetic construct
SEQUENCE: 484
DTEFMREALA EARAAAAAGE VPVGAVVVRD GAIIARAGNR TIRDRDPTAH AEVVALREAA  60
RALGNHRLTG CTLYVTLEPC AMCAGAISHA RVARLVYGAA DPKGGAVAHG PRFFEQPTCH  120
HRPEVTGGVL AEEAGALLRD FFRARR                                       146
```

```
SEQ ID NO: 485          moltype = AA  length = 164
FEATURE                 Location/Qualifiers
source                  1..164
                        mol_type = protein
                        organism = synthetic construct
SEQUENCE: 485
MSEQDEFYMR RAIELARKGE ENGEVPVGAV LVKDGEIIAE GWNQSIGSHD ATAHAEIVTL  60
RKAGQVLENY RLLDTTLYVT LEPCPMCAGA LLHSRVKRVV FGAPDLKAGA AGTVLNLFES  120
QASYHYADVE SGLLEEECRE QLQAFFKRRR KEKKALKQAQ KELE                   164

SEQ ID NO: 486          moltype = AA  length = 149
FEATURE                 Location/Qualifiers
source                  1..149
                        mol_type = protein
                        organism = synthetic construct
SEQUENCE: 486
MTDADFMALA LAEARAAAAA GEVPVGAVVV RDGVVLAAAG NRTLRDCDPT AHAEVVALRA  60
AARALGNYRL DGCTLYVTLE PCAMCAGAML HARLARVVYG AADPKTGAAG SVLDLFAQPR  120
LNHHTAVAGG VLAAECGALL ADFFRQRRG                                    149

SEQ ID NO: 487          moltype = AA  length = 164
FEATURE                 Location/Qualifiers
source                  1..164
                        mol_type = protein
                        organism = synthetic construct
SEQUENCE: 487
MSDEQYMRRA LELARQAEQQ GEVPVGAVLV RDGEVIAEGW NQSISSHDAT AHAEMMAIRA  60
AGAALENYRL LDTTLYVTLE PCPMCAGALL HSRVKRVVFG APDLKAGAAG TVLNLFESQA  120
SYHYADVESG LLEEECREQL QAFFKRRRKE IKALRQAEKE AAAK                   164

SEQ ID NO: 488          moltype = AA  length = 157
FEATURE                 Location/Qualifiers
source                  1..157
                        mol_type = protein
                        organism = synthetic construct
SEQUENCE: 488
MSSETSTDAA ADAAFMAEAL AEARAAAAAG EVPVGAVVVC GGRIVARAGN RTVRDNDPTA  60
HAEIVALREA ARVLGNHRLT GCTLYVTLEP CAMCAGAISH ARIARLVYGA DDPKGGAVRH  120
GPRFFAQPTC HHRPDVAGGV GEAEAAELLR AFFRARR                           157

SEQ ID NO: 489          moltype = AA  length = 148
FEATURE                 Location/Qualifiers
source                  1..148
                        mol_type = protein
                        organism = synthetic construct
SEQUENCE: 489
MTDADFMALA LEEARAAAAL GEVPVGAVVV KDGEVIARAG NRTIRDCDPT AHAEIVALRE  60
AARKLGNYRL DGCDLYVTLE PCAMCAGAMI HARLARLVYG AADPKTGAAG SVLDVFANPQ  120
LNHHTAVVGG VLADEAGALL REFFAARR                                     148

SEQ ID NO: 490          moltype = AA  length = 149
FEATURE                 Location/Qualifiers
source                  1..149
                        mol_type = protein
                        organism = synthetic construct
SEQUENCE: 490
MDDDARFMGE ALAEARAAAA AGEVPIGAVV VRDGAVVARA GNRTVRDNDP TAHAEVLALR  60
EAARALGSQR LTGCTLYVTL EPCAMCAGAI SHARVARLVY GAADPKGGAV AHGPRFFAQP  120
TCHHRPEVTG GVGEAEAAAL LRDFFRARR                                    149

SEQ ID NO: 491          moltype = AA  length = 146
FEATURE                 Location/Qualifiers
source                  1..146
                        mol_type = protein
                        organism = synthetic construct
SEQUENCE: 491
DRLFMEEALA EARAAAAAGE VPIGAVVVRD GEIVARAGNR TVRDCDPTAH AEIVALREAA  60
RALGNYRLTG CTLYVTIEPC AMCAGAMIHA RLDRLVYGAD DPKAGAVRSV LQVLDHPALN  120
HRVEVESGVL AAECAALLQE FFASRR                                       146

SEQ ID NO: 492          moltype = AA  length = 165
FEATURE                 Location/Qualifiers
source                  1..165
                        mol_type = protein
                        organism = synthetic construct
SEQUENCE: 492
DSLTRDELYM RRALELAALA EAEGEVPVGA VLVKDGEIVG EGWNRSIGSH DATAHAEIMA  60
LRQAGQALQN YRLLDTTLYV TLEPCPMCAG ALLHSRVKRV VFGASDLKAG AAGTVLNLFE  120
```

```
SQASYHYADV ESGLLEQECR EQLQAFFKRR RKEIKAQRQA EKAAQ                165

SEQ ID NO: 493         moltype = AA  length = 142
FEATURE                Location/Qualifiers
source                 1..142
                       mol_type = protein
                       organism = synthetic construct
SEQUENCE: 493
MRAALAEARR AAEAGEVPVG AVVVRDGAVL AAAGNRTVRD CDPTAHAEIV ALRAAARAAG  60
NHRLTGCTLY VTLEPCAMCA GAISHARVAR LVYGAADPKG GAVAHGPRFF EQPTCHHRPE  120
VTGGVLAEEA GALLRDFFRA RR                                         142

SEQ ID NO: 494         moltype = AA  length = 142
FEATURE                Location/Qualifiers
source                 1..142
                       mol_type = protein
                       organism = synthetic construct
SEQUENCE: 494
MSAALEEARR AAAAGEVPVG AVLVRDGAVL ARGGNRTIRD CDPTAHAEIV ALRAAARALG  60
NYRLPGTTLY VTLEPCAMCA GAMIHARVAR LVYGAADPKT GAAGSVFDVL RHPALNHRME  120
VEGGVLAEEC GALLRDFFRA RR                                         142

SEQ ID NO: 495         moltype = AA  length = 147
FEATURE                Location/Qualifiers
source                 1..147
                       mol_type = protein
                       organism = synthetic construct
SEQUENCE: 495
DDTEFMRLAL AEAEAAAAAG EVPVGAVVVR DGEVIARAGN RTIRDCDPTA HAEVVALREA  60
ARKLGNYRLA GCTLYVTLEP CAMCAGAMIH ARLDRVVYGA ADPKTGAAGS VLDLFATRQL  120
NHHTQVTGGV LAEECGALLR GFFEARR                                    147

SEQ ID NO: 496         moltype = AA  length = 161
FEATURE                Location/Qualifiers
source                 1..161
                       mol_type = protein
                       organism = synthetic construct
SEQUENCE: 496
DTLYMRRALE LAAQAEAEGE VPVGAVLVKD GEVIAEGWNR SIGDHDATAH AEIQTLRKAG  60
QVLQNYRLLD TTLYVTLEPC PMCAGALLHS RVKRIVYGAP DLKAGAAGTV LNLFESQASY  120
HYADVESGLL EDECREQLQA FFKRRRKEIK ALRQAEKAAE Q                    161

SEQ ID NO: 497         moltype = AA  length = 146
FEATURE                Location/Qualifiers
source                 1..146
                       mol_type = protein
                       organism = synthetic construct
SEQUENCE: 497
DDPYMALALE EARAAAAAGE VPIGAVVVRD GEVVARAGNR TVRDNDPTAH AEVVALREAA  60
RALGNHRLTG CTLYVTLEPC AMCAGAISHA RVARLVYGAD DPKGGAVRHG ARVFEHPQCH  120
HRPEVTGGVG AAEAGELLRG FFRARR                                     146

SEQ ID NO: 498         moltype = AA  length = 168
FEATURE                Location/Qualifiers
source                 1..168
                       mol_type = protein
                       organism = synthetic construct
SEQUENCE: 498
MDSKEKDEFF MRRALELARL GEEKGEVPVG AVLVKDGEII AEGWNQSIGE NDATAHAEIM  60
ALRKAGKALE NYRLLDTTLY VTLEPCPMCA GALLHSRVKR IVFGAPDLKA GAAGTVLNLF  120
ESQASYHYAD VESGLLEEEC REQLQAFFKR RRKEIKEKKK AEKAALEA              168

SEQ ID NO: 499         moltype = AA  length = 142
FEATURE                Location/Qualifiers
source                 1..142
                       mol_type = protein
                       organism = synthetic construct
SEQUENCE: 499
MRSALDLAAA AAAAGEVPVG AVVVRDGAIV GRGENRVLRD SDPTAHAEIV ALREAARALG  60
NYRLTGCTLY VTLEPCAMCA GAMIHARIDR LVYGAADPKA GAAGSVLDVL GHPALNHQME  120
VEGGVLAEEC GALLRDFFRA RR                                         142

SEQ ID NO: 500         moltype = AA  length = 142
FEATURE                Location/Qualifiers
source                 1..142
                       mol_type = protein
                       organism = synthetic construct
SEQUENCE: 500
MDAALAEARA AADAGEVPVG AVVVRDGVVL ARAGNRTVRD ADPTAHAEIV ALRAAARALG  60
```

```
NHRLGGCTLY VTLEPCAMCA GAISHARVAR LVYGADDPKG GAVRHGPRLF ASPTCHHRPE  120
VVSGVGEAEA AALLRDFFAA RR                                          142

SEQ ID NO: 501         moltype = AA  length = 142
FEATURE                Location/Qualifiers
source                 1..142
                       mol_type = protein
                       organism = synthetic construct
SEQUENCE: 501
MDAALEEARR AAAAGEVPVG AVLVRDGVVL ARAGNRTIRD CDPTAHAEIV ALREAARAAG  60
NYRLPGTTLY VTLEPCAMCA GAMIHARVDR LVYGAADPRA GAAGSVFDVV RHPALNHRME  120
VEGGVLADES AALLRGFFRA RR                                          142

SEQ ID NO: 502         moltype = AA  length = 166
FEATURE                Location/Qualifiers
source                 1..166
                       mol_type = protein
                       organism = synthetic construct
SEQUENCE: 502
MTSEDEKYMR RALELARQAE QEGEVPVGAV LVKDGEIVAE GWNRSIGDHD ATAHAEIETL  60
RKAGQVLENY RLLDTTLYVT LEPCPMCAGA LLHSRVKRVV FGAPDLKAGA AGTVLNLFES  120
QASYHYADVE SGLLEEECRE QLQAFFKRRR KEIKALRQAQ KEAEQK                166

SEQ ID NO: 503         moltype = AA  length = 146
FEATURE                Location/Qualifiers
source                 1..146
                       mol_type = protein
                       organism = synthetic construct
SEQUENCE: 503
DEPYMRLALD EARAAAAAGE VPIGAVVVRD GEVLARAGNR TVRDNDPTAH AEVLALREAA  60
RALGNHRLTG CTLYVTLEPC AMCAGAISHA RVARLVYGAD DPKGGAVAHG PRFFAQPTCH  120
HRPEVTGGVL AEEAGALLRD FFRARR                                      146

SEQ ID NO: 504         moltype = AA  length = 142
FEATURE                Location/Qualifiers
source                 1..142
                       mol_type = protein
                       organism = synthetic construct
SEQUENCE: 504
MDAALAEARA AADAGEVPVG AVVVRDGAVL ARAGNRTLRD ADPTAHAEIV ALRAAARALG  60
NHRLGGCTLY VTLEPCAMCA GAISHARLAR LVYGADDPKG GAVAHGPRFF GQPTCHHRPE  120
VVGGVGAAAA GDLLRGFFRA RR                                          142

SEQ ID NO: 505         moltype = AA  length = 157
FEATURE                Location/Qualifiers
source                 1..157
                       mol_type = protein
                       organism = synthetic construct
SEQUENCE: 505
RSSPEEAAMD DAGFMRLALA EAEAAAAAGE VPVGAVVVLG GEVIARAGNR TVRDNDPTAH  60
AEIVALREAA RKLGNYRLAG CTLYVTLEPC AMCAGAMIHA RLARLVYGAA DPKTGAAGSV  120
LDLVAHPALN HRMEVEGGVL AAECGALLRD FFAARRG                          157

SEQ ID NO: 506         moltype = AA  length = 164
FEATURE                Location/Qualifiers
source                 1..164
                       mol_type = protein
                       organism = synthetic construct
SEQUENCE: 506
MTRDEQYMRR ALELARQAEA EGEVPVGAVL VRDGEVIAEG WNRSIGAHDA TAHAEIMALR  60
QAGQVLENYR LLDTTLYVTL EPCPMCAGAL LHSRVKRVVY GAPDLKAGAA GTVLNLFESQ  120
ASYHYAEVEG GLLEEECREQ LQAFFKRRRK EIKAARQARR AAEE                  164

SEQ ID NO: 507         moltype = AA  length = 142
FEATURE                Location/Qualifiers
source                 1..142
                       mol_type = protein
                       organism = synthetic construct
SEQUENCE: 507
MRAALAEARA AAEAGEVPVG AVVVHEGRII ARAQNRVERD HDPTAHAEIL ALRAAAAALG  60
ATRLGGCTLY VTLEPCAMCA GAIAHARVAR LVYGADDPKG GAVAHGPRFF TQPTCHHRPE  120
VTGGVGEAEA AALLRDFFRA RR                                          142

SEQ ID NO: 508         moltype = AA  length = 148
FEATURE                Location/Qualifiers
source                 1..148
                       mol_type = protein
                       organism = synthetic construct
SEQUENCE: 508
```

```
MDDAGFMREA LAEAEAAAAA GEVPVGAVVV KDGEIIARAR NATVARNDPT AHAEILALRE  60
AARVLGNYRL TGCTLYATLE PCAMCAGAIL HARIARLVYG AADPKAGACG SVLDVIGHPR  120
LNHRVEVAGG VLAEECGALL REFFRSRR                                     148

SEQ ID NO: 509         moltype = AA  length = 161
FEATURE                Location/Qualifiers
source                 1..161
                       mol_type = protein
                       organism = synthetic construct
SEQUENCE: 509
DETYMRRALE LARQAEQAGE VPVGAVLVKD GEIVAEGWNQ SIGTHDATAH AEIMALRAAG  60
QALENYRLVD TTLYVTLEPC PMCAGALLHS RVKRVVFGAA DLKAGAAGTV LNLFESQASY  120
HYAEVESGLL EEECREQLQA FFKRRRKEIK ALKQAEKAAQ E                      161

SEQ ID NO: 510         moltype = AA  length = 164
FEATURE                Location/Qualifiers
source                 1..164
                       mol_type = protein
                       organism = synthetic construct
SEQUENCE: 510
MNSDDLYMRR ALELARQAEE EGEVPVGAVL VKDGEIVAEG WNRSIGSHDA TAHAEIETLR  60
KAGQVLQNYR LLDTTLYVTL EPCPMCAGAL LHSRVKRVVF GAPDLKAGAA GTVLNLFESQ  120
ASYHYADVES GLLEDECREQ LQAFFKRRRK EIKALRQAQK EAEE                   164

SEQ ID NO: 511         moltype = AA  length = 142
FEATURE                Location/Qualifiers
source                 1..142
                       mol_type = protein
                       organism = synthetic construct
SEQUENCE: 511
MDAALAEARA AADAGEVPVG AVLVRDGVVL ARAGNRTVRD CDPTAHAEIV ALRAAARALG  60
NYRLPGTTLY VTLEPCAMCA GAMIHARVDR LVFGARDPRA GAAGSVFDVL RHPALNHRVE  120
VVEGVRAEEC GALLRDFFRA RR                                           142

SEQ ID NO: 512         moltype = AA  length = 160
FEATURE                Location/Qualifiers
source                 1..160
                       mol_type = protein
                       organism = synthetic construct
SEQUENCE: 512
DRLFMRRALE LAAQAEAEGE VPVGAVLVKD GEVIAEGWNR SIGSHDATAH AEIETLRKAG  60
QVLENYRLLD TTLYVTLEPC PMCAGALLHS RVKRIVYGAP DLKAGAAGTV LNLFESQASY  120
HYADVESGLL EDECREQLQA FFKRRRKEIK AARQAKREQE                        160

SEQ ID NO: 513         moltype = AA  length = 149
FEATURE                Location/Qualifiers
source                 1..149
                       mol_type = protein
                       organism = synthetic construct
SEQUENCE: 513
MDDARFMAEA LAEARAAAAA GEVPVGAVVV RDGAVLARAG NRTVRDCDPT AHAEIVALRE  60
AARALGNYRL DGCTLYVTLE PCAMCAGAML HARLPRLVYG AADPKTGAAG SVLDLFAERR  120
LNHQTEVRGG VLAEACGALL TDFFRSRRA                                    149

SEQ ID NO: 514         moltype = AA  length = 146
FEATURE                Location/Qualifiers
source                 1..146
                       mol_type = protein
                       organism = synthetic construct
SEQUENCE: 514
DSEFMAEALA EARAAAEAGE VPIGAVVVCD GEIVARAGNR TIRDNDPTAH AEIVALREAA  60
RKLGNYRLTG CTVYVTLEPC AMCAGAMIHA RLDRLVYGAA DPKAGAAGSV LDVLGHPRLN  120
HQMAVESGVL ADECGALLRD FFRSRR                                       146

SEQ ID NO: 515         moltype = AA  length = 151
FEATURE                Location/Qualifiers
source                 1..151
                       mol_type = protein
                       organism = synthetic construct
SEQUENCE: 515
MDSESDLRFM REALAEARAA AAAGEVPVGA VVVRDGAILA RAGNRTLRDN DPTAHAEIVA  60
LRAAAAALGN HRLTGCTLYV TLEPCAMCAG AISHARIARL VYGAADPKGG AVAHGPRFFE  120
QPTCHHRPEV AGGVLAEEAG ALLRAFFAAR R                                 151

SEQ ID NO: 516         moltype = AA  length = 149
FEATURE                Location/Qualifiers
source                 1..149
                       mol_type = protein
                       organism = synthetic construct
```

```
SEQUENCE: 516
MSSDAGFMAE ALAEARAAAA AGEVPVGAVV VRDGAIVARA GNRTVRDNDP TAHAEVVALR  60
EAARALGNHR LGGCELYVTL EPCAMCAGAI SHARIARLYY GADDPKGGAV AHGARVFSHP  120
QCHHRPEVYD GIGAGEAAAL LRDFFAARR                                    149

SEQ ID NO: 517         moltype = AA  length = 148
FEATURE                Location/Qualifiers
source                 1..148
                       mol_type = protein
                       organism = synthetic construct
SEQUENCE: 517
DRDDRYMRLA LEEARAAAEA GEVPIGAVVV RDGEVLARAG NRTVRDCDPT AHAEIVALRE  60
AARVLGNYRL AGCTLYVTVE PCAMCAGAMI HARVDRLVYG ADDPKGGAVR SCLQVLDHPR  120
LNHRVEVTAG VLAEECAALL QSFFAARR                                     148

SEQ ID NO: 518         moltype = AA  length = 146
FEATURE                Location/Qualifiers
source                 1..146
                       mol_type = protein
                       organism = synthetic construct
SEQUENCE: 518
DSEFMAEALA EARAAAAAGE VPVGAVVVRD GEIVARAGNR TLRDNDPTAH AEIVALREAA  60
RALGNHRLTG CTLYVTLEPC AMCAGAISHA RIARLVYGAD DPKGGGVAHG ARVFEHPQCH  120
HRPEVVGGVG AAEAGELLRG FFAARR                                       146

SEQ ID NO: 519         moltype = AA  length = 164
FEATURE                Location/Qualifiers
source                 1..164
                       mol_type = protein
                       organism = synthetic construct
SEQUENCE: 519
DREEYLMRKA LELAAKAEQL GEVPVGAVLV KDGEIIAEGW NQSIGNHDAT AHAEIMTLRQ  60
AGQALENYRL LDTTLYVTLE PCPMCAGALL HSRVKRIVFG APDLKAGAAG TVLNLFESQA  120
SYHYADVESG LLEDECREQL QAFFKRRRKE IKALKQAKRD AEEN                   164

SEQ ID NO: 520         moltype = AA  length = 142
FEATURE                Location/Qualifiers
source                 1..142
                       mol_type = protein
                       organism = synthetic construct
SEQUENCE: 520
MDAALAEARA AADAGEVPVG AVVVRDGAVL ARAGNRTLRD ADPTAHAEIV ALRAAARALG  60
NHRLGGCTLY VTLEPCAMCA GAISHARLAR LHYGAADPKG GAVEHGPRFF AQPTCHHRPD  120
VYGGIGEGEA AALLRGFFAA RR                                           142

SEQ ID NO: 521         moltype = AA  length = 146
FEATURE                Location/Qualifiers
source                 1..146
                       mol_type = protein
                       organism = synthetic construct
SEQUENCE: 521
DEPYMRLALD EARAAAAAGE VPIGAVVVKD GEVIARARNR TLADNDPTAH AEIVALRAAA  60
AALGNHRLTG CELYVTLEPC AMCAGAISHA RIARLVYGAD DPKGGAVAHG PRFFAQPTCH  120
HRPEVVGGVG EGEAAELLRG FFAARR                                       146

SEQ ID NO: 522         moltype = AA  length = 148
FEATURE                Location/Qualifiers
source                 1..148
                       mol_type = protein
                       organism = synthetic construct
SEQUENCE: 522
DRDSRFMREA LAEARAAAEA GEVPIGAVVV RDGEIVARAG NRTVRDCDPT AHAEIVALRE  60
AARALGNYRL TGCTLYVTIE PCAMCAGAMI HARIDRLVYG AADPKAGAAG SVLDVLGHPR  120
LNHRMEVTAG VLAEECAALL RDFFAARR                                     148

SEQ ID NO: 523         moltype = AA  length = 142
FEATURE                Location/Qualifiers
source                 1..142
                       mol_type = protein
                       organism = synthetic construct
SEQUENCE: 523
MDAALEEARR AAAAGEVPVG AVLVHDGQIL ARAGNRTIRD NDPTAHAEIV VLREAARALG  60
NYRLEGCTLY VTLEPCAMCA GAMIHARLPR LVYGADDPKA GAAGSVLDVL NHPALNHRME  120
VEGGVLAAEC GALLRDFFRA RR                                           142

SEQ ID NO: 524         moltype = AA  length = 151
FEATURE                Location/Qualifiers
source                 1..151
                       mol_type = protein
```

```
                         organism = synthetic construct
SEQUENCE: 524
MSAADDIRFM REALAEARAA AAAGEVPVGA VVVRDGAILA RAGNRTIRDC DPTAHAEVVA  60
LREAARALGN HRLTGCTLYV TLEPCAMCAG AISQARVARL VYGADDPKGG AVAHGPRFFA  120
QPTCHHRPEV TGGVLAEEAG ALLRDFFRAR R                                151

SEQ ID NO: 525           moltype = AA  length = 148
FEATURE                  Location/Qualifiers
source                   1..148
                         mol_type = protein
                         organism = synthetic construct
SEQUENCE: 525
MTDADFMALA LEEARAAAAL GEVPVGAVVV KDGEVIARAG NRTIRDCDPT AHAEVVALRE  60
AARKLGNYRL PGLTLYVTLE PCAMCAGAMI HARLDRVVYG ADDPKGGAAR SVYRILDDPR  120
LNHQVAVTSG VLAEECGALL RDFFRARR                                    148

SEQ ID NO: 526           moltype = AA  length = 166
FEATURE                  Location/Qualifiers
source                   1..166
                         mol_type = protein
                         organism = synthetic construct
SEQUENCE: 526
MDSAAKDLCY MRRALELAAL AEAEGEVPVG AVLVRDGEIV GEGWNRSIGS HDATAHAEIM  60
ALRQAGQALQ NYRLLDTTLY VTLEPCPMCA GALLHSRVKR VVFGAPDLKA GAAGTVLNLF  120
ESQASYHYAD VEGGLLAEEC RAQLQAFFKR RRKEQKALRQ AQKEAA                166

SEQ ID NO: 527           moltype = AA  length = 147
FEATURE                  Location/Qualifiers
source                   1..147
                         mol_type = protein
                         organism = synthetic construct
SEQUENCE: 527
DEEFMREALA EAQAAADAGE VPIGAVVVCD GEIVARAGNR TIRDNDPTAH AEIVALREAA  60
RKLGNYRLAG CTLYVTLEPC AMCAGAMIHA RVDRLVYGAD DPKAGAAGSV LDVIGHPRLN  120
HRMEVTSGVL AEECGAMLRE FFRRRRA                                     147

SEQ ID NO: 528           moltype = AA  length = 148
FEATURE                  Location/Qualifiers
source                   1..148
                         mol_type = protein
                         organism = synthetic construct
SEQUENCE: 528
MDDAGFMRLA LAEARAAAAA GEVPVGAVVV RGGEVLAAAG NRTLRDCDPT AHAEVVALRA  60
AARALGNHRL DGCDLYVTLE PCAMCAGAIS HARIARLYYG ADDPKGGAVA HGPRFFAQPT  120
CHHRPEVYGG IGESEAAALL RDFFAARR                                    148

SEQ ID NO: 529           moltype = AA  length = 148
FEATURE                  Location/Qualifiers
source                   1..148
                         mol_type = protein
                         organism = synthetic construct
SEQUENCE: 529
MSDEDYMRLA LAEAQAAADA GEVPVGAVLV AGGEVVARGR NRMIADSDPT AHAEIVALRE  60
AARRLGNYRL TGCTLYVTLE PCAMCAGAIV HARLDRVVYG AADPKAGAAG SVLDVLGHPR  120
LNHRTEVTGG VLADECGALL KDFFRARR                                    148

SEQ ID NO: 530           moltype = AA  length = 163
FEATURE                  Location/Qualifiers
source                   1..163
                         mol_type = protein
                         organism = synthetic construct
SEQUENCE: 530
MSSEDEKYMR RALELARQAE EEGEVPVGAV LVKDGEIVAE GWNRSIGSHD ATAHAEIETL  60
RKAGQALENY RLLDTTLYVT LEPCPMCAGA LLHSRVKRIV FGAPDLKAGA AGTVLNLFES  120
QASYHYADVE SGLLEDECRE QLQAFFKRRR KEIKAARKAA KAE                   163

SEQ ID NO: 531           moltype = AA  length = 149
FEATURE                  Location/Qualifiers
source                   1..149
                         mol_type = protein
                         organism = synthetic construct
SEQUENCE: 531
MSDDAAFMGE ALAEARAAAA AGEVPIGAVV VCDGAIVARA GNRTVRDNDP TAHAEIVALR  60
EAAARLGNYR LTGCTLYVTL EPCAMCAGAM IHARIDRLVY GAADPKAGAA GSVLDVIGHP  120
RLNHRMEVEG GVLAAECGAL LRDFFASRR                                   149

SEQ ID NO: 532           moltype = AA  length = 142
FEATURE                  Location/Qualifiers
source                   1..142
```

```
                        mol_type = protein
                        organism = synthetic construct
SEQUENCE: 532
MRAALAEAER AAAAGEVPVG AVVVRDGAVL AAAGNRTVRD CDPTAHAEVL ALRAAARALG  60
NHRLTGCTLY VTLEPCAMCA GAISHARVAR LVYGADDPKG GAVAHGPRFF AQPTCHHRPE  120
VAGGLGAAAA GELLRAFFRA RR                                           142

SEQ ID NO: 533          moltype = AA  length = 142
FEATURE                 Location/Qualifiers
source                  1..142
                        mol_type = protein
                        organism = synthetic construct
SEQUENCE: 533
MRAALDEARA AAAAGEVPVG AVVVHEGRIV ARAQNRMRRD NDPTAHAEIV ALRAAAAALG  60
SMRLTGCTLY VTLEPCAMCA GAISHARIDR LVYGAADPKG GAVAHGPRFF EQPTCHHRPD  120
VVGGVLAEEA GALLRGFFAA RR                                           142

SEQ ID NO: 534          moltype = AA  length = 167
FEATURE                 Location/Qualifiers
source                  1..167
                        mol_type = protein
                        organism = synthetic construct
SEQUENCE: 534
MDSAAKDLCY MRRALELAAL AEAEGEVPVG AVLVKDGEIV GEGWNRSIGS HDATAHAEIM  60
ALRQAGQALQ NYRLLDTTLY VTLEPCPMCA GALLHSRVKR VVFGAPDLKA GAAGTVLNLF  120
ESQASYHYAD VESGLLEQEC REQLQAFFKR RRKEIKAQRD AQRAADE                167

SEQ ID NO: 535          moltype = AA  length = 160
FEATURE                 Location/Qualifiers
source                  1..160
                        mol_type = protein
                        organism = synthetic construct
SEQUENCE: 535
MNDEFYMRRA LELAALAEEH NEVPVGAVLV LNGEIIGEGW NRSIGQHDAT AHAEIMALRQ  60
AGKVLQNYRL LDTTLYVTLE PCPMCAGALV HSRVKRVVYG TPDLKAGAAG TVMNLLSYDA  120
VNHHVAITSG VLAEECREQL QAFFRRRRAE KKALKQAQRA                        160

SEQ ID NO: 536          moltype = AA  length = 161
FEATURE                 Location/Qualifiers
source                  1..161
                        mol_type = protein
                        organism = synthetic construct
SEQUENCE: 536
DDTFYMRRAL ELARQAEAEG EVPVGAVLVR DGEVIAEGWN RSIGDHDATA HAEIQVLRKA  60
GQVLQNYRLL DTTLYVTLEP CPMCAGALLH SRVKRVVYGA PDLKAGAAGT VLNLFESQAS  120
YHYADVESGL LEEECREQLQ AFFKRRRKEI KAARQAKRAA E                      161

SEQ ID NO: 537          moltype = AA  length = 142
FEATURE                 Location/Qualifiers
source                  1..142
                        mol_type = protein
                        organism = synthetic construct
SEQUENCE: 537
MRSALDLAAA AAAAGEVPVG AVVVRDGAIV GRGENRVLRD SDPTAHAEIV AMREAARALG  60
NYRLTGCTLY VTLEPCAMCA GAMIHARIDR LVYGAADPKA GAAGSVLDVL NHPRLNHQME  120
VEGGVLAAEC GAMLRDFFRA RR                                           142

SEQ ID NO: 538          moltype = AA  length = 148
FEATURE                 Location/Qualifiers
source                  1..148
                        mol_type = protein
                        organism = synthetic construct
SEQUENCE: 538
MDDDALMGLA LDEARAAAAA GEVPIGAVVA RDGEVVARAG NRTVRDCDPT AHAEIVALRE  60
AARKLGNYRL TGCTLYVTLE PCAMCAGAMI HARLDRLVYG AADPKTGAAG SVLDVLGHPA  120
LNHQTQVEGG VLAEECGALL RDFFRERR                                     148

SEQ ID NO: 539          moltype = AA  length = 165
FEATURE                 Location/Qualifiers
source                  1..165
                        mol_type = protein
                        organism = synthetic construct
SEQUENCE: 539
MTEEDKYFMR RAIELAKLAE ENGEVPVGAV LVKDGEIIAE GWNQSIGSHD ATAHAEMMAI  60
REAGKVLENY RLLDTTLYVT LEPCPMCAGA LLHSRVKRIV FGAPDLKAGA AGTVLNLFES  120
QASYHYADVE SGLLEEECRE QLQAFFKRRR KEIKALKKAQ KEAEE                  165

SEQ ID NO: 540          moltype = AA  length = 146
FEATURE                 Location/Qualifiers
```

```
source                 1..146
                       mol_type = protein
                       organism = synthetic construct
SEQUENCE: 540
DDDYMRLALA EARAAAEAGE VPIGAVVVCG GEVVARAGNR TVADCDPTAH AEIVALREAA  60
RKLGNYRLTG CTLYVTLEPC AMCAGAMIHA RLDRLVYGAD DPKAGAAGSV LDVLGHPALN  120
HQMQVTAGVL ADECAALLRD FFRARR                                       146

SEQ ID NO: 541         moltype = AA  length = 163
FEATURE                Location/Qualifiers
source                 1..163
                       mol_type = protein
                       organism = synthetic construct
SEQUENCE: 541
DDSFYMRRAL ELAALAEREG EVPVGAVLVK DGEIIAEGWN RSIGSHDATA HAEIETLRKA  60
GQALQNYRLL DTTLYVTLEP CPMCAGALLH SRVKRIVFGA PDLKAGAAGT VLNLFESQAS  120
YHYADVESGL LEEECREQLQ AFFKRRRKEI KAQRDAEKAA AEK                    163

SEQ ID NO: 542         moltype = AA  length = 142
FEATURE                Location/Qualifiers
source                 1..142
                       mol_type = protein
                       organism = synthetic construct
SEQUENCE: 542
MDAALAEARA AADAGEVPVG AVVVRDGAVL ARAGNRTLRD SDPTAHAEIV ALRAAARALG  60
NHRLGGCDLY VTLEPCAMCA GAISHARIAR LYYGADDPKG GAVAHGARVF AHPQCHHRPE  120
VYDGIGAAEA AALLRDFFAA RR                                           142

SEQ ID NO: 543         moltype = AA  length = 164
FEATURE                Location/Qualifiers
source                 1..164
                       mol_type = protein
                       organism = synthetic construct
SEQUENCE: 543
MTRDEQYMRR ALELARQAEA EGEVPVGAVL VKDGEIIAEG WNRSIGSHDA TGHAEIMALR  60
AAGQALENYR LLDTTLYVTL EPCPMCAGAL LHSRVKRVVF GAPDLKAGAA GTVLNLFESQ  120
ASYHYADVES GLLEEECREQ LQAFFKRRRK EIKALRQAEK AAAE                   164

SEQ ID NO: 544         moltype = AA  length = 151
FEATURE                Location/Qualifiers
source                 1..151
                       mol_type = protein
                       organism = synthetic construct
SEQUENCE: 544
MTDADFMALA LEEARAAAAL GEVPVGAVVV KDGEVIARAG NRTIRDCDPT AHAEIVALRE  60
AARKLGNYRL PGLALYVTLE PCAMCAGAMI HARLARLVYG AADPKTGAAG SVLDVLGHPA  120
LNHQTAVTGG VLAEEAGALL RDFFAARRAA G                                 151

SEQ ID NO: 545         moltype = AA  length = 142
FEATURE                Location/Qualifiers
source                 1..142
                       mol_type = protein
                       organism = synthetic construct
SEQUENCE: 545
MDAALAEARA AADAGEVPVG AVVVRDGAVL ARAGNRTLRD ADPTAHAEIV ALRAAARALG  60
NHRLPGCTLY VTLEPCAMCA GAISHARIAR LVYGAADPKG GAVAHGPRFF EQPTCHHRPE  120
VVGGLGETEA AALLRAFFAA RR                                           142

SEQ ID NO: 546         moltype = AA  length = 142
FEATURE                Location/Qualifiers
source                 1..142
                       mol_type = protein
                       organism = synthetic construct
SEQUENCE: 546
MDAALEEARR AAAAGEVPVG AVLVAGGRVL ARAGNRTIRD CDPTAHAEIV ALRAAARALG  60
NYRLPGTTLY VTLEPCAMCA GAMIHARVAR LVYGAADPKT GAAGSVFDVL GSGRLNHRVA  120
VEGGVRAEEC GALLRDFFRA RR                                           142

SEQ ID NO: 547         moltype = AA  length = 148
FEATURE                Location/Qualifiers
source                 1..148
                       mol_type = protein
                       organism = synthetic construct
SEQUENCE: 547
DDDERWMREA LAEARAAAEA GEVPVGAVVV RDGELIARGR NRVEADADPS AHAEIVALRE  60
AARRLGNHRL TGCTLYVTLE PCAMCAGAIS HARVARLVYG ADDPKGGAVR HGARVFEQPT  120
CHHRPEVVGG VLASESAALL RDFFRARR                                     148

SEQ ID NO: 548         moltype = AA  length = 165
```

```
FEATURE                Location/Qualifiers
source                 1..165
                       mol_type = protein
                       organism = synthetic construct
SEQUENCE: 548
MSAADEQFMR RAIELARQAE AEGEVPVGAV LVKDGEIVAE GWNRSIGAHD ATAHAEIETL  60
RKAGQALENY RLLDTTLYVT LEPCPMCAGA LLHSRVKRVV FGAPDLKAGA AGTVLNLFES  120
QASYHYADVE SGLLEEECRE QLQAFFKRRR KEIKALRQAQ KAAEE                  165

SEQ ID NO: 549         moltype = AA  length = 152
FEATURE                Location/Qualifiers
source                 1..152
                       mol_type = protein
                       organism = synthetic construct
SEQUENCE: 549
MSSAPSDADF MGLALEQARL AAAAGEVPVG AVVVRDGEVI AQAHNRTVAD CDPTAHAEVV  60
ALRAAARALG NHRLTGCTLY VTLEPCAMCA GAIAHARVAR VVYGAADPKG GAVEHGPRFF  120
AQPTCHHRPE VVGGVGAAEA GALLRDFFRA RR                                152

SEQ ID NO: 550         moltype = AA  length = 143
FEATURE                Location/Qualifiers
source                 1..143
                       mol_type = protein
                       organism = synthetic construct
SEQUENCE: 550
MDEALAEARR AAAAGEVPVG AVVVRDGVVL ARAGNRTVRD ADPTAHAEIV ALRAAAAALG  60
NYRLDGCTLY VTLEPCAMCA GAMVHARLAR LVYGAADPRA GAAGSVLDVL GHPALNHRME  120
VAGGVRAEEC AALLRDFFAA RRG                                          143

SEQ ID NO: 551         moltype = AA  length = 142
FEATURE                Location/Qualifiers
source                 1..142
                       mol_type = protein
                       organism = synthetic construct
SEQUENCE: 551
MDEALAEARR AAEAGEVPVG AVVVRDGAVL ARAGNRTVRD CDPTAHAEVL ALREAARALG  60
NHRLAGCTLY VTLEPCAMCA GAISHARVAR LVYGADDPKG GAVAHGPRFF GQPTCHHRPE  120
VAAGLGAAEA GALLRDFFAA RR                                           142

SEQ ID NO: 552         moltype = AA  length = 146
FEATURE                Location/Qualifiers
source                 1..146
                       mol_type = protein
                       organism = synthetic construct
SEQUENCE: 552
DTSFMRLALD EARAAADAGE VPVGAVVVCD GEVIARAGNR TVRDCDPTAH AEIVALREAA  60
RRLGNYRLAG CTLYVTLEPC AMCAGAMIHA RLDRLVYGAA DPKAGAAGSV LDVLGHPALN  120
HQTQVEGGVL AAECGALLRD FFRARR                                       146

SEQ ID NO: 553         moltype = AA  length = 161
FEATURE                Location/Qualifiers
source                 1..161
                       mol_type = protein
                       organism = synthetic construct
SEQUENCE: 553
DTLFMRRALE LAAQAEAEGE VPVGAVLVKD GEVIAEGWNR SIGSHDATAH AEIETLRKAG  60
QVLQNYRLLD TTLYVTLEPC PMCAGALLHS RVKRIVYGAP DLKAGAAGTV LNLFESQASY  120
HYAEVESGLL EEECREQLQA FFKRRRKEIK ALRQAEKEAE K                      161

SEQ ID NO: 554         moltype = AA  length = 148
FEATURE                Location/Qualifiers
source                 1..148
                       mol_type = protein
                       organism = synthetic construct
SEQUENCE: 554
MDDEFFMRQA LREARKAYDE GEVPVGAVVV RDGKVIARGR NQVERLKDPT AHAEMIALTA  60
AAAHLGSKWL KGCTLYVTVE PCAMCAGALV LARLERLVFG ARDPKAGACG SVLDIVRHPR  120
LNHRVEVVSG VLEEECGALL KEFFRRLR                                     148

SEQ ID NO: 555         moltype = AA  length = 163
FEATURE                Location/Qualifiers
source                 1..163
                       mol_type = protein
                       organism = synthetic construct
SEQUENCE: 555
MTRDEQYMRR ALALARQAEA EGEVPVGAVL VKDGEVIAEG WNRSIGRHDA TAHAEIETLR  60
KAGQVLGNYR LLDTTLYVTL EPCPMCAGAL LHSRVKRVVF GAPDLKAGAA GTVLNLFESQ  120
ASYHYADVES GLLEDECREQ LQAFFKRRRK EIKAARKAAK EAE                    163
```

```
SEQ ID NO: 556         moltype = AA  length = 142
FEATURE                Location/Qualifiers
source                 1..142
                       mol_type = protein
                       organism = synthetic construct
SEQUENCE: 556
MDAALEEARR AAAAGEVPVG AVLVRDGEVL ARAGNRTVRD NDPTAHAEIL VIREAARRLG  60
NYRLEGCVLY VTLEPCAMCA GAMVHARLPR LVYGAADPKA GAAGSVLDVL GHPALNHRVE  120
VTGGVLADAC GALLRDFFAA RR                                           142

SEQ ID NO: 557         moltype = AA  length = 142
FEATURE                Location/Qualifiers
source                 1..142
                       mol_type = protein
                       organism = synthetic construct
SEQUENCE: 557
MDEALAEARR AAAAGEVPVG AVLVRDGEVL ARGGNRTIRD CDPTAHAEIV ALREAARRAG  60
NYRLPGTTLY VTLEPCAMCA GAMIHARVAR LVYGAADPRA GAAGSVFDVL RHPALNHRME  120
VEGGVRAEEC GALLREFFRA RR                                           142

SEQ ID NO: 558         moltype = AA  length = 166
FEATURE                Location/Qualifiers
source                 1..166
                       mol_type = protein
                       organism = synthetic construct
SEQUENCE: 558
MTEKDEFYMK RAIELARKGE EEGEVPVGAV LVKDGEIIAE GWNRSIGSHD ATAHAEIETL  60
RKAGQALENY RLLDTTLYVT LEPCPMCAGA LLHSRVKRVV FGAPDLKAGA AGTVLNLFES  120
QASYHYADVE SGLLEEECRE QLQAFFKRRR KEIKALKKAK KEEQDK                 166

SEQ ID NO: 559         moltype = AA  length = 146
FEATURE                Location/Qualifiers
source                 1..146
                       mol_type = protein
                       organism = synthetic construct
SEQUENCE: 559
DDDFMALALE EARAAAEAGE VPIGAVVVCD GEVVARAGNR TVRDNDPTAH AEIVALREAA  60
RKLGNYRLAG CTLYVTLEPC AMCAGAMIHA RLDRVVYGAD DPKAGAARSV LNVLDHPALN  120
HRVAVEGGVL ADECGALLRE FFRARR                                       146

SEQ ID NO: 560         moltype = AA  length = 165
FEATURE                Location/Qualifiers
source                 1..165
                       mol_type = protein
                       organism = synthetic construct
SEQUENCE: 560
MTEEDKYFMQ RAIELARQAE LAGEVPVGAV LVKDGEIIAE GWNQSIGSHD ATAHAEIMAL  60
RQAGQVLQNY RLLDTTLYVT LEPCPMCAGA LLHSRVKRVV FGAPDLKAGA AGTVLNLFES  120
QASYHYADVE SGLLEQECRE QLQAFFKRRR KEIKALKQAQ KEAEN                  165

SEQ ID NO: 561         moltype = AA  length = 162
FEATURE                Location/Qualifiers
source                 1..162
                       mol_type = protein
                       organism = synthetic construct
SEQUENCE: 561
MTDEEYMRRA LELARQAEQQ GEVPVGAVLV KDGEVIAEGW NQSIGSHDAT AHAEIMALRA  60
AGQALENYRL LDTTLYVTLE PCPMCAGALL HSRVKRVVFG APDLKAGAAG TVLNLFESQA  120
SYHYADVESG LLEEECREQL QAFFKRRRKE IKAARQAKRE AE                     162

SEQ ID NO: 562         moltype = AA  length = 166
FEATURE                Location/Qualifiers
source                 1..166
                       mol_type = protein
                       organism = synthetic construct
SEQUENCE: 562
MSEQDEFYMR RAIELARQAE AEGEVPVGAV LVKDGEIVAE GWNRSIGSHD ATAHAEIETL  60
RKAGQALQNY RLLDTTLYVT LEPCPMCAGA LLHSRVKRVV FGAPDLKAGA AGTVLNLFES  120
QASYHYAEVE SGLLEEECRE QLQAFFKRRR KEIKALRQAQ KEAEEK                 166

SEQ ID NO: 563         moltype = AA  length = 161
FEATURE                Location/Qualifiers
source                 1..161
                       mol_type = protein
                       organism = synthetic construct
SEQUENCE: 563
DDTLYMKRAL ELARQAEAEG EVPVGAVLVK DGEVIAEGWN RSIGSHDATA HAEIETLRKA  60
GQALQNYRLL DTTLYVTLEP CPMCAGALLH SRVKRIVFGA PDLKAGAAGT VLNLFESQAS  120
YHYAEVESGL LEEECREQLQ AFFKRRRKEI KALRQAEKEA E                      161
```

```
SEQ ID NO: 564          moltype = AA  length = 162
FEATURE                 Location/Qualifiers
source                  1..162
                        mol_type = protein
                        organism = synthetic construct
SEQUENCE: 564
DETYMRRALE LARQAEEHGE VPVGAVLVKD GEIIAEGWNR SIGDHDATAH AEIMALREAG  60
KTLENYRLLD TTLYVTLEPC PMCAGALLHS RVKRVVYGAP DLKAGAAGTV LNLFESQASY  120
HYAEVESGLL EEECREQLQA FFKRRRKEIK AARKARREAE EK                     162

SEQ ID NO: 565          moltype = AA  length = 148
FEATURE                 Location/Qualifiers
source                  1..148
                        mol_type = protein
                        organism = synthetic construct
SEQUENCE: 565
MTDADFMALA LEEARAAAAL GEVPVGAVVV RDGAVIARAG NRTIRDCDPT AHAEIVALRA  60
AARALGNYRL DGCDLYVTLE PCAMCAGAMI HARLARLVYG AADPKTGAAG SVLDVFANPR  120
LNHHTAVVGG VLADEAAALL RGFFAARR                                     148

SEQ ID NO: 566          moltype = AA  length = 161
FEATURE                 Location/Qualifiers
source                  1..161
                        mol_type = protein
                        organism = synthetic construct
SEQUENCE: 566
DDEKWMRYAL SLADKAEALG EVPVGAVLVK DNQVIGEGWN QSISGHDATA HAEIMAIRDA  60
GKNLQNYRLI DCTLYVTLEP CPMCAGAIVH SRIKRVVFGA SDYKTGAAGS VFNLLSNEQL  120
NHQAEVTAGV LAEECGEKIS AFFKRRRKEK KAAKKAAKLA E                      161

SEQ ID NO: 567          moltype = AA  length = 164
FEATURE                 Location/Qualifiers
source                  1..164
                        mol_type = protein
                        organism = synthetic construct
SEQUENCE: 567
MTEEDKYFMR RAIELAKLAE ENGEVPVGAV LVKDGEIIAE GWNQSIGSHD ATAHAEMMAI  60
RQAGQVLENY RLLDTTLYVT LEPCPMCAGA LLHSRVKRIV FGAPDLKAGA AGTVLNLFES  120
QASYHYADVE SGLLEEECRE QLQAFFKRRR KEIKALKKAQ KEAE                   164

SEQ ID NO: 568          moltype = AA  length = 149
FEATURE                 Location/Qualifiers
source                  1..149
                        mol_type = protein
                        organism = synthetic construct
SEQUENCE: 568
MTDDERWMRE ALAEARAAEA AGEVPVGAVV VRDGELIARG RNRVLRDSDP TAHAEIVALR  60
EAARALGNYR LDGCTLYATL EPCAMCAGAM LHARLARLVY GAADPKAGAA GSVLDVLGHP  120
RLNHRMEVTG GVLAEEAGAL LREFFRARR                                    149

SEQ ID NO: 569          moltype = AA  length = 162
FEATURE                 Location/Qualifiers
source                  1..162
                        mol_type = protein
                        organism = synthetic construct
SEQUENCE: 569
DDSFYMRRAL ELAALAEAEG EVPVGAVLVK DGEIIAEGWN RSIGDHDATA HAEIQVLRKA  60
GQALQNYRLL DTTLYVTLEP CPMCAGALLH SRVKRIVYGA PDLKAGAAGT VLNLFESQAS  120
YHYAEVESGL LEEECREQLQ AFFKRRRKEI KALRQAEKEA QN                     162

SEQ ID NO: 570          moltype = AA  length = 146
FEATURE                 Location/Qualifiers
source                  1..146
                        mol_type = protein
                        organism = synthetic construct
SEQUENCE: 570
DEEFMREALA EAQAAADAGE VPIGAVVVCD GEIVARAGNR TIRDNDPTAH AEIVALREAA  60
RKLGNYRLAG CTLYVTLEPC AMCAGAMIHA RIDRLVYGAD DPKAGAAGSV LDVLGHPRLN  120
HQMQVERGVL AAECGAMLTR FFQARR                                       146

SEQ ID NO: 571          moltype = AA  length = 164
FEATURE                 Location/Qualifiers
source                  1..164
                        mol_type = protein
                        organism = synthetic construct
SEQUENCE: 571
MTEADEKFMR RAIELAREAE EHGEVPVGAV LVKDGEIIAE GWNRSIGEHD ATAHAEIETL  60
RKAGQVLENY RLLDTTLYVT LEPCPMCAGA LLHSRVKRIV FGAPDLKAGA AGTVLNLFES  120
```

```
QASYHYADVE SGLLEEECRE QLQAFFKRRR KEIKALRQAE KAAG                   164

SEQ ID NO: 572         moltype = AA  length = 142
FEATURE                Location/Qualifiers
source                 1..142
                       mol_type = protein
                       organism = synthetic construct
SEQUENCE: 572
MRDALALAAA AAAAGEVPVG AVVVHGGEIV GRGENRVLRD SDPTAHAEIV ALREAARALG  60
NYRLTGCDLY VTLEPCAMCA GAMIHARIAR LVYGAADPKA GAAGSVLDVL NHPRLNHRME  120
VTGGVLAEEC GALLRDFFRA RR                                           142

SEQ ID NO: 573         moltype = AA  length = 165
FEATURE                Location/Qualifiers
source                 1..165
                       mol_type = protein
                       organism = synthetic construct
SEQUENCE: 573
MTEEDKYFMQ RAIELARLAE ENGEVPVGAV LVKDGEIIAE GWNQSIGNHD ATAHAEIMTL  60
RQAGQVLQNY RLLDTTLYVT LEPCPMCAGA LLHSRVKRIV FGAPDLKAGA AGTVLNLFES  120
QASYHYADVE SGLLEDECRE QLQAFFKRRR KEIKALKKAK RDAEN                  165

SEQ ID NO: 574         moltype = AA  length = 149
FEATURE                Location/Qualifiers
source                 1..149
                       mol_type = protein
                       organism = synthetic construct
SEQUENCE: 574
MDPTDLAFMR EALAEARAAA EAGEFPIGAV VVCDGRIVAR AHNRPIALSD PTAHAEILAL  60
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 575         moltype = AA  length = 149
FEATURE                Location/Qualifiers
source                 1..149
                       mol_type = protein
                       organism = synthetic construct
SEQUENCE: 575
MDPTDLAFMR EALAEARAAA EAGEVPVGAV VVCDGRIVAR AHNRPIALSD PTAHAEILAL  60
REAARALGNI RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 576         moltype = AA  length = 147
FEATURE                Location/Qualifiers
source                 1..147
                       mol_type = protein
                       organism = synthetic construct
SEQUENCE: 576
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPKTGAAG SVLDVLGHPR  120
LNHRMEVEGG VLAAECGALL RDFFRAR                                      147

SEQ ID NO: 577         moltype = AA  length = 147
FEATURE                Location/Qualifiers
source                 1..147
                       mol_type = protein
                       organism = synthetic construct
SEQUENCE: 577
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPGCGAAG SVLDVLGHPR  120
LNHRMEVEGG VLAAECGALL RDFFRAR                                      147

SEQ ID NO: 578         moltype = AA  length = 147
FEATURE                Location/Qualifiers
source                 1..147
                       mol_type = protein
                       organism = synthetic construct
SEQUENCE: 578
MTDEYFMRQA LREARRAYDE GEVPVGAVVV RDGRVIARGR NQVERLKDPT AHAEMLALTA  60
AAGHLGSGRL TGCTLYVTVE PCAMCAGALV WARVERVVFG VRNPKTGACG SVFDIPGDRR  120
LNHRPEVVGG VLEAECAALM RDFFRER                                      147

SEQ ID NO: 579         moltype = AA  length = 149
FEATURE                Location/Qualifiers
source                 1..149
                       mol_type = protein
                       organism = synthetic construct
SEQUENCE: 579
MDPTDLAFMR EALAEARAAA EAGEVPVGAV VVCDGRIVAR AHNRPIALSD PTAHAEILAL  60
```

```
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 580         moltype = AA  length = 149
FEATURE                Location/Qualifiers
source                 1..149
                       mol_type = protein
                       organism = synthetic construct
SEQUENCE: 580
MDPTDLAFMR EALAEARAAA EAGEVPIGAV VVCDGRIVAR AHNRPIALSD PTAHAEILAL  60
REAARALGNY RLTGCTLYAT LEPCAMCAGA ILHARIARLV YGVANAGAGA CGSVLDVMNH  120
PRLNHRVEVT GGVLAEECGA LLSGFFRAR                                    149

SEQ ID NO: 581         moltype = AA  length = 147
FEATURE                Location/Qualifiers
source                 1..147
                       mol_type = protein
                       organism = synthetic construct
SEQUENCE: 581
MDDAGFMRLA LEEARAAAAA GEVPIGAVVV RDGEVLARAG NRTVRDCDPT AHAEIVALRE  60
AARRLGNYRL AGCTLYVTLE PCAMCAGAMI HARLDRLVYG VANPKTGAAG SVLDVLGHPR  120
LNHRMEVEGG VLAAECGALL RDFFRAR                                      147

SEQ ID NO: 582         moltype = AA  length = 147
FEATURE                Location/Qualifiers
source                 1..147
                       mol_type = protein
                       organism = synthetic construct
SEQUENCE: 582
MDDAGFMRLA LEEARAAAAA GEVPIGAVVV RDGEVLARAG NRTVRDCDPT AHAEIVALRE  60
AARRLGNYRL AGCTLYVTLE PCAMCAGAMI HARLDRLVYG VANPGAGAAG SVLDVLGHPR  120
LNHRMEVEGG VLAAECGALL RDFFRAR                                      147

SEQ ID NO: 583         moltype = AA  length = 147
FEATURE                Location/Qualifiers
source                 1..147
                       mol_type = protein
                       organism = synthetic construct
SEQUENCE: 583
MTDEYFMRQA LREARRAYDE GEVPVGAVVV RDGRVIARGR NQVERLKDPT AHAEMLALTA  60
AAGHLGSSRL TGCTLYVTVE PCAMCAGALV WARVERVVFG VRNPKTGACG SVFDIPGDRR  120
LNHRPEVVGG VLEAECAALM RDFFRER                                      147

SEQ ID NO: 584         moltype = AA  length = 147
FEATURE                Location/Qualifiers
source                 1..147
                       mol_type = protein
                       organism = synthetic construct
SEQUENCE: 584
MTDEYFMRQA LREARRAYDE GEVPVGAVVV RDGRVIARGR NQVRRLKDPT AHAEMLALTA  60
AAGHLGSPRL TGCTLYVTVE PCAMCAGALV WARVERVVFG VRNPKTGACG SVFDIPGDRR  120
LNHRPEVVGG VLEAECAALM RDFFRER                                      147

SEQ ID NO: 585         moltype = AA  length = 149
FEATURE                Location/Qualifiers
source                 1..149
                       mol_type = protein
                       organism = synthetic construct
SEQUENCE: 585
MDPTDLAFMR EALAEARAAA EAGEVPIGAV VVCDGRIVAR AHNRPIALSD PTAHAEILAL  60
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 586         moltype = AA  length = 149
FEATURE                Location/Qualifiers
source                 1..149
                       mol_type = protein
                       organism = synthetic construct
SEQUENCE: 586
MDPTDLAFMR EALAEARAAA EAGELPIGAV VVCDGRIVAR AHNRPIALSD PTAHAEILAL  60
REAARALGNY RLTGCTLYAT LEPCAMCAGA ILHARIARLV YGVANPGTGA CGSVLDVMNH  120
PRLNHRVEVT GGVLAEECGA LLSGFFRAR                                    149

SEQ ID NO: 587         moltype = AA  length = 149
FEATURE                Location/Qualifiers
source                 1..149
                       mol_type = protein
                       organism = synthetic construct
SEQUENCE: 587
```

```
MDPTDLAFMR EALAEARAAA EAGEMPVGAV VVCDGRIVAR AHNRPIALSD PTAHAEILAL  60
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 588          moltype = AA  length = 147
FEATURE                 Location/Qualifiers
source                  1..147
                        mol_type = protein
                        organism = synthetic construct
SEQUENCE: 588
MDDAGFMRLA LEEARAAAAA GEVPIGAVVV RDGEVLARAG NRTVRDCDPT AHAEIVALRE  60
AARRLGNYRL AGCTLYVTLE PCAMCAGAMI HARLDRLVYG VANPKAGAAG SVLDVLGHPR  120
LNHRMEVEGG VLAAECGALL RDFFRAR                                      147

SEQ ID NO: 589          moltype = AA  length = 147
FEATURE                 Location/Qualifiers
source                  1..147
                        mol_type = protein
                        organism = synthetic construct
SEQUENCE: 589
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPGRGAAG SVLDVLGHPR  120
LNHRMEVEGG VLAAECGALL RDFFRAR                                      147

SEQ ID NO: 590          moltype = AA  length = 147
FEATURE                 Location/Qualifiers
source                  1..147
                        mol_type = protein
                        organism = synthetic construct
SEQUENCE: 590
MDDAGFMRLA LEEARAAAAA GEVPIGAVVV RDGEVLARAG NRTVRDCDPT AHAEIVALRE  60
AARRLGNYRL AGCTLYVTLE PCAMCAGAMI HARLDRLVYG VANPGSGAAG SVLDVLGHPR  120
LNHRMEVEGG VLAAECGALL RDFFRAR                                      147

SEQ ID NO: 591          moltype = AA  length = 147
FEATURE                 Location/Qualifiers
source                  1..147
                        mol_type = protein
                        organism = synthetic construct
SEQUENCE: 591
MTDEYFMRQA LREARRAYDE GEVPVGAVVV RDGRVIARGR NQVIRLKDPT AHAEMLALTA  60
AAGHLGSPRL TGCTLYVTVE PCAMCAGALV WARVERVVFG VRNPKTGACG SVFDIPGDRR  120
LNHRPEVVGG VLEAECAALM RDFFRER                                      147

SEQ ID NO: 592          moltype = AA  length = 149
FEATURE                 Location/Qualifiers
source                  1..149
                        mol_type = protein
                        organism = synthetic construct
SEQUENCE: 592
MDPTDLAFMR EALAEARAAA EAGEIPVGAV VVCDGRIVAR AHNRPIALSD PTAHAEILAL  60
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 593          moltype = AA  length = 149
FEATURE                 Location/Qualifiers
source                  1..149
                        mol_type = protein
                        organism = synthetic construct
SEQUENCE: 593
MDPTDLAFMR EALAEARAAA EAGELPIGAV VVCDGRIVAR AHNRPIALSD PTAHAEILAL  60
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 594          moltype = AA  length = 149
FEATURE                 Location/Qualifiers
source                  1..149
                        mol_type = protein
                        organism = synthetic construct
SEQUENCE: 594
MDPTDLAFMR EALAEARAAA EAGEVPVGAV VVCDGRIVAR AHNRPIALSD PTAHAEILAL  60
REAARALGNV RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 595          moltype = AA  length = 149
FEATURE                 Location/Qualifiers
source                  1..149
                        mol_type = protein
                        organism = synthetic construct
```

```
SEQUENCE: 595
MDPTDLAFMR EALAEARAAA EAGEVPIGAV VVCDGRIVAR AHNRPIALSD PTAHAEILAL  60
REAARALGNS RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 596          moltype = AA  length = 147
FEATURE                 Location/Qualifiers
source                  1..147
                        mol_type = protein
                        organism = synthetic construct
SEQUENCE: 596
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPKRGAAG SVLDVLGHPR  120
LNHRMEVEGG VLAAECGALL RDFFRAR                                      147

SEQ ID NO: 597          moltype = AA  length = 147
FEATURE                 Location/Qualifiers
source                  1..147
                        mol_type = protein
                        organism = synthetic construct
SEQUENCE: 597
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPGSGAAG SVLDVLGHPR  120
LNHRMEVEGG VLAAECGALL RDFFRAR                                      147

SEQ ID NO: 598          moltype = AA  length = 147
FEATURE                 Location/Qualifiers
source                  1..147
                        mol_type = protein
                        organism = synthetic construct
SEQUENCE: 598
MDDAGFMRLA LEEARAAAAA GEVPVGAVVV RDGEVLARAG NRTVRDCDPT AHAEIVALRE  60
AARRLGNFRL AGCTLYVTLE PCAMCAGAMI HARLDRLVYG VANPGRGAAG SVLDVLGHPR  120
LNHRMEVEGG VLAAECGALL RDFFRAR                                      147

SEQ ID NO: 599          moltype = AA  length = 149
FEATURE                 Location/Qualifiers
source                  1..149
                        mol_type = protein
                        organism = synthetic construct
SEQUENCE: 599
MDPTDLAFMR EALAEARAAA EAGEVPVGAV VVCDGRIVAR AHNRPIALSD PTAHAEILAL  60
REAARALGNY RLTGCTLYAT LEPCAMCAGA ILHARIARLV YGVANDGAGA CGSVLDVMNH  120
PRLNHRVEVT GGVLAEECGA LLSGFFRAR                                    149

SEQ ID NO: 600          moltype = AA  length = 149
FEATURE                 Location/Qualifiers
source                  1..149
                        mol_type = protein
                        organism = synthetic construct
SEQUENCE: 600
MDPTDLAFMR EALAEARAAA EAGEFPVGAV VVCDGRIVAR AHNRPIALSD PTAHAEILAL  60
REAARALGNY RLTGCTLYAT LEPCAMCAGA ILHARIARLV YGVANPGTGA CGSVLDVMNH  120
PRLNHRVEVT GGVLAEECGA LLSGFFRAR                                    149

SEQ ID NO: 601          moltype = AA  length = 149
FEATURE                 Location/Qualifiers
source                  1..149
                        mol_type = protein
                        organism = synthetic construct
SEQUENCE: 601
MDPTDLAFMR EALAEARAAA EAGEVPIGAV VVCDGRIVAR AHNRPIALSD PTAHAEILAL  60
REAARALGNW RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 602          moltype = AA  length = 147
FEATURE                 Location/Qualifiers
source                  1..147
                        mol_type = protein
                        organism = synthetic construct
SEQUENCE: 602
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANAGSGAAG SVLDVLGHPR  120
LNHRMEVEGG VLAAECGALL RDFFRAR                                      147

SEQ ID NO: 603          moltype = AA  length = 147
FEATURE                 Location/Qualifiers
source                  1..147
                        mol_type = protein
```

```
                         organism = synthetic construct
SEQUENCE: 603
MTDEYFMRQA LREARRAYDE GEVPVGAVVV RDGRVIARGR NQVERLKDPT AHAEMLALTA  60
AAGHLGSGRL TGCTLYVTVE PCAMCAGALV WARVERVVFG VRNPKTGACG SVFDIPGDRR  120
LSHRPEVVGG VLEAECAALM RDFFRER                                      147

SEQ ID NO: 604           moltype = AA  length = 147
FEATURE                  Location/Qualifiers
source                   1..147
                         mol_type = protein
                         organism = synthetic construct
SEQUENCE: 604
MTDEYFMRQA LREARRAYDE GEVPVGAVVV RDGRVIARGR NQVRRLKDPT AHAEMLALTA  60
AAGHLGSRRL TGCTLYVTVE PCAMCAGALV WARVERVVFG VRNPKTGACG SVFDIPGDRR  120
LNHRPEVVGG VLEAECAALM RDFFRER                                      147

SEQ ID NO: 605           moltype = AA  length = 149
FEATURE                  Location/Qualifiers
source                   1..149
                         mol_type = protein
                         organism = synthetic construct
SEQUENCE: 605
MDPTDLAFMR EALAEARAAA EAGEIPIGAV VVCDGRIVAR AHNRPIALSD PTAHAEILAL  60
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 606           moltype = AA  length = 149
FEATURE                  Location/Qualifiers
source                   1..149
                         mol_type = protein
                         organism = synthetic construct
SEQUENCE: 606
MDPTDLAFMR EALAEARAAA EAGEFPVGAV VVCDGRIVAR AHNRPIALSD PTAHAEILAL  60
REAARALGNY RLTGCTLYAT LEPCAMCAGA ILHARIARLV YGVANPGAGA CGSVLDVMNH  120
PRLNHRVEVT GGVLAEECGA LLSGFFRAR                                    149

SEQ ID NO: 607           moltype = AA  length = 149
FEATURE                  Location/Qualifiers
source                   1..149
                         mol_type = protein
                         organism = synthetic construct
SEQUENCE: 607
MDPTDLAFMR EALAEARAAA EAGEIPVGAV VVCDGRIVAR AHNRPIALSD PTAHAEILAL  60
REAARALGNY RLTGCTLYAT LEPCAMCAGA ILHARIARLV YGVANAGAGA CGSVLDVMNH  120
PRLNHRVEVT GGVLAEECGA LLSGFFRAR                                    149

SEQ ID NO: 608           moltype = AA  length = 147
FEATURE                  Location/Qualifiers
source                   1..147
                         mol_type = protein
                         organism = synthetic construct
SEQUENCE: 608
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPGTGAAG SVLDVLGHPR  120
LNHRMEVEGG VLAAECGALL RDFFRAR                                      147

SEQ ID NO: 609           moltype = AA  length = 147
FEATURE                  Location/Qualifiers
source                   1..147
                         mol_type = protein
                         organism = synthetic construct
SEQUENCE: 609
MTDEYFMRQA LREARRAYDE GEVPVGAVVV RDGRVIARGR NQVERLKDPT AHAEMLALTA  60
AAGHLGSRSL TGCTLYVTVE PCAMCAGALV WARVERVVFG VRNPRAGACG SVFDIPGDRR  120
LNHRPEVVGG VLEAECAALM RDFFRER                                      147

SEQ ID NO: 610           moltype = AA  length = 147
FEATURE                  Location/Qualifiers
source                   1..147
                         mol_type = protein
                         organism = synthetic construct
SEQUENCE: 610
MTDEYFMRQA LREARRAYDE GEVPVGAVVV RDGRVIARGR NQVVRLKDPT AHAEMLALTA  60
AAGHLGSPRL TGCTLYVTVE PCAMCAGALV WARVERVVFG VRNPKTGACG SVFDIPGDRR  120
LNHRPEVVGG VLEAECAALM RDFFRER                                      147

SEQ ID NO: 611           moltype = AA  length = 149
FEATURE                  Location/Qualifiers
source                   1..149
```

```
                        mol_type = protein
                        organism = synthetic construct
SEQUENCE: 611
MDPTDLAFMR EALAEARAAA EAGEVPIGAV VVCDGRIVAR AHNRPIALSD PTAHAEILAL  60
REAARALGNY RLTGCTLYAT LEPCAMCAGA ILHARIARLV YGVANDGAGA CGSVLDVMNH  120
PRLNHRVEVT GGVLAEECGA LLSGFFRAR                                   149

SEQ ID NO: 612          moltype = AA  length = 149
FEATURE                 Location/Qualifiers
source                  1..149
                        mol_type = protein
                        organism = synthetic construct
SEQUENCE: 612
MDPTDLAFMR EALAEARAAA EAGEVPVGAV VVCDGRIVAR AHNRPIALSD PTAHAEILAL  60
REAARALGNY RLTGCTLYAT LEPCAMCAGA ILHARIARLV YGVANSGAGA CGSVLDVMNH  120
PRLNHRVEVT GGVLAEECGA LLSGFFRAR                                   149

SEQ ID NO: 613          moltype = AA  length = 149
FEATURE                 Location/Qualifiers
source                  1..149
                        mol_type = protein
                        organism = synthetic construct
SEQUENCE: 613
MDPTDLAFMR EALAEARAAA EAGEVPIGAV VVCDGRIVAR AHNRPIALSD PTAHAEILAL  60
REAARALGNT RLTGCTLYAT LEPCAMCAGA ILHARIARLV YGVANPGAGA CGSVLDVMNH  120
PRLNHRVEVT GGVLAEECGA LLSGFFRAR                                   149

SEQ ID NO: 614          moltype = AA  length = 147
FEATURE                 Location/Qualifiers
source                  1..147
                        mol_type = protein
                        organism = synthetic construct
SEQUENCE: 614
MTDEYFMRQA LREARRAYDE GEVPVGAVVV RDGRVIARGR NQVNRLKDPT AHAEMLALTA  60
AAGHLGSPRL TGCTLYVTVE PCAMCAGALV WARVERVVFG VRNPKAGACG SVFDIPGDRR  120
LNHRPEVVGG VLEAECAALM RDFFRER                                     147

SEQ ID NO: 615          moltype = AA  length = 147
FEATURE                 Location/Qualifiers
source                  1..147
                        mol_type = protein
                        organism = synthetic construct
SEQUENCE: 615
MTDEYFMRQA LREARRAYDE GEVPVGAVVV RDGRVIARGR NQVNRLKDPT AHAEMLALTA  60
AAGHLGSRSL TGCTLYVTVE PCAMCAGALV WARVERVVFG VRNPKTGACG SVFDIPGDRR  120
LNHRPEVVGG VLEAECAALM RDFFRER                                     147

SEQ ID NO: 616          moltype = AA  length = 149
FEATURE                 Location/Qualifiers
source                  1..149
                        mol_type = protein
                        organism = synthetic construct
SEQUENCE: 616
MDPTDLAFMR EALAEARAAA EAGEVPIGAV VVCDGRIVAR AHNRPIALSD PTAHAEILAL  60
REAARALGNY RLTGCTLYAT LEPCAMCAGA ILHARIARLV YGVANAGTGA CGSVLDVMNH  120
PRLNHRVEVT GGVLAEECGA LLSGFFRAR                                   149

SEQ ID NO: 617          moltype = AA  length = 149
FEATURE                 Location/Qualifiers
source                  1..149
                        mol_type = protein
                        organism = synthetic construct
SEQUENCE: 617
MDPTDLAFMR EALAEARAAA EAGEFPIGAV VVCDGRIVAR AHNRPIALSD PTAHAEILAL  60
REAARALGNY RLTGCTLYAT LEPCAMCAGA ILHARIARLV YGVANPGTGA CGSVLDVMNH  120
PRLNHRVEVT GGVLAEECGA LLSGFFRAR                                   149

SEQ ID NO: 618          moltype = AA  length = 149
FEATURE                 Location/Qualifiers
source                  1..149
                        mol_type = protein
                        organism = synthetic construct
SEQUENCE: 618
MDPTDLAFMR EALAEARAAA EAGEVPIGAV VVCDGRIVAR AHNRPIALSD PTAHAEILAL  60
REAARALGNI RLTGCTLYAT LEPCAMCAGA ILHARIARLV YGVANPGTGA CGSVLDVMNH  120
PRLNHRVEVT GGVLAEECGA LLSGFFRAR                                   149

SEQ ID NO: 619          moltype = AA  length = 147
FEATURE                 Location/Qualifiers
```

```
source                 1..147
                       mol_type = protein
                       organism = synthetic construct
SEQUENCE: 619
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANPGAGAAG SVLDVLGHPR  120
LNHRMEVEGG VLAAECGALL RDFFRAR                                      147

SEQ ID NO: 620         moltype = AA  length = 147
FEATURE                Location/Qualifiers
source                 1..147
                       mol_type = protein
                       organism = synthetic construct
SEQUENCE: 620
MDDAGFMRLA LEEARAAAAA GEVPVGAVVV RDGEVLARAG NRTVRDCDPT AHAEIVALRE  60
AARRLGNYRL AGCTLYVTLE PCAMCAGAMI HARLDRLVYG VANAGRGAAG SVLDVLGHPR  120
LNHRMEVEGG VLAAECGALL RDFFRAR                                      147

SEQ ID NO: 621         moltype = AA  length = 149
FEATURE                Location/Qualifiers
source                 1..149
                       mol_type = protein
                       organism = synthetic construct
SEQUENCE: 621
MDPTDLAFMR EALAEARAAA EAGEVPVGAV VVCDGRIVAR AHNRPIALRD PTAHAEVLAL  60
REAAAALGSY RLTGCTLYAT LEPCPMCAGA ILHARIARLV YGVANPKAGA CGSVLDVMNH  120
PRLNHRVEVT GGVLAEECGA LLSGFFRAR                                    149

SEQ ID NO: 622         moltype = AA  length = 149
FEATURE                Location/Qualifiers
source                 1..149
                       mol_type = protein
                       organism = synthetic construct
SEQUENCE: 622
MDPTDLAFMR EALAEARAAA EAGEVPVGAV VVCDGRIVAR AHNRPIALKD PTAHAEVLAL  60
REAAAALGSY RLTGCTLYAT LEPCPMCAGA ILHARIARLV YGVANPKAGA CGSVLDVMNH  120
PRLNHRVEVT GGVLAEECGA LLSGFFRAR                                    149

SEQ ID NO: 623         moltype = AA  length = 149
FEATURE                Location/Qualifiers
source                 1..149
                       mol_type = protein
                       organism = synthetic construct
SEQUENCE: 623
MDPTDLAFMR EALAEARAAA EAGEVPVGAV VVCDGRIVAR AHNRPIALND PTAHAEVLAL  60
REAGKALGSY RLTGCTLYAT LEPCPMCAGA ILHARIARLV YGVANPKAGA CGSVLDVMNH  120
PRLNHRVEVT GGVLAEECGA LLSGFFRAR                                    149

SEQ ID NO: 624         moltype = AA  length = 149
FEATURE                Location/Qualifiers
source                 1..149
                       mol_type = protein
                       organism = synthetic construct
SEQUENCE: 624
MDPTDLAFMR EALAEARAAA EAGEVPVGAV VVCDGRIVAR AHNRPIALRD PTAHAEVLAL  60
REAARALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 625         moltype = AA  length = 147
FEATURE                Location/Qualifiers
source                 1..147
                       mol_type = protein
                       organism = synthetic construct
SEQUENCE: 625
MDDAGFMRLA LEEARAAAAA GEVPVGAVVV RDGEVLARAG NRTVRDRDPT AHAEIVAIRE  60
AARRLGSYRL AGCTLYVTLE PCPMCAGAMI HARLDRLVYG VANPKAGAAG TVLDVLGHPR  120
LNHRMEVEGG VLAAECGALL RDFFRAR                                      147

SEQ ID NO: 626         moltype = AA  length = 147
FEATURE                Location/Qualifiers
source                 1..147
                       mol_type = protein
                       organism = synthetic construct
SEQUENCE: 626
MTDEYFMRQA LREARRAYDE GEVPVGAVVV RDGRVIARGR NQVRRLKDPT AHAEMLALTA  60
AAGHLGSRSL TGCTLYVTVE PCAMCAGALV WARVERVVFG VRNPKAGACG SVFDIPGDRR  120
LNHRPEVVGG VLEAECAALM RDFFRER                                      147

SEQ ID NO: 627         moltype = AA  length = 147
```

```
FEATURE                Location/Qualifiers
source                 1..147
                       mol_type = protein
                       organism = synthetic construct
SEQUENCE: 627
MTDEYFMRQA LREARRAYDE GEVPVGAVVV RDGRVIARGR NQVRRLKDPT AHAEMLALTA  60
AAGHLGSARL TGCTLYVTVE PCAMCAGALV WARVERVVFG VRNPRAGACG SVFDIPGDRR  120
LNHRPEVVGG VLEAECAALM RDFFRER                                      147

SEQ ID NO: 628         moltype = AA  length = 149
FEATURE                Location/Qualifiers
source                 1..149
                       mol_type = protein
                       organism = synthetic construct
SEQUENCE: 628
MDPTDLAFMR EALAEARAAA EAGEVPVGAV VVCDGRIVAR AHNRPIALND PTAHAEVLAL  60
REAARALGDY RLTGCTLYAT LEPCAMCAGA ILHARIARLV YGVANPKAGA CGSVLDVMNH  120
PRLNHRVEVT GGVLAEECGA LLSGFFRAR                                    149

SEQ ID NO: 629         moltype = AA  length = 149
FEATURE                Location/Qualifiers
source                 1..149
                       mol_type = protein
                       organism = synthetic construct
SEQUENCE: 629
MDPTDLAFMR EALAEARAAA EAGEVPVGAV VVCDGRIVAR AHNRPIALKD PTAHAEILAL  60
REAAAALGSY RLTGCTLYAT LEPCAMCAGA ILHARIARLV YGVANPKAGA CGSVLDVMNH  120
PRLNHRVEVT GGVLAEECGA LLSGFFRAR                                    149

SEQ ID NO: 630         moltype = AA  length = 149
FEATURE                Location/Qualifiers
source                 1..149
                       mol_type = protein
                       organism = synthetic construct
SEQUENCE: 630
MDPTDLAFMR EALAEARAAA EAGEVPVGAV VVCDGRIVAR AHNRPIALKD PTAHAEILAL  60
REAGRALGSY RLTGCTLYAT LEPCPMCAGA ILHARIARLV YGVANPKAGA CGSVLDVMNH  120
PRLNHRVEVT GGVLAEECGA LLSGFFRAR                                    149

SEQ ID NO: 631         moltype = AA  length = 149
FEATURE                Location/Qualifiers
source                 1..149
                       mol_type = protein
                       organism = synthetic construct
SEQUENCE: 631
MDPTDLAFMR EALAEARAAA EAGEVPVGAV VVCDGRIVAR AHNRPIALAD PTAHAEVLAL  60
REAARALGSY RLTGCTLYAT LEPCPMCAGA ILHARIARLV YGVANPKAGA CGSVLDVMNH  120
PKLNHRVEVT GGVLAEECGA LLSGFFRAR                                    149

SEQ ID NO: 632         moltype = AA  length = 149
FEATURE                Location/Qualifiers
source                 1..149
                       mol_type = protein
                       organism = synthetic construct
SEQUENCE: 632
MDPTDLAFMR EALAEARAAA EAGEVPVGAV VVCDGRIVAR AHNRPIALND PTAHAEILAL  60
REAGRALGSY RLTGCTLYAT LEPCPMCAGA ILHARIARLV YGVANPKAGA CGSVLDVMNH  120
PRLNHRVEVT GGVLAEECGA LLSGFFRAR                                    149

SEQ ID NO: 633         moltype = AA  length = 149
FEATURE                Location/Qualifiers
source                 1..149
                       mol_type = protein
                       organism = synthetic construct
SEQUENCE: 633
MDPTDLAFMR EALAEARAAA EAGEVPVGAV VVCDGRIVAR AHNRPIALRD PTAHAEILAL  60
REAGRALGNY RLTGCTLYAT LEPCPMCAGA ILHARIARLV YGVANPKAGA CGSVLDVMNH  120
PKLNHRVEVT GGVLAEECGA LLSGFFRAR                                    149

SEQ ID NO: 634         moltype = AA  length = 149
FEATURE                Location/Qualifiers
source                 1..149
                       mol_type = protein
                       organism = synthetic construct
SEQUENCE: 634
MDPTDLAFMR EALAEARAAA EAGEVPVGAV VVCDGRIVAR AHNRPIALND PTAHAEVLAL  60
REAAAALGSY RLTGCTLYAT LEPCPMCAGA ILHARIARLV YGVANPKAGA CGTVLDVMNH  120
PRLNHRVEVT GGVLAEECGA LLSGFFRAR                                    149
```

```
SEQ ID NO: 635         moltype = AA  length = 149
FEATURE                Location/Qualifiers
source                 1..149
                       mol_type = protein
                       organism = synthetic construct
SEQUENCE: 635
MDPTDLAFMR EALAEARAAA EAGEVPVGAV VVCDGRIVAR AHNRPIALND PTAHAEILAL  60
REAGRALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 636         moltype = AA  length = 149
FEATURE                Location/Qualifiers
source                 1..149
                       mol_type = protein
                       organism = synthetic construct
SEQUENCE: 636
MDPTDLAFMR EALAEARAAA EAGEVPVGAV VVCDGRIVAR AHNRPIALAD PTAHAEVLAL  60
REAARALGSY RLTGCTLYAT LEPCAMCAGA ILHARIARLV YGVANPKAGA CGSVLDVMNH  120
PKLNHRVEVT GGVLAEECGA LLSGFFRAR                                    149

SEQ ID NO: 637         moltype = AA  length = 147
FEATURE                Location/Qualifiers
source                 1..147
                       mol_type = protein
                       organism = synthetic construct
SEQUENCE: 637
MDDAGFMRLA LEEARAAAAA GEVPVGAVVV RDGEVLARAG NRTVRDRDPT AHAEVVALRE  60
AARRLGSYRL AGCTLYVTLE PCAMCAGAMI HARLDRLVYG VANPKAGAAG TVLDVLGHPR  120
LNHRMEVEGG VLAAECGALL RDFFRAR                                      147

SEQ ID NO: 638         moltype = AA  length = 147
FEATURE                Location/Qualifiers
source                 1..147
                       mol_type = protein
                       organism = synthetic construct
SEQUENCE: 638
MDDAGFMRLA LEEARAAAAA GEVPVGAVVV RDGEVLARAG NRTVRDRDPT AHAEIVAIRE  60
AARRLGSYRL AGCTLYVTLE PCAMCAGAMI HARLDRLVYG VANPKAGAAG TVLDVLGHPR  120
LNHRMEVEGG VLAAECGALL RDFFRAR                                      147

SEQ ID NO: 639         moltype = AA  length = 147
FEATURE                Location/Qualifiers
source                 1..147
                       mol_type = protein
                       organism = synthetic construct
SEQUENCE: 639
MDDAGFMRLA LEEARAAAAA GEVPVGAVVV RDGEVLARAG NRTVRDKDPT AHAEIVALRE  60
AARRLGSYRL AGCTLYVTLE PCAMCAGAMI HARLDRLVYG VANPKAGAAG TVLDVLGHPR  120
LNHRMEVEGG VLAAECGALL RDFFRAR                                      147

SEQ ID NO: 640         moltype = AA  length = 147
FEATURE                Location/Qualifiers
source                 1..147
                       mol_type = protein
                       organism = synthetic construct
SEQUENCE: 640
MTDEYFMRQA LREARRAYDE GEVPVGAVVV RDGRVIARGR NQVVRLKDPT AHAEMLALTA  60
AAGHLGSPRL TGCTLYVTVE PCAMCAGALV WARVERVVFG VRNPKTGACG SVFDIPGDRR  120
LSHRPEVVGG VLEAECAALM RDFFRER                                      147

SEQ ID NO: 641         moltype = AA  length = 149
FEATURE                Location/Qualifiers
source                 1..149
                       mol_type = protein
                       organism = synthetic construct
SEQUENCE: 641
MDPTDLAFMR EALAEARAAA EAGEVPVGAV VVCDGRIVAR AHNRPIALND PTAHAEILAL  60
REAARALGSY RLTGCTLYAT LEPCAMCAGA ILHARIARLV YGVANPKAGA CGSVLDVMNH  120
PKLNHRVEVT GGVLAEECGA LLSGFFRAR                                    149

SEQ ID NO: 642         moltype = AA  length = 149
FEATURE                Location/Qualifiers
source                 1..149
                       mol_type = protein
                       organism = synthetic construct
SEQUENCE: 642
MDPTDLAFMR EALAEARAAA EAGEVPVGAV VVCDGRIVAR AHNRPIALRD PTAHAEILAL  60
REAARALGSY RLTGCTLYAT LEPCAMCAGA ILHARIARLV YGVANPKAGA CGTVLDVMNH  120
PRLNHRVEVT GGVLAEECGA LLSGFFRAR                                    149
```

```
SEQ ID NO: 643          moltype = AA  length = 149
FEATURE                 Location/Qualifiers
source                  1..149
                        mol_type = protein
                        organism = synthetic construct
SEQUENCE: 643
MDPTDLAFMR EALAEARAAA EAGEVPVGAV VVCDGRIVAR AHNRPIALND PTAHAEVLAL  60
REAAAALGSY RLTGCTLYAT LEPCAMCAGA ILHARIARLV YGVANPKAGA CGTVLDVMNH  120
PRLNHRVEVT GGVLAEECGA LLSGFFRAR                                    149

SEQ ID NO: 644          moltype = AA  length = 147
FEATURE                 Location/Qualifiers
source                  1..147
                        mol_type = protein
                        organism = synthetic construct
SEQUENCE: 644
MTDEYFMRQA LREARRAYDE GEVPVGAVVV RDGRVIARGR NQVVRLKDPT AHAEMLALTA  60
AAGHLGSSRL TGCTLYVTVE PCAMCAGALV WARVERVVFG VRNPRTGACG SVFDIPGDRR  120
LNHRPEVVGG VLEAECAALM RDFFRER                                      147

SEQ ID NO: 645          moltype = AA  length = 147
FEATURE                 Location/Qualifiers
source                  1..147
                        mol_type = protein
                        organism = synthetic construct
SEQUENCE: 645
MTDEYFMRQA LREARRAYDE GEVPVGAVVV RDGRVIARGR NQVRRLKDPT AHAEMLALTA  60
AAGHLGSPSL TGCTLYVTVE PCAMCAGALV WARVERVVFG VRNPRTGACG SVFDIPGDRR  120
LNHRPEVVGG VLEAECAALM RDFFRER                                      147

SEQ ID NO: 646          moltype = AA  length = 149
FEATURE                 Location/Qualifiers
source                  1..149
                        mol_type = protein
                        organism = synthetic construct
SEQUENCE: 646
MDPTDLAFMR EALAEARAAA EAGEVPVGAV VVCDGRIVAR AHNRPIALKD PTAHAEILAL  60
REAARALGSY RLTGCTLYAT LEPCPMCAGA ILHARIARLV YGVANPKAGA CGSVLDVMNH  120
PRLNHRVEVT GGVLAEECGA LLSGFFRAR                                    149

SEQ ID NO: 647          moltype = AA  length = 149
FEATURE                 Location/Qualifiers
source                  1..149
                        mol_type = protein
                        organism = synthetic construct
SEQUENCE: 647
MDPTDLAFMR EALAEARAAA EAGEVPVGAV VVCDGRIVAR AHNRPIALND PTAHAEVLAL  60
REAGRALGSY RLTGCTLYAT LEPCPMCAGA ILHARIARLV YGVANPKAGA CGSVLDVMNH  120
PRLNHRVEVT GGVLAEECGA LLSGFFRAR                                    149

SEQ ID NO: 648          moltype = AA  length = 149
FEATURE                 Location/Qualifiers
source                  1..149
                        mol_type = protein
                        organism = synthetic construct
SEQUENCE: 648
MDPTDLAFMR EALAEARAAA EAGEVPVGAV VVCDGRIVAR AHNRPIALND PTAHAEVLAL  60
REAAKALGSY RLTGCTLYAT LEPCPMCAGA ILHARIARLV YGVANPKAGA CGSVLDVMNH  120
PKLNHRVEVT GGVLAEECGA LLSGFFRAR                                    149

SEQ ID NO: 649          moltype = AA  length = 149
FEATURE                 Location/Qualifiers
source                  1..149
                        mol_type = protein
                        organism = synthetic construct
SEQUENCE: 649
MDPTDLAFMR EALAEARAAA EAGEVPVGAV VVCDGRIVAR AHNRPIALKD PTAHAEILAL  60
REAAAALGDY RLTGCTLYAT LEPCPMCAGA ILHARIARLV YGVANPKAGA CGSVLDVMNH  120
PKLNHRVEVT GGVLAEECGA LLSGFFRAR                                    149

SEQ ID NO: 650          moltype = AA  length = 149
FEATURE                 Location/Qualifiers
source                  1..149
                        mol_type = protein
                        organism = synthetic construct
SEQUENCE: 650
MDPTDLAFMR EALAEARAAA EAGEVPVGAV VVCDGRIVAR AHNRPIALRD PTAHAEILAL  60
REAGRALGSY RLTGCTLYAT LEPCPMCAGA ILHARIARLV YGVANPKAGA CGSVLDVMNH  120
```

```
PKLNHRVEVT GGVLAEECGA LLSGFFRAR                                   149

SEQ ID NO: 651         moltype = AA  length = 147
FEATURE                Location/Qualifiers
source                 1..147
                       mol_type = protein
                       organism = synthetic construct
SEQUENCE: 651
MDDAGFMRLA LEEARAAAAA GEVPVGAVVV RDGEVLARAG NRTVRDRDPT AHAEIVALRE  60
AARRLGSYRL AGCTLYVTLE PCPMCAGAMI HARLDRLVYG VANPKAGAAG TVLDILGHPR  120
LNHRMEVEGG VLAAECGALL RDFFRAR                                     147

SEQ ID NO: 652         moltype = AA  length = 147
FEATURE                Location/Qualifiers
source                 1..147
                       mol_type = protein
                       organism = synthetic construct
SEQUENCE: 652
MDDAGFMRLA LEEARAAAAA GEVPVGAVVV RDGEVLARAG NRTVRDRDPT AHAEVVAIRE  60
AARRLGSYRL AGCTLYVTLE PCAMCAGAMI HARLDRLVYG VANPKAGAAG TVLDVLGHPR  120
LNHRMEVEGG VLAAECGALL RDFFRAR                                     147

SEQ ID NO: 653         moltype = AA  length = 147
FEATURE                Location/Qualifiers
source                 1..147
                       mol_type = protein
                       organism = synthetic construct
SEQUENCE: 653
MTDEYFMRQA LREARRAYDE GEVPVGAVVV RDGRVIARGR NQVNRLKDPT AHAEMLALTA  60
AAGHLGSPRL TGCTLYVTVE PCAMCAGALV WARVERVVFG VRNPRTGACG SVFDIPGDRR  120
LSHRPEVVGG VLEAECAALM RDFFRER                                     147

SEQ ID NO: 654         moltype = AA  length = 147
FEATURE                Location/Qualifiers
source                 1..147
                       mol_type = protein
                       organism = synthetic construct
SEQUENCE: 654
MTDEYFMRQA LREARRAYDE GEVPVGAVVV RDGRVIARGR NQVRRLKDPT AHAEMLALTA  60
AAGHLGSPQL TGCTLYVTVE PCAMCAGALV WARVERVVFG VRNPKTGACG SVFDIPGDRR  120
LNHRPEVVGG VLEAECAALM RDFFRER                                     147

SEQ ID NO: 655         moltype = AA  length = 149
FEATURE                Location/Qualifiers
source                 1..149
                       mol_type = protein
                       organism = synthetic construct
SEQUENCE: 655
MDPTDLAFMR EALAEARAAA EAGEVPVGAV VVCDGRIVAR AHNRPIALND PTAHAEILAL  60
REAGRALGNY RLTGCTLYAT LEPCPMCAGA ILHARIARLV YGVANPKAGA CGTVLDVMNH  120
PRLNHRVEVT GGVLAEECGA LLSGFFRAR                                   149

SEQ ID NO: 656         moltype = AA  length = 149
FEATURE                Location/Qualifiers
source                 1..149
                       mol_type = protein
                       organism = synthetic construct
SEQUENCE: 656
MDPTDLAFMR EALAEARAAA EAGEVPVGAV VVCDGRIVAR AHNRPIALRD PTAHAEILAL  60
REAARALGSY RLTGCTLYAT LEPCPMCAGA ILHARIARLV YGVANPKAGA CGTVLDVMNH  120
PRLNHRVEVT GGVLAEECGA LLSGFFRAR                                   149

SEQ ID NO: 657         moltype = AA  length = 149
FEATURE                Location/Qualifiers
source                 1..149
                       mol_type = protein
                       organism = synthetic construct
SEQUENCE: 657
MDPTDLAFMR EALAEARAAA EAGEVPVGAV VVCDGRIVAR AHNRPIALND PTAHAEVLAL  60
REAARALGSY RLTGCTLYAT LEPCAMCAGA ILHARIARLV YGVANPKAGA CGTVLDVMNH  120
PRLNHRVEVT GGVLAEECGA LLSGFFRAR                                   149

SEQ ID NO: 658         moltype = AA  length = 149
FEATURE                Location/Qualifiers
source                 1..149
                       mol_type = protein
                       organism = synthetic construct
SEQUENCE: 658
MDPTDLAFMR EALAEARAAA EAGEVPVGAV VVCDGRIVAR AHNRPIALND PTAHAEILAL  60
```

```
REAARALGSY RLTGCTLYAT LEPCAMCAGA ILHARIARLV YGVANPKAGA CGTVLDVMNH  120
PKLNHRVEVT GGVLAEECGA LLSGFFRAR                                    149

SEQ ID NO: 659         moltype = AA  length = 149
FEATURE                Location/Qualifiers
source                 1..149
                       mol_type = protein
                       organism = synthetic construct
SEQUENCE: 659
MDPTDLAFMR EALAEARAAA EAGEVPVGAV VVCDGRIVAR AHNRPIALAD PTAHAEILAL  60
REAAKALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 660         moltype = AA  length = 147
FEATURE                Location/Qualifiers
source                 1..147
                       mol_type = protein
                       organism = synthetic construct
SEQUENCE: 660
MTDEYFMRQA LREARRAYDE GEVPVGAVVV RDGRVIARGR NQVRRLKDPT AHAEMLALTA  60
AAGHLGSPRL TGCTLYVTVE PCAMCAGALV WARVERVVFG VRNPKTGACG SVFDIPGDRR  120
LSHRPEVVGG VLEAECAALM RDFFRER                                      147

SEQ ID NO: 661         moltype = AA  length = 147
FEATURE                Location/Qualifiers
source                 1..147
                       mol_type = protein
                       organism = synthetic construct
SEQUENCE: 661
MTDEYFMRQA LREARRAYDE GEVPVGAVVV RDGRVIARGR NQVRRLKDPT AHAEMLALTA  60
AAGHLGSARL TGCTLYVTVE PCAMCAGALV WARVERVVFG VRNPRTGACG SVFDIPGDRR  120
LNHRPEVVGG VLEAECAALM RDFFRER                                      147

SEQ ID NO: 662         moltype = AA  length = 147
FEATURE                Location/Qualifiers
source                 1..147
                       mol_type = protein
                       organism = synthetic construct
SEQUENCE: 662
MTDEYFMRQA LREARRAYDE GEVPVGAVVV RDGRVIARGR NQVIRLKDPT AHAEMLALTA  60
AAGHLGSPSL TGCTLYVTVE PCAMCAGALV WARVERVVFG VRNPRTGACG SVFDIPGDRR  120
LNHRPEVVGG VLEAECAALM RDFFRER                                      147

SEQ ID NO: 663         moltype = AA  length = 149
FEATURE                Location/Qualifiers
source                 1..149
                       mol_type = protein
                       organism = synthetic construct
SEQUENCE: 663
MDPTDLAFMR EALAEARAAA EAGEVPVGAV VVCDGRIVAR AHNRPIALND PTAHAEILAL  60
REAARALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 664         moltype = AA  length = 149
FEATURE                Location/Qualifiers
source                 1..149
                       mol_type = protein
                       organism = synthetic construct
SEQUENCE: 664
MDPTDLAFMR EALAEARAAA EAGEVPVGAV VVCDGRIVAR AHNRPIALND PTAHAEVLAL  60
REAARALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 665         moltype = AA  length = 149
FEATURE                Location/Qualifiers
source                 1..149
                       mol_type = protein
                       organism = synthetic construct
SEQUENCE: 665
MDPTDLAFMR EALAEARAAA EAGEVPVGAV VVCDGRIVAR AHNRPIALND PTAHAEVLAL  60
REAAKALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 666         moltype = AA  length = 149
FEATURE                Location/Qualifiers
source                 1..149
                       mol_type = protein
                       organism = synthetic construct
SEQUENCE: 666
```

```
MDPTDLAFMR EALAEARAAA EAGEVPVGAV VVCDGRIVAR AHNRPIALND PTAHAEVLAL  60
REAGRALGSY RLTGCTLYAT LEPCPMCAGA ILHARIARLV YGVANPKAGA CGSVLDVMNH  120
PKLNHRVEVT GGVLAEECGA LLSGFFRAR                                    149

SEQ ID NO: 667         moltype = AA  length = 147
FEATURE                Location/Qualifiers
source                 1..147
                       mol_type = protein
                       organism = synthetic construct
SEQUENCE: 667
MDDAGFMRLA LEEARAAAAA GEVPVGAVVV RDGEVLARAG NRTVRDKDPT AHAEIVAIRE  60
AARRLGSYRL AGCTLYVTLE PCPMCAGAMI HARLDRLVYG VANPKAGAAG TVLDVLGHPR  120
LNHRMEVEGG VLAAECGALL RDFFRAR                                      147

SEQ ID NO: 668         moltype = AA  length = 147
FEATURE                Location/Qualifiers
source                 1..147
                       mol_type = protein
                       organism = synthetic construct
SEQUENCE: 668
MTDEYFMRQA LREARRAYDE GEVPVGAVVV RDGRVIARGR NQVRRLKDPT AHAEMLALTA  60
AAGHLGSPSL TGCTLYVTVE PCAMCAGALV WARVERVVFG VRNPKTGACG SVFDIPGDRR  120
LNHRPEVVGG VLEAECAALM RDFFRER                                      147

SEQ ID NO: 669         moltype = AA  length = 147
FEATURE                Location/Qualifiers
source                 1..147
                       mol_type = protein
                       organism = synthetic construct
SEQUENCE: 669
MTDEYFMRQA LREARRAYDE GEVPVGAVVV RDGRVIARGR NQVIRLKDPT AHAEMLALTA  60
AAGHLGSRSL TGCTLYVTVE PCAMCAGALV WARVERVVFG VRNPRAGACG SVFDIPGDRR  120
LNHRPEVVGG VLEAECAALM RDFFRER                                      147

SEQ ID NO: 670         moltype = AA  length = 147
FEATURE                Location/Qualifiers
source                 1..147
                       mol_type = protein
                       organism = synthetic construct
SEQUENCE: 670
MTDEYFMRQA LREARRAYDE GEVPVGAVVV RDGRVIARGR NQVVRLKDPT AHAEMLALTA  60
AAGHLGSPSL TGCTLYVTVE PCAMCAGALV WARVERVVFG VRNPRTGACG SVFDIPGDRR  120
LNHRPEVVGG VLEAECAALM RDFFRER                                      147

SEQ ID NO: 671         moltype = AA  length = 149
FEATURE                Location/Qualifiers
source                 1..149
                       mol_type = protein
                       organism = synthetic construct
SEQUENCE: 671
MDPTDLAFMR EALAEARAAA EAGEVPVGAV VVCDGRIVAR AHNRPIALKD PTAHAEILAL  60
REAAAALGNY RLTGCTLYAT LEPCPMCAGA ILHARIARLV YGVANPKAGA CGSVLDVMNH  120
PLLNHRVEVT GGVLAEECGA LLSGFFRAR                                    149

SEQ ID NO: 672         moltype = AA  length = 149
FEATURE                Location/Qualifiers
source                 1..149
                       mol_type = protein
                       organism = synthetic construct
SEQUENCE: 672
MDPTDLAFMR EALAEARAAA EAGEVPVGAV VVCDGRIVAR AHNRPIALRD PTAHAEILAL  60
REAAAALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 673         moltype = AA  length = 149
FEATURE                Location/Qualifiers
source                 1..149
                       mol_type = protein
                       organism = synthetic construct
SEQUENCE: 673
MDPTDLAFMR EALAEARAAA EAGEVPVGAV VVCDGRIVAR AHNRPIALND PTAHAEILAL  60
REAARALGSY RLTGCTLYAT LEPCPMCAGA ILHARIARLV YGVANPKAGA CGTVLDVMNH  120
PKLNHRVEVT GGVLAEECGA LLSGFFRAR                                    149

SEQ ID NO: 674         moltype = AA  length = 149
FEATURE                Location/Qualifiers
source                 1..149
                       mol_type = protein
                       organism = synthetic construct
```

```
SEQUENCE: 674
MDPTDLAFMR EALAEARAAA EAGEVPVGAV VVCDGRIVAR AHNRPIALKD PTAHAEILAL  60
REAARALGSY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 675         moltype = AA  length = 149
FEATURE                Location/Qualifiers
source                 1..149
                       mol_type = protein
                       organism = synthetic construct
SEQUENCE: 675
MDPTDLAFMR EALAEARAAA EAGEVPVGAV VVCDGRIVAR AHNRPIALKD PTAHAEILAL  60
REAAAALGDY RLTGCTLYAT LEPCPMCAGA ILHARIARLV YGVANPKAGA CGTVLDVMNH  120
PRLNHRVEVT GGVLAEECGA LLSGFFRAR                                    149

SEQ ID NO: 676         moltype = AA  length = 147
FEATURE                Location/Qualifiers
source                 1..147
                       mol_type = protein
                       organism = synthetic construct
SEQUENCE: 676
MTDEYFMRQA LREARRAYDE GEVPVGAVVV RDGRVIARGR NQVERLKDPT AHAEILALRA  60
ACRHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 677         moltype = AA  length = 147
FEATURE                Location/Qualifiers
source                 1..147
                       mol_type = protein
                       organism = synthetic construct
SEQUENCE: 677
MTDEYFMRQA LREARRAYDE GEVPVGAVVV RDGRVIARGR NQVERLKDPT AHAEILALSA  60
ACRHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 678         moltype = AA  length = 147
FEATURE                Location/Qualifiers
source                 1..147
                       mol_type = protein
                       organism = synthetic construct
SEQUENCE: 678
MTDEYFMRQA LREARRAYDE GEVPVGAVVV RDGRVIARGR NQVERLKDAT AHAEILALRA  60
ACAHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 679         moltype = AA  length = 147
FEATURE                Location/Qualifiers
source                 1..147
                       mol_type = protein
                       organism = synthetic construct
SEQUENCE: 679
MTDEYFMRQA LREARRAYDE GEVPVGAVVV RDGRVIARGR NQVERLRDAT AHAEILALRA  60
ACEHLGSKYL TGCTLYVTVE PCAMCAGALV WARVERVVFG VRNPKAGACG SVLDIPGNRR  120
LNHRPEVVGG VLEAECAALM RDFFRER                                      147

SEQ ID NO: 680         moltype = AA  length = 149
FEATURE                Location/Qualifiers
source                 1..149
                       mol_type = protein
                       organism = synthetic construct
SEQUENCE: 680
MDPEDLAFMR KALEEARQAR DAGEVPVGAV VVLDGEIVAR AHNRTIQLSD PTAHAEILAL  60
REAARALGNY RLEGCTLYVT LEPCAMCAGA ILHARIERLV FGVANPKAGA AGSVLDVLNH  120
PRLNHRVEVT GGVLAEECGA LLRDFFRAR                                    149

SEQ ID NO: 681         moltype = AA  length = 149
FEATURE                Location/Qualifiers
source                 1..149
                       mol_type = protein
                       organism = synthetic construct
SEQUENCE: 681
MDPTDEAFMK KALDEAKKAA EAGEVPVGAV VVYDGKVVAR AHNRRIAESD PTAHAEILAL  60
REAARALGNY RLTGCTLYVT LEPCAMCAGA ILHARIARLV YGVPNPKAGA TGSVLNVLNH  120
PRLNHRVEVT GGVLAEECGD LLRGFFRAR                                    149

SEQ ID NO: 682         moltype = AA  length = 147
FEATURE                Location/Qualifiers
source                 1..147
                       mol_type = protein
```

```
                         organism = synthetic construct
SEQUENCE: 682
MDDEGWMQLA LEEARASRAA GEVPVGAVVV RDGEVLARAG NRTRELCDPT AHAEIVALRE  60
AARRLGNYRL PGCTLYVTLE PCAMCAGAML HARLDRLVYG VPNPKAGAAG SVLDVLGHPR  120
LNHRLEVTGG VLAAECGQLL RDFFRAR                                      147

SEQ ID NO: 683           moltype = AA  length = 147
FEATURE                  Location/Qualifiers
source                   1..147
                         mol_type = protein
                         organism = synthetic construct
SEQUENCE: 683
MTDEYFMRQA LREARRAYDE GEVPVGAVVV RDGRVIARGR NQVERLKDPT AHAEILALKA  60
ACAHLGSKYL TGCTLYVTVE PCAMCAGALV WARVERVVFG VRNPKAGACG SVLDIPGNRR  120
LNHRPEVVGG VLEAECAALM RDFFRER                                      147

SEQ ID NO: 684           moltype = AA  length = 149
FEATURE                  Location/Qualifiers
source                   1..149
                         mol_type = protein
                         organism = synthetic construct
SEQUENCE: 684
MDPTDVAFMQ QALDEARAAR EAGEVPVGAV VVYDGRVVAR AHNRTIARSD PTAHAEILAL  60
REAARALGNY RLAGCTLYVT LEPCAMCAGA ILHARIERLV YGVPNPKAGA TGSVLNVLNH  120
PRLNHRVEVT GGVLAEECGA LLRGFFRAR                                    149

SEQ ID NO: 685           moltype = AA  length = 149
FEATURE                  Location/Qualifiers
source                   1..149
                         mol_type = protein
                         organism = synthetic construct
SEQUENCE: 685
MDPEDLRFMR KALAEARKAK EAGEVPVGAV VVKDGKIVAQ AHNRTIALSD PTAHAEILAL  60
REAARALGNY RLTGCTLYAT LEPCAMCAGA ILHARIARLV YGVPNPKAGA SGSVLNVLNH  120
PRLNHQVEVT GGVLAEECGA LLRDFFRAR                                    149

SEQ ID NO: 686           moltype = AA  length = 149
FEATURE                  Location/Qualifiers
source                   1..149
                         mol_type = protein
                         organism = synthetic construct
SEQUENCE: 686
MDPKDLRFMQ KALAEAREAK AAGEVPVGAV VVRNGKIVAR AHNRTRALSD PTAHAEILAL  60
REAARALGNY RLEGCTLYVT LEPCAMCAGA ILHARIERLV YGVANPKAGA AGSVLDVLNH  120
PRLNHRVEVT GGVLAEECGA LLRGFFRAR                                    149

SEQ ID NO: 687           moltype = AA  length = 147
FEATURE                  Location/Qualifiers
source                   1..147
                         mol_type = protein
                         organism = synthetic construct
SEQUENCE: 687
MTDEYFMRQA LREARRAYDE GEVPVGAVVV RDGRVIARGR NQVERLKDPT AHAEILALRA  60
ACAHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 688           moltype = AA  length = 147
FEATURE                  Location/Qualifiers
source                   1..147
                         mol_type = protein
                         organism = synthetic construct
SEQUENCE: 688
MTDEYFMRQA LREARRAYDE GEVPVGAVVV RDGRVIARGR NQVERLQDPT AHAEILALRA  60
ACAHLGSKYL TGCTLYVTVE PCAMCAGALV WARVERVVFG VRNPKAGACG SVLDIPGNRR  120
LNHRPEVVGG VLEAECAALM RDFFRER                                      147

SEQ ID NO: 689           moltype = AA  length = 147
FEATURE                  Location/Qualifiers
source                   1..147
                         mol_type = protein
                         organism = synthetic construct
SEQUENCE: 689
MTDEYFMRQA LREARRAYDE GEVPVGAVVV RDGRVIARGR NQVERLRDPT AHAEVLALRA  60
ACAHLGSKYL TGCTLYVTVE PCAMCAGALV WARVERVVFG VRNPKAGACG SVLDIPGDRR  120
MNHRPEVVGG VLEAECAALM RDFFRER                                      147

SEQ ID NO: 690           moltype = AA  length = 147
FEATURE                  Location/Qualifiers
source                   1..147
```

```
                        mol_type = protein
                        organism = synthetic construct
SEQUENCE: 690
MTDEYFMRQA LREARRAYDE GEVPVGAVVV RDGRVIARGR NQVERLKDAT AHAEILALRA  60
ACRHLGSKYL TGCTLYVTVE PCAMCAGALV WARVERVVFG VRNPKAGACG SVLDIPGNRR  120
LNHRPEVVGG VLEAECAALM RDFFRER                                    147

SEQ ID NO: 691          moltype = AA  length = 149
FEATURE                 Location/Qualifiers
source                  1..149
                        mol_type = protein
                        organism = synthetic construct
SEQUENCE: 691
MDALDIEFMR KALAEARAAK EAGEVPVGAV VVRDGKIVAR AHNRTIALSD PTAHAEILAL  60
RAAARALGNY RLTGCTLYVT LEPCAMCAGA ILHARIERLV YGVPNPKAGA TGSVLNVLNH  120
PRLNHRVEVT GGVLAEECGR LLSDFFRAR                                  149

SEQ ID NO: 692          moltype = AA  length = 149
FEATURE                 Location/Qualifiers
source                  1..149
                        mol_type = protein
                        organism = synthetic construct
SEQUENCE: 692
MDPDDIAFMR EALAEARRAK EAGEVPVGAV VVKDGRIVAR AHNRTIAESD PTAHAEILAL  60
REAARQLGNY RLTGCTLYAT LEPCAMCAGA ILHARIARLV YGVPNPKAGA TGSVLDVMNH  120
PRLNHRVEVT GGVLADECGD LLRDFFRAR                                  149

SEQ ID NO: 693          moltype = AA  length = 149
FEATURE                 Location/Qualifiers
source                  1..149
                        mol_type = protein
                        organism = synthetic construct
SEQUENCE: 693
MDPEDIAFME QALAEARAAR DAGEVPVGAV VVLDGEIVAQ AHNRTRQLSD PTAHAEILAL  60
RQAARALGNY RLTGCTLYVT LEPCAMCAGA ILHARVERLV YGVANPKAGA TGSVLNVLNH  120
PRLNHRVEVT GGVLAEECGD LLRGFFRAR                                  149

SEQ ID NO: 694          moltype = AA  length = 149
FEATURE                 Location/Qualifiers
source                  1..149
                        mol_type = protein
                        organism = synthetic construct
SEQUENCE: 694
MDDQDLRFMK MALDEARKAK DAGEVPVGAV VVHEGEVVAR AHNRTIARSD PTAHAEIRAL  60
REAARALGNY RLTGCTLYVT LEPCAMCAGA ILHARIARLV YGVPNPKAGA TGSVLNVLNH  120
PRLNHRVEVT GGVLAEECGD LLRDFFRAR                                  149

SEQ ID NO: 695          moltype = AA  length = 147
FEATURE                 Location/Qualifiers
source                  1..147
                        mol_type = protein
                        organism = synthetic construct
SEQUENCE: 695
MDDEGWMRLA LEEARASRAA GEVPVGAVVV RDGQVLARAG NRTRERCDPT AHAEIVALRE  60
AARKLGNYRL AGCTLYVTLE PCAMCAGAML HARLDRLVYG VANPKAGAAG SVLDVLGHPR  120
LNHRLEVTGG VLEAECGQLL RDFFRAR                                    147

SEQ ID NO: 696          moltype = AA  length = 147
FEATURE                 Location/Qualifiers
source                  1..147
                        mol_type = protein
                        organism = synthetic construct
SEQUENCE: 696
MTDEYFMRQA LREARRAYDE GEVPVGAVVV RDGRVIARGR NQVERLRDPT AHAELLALRA  60
ACEHLGSKYL TGCTLYVTVE PCAMCAGALV WARVERVVFG VRNPKAGACG SVLDIPGDRR  120
LNHRPEVVGG VLEAECAALM RDFFRER                                    147

SEQ ID NO: 697          moltype = AA  length = 147
FEATURE                 Location/Qualifiers
source                  1..147
                        mol_type = protein
                        organism = synthetic construct
SEQUENCE: 697
MTDEYFMRQA LREARRAYDE GEVPVGAVVV RDGRVIARGR NQVERLRDAT AHAEILALRA  60
AARHLGSKYL TGCTLYVTVE PCAMCAGALV WARVERVVFG VRNPKAGACG SVLDIPGNRR  120
LNHRPEVVGG VLEAECAALM RDFFRER                                    147

SEQ ID NO: 698          moltype = AA  length = 149
FEATURE                 Location/Qualifiers
```

```
source                  1..149
                        mol_type = protein
                        organism = synthetic construct
SEQUENCE: 698
MDAEDLAFMR QALAEAREAK EAGEVPVGAV VVHDGRVVAR AHNRTIRLSD PTAHAEILAL  60
REAARALGNY RLAGCTLYVT LEPCAMCAGA ILHARIQRLV YGVPNPKAGA AGSVLDVLNH  120
PRLNHRVEVT GGVLAEECAA LLTDFFRAR                                    149

SEQ ID NO: 699          moltype = AA  length = 149
FEATURE                 Location/Qualifiers
source                  1..149
                        mol_type = protein
                        organism = synthetic construct
SEQUENCE: 699
MDPEDVEFMR KALAEAREAR QAGEVPVGAV VVHDGKIVAR AHNRPIALSD PTAHAEILAL  60
REAARALGNY RLEGCTLYVT LEPCAMCAGA ILHARIQRLV YGVPNPKAGA TGSVLNVMNH  120
PRLNHRVEVT GGVLAEECGA LLSDFFRAR                                    149

SEQ ID NO: 700          moltype = AA  length = 149
FEATURE                 Location/Qualifiers
source                  1..149
                        mol_type = protein
                        organism = synthetic construct
SEQUENCE: 700
MDPEDLRFMR EALDEAREAR EAGEVPVGAV VVRDGRIVAR AHNRTKELSD PTAHAEILAL  60
RAAARALGNY RLAGCTLYCT LEPCAMCAGA ILHARIARLV YGVPNPKAGA AGSVLDVLNH  120
PRLNHRVEVT GGVLAEECGA LLRGFFRAR                                    149

SEQ ID NO: 701          moltype = AA  length = 147
FEATURE                 Location/Qualifiers
source                  1..147
                        mol_type = protein
                        organism = synthetic construct
SEQUENCE: 701
MDDAGFMRLA LEEARAAAAA GEVPVGAVVV RDGEVLARAG NRTVRDADPT AHAEVVAIRE  60
AARRLGSYRL AGCTLYVTLE PCPMCAGAMI HARLDRLVYG VANPKAGAAG TVLDVLGHPR  120
LNHRMEVEGG VLAAECGALL RDFFRAR                                      147

SEQ ID NO: 702          moltype = AA  length = 147
FEATURE                 Location/Qualifiers
source                  1..147
                        mol_type = protein
                        organism = synthetic construct
SEQUENCE: 702
MTDEYFMRQA LREARRAYDE GEVPVGAVVV RDGRVIARGR NQVERLRDPT AHAEILALRA  60
ACAHLGSKYL TGCTLYVTVE PCAMCAGALV WARVERVVFG VRNPKAGACG SVLDIPGNRR  120
LNHRPEVVGG VLEAECAALM RDFFRER                                      147

SEQ ID NO: 703          moltype = AA  length = 147
FEATURE                 Location/Qualifiers
source                  1..147
                        mol_type = protein
                        organism = synthetic construct
SEQUENCE: 703
MTDEYFMRQA LREARRAYDE GEVPVGAVVV RDGRVIARGR NQVERLRDPT AHAELLALRA  60
ACAHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 704          moltype = AA  length = 147
FEATURE                 Location/Qualifiers
source                  1..147
                        mol_type = protein
                        organism = synthetic construct
SEQUENCE: 704
MTDEYFMRQA LREARRAYDE GEVPVGAVVV RDGRVIARGR NQVERLRDAT AHAEILALRA  60
AAAHLGSKYL TGCTLYVTVE PCAMCAGALV WARVERVVFG VRNPKAGACG SVLDIPGNRR  120
LNHRPEVVGG VLEAECAALM RDFFRER                                      147

SEQ ID NO: 705          moltype = AA  length = 147
FEATURE                 Location/Qualifiers
source                  1..147
                        mol_type = protein
                        organism = synthetic construct
SEQUENCE: 705
MTDEYFMRQA LREARRAYDE GEVPVGAVVV RDGRVIARGR NQVERLKDAT AHAEILALRA  60
ACAHLGSKYL TGCTLYVTVE PCAMCAGALV WARVERVVFG VRNPKAGACG SVLDIPGNRR  120
LNHRPEVVGG VLEAECAALM RDFFRER                                      147

SEQ ID NO: 706          moltype = AA  length = 149
```

```
FEATURE                Location/Qualifiers
source                 1..149
                       mol_type = protein
                       organism = synthetic construct
SEQUENCE: 706
MDPKDIRFMR KALAEAREAR DAGEVPVGAV VVHDGEIVAQ AHNRPIAESD PTAHAEILAL  60
REAARALGNY RLEGCTLYVT LEPCAMCAGA ILHARIARLV YGVANPKAGA AGSVLNVLNH  120
PRLNHRVEVT GGVLADECGD LLRDFFRAR                                    149

SEQ ID NO: 707         moltype = AA  length = 149
FEATURE                Location/Qualifiers
source                 1..149
                       mol_type = protein
                       organism = synthetic construct
SEQUENCE: 707
MDSEDIKFMR QALAEAREAR EAGEVPVGAV VVHDGRIVAR AHNRRILESD PTAHAEILAL  60
RQAARALGNY RLTGCTLYAT LEPCAMCAGA ILHARIERLV YGVANPKAGA TGSVLNVLNH  120
PRLNHRVEVT GGVLEEECGA LLRDFFRAR                                    149

SEQ ID NO: 708         moltype = AA  length = 149
FEATURE                Location/Qualifiers
source                 1..149
                       mol_type = protein
                       organism = synthetic construct
SEQUENCE: 708
MDPVDVRFMK KALAEAREAK EAGEVPVGAV VVKDGEVVAR AHNRTIARSD PTAHAEINAL  60
RAAARALGNY RLEGCTLYVT LEPCAMCAGA ILHARIQRLV YGVPNPKAGA AGSVLDVLNH  120
PRLNHRVEVT GGVLAEECGA LLSDFFRAR                                    149

SEQ ID NO: 709         moltype = AA  length = 149
FEATURE                Location/Qualifiers
source                 1..149
                       mol_type = protein
                       organism = synthetic construct
SEQUENCE: 709
MDPDDIKFMR QALAEARKAR EAGEVPVGAV VVKDGRVVAR AHNRTIALSD PTAHAEIRAL  60
REAARALGNY RLVGCTLYVT LEPCAMCAGA ILHARIARLV YGVPNPKAGA AGSVLDVMNH  120
PRLNHRVEVT GGVLAEECGA LMSDFFRAR                                    149

SEQ ID NO: 710         moltype = AA  length = 147
FEATURE                Location/Qualifiers
source                 1..147
                       mol_type = protein
                       organism = synthetic construct
SEQUENCE: 710
MDDEGWMQLA LEEARASRAA GEVPVGAVVV RDGEVLARAG NRTRERCDPT AHAEIVALRE  60
AARRLGNYRL PGCTLYVTLE PCAMCAGAML HARLDRLVYG VANPKAGAAG SVLDVLGHPR  120
LNHRMEVTGG VLADECGRLL RDFFRAR                                      147

SEQ ID NO: 711         moltype = AA  length = 147
FEATURE                Location/Qualifiers
source                 1..147
                       mol_type = protein
                       organism = synthetic construct
SEQUENCE: 711
MTDEYFMRQA LREARRAYDE GEVPVGAVVV RDGRVIARGR NQVERLRDAT AHAEILALKA  60
AAAHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 712         moltype = AA  length = 149
FEATURE                Location/Qualifiers
source                 1..149
                       mol_type = protein
                       organism = synthetic construct
SEQUENCE: 712
MDPEDIEFME QALAEAKAAR EAGEVPVGAV VVHDGKIVAR AHNRTRALSD PTAHAEILAL  60
REAARALGNY RLEGCTLYAT LEPCAMCAGA ILHARIERLV YGVANPKAGA TGSVLDVLNH  120
PRLNHRVEVT GGVLAEECGA LLSDFFRAR                                    149

SEQ ID NO: 713         moltype = AA  length = 149
FEATURE                Location/Qualifiers
source                 1..149
                       mol_type = protein
                       organism = synthetic construct
SEQUENCE: 713
MDPEDIAFMR MALAEARKAK EAGEVPVGAV VVLNGEIVAR AHNRPIALSD PTAHAEILAL  60
REAARALGNY RLPGCTLYVT LEPCAMCAGA ILHARIERLV YGVANPKAGA TGSVLDVLNH  120
PRLNHKVEVT GGVLAEECGA LLRGFFRAR                                    149
```

```
SEQ ID NO: 714         moltype = AA  length = 149
FEATURE                Location/Qualifiers
source                 1..149
                       mol_type = protein
                       organism = synthetic construct
SEQUENCE: 714
MDAEDLEFMQ QALDEAREAR EAGEVPVGAV VVLDGRIVAR AHNRPIAESD PTAHAEILAL  60
RAAARALGNY RLTGCTLYVT LEPCAMCAGA ILHARIERLV YGVPNPKAGA CGSVLNVMNH  120
PRLNHRVEVV GGVLAEECGA LLTGFFRAR                                    149

SEQ ID NO: 715         moltype = AA  length = 149
FEATURE                Location/Qualifiers
source                 1..149
                       mol_type = protein
                       organism = synthetic construct
SEQUENCE: 715
MDPKDIKFME KALEEARKAK EAGEVPVGAV VVKDGRIVAR AHNRTIELSD PTAHAEIRAL  60
REAARALGNY RLEGCTLYAT LEPCAMCAGA ILHARIERLV YGVPNPKAGA TGSVLDVLNH  120
PRLNHRVEVT GGVLAEECGA LLRGFFRAR                                    149

SEQ ID NO: 716         moltype = AA  length = 147
FEATURE                Location/Qualifiers
source                 1..147
                       mol_type = protein
                       organism = synthetic construct
SEQUENCE: 716
MDDEGWMRLA LEEARASRAA GEVPVGAVVV RDGEVLARAG NRTRELCDPT AHAEIVALRE  60
AARRLGNYRL PGCTLYVTLE PCAMCAGAMI HARLDRLVYG VANPKAGAAG SVLDVLGHPR  120
LNHRMEVTGG VLAEECGALM RDFFRAR                                      147

SEQ ID NO: 717         moltype = AA  length = 147
FEATURE                Location/Qualifiers
source                 1..147
                       mol_type = protein
                       organism = synthetic construct
SEQUENCE: 717
MTDEYFMRQA LREARRAYDE GEVPVGAVVV RDGRVIARGR NQVERLKDPT AHAEILALRA  60
ACAHLGSKYL TGCTLYVTVE PCAMCAGALV WARVERVVFG VRNPKAGACG SVLDIPGNRK  120
LNHRPEVVGG VLEAECAALM RDFFRER                                      147

SEQ ID NO: 718         moltype = AA  length = 147
FEATURE                Location/Qualifiers
source                 1..147
                       mol_type = protein
                       organism = synthetic construct
SEQUENCE: 718
MTDEYFMRQA LREARRAYDE GEVPVGAVVV RDGRVIARGR NQVERLRDAT AHAEILALRA  60
ACRHLGSKYL TGCTLYVTVE PCAMCAGALV WARVERVVFG VRNPKAGACG SVLDIPGNRR  120
LNHRPEVVGG VLEAECAALM RDFFRER                                      147

SEQ ID NO: 719         moltype = AA  length = 149
FEATURE                Location/Qualifiers
source                 1..149
                       mol_type = protein
                       organism = synthetic construct
SEQUENCE: 719
MDPEDIAFMR KALAEARKAK EAGEVPVGAV VVKDGKIVAR AHNRTIALSD PTAHAEILAL  60
REAARALGNY RLTGCTLYVT LEPCAMCAGA ILHARIEKLV YGVPNPKAGA CGSVLNVLNH  120
PRLNHRVEVT GGVLAEECGA LLKDFFRAR                                    149

SEQ ID NO: 720         moltype = AA  length = 149
FEATURE                Location/Qualifiers
source                 1..149
                       mol_type = protein
                       organism = synthetic construct
SEQUENCE: 720
MDPEDVRYMR KALAEARKAK EAGEVPVGAV VVHDGRVVAR AHNRTIALSD PTAHAEILAL  60
REAARALGNY RLEGCTLYAT LEPCAMCAGA ILHARIQRLV YGVANPKAGA AGSVLDVMNH  120
PRLNHRVEVT GGVLEEECGA LLSDFFRAR                                    149

SEQ ID NO: 721         moltype = AA  length = 149
FEATURE                Location/Qualifiers
source                 1..149
                       mol_type = protein
                       organism = synthetic construct
SEQUENCE: 721
MDPEDVAFMK KALAEARAAQ EAGEVPVGAV VVKDGEVVAR AHNRTRERSD PTAHAEILAL  60
REAARALGNY RLAGCTLYVT LEPCAMCAGA ILHARIERLV YGVANPKAGA AGSVLNVLNH  120
PRLNHRVEVT GGVLAEECGD LLRGFFRAR                                    149
```

```
SEQ ID NO: 722          moltype = AA  length = 149
FEATURE                 Location/Qualifiers
source                  1..149
                        mol_type = protein
                        organism = synthetic construct
SEQUENCE: 722
MDPTDLEFMR QALAEAREAR DAGEVPVGAV VVHDGRIVAR AHNRTRELSD PTAHAEILAL  60
RAAARALGNY RLTGCTLYAT LEPCAMCAGA ILHARIERLV YGVANPKAGA CGSVLHVLNH  120
PRLNHRVEVT GGVLAEECGR LLRGFFRAR                                    149

SEQ ID NO: 723          moltype = AA  length = 147
FEATURE                 Location/Qualifiers
source                  1..147
                        mol_type = protein
                        organism = synthetic construct
SEQUENCE: 723
MDDEGWMRLA LEEARAAKAA GEVPVGAVVV RDGEVLARAG NRTRLDCDPT AHAEIVALRE  60
AARQLGNYRL AGCTLYVTLE PCAMCAGAML HARLDRLVYG VPNPKAGAAG SVLDVLGHPR  120
LNHRLEVTGG VLAEECGQLM RDFFRAR                                      147

SEQ ID NO: 724          moltype = AA  length = 147
FEATURE                 Location/Qualifiers
source                  1..147
                        mol_type = protein
                        organism = synthetic construct
SEQUENCE: 724
MTDEYFMRQA LREARRAYDE GEVPVGAVVV RDGRVIARGR NQVERLRDAT AHAEILALRA  60
AAAHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 725          moltype = AA  length = 147
FEATURE                 Location/Qualifiers
source                  1..147
                        mol_type = protein
                        organism = synthetic construct
SEQUENCE: 725
MTDEYFMRQA LREARRAYDE GEVPVGAVVV RDGRVIARGR NQVERLRDAT AHAEILALRA  60
ASAHLGSKYL TGCTLYVTVE PCAMCAGALV WARVERVVFG VRNPKAGACG SVLDIPGDRR  120
LNHRPEVVGG VLEAECAALM RDFFRER                                      147

SEQ ID NO: 726          moltype = AA  length = 147
FEATURE                 Location/Qualifiers
source                  1..147
                        mol_type = protein
                        organism = synthetic construct
SEQUENCE: 726
MTDEYFMRQA LREARRAYDE GEVPVGAVVV RDGRVIARGR NQVERLRDPT AHAEILALRA  60
ACAHLGSKYL TGCTLYVTVE PCAMCAGALV WARVERVVFG VRNPKAGACG SVLDIPGNRR  120
MNHRPEVVGG VLEAECAALM RDFFRER                                      147

SEQ ID NO: 727          moltype = AA  length = 149
FEATURE                 Location/Qualifiers
source                  1..149
                        mol_type = protein
                        organism = synthetic construct
SEQUENCE: 727
MDPEDLAFMR KALAEARRAA EAGEVPVGAV VVHDGRIVAR AHNRREALSD PTAHAEILAL  60
REAARALGNY RLAGCTLYAT LEPCAMCAGA ILHARIARLV YGVPNPKAGA CGSVLDVLNH  120
PRLNHRVEVT GGVLAEECGA LLRDFFRAR                                    149

SEQ ID NO: 728          moltype = AA  length = 149
FEATURE                 Location/Qualifiers
source                  1..149
                        mol_type = protein
                        organism = synthetic construct
SEQUENCE: 728
MDPYDLAFMQ QALAEARQAK AAGEVPVGAV VVHDGRIVAR AHNRTIELSD PTAHAEILAL  60
RQAARALGNY RLEGCTLYCT LEPCAMCAGA ILHARIERLV YGVPNPKAGA AGSVLNVMNH  120
PRLNHRVEVT GGVLAEECGA LLRDFFRAR                                    149

SEQ ID NO: 729          moltype = AA  length = 149
FEATURE                 Location/Qualifiers
source                  1..149
                        mol_type = protein
                        organism = synthetic construct
SEQUENCE: 729
MDPEDIEFMQ KALAEAREAR EAGEVPVGAV VVKDGEVVAR AHNRVNALSD PTAHAEILAL  60
REAARALGNY RLTGCTLYAT LEPCAMCAGA ILHARIERLV YGVANPKAGA TGSVLNVLNH  120
```

```
PRLNHRVEVT GGVLAEECGD LLRDFFRAR                                 149

SEQ ID NO: 730          moltype = AA  length = 147
FEATURE                 Location/Qualifiers
source                  1..147
                        mol_type = protein
                        organism = synthetic construct
SEQUENCE: 730
MDDRGWMRLA LEEARAARAR GEVPVGAVVV RDGQVLARAG NRTRELCDPT AHAEIVALRE  60
AARRLGNYRL AGCTLYVTLE PCAMCSGAML HARLDRLVYG VANPKAGAAG SVLDVLGHPR  120
LNHRLEVEGG VLEEECGALL RDFFRAR                                   147

SEQ ID NO: 731          moltype = AA  length = 147
FEATURE                 Location/Qualifiers
source                  1..147
                        mol_type = protein
                        organism = synthetic construct
SEQUENCE: 731
MDDRGWMRLA LEEARASRAA GEVPVGAVVV RDGEVLARAG NRVRELCDPT AHAEIVALRE  60
AARRLGNYRL PGCTLYVTLE PCAMCAGAML HARLDRLVYG VANPKAGAAG SVLDVLGHPR  120
LNHRMEVTGG VLEEECGALM RDFFRAR                                   147

SEQ ID NO: 732          moltype = AA  length = 147
FEATURE                 Location/Qualifiers
source                  1..147
                        mol_type = protein
                        organism = synthetic construct
SEQUENCE: 732
MNDEGFMQLA LEEARAARAA GEVPVGAVVV RDGEVIASAG NRTRERCDPT AHAEIVALRA  60
AARKLGNYRL PGCTLYVTLE PCAMCAGAMI HARLDRLVYG VANPKAGAAG SVLDVLGHPR  120
LNHRMEVEGG VLAEECGRLL RDFFRAR                                   147

SEQ ID NO: 733          moltype = AA  length = 147
FEATURE                 Location/Qualifiers
source                  1..147
                        mol_type = protein
                        organism = synthetic construct
SEQUENCE: 733
MSDEHFMKQA LDEARKAKDR GEVPVGAVVV RDGEIIATGR NRVEELKDPT AHAEMLAITA  60
AAGHLGSKYL TGCTLYVTLE PCVMCAGACI WARVDRVVFG VRNPKAGACG SVFNVPGDPR  120
LNHHPEVTGG ILEDECAKLL RDFFRER                                   147

SEQ ID NO: 734          moltype = AA  length = 167
FEATURE                 Location/Qualifiers
source                  1..167
                        mol_type = protein
                        organism = synthetic construct
SEQUENCE: 734
MSEVDPTDLA FMREALAEAR AAAEAGEVPV GAVVVCDGRI VARAHNRPIA LSDPTAHAEI  60
LALREAARAL GNYRLTGCTL YATLEPCAMC AGAILHARIA RLVYGVANPK AGACGSVLDV  120
MNHPRLNHRV EVTGGVLAEE CGALLSGFFR APRRVFNAQK KAQSSTD             167

SEQ ID NO: 735          moltype = AA  length = 365
FEATURE                 Location/Qualifiers
source                  1..365
                        mol_type = protein
                        organism = synthetic construct
SEQUENCE: 735
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGVRNAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFTDEYFM RQALREARRA YDEGEVPVGA VVVRDGRVIA  240
RGRNQVERLK DPTAHAEMLA LTAAAGHLGS KYLTGCTLYV TVEPCAMCAG ALVWARVERV  300
VFGVRNPKAG ACGSVFDIPG DRRLNHRPEV VGGVLEAECA ALMRDFFREP RRVFNAQKKA  360
QSSTD                                                           365

SEQ ID NO: 736          moltype = AA  length = 147
FEATURE                 Location/Qualifiers
source                  1..147
                        mol_type = protein
                        organism = synthetic construct
SEQUENCE: 736
MDDEGWMRLA LEEARAAKAA GEVPVGAVVV RDGQVIARAG NRTRERCDPT AHAEIRALRE  60
AARRLGNYRL EGCTLYVTLE PCAMCAGAML HARLDRLVYG VANPKAGAAG SVLDVLGHPR  120
LNHRLEVTGG VLAEECGQLL RDFFRAR                                   147

SEQ ID NO: 737          moltype = AA  length = 147
FEATURE                 Location/Qualifiers
source                  1..147
```

```
                         mol_type = protein
                         organism = synthetic construct
SEQUENCE: 737
MDDAGWMQLA LEEARASRAA GEVPVGAVVV RDGEVLASAG NRTRELCDPT AHAEIVALRE  60
AARRLGNYRL SGCTLYVTLE PCAMCAGAML HARLDRLVYG VANPKAGAAG SVLDVLGHPR  120
LNHRMEVTGG VLAEECAALL RDFFRAR                                      147

SEQ ID NO: 738           moltype = AA  length = 147
FEATURE                  Location/Qualifiers
source                   1..147
                         mol_type = protein
                         organism = synthetic construct
SEQUENCE: 738
MDDEGWMRLA LEEARAARDA GEVPVGAVVV RDGQVIARAG NRTRQLCDPT AHAEIVALRA  60
AARRLGNYRL PGCTLYVTLE PCAMCAGAMV HARIDRLVYG VPNPKAGAAG SVLNVLHHPR  120
LNHRMEVTGG VLAEECGALL TDFFRAR                                      147

SEQ ID NO: 739           moltype = AA  length = 147
FEATURE                  Location/Qualifiers
source                   1..147
                         mol_type = protein
                         organism = synthetic construct
SEQUENCE: 739
MDDAGWMQLA LEEARASKAA GEVPVGAVVV RDGRILARAG NRTRELCDPT AHAEIVALRE  60
AARRLGNYRL PGCTLYVTLE PCAMCAGAML HARLDRLVYG VANPKAGAAG SVLDVLGHPR  120
LNHRLEVEGG VLAAECSALL RDFFRAR                                      147

SEQ ID NO: 740           moltype = AA  length = 167
FEATURE                  Location/Qualifiers
source                   1..167
                         mol_type = protein
                         organism = synthetic construct
SEQUENCE: 740
MSEVEFDDAG FMRLALEEAR AAAAAGEVPV GAVVVRDGEV LARAGNRTVR DCDPTAHAEI  60
VALREAARRL GNYRLAGCTL YVTLEPCAMC AGAMIHARLD RLVYGVANPK AGAAGSVLDV  120
LGHPRLNHRM EVEGGVLAAE CGALLRDFFR APRRVFNAQK KAQSSTD                167

SEQ ID NO: 741           moltype = AA  length = 147
FEATURE                  Location/Qualifiers
source                   1..147
                         mol_type = protein
                         organism = synthetic construct
SEQUENCE: 741
MDDRGWMKLA LEEARASRAA GEVPVGAVVV RDGRVLASAG NRTRERCDPT AHAEIVALRE  60
AARKLGNYRL AGCTLYVTLE PCAMCAGAML HARLDRLVYG VANPKAGAAG SVLDVLGHPR  120
LNHRMEVTGG VLAEECGALL RDFFRAR                                      147

SEQ ID NO: 742           moltype = AA  length = 147
FEATURE                  Location/Qualifiers
source                   1..147
                         mol_type = protein
                         organism = synthetic construct
SEQUENCE: 742
MDDEGWMQLA LDEARKARDA GEVPVGAVVV RDGRVLASAG NRTRERCDPT AHAEIVALRE  60
AARKLGNYRL PGCTLYVTLE PCAMCAGAML HARLDRLVYG VDNPKAGAAG SVLDVLGHPR  120
LNHRMEVVGG VLAEECGALL RDFFRAR                                      147

SEQ ID NO: 743           moltype = AA  length = 147
FEATURE                  Location/Qualifiers
source                   1..147
                         mol_type = protein
                         organism = synthetic construct
SEQUENCE: 743
MTDEYFMKQA LAEARKAYDA GEVPVGAVVV RDGEVIARGH NRVERLKDPT AHAEMLAITA  60
AAGHLGSKYL EGCTLYVTLE PCVMCAGALV WARVDRVVFG VPNPKAGACG SVFDIPGDPR  120
LNHRPEVTGG VLEAECAALI RDFFRER                                      147

SEQ ID NO: 744           moltype = AA  length = 167
FEATURE                  Location/Qualifiers
source                   1..167
                         mol_type = protein
                         organism = synthetic construct
SEQUENCE: 744
MSEVEFTDEY FMRQALREAR RAYDEGEVPV GAVVVRDGRV IARGRNQVER LKDPTAHAEM  60
LALTAAAGHL GSKYLTGCTL YVTVEPCAMC AGALVWARVE RVVFGVRNPK AGACGSVFDI  120
PGDRRLNHRP EVVGGVLEAE CAALMRDFFR EPRRVFNAQK KAQSSTD                167

SEQ ID NO: 745           moltype = AA  length = 364
FEATURE                  Location/Qualifiers
```

```
source                  1..364
                        mol_type = protein
                        organism = synthetic construct
SEQUENCE: 745
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGVRNAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFDEKWMR YALSLADKAE ALGEVPVGAV LVKDNQVIGE  240
GWNQSISGHD ATAHAEIMAI RDAGKNLQNY RLIDCTLYVT LEPCPMCAGA IVHSRIKRVV  300
FGVSNYKTGA AGSVFNLLSN EQLNHQAEVT AGVLAEECGE KISAFFKRPR RVFNAQKKAQ  360
SSTD                                                               364

SEQ ID NO: 746          moltype = AA  length = 147
FEATURE                 Location/Qualifiers
source                  1..147
                        mol_type = protein
                        organism = synthetic construct
SEQUENCE: 746
MDDEGWMQLA LEEARASRAA GEVPVGAVVV RDGEVVARAG NRTRELCDPT AHAEIVALRE  60
AARARGNYRL TGCTLYVTLE PCAMCAGAMI HARLDRLVYG VPNPKAGAAG SVLDVLGHPR  120
LNHRMEVTGG VLAEECGALL RDFFRAR                                      147

SEQ ID NO: 747          moltype = AA  length = 147
FEATURE                 Location/Qualifiers
source                  1..147
                        mol_type = protein
                        organism = synthetic construct
SEQUENCE: 747
MDDQGWMQLA LEEARASRAR GEVPVGAVVV RDGEVIARAG NRVRERCDPT AHAEIVALRE  60
AARALGNYRL PGCTLYVTLE PCAMCAGAML HARLDRLVYG VANPKAGAAG SVLDVLGHPR  120
LNHRLEVTGG VLEAECGALL RDFFRAR                                      147

SEQ ID NO: 748          moltype = AA  length = 147
FEATURE                 Location/Qualifiers
source                  1..147
                        mol_type = protein
                        organism = synthetic construct
SEQUENCE: 748
MDDEGWMRLA LEEARASRAR GEVPVGAVVV RDGEVLARAG NRTREKCDPT AHAEIVALRE  60
AARRLGNYRL AGCTLYVTLE PCAMCAGAML HARLDRLVYG VPNPKAGAAG SVLDVLGHPR  120
LNHRMEVVGG VLEAECGALL RDFFRAR                                      147

SEQ ID NO: 749          moltype = AA  length = 147
FEATURE                 Location/Qualifiers
source                  1..147
                        mol_type = protein
                        organism = synthetic construct
SEQUENCE: 749
MTDEHFMREA LREAQKAYDR GEVPVGAVVV RDGEIIARGR NQVEKLKDPT AHAEMLAITA  60
AAGHLGSKYL RGCTLYVTLE PCVMCAGALV WARVERVVFG VDNPKAGAAG SVFNVPGDPR  120
LNHRPEVVGG VLEAECAALL RDFFRER                                      147

SEQ ID NO: 750          moltype = AA  length = 366
FEATURE                 Location/Qualifiers
source                  1..366
                        mol_type = protein
                        organism = synthetic construct
SEQUENCE: 750
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGVRNAK TGAAGSLMDV  120
LHHPGMNHRV EITEGILADE CAALLSDFFR MRRQEIKAQK KAQSSTDSGG SSGGSSGSET  180
PGTSESATPE SSGGSSGGSS EVEFSDDAGF MREALAEARA AAAAGEVPVG AVVVKDGEII  240
ARAGNRTLRD NDPTAHAEIV ALRAAARALG NHRLTGCTLY VTLEPCAMCA GAISHARIAR  300
LVYGVDNPKG GAVAHGPRFF AQPTCHHRPE VTGGVGAEEA GALLRDFFRA PRRVFNAQKK  360
AQSSTD                                                             366

SEQ ID NO: 751          moltype = AA  length = 162
FEATURE                 Location/Qualifiers
source                  1..162
                        mol_type = protein
                        organism = synthetic construct
SEQUENCE: 751
MDDEFYMRRA LELAALAEEH NEVPVGAVLV LNGEIIGEGW NRSIGHHDAT AHAEIMALRQ  60
AGKKLENYRL LDTTLYVTLE PCPMCAGALL HSRVKRVVFG VPNLKAGAAG TVLNLFESQA  120
SYHYADVESG LLEQECREQL QAFFKRRRKE KKALKQAQKE AE                     162

SEQ ID NO: 752          moltype = AA  length = 147
FEATURE                 Location/Qualifiers
source                  1..147
```

```
                        mol_type = protein
                        organism = synthetic construct
SEQUENCE: 752
MDDRGWMRLA LEEARAARAA GEVPVGAVVV RDGEVLARAG NRTRELCDPT AHAEIRALRE  60
AARQLGNYRL AGCTLYVTLE PCAMCAGAML HARLDRLVYG VPNPKAGAAG SVLDVLGHPR  120
LNHRLEVEGG VLAAECAQLL RDFFRAR                                      147

SEQ ID NO: 753          moltype = AA  length = 147
FEATURE                 Location/Qualifiers
source                  1..147
                        mol_type = protein
                        organism = synthetic construct
SEQUENCE: 753
MDDAGWMQLA LEEARAAREA GEVPVGAVVV RDGEVIARAG NRTRELCDPT AHAEIVALRE  60
AARKLGNYRL AGCTLYVTLE PCAMCAGAML HARLDRLVYG VANPKAGAAG SVLDVLGHPR  120
LNHRMEVTGG VLAAECGRLL RDFFRAR                                      147

SEQ ID NO: 754          moltype = AA  length = 147
FEATURE                 Location/Qualifiers
source                  1..147
                        mol_type = protein
                        organism = synthetic construct
SEQUENCE: 754
MDDEGFMQLA LEEARAARAA GEVPVGAVVV KDGEVLARAG NRTRELCDPT AHAEIVALRE  60
AARALGNYRL SGCTLYVTLE PCAMCAGAMV HARLDRLVYG VPNPKAGAAG SVLDVLHHPR  120
LNHRMEVTGG VLAAECGALL RDFFRAR                                      147

SEQ ID NO: 755          moltype = AA  length = 147
FEATURE                 Location/Qualifiers
source                  1..147
                        mol_type = protein
                        organism = synthetic construct
SEQUENCE: 755
MSDEHFMRQA LEEARKAYDE GEVPVGAVVV RDGEVIARGR NQVEILKDPT AHAEMLALTA  60
AAGHLGSKYL RGCTLYVTLE PCVMCAGACI WARVDRVVFG VRNPKAGAAG SVFDVPGDPR  120
LNHRPEVVGG VLRDECAQLM RDFFRER                                      147

SEQ ID NO: 756          moltype = AA  length = 365
FEATURE                 Location/Qualifiers
source                  1..365
                        mol_type = protein
                        organism = synthetic construct
SEQUENCE: 756
MSEVEFTDEY FMRQALREAR RAYDEGEVPV GAVVVRDGRV IARGRNQVER LKDPTAHAEM  60
LALTAAAGHL GSKYLTGCTL YVTVEPCAMC AGALVWARVE RVVFGVRNPK AGACGSVFDI  120
PGDRRLNHRP EVVGGVLEAE CAALMRDFFR EPRRVFNAQK KAQSSTDSGG SSGGSSGSET  180
PGTSESATPE SSGGSSGGSS EVEFTDEYFM RQALREARRA YDEGEVPVGA VVVRDGRVIA  240
RGRNQVERLK DPTAHAEMLA LTAAAGHLGS KYLTGCTLYV TVEPCAMCAG ALVWARVERV  300
VFGVRNPKAG ACGSVFDIPG DRRLNHRPEV VGGVLEAECA ALMRDFFREP RRVFNAQKKA  360
QSSTD                                                              365

SEQ ID NO: 757          moltype = AA  length = 161
FEATURE                 Location/Qualifiers
source                  1..161
                        mol_type = protein
                        organism = synthetic construct
SEQUENCE: 757
MDEKWMRYAL SLADKAEALG EVPVGAVLVK DNQVIGEGWN QSISGHDATA HAEIMAIRDA  60
GKNLQNYRLI DCTLYVTLEP CPMCAGAIVH SRIKRVVFGV SNYKTGAAGS VFNLLSNEQL  120
NHQAEVTAGV LAEECGEKIS AFFKRRRKEK KAAKKAAKLA E                      161

SEQ ID NO: 758          moltype = AA  length = 147
FEATURE                 Location/Qualifiers
source                  1..147
                        mol_type = protein
                        organism = synthetic construct
SEQUENCE: 758
MNDQGWMRLA LEEARAARAA GEVPVGAVVV RDGEVLARAG NRVRLLCDPT AHAEIVALRE  60
AARRLGNYRL EGCTLYVTLE PCAMCAGAMI HARLDRLVYG VPNPKAGAAG SVLDVLGHPR  120
LNHRLEVTGG VLADECGALM RDFFRAR                                      147

SEQ ID NO: 759          moltype = AA  length = 147
FEATURE                 Location/Qualifiers
source                  1..147
                        mol_type = protein
                        organism = synthetic construct
SEQUENCE: 759
MDDEGWMRLA LEEARASKAA GEVPVGAVVV RDGEVIARAG NRTRELCDPT AHAEIVALRE  60
AARRLGNYRL AGCTLYVTLE PCAMCAGAMI HARLDRLVYG VPNPKAGAAG SVLDVLGHPR  120
```

```
LNHRMEVEGG VLAEECRALL TDFFRAR                                  147

SEQ ID NO: 760         moltype = AA  length = 147
FEATURE                Location/Qualifiers
source                 1..147
                       mol_type = protein
                       organism = synthetic construct
SEQUENCE: 760
MTDEHFMRQA LAEARKAYDE GEVPVGAVVV RDGEIVATGR NQVERLKDPT AHAEMLAITA  60
AAGHLGSKYL RGCTLYVTVE PCVMCAGACV WARVDRVVFG VRNPKAGACG SVFDIPGDPR  120
LNHHPEVTGG VLEDECRQLL RDFFRER                                  147

SEQ ID NO: 761         moltype = AA  length = 147
FEATURE                Location/Qualifiers
source                 1..147
                       mol_type = protein
                       organism = synthetic construct
SEQUENCE: 761
MTDEHFMRQA LEEARKAYDQ GEVPVGAVVV RDGEVIARGR NQVERLKDPT AHAEMLAITA  60
AAGTLGSKYL EGCTLYVTLE PCVMCAGACI WARVERVVFG VRNPKAGACG SVFDIPGDPR  120
LNHRPEVVGG VLEAECAALM RDFFRER                                  147

SEQ ID NO: 762         moltype = AA  length = 168
FEATURE                Location/Qualifiers
source                 1..168
                       mol_type = protein
                       organism = synthetic construct
SEQUENCE: 762
MSEVEFSDDA GFMREALAEA RAAAAAGEVP VGAVVVKDGE IIARAGNRTL RDNDPTAHAE  60
IVALRAAARA LGNHRLTGCT LYVTLEPCAM CAGAISHARI ARLVYGVDNP KGGAVAHGPR  120
FFAQPTCHHR PEVTGGVGAE EAGALLRDFF RAPRRVFNAQ KKAQSSTD           168

SEQ ID NO: 763         moltype = AA  length = 365
FEATURE                Location/Qualifiers
source                 1..365
                       mol_type = protein
                       organism = synthetic construct
SEQUENCE: 763
MSEVDPTDLA FMREALAEAR AAAEAGEVPV GAVVVCDGRI VARAHNRPIA LNDPTAHAEI  60
LALREAAKAL GNYRLTGCTL YATLEPCPMC AGAILHARIA RLVYGVANPK AGACGTVLDV  120
MNHPRLNHRV EVTGGVLAEE CGALLSGFFR APRRVFNAQK KAQSSTDSGG SSGGSSGSET  180
PGTSESATPE SSGGSSGGSS EVDPTDLAFM REALAEARAA AEAGEVPVGA VVVCDGRIVA  240
RAHNRPIALN DPTAHAEILA LREAAKALGN YRLTGCTLYA TLEPCPMCAG AILHARIARL  300
VYGVANPKAG ACGTVLDVMN HPRLNHRVEV TGGVLAEECG ALLSGFFRAP RRVFNAQKKA  360
QSSTD                                                          365

SEQ ID NO: 764         moltype = AA  length = 147
FEATURE                Location/Qualifiers
source                 1..147
                       mol_type = protein
                       organism = synthetic construct
SEQUENCE: 764
MDDAGFMREA LAEARAAAAA GEVPVGAVVV KDGEIIARAG NRTLRDNDPT AHAEIVALRA  60
AARALGNHRL TGCTLYVTLE PCAMCAGAIS HARIARLVYG VDNPKGGAVA HGPRFFAQPT  120
CHHRPEVTGG VGAEEAGALL RDFFRAR                                  147

SEQ ID NO: 765         moltype = AA  length = 147
FEATURE                Location/Qualifiers
source                 1..147
                       mol_type = protein
                       organism = synthetic construct
SEQUENCE: 765
MDDEGWMRLA LEEARKSRAA GEVPVGAVVV RDGEVLATAG NRTRELCDPT AHAEIVALRE  60
AARRLGNYRL PGCTLYVTLE PCAMCAGAMI HARLDRLVYG VANPKAGAAG SVLDVLGHPR  120
LNHRMEVEGG VLEAECAALL RDFFRAR                                  147

SEQ ID NO: 766         moltype = AA  length = 147
FEATURE                Location/Qualifiers
source                 1..147
                       mol_type = protein
                       organism = synthetic construct
SEQUENCE: 766
MDDEGWMQLA LEEARQSRAA GEVPVGAVVV RDGEVIARAG NRTREKCDPT AHAEIVALRE  60
AARKLGNYRL PGCTLYVTLE PCAMCAGAMV HARLDRLVYG VANPKAGAAG SVLDVLHHPR  120
LNHRMEVTGG VLAEECGALL RDFFRAR                                  147

SEQ ID NO: 767         moltype = AA  length = 147
FEATURE                Location/Qualifiers
source                 1..147
```

```
                         mol_type = protein
                         organism = synthetic construct
SEQUENCE: 767
MDDAGWMRLA LEEARKSRAR GEVPVGAVVV RDGQVLARAG NRTRELCDPT AHAEIVALRA  60
AARKLGNYRL PGCTLYVTLE PCAMCAGAMV HARLDRLVYG VRNPKAGAAG SVLDVLGHPR  120
LNHQMEVTGG VLADECAALL RDFFRAR                                      147

SEQ ID NO: 768           moltype = AA  length = 365
FEATURE                  Location/Qualifiers
source                   1..365
                         mol_type = protein
                         organism = synthetic construct
SEQUENCE: 768
MSEVEFDDAG FMRLALEEAR AAAAAGEVPV GAVVVRDGEV LARAGNRTVR DNDPTAHAEI  60
VALREAARRL GSYRLAGCTL YVTLEPCPMC AGAMIHARLD RLVYGVANPK AGAAGTVLDV  120
LGHPRLNHRM EVEGGVLAAE CGALLRDFFR APRRVFNAQK KAQSSTDSGG SSGGSSGSET  180
PGTSESATPE SSGGSSGGSS EVEFDDAGFM RLALEEARAA AAAGEVPVGA VVVRDGEVLA  240
RAGNRTVRDN DPTAHAEIVA LREAARRLGS YRLAGCTLYV TLEPCPMCAG AMIHARLDRL  300
VYGVANPKAG AAGTVLDVLG HPRLNHRMEV EGGVLAAECG ALLRDFFRAP RRVFNAQKKA  360
QSSTD                                                              365

SEQ ID NO: 769           moltype = AA  length = 147
FEATURE                  Location/Qualifiers
source                   1..147
                         mol_type = protein
                         organism = synthetic construct
SEQUENCE: 769
MDDAGFMELA LDEARAARAA GEVPVGAVVV RDGEVLARAG NRTRELCDPT AHAEIVALRE  60
AARKLGNYRL EGCTLYVTLE PCAMCAGAML HARLDRLVYG VANPKAGAAG SVLDVLGHPR  120
LNHRMEVTGG VLEDECAALL RDFFRAR                                      147

SEQ ID NO: 770           moltype = AA  length = 147
FEATURE                  Location/Qualifiers
source                   1..147
                         mol_type = protein
                         organism = synthetic construct
SEQUENCE: 770
MDDAGWMQLA LEEARAARAA GEVPVGAVVV RDGEVLARAG NRTRERCDPT AHAEIVALRA  60
AARHLGNYRL EGCTLYVTLE PCAMCAGAML HARLDRLVYG VDNPKAGAAG SVLDVLGHPR  120
LNHRLEVTGG VLADECGQLL RDFFRAR                                      147

SEQ ID NO: 771           moltype = AA  length = 147
FEATURE                  Location/Qualifiers
source                   1..147
                         mol_type = protein
                         organism = synthetic construct
SEQUENCE: 771
MNDKGWMRLA LEEARAARAA GEVPVGAVVV RDGEVIAAAG NRRRELCDPT AHAEIVALRE  60
AARRLGNYRL PGCTLYVTLE PCAMCAGAMI HARLDRLVFG VANPKAGAAG SVLDVLGHPR  120
LNHRLEVTGG VLEEECGQLL RDFFRAR                                      147

SEQ ID NO: 772           moltype = AA  length = 147
FEATURE                  Location/Qualifiers
source                   1..147
                         mol_type = protein
                         organism = synthetic construct
SEQUENCE: 772
MSDEHFMQQA LAEARKAYDL GEVPVGAVVV RDGRIIARGH NQVEKLKDPT AHAEMLAITA  60
AAGHLGSKYL EGCTLYVTLE PCIMCAGACV WARVERVVYG VRNPKAGACG SVFDIPGDPR  120
LNHHPEVTGG VLEAECARLM RDFFRER                                      147

SEQ ID NO: 773           moltype = AA  length = 147
FEATURE                  Location/Qualifiers
source                   1..147
                         mol_type = protein
                         organism = synthetic construct
SEQUENCE: 773
MSDEFFMKQA LEEARLAYDE GEVPVGAVVV RDGEVIARGR NQIEELKDPT AHAEMLAITA  60
AAGHLGSKYL LGCTLYVTLE PCVMCAGACV WARVDRVVYG VRNPKAGAAG SVFDIPGDPR  120
LNHHPEVVGG VLQAECAALM RDFFRER                                      147

SEQ ID NO: 774           moltype = AA  length = 365
FEATURE                  Location/Qualifiers
source                   1..365
                         mol_type = protein
                         organism = synthetic construct
SEQUENCE: 774
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGVRNAK TGAAGSLMDV  120
```

```
LHHPGMNHRV EITEGILADE CAALLSDFFR MRRQEIKAQK KAQSSTDSGG SSGGSSGSET  180
PGTSESATPE SSGGSSGGSS EVEFDDAGFM RLALEEARAA AAAGEVPVGA VVVRDGEVLA  240
RAGNRTVRDC DPTAHAEIVA LREAARRLGN YRLAGCTLYV TLEPCAMCAG AMIHARLDRL  300
VYGVANPKAG AAGSVLDVLG HPRLNHRMEV EGGVLAAECG ALLRDFFRAP RRVFNAQKKA  360
QSSTD                                                              365

SEQ ID NO: 775         moltype = AA  length = 365
FEATURE                Location/Qualifiers
source                 1..365
                       mol_type = protein
                       organism = synthetic construct
SEQUENCE: 775
MSEVEFTDEY FMRQALREAR RAYDEGEVPV GAVVVRDGRV IARGRNQVER LKDPTAHAEI  60
LALRAACRHL GSKYLTGCTL YVTVEPCAMC AGALVWARVE RVVFGVRNPK AGACGSVLDI  120
PGDRRLNHRP EVVGGVLEAE CAALMRDFFR EPRRVFNAQK KAQSSTDSGG SSGGSSGSET  180
PGTSESATPE SSGGSSGGSS EVEFTDEYFM RQALREARRA YDEGEVPVGA VVVRDGRVIA  240
RGRNQVERLK DPTAHAEILA LRAACRHLGS KYLTGCTLYV TVEPCAMCAG ALVWARVERV  300
VFGVRNPKAG ACGSVLDIPG DRRLNHRPEV VGGVLEAECA ALMRDFFREP RRVFNAQKKA  360
QSSTD                                                              365

SEQ ID NO: 776         moltype = AA  length = 149
FEATURE                Location/Qualifiers
source                 1..149
                       mol_type = protein
                       organism = synthetic construct
SEQUENCE: 776
MDPTDLAFMR EALAEARAAA EAGEVPVGAV VVCDGRIVAR AHNRPIALSD PTAHAEILAL  60
REAARALGNY RLTGCTLYAT LEPCAMCAGA ILHARIARLV YGVANPGTGA CGSVLDVMNH  120
PRLNHRVEVT GGVLAEECGA LLSGFFRAR                                    149

SEQ ID NO: 777         moltype = RNA  length = 20
FEATURE                Location/Qualifiers
source                 1..20
                       mol_type = other RNA
                       organism = synthetic construct
SEQUENCE: 777
gaacacaaag catagactgc                                              20

SEQ ID NO: 778         moltype = RNA  length = 20
FEATURE                Location/Qualifiers
source                 1..20
                       mol_type = other RNA
                       organism = synthetic construct
SEQUENCE: 778
ggcccagact gagcacgtga                                              20

SEQ ID NO: 779         moltype = RNA  length = 20
FEATURE                Location/Qualifiers
source                 1..20
                       mol_type = other RNA
                       organism = synthetic construct
SEQUENCE: 779
acatacttct gtaatacact                                              20

SEQ ID NO: 780         moltype = RNA  length = 20
FEATURE                Location/Qualifiers
source                 1..20
                       mol_type = other RNA
                       organism = synthetic construct
SEQUENCE: 780
ggacagcttt tcctagacag                                              20

SEQ ID NO: 781         moltype = RNA  length = 20
FEATURE                Location/Qualifiers
source                 1..20
                       mol_type = other RNA
                       organism = synthetic construct
SEQUENCE: 781
gagcagatcg ttgattgtag                                              20

SEQ ID NO: 782         moltype = DNA  length = 23
FEATURE                Location/Qualifiers
source                 1..23
                       mol_type = other DNA
                       organism = synthetic construct
SEQUENCE: 782
ctggtggtac ttgaatcaag cac                                          23

SEQ ID NO: 783         moltype = DNA  length = 26
```

```
FEATURE                Location/Qualifiers
source                 1..26
                       mol_type = other DNA
                       organism = synthetic construct
SEQUENCE: 783
gaaggagact tgtgcacatt ctatag                                        26

SEQ ID NO: 784         moltype = DNA  length = 20
FEATURE                Location/Qualifiers
source                 1..20
                       mol_type = other DNA
                       organism = synthetic construct
SEQUENCE: 784
atgtgggctg cctagaaagg                                               20

SEQ ID NO: 785         moltype = DNA  length = 20
FEATURE                Location/Qualifiers
source                 1..20
                       mol_type = other DNA
                       organism = synthetic construct
SEQUENCE: 785
cccagccaaa cttgtcaacc                                               20

SEQ ID NO: 786         moltype = DNA  length = 53
FEATURE                Location/Qualifiers
source                 1..53
                       mol_type = other DNA
                       organism = synthetic construct
SEQUENCE: 786
acactctttc cctacacgac gctcttccga tctcaagacc tggctgagct aac          53

SEQ ID NO: 787         moltype = DNA  length = 52
FEATURE                Location/Qualifiers
source                 1..52
                       mol_type = other DNA
                       organism = synthetic construct
SEQUENCE: 787
gactggagtt cagacgtgtg ctcttccgat ctaaattgtc cagccccatc tg           52

SEQ ID NO: 788         moltype = DNA  length = 54
FEATURE                Location/Qualifiers
source                 1..54
                       mol_type = other DNA
                       organism = synthetic construct
SEQUENCE: 788
acactctttc cctacacgac gctcttccga tcttgatcgg cttcctaact gaag         54

SEQ ID NO: 789         moltype = DNA  length = 52
FEATURE                Location/Qualifiers
source                 1..52
                       mol_type = other DNA
                       organism = synthetic construct
SEQUENCE: 789
gactggagtt cagacgtgtg ctcttccgat ctaagctcac cagaacagca aa           52

SEQ ID NO: 790         moltype = DNA  length = 53
FEATURE                Location/Qualifiers
source                 1..53
                       mol_type = other DNA
                       organism = synthetic construct
SEQUENCE: 790
acactctttc cctacacgac gctcttccga tctctggcct gggtcaatcc ttg          53

SEQ ID NO: 791         moltype = DNA  length = 52
FEATURE                Location/Qualifiers
source                 1..52
                       mol_type = other DNA
                       organism = synthetic construct
SEQUENCE: 791
gactggagtt cagacgtgtg ctcttccgat cttccctagg tgctggcttc ca           52

SEQ ID NO: 792         moltype = AA  length = 4
FEATURE                Location/Qualifiers
source                 1..4
                       mol_type = protein
                       organism = synthetic construct
SEQUENCE: 792
KRKR                                                                4
```

```
SEQ ID NO: 793          moltype = AA  length = 4
FEATURE                 Location/Qualifiers
source                  1..4
                        mol_type = protein
                        organism = synthetic construct
SEQUENCE: 793
KRRR                                                                      4

SEQ ID NO: 794          moltype = AA  length = 4
FEATURE                 Location/Qualifiers
source                  1..4
                        mol_type = protein
                        organism = synthetic construct
SEQUENCE: 794
KKRK                                                                      4

SEQ ID NO: 795          moltype = AA  length = 4
FEATURE                 Location/Qualifiers
source                  1..4
                        mol_type = protein
                        organism = synthetic construct
SEQUENCE: 795
KRRK                                                                      4

SEQ ID NO: 796          moltype = AA  length = 7
FEATURE                 Location/Qualifiers
source                  1..7
                        mol_type = protein
                        organism = synthetic construct
VARIANT                 7
                        note = X is any amino acid except D or E
SEQUENCE: 796
RXXKRKX                                                                   7

SEQ ID NO: 797          moltype = AA  length = 7
FEATURE                 Location/Qualifiers
source                  1..7
                        mol_type = protein
                        organism = synthetic construct
VARIANT                 7
                        note = X is any amino acid except D or E
SEQUENCE: 797
PXXKRKX                                                                   7

SEQ ID NO: 798          moltype = AA  length = 7
FEATURE                 Location/Qualifiers
source                  1..7
                        mol_type = protein
                        organism = synthetic construct
VARIANT                 7
                        note = X is any amino acid except D or E
SEQUENCE: 798
RXXKRRX                                                                   7

SEQ ID NO: 799          moltype = AA  length = 7
FEATURE                 Location/Qualifiers
source                  1..7
                        mol_type = protein
                        organism = synthetic construct
VARIANT                 7
                        note = X is any amino acid except D or E
SEQUENCE: 799
PXXKRRX                                                                   7

SEQ ID NO: 800          moltype = AA  length = 7
FEATURE                 Location/Qualifiers
source                  1..7
                        mol_type = protein
                        organism = synthetic construct
VARIANT                 6
                        note = X is any amino acid except D or E
SEQUENCE: 800
RXXKRXK                                                                   7

SEQ ID NO: 801          moltype = AA  length = 7
FEATURE                 Location/Qualifiers
source                  1..7
                        mol_type = protein
                        organism = synthetic construct
```

```
VARIANT                6
                       note = X is any amino acid except D or E
SEQUENCE: 801
PXXKRXK                                                         7

SEQ ID NO: 802         moltype = AA  length = 7
FEATURE                Location/Qualifiers
source                 1..7
                       mol_type = protein
                       organism = synthetic construct
VARIANT                6
                       note = X is any amino acid except D or E
SEQUENCE: 802
RXXKRXR                                                         7

SEQ ID NO: 803         moltype = AA  length = 7
FEATURE                Location/Qualifiers
source                 1..7
                       mol_type = protein
                       organism = synthetic construct
VARIANT                6
                       note = X is any amino acid except D or E
SEQUENCE: 803
PXXKRXR                                                         7

SEQ ID NO: 804         moltype = AA  length = 8
FEATURE                Location/Qualifiers
source                 1..8
                       mol_type = protein
                       organism = synthetic construct
SEQUENCE: 804
KRXWXXAF                                                        8

SEQ ID NO: 805         moltype = AA  length = 8
FEATURE                Location/Qualifiers
source                 1..8
                       mol_type = protein
                       organism = synthetic construct
SEQUENCE: 805
KRXFXXAF                                                        8

SEQ ID NO: 806         moltype = AA  length = 8
FEATURE                Location/Qualifiers
source                 1..8
                       mol_type = protein
                       organism = synthetic construct
SEQUENCE: 806
KRXYXXAF                                                        8

SEQ ID NO: 807         moltype = AA  length = 6
FEATURE                Location/Qualifiers
source                 1..6
                       mol_type = protein
                       organism = synthetic construct
VARIANT                6
                       note = X is W, F, or Y
SEQUENCE: 807
LGKRRX                                                          6

SEQ ID NO: 808         moltype = AA  length = 6
FEATURE                Location/Qualifiers
source                 1..6
                       mol_type = protein
                       organism = synthetic construct
VARIANT                6
                       note = X is W, F, or Y
SEQUENCE: 808
LGKRKX                                                          6
```

What is claimed is:

1. A polypeptide comprising a synthetic adenosine deaminase having the amino acid sequence with at least 85% identity to SEQ ID NO: 2.

2. The polypeptide of claim 1, wherein the synthetic adenosine deaminase has the amino acid sequence with at least 90% identity to SEQ ID NO: 2.

3. The polypeptide of claim 1, wherein the synthetic adenosine deaminase has the amino acid sequence of SEQ ID NO: 2.

4. The polypeptide of claim 1, wherein the synthetic adenosine deaminase has the amino acid sequence with at least 95% identity to SEQ ID NO: 2.

5. A nucleic acid encoding the polypeptide of claim 1 or a fusion protein thereof.

6. A cell comprising a polypeptide of claim 1.

* * * * *